(12) United States Patent
Fu et al.

(10) Patent No.: US 11,725,214 B2
(45) Date of Patent: Aug. 15, 2023

(54) METHODS FOR INCREASING GRAIN PRODUCTIVITY

(71) Applicant: Institute of Genetics and Developmental Biology Chinese Academy of Sciences, Beijing (CN)

(72) Inventors: Xiangdong Fu, Beijing (CN); Shuansuo Wang, Beijing (CN); Kun Wu, Beijing (CN); Qian Liu, Beijing (CN); Qian Qian, Beijing (CN); Ke Huang, Beijing (CN); Penggen Duan, Beijing (CN); Baolan Zhang, Beijing (CN); Yunhai Li, Beijing (CN)

(73) Assignee: INSTITUTE OF GENETICS AND DEVELOPMENTAL BIOLOGY CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 16/616,590

(22) PCT Filed: May 24, 2018

(86) PCT No.: PCT/GB2018/051414
§ 371 (c)(1),
(2) Date: Nov. 25, 2019

(87) PCT Pub. No.: WO2018/215779
PCT Pub. Date: Nov. 29, 2018

(65) Prior Publication Data
US 2021/0017532 A1    Jan. 21, 2021

(30) Foreign Application Priority Data

May 25, 2017 (WO) ................ PCT/CN2017/085986

(51) Int. Cl.
*C12N 15/82* (2006.01)
*C12N 9/48* (2006.01)
*C12Q 1/6895* (2018.01)

(52) U.S. Cl.
CPC ......... *C12N 15/8218* (2013.01); *C12N 9/485* (2013.01); *C12N 15/8213* (2013.01); *C12N 15/8261* (2013.01); *C12Q 1/6895* (2013.01); *C12Y 304/19012* (2013.01); *C12Q 2600/13* (2013.01)

(58) Field of Classification Search
None
See application file for complete search history.

(56) References Cited

U.S. PATENT DOCUMENTS 8,748,592 B1 *  6/2014  Song .................. C12N 15/1137
                                                536/24.5
2004/0123343 A1  6/2004 La Rosa et al.
2016/0348073 A1  12/2016 Meissner et al.

FOREIGN PATENT DOCUMENTS

| CN | 107164347 A   | 9/2017 |
| WO | WO2016054039 A1 | 4/2016 |
| WO | WO2016160721 A1 | 10/2016 |
| WO | WO2016161380 A1 | 10/2016 |

OTHER PUBLICATIONS

Wang et al, 2017, Cell Research:1142-1156.*
Li et al, 2014, Frontiers in Plant Science, 5:1-6.*
Liu et al, 2021, Int. J. Mol. Sci., 22:1-17.*
Anonymous, "B9G207", Mar. 24, 2009 (Mar. 24, 2009), Retrieved from the Internet: URL:https://www.uniprot.org/uniprot/B9G207.txt, XP055491423.*
Jiang et al, 2021, Plant Signaling and Behavior, 16:1-7.*
Jing Wang et al, "Tissue-Specific Ubiquitination by IPA1 Interacting Protein1 Modulates IPA1 Protein Levels to Regulate Plant Architecture in Rice", The Plant Cell, Apr. 8, 2017 (Apr. 8, 2017), p. 697-707, vol. 29, No. 4, XP055490457.
Na Li et al, "Ubiquitin-mediated control of seed size in plants", Frontiers in Plant Science, Jul. 11, 2014 (Jul. 11, 2014), pp. 1-6, vol. 5, XP055167715.
Xu Rongfang et al, "Rapid improvement of grain weightviahighly efficient CRISPR/Cas9-mediated multiplex genome editing in rice", Journal of Genetics and Genomics, Elsevier BV, NL, Jul. 29, 2016 (Jul. 29, 2016), p. 529-532, vol. 43, No. 8, , XP029715830.
Shuansuo Wang et al, "Non-canonical regulation of SPL transcription factors by a human OTUB1-like deubiquitinase defines a new plant type rice associated with higher grain yield", Cell Research—Xibao Yanjiu, Aug. 4, 2017 (Aug. 4, 2017), p. 1142-1156, vol. 27, No. 9, XP055490394.
Ke Huang et al, "Wide and Thick Grain 1 , which encodes an otubain-like protease with deubiquitination activity, influences grain size and shape in rice", The Plant Journal, Jun. 2017 (Jun. 16, 2017), p. 849-860, vol. 91, No. 5, 16 J, XP055490401.
Zang, Y., et al., "Rice UBC13, a candidate housekeeping gene, is required for K63-linked polyubiquitination and tolerance to DNA damage", Rice, (2012), pp. 1-11, vol. 5, No. 24.
Balakirev, M.Y., et al., (2003) "Otubains: a new family of cysteine proteases in the ubiquitin pathway", EMBO Reports, (2003), pp. 517-522, vol. 4.
Dong, H., et al., "Ubiquitylation activates a peptidase that promotes cleavage and destabilization of its activating E3 ligases and diverse growth regulatory proteins to limit cell proliferation in *Arabidopsis*", Genes and Development, Jan. 11, 2017, pp. 197-208, vol. 31.
Du, L., et al., "The ubiquitin receptor DA1 regulates seed and organ size by modulating the stability of the ubiquitin-specific protease UBP15/SOD2 in *Arabidopsis*", The Plant Cell, Feb. 2014, pp. 665-677, vol. 26.

(Continued)

*Primary Examiner* — Jason Deveau Rosen

(74) *Attorney, Agent, or Firm* — Greer, Burns & Crain, Ltd.

(57) ABSTRACT

The invention relates to methods for increasing plant yield, and in particular grain yield by reducing or abolishing the expression and/or activity of OTUB1 in a plant. Also described are genetically altered plants characterised by the above phenotype and methods of producing such plants.

12 Claims, 44 Drawing Sheets

Specification includes a Sequence Listing.

(56) References Cited

OTHER PUBLICATIONS

Duan, P., et al., "Natural Variation in the Promoter of GSE5 Contributes to Grain Size Diversity in Rice", Molecular Plant, May 2017, pp. 685-694, vol. 10.

Fan, C., et al., "GS3, a major QTL for grain length and weight and minor QTL for grain width and thickness in rice, encodes a putative transmembrane protein", Theor Appl Genet, Jan. 6, 2006, pp. 1164-1171, vol. 112.

Herhaus, L., et al., OTUB1 enhances TGFbeta signalling by inhibiting the ubiquitylation and degradation of active SMAD2/3, Nature Communications, (2013), pp. 1-13, vol. 2519, No. 4.

Li, N., "Ubiquitin-mediated control of seed size in plants", Frontiers in Plant Science, Jul. 11, 2014, pp. 1-6, vol. 5, No. 332.

Li, N., et al., "Signaling pathways of seed size control in plants", Current Opinion in Plant Biology, (2016), pp. 23-32, vol. 33.

Miao, H., et al., "Linking differential domain functions of the GS3 protein to natural variation of grain size in rice", Proc Natl Acad. Sci. USA, Nov. 9, 2010, pp. 19579-19584, vol. 107, No. 45.

Nakada, S., et al., "Non-canonical inhibition of DNA damage-dependent ubiquitination by OTUB1", Nature, Aug. 19, 2010, pp. 941-946, vol. 466.

Numan, S.M., et al., "A genomic and functional inventory of deubiquitinating enzymes", Cell, Dec. 2, 2005, pp. 773-786, vol. 123.

Shomura, A., et al., "Deletion in a gene associated with grain size increased yields during rice domestication", Nature Genetics, Aug. 2008, pp. 1023-1028, vol. 40.

Song, X.J., et al., "A QTL for rice grain width and weight encodes a previously unknown RING-type E3 ubiquitin ligase". Nature Genetics, May 2007, pp. 623-630, vol. 39, No. 5.

Weng J., et al., "Isolation and initial characterization of GW5, a major QTL associated with rice grain width and weight", Cell Research, Dec. 2008, pp. 1199-1209, vol. 18.

Xia, T., et al., "The Ubiquitin Receptor DA1 Interacts with the E3 Ubiquitin Ligase DA2 to Regulate Seed and Organ Size in *Arabidopsis*", The Plant Cell, Sep. 2013, pp. 3347-3359, vol. 25.

Xu, Y., et al., "Ubiquitin-Specific Protease14 Interacts with Ultraviolet-B Insensitive4 to Regulate Endoreduplication and Cell and Organ Growth in *Arabidopsis*", Plant Cell, May 2016, pp. 1200-1214, vol. 28.

Que, L., et al., "Characterization of OTUB1 activation and inhibition by different E2 enzymes", Department of Biophysics and Biophysical Chemistry, Nov. 20, 2019, pp. 1-29.

Genbank, "Predicted: Oryza sativa Japonica Group ubiquitin thioesterase otubain-like (LOC4346169)", Mar. 1, 2016, pp. 1-2, Accession No. XM_015794619.

Australian Examination Report dated Aug. 22, 2022 for Australian Application No. 2018274709.

* cited by examiner

Figure 1
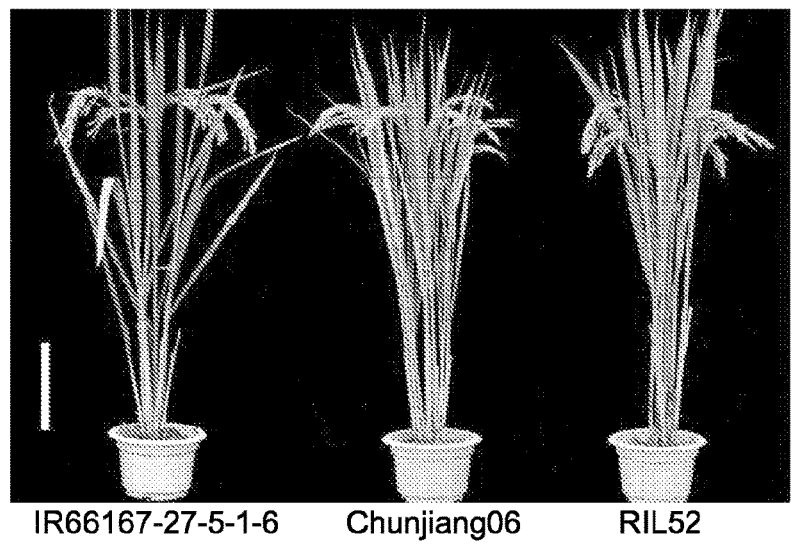
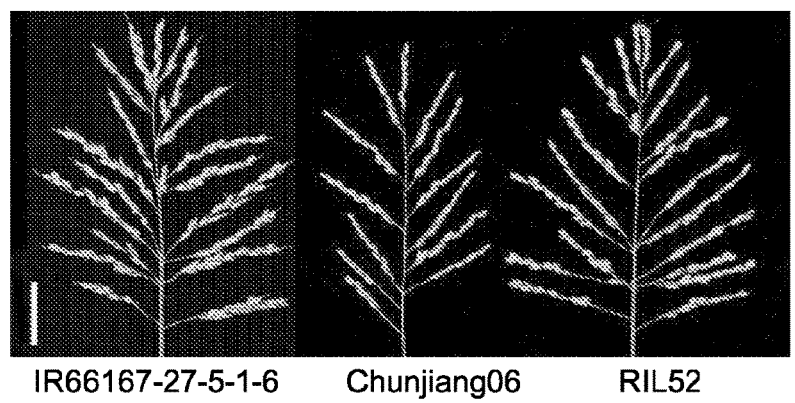
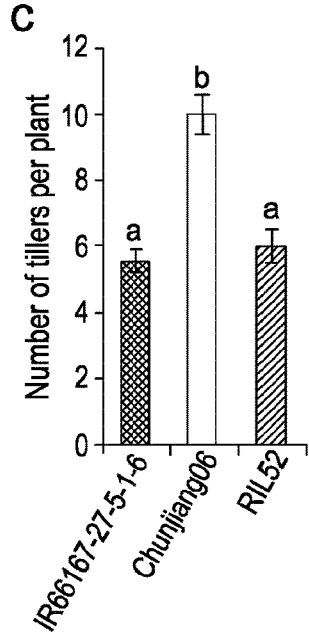 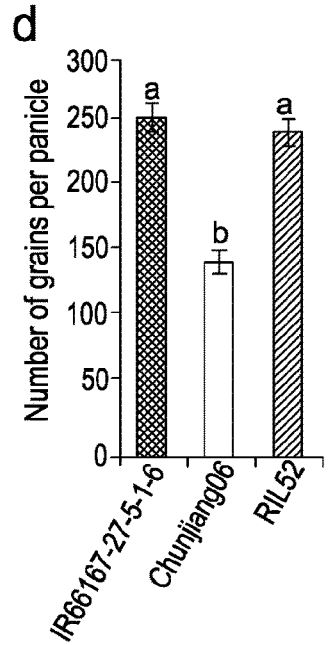 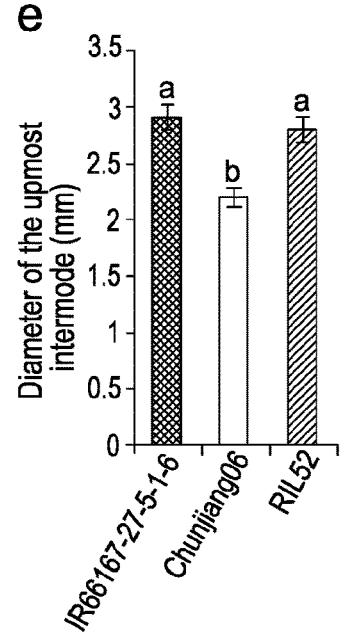

Figure 1
continued
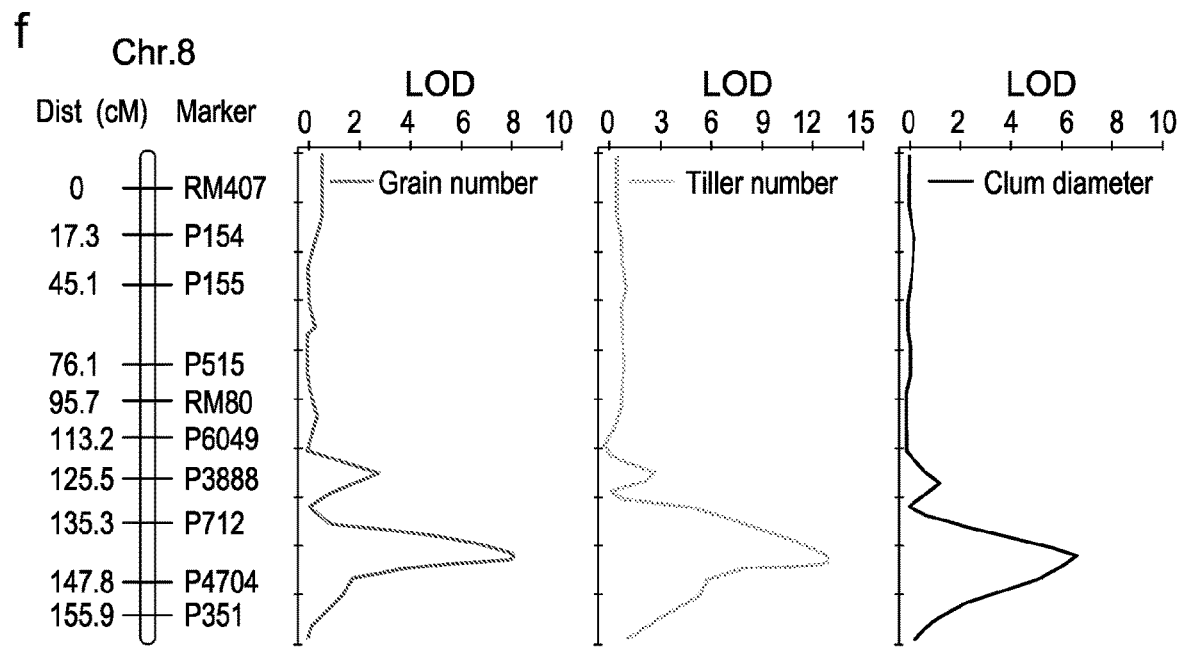
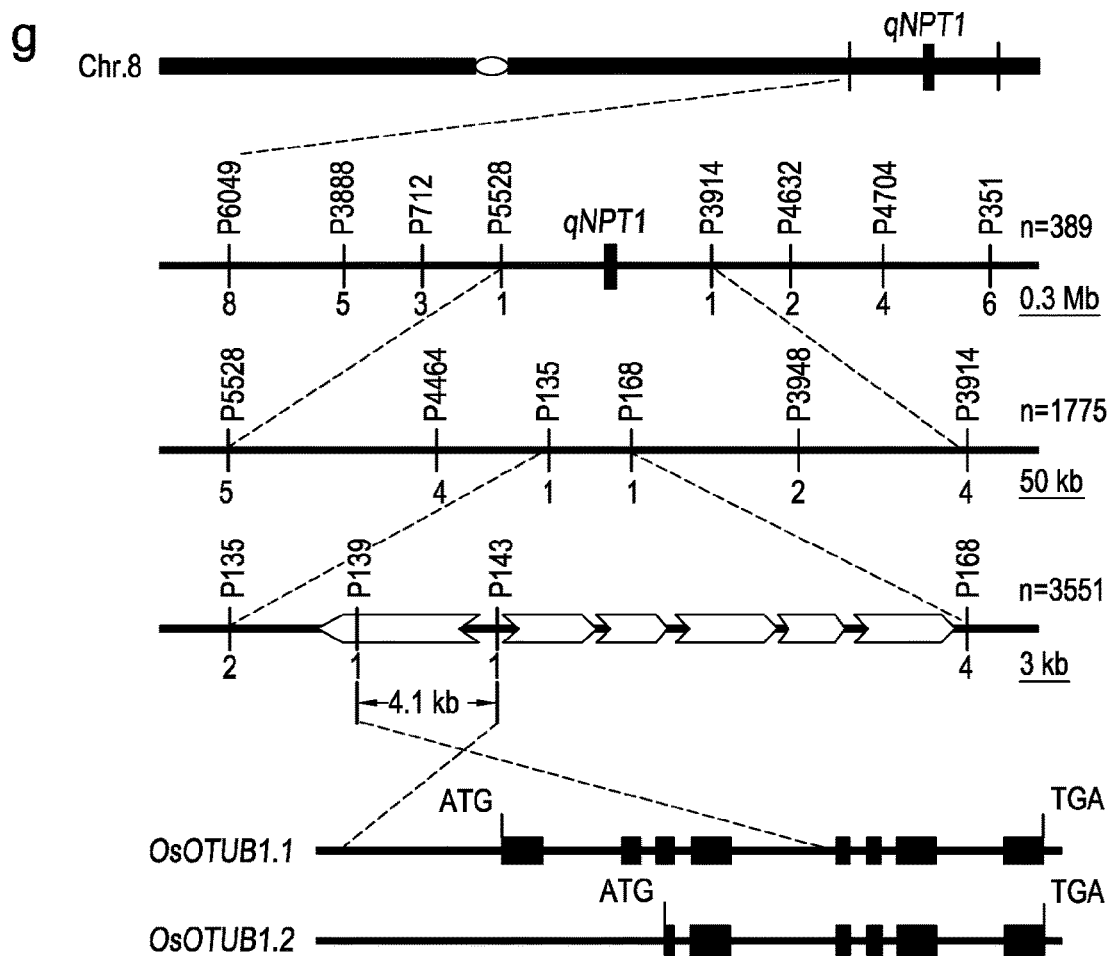

h

Figure 2
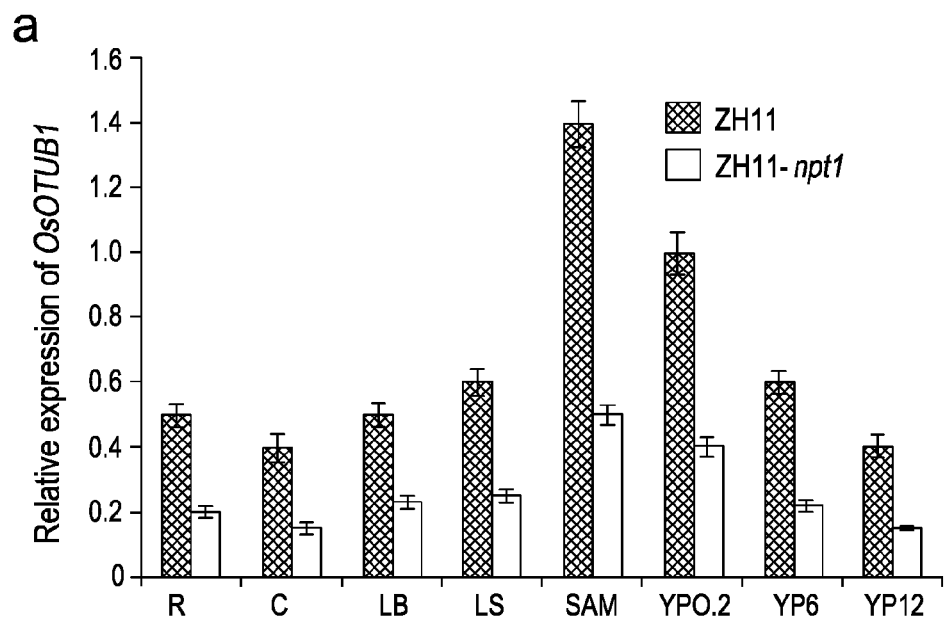
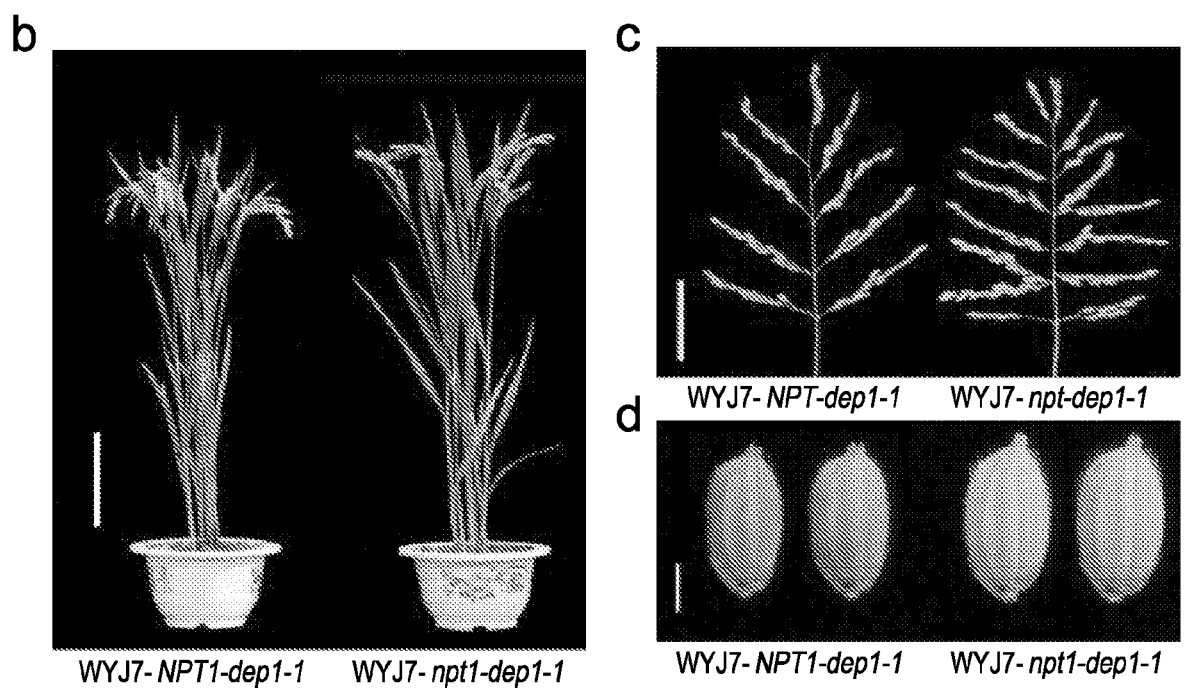

Figure 2
continued
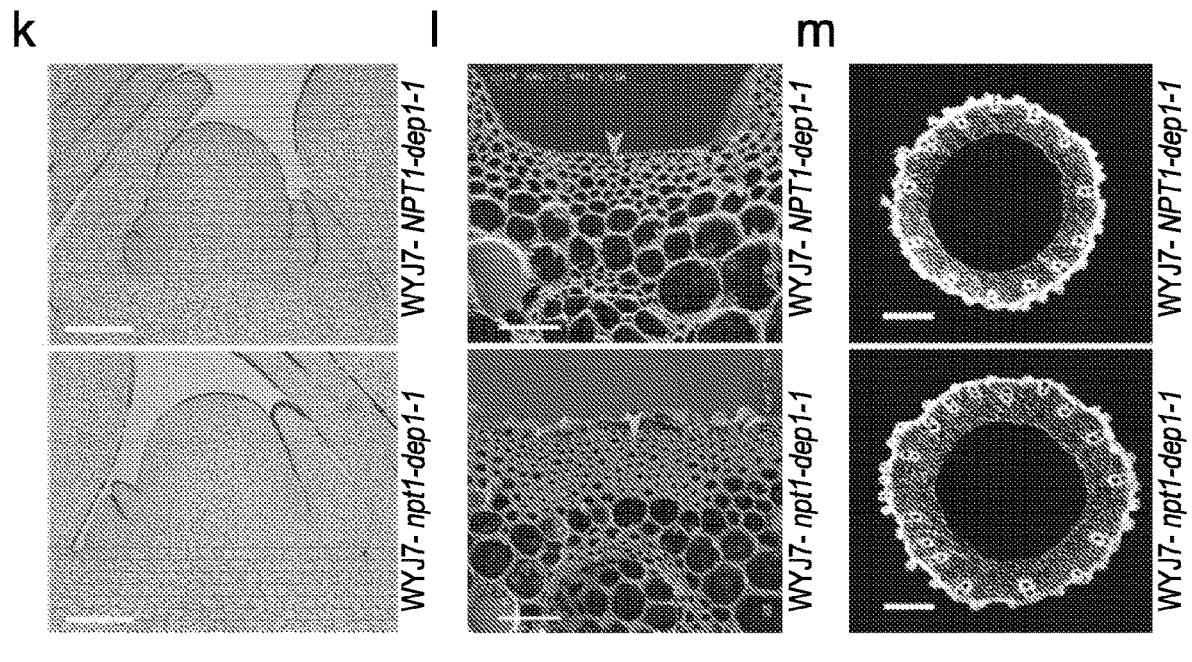
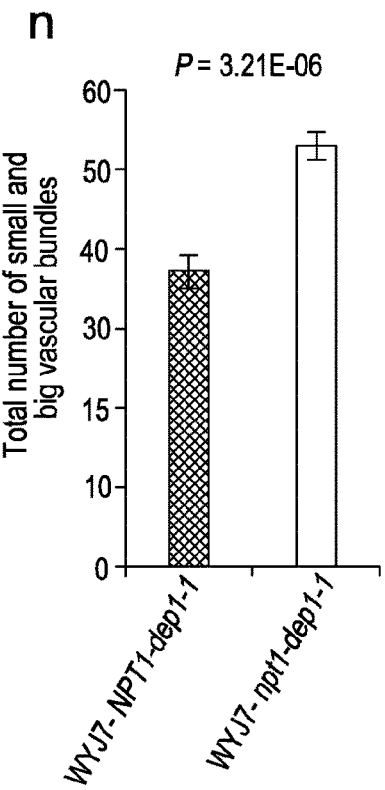
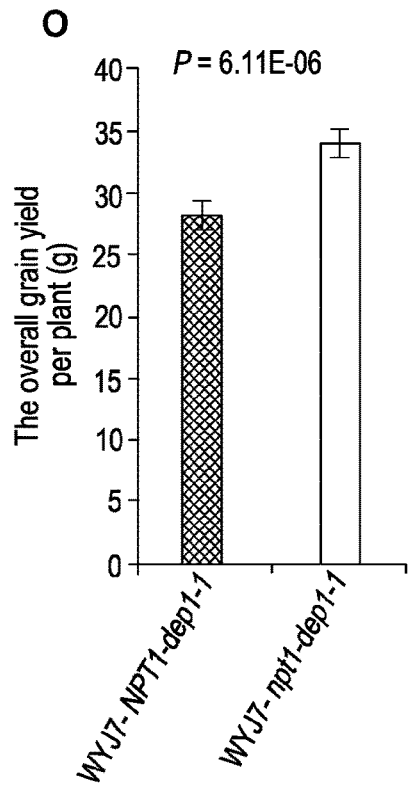

Figure 3
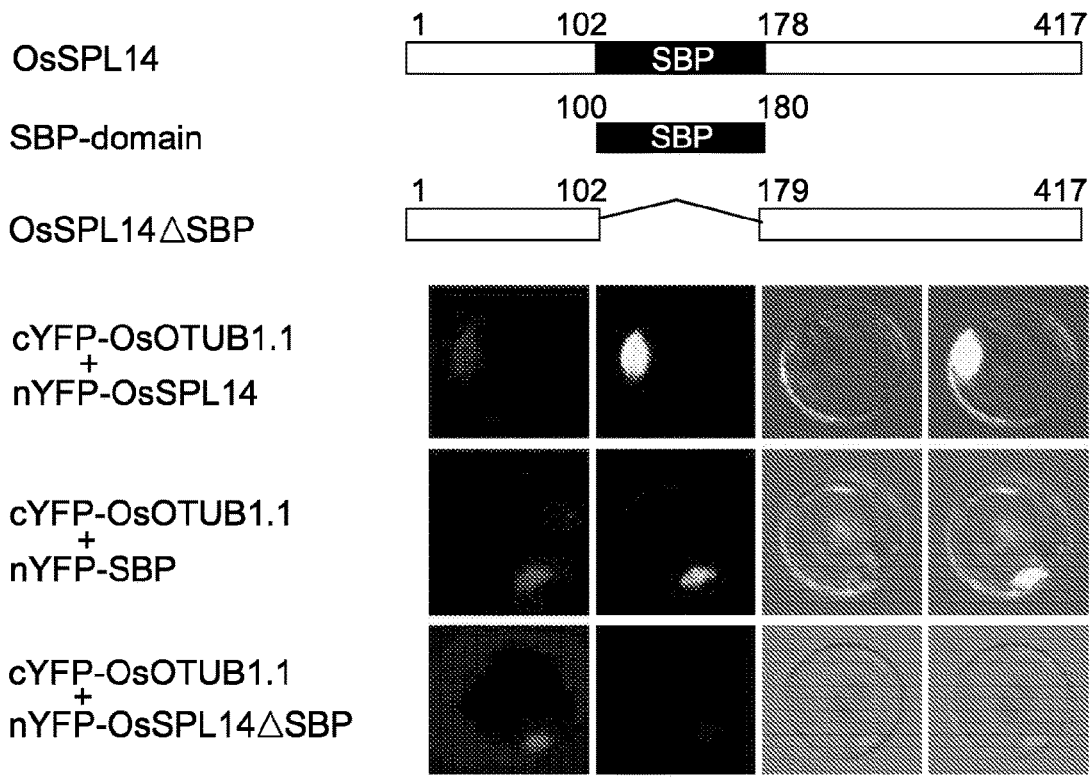
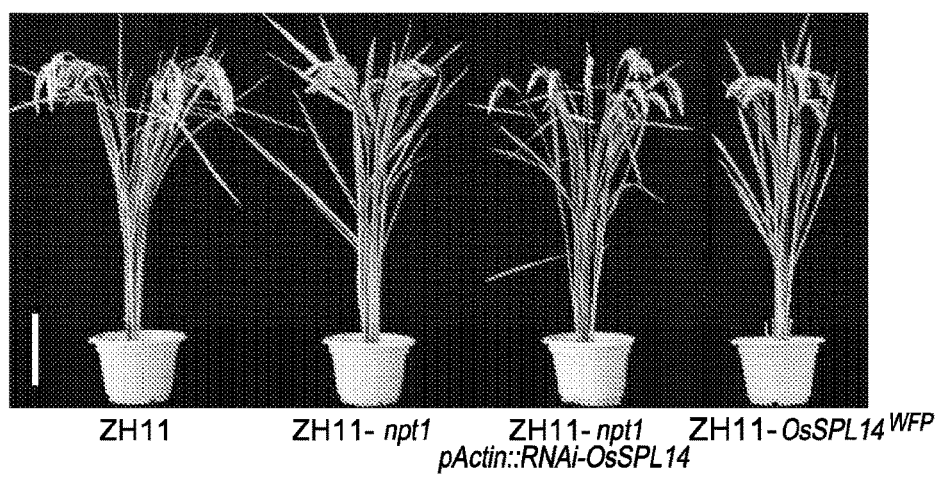
ZH11　　ZH11-*npt1*　　ZH11-*npt1*　　ZH11-*OsSPL14*[WFP]
　　　　　　　　　　*pActin::RNAi-OsSPL14*
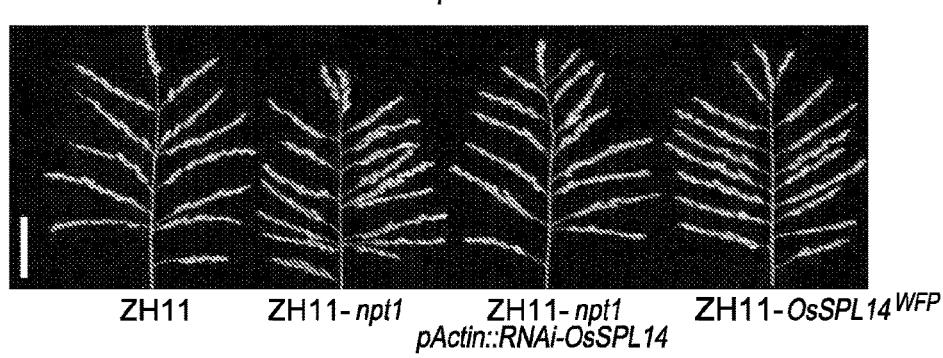
ZH11　　ZH11-*npt1*　　ZH11-*npt1*　　ZH11-*OsSPL14*[WFP]
　　　　　　　　　　*pActin::RNAi-OsSPL14* f

Figure 5

```
                              *         20         *         40         *         60         *         80
SEQ ID NO: 213 OTUB1    MAAEEPQQQK--------------------------QEPLGSDSEGVNCLA--DEAIMAQQDRIQQEIAVQN VSE  50
SEQ ID NO: 214 MmOTUB1  MAAEEPQQQK--------------------------QEPLGSDSEGVNCLA--DEAIMAQQDRIQQEIAVQN VSE  50
SEQ ID NO: 215 AtOTUB1  MQNQIDMVKD--------------------------EAEVAASISAIKGEE--GNCSSVEDQPSFQEE AAK YVD  51
SEQ ID NO: 216 GmOTUB1  MQSKEAVVEDGE------------------------IRKVTAVGSEIDGWTN GDDDIMQQYTIQSE AKK SVD  54
SEQ ID NO: 217 ZmOTUB1  MGDVPQAPHAAG-----GG-----EEWAGPDPNPSF-SLGGCSDPVSVELSNGGI RACCGEPDPD--IP GPK VE  68
SEQ ID NO: 218 SbOTUB1  MGDVPQAPHAAE-----GGGGGLEEGAVPDPNPSPSLSLGGCSDPVSLELSNGGI RACCGPDPD--IP GPK VE  74
SEQ ID NO: 219 HvOTUB1  ---------------------------------------------MGGI HACCGPDPDPK-P GPC IN  29
SEQ ID NO: 220 TuOTUB1  ---------------------------------------------MGGI HACCGPDPDHK-P GPC IN  29
SEQ ID NO: 221 OsOTUB1  ---------------------------------------------MGGI HSCCGPDPDLRAP GPK VD  30

*         100        *         120        *         140        *         160
OTUB1    ELALS YKE AEDDS  QKIKI HFKYSY IRKTF DGNCFYR GFS LE IID--SM  FKAVSAKS EI VSQ 128
MmOTUB1  ELALS YKE AEDDS  QKIKI HFKYSY IRKTF DGNCFYR GFS LE IID--SM  FKAVSAKS EI VSQ 128
AtOTUB1  K  LSSI EYC    IEKIK IG IGIRRTR DGNCFPR FS LE IES DK      VKN  KN H N 131
GmOTUB1  K  LSSI DYK    IEKIK IDE YARLRTR DGNCFPR FS LE VMKC DQ  D  QAN  KSRK   N 134
ZmOTUB1  K  LSSI EIC    II EKIK IGE YGALRRTR DGNCFYR FS LE IIET DK ALRS MVK  CNK ILS 148
SbOTUB1  K  LSSI EIC    II EKIK IGE YGALRRTR DGNCFYR FS LE IIET DK ALRS MVK  DKK ILS 154
HvOTUB1  K  LSSI EIC       EKIK IGE YDALRRTR DGNCFYR FS LE IET DK E    LKN  CKK ISG 109
TuOTUB1  K  LSSI EIC       EKIK IGE YDALRRTR DGNCFYR FS LE IET DK E    LKN  CKM ISG 109
OsOTUB1  K  LSSL EIC       EKIK IGE YDALRRTR DGNCFYR FS LE IER DK E    LRK  CKK  AS 110

*         180        *         200        *         220        *         240
OTUB1    GY   IEDP HN M       QVER---VA--D ASFN ST      L LTK  L ESKFE FI GR--TV E 202
MmOTUB1  GY   IEDP HN M       QVER---VA--D ASFN ST      L LTK  L ESKFE FI GR--TV E 202
AtOTUB1  GY DI EDP A PIEQ ID  T  ISYDE  NRSR SV      F VT  RT ADFFE FI G  ATV Q 211
GmOTUB1  GY DI EDF A FIEQ SV  I  DSHEE LRSR SV      F VT AR  TEFFE FI G  TV E 214
ZmOTUB1  GY   TEDF   PEHI SV     HIG----------------  F VT R  SIFFE FIS   TVV C 206
SbOTUB1  GY   TEDF   PIDHI SV    HIG----------------  F VT R  SIFFE FIS   TVV C 212
HvOTUB1  GY   BDF S PIEEL VV    H  GPEE ERTR TT      F VT R  AEFFE FI G  TVV Q 189
TuOTUB1  GY   BDF   PIERL VV    H  GPEE ERTR TT      F VT R  AEFFE FI G  TVA Q 189
OsOTUB1  GI   IEDF S I DE SV     H  GAEE ERTR MV      F VT R  AEFFE FI G  TVV Q 190

*         260        *         280        *         300        *         320
OTUB1    FCQQEVEPM CRESDHIHI ALAQAL S G YMDRG---EGG--TTN E IS EGS----------------EI  LIY 261
MmOTUB1  FCQQEVEPM CRESDHIHI ALAQAL S G YMDRG---EGG--TTN E IS EGS----------------EI  LIY 261
AtOTUB1  FC S VEPM  ESDHIHI AL AL VAIN YYLDR  SG TYN EM  VG--ITNEK-DE--EAGAN  LIY 284
GmOTUB1  FC S VEPM  ESDHVHI AL AL VAIN YYLDR  S TGG S N   I VAGDLPNASCSS----EKNI  LIY 290
ZmOTUB1  FC   VEPM  ESDHVHI AL AL ILN  YYLDR  C      I SANDSEGDAATTPAPATERK LIY 285
SbOTUB1  FC A VEPM  ESDHVHI AL AL VI  YYLDR  C  S N  I SSNASEGDAAMTSTPDAEKK LIY 291
HvOTUB1  FC   VEPM  ESDHVHI AL AL VI  YYLDR  C  GN      AANSSEGDAAMGLNPADEK  LIY 268
TuOTUB1  FC S VEPM  ESDHVHI AL AL VI  YYLDR  C  GN      AANSSEGDAAMGLNPAEKK  LIY 268
OsOTUB1  FC A VEPM  ESDHVHI AL AL VI  YYLDR  C SV    EANSSDCAAA------AEK  LIY 263

*         340        *         360        *         380        *         400
OTUB1    RPGHYDIL K--------------------------------------------------- 271
MmOTUB1  RPGHYDIL K--------------------------------------------------- 271
AtOTUB1  RPGHYDILY PSCKVSDNVGK---------------------------------------- 306
GmOTUB1  RPGHYDILY ---------------------------------------------------- 301
ZmOTUB1  RPGHYDILY ---------------------------------------------------- 296
SbOTUB1  RPGHYDILY ---------------------------------------------------- 302
HvOTUB1  RPGHYDILY ---------------------------------------------------- 279
TuOTUB1  RPGHYDILY ---------------------------------------------------- 279
OsOTUB1  RPGHYDILY ---------------------------------------------------- 274
```

Figure 9
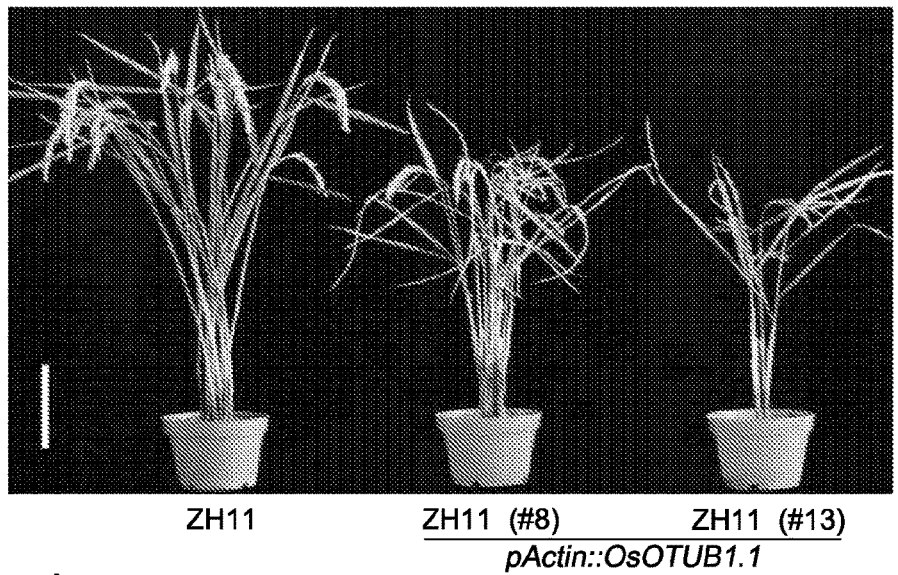
ZH11    ZH11 (#8)    ZH11 (#13)
         pActin::OsOTUB1.1
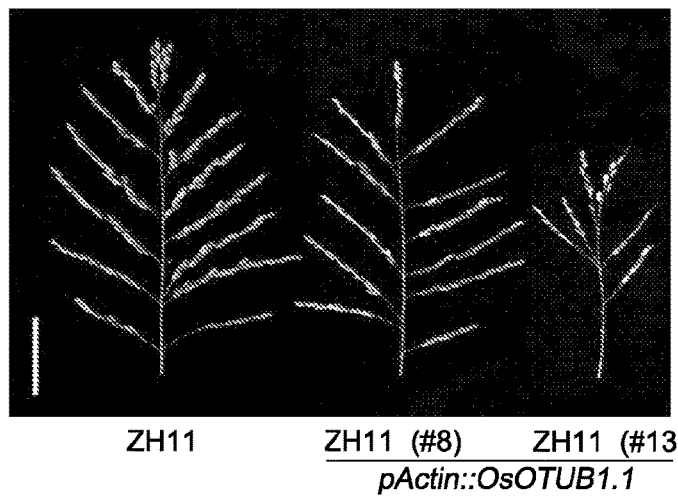
ZH11    ZH11 (#8)    ZH11 (#13)
         pActin::OsOTUB1.1
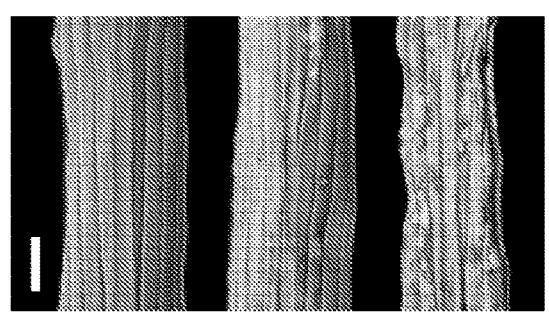
ZH11    ZH11 (#8)    ZH11 (#13)
         pActin::OsOTUB1.1
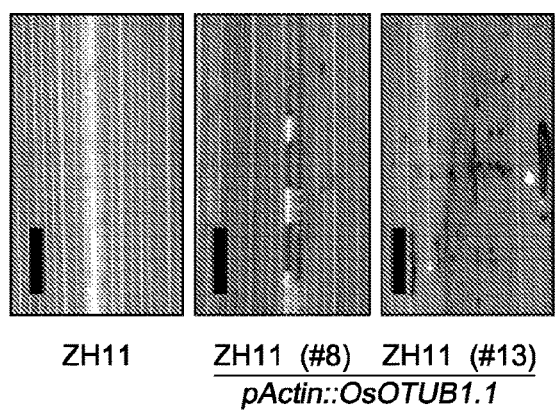
ZH11    ZH11 (#8)    ZH11 (#13)
         pActin::OsOTUB1.1

Figure 15
A
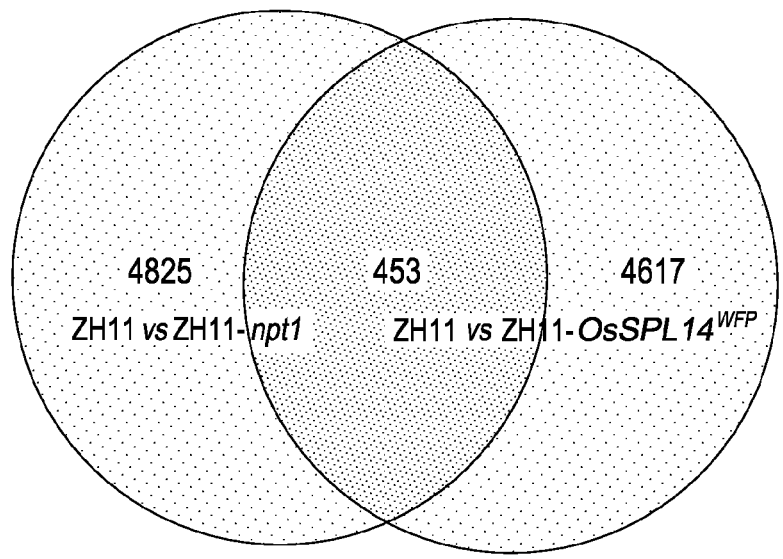
B
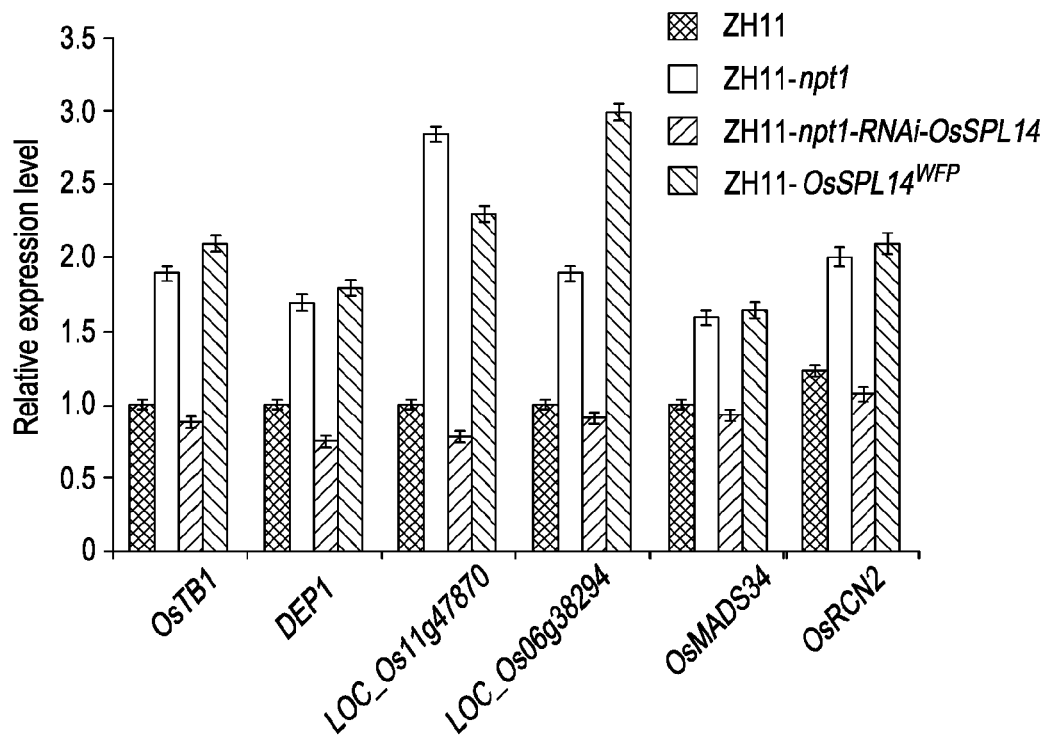

Figure 17

| | Forward (5'- 3') | Reverse (5'- 3') |
|---|---|---|
| OsSPL1 | Cgagctcatgtcgagtgggctcaagaa SEQ ID NO: 228 | Cgggatcctcacttggggcctgaacgca SEQ ID NO: 229 |
| OsSPL2 | Gcgtcgacaatggattgggacgccaagat SEQ ID NO: 230 | Cgggatccctaccacgatgagaaggaa SEQ ID NO: 231 |
| OsSPL3 | Gcgtcgacaatgggttcttttgggatgga SEQ ID NO: 232 | Cgggatccctataatgcaaatagaatct SEQ ID NO: 233 |
| OsSPL4 | Gcgtcgacaatggattggatgcctcctcc SEQ ID NO: 234 | Cgggatccttaatgaaatgacatgcagc SEQ ID NO: 235 |
| OsSPL5 | Cgagctcatggcggtgccagcggcggc SEQ ID NO: 236 | Cgggatccctagatgaaatccacctcga SEQ ID NO: 237 |
| OsSPL6 | Gcgtcgacaatggaggctgcccggtcgg SEQ ID NO: 238 | Cgggatcctcacattggtccacgttcta SEQ ID NO: 239 |
| OsSPL7 | Gcgtcgacaatggaaggaaacggctgcggc SEQ ID NO: 240 | Cgggatcctcagaccacgcgggcgccct SEQ ID NO: 241 |
| OsSPL8 | gcgtcgacaatgatgaacgttccatccgc SEQ ID NO: 242 | Cgggatccctagtgatcgaagtcgagat SEQ ID NO: 243 |
| OsSPL9 | Gcgtcgacaatggacgcccccggcggcggcg SEQ ID NO: 244 | Cgggatccctatgatgagtagttcctag SEQ ID NO: 245 |
| OsSPL10 | Ggactagtatgatgagcggtaggatgaa SEQ ID NO: 246 | Cgggatccctacatgaagtcgacctcga SEQ ID NO: 247 |
| OsSPL11 | Gcgtcgacaatggagtgcaacccgtctc SEQ ID NO: 248 | Cgggatcctcaatgtatctggttcagac SEQ ID NO: 249 |
| OsSPL12 | Gcgtcgacaatggcttcttttgggatgaa SEQ ID NO: 250 | Ggactagttcagtgcagatggccatagc SEQ ID NO: 251 |
| OsSPL13 | Cgagctcatggaccgcaaggacaaggc SEQ ID NO: 252 | Cgggatccttatctgatctggaacggcg SEQ ID NO: 253 |
| OsSPL15 | Gcgtcgacaatgcagagggaagtggggcc SEQ ID NO: 254 | Cgggatccttatatcgtaccaaaatcca SEQ ID NO: 255 |
| OsSPL16 | Gtcgacaatggagtgggatctcaagat SEQ ID NO: 256 | Ggatccctactgccatgagaacggca SEQ ID NO: 257 |
| OsSPL17 | Gcgtcgacaatggcgaccggcggcagcgg SEQ ID NO: 258 | Cgggatccctacagagaccagttcatgg SEQ ID NO: 259 |
| OsSPL18 | Cgagctcatggattgggatctcaagat SEQ ID NO: 260 | Cgggatccctactgccacgagaatggga SEQ ID NO: 261 |
| OsSPL19 | Cgagctcatggagtgggcggcggcggc SEQ ID NO: 262 | Cgggatccctacacctgccaagagaat SEQ ID NO: 263 |
| OsOTUB1 | Gattgaggagacgagccatc SEQ ID NO: 264 | Cttttcagatctgcgctcc SEQ ID NO: 265 |
| OsSPL14 | Cattgggtttgtgcattcag SEQ ID NO: 266 | Caacgacccatattccaacc SEQ ID NO: 267 |
| OsUBC13 | Ggggtgacttgaggtagtgg SEQ ID NO: 268 | Gcgacttcagttctccacct SEQ ID NO: 269 |
| OsTB1 | Gaaccactcatcgtccacca SEQ ID NO: 270 | Ctgatcctgctgatgctgct SEQ ID NO: 271 |
| DEP1 | Gcgagatcacgttcctcaag SEQ ID NO: 272 | Tgcagtttggcttacagcat SEQ ID NO: 273 |
| OsRCN2 | Caaccccacggtgaagatga SEQ ID NO: 274 | Acctgtggatgccgatgttt SEQ ID NO: 275 |
| OsMADS34 | Gagatcgacgtagaggcagc SEQ ID NO: 276 | Taggccatccactcaggagg SEQ ID NO: 277 |
| Os11g47870 | Agctgcacatcgtggactac SEQ ID NO: 278 | Ttgcagcaatggcttggaac SEQ ID NO: 279 |
| Os06g38294 | Tcgttcttgtggtggaggtg SEQ ID NO: 280 | Aggtagatggcgtaggtggt SEQ ID NO: 281 |
| Actin1 | Ccactatgttccctggcatt SEQ ID NO: 282 | Gtactcagccttggcaatcc SEQ ID NO: 283 |

Figure 17
continued

| | Forward (5'- 3') | Reverse (5'- 3') |
|---|---|---|
| DEP1-GTAC-motif | Aatttattccctttgctgtttcatttcgtacgtactccgcgctcgggatgcggccatagc SEQ ID NO: 284 | Gctatggccgcatcccgagcgcggagtacgtacgaaatgaaacagcaagggaataaatt SEQ ID NO: 285 |
| pOsOTUB1.1 | Gaattcgagttgaagttgttgctgctgtca SEQ ID NO: 286 | Ggtacccgagagctcgaccgacacg SEQ ID NO: 287 |
| gOsOTUB1.1 | Cccgggatgggcggggactactaccact SEQ ID NO: 288 | Gtcgactcacttcggggtagagaatgtcg SEQ ID NO: 289 |
| gOsOTUB1.2 | Cccgggatgttttcctacttggtattattt SEQ ID NO: 290 | Gtcgactcacttcggggtagagaatgtcg SEQ ID NO: 291 |
| OsOTUB1.1-OE | Cccgggatgggcggggactactaccact SEQ ID NO: 292 | Gtcgactcacttcgggtagagaatgtcg SEQ ID NO: 293 |
| OsOTUB1.2-OE | Cccgggatgttttcctacttggaacatatc SEQ ID NO: 294 | Gtcgactcacttcgggtagagaatgtcg SEQ ID NO: 295 |
| OsOTUB1.1-GFP | Cccgggatgggcggggactactaccact SEQ ID NO: 296 | Gtcgaccttcgggtagagaatgtcgtag SEQ ID NO: 297 |
| OsOTUB1.2-GFP | Cccgggatgttttcctacttggaacatatc SEQ ID NO: 298 | Gtcgaccttcgggtagagaatgtcgtag SEQ ID NO: 299 |
| CRISPR-OsOTUB1 | Cagctggaaagtgttctgcgtttagagctagaaat SEQ ID NO: 300 | Gcagaacactttccagctgcggcagccaagccagca SEQ ID NO: 301 |
| OsUBC13-OE | Gtcgacatggccaacagcaacctcccccgg SEQ ID NO: 302 | Ctgcagttatgcaccgctggcatacaggcg SEQ ID NO: 303 |
| RNAi-OsUBC13-L | Actagtcccggcgaatcatcaaggagac SEQ ID NO: 304 | Agatctgaactgtccgaatctgaagggc SEQ ID NO: 305 |
| RNAi-OsUBC13-R | Tctagacccggcgaatcatcaaggagac SEQ ID NO: 306 | Ggatccgaactgtccgaatctgaagggc SEQ ID NO: 307 |
| OsSPL14-OE | Gaattcctatggagatggccagtggaggag SEQ ID NO: 308 | Ggatcccctacagagaccaatccatcgtgtt SEQ ID NO: 309 |
| RNAi-OsSPL14-L | Actagtaagaacaaggggaagggcgtg SEQ ID NO: 310 | Agatctaaaggggtttgcggcctcct SEQ ID NO: 311 |
| RNAi-OsSPL14-R | Tctagaaagaacaaggggaagggcgtg SEQ ID NO: 312 | Ggatccaaaggggtttgcggcctcct SEQ ID NO: 313 |
| BD-OsOTUB1.1 | Ggatccatgggcggggactactaccact SEQ ID NO: 314 | Gaattctcacttcgggtagagaatgtcg SEQ ID NO: 315 |
| BD-OsOTUBΔC | Ggatccatgttggaacatatcctagagac SEQ ID NO: 316 | Gaattctcacttcgggtagagaatgtcg SEQ ID NO: 317 |
| AD-OsUBC13 | Ggatccatggccaacagcaacctcccccgg SEQ ID NO: 318 | Gtcgactgcaccgctggcatacaggcg SEQ ID NO: 319 |
| BD-OsSPL14ΔN2 | Gaattcatgccgccgcggtgccaggtgga SEQ ID NO: 320 | Ggatcccctacagagaccaatccatcgtgtt SEQ ID NO: 321 |
| cYFP-OsOTUB1.1 | Gtcgacaatgggcggggactactaccact SEQ ID NO: 322 | Ggatcctcacttcgggtagagaatgtcg SEQ ID NO: 323 |
| nYFP-OsUBC13 | Gtcgacaatggccaacagcaacctcccccgg SEQ ID NO: 324 | Ggatccttatgcaccgctggcatacaggcg SEQ ID NO: 325 |
| nYFP-OsSPL14 | Gagctcatggagatggccagtggaggag SEQ ID NO: 326 | Ggatcccctacagagaccaatccatcgtgtt SEQ ID NO: 327 |

Figure 17 continued

| | Forward (5'- 3') | Reverse (5'- 3') |
|---|---|---|
| nYFP-OsSPL14ΔN1 | Gagctcatggcaggcggcggcggcactgg SEQ ID NO: 328 | Ggatccctacagagaccaatccatcgtgtt SEQ ID NO: 329 |
| nYFP-OsSPL14ΔN2 | Gagctcatgccgccgcggtgccaggtgga SEQ ID NO: 330 | Ggatccctacagagaccaatccatcgtgtt SEQ ID NO: 331 |
| nYFP-OsSPL14ΔN3 | Gagctcatgagctttacgttggatttctc SEQ ID NO: 332 | Ggatccctacagagaccaatccatcgtgtt SEQ ID NO: 333 |
| nYFP-OsSPL14ΔN4 | Gagctcatgtgggatactactacccacagt SEQ ID NO: 334 | Ggatccctacagagaccaatccatcgtgtt SEQ ID NO: 335 |
| nYFP-OsSPL14ΔC1 | Gagctcatggagatggccagtggaggag SEQ ID NO: 336 | Ggatccctaccatggctgggttgacagaa SEQ ID NO: 337 |
| nYFP-OsSPL14ΔC2 | Gagctcatggagatggccagtggaggag SEQ ID NO: 338 | Ggatccctatctgaacctgcgatgctcac SEQ ID NO: 339 |
| nYFP-OsSPL14ΔC3 | Gagctcatggagatggccagtggaggag SEQ ID NO: 340 | Ggatccctacggcggcggcggcggcggcg SEQ ID NO: 341 |
| nYFP-OsSPL14ΔC4 | Gagctcatggagatggccagtggaggag SEQ ID NO: 342 | Ggatccctatgccgcggcggcgtcctcga SEQ ID NO: 343 |
| nYFP-SBP | Gagctcatgccgccgcggtgccaggtgga SEQ ID NO: 344 | Ggatccctaggtttgcggcctcctccggc SEQ ID NO: 345 |
| YFP-SPL14ΔSBP-1 | Gagctcatggagatggccagtggaggag SEQ ID NO: 346 | Gcgtgatgccaaagggglttgcacgcccttcccctlgttct SEQ ID NO: 347 |
| YFP-SPL14ΔSBP-2 | Caaaccccttlggcatcacgc SEQ ID NO: 348 | Ggatccctacagagaccaatccatcgtgtt SEQ ID NO: 349 |

Figure 18

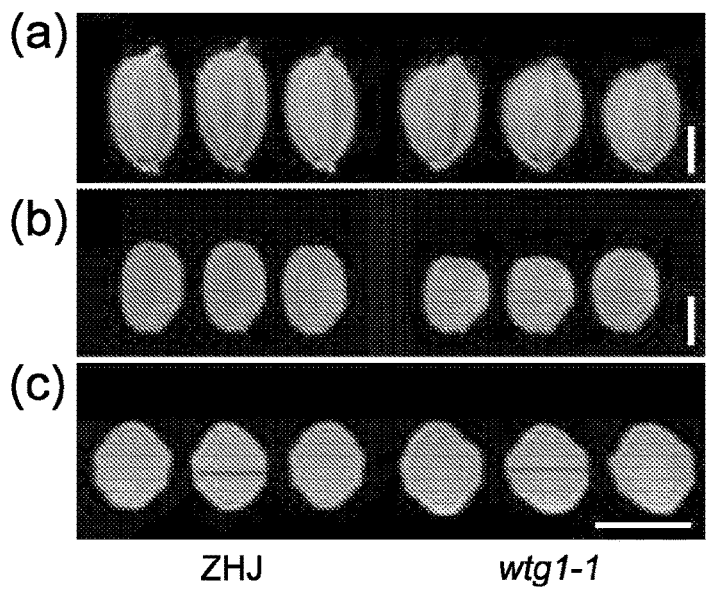

ZHJ  wtg1-1

Figure 18
continued
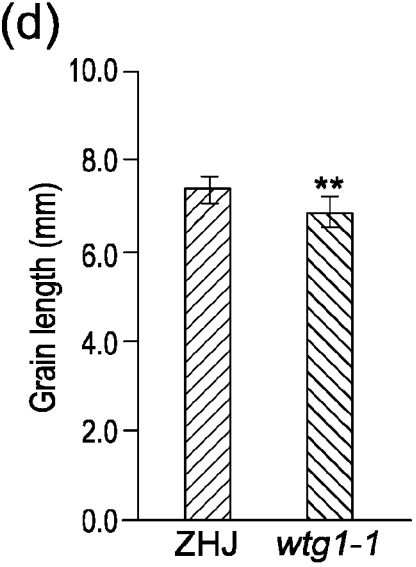
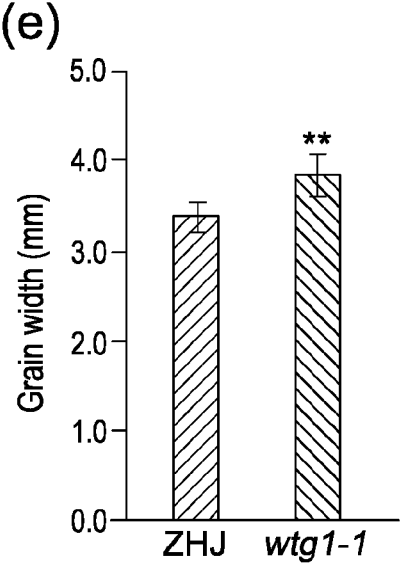
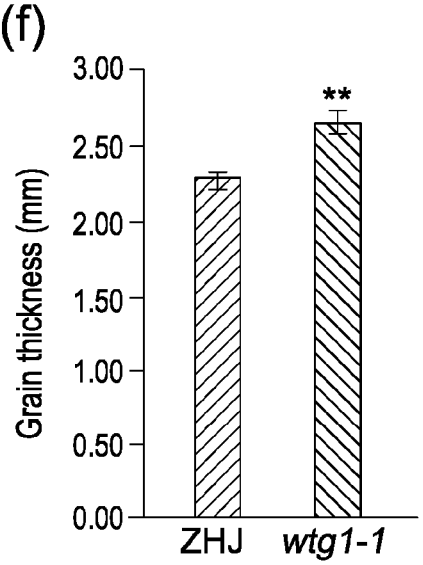
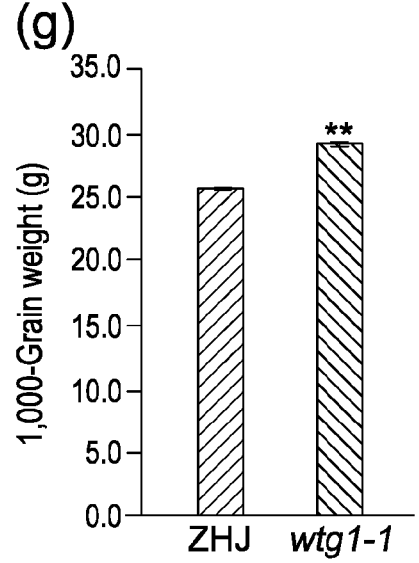

Figure 19
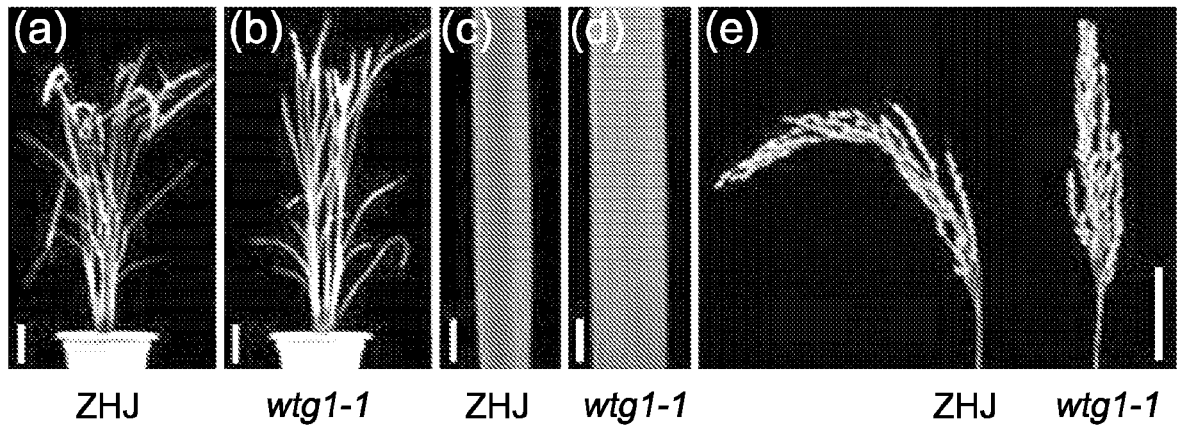
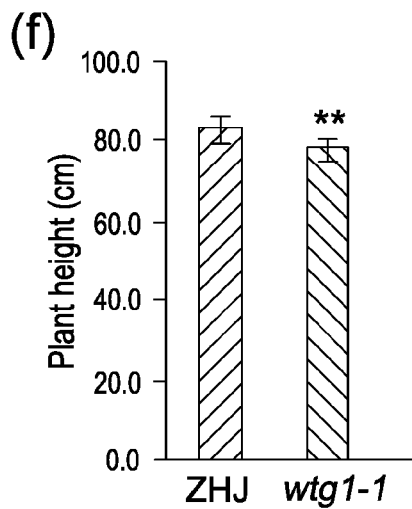
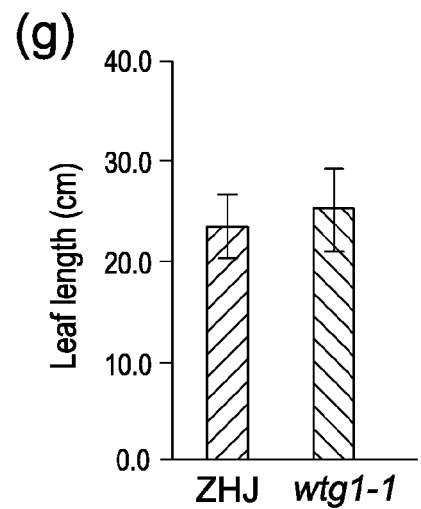
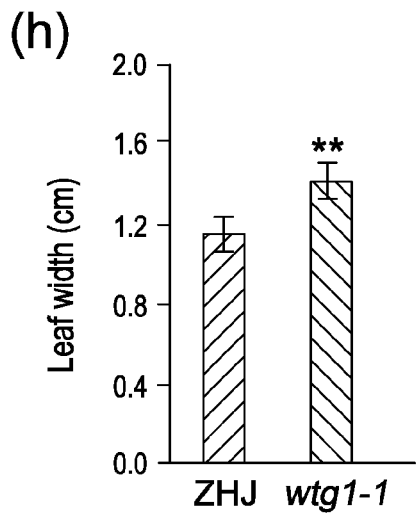
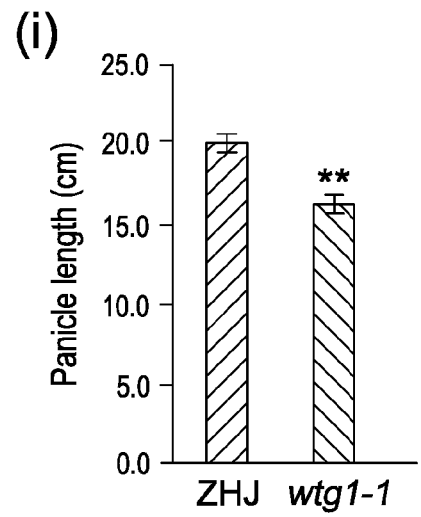

Figure 19
continued
(j)
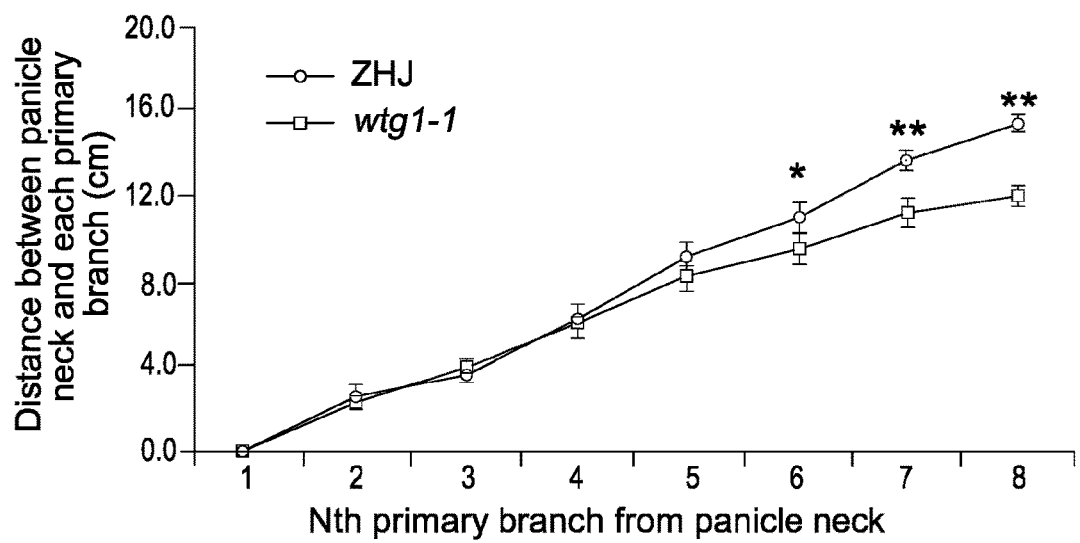
(k)
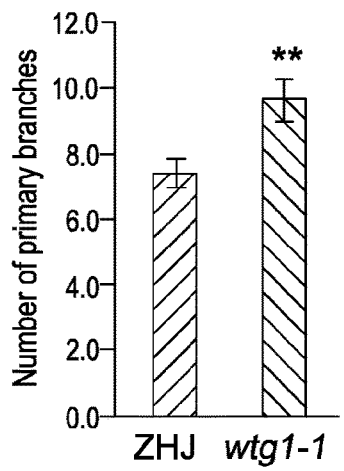
(l)
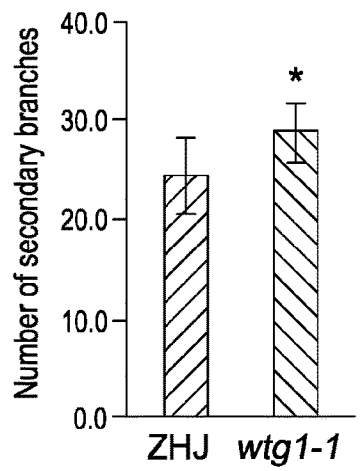
(m)
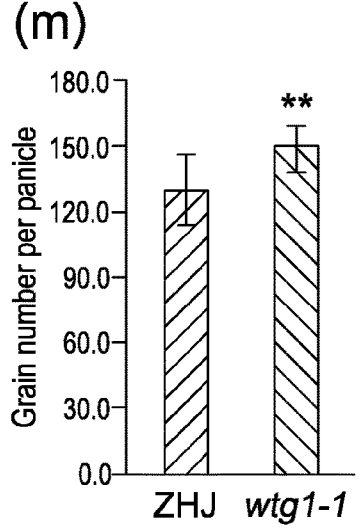

| No. | Chromosome | Position | ZHJ | wtg-1-1 | Gene | Note | SNP/INDEL index |
|---|---|---|---|---|---|---|---|
| Deletion1 | Chr.8 | 26885556 - 26885559 | TTAC | - | LOC_Os08g42540 | deletion | 1 |

Figure 25

```
SEQ ID NO: 350  C.elegans         1 ------------------------MANE QKSDDN QAA A VT---------D IV
SEQ ID NO: 351  OTUB2             1 ------------------------------------------------------
SEQ ID NO: 352  Mus musculus      1 ------------------------------------------------------
SEQ ID NO: 353  OTUB1             1 ---------------------M EEQ-----QQKQ LGS SEGVNCLA  A-
SEQ ID NO: 354  D.melanogaster    1 -------------------------------------M PFTH-----NDGNR  L-
SEQ ID NO: 355  C.reinhardtii     1 ------ A------------------STE AAEPPV G EA ---------DRPS A-
SEQ ID NO: 356  Zea mays          1 ------  VPQ---- HAA  EE  PDP PS PSL GCSD  V-  L    Y RA -
SEQ ID NO: 357  LOC_Os08g42540    1 -----------------------------------------------    Y HS -
SEQ ID NO: 358  Hordeum vulgare   1 ------  A P  A  L E    SDGA  D  SHR---L   P  V -  L    Y HA -
SEQ ID NO: 359  Triticum urartu   1 ------  A P  A  L E    SDGA  D  SHR---L   T V -  L    Y HA -
SEQ ID NO: 360  A.thaliana        1   NQID  VKDEAEVA SISAIK  EE -----------------------------GNCS-
SEQ ID NO: 361  Glycine max       1   SKEAVVEDGEIKSVTA GSEIDG TN----------------------FG DD-
                consensus         1   ..     ...   .............                  ..  ...............

C.elegans        26 LQ   LKTIED QKS  L ATLA FS I C   DNE  AAFLS ATE S  V GE I R Y
                OTUB2             1 ----------MSETSFNLISE CDIL ILRDH-PE-NR YRR  IEE SKRFT  R K K
                Mus musculus      1 ----------MSETSFNLISE CDIL ILRDH-PE-NR YQR QE  SKRFTS  R K K
                OTUB1            30 IMA  DR  QQ IAVQN LV SERLE  V YK  YAED-DN  Y Q   D HKK  SY  K  P
                D.melanogaster   15 IIQ KR  EK ISDTT  L SEQL  TC Y   SG--DE  FTA QD SKK KF    RP
                C.reinhardtii    26 ILQ  NQ RA QA VSEY  QE N GA K  EN -NQNFVQ  GK E  RTF     P
                Zea mays         50 C EPD   --IP G  L C  D K  L SG LA E FQ G-SP L  K  KLL G  G LR    R
                LOC_Os08g42540   10 C  PD  LRAE G  L Y  D K  L STLA E FQ G-SP L  K  KLL G  QT AL     R
                Hordeum vulgare  50 C  PD   P-KF G  QV YI  N  P L SA LA   FQ G-SP L  K  TKLG  Q TAL    R
                Triticum urartu  50 C  PD   P-KF G  QV YI  N  P L SA LA   FQ G-SP L  K  TKLG  Q TAL    R
                A.thaliana       31 SVED  SF  E   AA   PY  D   P L SS LA E YQ G-SP IL EK KILDS  IG I    R
                Glycine max      34 IM Q  YT  A  RAK V PF  D   P L SS LA   KL G-SP ILLEK   V L D   A L     R
                consensus        61 ..........      .....*...*......*..*

C.elegans        86         ILVGLI  IM KDR-- RL  KFIASSRDWTR   E  FPD W CT  CDF  K FL
                OTUB2            49         ALGY   SL GKS--R I FKF ER L TPND LAA FE  HK RN   NA YSVV
                Mus musculus     49         ALGY   SL GKS--R ILKF ER L TPND LAA FE  HK RN   NA YSVV
                OTUB1            89         A G   AL DDS--K LQ F AVSAKS ED  SQ FT  T I  HNT  OLI
                D.melanogaster   73         FR A AYS L YLISNT--SAYQEF  LA ES EK  Q  FPS  L  HET  VI
                C.reinhardtii    85         F G  TYA L GL QNS L  AN  FMSV QSW AK  EG FQ LV   AME LL  V
                Zea mays        107         Y        L ETQ   K   AD IMVK  E    TLLS G Y I  P DP  I   L
                LOC_Os08g42540   69         Y        L ETQ   K  VE IL K  Q   K   AD GY I  P DP  I  DQL
                Hordeum vulgare 108         Y                E RA  V  IL  I  Q K TLSG G Y I  P DP  M  EL
                Triticum urartu 108         Y                E RA  V  IL  I  Q K TLSG G Y I  P DP  M  EL
                A.thaliana       90         F         E   SQ A  V D IV  K R  QN  GYTD     P   AL  Q L
                Glycine max      93         F        E   M C  Q  E ID IQA  K S  A  QTL YA DL     AL  Q L
                consensus       121 ****.*.......*...........*....*...........
```

Figure 25
continued

```
C.elegans       144 EKIHSGVH-----TEEAVYTILNEDGSANYILMFFRLITSAFLKQNSEEYAPFIDEG---
OTUB2           107 ELVEKDG------SVSSLIKVFNDQSASDHIVQFLRLLTSAFIRNRADFFRHFIDEE---
Mus musculus    107 ELVEKDS------SVSSLIKVFNDQSSSDRIVQFLRLLTSAFIRNRADFFRHFIDEE---
OTUB1           147 EQVEKQT------SVADLLASFNDQSTSDYLVVYLRLLISGYLQESKFTEHFIEGG---
D.melanogaster  131 QRVSPDNAGGHSTVQDEIHKIFNEDGYSDYVVVYLRLITSGKLQEEADFYQNFIEKD---
C.reinhardtii   145 KEVTKAS--D-QFAQEKLIVNMRDMVSNMIVDFLRLVTSCEVQRREDFFPFILGMYDE
Zea mays        167 ESVLQGH--ETPIGPEELLERTRDPQVSDYVVMFRFVTSGEIQRRSDFFEPFISGLTN-
LOC_Os08g42540  129 ESVLQGH--ESSIGAEELLERTRDQMVSDYVVMFRFVTSGEIQRRAEFFEPFISGLTN-
Hordeum vulgare 168 QNVLQGH--GISIGPEELLERTRDQTTSDYVVMFRFVTSGEIQRRAEFFEPFISGLTN-
Triticum urartu 168 QNVLQGH--ETSIGPEELLERTRDQTTSDYVVMFRFVTSGEIQRRAEFFEPFISGLTN-
A.thaliana      150 DDILQGT--RESISYDELVNESRDQSVSDYIVMFRFVTAGDIRTRADFFEPFITGLSN-
Glycine max     153 ESVIQGK--ETSISHEELVLRSRDQSISDYVVMFRFVTSARIQRAEFFEPFILGLTN-
consensus       181 ........ .......................*..*..............**......

C.elegans       196 --MTVAQYCEQEIEPNWKDADHLAIKSLIKRAGTRVRIEYMDRTAAPNGGW----------
OTUB2           158 --MDIKDFCTHEVEPMATRCDWIQITALSQRLSIALQVEYVDEMD------------TAL
Mus musculus    158 --MDIKDFCTHEVEPMAMECDWVQITALSQRLNIALQVEYVDEMD------------TAL
OTUB1           198 --RIVKEFCQQEVEPMCKESDWIHIIALAQRLSVSIQVEYMDRGEG----------GII
D.melanogaster  188 --LITEAFRHLEVEPMYKESDWIHIIALCTALGAGVEVEYLDRGEG----------GTV
C.reinhardtii   202 PPATVELFCQRHVEPMGEESDRLHIVAVIERLQIPVRVVYLDSSGLPASGGGGSRAGALEA
Zea mays        224 --STVVQFCKASVEPMGEESDRVHIIALSDALGVPIRVMYLDRSSCDTGN-------LSV
LOC_Os08g42540  186 --STVVQFCRASVEPMGEESDRVHIIALSDALGVPIRVMYLDRSSCDAGN-------ISV
Hordeum vulgare 225 --STVVQFCRSSVEPMGEESDRVHIIALSDALGVPIRVMYLDRSSCDTGN-------LSV
Triticum urartu 225 --STVVQFCRSSVEPMGEESDRVHIIALSDALGVPIRVMYLDRSSCDTGN-------LSV
A.thaliana      207 --ATVDQFCRSSVEPMGEESDMHIITALSDALGVAIRVVYLDRSSCDSGG-------VTV
Glycine max     210 --TTVEQFCRSSVEPMGEESDMHITALSDALGIPIRVVYLDRSSCDTGG-------VSV
consensus       241 ............***....**..*......*........*.*........ ........

C.elegans       245 --RYDIPS-------------DDQQIADEITLLYRPGYIVIYKDSTEASEIEN-
OTUB2           204 NHHVF-----------------FERATESVYLLYKTSNINILAADKS--------
Mus musculus    204 NHHVF-----------------FERAIPSVYLLYKTSNINILAAEKN--------
OTUB1           245 NPHIF-----------------FEGSEPKVYLLYRPGYDILYK------------
D.melanogaster  235 KAHNY-----------------HEGSEPRIYLIYRPGYDILYPN------------
C.reinhardtii   262 SCHDFVPDS-----------CPPGTAPRVHLLYRPGYDILYANSG-----------
Zea mays        275 NHHDFIPSANDSGGDAATTPAPATEKPYITLLYRPGYDILYPK-----------
LOC_Os08g42540  237 NHHDFSPEANSSDGRA-------ARKPYITLLYRPGYDILYPK-----------
Hordeum vulgare 276 NHHDFIPAANSSEGDAAMGLNPADEKPYITLLYRPGYDILYPK-----------
Triticum urartu 276 NHHDFIPAANSSEGDAAMGLNPAEEKPYITLLYRPGYDILYPK-----------
A.thaliana      258 NHHDFVPVGITNE---K---DEERSAPFITLLYRPGYDILYPKPSCKVSDNVGN
Glycine max     261 NHHDFMPVAGDLPNASC----SSEKNIPFITLLYRPGYDILYPTK-----------
consensus       301 ..*...... ................*....*...*..**...*... .. .
```

Figure 27

| | Primers | Primer sequence |
|---|---|---|
| | \multicolumn{2}{l}{dCAPS1 marker for the wtg1-1 mutation identification} | |
| SEQ ID NO: 362 | WTG1-dF | CACAAAGTAACAATAAAGTC (Hpy188I) |
| SEQ ID NO: 363 | WTG1-dR | GCTGATGATCTTATCATTTGCTTC |
| | Primers for altered splicing identification | |
| SEQ ID NO: 364 | WTG1-F1 | ATGGGCGGGGACTACTAC |
| SEQ ID NO: 365 | WTG1-R1 | TCACTTCGGGTAGAGAATGT |
| | Primers for plasmid constructs | |
| SEQ ID NO: 366 | C99-WTG1-GF | AGCGCAACGAATTCGAGCTCGGTCACATCAAACACCGGAC |
| SEQ ID NO: 367 | C99-WTG1-GR | GGCCAGTGCCAAGCTTAGCAGCAACATCAACTAGGGGCCT |
| SEQ ID NO: 368 | 003-CDSWTG1-F | GCAGGAATTCAAGCTTATGGGCGGGGACTACTAC |
| SEQ ID NO: 369 | 003-CDSWTG1-R | AGTCACTATGGTCGACTCACTTCGGGTAGAGAATGT |
| SEQ ID NO: 370 | C43-CDSWTG1-F | TGAACTATACAAGGCGCGCCAATGGGCGGGGACTACTAC |
| SEQ ID NO: 371 | C43-CDSWTG1-R | CGCTCTAGAACTAGTTAATTAATCACTTCGGGTAGAGAATGT |
| SEQ ID NO: 372 | proWTG1-F | CGGGGCGTAATCTAGATGCTACCAAGTCCCACGTAT |
| SEQ ID NO: 373 | proWTG1-R | GGATCGATCCTCTAGAAAAGCTTCGATAAAAGCAGT |
| SEQ ID NO: 374 | MBP-WTG1-F | TCGGATCCTCTAGAGTCGACATGGGCGGGGACTACTAC |
| SEQ ID NO: 375 | MBP-WTG1-R | GGCCAGTGCCAAGCTTGCTCACTTCGGGTAGAGAATGT |
| SEQ ID NO: 376 | MBP-wtg1-F | TCGGATCCTCTAGAGTCGACATGGGCGGGGACTACTACCA |
| SEQ ID NO: 377 | MBP-wtg1-R | GGCCAGTGCCAAGCTTGCCTAGCTCATACAAAAATTATTCC |
| SEQ ID NO: 378 | MBP-WTG1-MutF | TCGGATCCTCTAGAGTCGACATGGGCGGGGACTACTACCA |
| SEQ ID NO: 379 | MBP-WTG1-MutR | GGCCAGTGCCAAGCTTGCTCACTTCGGGTAGAGAATGTCGTAGCGAC |
| SEQ ID NO: 380 | MBP-WTG1-MutF1 | GAGGAGAAGGAAACAGCTTTTATCG |
| SEQ ID NO: 381 | MBP-WTG1-MutR1 | CGATAAAAGCTGTTTCCTTCTCCTC |

Figure 27
continued

|  | Primers | Primer sequence |
|---|---|---|
|  | \multicolumn{2}{l\|}{Primers for quantitative real-time RT-PCR} |
| SEQ ID NO: 382 | ACTIN1-F | ACATCGCCCTGGACTATGACCA |
| SEQ ID NO: 383 | ACTIN1-R | GTCGTACTCAGCCTTGGCAAT |
| SEQ ID NO: 384 | WTG1-QF | TGGTTCAGTTCTGCAAGGCT |
| SEQ ID NO: 385 | WTG1-QR | CCAGGACGGTAGAGCAAAGT |
| SEQ ID NO: 386 | LIC-QF | GGAGTTTCGAGCGTATCTGGAA |
| SEQ ID NO: 387 | LIC-QR | TGGACAGAGGAAGCAGGAGACT |
| SEQ ID NO: 388 | BRD1-QF | TCAACCTTCCTGGAACCAAC |
| SEQ ID NO: 389 | BRD1-QR | TCTGTGAGCTTCTCCCTGGT |
| SEQ ID NO: 390 | BZR1-QF | GACAACAACGAGGTGCTCAA |
| SEQ ID NO: 391 | BZR1-QR | GCTTACATCCCTTGCGGTAG |
| SEQ ID NO: 392 | D1-QF | CGGCCCTAGACCAGAAACTTG |
| SEQ ID NO: 393 | D1-QR | CTTCCCTGGAGCGTCTCATGC |
| SEQ ID NO: 394 | D2-QF | AGCTGCCTGGCACTAGGCTCTACAGATCAC |
| SEQ ID NO: 395 | D2-QR | ATGTTGTCGGAGATGAGCTCGTCGGTGAGC |
| SEQ ID NO: 396 | D11-QF | TGGCGATGACATTCCGATG |
| SEQ ID NO: 397 | D11-QR | GCAACTGCAAACCTGTCAGGA |
| SEQ ID NO: 398 | D61-QF | GTTGGACGGCCTTACGTTTATC |
| SEQ ID NO: 399 | D61-QR | GCTGGTAAACTCCAGCAAGC |
| SEQ ID NO: 400 | GS2-QF | GCCATTTCCCCTTTCAAGCTAT |
| SEQ ID NO: 401 | GS2-QR | GACCATGAATCCCTTCCCTTTG |
| SEQ ID NO: 402 | GL7-QF | CACAGGGAAGATGCAAGGTG |
| SEQ ID NO: 403 | GL7-QR | GGCCCCGTGTTGAGGAATAT |
| SEQ ID NO: 404 | SPL13-QF | CCGCCGTTCCAGATCAGATA |
| SEQ ID NO: 405 | SPL13-QR | AAGAAGGGACGTAGGTGGTG |
| SEQ ID NO: 406 | SRS5-QF | GAGTTCGACGATGGTGACG |
| SEQ ID NO: 23 | SRS5-QR | TCAAAACCAGACACACAAACTG |

METHODS FOR INCREASING GRAIN PRODUCTIVITY

REFERENCE TO A SEQUENCE LISTING SUBMITTED VIA EFS-WEB

The content of the ASCII text file of the sequence listing named "15D7105.txt" which is 272 kb in size was created on Nov. 21, 2019 and electronically submitted via EFS-Web on Nov. 25, 2019 during the filing of this application is incorporated herein by reference in its entirety.

CROSS-REFERENCE TO RELATED APPLICATIONS

This application is the U.S. National phase application corresponding to PCT/GB2018/051414 which was assigned an international filing date of May 24, 2018 and associated with publication WO 2018/215779 A1 and which claims priority to PCT/CN2017/085986 filed on May 25, 2017, the disclosures of which are expressly incorporated herein by reference.

FIELD OF THE INVENTION

The invention relates to methods for increasing plant yield, and in particular grain yield by reducing the expression and/or activity of OTUB1 and consequently modifying the levels of at least one SQUAMOSA promoter-binding protein-like (SBP-domain) transcription factor in a plant. Also described are genetically altered plants characterised by the above phenotype and methods of producing such plants.

BACKGROUND OF THE INVENTION

Rice is an important food consumed by the world population. Rice grain size and shape are key agronomic traits determining grain yield and grain appearance. In rice, grain length, width and thickness are associated with grain size and shape. Several important genes that influence grain size and shape have been characterized in rice (Fan et al., 2006, Song et al., 2007, Shomura et al., 2008, Weng et al., 2008, Che et al., 2015, Duan et al., 2015, Hu et al., 2015, Wang et al., 2015 and Si et al., 2016), but the molecular mechanisms that determine grain size and shape are still limited.

Several factors that affect cell proliferation determine grain size in rice. For example, loss-of-function of GRAIN SIZE 3 (GS3) results in long grains as a result of increased cell number (Fan et al., 2006, Mao et al., 2010). GS3 encodes a putative G protein y subunit. Similarly, a putative protein phosphatase (OsPPKL1) encoded by GL3.1/qGL3 restricts cell proliferation, and its loss-of-function mutant exhibits long grains (Hu et al., 2012, Qi et al., 2012, Zhang et al., 2012). By contrast, the putative serine carboxypeptidase encoded by GS5 and the transcriptional factor OsSPL16 mainly promote grain growth by influencing cell number (Li et al., 2011b, Wang et al., 2012). The OsMKK4-OsMPK6 module influences grain growth by increasing cell number (Duan et al., 2014, Liu et al., 2015). The cell expansion process also plays a crucial role in determining grain size. High expression of the transcription factor SPL13 causes long grains as a result of long cells (Si et al., 2016). The Growth-Regulating Factor 4 (OsGRF4) encoded by GS2 associates with transcriptional coactivators (OsGIF1/2/3) to increase grain size predominantly by influencing cell size (Che et al., 2015, Duan et al., 2015, Hu et al., 2015, Li et al., 2016, Sun et al., 2016). These studies suggest that the transcriptional regulation is important for grain growth in rice. High expression of GW7/GL7/SLG7, which is likely involved in the organization of microtubules, causes long grains as a result of longer cells and/or more cells (Wang et al., 2015a, Wang et al., 2015b, Zhou et al., 2015). Thus, cell proliferation and cell expansion processes coordinately influence grain size in rice.

The ubiquitin-proteasome pathway is crucial for seed growth in rice and other plant species (Li and Li, 2014, Li and Li, 2016). Ubiquitin can be added to target proteins by ubiquitination. The deubiquitinating enzymes (DUBs), such as otubain protease, ubiquitin-specific protease, ubiquitin C-terminal hydrolase, Josephins and JAMMs, can cleave off ubiquitin from ubiquitinated proteins (Nijman et al., 2005). In rice, the functionally-unknown protein encoded by qSW5/GW5 has been suggested to be involved in the ubiquitin pathway, and the disruption of qSW5 results in wide grains (Shomura et al., 2008, Weng et al., 2008). It should be noted that a previously unrecognized gene GSES in the qSW5/GW5 locus has been recently reported to restrict grain width (Duan et al., 2017). GSES encodes a plasma membrane-associated protein with IQ domains, and low expression of GSES in some indica varieties and most *japonica* varieties causes wide grains (Duan et al., 2017). The RING-type E3 ubiquitin ligase encoded by GW2 limits grain growth, and its loss-of-function mutant has wide grains (Song et al., 2007). Similarly, its *Arabidopsis* homolog DA2 restricts seed growth through maternal integuments (Xia et al., 2013). DA2 and another E3 ubiquitin ligase BB/EOD1 physically interact with the ubiquitin receptor DA1 to repress seed and organ growth (Li et al., 2008, Xia et al., 2013). DA1 also possesses the peptidase activity that can cleave the ubiquitin-specific protease (UBP15/SOD2) (Du et al., 2014, Dong et al., 2017). Thus, modification of proteins by ubiquitin is essential for seed size determination in plants.

Rice feeds more than half the world's population. Despite the major strides in grain yield delivered by the exploitation of semi-dwarfism and utility of heterosis[1-3], increasing rice yield potential over that of existing elite cultivars is a major challenge for breeders[4]. Towards breaking the yield ceiling of current rice varieties, the ideotype approach has been proposed and used in rice breeding programs[4-7]. Since the early 1990s, a number of the "new plant type" (NPT) rice varieties have been bred at the International Rice Research Institute (IRRI); the architecture of these plants differs from that of conventional varieties: they form larger panicles, fewer sterile tillers and stronger culms. Although several NPT rice strains have been commercially released[6,7], the genetic basis of their phenotype was as yet explained only at the level of quantitative trait loci (QTL)[8]. We have found that NPT1 encodes the OTUB1 gene, an otubain-like protease with deubiquitination activity.

Independently, and to further elucidate the mechanisms of grain size and shape determination, we have identified several rice grain size mutants (Duan et al., 2014, Fang et al., 2016). We have now characterized a wide and thick grain 1 (wtg1-1) mutant that produces wide, thick, short and heavy grains. WTG1 encodes OTUB1, the same gene as present at the rice NPT locus. Overexpression of WTG1 causes narrow, thin and long grains. Thus, our findings define the otubain-like protease WTG1 as an important factor that determines grain size and shape, as well as other important agronomic traits including overall crop yield.

There therefore exists a need to increase grain yield in commercially valuable crops such as rice. The present invention addresses this need.

SUMMARY OF THE INVENTION

We have surprisingly identified that the OTUB1 gene (also known as and referred to herein in as "NPT1", "DEP5" and "WTG1"; such terms can be used interchangeably) underpins a grain yield quantitative trait. In particular, we have identified that down-regulating or abolishing the expression or deubiquitinase activity of this protein enhances meristematic activity, increases grain number per panicle, enhances grain weight and width and importantly, increases grain yield.

In one aspect, there is provided a method of increasing grain yield in a plant, the method comprising reducing the expression of at least one nucleic acid encoding an otubain-like protease (OTUB1) and/or reducing the activity of an otubain-like protease. Preferably, said increase in grain yield comprises an increase in at least one of grain number, grain number per panicle, grain weight, grain width, grain thickness and/or thousand kernel weight.

The method may comprise introducing at least one mutation into at least one nucleic acid sequence encoding an OTUB1 polypeptide and/or the promoter of the OTUB1 polypeptide. The mutation may be a loss of function or a partial-loss of function mutation, and/or an insertion, deletion and/or substitution. Preferably, the mutation is then any mutation that can reduce the expression or activity of OTUB1.

Where the method comprises introducing a mutation, the mutation may be introduced using targeted genome modification, preferably ZFNs, TALENs or CRISPR/Cas9. Alternatively, in certain embodiments, the mutation may be introduced using mutagenesis, preferably TILLING or T-DNA insertion.

In other embodiments, the method may comprise using RNA interference to reduce or abolish the expression of an OTUB1 nucleic acid.

In certain embodiments, said increase in yield is relative to a wild-type or control plant.

In certain embodiments, the mutation reduces or abolishes the deubiquitinase activity of OTUB1.

Also provided by the invention is a genetically altered plant, part thereof or plant cell, wherein said plant comprises at least one mutation in at least one nucleic acid encoding a OTUB1 polypeptide and/or the OTUB1 promoter.

The plant may be characterised by a reduction or the absence of expression of the OTUB1 polypeptide. Alternatively, or in addition, said plant may be characterised by a reduction or absence of OTUB1 deubiquitinase activity.

In certain embodiments, said plant is characterised by an increase in grain yield, preferably when said plant is compared to a control or wild-type plant. Said increase in grain yield may comprise an increase in at least one of grain number, grain number per panicle, grain weight, grain width, grain thickness, thousand kernel weight and/or a decrease in grain length.

In certain embodiments, said mutation is a loss or partial loss of function mutation. Preferably said mutation is an insertion, deletion and/or substitution. Preferably, the mutation is then any mutation that can reduce the expression or activity of OTUB1.

In certain embodiments, the mutation may be introduced using targeted genome modification, preferably ZFNs, TAL-ENs or CRISPR/Cas9. Alternatively, the mutation may be introduced using mutagenesis, preferably TILLING or T-DNA insertion.

In certain embodiments, the plant comprises an RNA interference construct that reduces the expression of an OTUB1 polypeptide. In one example, the RNA interference construct comprises or consists of SEQ ID NO: 210 or a variant thereof, as defined herein.

The plant part is preferably grain or a seed.

Also provided by the present invention is a method of producing a plant with increased grain yield, the method comprising introducing at least one mutation into at least one nucleic acid sequence encoding an OTUB1 polypeptide and/or the promoter of the OTUB1 polypeptide. The mutation may be a loss or partial loss of function mutation, and is preferably an insertion, deletion and/or substitution. Preferably, the mutation is then any mutation that can reduce the expression or activity of OTUB1.

In certain embodiments, the mutation is introduced using targeted genome modification, preferably ZFNs, TALENs or CRISPR/Cas9. Alternatively, the mutation is introduced using mutagenesis, preferably TILLING or T-DNA insertion.

Also provided by the present invention is a method of producing a plant with increased grain yield, the method comprising introducing and expressing in said plant an RNA interference construct that reduces or abolishes the expression of an OTUB1 nucleic acid. In one example, the RNA interference construct comprises or consists of SEQ ID NO: 210 or a variant thereof, as defined herein.

Methods of the invention may further comprise measuring an increase in at least one of grain yield, wherein said measurement comprises measuring an increase in at least one of grain number, grain number per panicle, grain weight, grain width, grain thickness, thousand kernel weight and/or a decrease in grain length. Preferably said increase is compared to a control or wild-type plant.

Methods of the invention may further comprise measuring a reduction or absence in the expression of an OTUB1 nucleic acid and/or measuring a reduction or absence in activity, preferably deubiquitinase activity, of an OTUB1 polypeptide.

Methods of the invention may further comprise regenerating a plant and screening for an increase in grain yield.

The invention further provides a plant, plant part or plant cell obtained or obtainable by any one or more of the methods described above.

Further provided is a method for identifying and/or selecting a plant that will have increased grain yield, preferably compared to a wild-type or control plant, the method comprising detecting in the plant or plant germplasm at least one polymorphism in the OTUB1 gene and/or OTUB1 promoter and selecting said plant or progeny thereof. The polymorphism may be an insertion, deletion and/or substitution. The method may further comprise introgressing the chromosomal region comprising at least one polymorphism in the OTUB1 gene and/or OTUB1 promoter into a second plant or plant germplasm to produce an introgressed plant or plant germplasm.

In one embodiment of any of the above-described aspects, the OTUB1 polypeptide may comprise or consist of the amino acid sequence of SEQ ID NO: 1 or a functional homologue or variant thereof. In another embodiment, the OTUB1 nucleic acid comprises or consists of a nucleic acid sequence that encodes SEQ ID NO: 1. In a preferred embodiment, the OTUB1 nucleic acid comprises or consists of a nucleic acid sequence selected from SEQ ID NO: 2 to 5 or a functional variant or homologue thereof. In one example, the homologue may have a nucleic acid sequence that encodes an OTUB1 polypeptide as defined in SEQ ID NO: 14 to 20 or a functional variant thereof, as defined herein. Preferably, the OTUB1 homologue nucleic acid sequence is selected from one of SEQ ID NO: 7 to 13, or a functional variant thereof, as defined herein.

In other embodiments of any of the above-described aspects, the nucleic acid sequence of the OTUB1 promoter may comprise or consist of SEQ ID NO: 6 or a functional variant or homologue thereof. In one embodiment, the homologue is selected from SEQ ID NO: 21 to 27 or a functional variant thereof, as defined herein.

The plant is preferably selected from rice, wheat, maize, soybean, sorghum, brassica and barley. In one example, the plant is rice. In another example, the plant is wheat. In a further example the plant is maize.

Still further provided by the invention is a nucleic acid construct comprising a nucleic acid sequence encoding at least one DNA-binding domain that can bind to at least one target sequence in the OTUB1 gene and/or promoter. In one example, the sequence of the DNA-binding domain is selected from SEQ ID NO: 28, 34, 38, 42, 45, 48, 51, 54, 57, 60, 63, 66, 69, 72, 75, 78, 81, 84, 87, 90, 93, 96, 99, 102, 106, 110, 114, 118, 122, 126, 130, 134, 138, 142 and 146 or a sequence that is at least 90% identical to one of SEQ ID NO: 28, 34, 38, 42, 45, 48, 51, 54, 57, 60, 63, 66, 69, 72, 75, 78, 81, 84, 87, 90, 93, 96, 99, 102, 106, 110, 114, 118, 122, 126, 130, 134, 138, 142 and 146.

In one embodiment, the nucleic acid construct comprises at least one protospacer element, wherein the protospacer element comprises the DNA-binding domain. In one embodiment, the sequence of the protospacer element is selected from SEQ ID NOs: 29, 35, 39, 43, 46, 49, 52, 55, 58, 61, 64, 67, 70, 73, 76, 82, 85, 88, 91, 94, 97, 100, 103, 107, 111, 115, 119, 123, 127, 131, 135, 139, 143 and 147 or a sequence that is at least 90% identical to SEQ ID NOs: 29, 35, 39, 43, 46, 49, 52, 55, 58, 61, 64, 67, 70, 73, 76, 82, 85, 88, 91, 94, 97, 100, 103, 107, 111, 115, 119, 123, 127, 131, 135, 139, 143 and 147.

The construct may further comprise a nucleic acid sequence encoding a CRISPR RNA (crRNA) sequence, wherein said crRNA sequence comprises the protospacer element sequence and additional nucleotides. The construct may further comprise a nucleic acid sequence encoding a transactivating RNA (tracrRNA). In one embodiment, the tracrRNA comprises of consists of SEQ ID NO: 30 or a functional variant thereof.

In another embodiment, the nucleic acid construct comprises a nucleic acid sequence encoding at least one single-guide RNA (sgRNA), wherein said sgRNA comprises the tracrRNA sequence and the crRNA sequence or protospacer sequence. In one embodiment, the sequence of the sgRNA comprises or consists of a sequence selected from 31, 36, 40, 44, 47, 50, 53, 56, 59, 62, 65, 68, 71, 74, 77, 80, 83, 86, 89, 92, 95, 98, 101, 104, 108, 112, 116, 120, 124, 128, 132, 136, 140, 144 and 148 or a sequence that is at least 90% identical to 31, 36, 40, 44, 47, 50, 53, 56, 59, 62, 65, 68, 71, 74, 77, 80, 83, 86, 89, 92, 95, 98, 101, 104, 108, 112, 116, 120, 124, 128, 132, 136, 140, 144 and 148.

In a further aspect of the invention there is provided a nucleic acid construct comprising at least one nucleic acid encoding a sgRNA molecule, wherein the sgRNA molecule binds to a target sequence selected from SEQ ID NO: 28, 34, 38, 42, 45, 48, 51, 54, 57, 60, 63, 66, 69, 72, 75, 78, 81, 84, 87, 90, 93, 96, 99, 102, 106, 110, 114, 118, 122, 126, 130, 134, 138, 142 and 146 or a variant thereof. In a preferred embodiment, the sequence of the sgRNA nucleic acid is selected from 31, 36, 40, 44, 47, 50, 53, 56, 59, 62, 65, 68, 71, 74, 77, 80, 83, 86, 89, 92, 95, 98, 101, 104, 108, 112, 116, 120, 124, 128, 132, 136, 140, 144 and 148 or a variant thereof.

In one example, the sequence of the nucleic acid construct is selected from SEQ ID NO: 33, 37, 41, 105, 109, 113, 117, 121, 125, 129, 133, 137, 141, 145 and 149 or a variant thereof, wherein said variant has at least 75%, more preferably at least 80%, even more preferably at least 90% and most preferably at least 95% sequence identity to SEQ ID NO: 33, 37, 41, 105, 109, 113, 117, 121, 125, 129, 133, 137, 141, 145 and 149.

In certain embodiments, the construct may be operably linked to a promoter; preferably a constitutive promoter.

In certain embodiments, the nucleic acid construct further comprises a nucleic acid sequence encoding a CRISPR enzyme. In one example, the CRISPR enzyme may be a Cas protein; preferably Cas9 or a functional variant thereof.

In an alternative embodiment, the nucleic acid construct encodes a TAL effector. In certain embodiments, the nucleic acid construct comprises a nucleic acid sequence encoding at least one DNA-binding domain that can bind to at least one target sequence in the OTUB1 gene and/or promoter. In one example, the sequence of the DNA-binding domain is selected from SEQ ID NO: 28, 34, 38, 42, 45, 48, 51, 54, 57, 60, 63, 66, 69, 72, 75, 78, 81, 84, 87, 90, 93, 96, 99, 102, 106, 110, 114, 118, 122, 126, 130, 134, 138, 142 and 146 or a sequence that is at least 90% identical to one of SEQ ID NO: 28, 34, 38, 42, 45, 48, 51, 54, 57, 60, 63, 66, 69, 72, 75, 78, 81, 84, 87, 90, 93, 96, 99, 102, 106, 110, 114, 118, 122, 126, 130, 134, 138, 142 and 146, and further comprises a sequence encoding an endonuclease or DNA-cleavage domain thereof. The endonuclease may be FokI.

In a further aspect of the invention, there is provided a single guide (sg) RNA molecule wherein said sgRNA comprises a crRNA sequence and a tracrRNA sequence, wherein the sgRNA sequence can bind to at least one sequence selected from SEQ ID NOs: 28, 34, 38, 42, 45, 48, 51, 54, 57, 60, 63, 66, 69, 72, 75, 78, 81, 84, 87, 90, 93, 96, 99, 102, 106, 110, 114, 118, 122, 126, 130, 134, 138, 142 and 146 or a or a sequence that is at least 90% identical to one of SEQ ID NO: 28, 34, 38, 42, 45, 48, 51, 54, 57, 60, 63, 66, 69, 72, 75, 78, 81, 84, 87, 90, 93, 96, 99, 102, 106, 110, 114, 118, 122, 126, 130, 134, 138, 142 and 146.

Also provided is an isolated plant cell transfected with at least one nucleic acid construct as defined herein; or an isolated plant cell transfected with at least one nucleic acid construct as defined herein and a second nucleic acid construct, wherein said second nucleic acid construct comprises a nucleic acid sequence encoding a Cas protein, preferably a Cas9 protein or a functional variant thereof. The second nucleic acid construct may be transfected before, after or concurrently with the nucleic acid construct as defined herein. In another aspect of the invention, there is provided an isolated plant cell transfected with the sgRNA molecule as defined above.

Also provided is a genetically modified plant, wherein said plant comprises the transfected cell as defined herein. The nucleic acid encoding the sgRNA and/or the nucleic acid encoding a Cas protein may be integrated in a stable form.

The invention yet further provides a method of increasing grain yield in a plant, the method comprising introducing and expressing in a plant the nucleic acid construct or sgRNA molecule as described herein, wherein preferably said increase is relative to a control or wild-type plant. Also provided is a plant obtained or obtainable by this method.

The invention further provides a method for obtaining the genetically modified plant as defined herein, the method comprising:
a) selecting a part of the plant;
b) transfecting at least one cell of the part of the plant of paragraph (a) with the nucleic acid construct or sgRNA as defined herein;
c) regenerating at least one plant derived from the transfected cell or cells;
d) selecting one or more plants obtained according to paragraph (c) that show reduced expression of at least one OTUB1 nucleic acid in said plant.

In a further aspect of the invention, there is provided a method of modifying, preferably increasing the levels of at least one SQUAMOSA promoter-binding protein-like (SBP-domain) transcription factor, the method comprising increasing the expression or activity of UBC13 or decreasing or abolishing the expression or activity of OTUB1, as described herein.

DESCRIPTION OF THE FIGURES

The invention is further described in the following non-limiting figures:

FIG. 5 shows a phylogenic analysis. The human OTUB 1 sequence and its orthologs in mouse (MmOTUB 1), Arabidopsis thaliana (AtOTUB 1), soybean (GmOTUB 1), maize (ZmOTUB 1), sorghum (SbOTUB 1), barley (HvOTUB 1), wild einkorn wheat (TuOTUB 1) and rice (OsOTUB 1) were obtained from ncbi.nlm.nih.gov. The numbers on the right indicate the position of the residues within each protein. Identical residues indicated by dark shading, conserved ones by light shading and variables ones by no shading.

FIG. 15 shows OsOTUB1 and OsSPL14 antagonistically regulate common target genes. (a) The number and overlap of OsSPL14-activated and OsOTUB1-repressed target genes. RNA-seq was performed by using young panicles (<0.2 cm in length) of the NILs plants. (b) The abundance of OsSPL14-regulated gene examined in the young panicle, relative to the level in ZH11. Data shown as mean±s.e.m. (n=3).

FIG. 17 shows the primer sequences used for DNA constructs and transcripts analysis.

FIG. 18 shows that WTG1 influences grain size, shape and weight.

(a) Paddy rice grains of Zhonghuajing (ZHJ) and wtg1-1.

(b) Brown rice grains of ZHJ and wtg1-1.

(c) Cross-section of ZHJ and wtg1-1 brown rice grains. The red lines indicate the grain thickness.

(d) ZHJ and wtg1-1 grain length (n≥50).

(e) ZHJ and wtg1-1 grain width (n≥50).

(f) ZHJ and wtg1-1 grain width (n≥50).

(g) 1000-grain weight of ZHJ and wtg1-1. The weights of three sample batches were measured (n=3).

Values in (d-g) are means±SD. **P<0.01 compared with parental line (ZHJ) by Student's t-test.

Bars: 3 mm (a-c).

FIG. 19 shows that WTG1 influences panicle size, panicle shape and grain number per panicle.

(a, b) ZHJ (a) and wtg1-1 (b) plants. Plants grown in the paddy were dug up and placed in pots for the purpose of full plant photography.

(c, d) Flag leaves of ZHJ (c) and wtg1-1 (d).

(e) Panicles of ZHJ (left) and wtg1-1 (right).

(f) Plant height of ZHJ and wtg1-1 (n≥10).

(g, h) Leaf length (g) and width (h) of ZHJ and wtg1-1 (n≥10).

(i) Panicle length of ZHJ and wtg1-1 (n≥10).

(j) Distance between each primary branch and panicle neck (n≥10).

(k, l) The primary panicle branch number (k) and the secondary panicle branch number (l) (n≥10).

(m) Grain number per panicle (n≥10).

Values in (f-m) are means±SD. **P<0.01 compared with ZHJ by Student's t-test.

Bars: 10 cm (a, b); 1 cm (c, d); 5 cm (e).

Figure 20:
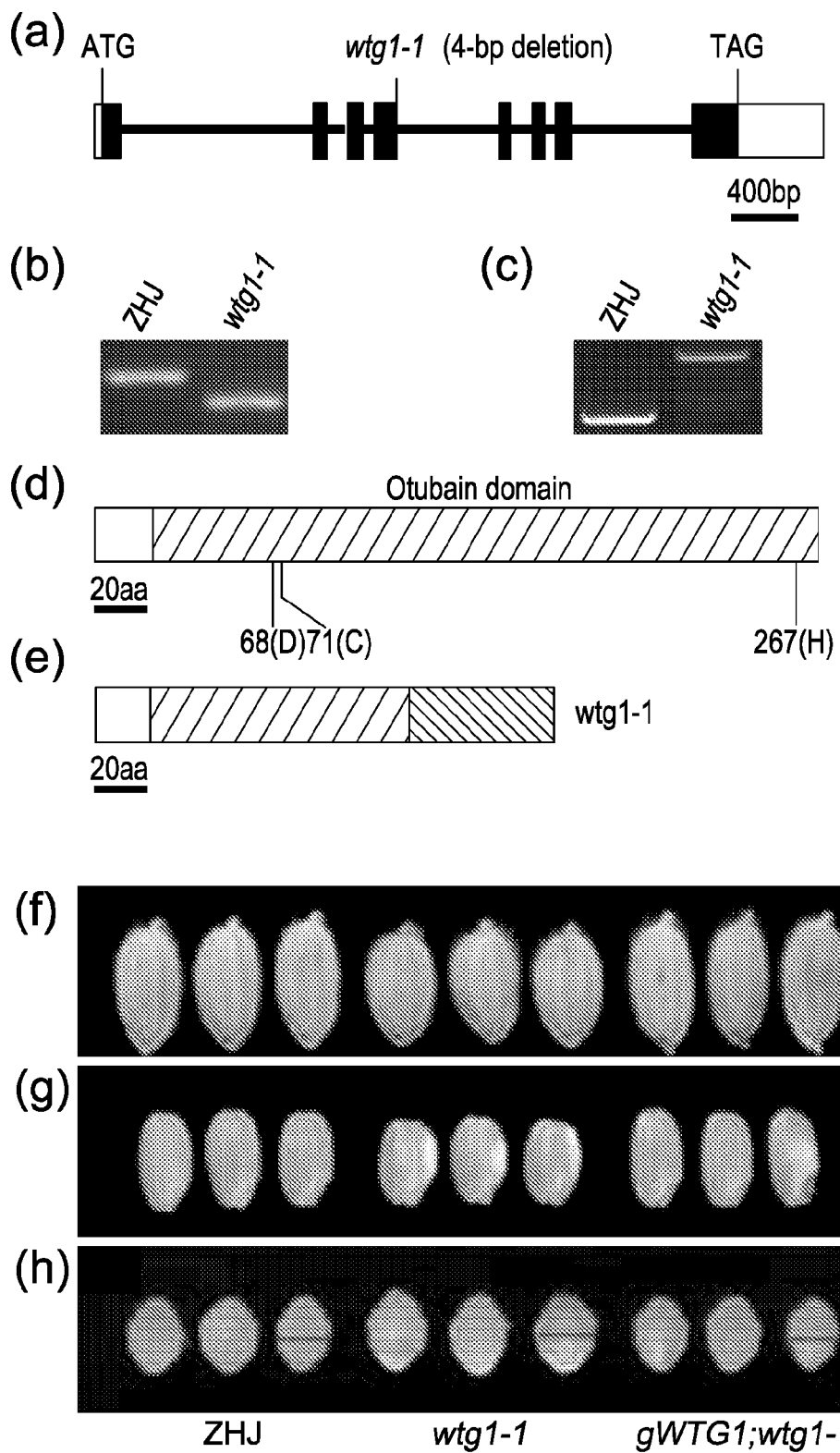
Figure 20:
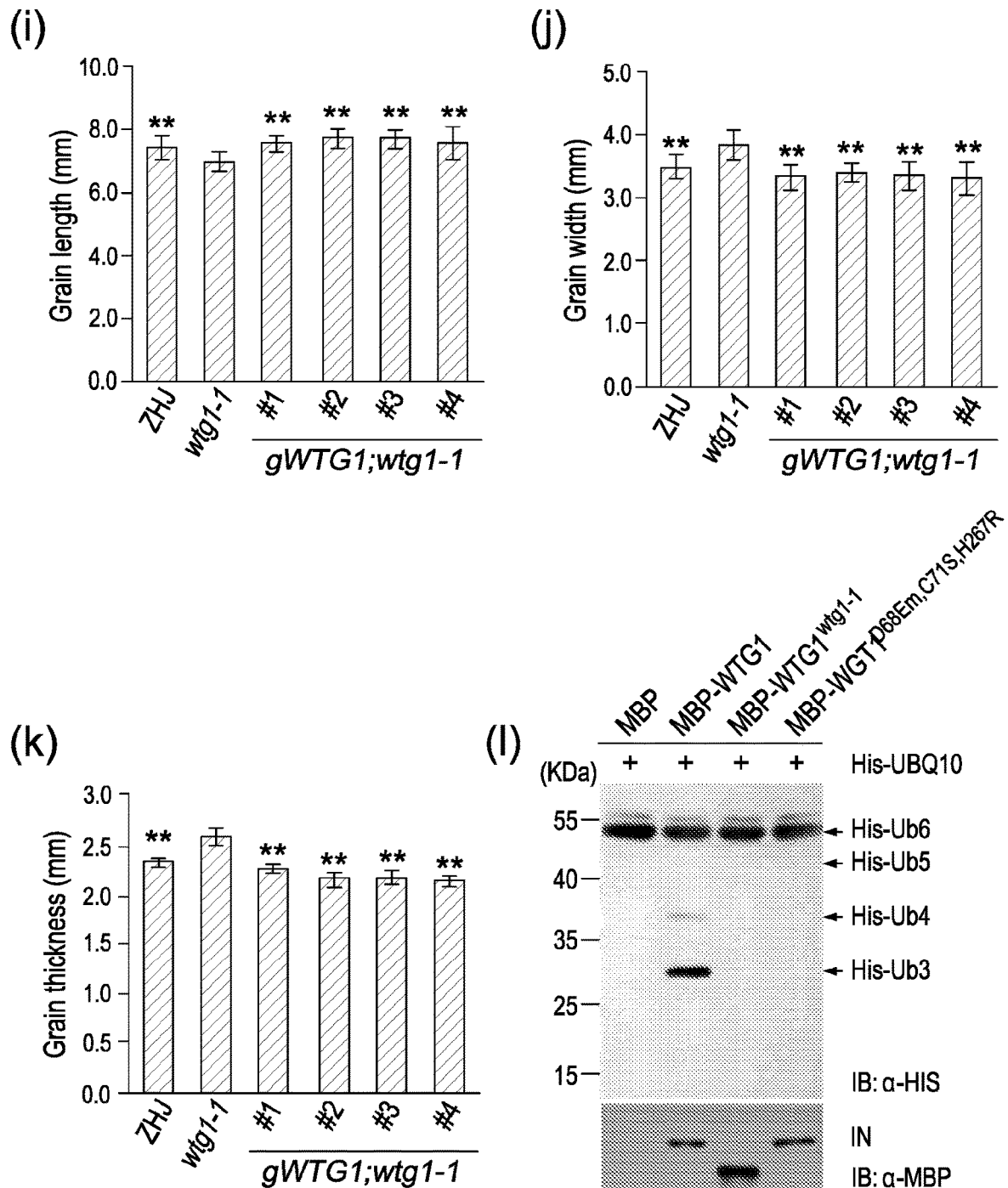

FIG. 20 shows that WTG1 encodes an otubain-like protease with deubiquitination activity.

(a) The WTG1 gene. Open boxes show the 5' and 3' untranslated regions. The closed boxes show the coding sequence. The start codon (ATG) and the stop codon (TAG) are indicated. The wtg1-1 contains the 4-bp deletion in the exon-intron junction region of the fourth intron.

(b) The dCAPS1 marker was developed based on the wtg1-1 mutation. The restriction enzyme Hpy188I was used to digest PCR products.

(c) RT-PCR analysis of WTG1 in ZHJ and wtg1-1 panicles. The wtg1-1 mutation resulted in the altered splicing of WTG1.

(d, e) The WTG1 protein (d) and the mutated wtg1-1 protein (e). The WTG1 protein possesses an otubain domain. The mutated wtg1-1 protein has the N-terminal region, a part of otubain domain and a unrelated peptide (green box).

(f) Paddy rice grains of ZHJ, wtg1-1 and gWTG1;wtg1-1. gWTG1;wtg1-1 represents that the genomic sequence of the WTG1 gene was transformed into the wtg1-1 mutant.

(g) Brown rice grains of ZHJ, wtg1-1 and gWTG1;wtg1-1.

(h) Cross-section of ZHJ, wtg1-1 and gWTG1;wtg1-1 brown rice grains. The red lines show the grain thickness.

(i-k) Grain length (i), grain width (j) and grain thickness (k) of ZHJ, wtg1-1 and gWTG1;wtg1-1 (n≥50).

(l) WTG1 has deubiquitination activity in vitro. MBP-WTG1 cleaved His-UBQ10 in vitro, but MBP, MBP-WTG1$^{wtg1-1}$ and MBP-WTG1$^{D68E;C71S;H267R}$ did not cleave His-UBQ10. Anti-His and anti-MBP antibodies were used to detect His-UBQ, cleaved His-UBQ, MBP, MBP-WTG1$^{wtg1-1}$ and MBP-WTG1$^{D68E;C71S;H267R}$, respectively.

Values in (i-k) are means±SD. **P<0.01 compared with parental line (ZHJ) by Student's t-test.

Bars: 3 mm (f-h).

Figure 21:
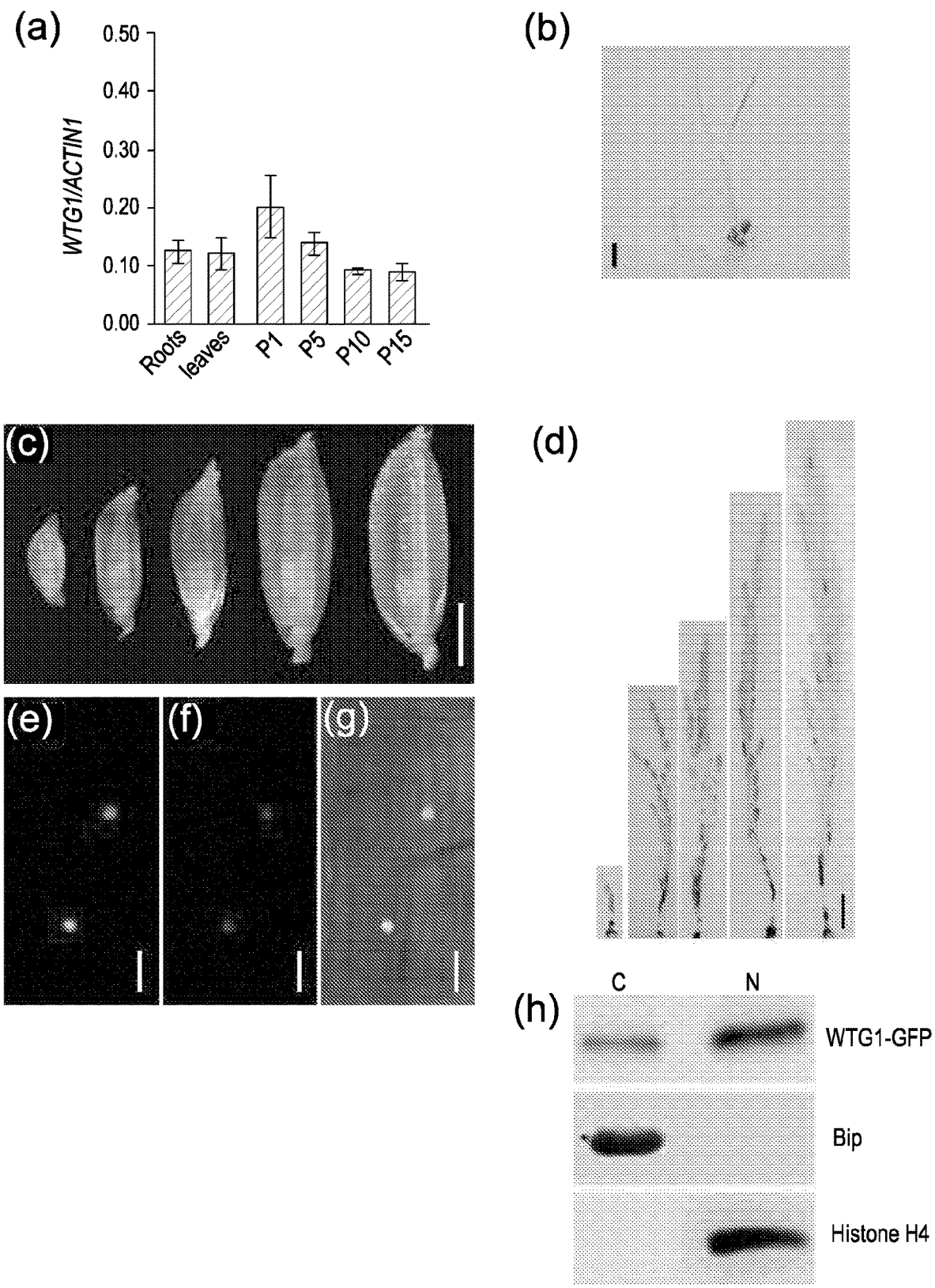

FIG. 21 shows the expression and subcellular localization of WTG1.

(a) WTG1 expression in roots and leaves of young seedlings and developing panicles of 1 cm (P1) to 15 cm (P15) was analyzed by Quantitative real-time RT-PCR. Values given are means±SD of three replicates.

(b-d) Expression of WTG1 was investigated using proWTG1:GUS transgenic plants. GUS activity in 8-d-old seedlings (b), the developing spikelet hulls (c) and the developing panicles (d).

(e-g) Subcellular localization of GFP-WTG1 in pro35S:GFP-WTG1 root cells. GFP fluorescence of GFP-WTG1 (e), DAPI staining (f), and merged (g) images are shown.

(h) Subcellular fractionation and immunoblot assays. The pro35S:GFP-WTG1 leaves were used to isolate the cytoplasmic protein fraction (C) and the nuclear protein fraction (N). Immunoblotting was carried out with an antibody against GFP. Bip, a luminal-binding protein, was used as cytoplasmic marker. Histone H4 was used as nuclear marker.

Bars: 5 mm (b), 2 mm (c), 10 mm (d) and 10 μm (e-g).

Figure 22:
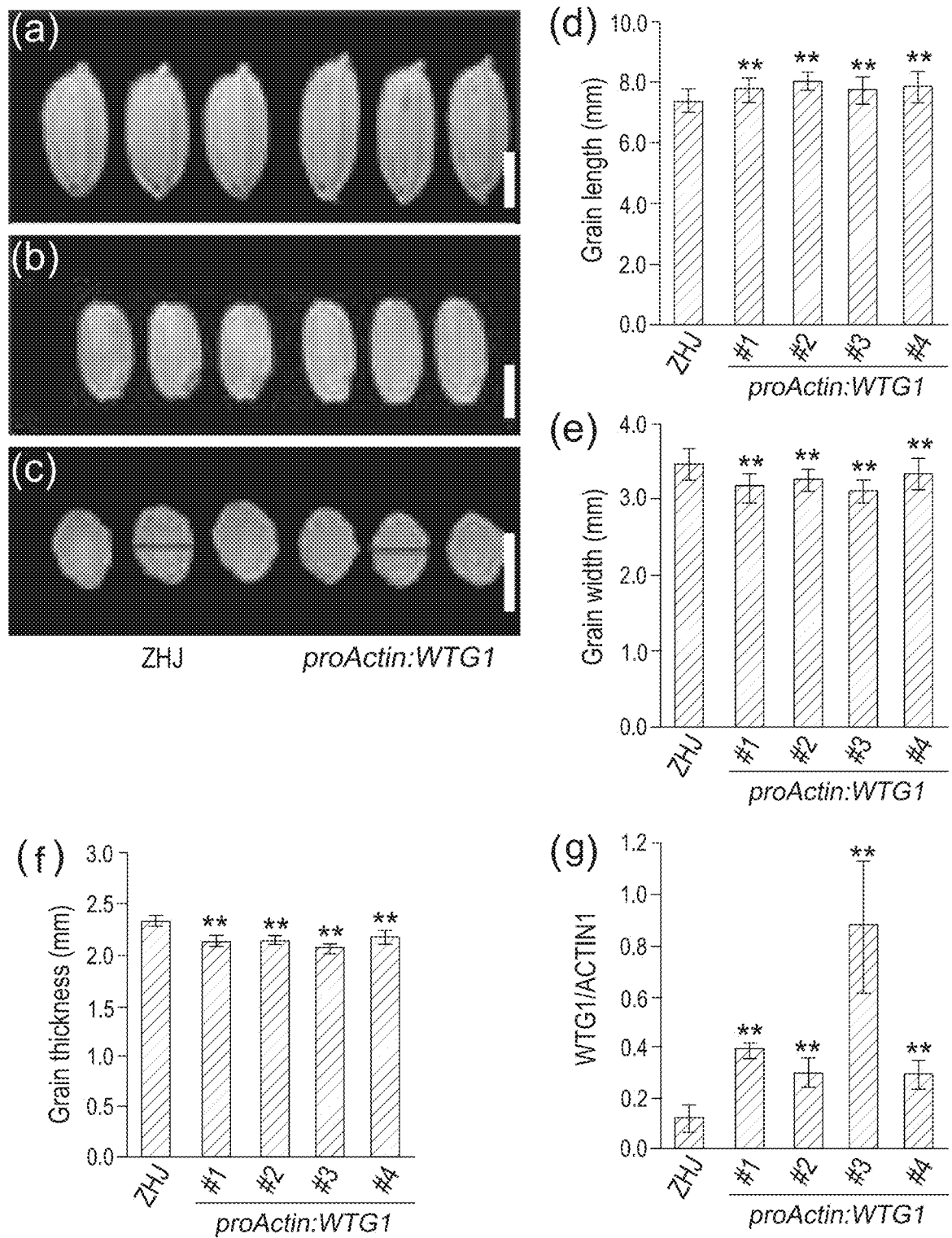

FIG. 22 shows that the overexpression of WTG1 causes narrow, thin and long grains.

(a) Paddy rice grains of Zhonghuajing (ZHJ) and proActin:WTG1 transgenic lines.

(b) Brown rice grains of ZHJ and proActin:WTG1 transgenic lines.

(c) Cross-section of ZHJ and proActin:WTG1 transgenic grains. The red lines indicate the grain thickness.

(d-f) Length (d), width (e) and thickness (f) of ZHJ and proActin:WTG1 grains (n≥40).

(g) Expression level of WTG1 in ZHJ and proActin:WTG1 transgenic lines. Three replicates were examined.

Values in (d-g) are means±SD. **P<0.01 compared with parental line (ZHJ) by Student's t-test.

Bars: 3 mm (a-c).

Figures 23, 24:
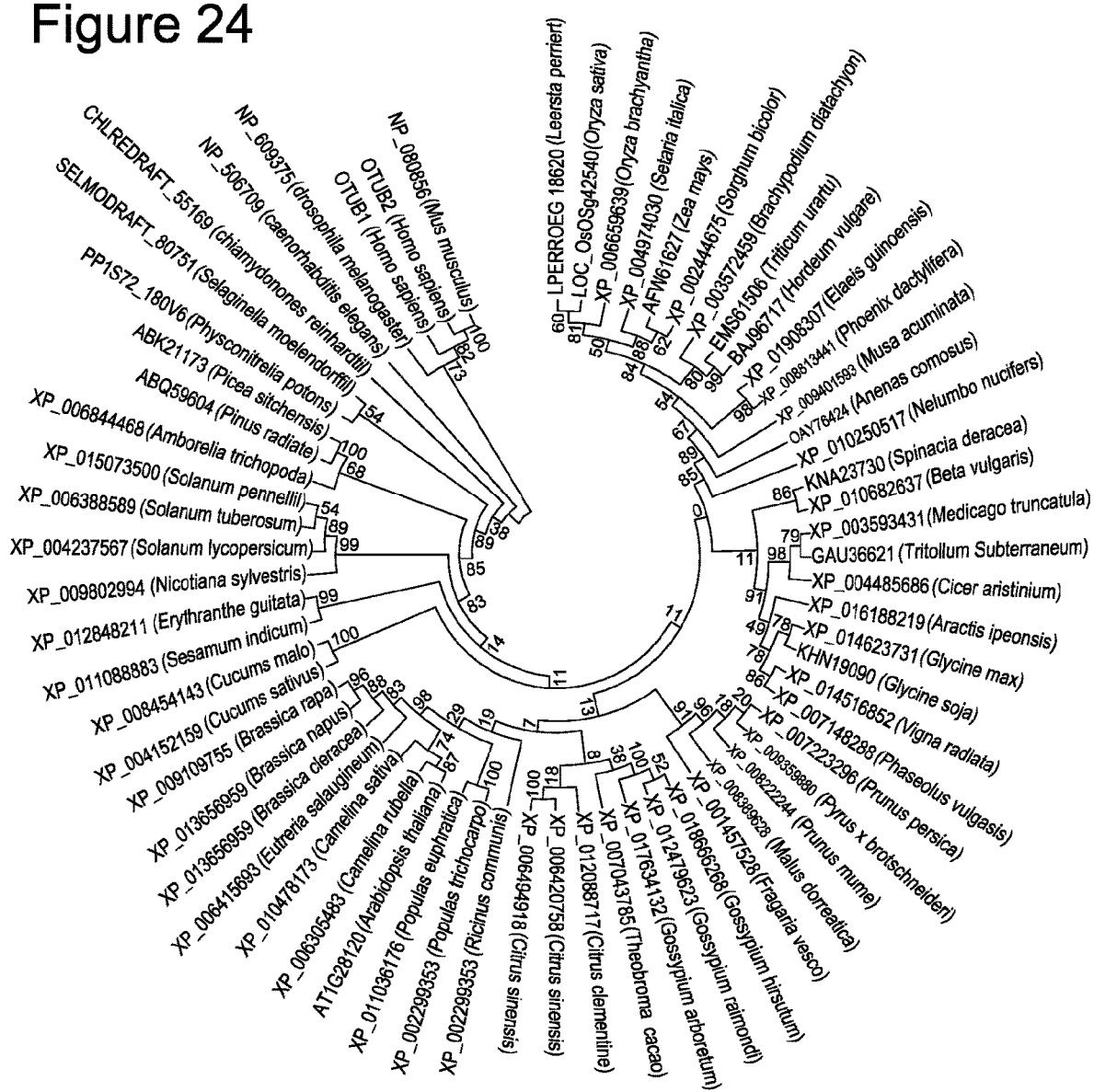

FIG. 23 shows the identification of the wtg1-1 mutation using the MutMap approach. The whole genome sequencing reveals the one deletion in the LOC-Os08g42540 gene, which has a SNP/INDEL-index=1.

FIG. 24 shows a phylogenetic tree of WTG1 and its homologs.

WTG1 homologs were obtained from the database searches (blast.ncbi.nlm.nih.gov). The phylogenetic tree of WTG1 homologs was constructed using the neighbor-joining method of MEGA7.0 software. Numbers at notes indicate the percentage of 1000 bootstrap replicates.

FIG. 25 shows an alignment of WTG1 and its homologs. Proteins from *Oryza sativa* (MSU_Locus: LOC_Os08g42540), *Caenorhabditis elegans* (*C. elegans*, NP_506709), *Homo sapiens* (OTUB1, AK000120; OTUB2, AK025569), *Mus musculus* (*Mus musculus*, NP_080856), *Drosophila melanogaster* (*D. melanogaster*, NP_609375), *Chlamydomonas reinhardtii* (*C. reinhardtii*, CHLREDRAFT_55169), *Zea mays* (*Zea mays*, ACG38232), *Hordeum vulgare* (*Hordeum vulgare*, BAJ96717), *Triticum urartu* (*Triticum urartu*, EMS61506), *Arabidopsis thaliana* (*A. thaliana*, At1g28120), and *Glycine max* (*Glycine max*, XP_014623731) were used to perform alignment. The red triangles represent the conserved amino acids in the putative catalytic triad of the cysteine protease, and the red boxes show the conserved sequences in the otubain-like domain.

Figure 26:
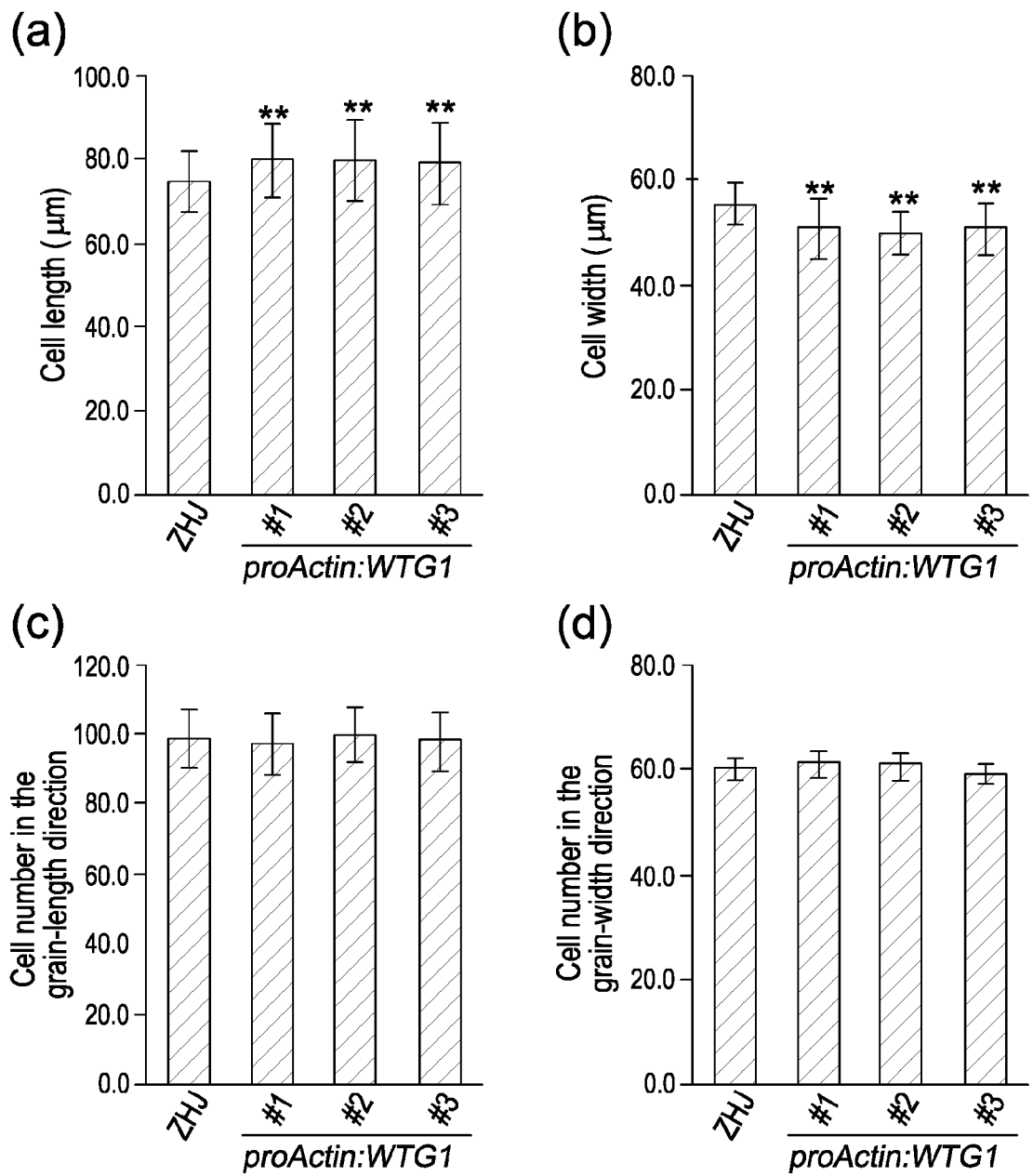

FIG. 26 shows the overexpression of WTG1 influences cell expansion in spikelet hulls.

(a, b) Average length (a) and width (b) of outer epidermal cells in lemmas of ZHJ and proActin:WTG1 transgenic plants. More than 100 cells were measured (n>100).

(c) The number of outer epidermal cells in the grain-length direction of lemmas. Twenty grains were used to calculate cell number (n=20).

(d) The number of outer epidermal cells in the grain-width direction. Twenty grains were used to count cell number (n=20).

Values in (a-d) are given as mean±SD. **P<0.01 compared with parental line (ZHJ) by Student's t-test.

FIG. 27 shows the primers used in Example 2.

Figure 28:
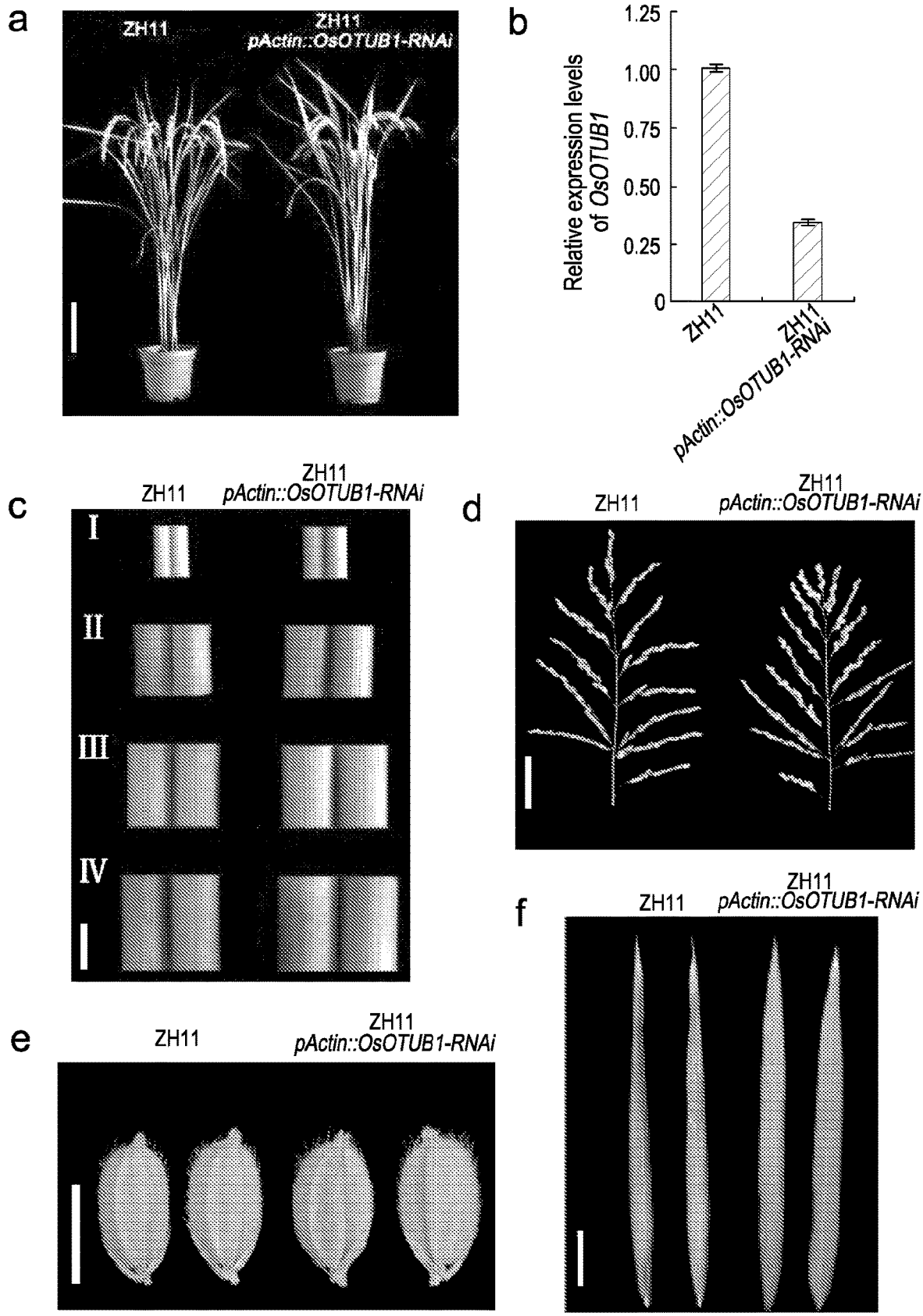

FIG. 28 shows the RNAi silencing of OsOTUB1. (a) RNAi silencing of OsOTUB1 exhibited ZH11-npt1-like phenotype, Scale bar, 20 cm. (b) OsOTUB1 expression levels in transgenic plants. (c) Culm thickness of transgenic plants, Scale bar, 5 mm. (d) Panicle architecture of transgenic plants, Scale bar, 5 cm. (e) Grain shape of transgenic plants, Scale bar, 5 mm. (f) Flag leaf shape of transgenic plants, Scale bar, 5 cm.

Figure 29:
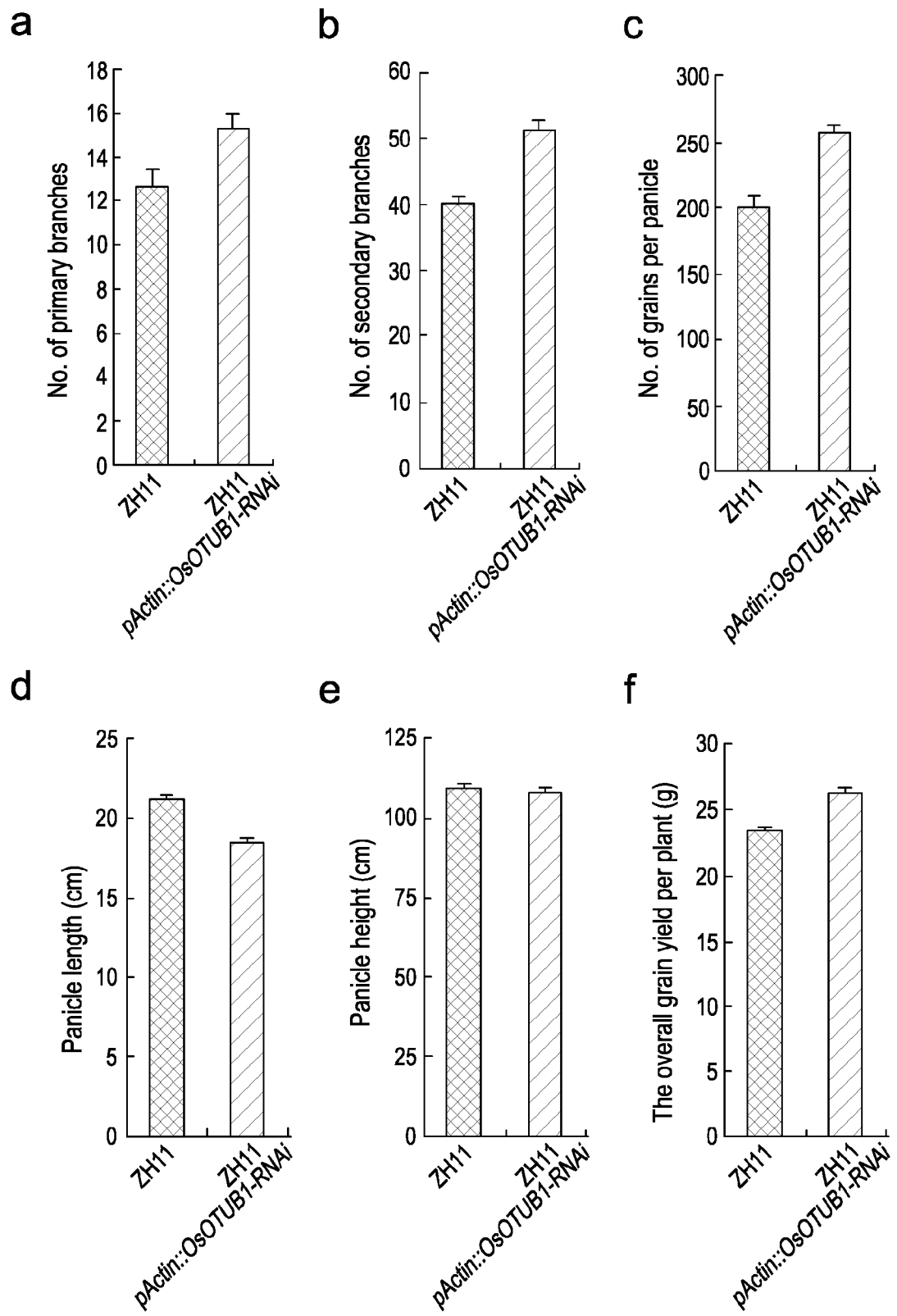

FIG. 29 shows the phenotype of plants with reduced levels of OTUB1 expression through RNAi. (a) Number of primary branches per panicle. (b) Number of secondary branches per panicle. (c) Number of grains per panicle. (d) Panicle length. (e) Plant height. (f) Overall grain yield per plant.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The practice of the present invention will employ, unless otherwise indicated, conventional techniques of botany, microbiology, tissue culture, molecular biology, chemistry, biochemistry and recombinant DNA technology, bioinformatics which are within the skill of the art. Such techniques are explained fully in the literature.

As used herein, the words "nucleic acid", "nucleic acid sequence", "nucleotide", "nucleic acid molecule" or "polynucleotide" are intended to include DNA molecules (e.g., cDNA or genomic DNA), RNA molecules (e.g., mRNA), natural occurring, mutated, synthetic DNA or RNA molecules, and analogs of the DNA or RNA generated using nucleotide analogs. It can be single-stranded or double-stranded. Such nucleic acids or polynucleotides include, but are not limited to, coding sequences of structural genes, anti-sense sequences, and non-coding regulatory sequences that do not encode mRNAs or protein products. These terms also encompass a gene. The term "gene" or "gene sequence" is used broadly to refer to a DNA nucleic acid associated with a biological function. Thus, genes may include introns and exons as in the genomic sequence, or may comprise only a coding sequence as in cDNAs, and/or may include cDNAs in combination with regulatory sequences.

The terms "polypeptide" and "protein" are used interchangeably herein and refer to amino acids in a polymeric form of any length, linked together by peptide bonds.

The aspects of the invention involve recombination DNA technology and exclude embodiments that are solely based on generating plants by traditional breeding methods.

Methods of Increasing Yield

Accordingly, in a first aspect of the invention, there is provided a method of increasing yield in a plant, the method comprising reducing or abolishing the expression of at least one nucleic acid encoding a otubain-like protease (referred to herein as "OTUB1" (for ovarian tumour domain-containing ubiquitin aldehyde binding protein 1)) and/or reducing or abolishing the activity of a OTUB1 polypeptide in said plant. Preferably, there is provided a method of increasing grain yield. OTUB1 may also be referred to herein as "NPT1", "DEP5" or "WTG1 and such terms may be used interchangeably. In one embodiment, the method reduces but does not abolish the expression and/or activity of OTUB1.

The term "yield" in general means a measurable produce of economic value, typically related to a specified crop, to an area, and to a period of time. Individual plant parts directly contribute to yield based on their number, size and/or weight. The actual yield is the yield per square meter for a crop and year, which is determined by dividing total production (includes both harvested and appraised production) by planted square metres.

The term "increased yield" as defined herein can be taken to comprise any or at least one of the following and can be measured by assessing one or more of (a) increased biomass (weight) of one or more parts of a plant, aboveground (harvestable parts), or increased root biomass, increased root volume, increased root length, increased root diameter or increased root length or increased biomass of any other harvestable part. Increased biomass may be expressed as g/plant or kg/hectare (b) increased seed yield per plant, which may comprise one or more of an increase in seed biomass (weight) per plant or an individual basis, (c) increased seed filling rate, (d) increased number of filled seeds, (e) increased harvest index, which may be expressed as a ratio of the yield of harvestable parts such as seeds over the total biomass, (f) increased viability/germination efficiency, (g) increased number or size or weight of seeds or pods or beans or grain (h) increased seed volume (which may be a result of a change in the composition (i.e. lipid (also referred to herein as oil)), protein, and carbohydrate total content and composition), (i) increased (individual or average) seed area, (j) increased (individual or average) seed length, (k) increased (individual or average) seed width, (l) increased (individual or average) seed perimeter, (m) increased growth or increased branching, for example inflorescences with more branches, (n) increased fresh weight or grain fill (o) increased ear weight (p) increased thousand kernel weight (TKVV), which may be taken from the number of filled seeds counted and their total weight and may be as a result of an increase in seed size and/or seed weight (q) decreased number of barren tillers per plant and (r) sturdier or stronger culms or stems. All parameters are relative to a wild-type or control plant.

Preferably, increased yield comprises at least one of an increase in at least one of grain number, grain number per ear or per panicle, grain weight, grain width and grain thickness, thousand kernel weight. Yield is increased relative to a control or wild-type plant. For example, the yield is increased by 2%, 3%, 4%, 5%, 6%, 7%, 8%, 9%, 10%, 11%, 12%, 13%, 14%, 15%, 16%, 17%, 18%, 19% or 20%, 25%, 30%, 35%, 40%, 45%, 50%, 55%, 60%, 65%, 70%, 75%, 80%, 85%, 90% or 95% compared to a control or wild-type plant. In one embodiment, yield may be increased by between 20-50%, more preferably between 5 and 15% or more compared to a control plant. An increase in grain yield can be measured by assessing one or more of grain number, grain number per panicle, grain weight, grain width and grain thickness, thousand kernel weight and/or the number of fertile tillers per plant. The skilled person would be able to measure any of the above grain yield parameters using known techniques in the art.

The terms "seed" and "grain" as used herein can be used interchangeably. The terms "increase", "improve" or "enhance" as used herein are also interchangeable As used herein, the terms "reducing" means a decrease in the levels of OTUB1 expression and/or activity by up to or more than 10%, 20%, 30%, 40%, 50%, 60%, 70%, 80% or 90% when compared to the level in a wild-type or control plant. Reducing may or may not encompass abolishes expression, preferably it does not. The term "abolish" expression means that no expression of OTUB1 is detectable or that no functional OTUB1 polypeptide is produced. Methods for determining the level of OTUB1 expression and/or activity would be well known to the skilled person. These reductions can be measured by any standard technique known to the skilled person. For example, a reduction in the expression and/or content levels of at least OTUB1 expression may be a measure of protein and/or nucleic acid levels and can be measured by any technique known to the skilled person, such as, but not limited to, any form of gel electrophoresis or chromatography (e.g. HPLC). In one embodiment, the mutation reduces or abolishes the deubiquitinase activity of OTUB1. Accordingly, the method may comprise measuring the deubiquitinase activity of the protein using techniques standard in the art, such as the use of a fluorescent deubiquitinase substrate.

In a preferred embodiment of any aspect of the invention described herein, the expression and/or activity of OTUB1 is reduced, and not abolished.

By "at least one mutation" is meant that where the OTUB1 gene is present as more than one copy or homoeologue (with the same or slightly different sequence) there is at least one mutation in at least one gene. Preferably all genes are mutated.

In one embodiment, the method comprises introducing at least one mutation into the, preferably endogenous, gene encoding OTUB1 and/or the OTUB1 promoter. Preferably said mutation is in the coding region of the OTUB1 gene. Alternatively, said mutation is in an intronic sequence or the 5'UTR. In a further embodiment, at least one mutation or structural alteration may be introduced into the OTUB1 promoter such that the OTUB1 gene is either not expressed (i.e. expression is abolished) or expression is reduced, as defined herein. In an alternative embodiment, at least one mutation may be introduced into the OTUB1 gene such that the altered gene does not express a full-length (i.e. expresses a truncated) OTUB1 protein or does not express a fully functional OTUB1 protein. In this manner, the activity of the OTUB1 polypeptide can be considered to be reduced or abolished as described herein. In any case, the mutation may result in the expression of OTUB1 with no, significantly reduced or altered biological activity in vivo. Alternatively, OTUB1 may not be expressed at all.

In one embodiment, the sequence of the OTUB1 gene comprises or consists of a nucleic acid sequence as defined in any of SEQ ID NO: 2 to 5 or a functional variant or homologue thereof and encodes a polypeptide as defined in SEQ ID NO: 1 or a functional variant or homologue thereof.

By "OTUB1 promoter" is meant a region extending for at least 2.5 kbp upstream of the ATG codon of the OTUB1 ORF. In one embodiment, the sequence of the OTUB1 promoter comprises or consists of a nucleic acid sequence as defined in SEQ ID NO: 6 or a functional variant or homologue thereof. Examples of promoter homologues are shown in SEQ ID NOs: 21 to 27.

In the above embodiments an 'endogenous' nucleic acid may refer to the native or natural sequence in the plant genome. In one embodiment, the endogenous sequence of the OTUB1 gene comprises any of SEQ ID NOs: 2, 3, 4 or 5 and encodes an amino acid sequence as defined in SEQ ID NO: 1 or homologs thereof. Also included in the scope of this invention are functional variants (as defined herein) and homologs of the above identified sequences. Examples of homologs are shown in SEQ ID NOs: 7 to 27. Accordingly, in one embodiment, the homolog encodes a polypeptide selected from SEQ ID NOs: 14 to 20 or the homolog comprises or consists of a nucleic acid sequence selected from SEQ ID NOs 7 to 13.

The term "functional variant" (or "variant") as used herein with reference to any of SEQ ID NOs: 2 to 210 refers to a variant sequence or part of the sequence which retains the biological function of the full non-variant sequence. A functional variant also comprises a variant of the gene of interest which has sequence alterations that do not affect function, for example in non-conserved residues. Also encompassed is a variant that is substantially identical, i.e. has only some sequence variations, for example in non-conserved residues, compared to the wild type sequences as shown herein and is biologically active. Alterations in a nucleic acid sequence which result in the production of a different amino acid at a given site that do not affect the functional properties of the encoded polypeptide are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

In one embodiment, a functional variant has at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to the non-variant nucleic acid or amino acid sequence.

The term homolog, as used herein, also designates a OTUB1 promoter or OTUB1 gene orthologue from other plant species. A homolog may have, in increasing order of preference, at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to the amino acid represented by any of SEQ ID NO: 1 or to the nucleic acid sequences as shown by SEQ ID NOs: 2 or 6. In one embodiment, overall sequence identity is at least 37%. In one embodiment, overall sequence identity is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, most preferably 90%, 91%, 92%, 93%, 94%, 95%, 96%, 97%, 98%, or at least 99%.

Functional variants of OTUB1 homologs as defined above are also within the scope of the invention.

The "OTUB1" (for ovarian tumour domain-containing ubiquitin aldehyde binding protein 1)) encodes a otubain-like protease. As discussed above, "OTUB1" may also be referred to herein as "NPT1", "DEP5" or "WTG1 and such terms may be used interchangeably.

OTUB1 is characterised by a number of conserved domains, including but not limited to an otubain-like domain.

In a further embodiment, the sequence of the otubain-like domain is as follows:

SEQ ID NO: 211
PYVGDKEPLSTLAAEFQSGSPILQEKIKLLGEQYDALRRTRGDGNCF
YRSFMFSYLEHILETQDKAEVERILKKIEQCKKTLADLGYIEFTFED

```
                                                    -continued
FFSIF1DQLESVLQGHESSIGAEELLERTRDQMVSDYVVMFFRFVTS

GEIQRRAEFFEPFISGLTNSTVVQFCKASVEPMGEESDHVHIIALSD

ALGVPIRVMYLDRSSCDAGNISVNHHDFSPEANSSDGAAAAEKPYIT

LLYRPGHYDILYP
```

Wherein the amino acids highlighted in bold in SEQ ID NO: 211 forms a catalytic triad.

```
or
                                              SEQ ID NO: 212
SPILQEKIKLLGEQYDALRRTRGDGNCFYRSFMFSYLEHILETQDKA

EVERILKKIEQCKKTLADLGYIEFTFEDFFSIF1DQLESVLQGHESS

IGAEELLERTRDQMVSDYVVMFFRFVTSGEIQRRAEFFEPFISGLTN

STVVQFCKASVEPMGEESDHVHIIALSDALGVPIRVMYLDRSSCDAG

NISVNHHDFSPEANSSDGAAAAEKPYITLLYRPGHYDILYPK
```

Accordingly, in one embodiment, the OTUB1 nucleic acid (coding) sequence encodes a OTUB1 protein comprising at least one SBP-domain and/or otubain-like domain as defined below, or a variant thereof, wherein the variant has at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to SEQ ID NO 211 or 212. In a preferred embodiment, the OTUB1 polypeptide is characterised by at least one otubain-like domain and has at least 75% homology to SEQ ID NO 211 or 212. In a further embodiment, the OTUB1 protein comprises a catalytic triad, and preferably the OTUB1 protein comprises SEQ ID NO: 211 and/or SEQ ID NO: 212 or a variant thereof as defined above, wherein the sequence of the variant comprises at least a aspartate and cysteine (preferably at positions 4 and 7) and/or a histidine in SEQ ID NO: 211 (preferably at the first position).

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognised that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Non-limiting examples of algorithms that are suitable for determining percent sequence identity and sequence similarity are the BLAST and BLAST 2.0 algorithms.

Suitable homologues can be identified by sequence comparisons and identifications of conserved domains. There are predictors in the art that can be used to identify such sequences. The function of the homologue can be identified as described herein and a skilled person would thus be able to confirm the function, for example when overexpressed in a plant.

Thus, the nucleotide sequences of the invention and described herein can also be used to isolate corresponding sequences from other organisms, particularly other plants, for example crop plants. In this manner, methods such as PCR, hybridization, and the like can be used to identify such sequences based on their sequence homology to the sequences described herein. Topology of the sequences and the characteristic domains structure can also be considered when identifying and isolating homologs.

Sequences may be isolated based on their sequence identity to the entire sequence or to fragments thereof. In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen plant. The hybridization probes may be genomic DNA fragments, cDNA fragments, RNA fragments, or other oligonucleotides, and may be labeled with a detectable group, or any other detectable marker. Methods for preparation of probes for hybridization and for construction of cDNA and genomic libraries are generally known in the art and are disclosed in Sambrook, et al., (1989) Molecular Cloning: A Library Manual (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Duration of hybridization is generally less than about 24 hours, usually about 4 to 12. Stringent conditions may also be achieved with the addition of destabilizing agents such as formamide.

In a further embodiment, a variant as used herein can comprise a nucleic acid sequence encoding a OTUB1 polypeptide as defined herein that is capable of hybridising under stringent conditions as defined herein to a nucleic acid sequence as defined in any of SEQ ID NOs: 2 to 5.

In one embodiment, the method comprises reducing or abolishing, preferably reducing, the expression of at least one nucleic acid encoding a OTUB1 polypeptide or reducing or abolishing the activity of an OTUB1 polypeptide, as described herein, wherein the method comprises introducing at least one mutation into at least one OTUB1 gene and/or promoter, wherein the OTUB1 gene comprises or consists of
  a. a nucleic acid sequence encoding a polypeptide as defined in one of SEQ ID NOs: 1 and 14 to 20; or
  b. a nucleic acid sequence as defined in one of SEQ ID NOs: 2 to 13; or
  c. a nucleic acid sequence with at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to either (a) or (b); or
  d. a nucleic acid sequence encoding a OTUB1 polypeptide as defined herein that is capable of hybridising under stringent conditions as defined herein to the nucleic acid sequence of any of (a) to (c).
and wherein the OTUB1 promoter comprises or consists of
  e. a nucleic acid sequence as defined in one of SEQ ID NOs: 6 and 21 to 27
  f. a nucleic acid sequence with at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to (e); or
  g. a nucleic acid sequence capable of hybridising under stringent conditions as defined herein to the nucleic acid sequence of any of (e) to (f).

In a preferred embodiment, the mutation that is introduced into the endogenous OTUB1 gene or promoter thereof to silence, reduce, or inhibit the biological activity and/or expression levels of the OTUB1 gene or protein can be selected from the following mutation types
  1. a "missense mutation", which is a change in the nucleic acid sequence that results in the substitution of one amino acid for another amino acid;
  2. a "nonsense mutation" or "STOP codon mutation", which is a change in the nucleic acid sequence that results in the introduction of a premature STOP codon and, thus, the termination of translation (resulting in a truncated protein); in plants, the translation stop codons may be selected from "TGA" (UGA in RNA), "TAA" (UAA in RNA) and "TAG" (UAG in RNA); thus any nucleotide substitution, insertion, deletion which results in one of these codons to be in the mature mRNA being translated (in the reading frame) will terminate translation.
  3. an "insertion mutation" of one or more nucleotides or one or more amino acids, due to one or more codons having been added in the coding sequence of the nucleic acid;
  4. a "deletion mutation" of one or more nucleotides or of one or more amino acids, due to one or more codons having been deleted in the coding sequence of the nucleic acid;
  5. a "frameshift mutation", resulting in the nucleic acid sequence being translated in a different frame downstream of the mutation. A frameshift mutation can have various causes, such as the insertion, deletion or duplication of one or more nucleotides.
  6. a "splice site" mutation, which is a mutation that results in the insertion, deletion or substitution of a nucleotide at the site of splicing.

As used herein, an "insertion", "deletion" or "substitution" may refer to the insertion, deletion or substitution of at least one, two, three, four, five, six, seven, eight, nine or ten nucleotides. In one specific embodiment, said mutation may comprise the substitution of at least one of the following:
  C to T at position 1135 of SEQ ID NO: 2 or 5;
  G to C at position 1462 of SEQ ID NO: 2 or 5; and/or
  G to C at position 1798 of SEQ ID NO: 2 or 5

In a further additional or alternative embodiment, said mutation is the insertion of a single amino acid, preferably, T, at position 2234 of SEQ ID NO: 2 or 5.

In a further additional or alternative embodiment, said mutation is a deletion of at least four nucleotides, preferably the four nucleotides underlined in SEQ ID NO: 3. This mutation is a mutation in the exon-intron splicing sequence, which results in a mutated CDS sequence containing the fourth intron sequence as defined in SEQ ID NO: 153 (the fourth intron is underlined). As a result, the wtg mutation resulted in premature termination of the predicted protein (as described in SEQ ID NO: 154).

In a further additional or alternative embodiment, said mutation may be a G to A substitution at position 1824 of SEQ ID NO: 155.

In general, the skilled person will understand that at least one mutation as defined above and which leads to the insertion, deletion or substitution of at least one nucleic acid or amino acid compared to the wild-type OTUB1 promoter or OTUB1 nucleic acid or protein sequence can affect the biological activity of the OTUB1 protein. Preferably said mutation abolishes or reduces the deubiquitinase activity of OTUB1.

In one embodiment, the mutation is introduced into the SBP-domain and/or an otubain-like domain. Preferably said mutation is a loss or partial loss of function mutation such as a premature stop codon, or an amino acid change in a highly conserved region that is predicted to be important for protein structure. In another embodiment, the mutation is introduced into the OTUB1 promoter and is at least the deletion and/or insertion of at least one nucleic acid. Other major changes such as deletions that remove functional regions of the promoter are also included as these will reduce the expression of OTUB1. In one embodiment, the mutation may be introduced into at least one amino acid that makes the catalytic triad, as defined above. For example, said mutation may be at least one, preferably all of the following:
  a D to E at position 68 of SEQ ID NO: 1
  a C to S at position 71 of SEQ ID NO: 1 and/or
  a H to R at position 267 of SEQ ID NO: 1.

In one embodiment a mutation may be introduced into the OTUB1 promoter and at least one mutation is introduced into the OTUB1 gene.

In one embodiment, the mutation is introduced using mutagenesis or targeted genome editing. That is, in one embodiment, the invention relates to a method and plant that has been generated by genetic engineering methods as described above, and does not encompass naturally occurring varieties.

Targeted genome modification or targeted genome editing is a genome engineering technique that uses targeted DNA double-strand breaks (DSBs) to stimulate genome editing through homologous recombination (HR)-mediated recombination events. To achieve effective genome editing via introduction of site-specific DNA DSBs, four major classes of customisable DNA binding proteins can be used: meganucleases derived from microbial mobile genetic elements, ZF nucleases based on eukaryotic transcription factors, transcription activator-like effectors (TALEs) from Xanthomonas bacteria, and the RNA-guided DNA endonuclease Cas9 from the type II bacterial adaptive immune system CRISPR (clustered regularly interspaced short palindromic repeats). Meganuclease, ZF, and TALE proteins all recognize specific DNA sequences through protein-DNA interactions. Although meganucleases integrate nuclease and DNA-binding domains, ZF and TALE proteins consist of individual modules targeting 3 or 1 nucleotides (nt) of DNA, respectively. ZFs and TALEs can be assembled in desired combinations and attached to the nuclease domain of FokI to direct nucleolytic activity toward specific genomic loci.

Upon delivery into host cells via the bacterial type III secretion system, TAL effectors enter the nucleus, bind to effector-specific sequences in host gene promoters and activate transcription. Their targeting specificity is determined by a central domain of tandem, 33-35 amino acid repeats. This is followed by a single truncated repeat of 20 amino acids. The majority of naturally occurring TAL effectors examined have between 12 and 27 full repeats.

These repeats only differ from each other by two adjacent amino acids, their repeat-variable di-residue (RVD). The RVD that determines which single nucleotide the TAL effector will recognize: one RVD corresponds to one nucleotide, with the four most common RVDs each preferentially associating with one of the four bases. Naturally occurring recognition sites are uniformly preceded by a T that is required for TAL effector activity. TAL effectors can be fused to the catalytic domain of the FokI nuclease to create a TAL effector nuclease (TALEN) which makes targeted DNA double-strand breaks (DSBs) in vivo for genome editing. The use of this technology in genome editing is well described in the art, for example in U.S. Pat. Nos. 8,440,431, 8,440,432 and 8,450,471. Cermak T et al. describes a set of customized plasmids that can be used with the Golden Gate cloning method to assemble multiple DNA fragments. As described therein, the Golden Gate method uses Type IIS restriction endonucleases, which cleave outside their recognition sites to create unique 4 bp overhangs. Cloning is expedited by digesting and ligating in the same reaction mixture because correct assembly eliminates the enzyme recognition site. Assembly of a custom TALEN or TAL effector construct and involves two steps: (i) assembly of repeat modules into intermediary arrays of 1-10 repeats and (ii) joining of the intermediary arrays into a backbone to make the final construct. Accordingly, using techniques known in the art it is possible to design a TAL effector that targets a OTUB1 gene or promoter sequence as described herein.

Another genome editing method that can be used according to the various aspects of the invention is CRISPR. The use of this technology in genome editing is well described in the art, for example in U.S. Pat. No. 8,697,359 and references cited herein. In short, CRISPR is a microbial nuclease system involved in defense against invading phages and plasmids. CRISPR loci in microbial hosts contain a combination of CRISPR-associated (Cas) genes as well as non-coding RNA elements capable of programming the specificity of the CRISPR-mediated nucleic acid cleavage (sgRNA). Three types (I-III) of CRISPR systems have been identified across a wide range of bacterial hosts. One key feature of each CRISPR locus is the presence of an array of repetitive sequences (direct repeats) interspaced by short stretches of non-repetitive sequences (spacers). The non-coding CRISPR array is transcribed and cleaved within direct repeats into short crRNAs containing individual spacer sequences, which direct Cas nucleases to the target site (protospacer). The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer.

One major advantage of the CRISPR-Cas9 system, as compared to conventional gene targeting and other programmable endonucleases is the ease of multiplexing, where multiple genes can be mutated simultaneously simply by using multiple sgRNAs each targeting a different gene. In addition, where two sgRNAs are used flanking a genomic region, the intervening section can be deleted or inverted (Wiles et al., 2015).

Cas9 is thus the hallmark protein of the type II CRISPR-Cas system, and is a large monomeric DNA nuclease guided to a DNA target sequence adjacent to the PAM (protospacer adjacent motif) sequence motif by a complex of two non-coding RNAs: CRISPR RNA (crRNA) and trans-activating crRNA (tracrRNA). The Cas9 protein contains two nuclease domains homologous to RuvC and HNH nucleases. The HNH nuclease domain cleaves the complementary DNA strand whereas the RuvC-like domain cleaves the non-complementary strand and, as a result, a blunt cut is introduced in the target DNA. Heterologous expression of Cas9 together with an sgRNA can introduce site-specific double strand breaks (DSBs) into genomic DNA of live cells from various organisms. For applications in eukaryotic organisms, codon optimized versions of Cas9, which is originally from the bacterium *Streptococcus pyogenes*, have been used.

The single guide RNA (sgRNA) is the second component of the CRISPR/Cas system that forms a complex with the Cas9 nuclease. sgRNA is a synthetic RNA chimera created by fusing crRNA with tracrRNA. The sgRNA guide sequence located at its 5' end confers DNA target specificity. Therefore, by modifying the guide sequence, it is possible to create sgRNAs with different target specificities. The canonical length of the guide sequence is 20 bp. In plants, sgRNAs have been expressed using plant RNA polymerase III promoters, such as U6 and U3. Accordingly, using techniques known in the art it is possible to design sgRNA molecules that targets a OTUB1 gene or promoter sequence as described herein. In one embodiment, the method comprises using any of the nucleic acid constructs or sgRNA molecules described herein.

Cas9 expression plasmids for use in the methods of the invention can be constructed as described in the art.

Alternatively, more conventional mutagenesis methods can be used to introduce at least one mutation into a OTUB1 gene or OTUB1 promoter sequence. These methods include both physical and chemical mutagenesis. A skilled person will know further approaches can be used to generate such mutants, and methods for mutagenesis and polynucleotide alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein.

In one embodiment, insertional mutagenesis is used, for example using T-DNA mutagenesis (which inserts pieces of the T-DNA from the *Agrobacterium tumefaciens* T-Plasmid into DNA causing either loss of gene function or gain of gene function mutations), site-directed nucleases (SDNs) or transposons as a mutagen. Insertional mutagenesis is an alternative means of disrupting gene function and is based on the insertion of foreign DNA into the gene of interest (see Krysan et al, The Plant Cell, Vol. 11, 2283-2290, December 1999). Accordingly, in one embodiment, T-DNA is used as an insertional mutagen to disrupt OTUB1 gene or OTUB1 promoter expression. T-DNA not only disrupts the expression of the gene into which it is inserted, but also acts as a marker for subsequent identification of the mutation. Since the sequence of the inserted element is known, the gene in which the insertion has occurred can be recovered, using various cloning or PCR-based strategies. The insertion of a piece of T-DNA in the order of 5 to 25 kb in length generally produces a disruption of gene function. If a large enough population of T-DNA transformed lines is generated, there are reasonably good chances of finding a transgenic plant carrying a T-DNA insert within any gene of interest. Transformation of spores with T-DNA is achieved by an *Agrobacterium*-mediated method which involves exposing plant cells and tissues to a suspension of *Agrobacterium* cells.

The details of this method are well known to a skilled person. In short, plant transformation by *Agrobacterium* results in the integration into the nuclear genome of a sequence called T-DNA, which is carried on a bacterial plasmid. The use of T-DNA transformation leads to stable single insertions. Further mutant analysis of the resultant transformed lines is straightforward and each individual insertion line can be rapidly characterized by direct sequencing and analysis of DNA flanking the insertion. Gene expression in the mutant is compared to expression of the OTUB1 nucleic acid sequence in a wild type plant and phenotypic analysis is also carried out.

In another embodiment, mutagenesis is physical mutagenesis, such as application of ultraviolet radiation, X-rays, gamma rays, fast or thermal neutrons or protons. The targeted population can then be screened to identify an OTUB1 mutant with reduced expression or activity.

In another embodiment of the various aspects of the invention, the method comprises mutagenizing a plant population with a mutagen. The mutagen may be a fast neutron irradiation or a chemical mutagen, for example selected from the following non-limiting list: ethyl methanesulfonate (EMS), methylmethane sulfonate (MMS), N-ethyl-N-nitrosurea (ENU), triethylmelamine (1'EM), N-methyl-N-nitrosourea (MNU), procarbazine, chlorambucil, cyclophosphamide, diethyl sulfate, acrylamide monomer, melphalan, nitrogen mustard, vincristine, dimethylnitosamine, N-methyl-N'-nitro-Nitrosoguanidine (MN NG), nitrosoguanidine, 2-aminopurine, 7,12 dimethyl-benz(a)anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9 [3-(ethyl-2-chloroethyl)aminopropylamino]acridine dihydrochloride (ICR-170) or formaldehyde. Again, the targeted population can then be screened to identify a OTUB1 gene or promoter mutant.

In another embodiment, the method used to create and analyse mutations is targeting induced local lesions in genomes (TILLING), reviewed in Henikoff et al, 2004. In this method, seeds are mutagenised with a chemical mutagen, for example EMS. The resulting M1 plants are self-fertilised and the M2 generation of individuals is used to prepare DNA samples for mutational screening. DNA samples are pooled and arrayed on microtiter plates and subjected to gene specific PCR. The PCR amplification products may be screened for mutations in the OTUB1 target gene using any method that identifies heteroduplexes between wild type and mutant genes. For example, but not limited to, denaturing high pressure liquid chromatography (dHPLC), constant denaturant capillary electrophoresis (CDCE), temperature gradient capillary electrophoresis (TGCE), or by fragmentation using chemical cleavage. Preferably, the PCR amplification products are incubated with an endonuclease that preferentially cleaves mismatches in heteroduplexes between wild type and mutant sequences. Cleavage products are electrophoresed using an automated sequencing gel apparatus, and gel images are analyzed with the aid of a standard commercial image-processing program. Any primer specific to the OTUB1 nucleic acid sequence may be utilized to amplify the OTUB1 nucleic acid sequence within the pooled DNA sample. Preferably, the primer is designed to amplify the regions of the OTUB1 gene where useful mutations are most likely to arise, specifically in the areas of the OTUB1 gene that are highly conserved and/or confer activity as explained elsewhere. To facilitate detection of PCR products on a gel, the PCR primer may be labeled using any conventional labeling method. In an alternative embodiment, the method used to create and analyse mutations is EcoTILLING. EcoTILLING is molecular technique that is similar to TILLING, except that its objective is to uncover natural variation in a given population as opposed to induced mutations. The first publication of the EcoTILLING method was described in Comai et al. 2004.

Rapid high-throughput screening procedures thus allow the analysis of amplification products for identifying a mutation conferring the reduction or inactivation of the expression of the OTUB1 gene as compared to a corresponding non-mutagenised wild type plant. Once a mutation is identified in a gene of interest, the seeds of the M2 plant carrying that mutation are grown into adult M3 plants and screened for the phenotypic characteristics associated with the target gene OTUB1. Loss of and reduced function mutants with increased grain yield compared to a control can thus be identified.

Plants obtained or obtainable by such method which carry a functional mutation in the endogenous OTUB1 gene or promoter locus are also within the scope of the invention In an alternative embodiment, the expression of the OTUB1 gene may be reduced at either the level of transcription or translation. For example, expression of a OTUB1 nucleic acid or OTUB1 promoter sequence, as defined herein, can be reduced or silenced using a number of gene silencing methods known to the skilled person, such as, but not limited to, the use of small interfering nucleic acids (siNA) against OTUB1. "Gene silencing" is a term generally used to refer to suppression of expression of a gene via sequence-specific interactions that are mediated by RNA molecules. The degree of reduction may be so as to totally abolish production of the encoded gene product, but more usually the abolition of expression is partial, with some degree of expression remaining. The term should not therefore be taken to require complete "silencing" of expression.

In one embodiment, the siNA may include, short interfering RNA (siRNA), double-stranded RNA (dsRNA), micro-RNA (miRNA), antagomirs and short hairpin RNA (shRNA) capable of mediating RNA interference.

The inhibition of expression and/or activity can be measured by determining the presence and/or amount of OTUB1 transcript using techniques well known to the skilled person (such as Northern Blotting, RT-PCR and so on).

Transgenes may be used to suppress endogenous plant genes. This was discovered originally when chalcone synthase transgenes in petunia caused suppression of the endogenous chalcone synthase genes and indicated by easily visible pigmentation changes. Subsequently it has been described how many, if not all plant genes can be "silenced" by transgenes. Gene silencing requires sequence similarity between the transgene and the gene that becomes silenced. This sequence homology may involve promoter regions or coding regions of the silenced target gene. When coding regions are involved, the transgene able to cause gene silencing may have been constructed with a promoter that would transcribe either the sense or the antisense orientation of the coding sequence RNA. It is likely that the various examples of gene silencing involve different mechanisms that are not well understood. In different examples there may be transcriptional or post-transcriptional gene silencing and both may be used according to the methods of the invention.

The mechanisms of gene silencing and their application in genetic engineering, which were first discovered in plants in the early 1990s and then shown in *Caenorhabditis elegans* are extensively described in the literature.

RNA-mediated gene suppression or RNA silencing according to the methods of the invention includes co-suppression wherein over-expression of the target sense RNA or mRNA, that is the OTUB1 sense RNA or mRNA, leads to a reduction in the level of expression of the genes concerned. RNAs of the transgene and homologous endogenous gene are co-ordinately suppressed. Other techniques used in the methods of the invention include antisense RNA to reduce transcript levels of the endogenous target gene in a plant. In this method, RNA silencing does not affect the transcription of a gene locus, but only causes sequence-specific degradation of target mRNAs. An "antisense" nucleic acid sequence comprises a nucleotide sequence that is complementary to a "sense" nucleic acid sequence encoding a OTUB1 protein, or a part of the protein, i.e. complementary to the coding strand of a double-stranded cDNA molecule or complementary to an mRNA transcript sequence. The antisense nucleic acid sequence is preferably complementary to the endogenous OTUB1 gene to be silenced. The complementarity may be located in the "coding region" and/or in the "non-coding region" of a gene. The term "coding region" refers to a region of the nucleotide sequence comprising codons that are translated into amino acid residues. The term "non-coding region" refers to 5' and 3' sequences that flank the coding region that are transcribed but not translated into amino acids (also referred to as 5' and 3' untranslated regions).

Antisense nucleic acid sequences can be designed according to the rules of Watson and Crick base pairing. The antisense nucleic acid sequence may be complementary to the entire OTUB1 nucleic acid sequence as defined herein, but may also be an oligonucleotide that is antisense to only a part of the nucleic acid sequence (including the mRNA 5' and 3' UTR). For example, the antisense oligonucleotide sequence may be complementary to the region surrounding the translation start site of an mRNA transcript encoding a polypeptide. The length of a suitable antisense oligonucleotide sequence is known in the art and may start from about 50, 45, 40, 35, 30, 25, 20, 15 or 10 nucleotides in length or less. An antisense nucleic acid sequence according to the invention may be constructed using chemical synthesis and enzymatic ligation reactions using methods known in the art. For example, an antisense nucleic acid sequence (e.g., an antisense oligonucleotide sequence) may be chemically synthesized using naturally occurring nucleotides or variously modified nucleotides designed to increase the biological stability of the molecules or to increase the physical stability of the duplex formed between the antisense and sense nucleic acid sequences, e.g., phosphorothioate derivatives and acridine-substituted nucleotides may be used. Examples of modified nucleotides that may be used to generate the antisense nucleic acid sequences are well known in the art. The antisense nucleic acid sequence can be produced biologically using an expression vector into which a nucleic acid sequence has been subcloned in an antisense orientation (i.e., RNA transcribed from the inserted nucleic acid will be of an antisense orientation to a target nucleic acid of interest). Preferably, production of antisense nucleic acid sequences in plants occurs by means of a stably integrated nucleic acid construct comprising a promoter, an operably linked antisense oligonucleotide, and a terminator.

The nucleic acid molecules used for silencing in the methods of the invention hybridize with or bind to mRNA transcripts and/or insert into genomic DNA encoding a polypeptide to thereby inhibit expression of the protein, e.g., by inhibiting transcription and/or translation. The hybridization can be by conventional nucleotide complementarity to form a stable duplex, or, for example, in the case of an antisense nucleic acid sequence which binds to DNA duplexes, through specific interactions in the major groove of the double helix. Antisense nucleic acid sequences may be introduced into a plant by transformation or direct injection at a specific tissue site. Alternatively, antisense nucleic acid sequences can be modified to target selected cells and then administered systemically. For example, for systemic administration, antisense nucleic acid sequences can be modified such that they specifically bind to receptors or antigens expressed on a selected cell surface, e.g., by linking the antisense nucleic acid sequence to peptides or antibodies which bind to cell surface receptors or antigens. The antisense nucleic acid sequences can also be delivered to cells using vectors.

RNA interference (RNAi) is another post-transcriptional gene-silencing phenomenon which may be used according to the methods of the invention. This is induced by double-stranded RNA in which mRNA that is homologous to the dsRNA is specifically degraded. It refers to the process of sequence-specific post-transcriptional gene silencing mediated by short interfering RNAs (siRNA). The process of RNAi begins when the enzyme, DICER, encounters dsRNA and chops it into pieces called small-interfering RNAs (siRNA). This enzyme belongs to the RNase III nuclease family. A complex of proteins gathers up these RNA remains and uses their code as a guide to search out and destroy any RNAs in the cell with a matching sequence, such as target mRNA.

Artificial and/or natural microRNAs (miRNAs) may be used to knock out gene expression and/or mRNA translation. MicroRNAs (miRNAs) miRNAs are typically single stranded small RNAs typically 19-24 nucleotides long. Most plant miRNAs have perfect or near-perfect complementarity with their target sequences. However, there are natural targets with up to five mismatches. They are processed from longer non-coding RNAs with characteristic fold-back structures by double-strand specific RNases of the Dicer family Upon processing, they are incorporated in the RNA-induced silencing complex (RISC) by binding to its main component, an Argonaute protein. miRNAs serve as the specificity components of RISC, since they base-pair to target nucleic acids, mostly mRNAs, in the cytoplasm. Subsequent regulatory events include target mRNA cleavage and destruction and/or translational inhibition. Effects of miRNA overexpression are thus often reflected in decreased mRNA levels of target genes. Artificial microRNA (amiRNA) technology has been applied in *Arabidopsis thaliana* and other plants to efficiently silence target genes of interest. The design principles for amiRNAs have been generalized and integrated into a Web-based tool (wmd.weigelworld.org).

Thus, according to the various aspects of the invention a plant may be transformed to introduce a RNAi, shRNA, snRNA, dsRNA, siRNA, miRNA, ta-siRNA, amiRNA or cosuppression molecule that has been designed to target the expression of an OTUB1 nucleic acid sequence and selectively decreases or inhibits the expression of the gene or stability of its transcript. Preferably, the RNAi, snRNA, dsRNA, shRNA siRNA, miRNA, amiRNA, to-siRNA or cosuppression molecule used according to the various aspects of the invention comprises a fragment of at least 17 nt, preferably 22 to 26 nt and can be designed on the basis of the information shown in any of SEQ ID NOs:1 to 12. Guidelines for designing effective siRNAs are known to the skilled person. Briefly, a short fragment of the target gene sequence (e.g., 19-40 nucleotides in length) is chosen as the target sequence of the siRNA of the invention. The short fragment of target gene sequence is a fragment of the target gene mRNA. In preferred embodiments, the criteria for choosing a sequence fragment from the target gene mRNA to be a candidate siRNA molecule include 1) a sequence from the target gene mRNA that is at least 50-100 nucleotides from the 5' or 3' end of the native mRNA molecule, 2) a sequence from the target gene mRNA that has a G/C content of between 30% and 70%, most preferably around 50%, 3) a sequence from the target gene mRNA that does not contain repetitive sequences (e.g., AAA, CCC, GGG, TTT, AAAA, CCCC, GGGG, TTTT), 4) a sequence from the target gene mRNA that is accessible in the mRNA, 5) a sequence from the target gene mRNA that is unique to the target gene, 6) avoids regions within 75 bases of a start codon. The sequence fragment from the target gene mRNA may meet one or more of the criteria identified above. The selected gene is introduced as a nucleotide sequence in a prediction program that takes into account all the variables described above for the design of optimal oligonucleotides. This program scans any mRNA nucleotide sequence for regions susceptible to be targeted by siRNAs. The output of this analysis is a score of possible siRNA oligonucleotides. The highest scores are used to design double stranded RNA oligonucleotides that are typically made by chemical synthesis. In addition to siRNA which is complementary to the mRNA target region, degenerate siRNA sequences may be used to target homologous regions. siRNAs according to the invention can be synthesized by any method known in the art. RNAs are preferably chemically synthesized using appropriately protected ribonucleoside phosphoramidites and a conventional DNA/RNA synthesizer. Additionally, siRNAs can be obtained from commercial RNA oligonucleotide synthesis suppliers.

siRNA molecules according to the aspects of the invention may be double stranded. In one embodiment, double stranded siRNA molecules comprise blunt ends. In another embodiment, double stranded siRNA molecules comprise overhanging nucleotides (e.g., 1-5 nucleotide overhangs, preferably 2 nucleotide overhangs). In some embodiments, the siRNA is a short hairpin RNA (shRNA); and the two strands of the siRNA molecule may be connected by a linker region (e.g., a nucleotide linker or a non-nucleotide linker). The siRNAs of the invention may contain one or more modified nucleotides and/or non-phosphodiester linkages. Chemical modifications well known in the art are capable of increasing stability, availability, and/or cell uptake of the siRNA. The skilled person will be aware of other types of chemical modification which may be incorporated into RNA molecules.

In one embodiment, recombinant DNA constructs as described in U.S. Pat. No. 6,635,805, incorporated herein by reference, may be used.

The silencing RNA molecule is introduced into the plant using conventional methods, for example a vector and *Agrobacterium*-mediated transformation. Stably transformed plants are generated and expression of the OTUB1 gene compared to a wild type control plant is analysed.

Silencing or reducing expression levels of OTUB1 nucleic acid may also be achieved using virus-induced gene silencing.

Thus, in one embodiment of the invention, the plant expresses a nucleic acid construct comprising a RNAi, shRNA snRNA, dsRNA, siRNA, miRNA, ta-siRNA, amiRNA or co-suppression molecule that targets the OTUB1 nucleic acid sequence as described herein and reduces expression of the endogenous OTUB1 nucleic acid sequence. A gene is targeted when, for example, the RNAi, snRNA, dsRNA, siRNA, shRNA miRNA, ta-siRNA, amiRNA or cosuppression molecule selectively decreases or inhibits the expression of the gene compared to a control plant. Alternatively, a RNAi, snRNA, dsRNA, siRNA, miRNA, ta-siRNA, amiRNA or cosuppression molecule targets a OTUB1 nucleic acid sequence when the RNAi, shRNA snRNA, dsRNA, siRNA, miRNA, ta-siRNA, amiRNA or co-suppression molecule hybridises under stringent conditions to the gene transcript. In one example, the plant expresses a nucleic acid construct comprising an RNAi, wherein the sequence of the RNAi comprises or consists of SEQ ID NO: 210 or a functional variant thereof, as defined herein. There is also provided the use of this nucleic acid construct comprising an RNAi, wherein the sequence of the RNAi comprises or consists of SEQ ID NO: 210 or a functional variant thereof to reduce or abolish (but preferably reduce) the expression of OTUB1 and consequently increase grain yield, as described above.

A further approach to gene silencing is by targeting nucleic acid sequences complementary to the regulatory region of the gene (e.g., the promoter and/or enhancers) of OTUB1 to form triple helical structures that prevent transcription of the gene in target cells. Other methods, such as the use of antibodies directed to an endogenous polypeptide for inhibiting its function in planta, or interference in the signaling pathway in which a polypeptide is involved, will be well known to the skilled man. In particular, it can be envisaged that manmade molecules may be useful for inhibiting the biological function of a target polypeptide, or for interfering with the signaling pathway in which the target polypeptide is involved.

In one embodiment, the suppressor nucleic acids may be anti-sense suppressors of expression of the OTUB1 polypeptides. In using anti-sense sequences to down-regulate gene expression, a nucleotide sequence is placed under the control of a promoter in a "reverse orientation" such that transcription yields RNA which is complementary to normal mRNA transcribed from the "sense" strand of the target gene.

An anti-sense suppressor nucleic acid may comprise an anti-sense sequence of at least 10 nucleotides from the target nucleotide sequence. It may be preferable that there is complete sequence identity in the sequence used for down-regulation of expression of a target sequence, and the target sequence, although total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a variant of such a sequence.

The sequence need not include an open reading frame or specify an RNA that would be translatable. It may be preferred for there to be sufficient homology for the respective anti-sense and sense RNA molecules to hybridise. There may be down regulation of gene expression even where there is about 5%, 10%, 15% or 20% or more mismatch between the sequence used and the target gene. Effectively, the homology should be sufficient for the down-regulation of gene expression to take place.

Suppressor nucleic acids may be operably linked to tissue-specific or inducible promoters. For example, integument and seed specific promoters can be used to specifically down-regulate an OTUB1 nucleic acid in developing ovules and seeds to increase final seed size.

Nucleic acid which suppresses expression of an OTUB1 polypeptide as described herein may be operably linked to a heterologous regulatory-sequence, such as a promoter, for example a constitutive, inducible, tissue-specific or developmental specific promoter. The construct or vector may be transformed into plant cells and expressed as described herein. Plant cells comprising such vectors are also within the scope of the invention.

In another aspect, the invention relates to a silencing construct obtainable or obtained by a method as described herein and to a plant cell comprising such construct.

Thus, aspects of the invention involve targeted mutagenesis methods, specifically genome editing, and in a preferred embodiment exclude embodiments that are solely based on generating plants by traditional breeding methods.

In a further embodiment, the method may comprise reducing and/or abolishing the activity of OTUB1. In one example this may comprise reducing OTUB1's ability to interact with UBC13 by reducing and/or abolishing its inhibition as described herein and/or reduce OTUB1's ability to deubiquitinase SPL14, leading to the accumulation of SPL14.

In another aspect, the invention extends to a plant obtained or obtainable by a method as described herein.

In a further aspect of the invention, there is provided a method of increasing cell proliferation in the spikelet hull of a plant, preferably in the grain-length direction and/or decreasing cell number in the grain-width direction, resulting in a decrease in cell length but an increase in cell width, the method comprising reducing or abolishing the expression of at least one nucleic acid encoding OTUB1 polypeptide and/or reducing the activity of a OTUB1 polypeptide in said plant using any of the methods described herein. The terms "increase", "improve" or "enhance" as used herein are interchangeable. In one embodiment, cell proliferation is increased by at least 2%, 3%, 4%, 5%, 6%, 7%, 8%, 9%, 10% 11%, 12%, 13%, 14%, 15%, 16%, 17%, 18%, 19%, 20%, 30%, 40% or 50% in comparison to a control plant.

Genetically Altered or Modified Plants and Methods of Producing Such Plants

In another aspect of the invention there is provided a genetically altered plant, part thereof or plant cell characterised in that the plant does not express OTUB1, has reduced levels of OTUB1 expression, does not express a functional OTUB1 protein or expresses a OTUB1 protein with reduced function and/or activity. For example, the plant is a reduction (knock down) or loss of function (knock out) mutant wherein the function of the OTUB1 nucleic acid sequence is reduced or lost compared to a wild type control plant. Preferably, the plant is a knock down and not a knock out, meaning that the plant has reduced levels of OTUB1 expression or expresses a OTUB1 protein with reduced function and/or activity. To this end, a mutation is introduced into either the OTUB1 gene sequence or the corresponding promoter sequence which disrupts the transcription of the gene. Therefore, preferably said plant comprises at least one mutation in the promoter and/or gene for OTUB1. In one embodiment the plant may comprise a mutation in both the promoter and gene for OTUB1.

In a further aspect of the invention, there is provided a plant, part thereof or plant cell characterised by an increased grain yield compared to a wild-type or control pant, wherein preferably, the plant comprises at least one mutation in the OTUB1 gene and/or its promoter. Preferably said increase in grain yield comprises an increase in grain number, grain number per panicle, grain weight, grain width, grain thickness, thousand kernel weight and/or a decrease in grain length.

The plant may be produced by introducing a mutation, preferably a deletion, insertion or substitution into the OTUB1 gene and/or promoter sequence by any of the above described methods. Preferably said mutation is introduced into a least one plant cell and a plant regenerated from the at least one mutated plant cell.

Alternatively, the plant or plant cell may comprise a nucleic acid construct expressing an RNAi molecule targeting the OTUB1 gene as described herein. In one example, the sequence of the RNAi comprises or consists of SEQ ID NO: 210 or a variant thereof, as defined herein. In one embodiment, said construct is stably incorporated into the plant genome. These techniques also include gene targeting using vectors that target the gene of interest and which allows for integration of a transgene at a specific site. The targeting construct is engineered to recombine with the target gene, which is accomplished by incorporating sequences from the gene itself into the construct. Recombination then occurs in the region of that sequence within the gene, resulting in the insertion of a foreign sequence to disrupt the gene. With its sequence interrupted, the altered gene will be translated into a nonfunctional protein, if it is translated at all.

In another aspect of the invention there is provided a method for producing a genetically altered plant as described herein. In one embodiment, the method comprises introducing at least one mutation into the OTUB1 gene and/or OTUB1 promoter of preferably at least one plant cell using any mutagenesis technique described herein. Preferably said method further comprising regenerating a plant from the mutated plant cell.

The method may further comprise selecting one or more mutated plants, preferably for further propagation. Preferably said selected plants comprise at least one mutation in the OTUB1 gene and/or promoter sequence. Preferably said plants are characterised by abolished or a reduced level of OTUB1 expression and/or a reduced level of OTUB1 polypeptide activity. Expression and/or activity levels of OTUB1 can be measured by any standard technique known to the skilled person. In one embodiment the deubiquitinase activity of OTUB1 could be measured. A reduction is as described herein.

The selected plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

In a further aspect of the invention there is provided a plant obtained or obtainable by the above described methods.

For the purposes of the invention, a "genetically altered plant" or "mutant plant" is a plant that has been genetically altered compared to the naturally occurring wild type (WT) plant. In one embodiment, a mutant plant is a plant that has been altered compared to the naturally occurring wild type (WT) plant using a mutagenesis method, such as any of the mutagenesis methods described herein. In one embodiment, the mutagenesis method is targeted genome modification or genome editing. In one embodiment, the plant genome has been altered compared to wild type sequences using a mutagenesis method. Such plants have an altered phenotype as described herein, such as an increased seed yield. Therefore, in this example, increased seed yield is conferred by the presence of an altered plant genome, for example, a mutated endogenous OTUB1 gene or OTUB1 promoter sequence. In one embodiment, the endogenous promoter or gene sequence is specifically targeted using targeted genome modification and the presence of a mutated gene or promoter sequence is not conferred by the presence of transgenes expressed in the plant. In other words, the genetically altered plant can be described as transgene-free.

A plant according to the various aspects of the invention, including the transgenic plants, methods and uses described herein may be a monocot or a dicot plant. Preferably, the plant is a crop plant. By crop plant is meant any plant which is grown on a commercial scale for human or animal consumption or use. In a preferred embodiment, the plant is a cereal. In another embodiment the plant is *Arabidopsis*.

In a most preferred embodiment, the plant is selected from rice, wheat, maize, barley, brassica, such as Brassica Napus, soybean and sorghum. In one example, the wheat is wild einkorn wheat. In another example, the plant is rice, preferably the *japonica* or indica varieties. In another embodiment, the plant carries a mutant dep-1 allele or a functional variant or homologue thereof. Preferably the plant (endogenously) carries or expresses a nucleic acid sequence comprising or consisting of SEQ ID NO: 156 or 158 that encodes a polypeptide as defined in SEQ ID NO: 157 or 159.

The term "plant" as used herein encompasses whole plants, ancestors and progeny of the plants and plant parts, including seeds, fruit, shoots, stems, leaves, roots (including tubers), flowers, tissues and organs, wherein each of the aforementioned comprise the nucleic acid construct as described herein. The term "plant" also encompasses plant cells, suspension cultures, callus tissue, embryos, meristematic regions, gametophytes, sporophytes, pollen and microspores, again wherein each of the aforementioned comprises the nucleic acid construct as described herein.

The invention also extends to harvestable parts of a plant of the invention as described herein, but not limited to seeds, leaves, fruits, flowers, stems, roots, rhizomes, tubers and bulbs. The aspects of the invention also extend to products derived, preferably directly derived, from a harvestable part of such a plant, such as dry pellets or powders, oil, fat and fatty acids, starch or proteins. Another product that may derived from the harvestable parts of the plant of the invention is biodiesel. The invention also relates to food products and food supplements comprising the plant of the invention or parts thereof. In one embodiment, the food products may be animal feed. In another aspect of the invention, there is provided a product derived from a plant as described herein or from a part thereof.

In a most preferred embodiment, the plant part or harvestable product is a seed or grain. Therefore, in a further aspect of the invention, there is provided a seed produced from a genetically altered plant as described herein. In an alternative embodiment, the plant part is pollen, a propagule or progeny of the genetically altered plant described herein. Accordingly, in a further aspect of the invention there is provided pollen, a propagule or progeny of the genetically altered plant as described herein.

A control plant as used herein according to all of the aspects of the invention is a plant which has not been modified according to the methods of the invention. Accordingly, in one embodiment, the control plant does not have reduced expression of a OTUB1 nucleic acid and/or reduced activity of a OTUB1 polypeptide. In an alternative embodiment, the plant been genetically modified, as described above. In one embodiment, the control plant is a wild type plant. The control plant is typically of the same plant species, preferably having the same genetic background as the modified plant.

Genome Editing Constructs for Use with the Methods for Targeted Genome Modification Described Herein By "crRNA" or CRISPR RNA is meant the sequence of RNA that contains the protospacer element and additional nucleotides that are complementary to the tracrRNA.

By "tracrRNA" (transactivating RNA) is meant the sequence of RNA that hybridises to the crRNA and binds a CRISPR enzyme, such as Cas9 thereby activating the nuclease complex to introduce double-stranded breaks at specific sites within the genomic sequence of at least one OTUB1 nucleic acid or promoter sequence.

By "protospacer element" is meant the portion of crRNA (or sgRNA) that is complementary to the genomic DNA target sequence, usually around 20 nucleotides in length. This may also be known as a spacer or targeting sequence.

By "sgRNA" (single-guide RNA) is meant the combination of tracrRNA and crRNA in a single RNA molecule, preferably also including a linker loop (that links the tracrRNA and crRNA into a single molecule)."sgRNA" may also be referred to as "gRNA" and in the present context, the terms are interchangeable. The sgRNA or gRNA provide both targeting specificity and scaffolding/binding ability for a Cas nuclease. A gRNA may refer to a dual RNA molecule comprising a crRNA molecule and a tracrRNA molecule.

By "TAL effector" (transcription activator-like (TAL) effector) or TALE is meant a protein sequence that can bind the genomic DNA target sequence (a sequence within the OTUB1 gene or promoter sequence) and that can be fused to the cleavage domain of an endonuclease such as FokI to create TAL effector nucleases or TALENS or meganucleases to create megaTALs. A TALE protein is composed of a central domain that is responsible for DNA binding, a nuclear-localisation signal and a domain that activates target gene transcription. The DNA-binding domain consists of monomers and each monomer can bind one nucleotide in the target nucleotide sequence. Monomers are tandem repeats of 33-35 amino acids, of which the two amino acids located at positions 12 and 13 are highly variable (repeat variable diresidue, RVD). It is the RVDs that are responsible for the recognition of a single specific nucleotide. HD targets cytosine; NI targets adenine, NG targets thymine and NN targets guanine (although NN can also bind to adenine with lower specificity).

In another aspect of the invention there is provided a nucleic acid construct wherein the nucleic acid construct comprises a nucleic acid sequence that encodes at least one DNA-binding domain. In one embodiment, the DNA-binding domain can bind to a sequence in the OTUB1 gene and/or promoter. Preferably said sequence is selected from SEQ ID NOs: 28, 34, 38, 42, 45, 48, 51, 54, 57, 60, 63, 66, 69, 72, 75, 78, 81, 84, 87, 90, 93, 96, 99, 102, 106, 110, 114, 118, 122, 126, 130, 134, 138, 142 and 146. In this example, SEQ ID NOs: 28 (rice), 34 (rice), 38 (rice), 102 (wheat), 106 (wheat), 110 (barley), 114 (barley), 118 (maize), 122 (maize), 126 (sorghum), 130 (sorghum), 134 (soybean), 138 (soybean), 142(brassica) and 146 (brassica) are target sequences in a OTUB1 gene, and SEQ ID NOs: 42, 45, 48, 51, 54, 57, 60, 63, 66, 69, 72, 75, 78, 81, 84, 87, 90, 93, 96 and 99 are target sequences in the OTUB1 promoter, preferably the rice promoter. In one embodiment, the nucleic acid construct comprises one or more DNA-binding domains, such that the construct can bind to one or more, preferably at least two or three sequences in the OTUB1 gene, wherein the sequences are selected from (i) SEQ ID NOs: 28 (rice), 34 (rice), and 38 (rice);
(ii) SEQ ID NOs: 102 (wheat) and 106 (wheat);
(iii) SEQ ID NOs: 110 (barley) and 114 (barley);
(iv) SEQ ID NOs: 118 (maize) and 122 (maize);
(v) SEQ ID NOs: 126 (sorghum) and 130 (sorghum);
(vi) SEQ ID NOs: 134 (soybean) and 138 (soybean); or
(vii) SEQ ID NOs: 142(brassica) and 146 (brassica).

In an alternative or additional embodiment, the nucleic acid construct comprises one or more DNA-binding domains, wherein the one or more DNA-binding domains can bind to at least one sequence selected from SEQ ID NOs: 42, 45, 48, 51, 54, 57, 60, 63, 66, 69, 72, 75, 78, 81, 84, 87, 90, 93, 96 and 99.

In a further embodiment, said construct further comprises a nucleic acid encoding a SSN, such as FokI or a Cas protein.

In one embodiment, the nucleic acid construct encodes at least one protospacer element wherein the sequence of the protospacer element is selected from SEQ ID NOs: 29, 35, 39, 43, 46, 49, 52, 55, 58, 61, 64, 67, 70, 73, 76, 82, 85, 88, 91, 94, 97, 100, 103, 107, 111, 115, 119, 123, 127, 131, 135, 139, 143 and 147 or a variant thereof. In on example, the nucleic acid construct may comprise one, two or three protospacer sequences, wherein the sequence of the protospacer sequences is selected from (i) SEQ ID NOs: 29 (rice), 35 (rice), and 39 (rice);
(ii) SEQ ID NOs: 103 (wheat) and 107 (wheat);
(iii) SEQ ID NOs: 111 (barley) and 115 (barley);
(iv) SEQ ID NOs: 119 (maize) and 123 (maize);
(v) SEQ ID NOs: 125 (sorghum) and 131 (sorghum);
(vi) SEQ ID NOs: 135 (soybean) and 139 (soybean); and
(vii) SEQ ID NOs: 143 (brassica) and 147 (brassica).

In a further embodiment, the nucleic acid construct comprises a crRNA-encoding sequence. As defined above, a crRNA sequence may comprise the protospacer elements as defined above and preferably additional nucleotides that are complementary to the tracrRNA. An appropriate sequence for the additional nucleotides will be known to the skilled person as these are defined by the choice of Cas protein.

In another embodiment, the nucleic acid construct further comprises a tracrRNA sequence. Again, an appropriate tracrRNA sequence would be known to the skilled person as this sequence is defined by the choice of Cas protein. Nonetheless, in one embodiment said sequence comprises or consists of a sequence as defined in SEQ ID NO: 30 or a variant thereof.

In a further embodiment, the nucleic acid construct comprises at least one nucleic acid sequence that encodes a sgRNA (or gRNA). Again, as already discussed, sgRNA typically comprises a crRNA sequence or protospacer sequence and a tracrRNA sequence and preferably a sequence for a linker loop. In a preferred embodiment, the nucleic acid construct comprises at least one nucleic acid sequence that encodes a sgRNA sequence as defined in any of SEQ ID NOs: 31, 36, 40, 44, 47, 50, 53, 56, 59, 62, 65, 68, 71, 74, 77, 80, 83, 86, 89, 92, 95, 98, 101, 104, 108, 112, 116, 120, 124, 128, 132, 136, 140, 144 and 148 or variant thereof.

In a further embodiment, the nucleic acid construct comprises or consists of a sequence selected from SEQ ID NO: 33, 37, 41, 105, 109, 113, 117, 121, 125, 129, 133, 137, 141, 145 and 149.

In a further embodiment, the nucleic acid construct may further comprise at least one nucleic acid sequence encoding an endoribonuclease cleavage site. Preferably the endoribonuclease is Csy4 (also known as Cas6f). Where the nucleic acid construct comprises multiple sgRNA nucleic acid sequences the construct may comprise the same number of endoribonuclease cleavage sites. In another embodiment, the cleavage site is 5' of the sgRNA nucleic acid sequence. Accordingly, each sgRNA nucleic acid sequence is flanked by a endoribonuclease cleavage site.

The term 'variant' refers to a nucleotide sequence where the nucleotides are substantially identical to one of the above sequences. The variant may be achieved by modifications such as insertion, substitution or deletion of one or more nucleotides. In a preferred embodiment, the variant has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to any one of the above described sequences. In one embodiment, sequence identity is at least 90%. In another embodiment, sequence identity is 100%. Sequence identity can be determined by any one known sequence alignment program in the art.

The invention also relates to a nucleic acid construct comprising a nucleic acid sequence operably linked to a suitable plant promoter. A suitable plant promoter may be a constitutive or strong promoter or may be a tissues-specific promoter. In one embodiment, suitable plant promoters are selected from, but not limited to, cestrum yellow leaf curling virus (CmYLCV) promoter or switchgrass ubiquitin 1 promoter (PvUbi1) wheat U6 RNA polymerase III (TaU6) CaMV35S, wheat U6 or maize ubiquitin (e.g. Ubi1) promoters. Alternatively, expression can be specifically directed to particular tissues of wheat seeds through gene expression-regulating sequences. In one embodiment, the promoter is selected from the U3 promoter (SEQ ID NO: 163), the U6a promoter (SEQ ID NO: 164), the U6b promoter (SEQ ID NO: 165), the U3b promoter in dicot plants (SEQ ID NO: 166) and the U6-1 promoter in dicot plants (SEQ ID NO: 167).

The nucleic acid construct of the present invention may also further comprise a nucleic acid sequence that encodes a CRISPR enzyme. By "CRISPR enzyme" is meant an RNA-guided DNA endonuclease that can associate with the CRISPR system. Specifically, such an enzyme binds to the tracrRNA sequence. In one embodiment, the CRIPSR enzyme is a Cas protein ("CRISPR associated protein), preferably Cas 9 or Cpf1, more preferably Cas9. In a specific embodiment Cas9 is codon-optimised Cas9 (optimised for the plant in which it is expressed). In one example, Cas9 has the sequence described in SEQ ID NO: 150 or a functional variant or homolog thereof. In another embodiment, the CRISPR enzyme is a protein from the family of Class 2 candidate x proteins, such as C2c1, C2C2 and/or C2c3. In one embodiment, the Cas protein is from *Streptococcus pyogenes*. In an alternative embodiment, the Cas protein may be from any one of *Staphylococcus aureus, Neisseria meningitides, Streptococcus thermophiles* or *Treponema denticola*.

The term "functional variant" as used herein with reference to Cas9 refers to a variant Cas9 gene sequence or part of the gene sequence which retains the biological function of the full non-variant sequence, for example, acts as a DNA endonuclease, or recognition or/and binding to DNA. A functional variant also comprises a variant of the gene of interest which has sequence alterations that do not affect function, for example non-conserved residues. Also encompassed is a variant that is substantially identical, i.e. has only some sequence variations, for example in non-conserved residues, compared to the wild type sequences as shown herein and is biologically active. In one embodiment, a functional variant of SEQ ID NO: 150 has at least 90%, 91%, 92%, 93%, 94%, 95%, 96%, 97%, 98%, or 99% overall sequence identity to the amino acid represented by SEQ ID NO: 150. In a further embodiment, the Cas9 protein has been modified to improve activity.

Suitable homologs or orthologs can be identified by sequence comparisons and identifications of conserved domains. The function of the homolog or ortholog can be identified as described herein and a skilled person would thus be able to confirm the function when expressed in a plant.

In a further embodiment, the Cas9 protein has been modified to improve activity. For example, in one embodiment, the Cas9 protein may comprise the D10A amino acid substitution, this nickase cleaves only the DNA strand that is complementary to and recognized by the gRNA. In an alternative embodiment, the Cas9 protein may alternatively or additionally comprise the H840A amino acid substitution, this nickase cleaves only the DNA strand that does not interact with the sRNA. In this embodiment, Cas9 may be used with a pair (i.e. two) sgRNA molecules (or a construct expressing such a pair) and as a result can cleave the target region on the opposite DNA strand, with the possibility of improving specificity by 100-1500 fold. In a further embodiment, the cas9 protein may comprise a D1135E substitution.

The Cas 9 protein may also be the VQR variant. Alternatively, the Cas protein may be comprise a mutation in both nuclease domains, HNH and RuvC0like and therefore is catalytically inactive. Rather than cleaving the target strand, this catalytically inactive Cas protein can be used to prevent the transcription elongation process, leading to a loss of function of incompletely translated proteins when co-expressed with a sgRNA molecule. An example of a catalytically inactive protein is dead Cas9 (dCas9) caused by a point mutation in RuvC and/or the HNH nuclease domains (Komor et al., 2016 and Nishida et al., 2016).

In a further embodiment, a Cas protein, such as Cas9 may be further fused with a repression effector, such as a histone-modifying/DNA methylation enzyme or a Cytidine deaminase (Komor et al.2016) to effect site-directed mutagenesis. In the latter, the cytidine deaminase enzyme does not induce dsDNA breaks, but mediates the conversion of cytidine to uridine, thereby effecting a C to T (or G to A) substitution. These approaches may be particularly valuable to target glutamine and proline residues in gliadins, to break the toxic epitopes while conserving gliadin functionality.

In a further embodiment, the nucleic acid construct comprises an endoribonuclease. Preferably the endoribonuclease is Csy4 (also known as Cas6f) and more preferably a codon optimised csy4, for example as defined in SEQ ID NO: 168. In one embodiment, where the nucleic acid construct comprises a cas protein, the nucleic acid construct may comprise sequences for the expression of an endoribonuclease, such as Csy4 expressed as a 5' terminal P2A fusion (used as a self-cleaving peptide) to a cas protein, such as Cas9, for example, as defined in SEQ ID NO: 169.

In one embodiment, the cas protein, the endoribonuclease and/or the endoribonuclease-cas fusion sequence may be operably linked to a suitable plant promoter. Suitable plant promoters are already described above, but in one embodiment, may be the *Zea mays* Ubiquitin 1 promoter.

Suitable methods for producing the CRISPR nucleic acids and vectors system are known, and for example are published in Molecular Plant (Ma et al., 2015, Molecular Plant, DOI:10.1016/j.molp.2015.04.007), which is incorporated herein by reference.

In an alternative aspect of the invention, the nucleic acid construct comprises at least one nucleic acid sequence that encodes a TAL effector, wherein said effector targets a OTUB1 gene and/or promoter sequence selected from SEQ ID NO: 28, 34, 38, 42, 45, 48, 51, 54, 57, 60, 63, 66, 69, 72, 75, 78, 81, 84, 87, 90, 93, 96, 99, 102, 106, 110, 114, 118, 122, 126, 130, 134, 138, 142 and 146. Methods for designing a TAL effector would be well known to the skilled person, given the target sequence. Examples of suitable methods are given in Sanjana et al., and Cermak T et al, both incorporated herein by reference. Preferably, said nucleic acid construct comprises two nucleic acid sequences encoding a TAL effector, to produce a TALEN pair. In a further embodiment, the nucleic acid construct further comprises a sequence-specific nuclease (SSN). Preferably such SSN is a endonuclease such as FokI. In a further embodiment, the TALENs are assembled by the Golden Gate cloning method in a single plasmid or nucleic acid construct.

In another aspect of the invention, there is provided a sgRNA molecule, wherein the sgRNA molecule comprises a crRNA sequence and a tracrRNA sequence and wherein the crRNA sequence can bind to at least one sequence selected from SEQ ID NOs: 28, 34, 38, 42, 45, 48, 51, 54, 57, 60, 63, 66, 69, 72, 75, 78, 81, 84, 87, 90, 93, 96, 99, 102, 106, 110, 114, 118, 122, 126, 130, 134, 138, 142 and 146 or a variant thereof. In one embodiment, the nucleic sequence of the sgRNA molecule is defined in any of SEQ ID NO: 31, 36, 40, 44, 47, 50, 53, 56, 59, 62, 65, 68, 71, 74, 77, 80, 83, 86, 89, 92, 95, 98, 101, 104, 108, 112, 116, 120, 124, 128, 132, 136, 140, 144 and 148 or variant thereof. In other words, the RNA sequence of the sgRNA is encoded by a nucleic acid sequence selected from SEQ ID NO: 31, 36, 40, 44, 47, 50, 53, 56, 59, 62, 65, 68, 71, 74, 77, 80, 83, 86, 89, 92, 95, 98, 101, 104, 108, 112, 116, 120, 124, 128, 132, 136, 140, 144 and 148. In one example only, the RNA sequence of one sgRNA of the invention is defined in SEQ ID NO: 32 or a variant thereof. A "variant" is as defined herein. In one embodiment, the sgRNA molecule may comprise at least one chemical modification, for example that enhances its stability and/or binding affinity to the target sequence or the crRNA sequence to the tracrRNA sequence. Such modifications would be well known to the skilled person, and include for example, but not limited to, the modifications described in Randar et al., 2015, incorporated herein by reference. In this example the crRNA may comprise a phosphorothioate backbone modification, such as 2'-fluoro (2'-F), 2'-O-methyl (2'-O-Me) and S-constrained ethyl (cET) substitutions.

In another aspect of the invention, there is provided an isolated nucleic acid sequence that encodes for a protospacer element (as defined in any of SEQ ID NOs: 29, 35, 39, 43, 46, 49, 52, 55, 58, 61, 64, 67, 70, 73, 76, 82, 85, 88, 91, 94, 97, 100, 103, 107, 111, 115, 119, 123, 127, 131, 135, 139, 143 and 147), or a sgRNA (as described in any of SEQ ID NO: 31, 36, 40, 44, 47, 50, 53, 56, 59, 62, 65, 68, 71, 74, 77, 80, 83, 86, 89, 92, 95, 98, 101, 104, 108, 112, 116, 120, 124, 128, 132, 136, 140, 144 and 148).

In another aspect of the invention, there is provided a plant or part thereof or at least one isolated plant cell transfected with at least one nucleic acid construct as described herein. Cas9 and sgRNA may be combined or in separate expression vectors (or nucleic acid constructs, such terms are used interchangeably). In other words, in one embodiment, an isolated plant cell is transfected with a single nucleic acid construct comprising both sgRNA and Cas9 as described in detail above. In an alternative embodiment, an isolated plant cell is transfected with two nucleic acid constructs, a first nucleic acid construct comprising at least one sgRNA as defined above and a second nucleic acid construct comprising Cas9 or a functional variant or homolog thereof. The second nucleic acid construct may be transfected below, after or concurrently with the first nucleic acid construct. The advantage of a separate, second construct comprising a cas protein is that the nucleic acid construct encoding at least one sgRNA can be paired with any type of cas protein, as described herein, and therefore are not limited to a single cas function (as would be the case when both cas and sgRNA are encoded on the same nucleic acid construct).

In one embodiment, the nucleic acid construct comprising a cas protein is transfected first and is stably incorporated into the genome, before the second transfection with a nucleic acid construct comprising at least one sgRNA nucleic acid. In an alternative embodiment, a plant or part thereof or at least one isolated plant cell is transfected with mRNA encoding a cas protein and co-transfected with at least one nucleic acid construct as defined herein.

Cas9 expression vectors for use in the present invention can be constructed as described in the art. In one example, the expression vector comprises a nucleic acid sequence as defined in SEQ ID NO: 150 or a functional variant or homolog thereof, wherein said nucleic acid sequence is operably linked to a suitable promoter. Examples of suitable promoters include the Actin, CaMV35S, wheat U6 or maize ubiquitin (e.g. Ubi1) promoter.

In an alternative aspect of the present invention, there is provided an isolated plant cell transfected with at least one nucleic acid construct or sgRNA molecule as described herein.

In a further aspect of the invention, there is provided a genetically modified or edited plant comprising the transfected cell described herein. In one embodiment, the nucleic acid construct or constructs may be integrated in a stable form. In an alternative embodiment, the nucleic acid construct or constructs are not integrated (i.e. are transiently expressed). Accordingly, in a preferred embodiment, the genetically modified plant is free of any sgRNA and/or Cas protein nucleic acid. In other words, the plant is transgene free.

The term "introduction", "transfection" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The resulting transformed plant cell may then be used to regenerate a transformed plant in a manner known to persons skilled in the art. The transfer of foreign genes into the genome of a plant is called transformation. Transformation of plants is now a routine technique in many species. Any of several transformation methods known to the skilled person may be used to introduce the nucleic acid construct or sgRNA molecule of interest into a suitable ancestor cell. The methods described for the transformation and regeneration of plants from plant tissues or plant cells may be utilized for transient or for stable transformation.

Transformation methods include the use of liposomes, electroporation, chemicals that increase free DNA uptake, injection of the DNA directly into the plant (microinjection), gene guns (or biolistic particle delivery systems (bioloistics)) as described in the examples, lipofection, transformation using viruses or pollen and microprojection. Methods may be selected from the calcium/polyethylene glycol method for protoplasts, ultrasound-mediated gene transfection, optical or laser transfection, transfection using silicon carbide fibers, electroporation of protoplasts, microinjection into plant material, DNA or RNA-coated particle bombardment, infection with (non-integrative) viruses and the like. Transgenic plants, can also be produced via *Agrobacterium tumefaciens* mediated transformation, including but not limited to using the floral dip/*Agrobacterium* vacuum infiltration method as described in Clough & Bent (1998) and incorporated herein by reference.

Accordingly, in one embodiment, at least one nucleic acid construct or sgRNA molecule as described herein can be introduced to at least one plant cell using any of the above described methods. In an alternative embodiment, any of the nucleic acid constructs described herein may be first transcribed to form a preassembled Cas9-sgRNA ribonucleoprotein and then delivered to at least one plant cell using any of the above described methods, such as lipofection, electroporation or microinjection.

Optionally, to select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility is growing the seeds, if appropriate after sterilization, on agar plates using a suitable selection agent so that only the transformed seeds can grow into plants. As described in the examples, a suitable marker can be bar-phosphinothricin or PPT. Alternatively, the transformed plants are screened for the presence of a selectable marker, such as, but not limited to, GFP, GUS (β-glucuronidase). Other examples would be readily known to the skilled person. Alternatively, no selection is performed, and the seeds obtained in the above-described manner are planted and grown and OTUB1 expression or protein levels measured at an appropriate time using standard techniques in the art. This alternative, which avoids the introduction of transgenes, is preferable to produce transgene-free plants.

Following DNA transfer and regeneration, putatively transformed plants may also be evaluated, for instance using PCR to detect the presence of the gene of interest, copy number and/or genomic organisation. Alternatively or additionally, integration and expression levels of the newly introduced DNA may be monitored using Southern, Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques.

In a further related aspect of the invention, there is also provided, a method of obtaining a genetically modified plant as described herein, the method comprising
  a. selecting a part of the plant;
  b. transfecting at least one cell of the part of the plant of paragraph (a) with at least one nucleic acid construct as described herein or at least one sgRNA molecule as described herein, using the transfection or transformation techniques described above;
  c. regenerating at least one plant derived from the transfected cell or cells;
  d. selecting one or more plants obtained according to paragraph (c) that show silencing or reduced expression of OTUB1.

In a further embodiment, the method also comprises the step of screening the genetically modified plant for SSN (preferably CRISPR)-induced mutations in the OTUB1 gene or promoter sequence. In one embodiment, the method comprises obtaining a DNA sample from a transformed plant and carrying out DNA amplification to detect a mutation in at least one OTUB1 gene or promoter sequence.

In a further embodiment, the methods comprise generating stable T2 plants preferably homozygous for the mutation (that is a mutation in in at least one OTUB1 gene or promoter sequence).

Plants that have a mutation in at least one OTUB1 gene or promoter sequence can also be crossed with another plant also containing at least one mutation in at least one OTUB1 gene or promoter sequence to obtain plants with additional mutations in the OTUB1 gene or promoter sequence. The combinations will be apparent to the skilled person. Accordingly, this method can be used to generate a T2 plants with mutations on all or an increased number of homoelogs, when compared to the number of homoeolog mutations in a single T1 plant transformed as described above.

A plant obtained or obtainable by the methods described above is also within the scope of the invention.

A genetically altered plant of the present invention may also be obtained by transference of any of the sequences of the invention by crossing, e.g., using pollen of the genetically altered plant described herein to pollinate a wild-type or control plant, or pollinating the gynoecia of plants described herein with other pollen that does not contain a mutation in at least one of the OTUB1 gene or promoter sequence. The methods for obtaining the plant of the invention are not exclusively limited to those described in this paragraph; for example, genetic transformation of germ cells from the ear of wheat could be carried out as mentioned, but without having to regenerate a plant afterward.

Method of Screening Plants for Naturally Occurring Increased Grain Yield Phenotypes In a further aspect of the invention, there is provided a method for screening a population of plants and identifying and/or selecting a plant that will have reduced OTUB1 expression and/or an increased grain yield phenotype, preferably an increased grain number, grain number per panicle, grain weight, grain width, grain thickness, thousand kernel weight and/or a decrease in grain length (compared to a control or wild-type plant), the method comprising detecting in the plant or plant germplasm at least one polymorphism (preferably a "low OTUB1 expresser polymorphism) in the promoter of the OTUB1 gene or the OTUB1 gene. Preferably, said screening comprises determining the presence of at least one polymorphism, wherein said polymorphism is at least one insertion and/or at least one deletion and/or substitution.

In one specific embodiment, said polymorphism may comprise the substitution of at least one of the following:
  C to T at position 1135 of SEQ ID NO: 2 or 5;
  G to C at position 1462 of SEQ ID NO: 2 or 5; and/or
  G to C at position 1798 of SEQ ID NO: 2 or 5

In a further additional or alternative embodiment, said polymorphism is the insertion of a single amino acid, preferably, T, at position 2234 of SEQ ID NO: 2 or 5.

In a further additional or alternative embodiment, said polymorphism may be a G to A substitution at position 1824 of SEQ ID NO: 155.

As a result, the above-described plants will display an increased grain yield phenotype as described above.

Suitable tests for assessing the presence of a polymorphism would be well known to the skilled person, and include but are not limited to, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs—which are also referred to as Microsatellites), and Single Nucleotide Polymorphisms (SNPs). In one embodiment, Kompetitive Allele Specific PCR (KASP) genotyping is used.

In one embodiment, the method comprises
  a) obtaining a nucleic acid sample from a plant and
  b) carrying out nucleic acid amplification of one or more OTUB1 promoter alleles using one or more primer pairs.

In a further embodiment, the method may further comprise introgressing the chromosomal region comprising at least one of said low-OTUB1-expressing polymorphisms or the chromosomal region containing the repeat sequence deletion as described above into a second plant or plant germplasm to produce an introgressed plant or plant germplasm. Preferably the expression of OTUB1 in said second plant will be reduced or abolished (compared to a control or wild-type plant), and more preferably said second plant will display an increase in grain yield, preferably an increase in at least one of grain number, grain number per panicle, grain weight, grain width, grain thickness, thousand kernel weight and/or a decrease in grain length.

In one embodiment, the plant may endogenously express SEQ ID NO: 2 or 4 and the levels of OTUB1 nucleic acid and/or activity of the OTUB1 protein reduced or further reduced by any method described herein.

Accordingly, in a further aspect of the invention there is provided a method for increasing yield, preferably seed or grain yield in a plant, the method comprising
  a. screening a population of plants for at least one plant with at least one of the above described polymorphisms;
  b. further reducing or abolishing the expression of at least one OTUB1 nucleic acid and/or reducing the activity of a OTUB1 polypeptide in said plant by introducing at least one mutation into the nucleic acid sequence encoding OTUB1 or at least one mutation into the promoter of OTUB1 as described herein or using RNA interference as described herein.

By "further reducing" is meant reducing the level of OTUB1 expression to a level lower than that in the plant with the at least one of the above-described OTUB1 polymorphisms. The terms "reducing" means a decrease in the levels of OTUB1 expression and/or activity by up to 10%, 20%, 30%, 40%, 50%, 60%, 70%, 80% or 90% when compared to the level in a control plant.

UBC13

The inventors have also surprisingly identified that increasing the expression of the E2 ubiquitin-conjugating protein, UBC13, results in a phenotype similar to that observed in plants carrying the npt1 allele, such as increased grain number, thousand kernel weight and culm diameter and a decrease in tiller number. Accordingly, overexpression of
UBC13 will also increase grain yield. Therefore, in a further aspect of the invention, there is provided a method of modifying, preferably increasing the levels of at least one SQUAMOSA promoter-binding protein-like (SBP-domain) transcription factor, the method comprising increasing the expression or activity of UBC13 as described herein or decreasing or abolishing the expression or activity of OTUB1, as described herein. In one embodiment, the SBP-domain transcription factor is SPL14.

The terms "increase", "improve" or "enhance" as used herein are interchangeable. In one embodiment, grain length is increased by at least 2%, 3%, 4%, 5%, 6%, 7%, 8%, 9%, 10% 11%, 12%, 13%, 14%, 15%, 16%, 17%, 18%, 19%, 20%, 30%, 40% or 50% compared to a control plant. Preferably, the increase is at least 5-50%.

Accordingly, in another aspect of the invention there is provided a nucleic acid construct comprising a nucleic acid sequence encoding a polypeptide as defined in SEQ ID NO: 161 or a functional variant or homolog thereof, wherein said sequence is operably linked to a regulatory sequence, wherein preferably said regulatory sequence is a tissue-specific promoter or a constitutive promoter. In a further embodiment, the nucleic acid construct comprises a nucleic acid sequence as defined in SEQ ID NO: 160 (cDNA) or 162 (genomic) or a functional variant or homolog thereof. A functional variant or homolog is as defined above.

The term "operably linked" as used herein refers to a functional linkage between the promoter sequence and the gene of interest, such that the promoter sequence is able to initiate transcription of the gene of interest.

A "plant promoter" comprises regulatory elements, which mediate the expression of a coding sequence segment in plant cells. Accordingly, a plant promoter need not be of plant origin, but may originate from viruses or microorganisms, for example from viruses which attack plant cells. The "plant promoter" can also originate from a plant cell, e.g. from the plant which is transformed with the nucleic acid sequence to be expressed in the inventive process and described herein. This also applies to other "plant" regulatory signals, such as "plant" terminators. The promoters upstream of the nucleotide sequences useful in the methods of the present invention can be modified by one or more nucleotide substitution(s), insertion(s) and/or deletion(s) without interfering with the functionality or activity of either the promoters, the open reading frame (ORF) or the 3'-regulatory region such as terminators or other 3' regulatory regions which are located away from the ORF. It is furthermore possible that the activity of the promoters is increased by modification of their sequence, or that they are replaced completely by more active promoters, even promoters from heterologous organisms. For expression in plants, the nucleic acid molecule must, as described above, be linked operably to or comprise a suitable promoter which expresses the gene at the right point in time and with the required spatial expression pattern. The term "operably linked" as used herein refers to a functional linkage between the promoter sequence and the gene of interest, such that the promoter sequence is able to initiate transcription of the gene of interest.

In one embodiment, the promoter is a constitutive promoter. A "constitutive promoter" refers to a promoter that is transcriptionally active during most, but not necessarily all, phases of growth and development and under most environmental conditions, in at least one cell, tissue or organ. Examples of constitutive promoters include but are not limited to actin, HMGP, CaMV19S, GOS2, rice cyclophilin, maize H3 histone, alfalfa H3 histone, 34S FMV, rubisco small subunit, OCS, SAD1, SAD2, nos, V-ATPase, super promoter, G-box proteins and synthetic promoters.

In another aspect of the invention there is provided a vector comprising the nucleic acid sequence described above.

In a further aspect of the invention, there is provided a host cell comprising the nucleic acid construct. The host cell may be a bacterial cell, such as *Agrobacterium tumefaciens*, or an isolated plant cell. The invention also relates to a culture medium or kit comprising a culture medium and an isolated host cell as described below.

In another embodiment, there is provided a transgenic plant expressing the nucleic acid construct as described above. In one embodiment, said nucleic acid construct is stably incorporated into the plant genome.

The nucleic acid sequence is introduced into said plant through a process called transformation as described above.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

A suitable plant is defined above.

In another aspect, the invention relates to the use of a nucleic acid construct as described herein to increase grain yield, preferably grain number and/or thousand kernel weight.

In a further aspect of the invention there is provided a method of increasing grain yield, preferably grain number and/or thousand kernel weight, the method comprising introducing and expressing in said plant the nucleic acid construct described herein.

In another aspect of the invention there is provided a method of producing a plant with increased grain yield, preferably grain number and/or thousand kernel weight, the method comprising introducing and expressing in said plant the nucleic acid construct described herein.

Said increase is relative to a control or wild-type plant.

While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

The foregoing application, and all documents and sequence accession numbers cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

The invention is now described in the following non-limiting examples.

EXAMPLE 1

Achieving an increase in grain productivity has long been the over-riding focus of cereal breeding programs. Here we show that a rice grain yield quantitative trait locus qNPT1 that acts through the determination of the new plant type (NPT) architecture characterized by fewer barren tillers, sturdier culms and larger panicles, encodes a deubiquitinating enzyme with homology to human OTUB1. Down-regulating OsOTUB1 enhances meristematic activity, resulting in reduced tiller number per plant, increased grain number per panicle, enhanced grain weight and a consequent increase in grain yield. OsOTUB1 interacts with OsUBC13 and SBP-domain transcription factor OsSPL14, limits Lys63-linked ubiquitin at OsSPL14 to regulate its proteasome-dependent degradation. Conversely, loss-of-function of OsOTUB1 results in the accumulation of a high level of OsSPL14, which in turn controls NPT architecture and boosts grain yield. Pyramiding of high-yielding npt1 and dep1-1 alleles provides a new strategy for increasing rice yield potential above that which is currently achievable.

A set of 670 recombinant inbred lines (RILs) was bred from the cross between the *japonica* rice variety Chunjiang06 and a selected NPT line (IR66167-27-5-1-6), from which RIL52 was selected on the basis that it had the NPT phenotype with respect to enhanced grain number, reduced tiller number and thickened culm (FIG. 1a-1e). A subsequent QTL analysis identified the locus qNPT1 (New Plant Type 1) as being pleiotropically responsible for all three traits (FIG. 1f). The positional cloning of qNPT1 was performed by using $BC_2F_2$ and $BC_2F_3$ progenies developed from the backcross between RIL52 and the indica variety Zhefu802 (the recurrent parent). The candidate region was narrowed to a ~4.1 Kbp segment flanked by the markers P139 and P143, which harbors the promoter and part of the coding sequence of the gene at LOC_Os08g42540 (FIG. 1g). This gene is predicted to encode a deubiquitinating enzyme with homology to human OTUB1 (ovarian tumour domain-containing ubiquitin aldehyde binding protein 1) (FIG. 5), a protein associated with the regulation of p53 stability and DNA damage repair[9-12]. On this basis, LOC_Os08g42540 is hereafter referred to as OsOTUB1. A sequence comparison revealed five nucleotide variants distinguished the alleles responsible for the NPT vs the conventional phenotype (FIG. 1h): three of these were single nucleotide polymorphisms (SNPs), one was an insertion-deletion polymorphism (Indel) in intronic sequence and one was an SNP in the promoter region.

Figure 1:
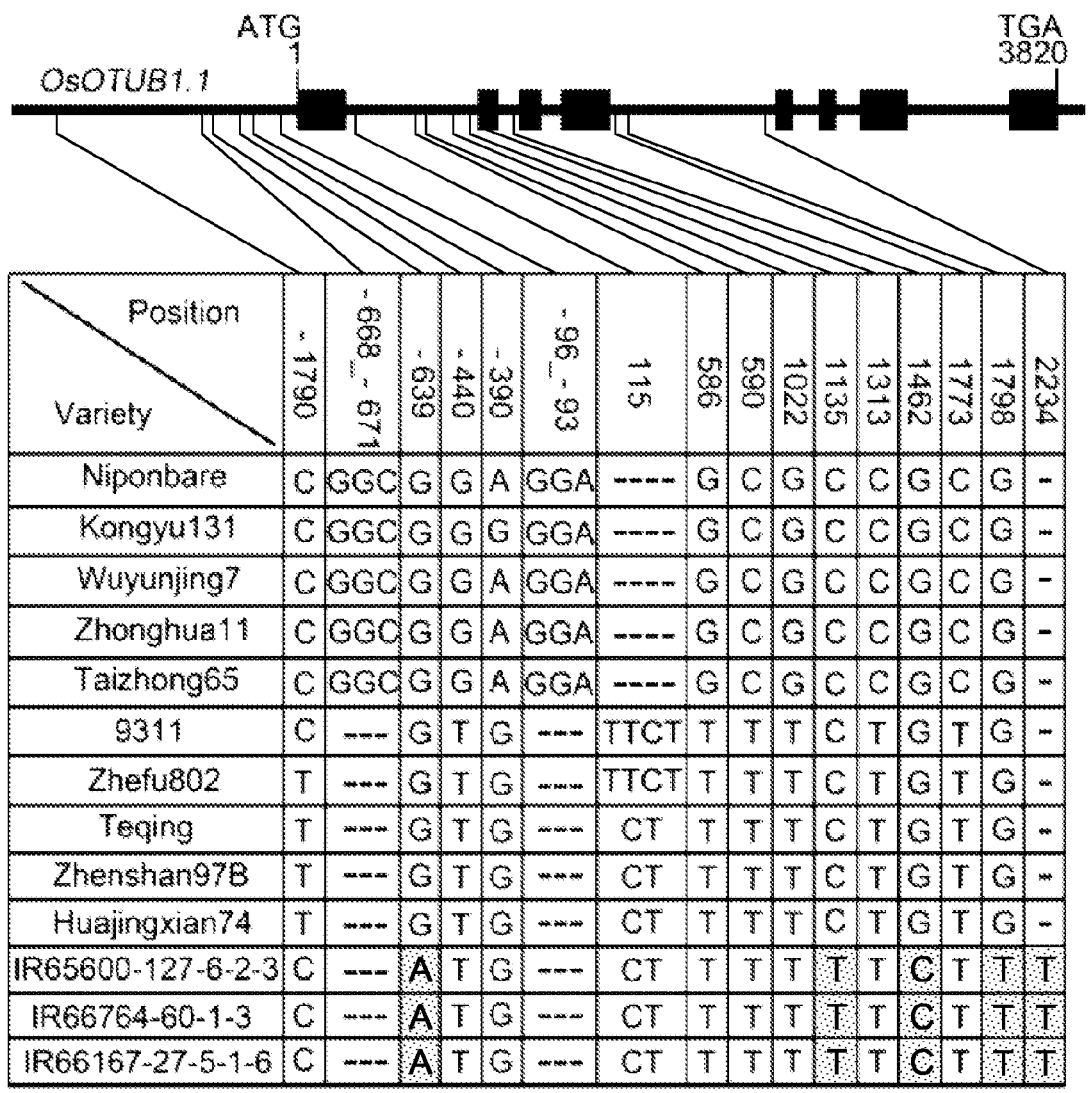
FIG. 1 shows the positional cloning of qNPT1. (a) Mature plant appearance. The RIL52 was a selection from the cross Chunjiang06 (CJ06)×IR66167-27-5-1-6. Scale bar: 20 cm. (b) Panicle morphology. Scale bar: 5 cm. (c-e) Comparison of RIL52 with its parents with respect to (c) grain number, (d) tiller number and (e) culm diameter. Data shown as mean±s.e.m. (n=30). The presence of the same lowercase letter denotes a non-significant difference between means (P<0.05). (f), QTL mapping for grain number, tiller number and culm diameter. (g) Positional cloning of qNPT1. The locus was mapped to a ~4.1 Kbp genomic region flanked by P139 and P143. The numbers below the lines indicate the number of recombinants between qNPT1 and an adjacent marker shown. The candidate gene was predicted to generate two alternative transcripts. (h) Sequence variants at the NPT1 locus in both the promoter and coding regions shown in g.
Figure 2:
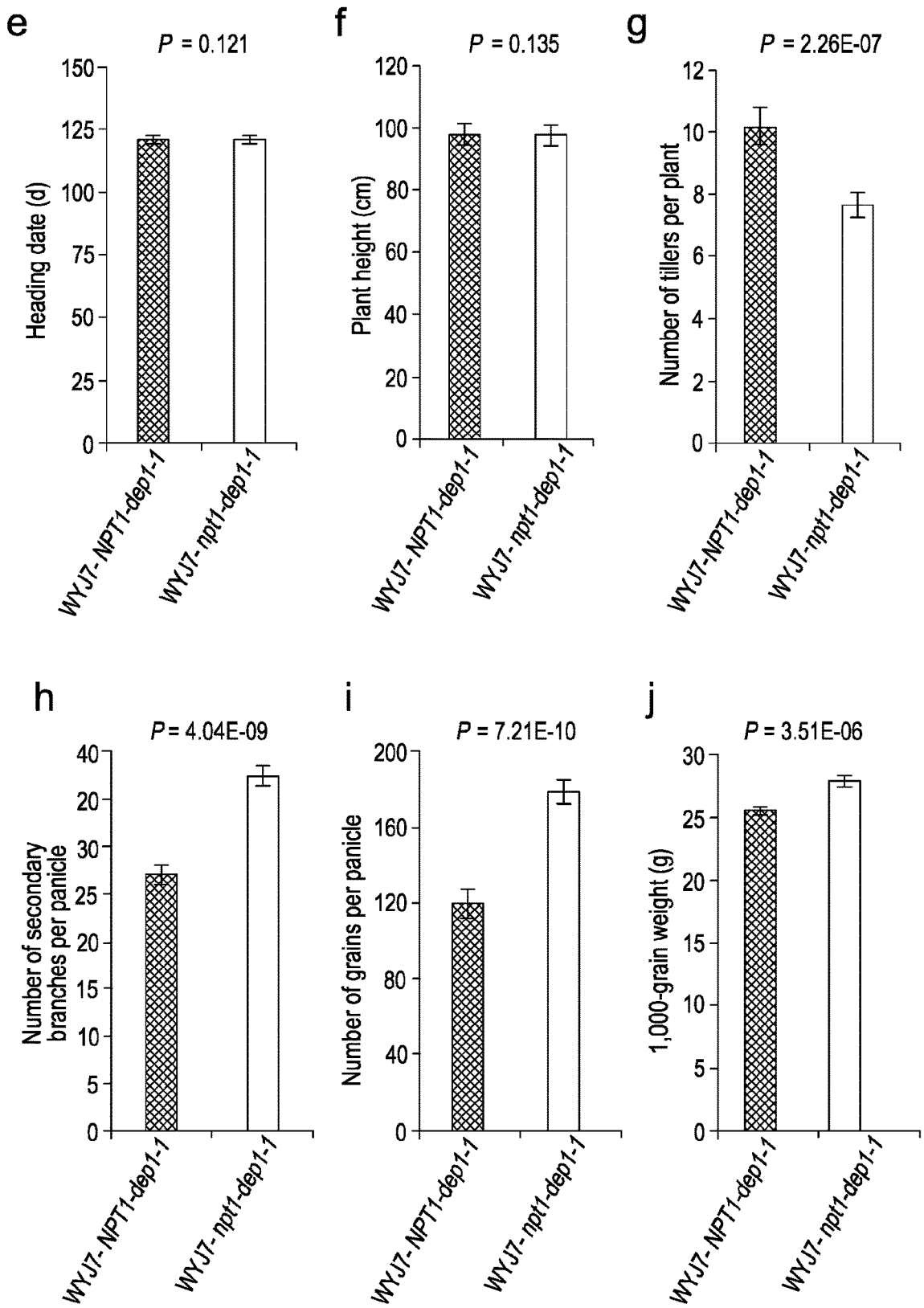
FIG. 2 shows the abundance of OsOTUB1 transcript is associated with panicle branching and grain yield. (a) Levels of OsOTUB1 transcript present in organs of the NIL plants. R: root; C: culm; LB: leaf blade; LS: leaf sheath; SAM: shoot apical meristem; YP0.2, YP6, YP12: young panicles, of mean length, respectively, 0.2 cm, 6 cm and 12 cm. Relative expression levels were expressed as the relative copies per 1,000 copies of rice Actin1. Data shown as mean±s.e.m. (n=3). (b) Plant morphology. Scale bar: 20 cm. (c) Panicle morphology. Scale bar: 5 cm. (d) Grain morphology. Scale bar: 2 mm. (e-j) A quantitative comparison of the two NILs. (e) Heading date. (f) Plant height. (g) The number of tillers per plant. (h) The number of secondary branches per panicle. (i) The number of grains per panicle. (j) 1,000 grain weight. (k) The image of the shoot apical meristem. Scale bar: 50 μm. (l), Scanning electron microscope image of culm. Scale bar: 25 μm. (m) Culm vascular system. (n) Total number of big and small vascular bundles shown in m. (o) The overall grain yield per plant. Data shown as mean±s.e.m. (n=288). All phenotypic data were measured from the paddy-grown plants under normal cultivation conditions. A Student's t-test was used to generate the P values.
Figure 6:
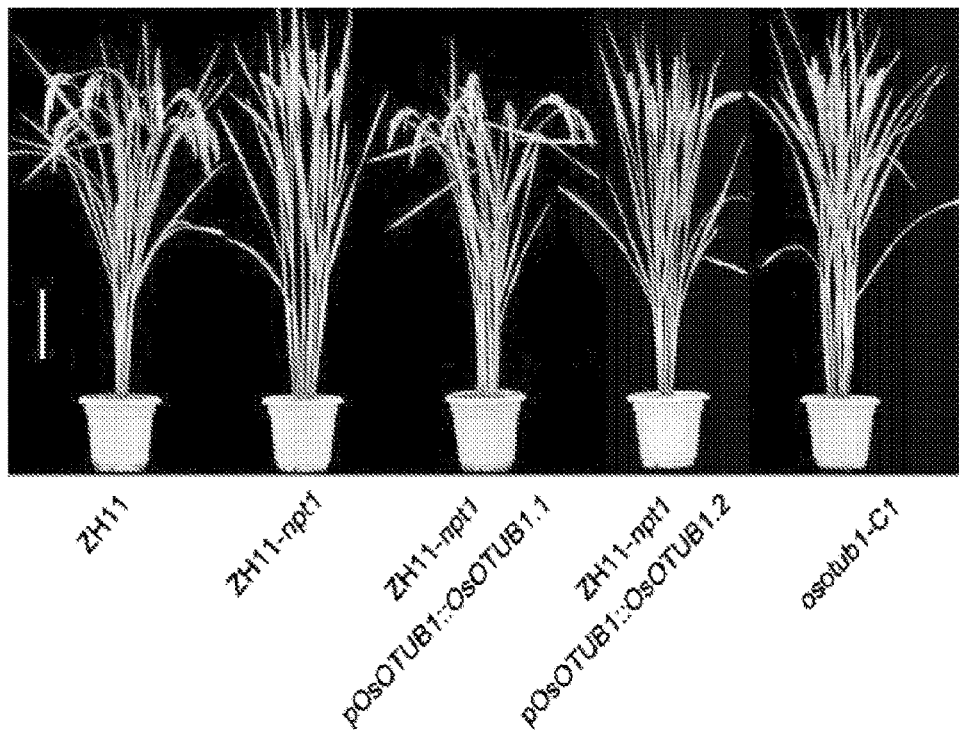
FIG. 6 shows the effect of functional OsOTUB1 on plant architecture and grain yield. (a) Mature plant morphology. Scale bar: 20 cm. (b) Loss-of-function mutations of OsOTUB1 generated by CRISPR/Cas9. (c) Heading date. (d) Plant height. (e) Diameter of the uppermost internode. (f) The number of tillers per plant. (g) Panicle length. (h) The number of primary branches per panicle. (i), The number of secondary branches per panicle. (j) The number of grains per panicle. (k) 1,000-grain weight. (l) The overall grain yield per plant. Data shown as mean±s.e.m. (n=288). All phenotypic data were measured from the paddy-grown plants under normal cultivation conditions. The presence of the same lowercase letter denotes a non-significant difference between means (P<0.05).
Figure 6:
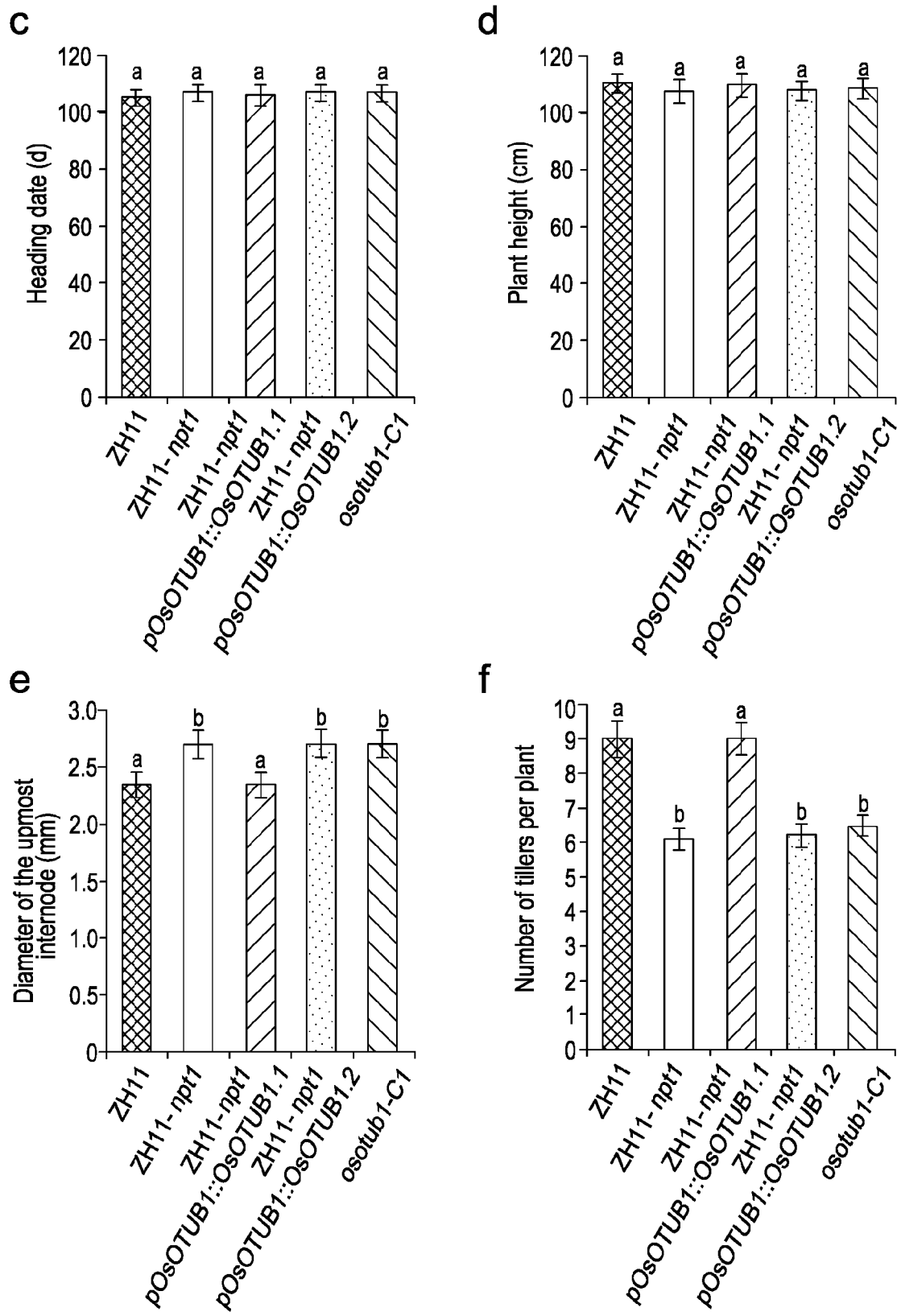
Figure 6:
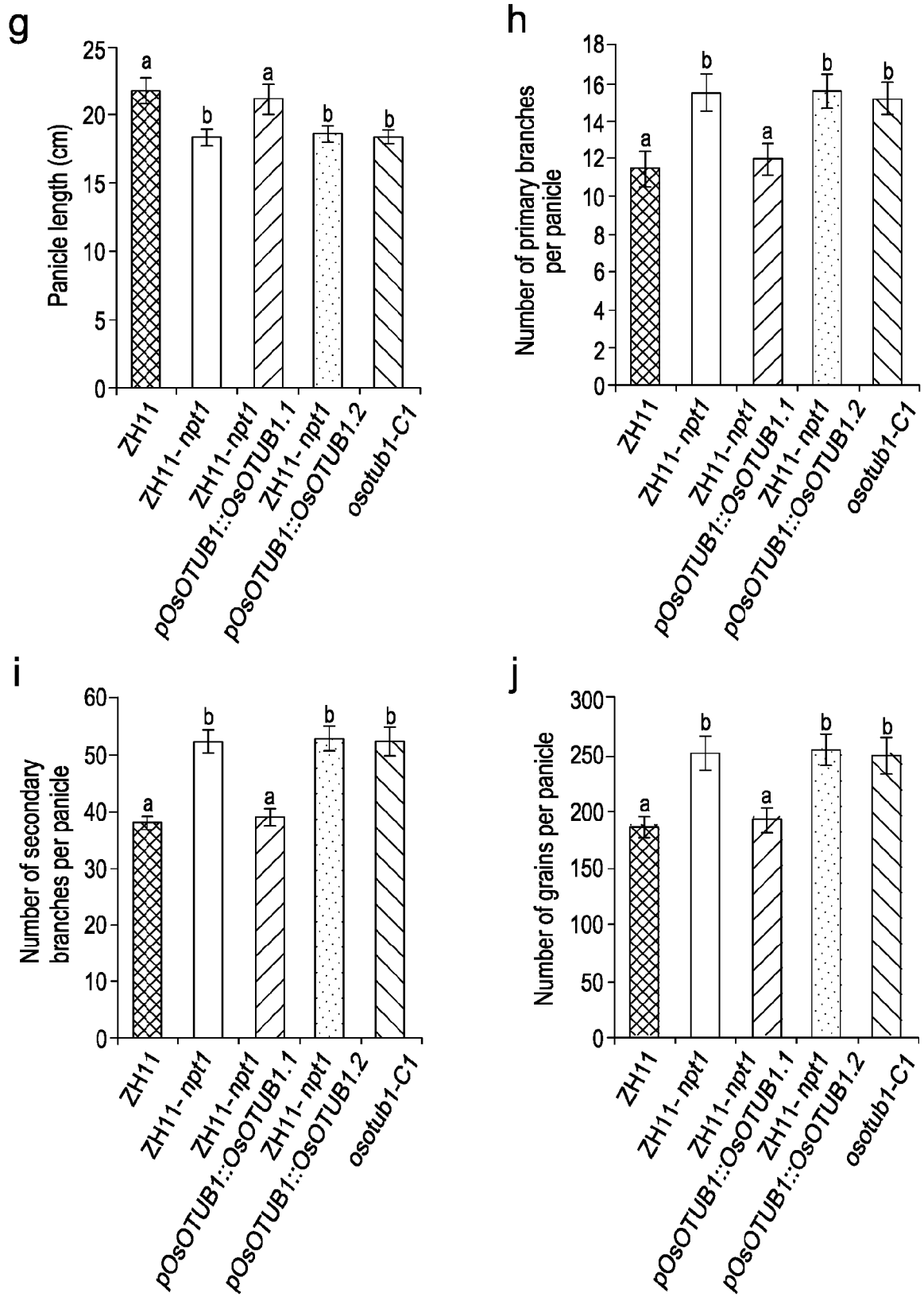
Figure 6:
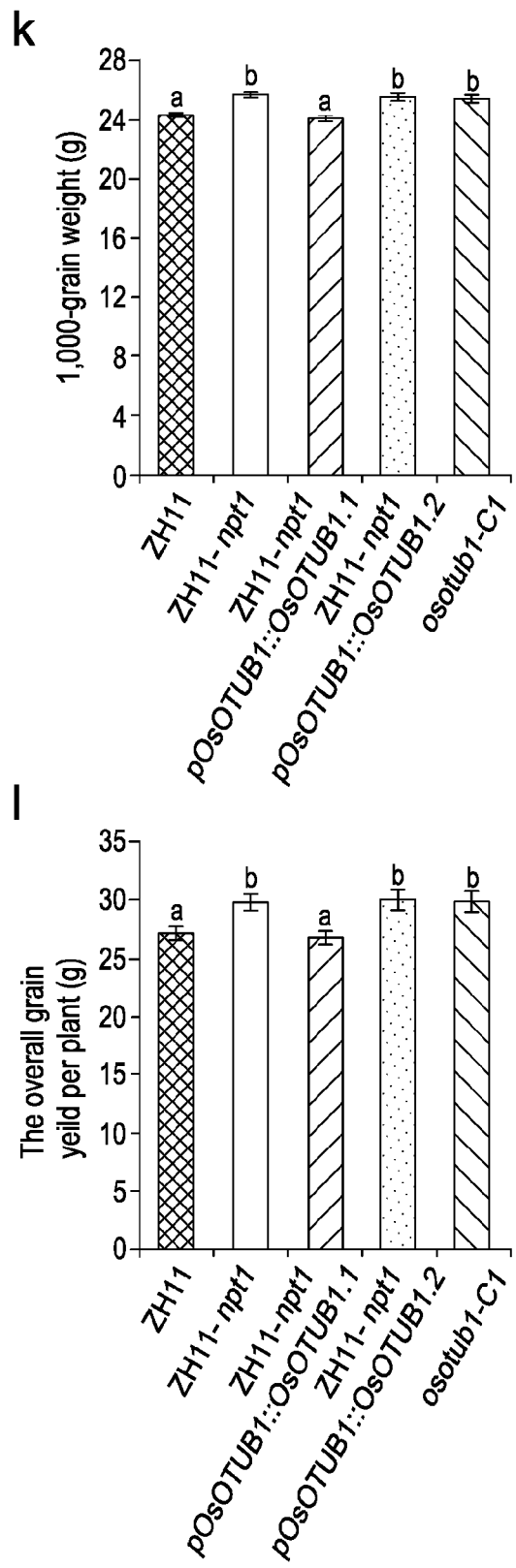
Figure 7:
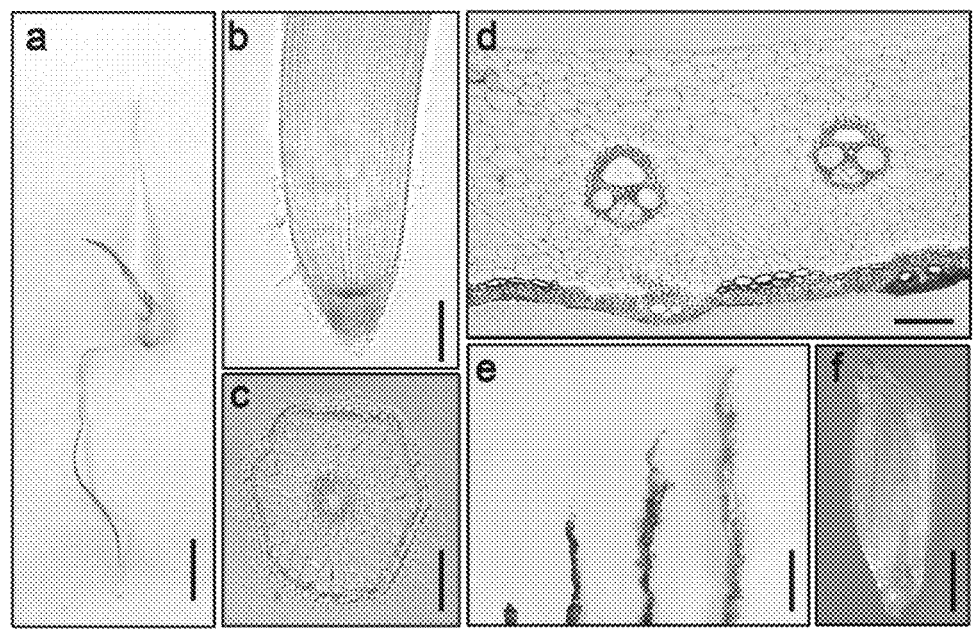
FIG. 7 shows an analysis of pOsOTUB1::GUS expression. (a) GUS expression in five day old seedlings. Scale bar: 1 cm. (b) The root tips of plants shown in a. Scale bar: 200 μm. (c) Cross-section of the GUS-stained root elongation zone shown in a. Scale bar: 200 μm. (d) Cross-section of the culm. Scale bar: 100 μm. (e) Various stages of the panicle development. Scale bar: 1 cm. (f) Spikelet hull before fertilization. Scale bar: 1 mm.
Figure 8:
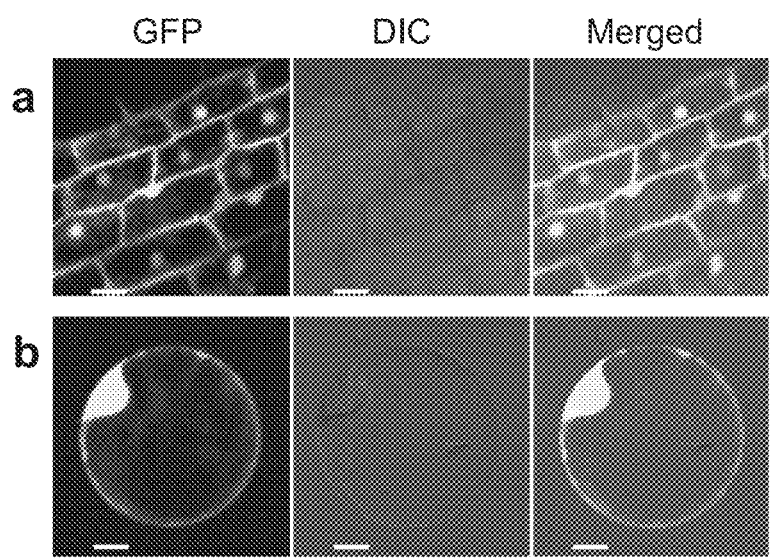
FIG. 8 shows the subcellular localization of OsOTUB1.1-GFP. (a) Expression of OsOTUB1-GFP in the root elongation zone. Scale bar: 20 μm. (b) GFP expression in protoplasts isolated form the leaf sheath of ZH11 plants overexpressing OsOTUB1.1-GFP. Scale bar: 10 μm. Panels (from left to right): GFP signal, differential interference contrast (DIC), merged channel.
Figure 9:
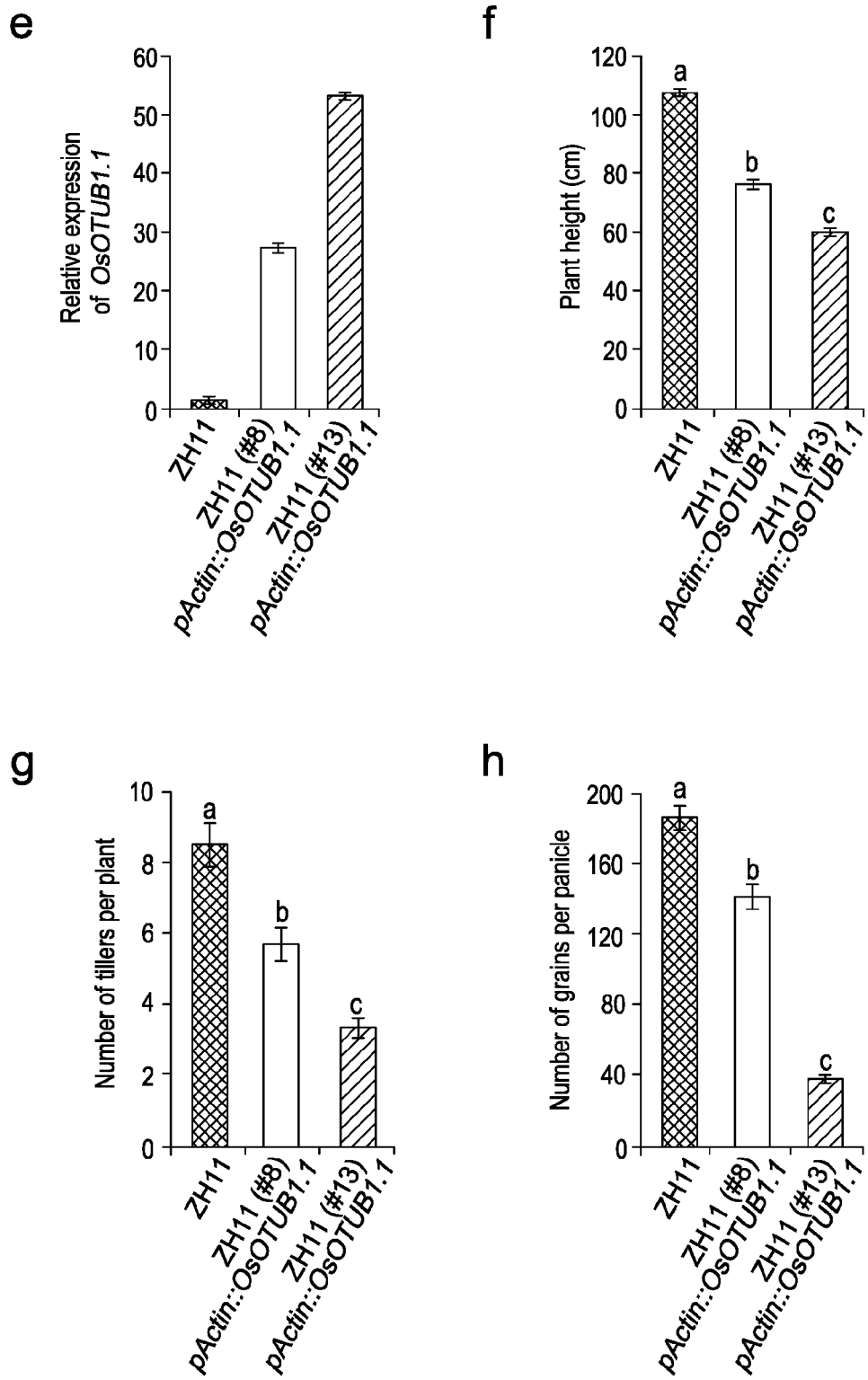
FIG. 9 shows the phenotype of ZH11 plants overexpressing OsOTUB1.1. (a) Two independent transgenic lines showed a reduced tiller number and dwarfism. Scale bar: 10 cm. (b) Panicle size was reduced. Scale bar: 5 cm. (c) Leaves suffered from necrosis. Scale bar: 3 mm. (d) Apoptosis was induced in the flag leaf, as assayed by Evans Blue staining. Scale bar: 3 mm. (e) Abundance of OsOTUB1.1 transcript in the young panicle. Transcription relative to the level of the ZH11 plants set to be one. Data shown as mean±s.e.m. (n=3). (f) Plant height. (g) Number of tillers per plant. (h) Number of grains per panicle. Data shown as mean±s.e.m. (n=60). All phenotypic data were measured from the paddy-grown rice plants under normal cultivation conditions. The presence of the same lowercase letter denotes a non-significant difference between means (P<0.05, panels f to h).

We next generated a near-isogenic line (NIL) ZH11-npt1, which harbors a ~240 Kbp segment including the npt1 allele from IR66167-27-5-1-6 in the background of the *japonica* rice variety Zhonghua11 (ZH11) (FIG. 6). Quantitative RT-PCR analysis revealed that the peak abundance of OsOTUB1 transcript was found in the shoot meristem and young panicles (FIG. 2a). Histochemical GUS assays targeting the OsOTUB1 promoter showed that the gene was strongly expressed in vascular tissue, as well as in the root cap and quiescent center (QC) cells (FIG. 7). The abundance of OsOTUB1 transcript in ZH11-npt1 was lower than in ZH11 (FIG. 2a). The phenotype of an OsOTUB1 knock-out, generated using the CRISPR/Cas9[13], was similar to that of ZH11-npt1, resulting in a reduced tiller number, an increased grain number, an enhanced grain weight and a consequent increase in grain yield (FIG. 6). In transgenic plants carrying the pOsOTUB1::OsOTUB1-GFP construct, GFP signal was detectable in both the nucleus and cytoplasm of root and leaf sheath cells (FIG. 8). The Rice Annotation Project Database predicts that the OsOTUB1 gene generates two alternatively spliced transcripts (FIG. 1g). The phenotype of transgenic ZH11-npt1 expressing OsOTUB1.1 cDNA driven by its native promoter was similar to that of ZH11, while that of those overexpressing OsOTUB1.2 was similar to that of ZH11-npt1 (FIG. 6). In addition, the transgenic ZH11 plants over-expressing OsOTUB1.1 were dwarfed in stature, set fewer grains and displayed leaf necrosis (FIG. 9). These results indicate that the loss-of-function of OsOTUB1 is associated with the ideotype architecture.

Haplotype analysis revealed that the npt1 allele has not been exploited by breeders of elite indica and temperate *japonica* varieties (FIG. 1h). Since the high-yielding dep1-1 allele has been heavily used by Chinese breeders[14, 15], it was therefore of interest to evaluate the effect of combining npt1 and dep1-1. NILs for allelic combinations of qNPT1 and qDEP1 loci were created in the elite *japonica* rice variety Wuyunjing7 (which carries NPT1 and dep1-1 alleles, hereafter referred to as WYJ7-NPT1-dep1-1). The WYJ7-npt1-dep1-1 and WYJ7-NPT1-dep1-1 plants did not differ from one another with respect to heading date and plant height (FIGS. 2b, 2e and 2f), whereas WYJ7-npt1-dep1-1 plants formed fewer tillers and set a larger number of heavier grains than WYJ7-NPT1-dep1-1 ones (FIG. 2g-2j). The shoot apical meristems formed by WYJ7-npt1-dep1-1 plants was larger than that formed by WYJ7-NPT1-dep1-1 ones (FIG. 2k), which implied that npt1 and dep1-1 acted synergistically to enhance meristematic activity[5]. The WYJ7-npt1-dep1-1 plants were also characterized by a greater number of vascular bundles, a thicker culm and a thicker parenchyma and sclerenchyma cell wall (FIG. 2l-2n). Importantly, over three successive seasons, the overall grain yield of WYJ7-npt1-dep1-1 plants was 10.4% greater than that of WYJ7-NPT1-dep1-1 plants (FIG. 2o). Therefore, pyramiding of the npt1 and dep1-1 alleles represents an effective means of boosting grain yield of rice.

Figure 10:
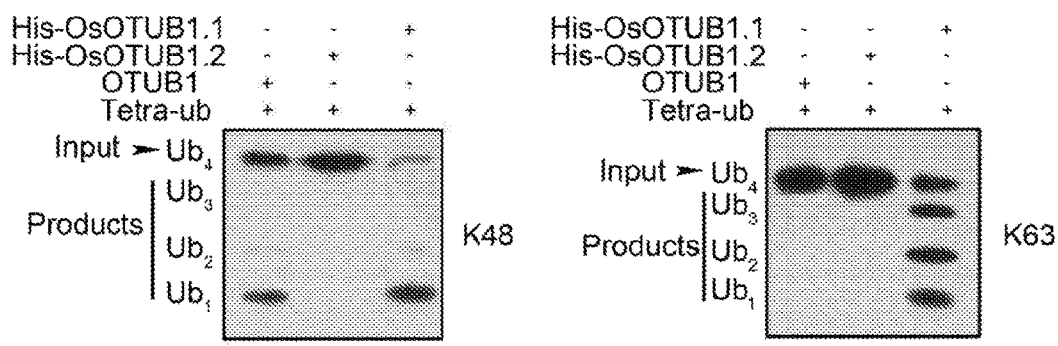
FIG. 10 shows OsOTUB1 displayed cleavage activity for K48- and K63-linked ubiquitin tetramers. Cleavage activity for K48- and K63-linked ubiquitin tetramers (Tetra-ub) were analyzed using OTUB1, His-OsOTUB1.1 or OsOTUB1.2. The inputs ($Ub_4$) and their cleavage products [trimers ($Ub_3$), dimers ($Ub_2$) and monomers ($Ub_1$)] were labeled on the left. The products were visualized by western blotting using an anti-ubiquitin antibody.
Figure 11:
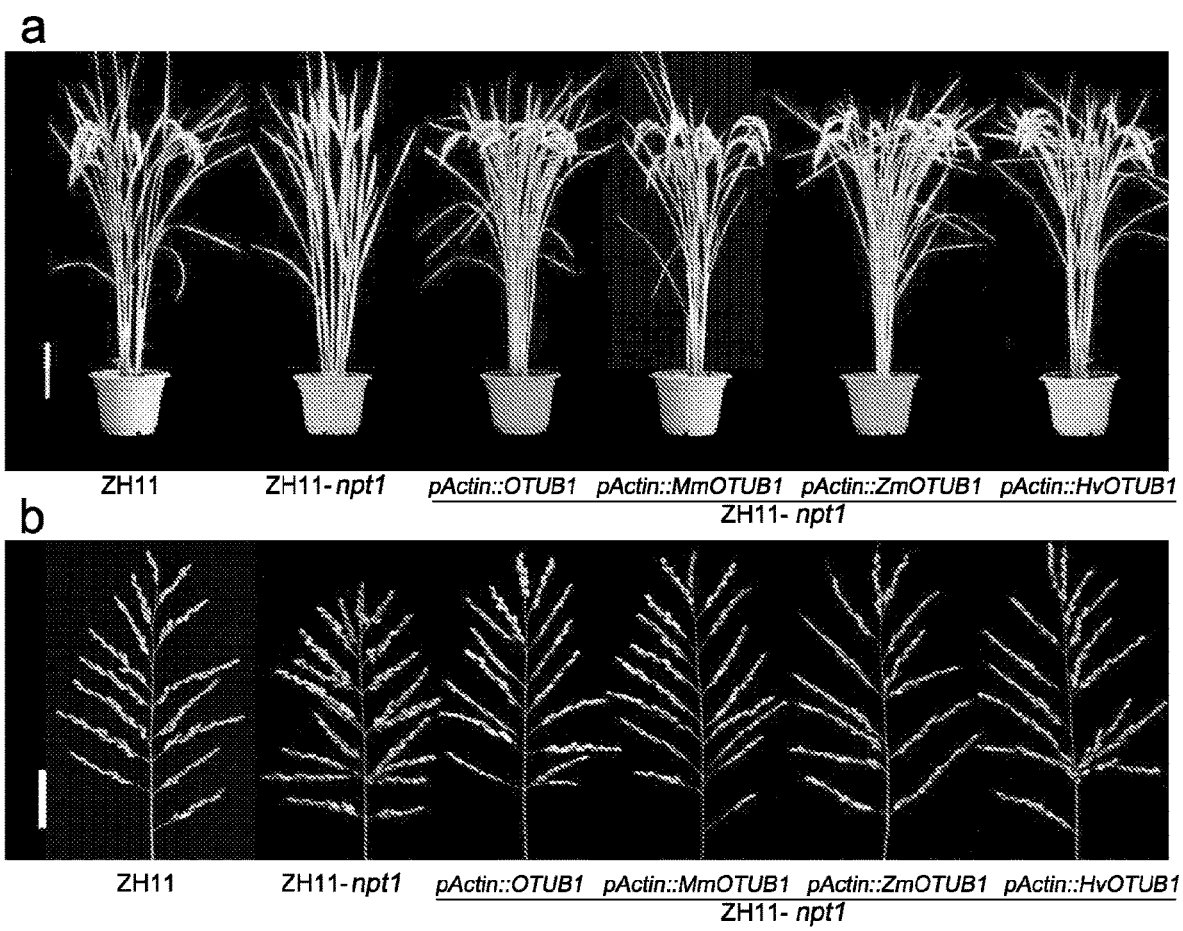
FIG. 11 shows the effect of expressing human OTUB1 or its orthologs on the plant architecture of ZH11-nptl. (a) Plant morphology. Scale bar: 20 cm. (b) Panicle morphology. Scale bar: 5 cm. (c) The abundance of OTUB1 (or its orthologs) transcript in the young panicles, relative to the level of OsOTUB1 in ZH11-npt1 plants. Data shown as mean±s.e.m. (n=3). (d) Number of tillers per plant. (e) Number of grains per panicle. (f) Diameter of the uppermost internode. Data shown as mean±s.e.m. (n=30). All phenotypic data were measured from the paddy-grown rice plants under normal cultivation conditions. The presence of the same lowercase letter denotes a non-significant difference between means (P<0.05, panels d to f).
Figure 11:
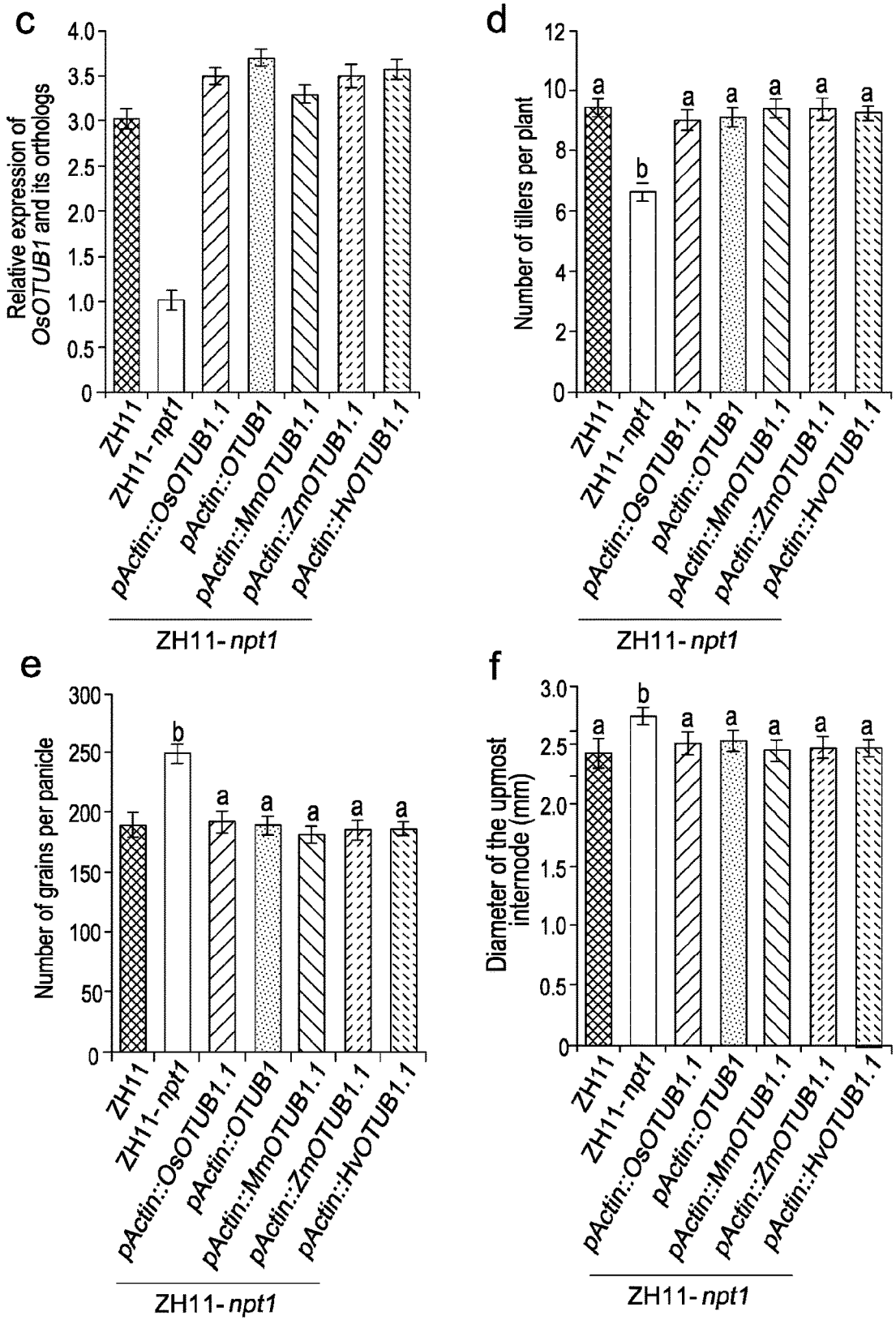
Figure 12:
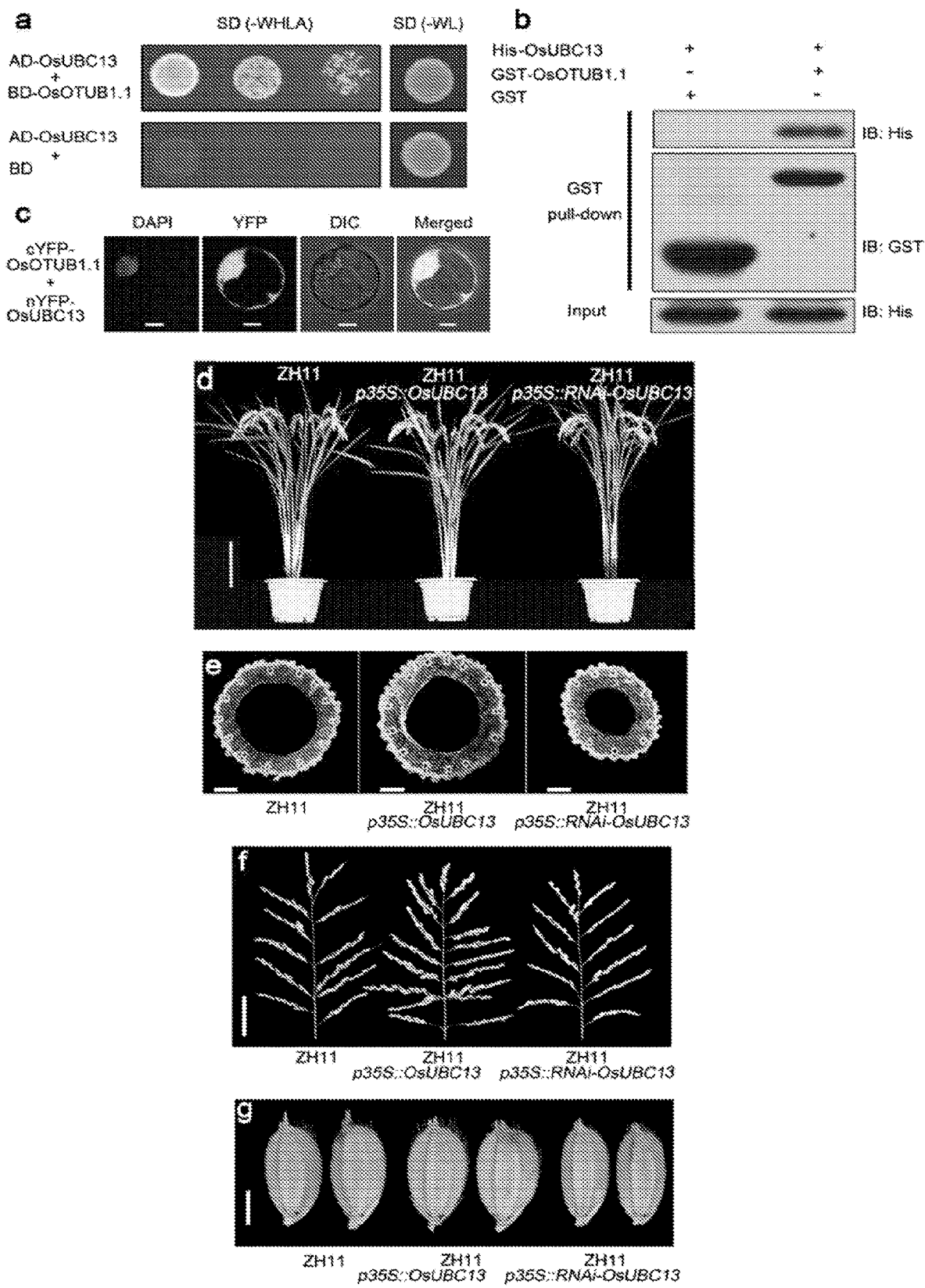
FIG. 12 shows the interaction between OsOTUB1 and OsUBC13 regulates plant architecture. (a) Yeast two-hybrid assays. (b) Pull-down assays using recombinant GST-OsOTUB1 and His-OsUBC13. (c) BiFC assays in rice protoplasts. Scale bar: 10 pm. (d) The morphology of the transgenic ZH11 plants. Scale bar: 20 cm. (e) Cross-section of the upmost internodes. Scale bar: 500 μm. (f) The effect of OsUBC13 on panicle branching. Scale bar: 5 cm. (g) Grain size and shape. Scale bar: 2 mm. (h) The abundance of OsOTUB1 transcript in the young panicle, relative to the level in ZH11. Data shown as mean±s.e.m. (n=3). (i), Number of tillers per plant. (j) Number of grains per panicle. (k) 1,000-grain weight. (l) Diameter of the uppermost internode. Data shown as mean±s.e.m. (n=30). All phenotypic data were measured from the paddy-grown rice plants under normal cultivation conditions. The presence of the same lowercase letter denotes a non-significant difference between means (P<0.05, panels i to l).
Figure 12:
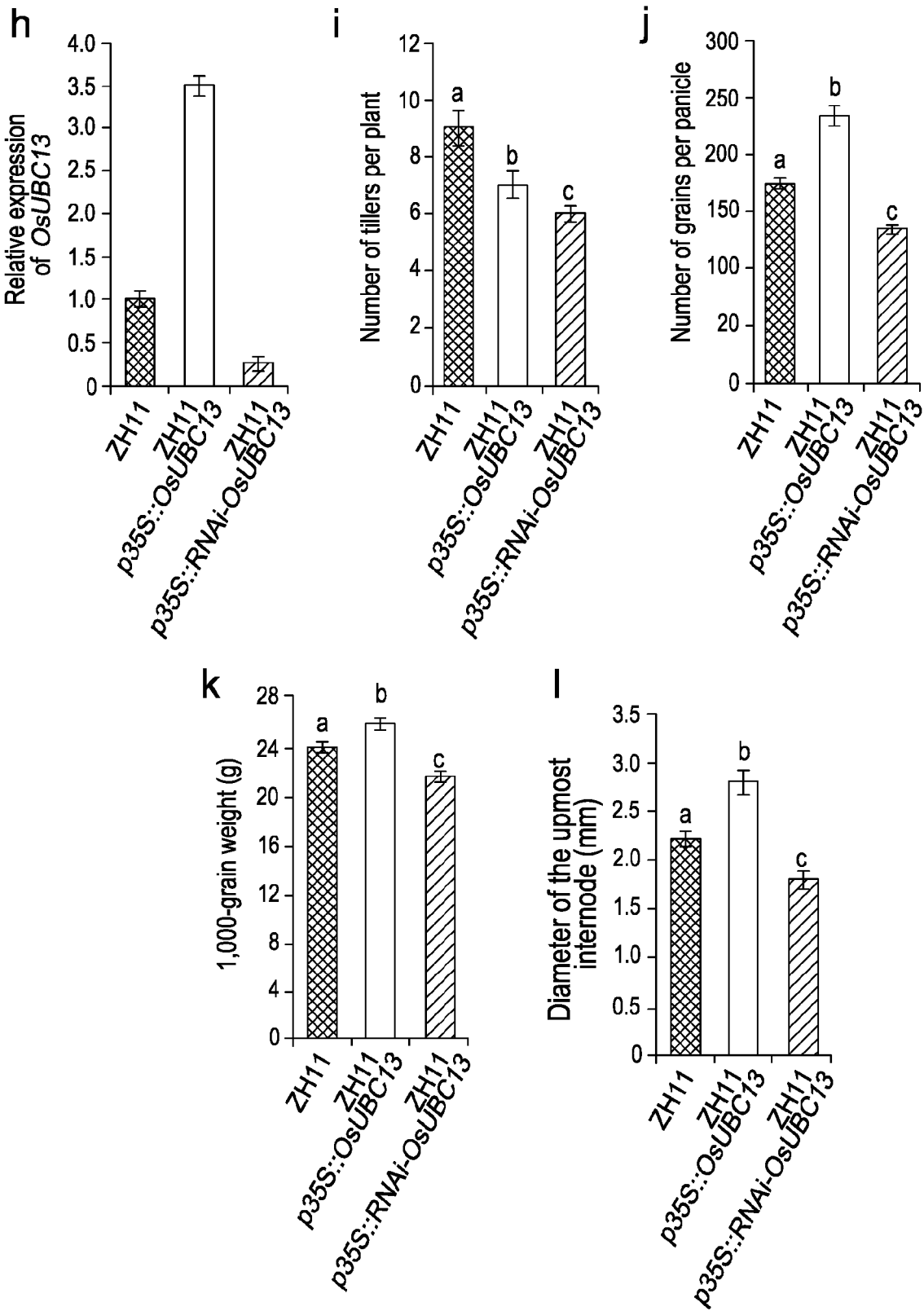

Given the predicted deubiquitinase activity of OsOTUB1, we next examined its ability to cleave linear Lys48- and Lys63-linked tetra-ubiquitin. Consistent with the behavior of its human homolog, it showed a strong cleavage activity when presented with Lys48-linked tetra-ubiquitin[16, 17], but unlike OTUB1, it also displayed a moderate level of activity when presented with the Lys63-linked forms (FIG. 10). The ZH11-npt1 plants expressing either OTUB1 or its orthologs from mouse, maize or barley driven by the OsOTUB1 promoter, exhibited a phenotype indistinguishable from that of ZH11 or transgenic ZH11-npt1 plants expressing OsOTUB1.1 (FIG. 11), suggesting that OTUB1 orthologs from all of these species are functionally interchangeable. It is known that OTUB1 interacts with UBC13 to inhibit double strand break-induced chromatin ubiquitination[9, 10], and the same interactions in vitro and in vivo were established between OsOTUB1 and OsUBC13 (FIG. 12). Overexpression of OsUBC13 resulted in a phenotype similar to that of plants carrying the npt1 allele, at least with respect to grain number, tiller number and culm diameter (FIG. 12). In contrast, the constitutive expression of an RNAi directed at OsUBC13 produced a phenotype reminiscent of plants in which OsOTUB1.1 cDNA was over-expressed (FIG. 9 and FIG. 12).

Figure 3:
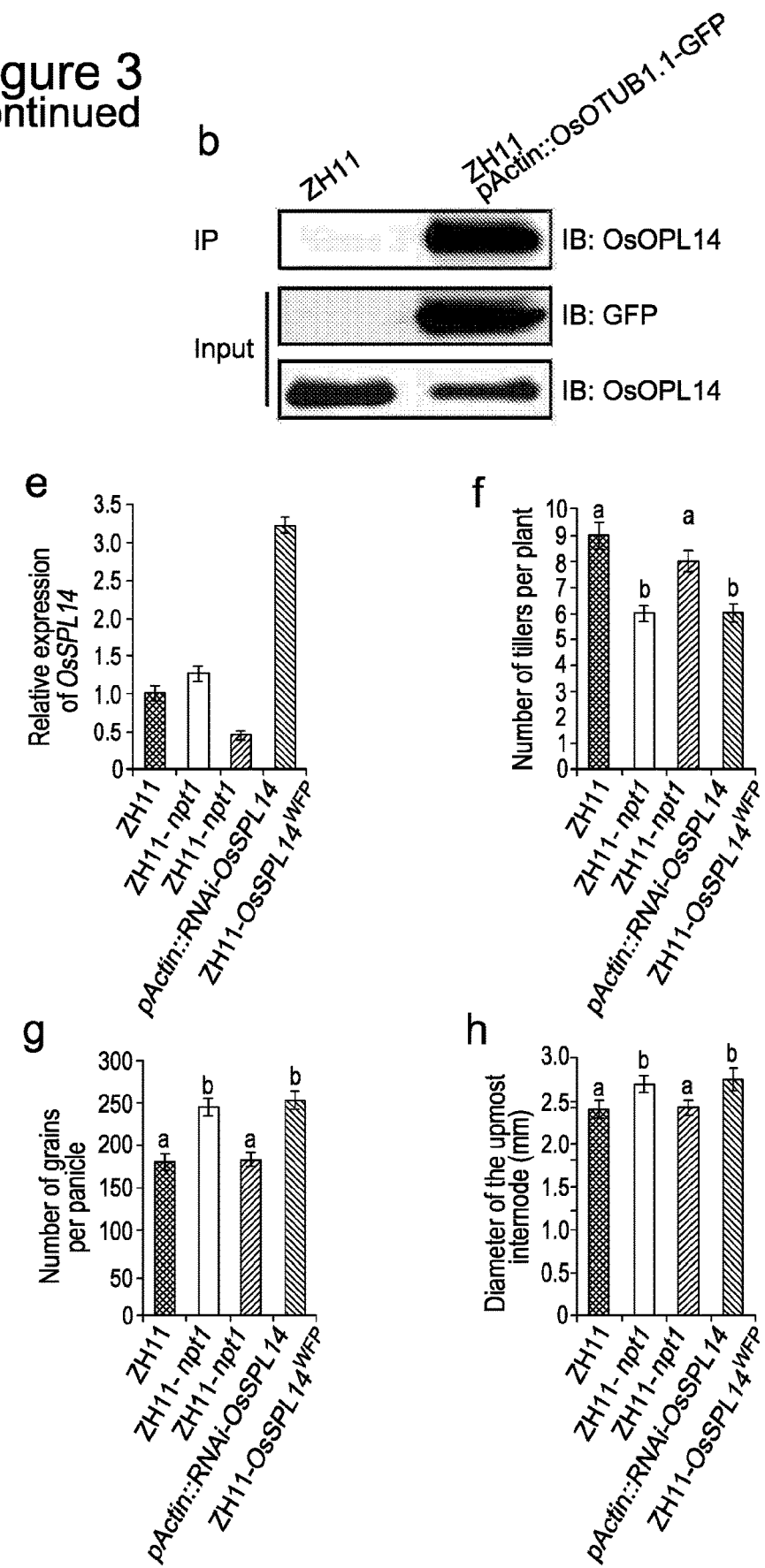
FIG. 3 shows the OsOTUB1-OsSPL14 interaction controls plant architecture. (a) BiFC assays. The N-terminus of YFP-tagged OsSPL14, SBP-domain or a deleted version of OsSPL14 was co-transformed into rice protoplasts along with the C-terminus of YFP-tagged OsOTUB1.1. Panels (from left to right): DAPI staining, YFP signal, differential interference contrast, merged channel. Scale bar: 10 μm. (b) Co-immunoprecipitation of OsOTUB1.1-GFP and OsSPL14. IB, Immunoblot; IP, immunoprecipitation. (c) Plant morphology. Scale bar: 20 cm. (d) Panicle morphology. Scale bar: 5 cm. (e) OsSPL14 transcript abundance. Transcription relative to the level of the ZH11 plants set to be one. Data shown as mean±s.e.m. (n=3). (f) The number of tillers per plant. (g) The number of grains per panicle. (h) Culm diameter. All phenotypic data were measured from the field-grown plants under normal cultivation conditions. Data in f-h shown as mean±s.e.m. (n=120). The presence of the same lowercase letter denotes a non-significant difference between means (P<0.05).
Figure 13:
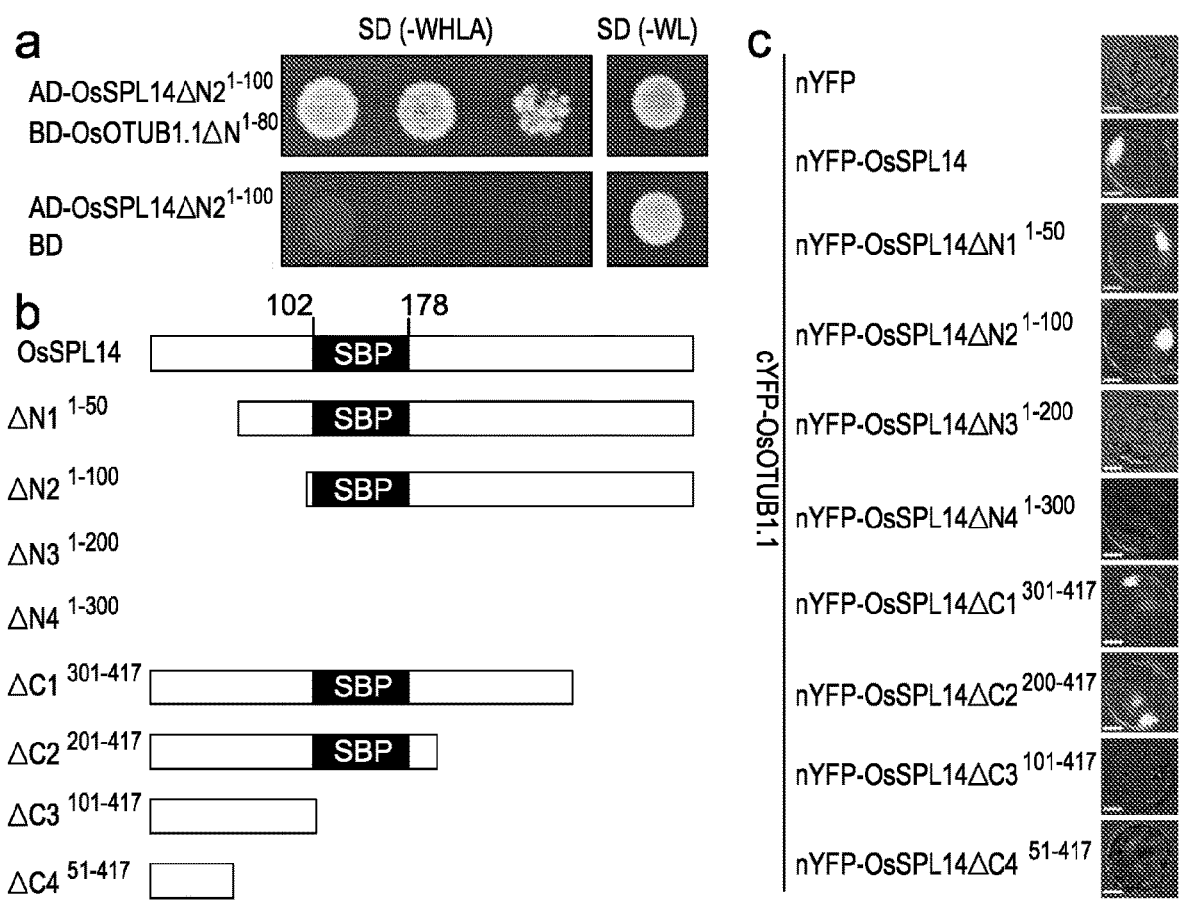
FIG. 13 shows that the SBP domain is required for the OsSPL14-OsOTUB1 interaction. (a) Yeast two-hybrid assays confirm the interaction between the C-termini of OsOTUB1 and OsSPL14. (b) Schematic representation of the deleted and non-deleted versions of OsSPL14 proteins used for the BiFC assays. (c) BiFC assays. Scale bar: 10 μm.
Figure 14:
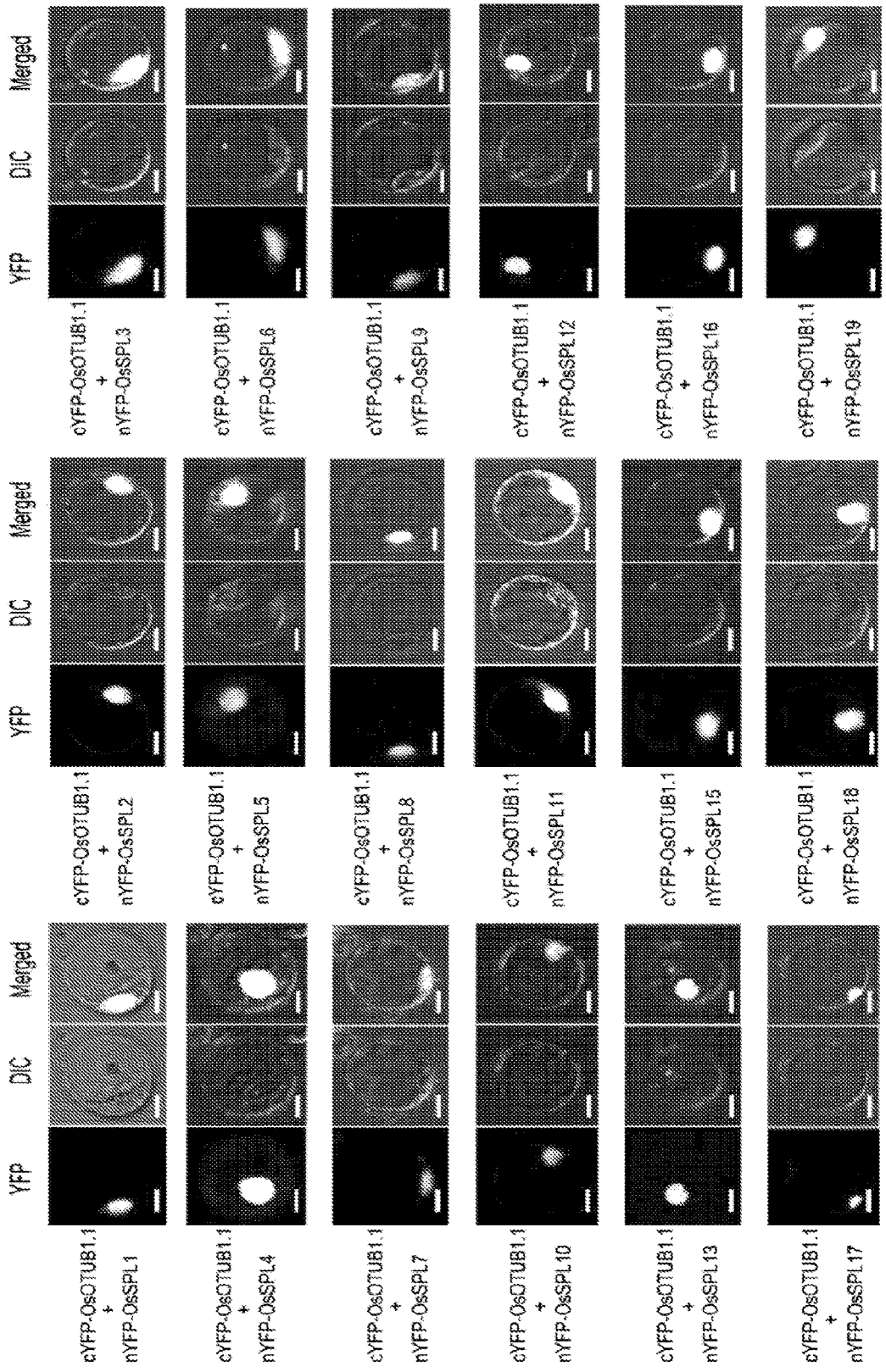
FIG. 14 shows OsOTUB1 interacts with the rice SPL transcription factors. BiFC assays were performed using rice protoplasts, the C-terminus of YFP-tagged OsOTUB1.1 was co-transformed with the N-terminus of YFP-tagged OsSPLs. Panels (left to right): YFP, differential interference contrast, merged channel. Panels (from left to right): YFP signal, differential interference contrast (DIC), merged channel. Scale bar: 10 μm.

A yeast two-hybrid screen targeting proteins interacting with OsOTUB1 identified 72 candidate interactors which included a rice homolog of the SQUAMOSA promoter-binding protein-like (SBP-domain) transcription factor OsSPL14, known to control plant architecture with reduced tiller number, thickened culm and enhanced grain number[18, 19]. Bimolecular fluorescence complementation (BiFC) and co-immunoprecipitation assays showed that the OsSPL14-OsOTUB1 interaction clearly occurred in planta (FIG. 3a, 3b). A deletion analysis revealed that the conserved SBP domain was both necessary and sufficient for the in vitro and in vivo interactions (FIG. 3a and FIG. 13). Further BiFC assays demonstrated that OsOTUB1 was able to interact with the full set of rice SPL transcription factors (FIG. 14), consistent with data showing that the abundance of OsSPL7, OsSPL13, OsSPL14 and OsSPL16 transcript is correlated with one or more of a reduction in tiller number, an increase in grain number or an enhancement to grain weight[18-23]. The presence of either the npt1 or the OsSPL14$^{WFP}$ allele associated with a high OsSPL14 transcript level[19], was shown to generate the NPT's architecture, while the phenotype of ZH11-npt1 plants in which OsSPL14 had been silenced by RNAi was similar to that of ZH11 plants (FIG. 3c-3h). Comparative RNA-seq based transcriptomic analysis of ZH11, ZH11-npt1 and ZH11-OsSPL 14$^{WFP}$ revealed that the transcript levels of 453 common target genes was higher in both ZH11-npt1 and ZH11-OsSPL14$^{WFP}$ than in ZH11 (FIG. 15), a result which was validated using qRT-PCR[22-24]. In contrast, the abundance of target genes examined was greatly reduced in ZH11-npt1 silenced for OsSPL14 (FIG. 15). Thus, OsOTUB1 and OsSPL14 act antagonistically to control plant architecture through regulation of common target genes.

Figure 4:
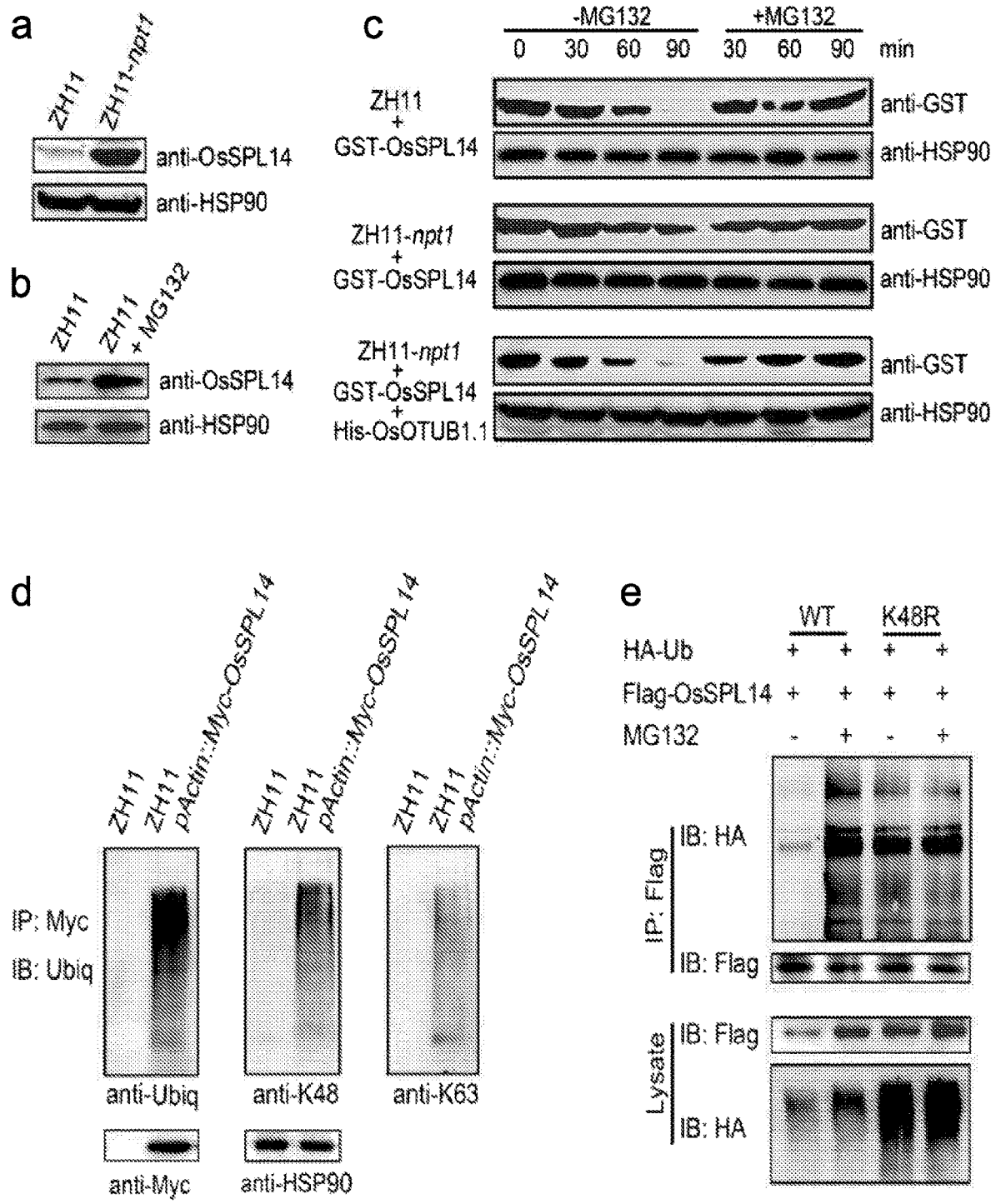
FIG. 4 shows that OsOTUB1 promotes the degradation of OsSPL14. (a) The accumulation of OsSPL14 in ZH11 and ZH11-npt1 plants. The abundance of HSP90 protein was used as the loading control. (b) Treatment with the proteasome inhibitor MG132 stabilizes OsSPL14. Total proteins were extracted from young panicles (<0.2 cm in length) of ZH11 plants exposed to either 0 or 50 μM MG132. The immunoblot was probed with either anti-OsSPL14 or anti-HSP90 antibodies. (c) OsOTUB1 destabilizes OsSPL14. The lysates from young panicles of ZH11 and ZH11-npt1 plants were co-incubated with GST-OsSPL14 in the presence or absence of His-OsOTUB1. The lysates were harvested at various times and immunoblotted to assess the accumulation of OsSPL14 and HSP90. (d) Ubiquitination of OsSPL14. The protein extracts from young panicles were immunoprecipitated using an anti-Myc antibody, then analyzed using either anti-ubiquitin, anti-K48 ubiquitin or anti-K63 ubiquitin chain conjugates. (e) Flag-OsSPL14 can be modified with K48-ubiquitin linkage. The rice protoplasts were co-transfected with Flag-OsSPL14 and HA-ubiquitin (either HA-tagged WT or K48R ubiquitins), and the ubiquitinated forms of Flag-OsSPL14 were immunoprecipitated using an anti-Flag antibody and then analyzed using an anti-HA antibody. (f) K63-linked ubiquitination of OsSPL14 was regulated by OsOTUB1. The rice protoplasts were co-transfected with Flag-OsSPL14 and HA-ubiquitin (either HA-tagged WT, K48R, K63R, K48O or K63O ubiquitins) in the presence or absence of Myc-OsOTUB1, lysates were harvested and immunoblotted to assess the accumulation of OsSPL14, and analyzed ubiquitinated forms of Flag-OsSPL14 as described in e.
Figure 4:
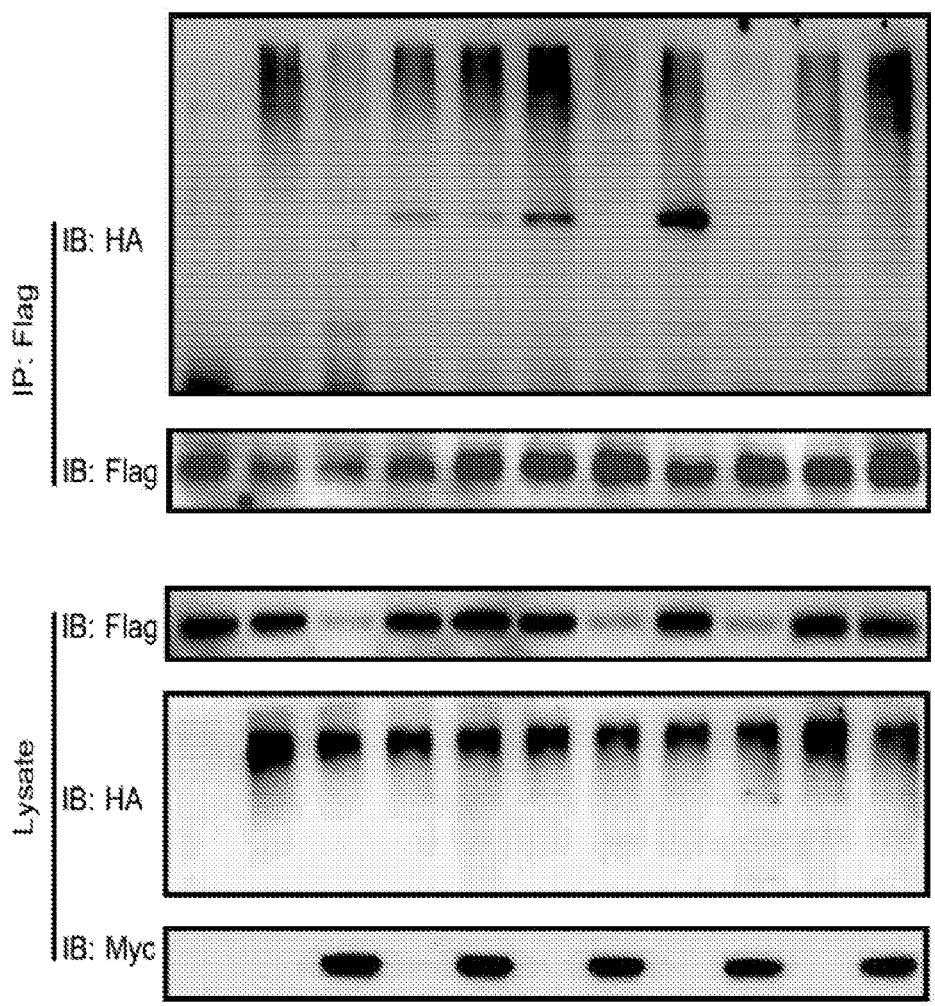
Figure 16:
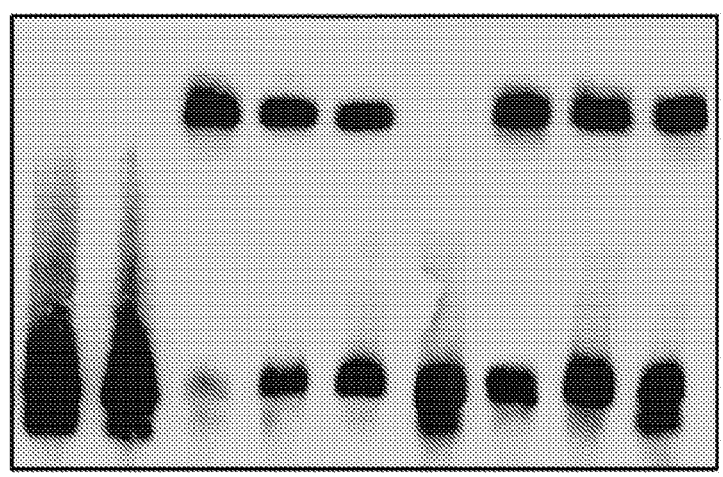
FIG. 16 shows the effect of the OsSPL14-OsOTUB1 interaction on the DNA binding affinity of OsSPL14. Competition for OsSPL14-GST protein binding was performed either with 10×, 20× and 50× unlabeled probes containing the GTAC-box motifs from the promoter of the DEP1 gene, or with 1×, 2× and 4× unlabeled Myc-OsOTUB1.1 fusion proteins, respectively.

EMSA assays revealed that the OsOTUB1-OsSPL14 interaction was unlikely to affect the binding affinity of OsSPL14 to its targeting GTAC motifs (FIG. 16). There was no difference in the abundance of OsSPL14 transcript between ZH11 and ZH11-npt1 (FIG. 3e), but the accumulation of OsSPL14 was much higher in the latter genotype (FIG. 4a). When exposed to the proteasome inhibitor MG132, OsSPL14 accumulation was obviously increased in ZH11 (FIG. 4b). These results suggest that OsOTUB1, unlike OTUB1 that regulates stability of p53 and SMAD proteins[11, 12], promoted the degradation of OsSPL14. When lysates prepared from young panicles of ZH11 were challenged with GST-OsSPL14, the titer of GST-OsSPL14 decreased over time, but the opposite occurred when a MG132 treatment was included (FIG. 4c). The stable accumulation of GST-OsSPL14 was greater when the lysates were prepared from ZH11-npt1 than from ZH11 panicles, whereas the degradation of GST-OsSPL14 was accelerated in lysates made from ZH11-npt1 panicles in the presence of His-OsOTUB1 (FIG. 4c). A western blotting analysis showed that it was possible to detect the presence of polyubiquitinated forms of Myc-OsSPL14 immunoprecipitated from young panicles by using an antibody that recognizes either total ubiquitin, Lys48-polyubiquitin or Lys63-polyubiquitin conjugates (FIG. 4d). The implication is that OsSPL14 is modulated by both Lys48- and Lys63-linked ubiquitination[25].

The analysis was extended to investigate endogenous E3 ligase-mediated ubiquitination of OsSPL14. In the presence of WT ubiquitin, the MG132 treatment of rice protoplasts expressing Flag-OsSPL14 resulted in an enhanced accumulation of polyubiquitinated Flag-OsSPL14; however, in the presence of K48R-ubiquitins, there was no perceptible effect of the MG132 treatment in the accumulation of polyubiquitinated Flag-OsSPL14 (FIG. 4e). This observation was consistent with the notion that Lys48-linked ubiquitin of OsSPL14 is required for its proteasome-mediated degradation. In the presence of Myc-OsOTUB1.1, the titer of ubiquitinated Flag-OsSPL14 was clearly decreased in the presence of either K48R or K63O mutations, but it remained unaffected by the presence of either K48O or K63R mutations (FIG. 4f). Moreover, Myc-OsOTUB1 promoted the degradation of Flag-OsSPL14 only in the presence of either WT-, K63O- or K48R-linked ubiquitins (FIG. 4f), indicating that the stabilization of OsSPL14 is correlated with Lys63-linked ubiquitination. Collectively, these results suggest that OsOTUB1-mediated inhibition of Lys63-linked ubiquitination of OsSPL14 is required for its proteasome-dependent degradation.

The miR156-targeted SBP-domain transcription factors play the important roles in the regulation of stem cell function and flowering in plants[26-28]. Non-canonical OsOTUB1-mediated regulation of SBP-domain transcription factors establishes a new framework for studying meristem cell fate, inflorescence architecture and flower development. Our findings shed light on the molecular basis of an ideotype approach in rice breeding programs, the manipulation of the OsOTUB1-OsSPL14 module also provides a potential strategy to facilitate the breeding of new rice varieties with higher grain productivity.

Plant materials and growing conditions. A set of 670 RILs population was bred from a cross between the Chinese temperate *japonica* rice variety Chunjiang06 and the NPT selection IR66167-27-5-1-6. The rice accessions used for the sequence diversity analysis have been described elsewhere[14, 21]. The NILs plants carrying either npt1, OsSPL14$^{WFP19, 29}$, or allelic combinations of the qNPT1 and qDEP1 loci were bred by crossing RIL52 seven times with either Zhonghua11 or Wuyunjing7. Paddy-grown plants were spaced 20 cm apart and were grown during the standard growing season at three experimental stations, one in Lingshui (Hainan Province), one in Hefei (Anhui Province) and one in Beijing.

Transgene constructs. The OsOTUB1.1 and OsOTUB1.2 coding sequences, their UTRs (5': from the transcription start site to −2.8 Kbp; 3': 1.5 Kbp downstream of the termination site) were amplified from ZH11 genomic DNA (gDNA), and introduced into the pCAMBIA2300 vector (CAMBIA) to generate pOsOTUB1::OsOTUB1.1 and pOsOTUB1::OsOTUB1.2. Full length human OTUB1 cDNA (and that of its mouse, barley and maize orthologs) were amplified from the relevant cDNA template and then subcloned into pActin::nos vector[14], while OsOTUB1.1 cDNA and its 5'-UTR was introduced into the p35S::GFP-nos vector[21] to generate pOsOTUB1::OsOTUB1.1-GFP-nos construct. To form p35S::Myc-OsSPL14, OsSPL14 cDNA was amplified from a template of ZH11 cDNA and cloned into p35S::Myc-nos. The gRNA constructs required for the CRISPR/Cas9-enabled knock-out of OsOTUB1 were generated as described elsewhere[13]. An 300 bp fragment of OsSPL14 cDNA and an 300 bp fragment of OsUBC13 cDNA were amplified from ZH11 cDNA and used to construct the pActin::RNAi-OsSPL14 and pActin::RNAi-OsUBC13 transgenes as described elsewhere[14]. The transgenic rice plants were generated by *Agrobacterium*-mediated transformation as previously described[5]. The relevant primer sequences were given in FIG. 17.

Quantitative real time PCR (qRT-PCR) analysis. Total RNA was extracted from plant tissues using TRIzol reagent (Invitrogen), and treated with RNase-free DNase I (Invitrogen) according to the manufacturer's protocol. The resulting RNA was reverse-transcribed using a cDNA synthesis kit (TRANSGEN). Subsequent qRT-PCR was performed as described elsewhere[21], including three independent RNA preparations as biological replicates. The rice Actin1 was used as a reference. The relevant primer sequences were given in FIG. 17.

Yeast two-hybrid assays. Yeast two-hybrid assays were performed as described elsewhere[14, 21]. The full length OsOTUB1.1 cDNA and an OsOTUB1 C-terminal fragment were amplified from ZH11 cDNA and inserted into pGBKT7 (Takara Bio Inc.), while the full length OsUBC13 cDNA and an OsSPL14 C-terminal fragment were inserted into pGADT7 (Takara Bio Inc.). Each of these plasmids was validated by sequencing before being transformed into yeast strain AH109. The required β-galactosidase assays were performed according to the manufacturer's (Takara Bio Inc.) protocol. Cells harboring either an empty pGBKT7 or an empty pGADT7 were used as the negative control. The entire OsOTUB1 sequence or a C-terminal fragment were used as the bait to screen a cDNA library prepared from poly(A)-containing RNA isolated from rice young panicles (<0.2 cm in length). The experimental procedures for screening and plasmid isolation followed the manufacturer's (Takara Bio Inc.) protocol. The relevant primer sequences are listed in FIG. 17.

BiFC assays. OsOTUB1.1, OsUBC13, OsSPL1 through OsSPL13 and OsSPL15 through OsSPL19 full length cDNAs, along with both deleted and non-deleted versions of OsSPL14 were amplified from ZH11 cDNA, and the amplicons inserted into the pSY-735-35S-cYFP-HA or pSY-736-35S-nYFP-EE vectors[30] to generate a set of fusion constructs. Two vectors for testing the protein-protein interaction (e.g., nYFP-OsSPL14 and cYFP-OsOTUB1) were co-transfected into rice protoplasts. After incubation in the dark for 14 h, the YFP signal was examined and photographed under a confocal microscope (Zeiss LSM710) as described elsewhere[31]. Each BiFC assay was repeated at least three times. The relevant primer sequences are listed in FIG. 17.

In vitro pull-down. The recombinant GST-OsOTUB1 fusion protein was immobilized on glutathione sepharose beads and incubated with His-OsUBC13 for 30 min at 4° C. The glutathione sepharose beads were washed three times, and eluted by the elution buffer (50 mM Tris-HCl, 10 mM reduced glutathione, pH 8.0). The supernatant was subjected to immunoblotting analysis by using anti-His and anti-GST antibodies (Santa Cruz).

Co-immunoprecipitation and western blotting. Myc-OsSPL14 was extracted from young panicles (<0.2 cm in length) of transgenic ZH11 plants harboring pActin::Myc-OsSPL14 using a buffer composed of 50 mM HEPES (pH7.5), 150 mM KCl, 1 mM EDTA, 0.5% Triton-X 100, 1 mM DTT and proteinase inhibitor cocktail (Roche Life-Science, Basel, Switzerland). The agarose-conjugated anti-Myc antibodies (Sigma-Aldrich) was added and the reaction was held at 4° C. for at least 4 hours, and then washed 5~6 times with TBS-T buffer and eluted with 2× loading buffer. The immunoprecipitates and lysates were subjected to SDS-PAGE and the separated proteins were transferred to a nitrocellulose membrane (GE Healthcare). The Myc-OsSPL14 fusion proteins were detected by probing the membrane with an anti-Myc antibody (Santa Cruz), while its polyubiquitinated forms were detected by probing with either antibodies that recognize total ubiquitin conjugates, antibodies that specifically recognize Lys48-polyubiquitin conjugates, or antibodies that specifically recognize Lys63-polyubiquitin conjugates (Abcam).

Analysis of the degradation of OsSPL14. Lysates obtained from young panicles (<0.2 cm in length) harvested from ZH11 and ZH11-npt1 plants were incubated with the appropriated recombinant GST-OsSPL14 fusion protein in the presence or absence of recombinant His-OsOTUB1 fusion protein. Protein was extracted from lysates which had either been exposed or not to 50 μM MG132 for a preset series of times, and subjected to SDS-PAGE and western blotting based on an anti-GST antibody (Santa Cruz). As a loading control, the abundance of HSP90 was detected by probing with an anti-HSP90 antibody (BGI). The lysis buffer contains 25 mM Tris-HCl (pH 7.5), 10 mM NaCl, 10 mM MgCl2, 4 mM PMSF, 5 mM DTT and 10 mM ATP as described elsewhere[32].

Linear K48- and K63-linked tetra-ubiquitin cleavage assays. A ~1 μg aliquot of recombinant GST-OsOTUB1.1, GST-OsOTUB1.2 or OTUB1 was added to 20 μL of 50 mM Tris-HCl (pH7.4), 150 mM NaCl, 0.5 mM dithiothreitol containing 2.5 μg of linear K48- and K63-linked tetra-ubiquitin (Boston Biochem) and held for 1 h at 37° C. The reaction products were analyzed by western blotting based on an anti-ubiquitin antibody (Abcam) as described elsewhere[16].

Analysis of in vitro ubiquitination. The rice protoplasts prepared from ZH11-npt1 young panicles (<0.2 cm in length) were transfected with plasmids pUC19-35S-Flag-OsSPL14-RBS (33) and pUC19-355-HA-Ubiq-RBS (either HA-tagged ubiquitin (WT), K48R (K48 mutated to arginine), K63R (K63 mutated to arginine), K48O (ubiquitin with only K48, with the other lysine residues mutated to arginine), or K63O (ubiquitin with only K63, with the other lysine residues mutated to arginine) in the presence or absence of plasmid pUC19-35S-Myc-OsOTUB1-RBS. After 15 h, the protoplasts were lysed in the extraction buffer [50 mM Tris-HCl (pH7.4), 150 mM KCl, 1 mM EDTA, 0.5% Trition-X 100, 1 mM DTT] containing proteinase inhibitor cocktail (Roche LifeScience). The resulting lysates was challenged with agarose-conjugated anti-Flag antibodies (Sigma-Aldrich) for at least 4 h at 4° C., then rinsed 5-6 times in the extraction buffer and eluted with 3× Flag peptide (Sigma-Aldrich). The immunoprecipitates were separated by SDS-PAGE and transferred to a nitrocellulose membrane (GE Healthcare), which was used for a western blotting analysis by using anti-HA and anti-Flag conjugates antibodies (Sigma-Aldrich).

EXAMPLE 2

Results

The wtg1-1 Mutant Produces Wide, Thick, Short and Heavy Grains

To understand how grain size is determined in rice, we mutagenized the *japonica* variety Zhonghuajing (ZHJ) with the γ-ray and isolated a wide and thick grain 1 (wtg1-1) mutant in M2 populations. The wtg1-1 grains were wider than ZHJ grains (FIGS. 18a, b, e). ZHJ grain width was 3.41 mm, while wtg1-1 grain width was 3.84 mm (FIG. 18e). By contrast, the length of wtg1-1 grains was reduced in comparison with that of ZHJ (FIGS. 18a, b, d). The length of ZHJ grains was 7.47 mm, whereas the length of wtg1-1 grains was 6.89 mm. The wtg1-1 grains were obviously thicker than ZHJ grains (FIG. 18c). The average thickness of ZHJ and wtg1-1 grains was 2.27 mm and 2.66 mm, respectively (FIG. 18f). Importantly, wtg1-1 grains were significantly heavier than ZHJ grains (FIG. 18g). The 1000-grain weight of ZHJ and wtg1-1 was 25.56 g and 29.09 g, respectively. These results indicate that WTG1 affects grain width, thickness and length as well as grain weight.

The wtg1-1 Mutant Increases Grain Number Per Panicle

Mature wtg1-1 plants were slightly short in comparison with wild-type plants (FIGS. 19a, b, f). The wtg1-1 plants produced wide leaves compared with ZHJ plants, while the length of wtg1-1 leaves was similar to that of ZHJ leaves (FIGS. 19c, d, g, h). The wtg1-1 panicles were short, thick and dense in comparison with wild-type panicles, showing an erect panicle phenotype (FIGS. 19e, i). The axis length of wtg1-1 panicles was decreased in comparison with that of wild-type panicles (FIG. 19j), showing that WTG1 influences panicle size. As panicle branches determine panicle structure and shape, we examined primary and secondary panicle branches of the wild type and wtg1-1. The wtg1-1 panicles had more primary and secondary panicle branches than ZHJ (FIGS. 19k, l). We examined the number of grains per panicle in ZHJ and wtg1-1. As shown in FIG. 2M, the number of grains per panicle in wtg1-1 was higher than that in ZHJ. Thus, these data indicate that the increased number of primary and secondary panicle branches in wtg1-1 causes an increase in grain number per panicle.

Identification of the WTG1 Gene

We sought to identify the wtg1-1 mutation using the MutMap method (Abe et al., 2012), which has been used to clone genes in rice. We crossed wtg1-1 with ZHJ and generated an $F_2$ population. In the $F_2$ population, the progeny segregation indicated that a single recessive mutation determines the phenotypes of wtg1-1. We extracted DNA from fifty $F_2$ plants that showed the wide and thick grain phenotypes, and the same amount of DNA was mixed for the whole genome sequencing. We also sequenced ZHJ as a control. 6.2 Gbp and 5.4 Gbp of short reads were generated for ZHJ and the pooled $F_2$ plants, respectively. We detected 1399 SNPs and 157 INDELs between the pooled $F_2$ and ZHJ. We then calculated the SNP/INDELratio in the pooled $F_2$ plants. Considering that all mutant plants in the $F_2$ population should possess the causative SNP/INDEL, the SNP/INDEL ratio for this causative mutation in bulked $F_2$ plants should be 1. Among them, only one INDEL shows a SNP/INDEL-ratio=1. This INDEL contains a 4-bp deletion in the gene (LOC_Os08g42540) (Figures a, 23). We further confirmed this deletion in wtg1-1 by developing the marker dCAPS1 (FIG. 20b). Thus, these analyses suggest that LOC_Os08g42540 could be the WTG1 gene.

To confirm that WTG1 is the LOC_Os08g42540 gene, we conducted genetic complementation test. The genomic fragment containing the 2337 bp of 5' flanking sequence, the LOC_Os08g42540 gene and 1706 bp of 3' flanking sequence (gWTG1) was transformed into the wtg1-1 mutant. The gWTG1 construct complemented the phenotypes of the wtg1-1 mutant (FIGS. 20f-k). The grain width, grain thickness and grain length of gWTG1;wtg1-1 transgenic plants were comparable with those of ZHJ. Therefore, this genomic complementation experiment confirmed that the WTG1 gene is LOC_Os08g42540.

WTG1 Encodes an Otubain-Like Protease with Deubiquitination Activity

The WTG1 gene encodes an unknown protein with a predicted otubain domain (FIG. 20d). WTG1 homologues were found in *Chlamydomonas reinhardtii, Physcomitrella patens, Selaginella moellendorffii*, other plant species and animals (FIG. 24). The homologs in the grass family (e.g. wheat, Brachypodium, maize and sorghum) have high amino acid sequence identity with WTG1 (FIG. 24). WTG1 also shares similarity with human otubain 1/2 proteins (OTUB1/2) (FIG. 25), which are involved in multiple physiology and developmental processes (Nakada et al., 2010, Herhaus et al., 2013). In wtg1-1, the 4-bp deletion happens in the exon-intron junction region of the fourth intron (FIG. 20a). The wtg1-1 mutation resulted in altered splicing of WTG1, which in turn caused a premature stop codon (FIG. 20c). The protein encoded by the wtg1-1 allele lacks half of the predicted otubain domain and also contains a completely unrelated peptide (FIG. 20e), suggesting that wtg1-1 is a loss-of-function allele.

In animals, otubain proteins have been known to possess deubiquitination activity because they have the histidine, cysteine and aspartate residues in the conserved catalytic domain of cysteine proteases (FIG. 25) (Balakirev et al., 2003). WTG1 shares similarity with human otubain proteins and has an otubain-like domain (FIGS. 20d, 25), suggesting that WTG1 could be an otubain-like protease. Therefore, we carefully examined the amino acid sequence of WTG1 and found that WTG1 contains the conserved aspartate (D68), cysteine (C71) and histidine (H267) residues in the predicted otubain domain, which define catalytic triad of ubiquitin protease in animals (FIGS. 20d, 25) (Balakirev et al., 2003). We then investigated whether WTG1 has deubiquitination activity. We expressed WTG1, WTG1$^{wtg1-1}$ encoded by the wtg1-1 allele and WTG1$^{D68E;C71S;H267R}$ with mutations in the conserved amino acids as MBP (maltose binding protein)-tagged proteins (MBP-WTG1, MBP-WTG1$^{wtg1-1}$ and WTG1$^{D68E;C71S;H267R}$), and UBQ10 (hexameric polyubiquitin) as a His-tagged protein (His-UBQ10). Deubiquitination assays showed that MBP-WTG1 was capable of cleaving His-UBQ10, but MBP-WTG1$^{wtg1-1}$, MBP-WTG1$^{D68E;C71S;H267R}$ and MBP did not cleave His-UBQ10 (FIG. 20I). These results show that WTG1 has deubiquitination activity, WTG1$^{wtg1-1}$ lacks deubiquitination activity, and the conserved aspartate (D68), cysteine (C71) and histidine (H267) residues are essential for the deubiquitination activity of WTG1. Thus, WTG1 is an otubain-like protease with deubiquitination activity.

Expression and Subcellular Localization of WTG1

We examined the expression of WTG1 using quantitative real-time RT-PCR analysis. As shown in FIG. 21a, the WTG1 gene expressed in leaves, developing panicles and roots. We generated the WTG1 promoter:GUS transgenic plants (proWTG1:GUS) and examined the expression patterns of WTG1 in different tissues. We observed the GUS staining in leaves and roots of proWTG1:GUS young seedlings (FIG. 21b). GUS staining in developing panicles was also detectable (FIG. 21d). GUS activity in younger panicles was stronger than that in older panicles (FIG. 21d), consistent with the function of WTG1 in influencing the number of panicle branches. During spikelet hull development, expression of WTG1 started from the tips, then spread down the whole spikelet hulls, and finally disappeared at later development stages. Therefore, the expression pattern of WTG1 supports its functions in panicle and spikelet hull development.

We then generated pro35S:GFP-WTG1 transgenic plants and investigated the subcellular localization of WTG1. As shown in FIGS. 5e-g, GFP signal in pro35S:GFP-WTG1 roots was predominantly detected in nuclei. We further asked whether GFP-WTG1 could localize exclusively to nuclei. We prepared cytoplasmic and nuclear protein fractions from pro35S:GFP-WTG1 transgenic plants. Unexpectedly, GFP-WTG1 fusion proteins were present in both the nuclear fraction and the cytoplasmic fraction, although GFP signal in pro35S:GFP-WTG1 plants could not be obviously observed in the cytoplasm (FIG. 21h). Thus, these findings indicate that WTG1 is localized in both the nucleus and the cytoplasm in rice.

Overexpression of WTG1 Results in Narrow, Thin and Long Grains Due to Narrow and Long Cells in Spikelet Hulls To further reveal functions of WTG1 in grain size and shape control, we conducted the proActin:WTG1 construct and transformed it to the wild type (ZHJ). As shown in FIG. 22g, proActin:WTG1 transgenic lines had higher expression levels of WTG1 than the wild type (ZHJ). We then investigated the grain size and shape phenotypes of proActin:WTG1 transgenic lines. As shown in FIGS. 22a-f, proActin:WTG1 transgenic lines formed narrow, thin and long grains compared with ZHJ. Expression levels of WTG1 in proActin:WTG1 transgenic lines were associated with the grain size and shape phenotypes (FIGS. 22d-g). These data further reveal that WTG1 functions to influence grain size and shape.

Considering that proActin:WTG1 transgenic lines showed narrow and long grains, we asked whether WTG could affect cell expansion. We examined the size of outer epidermal cells in ZHJ and proActin:WTG1 spikelet hulls. Outer epidermis of proActin:WTG1 spikelet hulls contained narrow and long cells compared with that of ZHJ spikelet hulls (FIGS. 26a, b). By contrast, outer epidermis of proActin:WTG1 spikelet hulls had a similar number of epidermal cells in both grain-width and grain-length directions to that of wild-type spikelet hulls (FIGS. 26c, d). These results further reveal that WTG1 determines grain size and shape by affecting cell size and shape in spikelet hulls.

Discussion

Grain size and shape are crucial for grain yield and grain appearance in crops. Grain width, thickness and length coordinately determine grain size and shape in rice.

However, the molecular mechanisms underlying grain size and shape determination are still limited in rice. In this study, we isolate a wide and thick grain mutant (wtg1-1), which shows thick, wide, short and heavy grains compared with the wild type. WTG1 encodes an otubain-like protease with deubiquitination activity. Overexpression of WTG1 causes narrow, thin and long grains. Thus, our findings identify the otubain-like protease as an important factor that influences rice grain size and shape, suggesting that it has the potential to increase grain yield and improve grain size and shape.

The wtg1-1 mutant formed thick, wide and short grains (FIGS. 18a-f), indicating that WTG1 acts as a factor that influences rice grain size and shape. The wtg1-1 grains were heavier than ZHJ grains (FIG. 18g), indicating that WTG1 plays a key role in determining grain weight. The wtg1-1 mutant showed short, thick and dense panicles compared with the wild type (FIG. 19e), suggesting the function of WTG1 in influencing panicle size and shape. The wtg1-1 mutation caused an increase in grain number per panicle as a result of increases in both primary and secondary panicle branches (FIGS. 19k, l, m). Previous studies showed that an increase in grain number per panicle usually causes a reduction in grain size and weight (Huang et al., 2009). By contrast, several rice mutants have been described to increase grain size as well as grain number per panicle (Li et al., 2011a, Hu et al., 2015). Here our results show that the wtg1-1 mutant produced heavy grains and increased grain number per panicle.

The WTG1 gene encodes an otubain-like protease. The homologs of WTG1 are found in plant species and animals. Homologs of WTG1 in humans are members of the ovarian tumor domain protease (OTU) family of deubiquitinating enzymes (DUBs). OTUB1 is involved in DNA damage repair and transforming growth factor-b (TGFb) signaling pathways (Nakada et al., 2010, Herhaus et al., 2013). OTUB1 has deubiquitination activity and functions to remove attached ubiquitin chains or molecules from their targets. The OTU domain of OTUB1 has three conserved amino acids (D88/C91/H265) (Balakirev et al., 2003). Similarly, WTG1 contains the predicted catalytic triad (D68/C71/H267) in the predicted otubain domain, suggesting that WTG1 may have deubiquitination activity. Consistent with this, our biochemical data showed that WTG1 can cleave polyubiquitins, revealing that WTG1 is a functional deubiquitinating enzyme. By contrast, the mutations in the predicted catalytic triad (WTG1$^{D68E;C71S;H267R}$) disrupted the deubiquitination activity of WTG1 (FIG. 20I), revealing that these conserved amino acids are crucial for deubiquitination activity. In addition, the protein encoded by the wtg1-1 allele (WTG1$^{wtg1-1}$) did not show any deubiquitination activity, indicating that wtg1-1 is a loss-of-function allele. It is possible that WTG1 might remove ubiquitin chains from its targets and prevent the degradation of its targets.

The wtgl-1 mutant produced wide, thick and short grains, while overexpression of WTG1 caused narrow, thin and long grains. In addition, the wtgl-1 grains were significantly heavier than the wild type, and wtgl-1 mutant exhibited the increased grain number per panicle, suggesting that it has the potential to increase grain yield. Thus, it is worthwhile to test whether WTG1 and its homologs in crops (e.g. maize and wheat) could be utilized to improve grain yield and grain size and shape in the future. It has been known that grain size and shape traits have been selected by crop breeders during domestication. We found that rice varieties contain multiple SNPs in the WTG1 gene region (ricevarmap.ncpgr.cn).

MATERIALS AND METHODS

Plant materials and growth conditions

Grains of the *japonica* variety Zhonghuajing (ZHJ) were irradiated with the γ-rays, and the wide and thickness grain 1 (wtgl-1) mutant was identified from this M2 population. Rice plants were grown in the paddy fields with 20 cm×20 cm density. A total of 48 rice seedlings were transplanted from the nursery bed to the paddy per plot (1.92 m$^2$). Rice plants were cultivated in the paddy fields of Lingshui (110° 03'E, 18° 51N, altitude of 10m, Hainan, China) from December 2015 to April 2016 and Hangzhou (119° 95'E, 30° 07'N, altitude of 12m, Zhejiang, China) from July 2016 to November 2016, respectively. The soil type is the sandy loam soil in Lingshui, while the soil type is the clay loam soil in Hangzhou. During growing seasons, the temperature ranged between 9° C. and 32° C. in Lingshui, and the temperature ranged between 12° C. and 39° C. in Hangzhou (data.cma.cn). Nitrogenous, phosphorus and potassium fertilizers (120 kg per hectare for each) were applied in the rice growth cycle.

Morphological and Cellular Analysis

The ZHJ and wtg1-1 plants grown in the paddy fields were dug out and putted into pots for taking photographs. MICROTEK Scan Marker i560 (MICROTEK, Shanghai, China) was used to scan mature grains. WSEEN Rice Test System (WSeen, Zhejiang, China) was used to auto-measure grain width and length. Grain thickness was measured using the digital caliper (JIANYE TOOLS, Zhejinag, China). Grains from 30 main panicles were used to measure grain weight. A total of 1000 dry seeds were weighed using electronic analytical balance. Grain weight was investigated with three replicates.

Identification of WTG1

To clone the WTG1 gene, we crossed wtg1-1 with ZHJ to produce F$_2$ population. In F$_2$ population, we selected 50 plants that showed wtg1-1 phenotypes and pooled their DNAs in the equal ratio for the whole genome resequencing using NextSeq 500 (Illumina, America). The MutMap was performed according to a previous study (Abe et al., 2012), and the SNP/INDEL-ratio was calculated according to a previous report (Fang et al., 2016). There is only one INDEL that shows a SNP/INDEL-ratio=1. This INDEL has the 4-bp deletion that happens in the exon-intron junction region of the fourth intron of LOC_Os08g42540. The dCAPS1 marker was further developed based on this 4-bp deletion. Thus, LOC_Os08g42540 is a candidate gene for WTG1.

Constructs and Plant Transformation

The primers 099-WTG1-GF and 099-WTG1-GR were used to amplify the genomic sequence of WTG1 containing the 2337-bp of 5' flanking sequence, the WTG1 gene and the 1706-bp of 3' flanking sequence. The genomic sequence was then inserted to the PMDC99 vector using the GBclonart Seamless Clone Kit (GB2001-48, Genebank Biosciences) to generate the gWTG1 construct. The primers 003-CD-SWTG1-F and 003-CDSWTG1-R were used to amplify the CDS of the WTG1 gene. The CDS was inserted to the pIPKb003 vector with the ACTIN promoter using the GBclonart Seamless Clone Kit (GB2001-48, Genebank Biosciences) to construct the proACT/N:WTG1 plasmid. The primers C43-CDSWTG1-F and C43-CDSWTG1-R were used to amplify the CDS of the WTG1 gene was amplified. The CDS was inserted to the PMDC43 vector using the GBclonart Seamless Clone Kit (GB2001-48, Genebank Biosciences) to generate the pro35S:GFP-WTG1 plasmid. The primers proWTG1-F and proWTG1-R were used to amplify the 3798-bp 5'-flanking sequence of WTG1. The promoter sequence was then inserted to the pMDC164 vector using the GBclonart Seamless Clone Kit (GB2001-48, Genebank Biosciences) to produce the proWTG1:GUS plasmid. The plasmids gWTG1, proACT/N:WTG1, pro35S:GFP-WTG1 and proWTG1:GUS were introduced into the *Agrobacterium tumefaciens* GV3101, respectively. The gWTG1 was transferred into wtg1-1, and proACT/N:WTG1, pro35S: GFP-WTG1 and proWTG1:GUS were transferred into ZHJ as described previously (Hiei et al., 1994).

GUS Staining and Subcellular Localization of WTG1

GUS staining of different tissues (proWTG1:GUS) were conducted as described previously (Xia et al., 2013, Fang et al., 2016). Roots of pro35S:GFP-WTG1 transgenic lines were used to observe the GFP fluorescence. Zeiss LSM 710 confocal microscopy was used to observe the GFP fluorescence. Root cell nuclei were marked with 4',6-diamidino-2-phenylindole (DAPI) (1 µg/ml).

RNA Isolation, Reverse Transcription and Quantitative Real-Time RT-PCR

Young panicles of ZHJ and wtg1-1 and seedlings of ZHJ and proACTIN:WTG1 transgenic lines were used to isolate total RNA using an RNA extraction kit (Tiangen, China). RNA (2 µg) was reversely transcribed into the complementary DNA with FastQuant RT Kit (Tiangen, China) according to the user manual. Quantitative real-time RT-PCR was conducted as described previously (Wang et al., 2016). Three replicates for each sample were tested. The list of primers was shown in the supplementary Table 1.

Deubiquitination Assays

The coding sequences of WTG1 and wtg1-1 were amplified from the complementary DNA transcripted from young panicle total RNA using the primers MBP-WTG1-F/R and MBP-WTG1-F/MBP-wtg1-R, and cloned to the vector pMAL-C2 using GBclonart Seamless Clone Kit (GB2001-48, Genebank Biosciences) to construct MBP-WTG1 and MBP-WTG1$^{wtg1-1}$ plasmids, respectively. For the MBP-WTG1$^{D68E;C71S;H267R}$ construct, the primers MBP-WTG1-MutF and MBP-WTG1-MutR1 (with two mutation sites) were used to amplify the first part of WTG1$^{D68E,C71S,H267R}$, and the primers MBP-WTG1-MutF1(with two mutation sites) and MBP-WTG1-MutR (with one mutation site) were used to amplify the second part of WTG1$^{D68E;C71S;H267R}$. These two products were then mixed as templates, and the primers MBP-WTG1-MutF and MBP-WTG1-MutR were used to amplify the complete sequence of WTG1$^{D68E;C71S;H267R}$. Finally, the sequence of WTG1$^{D68E;C71S;H267R}$ was cloned to the vector pMAL-C2 using GBclonart Seamless Clone Kit (GB2001-48, Genebank Biosciences) to construct the MBP-WT-G1$^{D68E;C71S;H267R}$ plasmid. The His-UBQ10 plasmid was constructed according to a previous study (Xu et al., 2016). The MBP-WTG1, MBP-WTG1$^{wtg1-1}$ and MBP-WT-G1$^{D68E;C71S;H267R}$ plasmids were transferred into *Escherichia coli* BL21. Induction, isolation and purification of MBP-WTG1, MBP-WTG1$^{wtg1-1}$ and MBP-WT-G1$^{D68E;C71S;H267R}$ proteins were conducted according to previous studies (Xia et al., 2013). 15 µl of His-UBQ10 was incubated with 2 µl of purified MBP, MBP-WTG1, MBP-WTG1$^{wtg1-1}$ and WTG1$^{D68E;C71S;H267R}$ in 100 µl reaction buffer (50 mM Tris-HCl, PH7.4, 100 mM NaCl, 1 mM DTT) at 30° C. for 20 minutes, respectively. Cleaved ubiquitin products, MBP-WTG1, MBP-WTG1$^{wtg1-1}$ and WT-G1$^{D68E;C71S;H267R}$ were analyzed by SDS-PAGE. Anti-His and anti-MBP antibodies were used to detect the cleaved ubiquitin and MPB-tagged proteins, respectively.

Protein Extractions and Western Blot Analysis

The leaves from pro35S:GFP-WTG1 transgenic plants were used to prepare cytoplasmic and nuclear protein fractions according to a previous method (Alvarez-Venegas and Avramova, 2005). Anti-GFP (Beyotime), anti-Bip (Abcam) and anti-H4 (Active Motif) antibodies were used to detect GFP-WTG1, Bip and histine H4, respectively.

EXAMPLE 3

To obtain OsOTUB1 knockdown transgenic plants, an RNAi strategy was employed. We inserted two same segments of OsOTUB1 coding region head-to-head into the intermediate vector pUCCRNAi which had an intron from GA20 oxidase of potato. With the aid of pUCCRNAi-OsOTUB1, the RNA interference structure was introduced into the plant binary vector pCambia-actin-2300 to generate pActin::OsOTUB1-RNAi construct. Then the OsOTUB1-RNAi construct was transformed into rice using *Agrobacterium tumefaciens* mediated transformation system. Transgenic plants were selected in half-strength Murashige and Skoog (MS) medium containing 50 mg/L G418 and G418-resistant plants were transplanted into soil and grown in the field. qRT-PCR was used to identify OsOTUB1 knockdown T2 homozygous transgenic plants. As shown in FIG. 28a, RNAi silencing of OsOTUB1 exhibited a ZH11-npt1-like phenotype. Furthermore, as shown in FIG. 28b, plants expressing the RNAi showed an increase in the number of primary branches per panicle, the number of secondary branches per panicle, the number of grains per panicle, and importantly, an increase in overall grain yield per plant.

```
SEQUENCE LISTING
Arabidopsis thaliana (AtOTUB1),
soybean (GmOTUB1),
maize (ZmOTUB1),
sorghum (SbOTUB1),
barley (HvOTUB1),
wild einkorn wheat (TuOTUB1)
rice (OsOTUB1)
SEQ ID NO: 1 OsOTUB1 polypeptide
MGGDYYHSCCGDPDPDLRAPEGPKLPYVGDKEPLSTLAAEFQSGSPILQEKIKLL

GEQYDALRRTRGDGNCFYRSFMFSYLEHILETQDKAEVERILKKIEQCKKTLADL

GYIEFTFEDFFSIFIDQLESVLQGHESSIGAEELLERTRDQMVSDYVVMFFRFVT

SGEIQRRAEFFEPFISGLTNSTVVQFCKASVEPMGEESDHVHIIALSDALGVPIR

VMYLDRSSCDAGNISVNHHDFSPEANSSDGAAAAEKPYITLLYRPGHYDILYPK

SEQ ID NO: 2 OsOTUB1 nucleic acid (cDNA from Zhefu802)
atgggcggggactactaccactcgtgctgcggcgaccccgaccccgacctccgcgcgcccgagggcccaagct gccgtacgtcggggacaaggaacctctctccactttagccgctgagtttcagtctggcagccccatttacagg agaaaataaagttgcttggtgaacagtatgatgctttaagaaggacacgaggagatggaaactgcttttatcga agctttatgttttcctacttggaacatatcctagagacacaagacaaagctgaggttgagcgcattctaaaaaa aattgagcagtgcaagaagactcttgcagatcttggatacattgagttcacctttgaagatttcttctctatat tcattgatcagctggaaagtgttctgcagggacatgaatcctccatagggccgaagagcttctagaaagaacc agggatcagatggtttctgattatgttgtcatgttctttaggtttgtcacctctggtgaaatccaaaggagggc tgagttcttcgaaccattcatctctggcttgacaaattcgactgtggttcagttctgcaaggcttccgtggagc cgatgggcgaggaaagtgaccatgtccacataattgccctatcagatgcgttgggtgtgccaatccgtgtgatg tacctagacagaagctcatgtgatgctggaaatataagtgtgaaccaccatgatttcagccctgaggccaattc atcggacggtgctgctgctgctgagaaaccttacattactttgctctaccgtcctggtcactacgacattctct acccgaagtga SEQ ID NO: 3 OsOTUB1 nucleic acid (genomic from Zhefu802)
atgggcggggactactaccactcgtgctgcggcgaccccgaccccgacctccgcgcgcccgagggcccaagct gccgtacgtcggggacaaggtgagatgttgacgcctctctctctttctctgtctctctcgctcgctttgactca
```

-continued

```
tctgcgctttgactcatctgcggtcgatagatttgttcatgtggtagaaatgggtctgaatcgtggtaagacgc
ccagtgttgccatgccagtatccgctagttgtgccagcaggtgaggcgatagatcagtcctgttagtctagttg
gatgctgattgttggtcatcattactgttgtattggtgctccatttctatgtgaattgacattttaaggcgtct
atacaagcagtggggactagaatttggataacaagtaacaatttccccttattgcgtcatcttaaaggataaga
ggagttatcagatgctggattttctcctttattttagtcgtggtgcctggaataatggagattggctgaacaa
gttcatatcagttgtgtccattttcatcctctggatggtcagtccttaagtattgtcaggcgctattgttgtga
gttgtaactgttgtacttgatttttagcttcgttggtgaactgatgtttggaggttcatgcagaagtcagaac
catggggaattagaatttggatgaacagacagcaattacctttcgtgttctcttctaggaaaagaagggtttat
ctgttatcatttgctggatgtgctccttacttaatatttatgcatggaataatagagatggccaaacaagtttg
ctccatagcgtattatgattctaggataaaagtggtgtcatcctttaatcgtcacacctaggacaataaatgtg
aaggacgaacttgttgatgcagaataatagcctatgctagtcaattcagcacagaaactgaggttaaatgtgtc
ccaaaagtttcagttaaggttcacactaggatttacacgaacagaacaaatctgcaaatatagtccatatgaga
aggtggagagctacatacacaatttcatatgaaatggaaaatgatgttggcactaaacttggatttaggtca
agtagttagatatttgatgcctcaaattcattttgttctgttaattgcaagcaccttttcacaatggaggacac
taatgcattgctatgattatctctgtgtttgtacagttattttaggctatcgtatgactttcttctgctttcat
ttgtgttcattattgatatcttttgaaccttgcaggaacctctctccactttagccgctgagtttcagtctggc
agccccatttacaggagaaaataaaggtccatatggatttggcagttataatatgtaatagacatattttggt
tgatctatcgtatcaatggatggtgcttcaatttgttcttataatttcttgcttggtctgcagttgcttggtga
acagtatgatgcttaagaaggacacgaggagatggaaactgcttttatcgaagctttatgttttcctacttgg
tattattttggtctgtttccatacaaactttgactattttataagctgatgatcttatcatttgcttctagga
acatatcctagagacacaagacaaagctgaggttgagcgcattctaaaaaaaattgagcagtgcaagaagactc
ttgcagatcttggatacattgagttcacctttgaagatttcttctctgtaagtctttattgttactttgtgtgg
tcctccttacttatcctgttcaattgctgttttgcaacttatgccagatgtattccctctgaatagtatgaaga
tctgtccgattattttcatgtatgcttgtttgcatttccttttagatgttcctggaataatttttgtatgagc
tagttataatgagagcttgtgcattttcctgtcatgcaacaaattaaatactagtgtctaatccttgtgcattg
ttaataactttgaaaatgattagccttgaagattggtccattatatatatgttcacttgtttcttagttaggat
cactcaccagtcacccttctgaagttcataatgtatcacttataagtaagctagcaaaacaaaatttggactgt
ttgtagccacccagaacccaaatagatggatttcacattattttctactggctttgggagttatttgatcgatg
ctagtacaacgttgaaatttgggtagttgagatgcgttttcacaaaggactccttattggtgcttgatctac
aactggtgttttactttttacaaaaaaatgtaatctccttgcagtgcactcaaattattgcaacctccttcct
tatgttcccaccctcattattttcagatattcattgatcagctggaaagtgttctgcagggacatgaatcctcc
atagggtaaatatcctagagttatatttgtatccttaatgcatatgaccaataatcatgtattaacaacaaagc
aattttgtaattgtttataaagtatggcatgtccatcataaatgttttccttctgtagtgaatctattttgtt
ttcctgtatccttagggccgaagagcttctagaaagaaccagggatcagatggtttctgattatggtttgtaca
tccagatatgtgtagtatgcctttctctgctttgctctcattatttaactatgtcttctttagttgtcatgttc
tttaggtttgtcacctctggtgaaatccaaaggagggctgagttcttcgaaccattcatctctggcttgacaaa
ttcgactgtggttcaggttagctccatacttccatttttatgagggtttgtacagtcgttggggaggtattatga
ggtacaatacctccaggtaccgggagttaccacacataagcataaaatgtgtggtgcctctccaaggaccacaa
gaaatctcttcattatatttgtaatgcacagagcagagagtacagacaaatagacctgcactctgcattttcat
taagtatttagatgtgagattattctatgttttatctctcttgttagtattttttgctctgttttataatggaa
gttcatttcttgggaactgtcattcacaaaacaatgagttatcgtaccctgccatttagtagggaatttggtg
```

```
gtaaaaaaccattaacttttttcttcaattttgtgccttctgcacaaggtgggatagggcatatattgtggaaca aaagagtgcacaatgactaattatttagtatgcatcacactggagtatgatatactagtggaaaggttatggca aaataccatgatagtagcttgatagattagcaggtccgtaagtattttttccaatgataatgttttattcattaa actgtagcaggataaaatctacttatgcaccttttttcatgagtagcaaacaatgcattctctggtttgaaaa acttgttcaagttgcagtgtgttattccaatccgtgtttgtgtgacaagcaattgctggagttactgatcctga gttcaattcaatttgcagttctgcaaggcttccgtgggagccgatgggcgaggaaagtgaccatgtccacataat tgccctatcagatgcgttgggtgtgccaatccgtgtgatgtacctagacagaagctcatgtgatgctggaaata taagtgtgaaccaccatgatttcagccctgaggccaattcatcggacggtgctgctgctgctgagaaaccttac attactttgctctaccgtcctggtcactacgacattctctacccgaagtga SEQ ID NO: 4 OsOTUB1 nucleic acid (cDNA from IR66167-27-5-1-6)
atgggcggggactactaccactcgtgctgcggcgaccccgaccccgacctccgcgcgcccgaggggcccaagct gccgtacgtcggggacaaggaacctctctccactttagccgctgagtttcagtctggcagccccatttttacagg agaaaataaagttgcttggtgaacagtatgatgctttaagaaggacacgaggagatggaaactgcttttatcga agctttatgttttcctacttggaacatatcctagagacacaagacaaagctgaggttgagcgcattctaaaaaa aattgagcagtgcaagaagactcttgcagatcttggatacattgagttcacctttgaagatttcttctctatat tcattgatcagctggaaagtgttctgcagggacatgaatcctccatagggccgaagagcttctagaaagaacc agggatcagatggtttctgattatgttgtcatgttctttaggtttgtcacctctggtgaaatccaaaggagggc cgagttcttcgaaccattcatctctggcttgacaaattcgactgtggttcagttctgcaaggcttccgtggagc cgatgggcgaggaaagtgaccatgtccacataattgccctatcagatgcgttgggtgtgccaatccgtgtgatg tacctagacagaagctcatgtgatgctggaaatataagtgtgaaccaccatgatttcagccctgaggccaattc atcggacggtgctgctgctgctgagaaaccttacattactttgctctaccgtcctggtcactacgacattctct acccgaagtga SEQ ID NO: 5 OsOTUB1 nucleic acid (genomic from IR66167-27-5-1-6)
atgggcggggactactaccactcgtgctgcggcgaccccgaccccgacctccgcgcgcccgaggggcccaagct gccgtacgtcggggacaaggtgagatgttgacgcctctctctctctgtctctctcgctcgctttgactcatc tgcgctttgactcatctgcggtcgatagatttgttcatgtggtagaaatgggtctgaatcgtggtaagacgccc agtgttgccatgccagtatccgctagttgtgccagcaggtgaggcgatagatcagtcctgttagtctagttgga tgctgattgttggtcatcattactgttgtattggtgctccatttctatgtgaattgacattttaaggcgtctat acaagcagtggggactagaatttggataacaagtaacaatttccccttattgcgtcatcttaaaggataagagg agttatcagatgctggattttctcctttatttttagtcgtggtgcctggaataatggagattggctgaacaagt tcatatcagttgtgtccattttcatcctctggatggtcagtccttaagtattgtcaggcgctattgttgtgagt tgtaactgttgtacttgattttttagcttcgttggtgaactgatgtttggaggttcatgcagaagtcagaacca tggggaattagaatttggatgaacagacagcaattacctttcgtgttctcttctaggaaaagaagggtttatct gttatcatttgctggatgtgctccttacttaatatttatgcatggaataatagagatggccaaacaagtttgct ccatagcgtattatgattctaggataaaagtggtgtcatcctttaatcgtcacacctaggacaataaatgtgaa ggacgaacttgttgatgcagaataatagcctatgctagtcaattcagcacagaaactgaggttaaatgtgtccc aaaagtttcagttaaggttcacactaggatttacacgaacagaacaaatctgcaaatatagtccatatgagaag gtggagagctacatacacacaatttcatatgaaatggaaaatgatgttggcactaaacttggatttaggtcaag tagttagatatttgatgcctcaaatttattttgttctgttaattgcaagcaccttttcacaatggaggacacta atgcattgctatgattatctctgtgtttgtacagttattttaggctatcgtatgactttcttctgctttcatt gtgttcattattgatatcttttgaaccttgcaggaacctctctccactttagccgctgagtttcagtctggcag
```

-continued

```
ccccattttacaggagaaaataaaggtccatatggatttggcagttataatatgtaatagacatattttggttg
atctatcgtatcaatggatggtgcttcaatttgttcttataattccttgcttggtctccagttgcttggtgaac
agtatgatgctttaagaaggacacgaggagatggaaactgcttttatcgaagctttatgttttcctacttggta
ttattttttggtctgtttccatacaaactttgactatttttataagctgatgatcttatcatttgcttctaggaac
atatcctagagacacaagacaaagctgaggttgagcgcattctaaaaaaaattgagcagtgcaagaagactctt
gcagatcttggatacattgagttcacctttgaagatttcttctctgtaagtctttattgttactttgtgtggtc
ctccttacttatcctgttcaatttctgttttgcaacttatgccagatgtattccctctgaatagtatgaagatc
tgtccgattatttttcatgtatgcttgtttgcatttccttttttagatgttcctggaataattttttgtatgagcta
gttataatgagagcttgtgcattttcctgtcatgcaacaaattaaatactagtgtctaatccttgtgcattgtt
aataactttgaaaatgattagccttgaagattggtccattatatatatgttcacttgtttcttagttaggatca
ctcaccagtcacccttctgaagttcataatgtatcacttataagtaagctagcaaaacaaaatttggactgttt
gtagccacccagaacccaaatagatggatttcacattattttctactggctttgggagttatttgatcgatgct
agtacaacgttgaaattttgggtagttgagatgcatttttcacaaaggactccttttattggtgcttgatctaca
actggtgttttacttttttacaaaaaaatgtaatctccttgcagtgcactcaaattattgcaacctccttcctt
atgttcccaccctcattattttcagatattcattgatcagctggaaagtgttctgcagggacatgaatcctcca
tagggtaaatatcctagagttatatttgtatccttaatgcatatgaccaataatcatgtattaacaacaaagca
ttttttgtaattgtttataaagtatggcatgtccatcataaatgttttccttctgtagtgaatctattttgttt
tcctgtatccttagggccgaagagcttctagaaagaaccagggatcagatggtttctgattatggtttgtacat
ccagatatgtgtagtatgcctttctctgctttgctctcattatttaactatgtcttctttagttgtcatgttct
ttaggtttgtcacctctggtgaaatccaaaggagggccgagttcttcgaaccattcatctctggcttgacaaat
tcgactgtggttcaggttagctccatacttccattgtatgagggtttgtacagttgttggggaggtattatgag
gtacaatacctccaggtaccgggagttaccacacataagcataaaatgtgtggtgcctctccaaggaccacaag
aaatctcttcattatatttgtaatgcacagagcagagagtacagacaaatagacctgcactctgcattttcatt
aagtatttagatgtgagattattctatgttttatctctcttgttagtattttttgctctgttttataatggaag
ttcattttcttgggaactgtcattcacaaaacaatgagttatcgtaccctgccatttagtagggaatttggtgg
taaaaaaccattaacttttttcttcaattttgtgccttctgcacaaggtgggatagggcatatattgtggaacaa
aagagtgcacaatgactaattatttagtatgcatcacactggagtatgatatactagtggaaaggttatggcaa
ataccatgatagtagcttgatagattagcaggtccgtaagtattttttccaatgataatgttttattcattaaa
ctgtagcaggataaaatctacttatgcacctttttttcatgagtagcaaacaatgcattctctggtttgaaaaa
cttgttcaagttgcagtgtgttattccaatccgtgtttgtgtgacaagcaattgctggagttactgatcctgag
ttcaattcaatttgcagttctgcaaggcttccgtggagccgatgggcgaggaaagtgaccatgtccacataatt
gccctatcagatgcgttgggtgtgccaatccgtgtgatgtacctagacagaagctcatgtgatgctggaaatat
aagtgtgaaccaccatgatttcagccctgaggccaattcatcggacggtgctgctgctgctgagaaaccttaca
ttactttgctctaccgtcctggtcactacgacattctctacccgaagtga
```

SEQ ID NO: 6 OsOTUB1 promoter sequence from Zhefu802
```
gagttgaagttgttgctgctgtcataagtactatctgctaaatgggcacactcctagcattattagaactgaga
aatatcccaagcaatgaaagcgacaaaaaagtacccgtttgaagacatgattgacatggtcacatcaaacaccg
gacatcaacatctaaatgtacataacaaggccaaaataatttttcgatgctggttggtgctaccaagtcccacgt
atgatacttaagaatcaatcatgaatattacaaatcaagtcaaactacgttatgtattgaactcttataattac
tgcaacatatcacactggaatttcctatggtaattcctcgccagccttatcctacccatcccttgcagtatatt
aagagcatcaacaacaaacatgattcaagacaacttttattaacactgaacaacataaattgggaacaaaacaa
```

-continued accacttggaggcatgattaggataatcggtattaaagaactggacatcacaattcacaactagatgttgaaat
aataccctgtctcttctttggctcatggcaggtgtcagtgaaatatactgatgctccaagagagctggaagcacc
gtttccacgtaatcaaaatgtccttttcgtttgctgcaatcaaccttaaagggctcttttgatgctatctcttc
aggcatgtcctttacaacttccacataacctctggtttgctcaatgaagtaatcaacatcgaaaacgtctgcaa
atccactgacagagaataccaataagtgatgaactaccttttgaacagaaataaactgcataactacaagtagc
acagtcgttcatcttgtagagtgattctcatacctagattcattccagtaggcagcaacctcaaacttgggcag
aaccattgttgcgttgagaaggcgcgcaaccgcaattccatcacatagctgaagaaacattcggaagaataatt
acaaccaggagtaacataataacatagccagttgaaatcacattcgccttgcaatgtgaaaattttcataaata
atctgaaaatttagttatgccactatatatcatgcaacctgcctccacgacattttaatcatggagtagaagat
aaaacatatgatcccccctcattgaccctactatcttactacttgtgcatggccgaacgatctaacagcgaaatc
cagaaagccaacactcatttgatcccactaacaacggaagagagaaacgctagccgagatcgcttaacgtacat
cgcgtcgcagctggttgagcccgccgtagcagtcgatccggatgtacccattcctcctcgacggagctgcagaa
gaagaggaggttcaaaaccgcaatcaccaccacagtctcaagcagagatgtccactacccggatccttaaaccc
aaaccacaaatcacggcgaggtctcacccggcattgccgcccgccaccacccgcacgaccgccactccgccacc
cgccgctgcgcccatatgacccgcgaccccgacgccgacggcgactcctccctaaagaccaaaagcgagtaagc
gagatccgtaagcttctggaacaatctcgagcatcagctgcaagaggtgaggctgggccgcgtacctggaggtg
ggaagagtgaagaagaaaggcggagaggagggtggagagaggaggaagtagagcgcggggcgaggaagatgac
cggtaggaggatgcggacgcggctgcgcgccaccacgccgccggcgacgccgacgacgacatcgcctcgccgc
gagaagcactggatctgatcggccgccgcctccacgccggagtggagagcgtatataagctcgtcagaatgtgg
gcccgtggctatgtgggcccaccatgtcatcgacgcttatcaagatcgagcggtggcgtgaggaaaccggtagg
ggtgggggggctaaccaatcggaaacgcgtaataactcacccgcggttcactttctccttatgacacgtgggcc
catctcttcctggacccacctgtcagttacccttacggcctccactctgaggatctaaacgtaaaaacgaattt
atcggagggcttatccgcgaggggaaaaaaacgcgcactttatttctcgccttcgccgagatctcggaagagaag
aacacgcaccgcggggagaggggagagaagcggaaagctccaccgaatcgaagcccccacacacgcgaagctgg
cgcgggaggcggccgacgcgagcgcccggaagcgcaaggcggcgacggcggcggggagggcgacgccgcggcg
acggtcccggaggaggcggtgatgggggaggcggcggcggcagccgcggccccgagccggtcgtcgaggggggg
aggagggggggggagggggttgaatcctaaccctagcggcggtggggaggaggtggtggagggtgctcggact
ccgtgtcggtcgagctctcg SEQ ID NO: 7 TuOTUB1 cDNA sequence
Atgggcggggactactaccacgcctgctgcggcgacccggaccccgaccacaagcccgagggaccccaggtgcc
gtacatcggtaacaaggaacctctctccgccttagcagcagagttccagtctggcagcccccattttacaggaga
aaataaagttgcttggtgaacaatatgatgctttaaggcgaacacgaggagatggaaactgcttttatcgaagc
tttatgttctcctacctggaacatatcctagagacacaagatagagctgaggttgagcgcatcctaaaaaacat
tgaacagtgcaagatgacactttcaggtcttggatacattgaattcacttttgaagacttcttctctatgttca
ttgaggagctgcaaaatgttctgcagggacacgaaacttctatttgggcctgaagaacttctagaaagaaccagg
gatcaaacgacttctgattatgttgtcatgttctttaggtttgttacctctggtgaaattcaaaggagggctga
gttcttttgaaccatttatttctggcttgacaaattcgaccgtggctcagttttgcaagtcttctgtggagccaa
tgggcgaggaaagcgaccatgtgcacattattgctctgtcagatgcgttaggggtgccaatccgcgtgatgtac
ctagaccgaagctcctgtgacacaggcaatctaagtgtgaaccaccatgatttcattcctgcagccaattcctc
tgaaggtgatgctgcaatgggattaaatccggctgaggagaaaccttacattactctgctctaccggcctggtc
actatgatattctctacccaaag -continued SEQ ID NO: 8 HvOTUB1 cDNA sequence
Atgggcggggactactaccacgcctgctgcggcgaccccgaccccgaccccaagcccgagggaccccaggtgcc gtacatcggtaacaaggaacctctctccgccttagcagcagagttccagtctggcagccccattttacaggaga aaataaagttgcttggtgaacaatatgatgctttaagacggacacgaggagatggaaactgcttttatcgaagc tttatgttctcctacctggaacatatccttgagacacaagacagagctgaggttgagcgcatcctaaaaaacat tgaacaatgcaagaagacactttcaggtcttggatacattgagttcacttttgaggacttcttctctatgttca ttgaggagctgcaaaatgttctgcagggacacggaacttctattgggcctgaagaacttctagaaagaaccagg gatcagacgacttctgattatgttgtcatgttctttagatttgttacctctggtgaaattcaaaggagggctga gttctttgaaccatttatttctggcttgacaaattcgaccgtggttcagttttgcaagtcttctgtggagccaa tgggcgaggaaagtgaccatgtgcacattattgctctgtcagatgcgttaggggtgccaatccgcgtgatgtac ctagaccgaagctcttgtgacacaggcaatctaagtgtgaaccaccatgatttcatccctgcagccaattcctc tgaaggtgatgctgcaatgggattaaatcctgctgatgagaaaccttacattactctgctctaccggcctggtc actatgacattctctacccgaagtga SEQ ID NO: 9 ZmOTUB1 cDNA sequence
atgggcgacgttccacaggcgccgcacgctgcgggaggtggagaagagtgggcggggccggaccctaaccctag cccgagcctcggcggctgctcggaccccgtgtcggtggagctctccatgggcggggactactaccgcgcctgct gcggcgagcccgatcccgacatccccgaggggcccaagctgccgtgcgttggggacaaggaacctctctcctct ttagcagctgagtttcagtctggcagccccattttacaagagaaaattaagttgcttggcgagcaatatggtgc tttaagacgtacacgtggagatggaaactgcttttatcgaagctttatgttttcctacctggaacacatcctag agacacaagacaaagctgaggctgatcgcatcatggtaaaaattgaggaatgcaagaaaacactcctctctctt ggatatattgagttcacttttgaggacttcttttcgatattcattgaactgctggaaagtgttctgcagggaca tgaaactcctatagggtttgtcacttctggtgaaattcaaaggaggctctgacttctttgaaccgttcatatctg gcttgacaaattcaaccgtggttcagttctgcaaggcttctgtggaacctatgggtgaggaaagtgaccatgtg cacataattgccctatcagatgcactaggcgtaccaatccgtgttatgtacctagaccgaagctcgtgtgacac tggcaacctgagcgtgaatcaccacgatttcatcccgtcggccaatgattcggagggtgatgcggccacgacac ctgctcctgccacagagaaaccgtacatcactttgctctaccgtcctggccactacgatattctctacccaaag tga SEQ ID NO: 10 SbOTUB1 cDNA sequence
atgggcgacgtgccccaggcgccgcacgccgcggaaggaggaggaggaggactggaggaggggcggtgcccga ccctaaccctagcccgagcctgagcctcggcggctgctcggaccccgtgtcgctggagctctccatgggcgggg actactaccgcgcctgctgcggcgaccccgaccccgacatccccgaggggcccaagctgccgtgcgttggggaa aaggaacctctctcctcttagcagccgagtttcagtctggcagccccattttacaagagaaaattaagttgct tggcgaacaatatggtgctttaagacggacacgtggagatggaaactgcttttatcgaagctttatgttctcct acttggaacacatcctagagacacaagacaaagctgaggctgatcgcatcatggtaaaaattgaggattgcaag aagacgctcctgtctcttggatatattgagttcacttttgaggatttctttgcgatattcattgatatgctgga aagtgttctgcagggacatgaaactcctatagggtttgtcacttctggtgaaattcaaaggaggtctgacttct ttgaaccattcatatctggcttgacaaattcaactgtggttcagttctgcaaggcttctgtggaacctatgggt gaggaaagtgaccatgttcacataattgccctatcggatgcactaggtgtacctatccgtgttatgtacctaga ccgaagctcgtgtgatactggcaatctgagtgtgaatcaccatgatttcatcccttcgtccaatgcttctgagg gtgatgctgcgatgacatctactcctgacgctgagaaacccttacatcactttgctctaccgtcctggtcactat gatattctctacccaaagtga -continued SEQ ID NO: 11 AtOTUB1 cDNA sequence
atgcagaatcagattgatatggtgaaggatgaagcggaagtagctgcatcgatttcagcaattaagggtgaaga atggggaaattgttcatcagtggaagatcaaccatcttttcaagaagaagaagctgctaaagttccttatgttg gtgataaggaacctctgtctagtttagctgcagagtatcaatcagggagtcccattttgctggagaagattaag atactggacagtcaatatatcggaatccggcgaacaagaggagatggaaattgcttcttccgaagttttatgtt ctcttaccttgagcatatattggaatcacaagatcgtgctgaagtcgatcgtatcaaggtcaatgttgagaaat gtagaaagactctgcaaaacttaggttatacagattttacatttgaggacttcttttgcgttgttccttgagcaa ctagatgacattctccaaggaactgaagagtctataagctacgatgagctggttaacagaagtagagatcagtc agtctcagattacattgtaatgttcttttaggtttgttactgctggtgatatacgaacgcgtgccgatttttcg agccttttataacaggcttatcaaatgcaacagtggatcagttttgcaagtcctcggtcgaaccaatggggaa gagagtgaccatattcacataactgctttgtcggacgcacttggtgttgcaatccgtgttgtgtatcttgaccg tagctcatgtgatagtggggcgtcactgtgaatcatcatgactttgttcctgtgggcattaccaatgagaaag atgaagaagcttctgctccatttataaccttgctgtatcgtccaggccattacgatatcctctaccccaagcca tcttgtaaggtatcagacaatgtggggaaa SEQ ID NO: 12 GmOTUB1 cDNA sequence
Atgcagagtaaagaagctgttgtggaagatggggaaataaagagtgtgactgctgtagggtctgaaattgatgg gtggaccaattttggggacgatgacataatgcagcagcagtatacaattcagtctgaagaggctaagaaagttc catctgtgggcgacaaggaaccactgagtagcttagctgctgaatataaatcaggcagtcctatcttgctggag aaaataaaggtgcttgatgagcaatacgctgccattcgtcgtactcgaggagatggaaactgcttctttcgaag cttatgttttcatatcttgagcatgttatgaaatgtcaagaccaagcagaagttgatcgtatccaagccaatg ttgaaaaagtagaaaagcactgcagaccttgggttatgcagacttgacttttgaagattttttgcgttattc cttgagcagctggaatctgttattcaaggaagagacttccataagtcatgaagagcttgttcttagaagccg agatcagtcagtatctgattatgtcgttatgttcttcagatttgttacctctgccgcaatacaaaagcgcacag aatttttgaaccattcatactaggcttaactaatacaacggtcgagcagttttgcaaatcatctgttgaacca atgggtgaagagagcgaccatgtgcacattactgccctttcagatgcattgggcattccagtccgtgttgtgta ccttgaccgcagctcaagtgatactggtggtgtcagtgtaaatcatcatgatttcatgccagtggctggtgatc tcccaaatgctagttgcagctctgaaaagaacattcctttcatcacactactatatcgtcctggtcactatgac atcctctatccaaaatga SEQ ID NO: 13 brassica napus cDNA sequence
Atgcagaatcagaatgatacggtgaaggatgatgcggagctcgctgcttccatctcggctgaacaatggggatg ctgttcagtggaggaaccatcttttcaagatgatgaagctgctaaagttccttatgttggtgataaggagccta tgtctagtttagctgcagagtaccaagcagggagccccattttgcttgagaagataaaggtactggacagtcaa tatgttgcaatcaggcgaacaagaggagatggaaactgcttcttccgaagttttatgttctcttaccttgagca tattttggaatcacaagatggtgctgaagttgaccgtatcaagctcaatgttgaaaaatgtagaaagaatctgc agaacttaggctacacagatttcacatttgaggacttcttttgcgttgttccttgagcaactagatgacatcctc caaggaggcgaagagtctataagctatgatgagctggttaacagaagtagagatcagtctgtttccgactacat tgtgatgttcttcaggtttgttactgctggtgaaataaaaacgcgtgctgagttcttcgagccttttataacag gattatctaataccacagtggatcagttttgcaagacatcagttgaaccgatggggaagagagtgaccatatt cacataacagctttgtcggacgcgcttggtgttgcaatccgggttgtgtatcttgaccgtagctcatgtgatac tggaggtggtgtcactgtgaaccatcacgactttgttcccgttggcagtggcactaatgagaagaagaagctt cttctgctgctcccttataacattgctctatcgtccaggccattacgatatcctctaccccaaggtattggag aatgtggaaaaatga SEQ ID NO: 14 TuOTUB1 amino acid
MGGDYYHACCGDPDPDHKPEGPQVPYIGNKEPLSALAAEFQSGSPILQEKIKLLG

EQYDALRRTRGDGNCFYRSFMFSYLEHILETQDRAEVERILKNIEQCKMTLSGLG

YIEFTFEDFFSMFIEELQNVLQGHETSIGPEELLERTRDQTTSDYVVMFFRFVTS

GEIQRRAEFFEPFISGLTNSTVAQFCKSSVEPMGEESDHVHIIALSDALGVPIRV

MYLDRSSCDTGNLSVNHHDFIPAANSSEGDAAMGLNPAEEKPYITLLYRPGHYDI

LYPK

SEQ ID NO: 15 HvOTUB1 amino acid
MGGDYYHACCGDPDPDPKPEGPQVPYIGNKEPLSALAAEFQSGSPILQEKIKLLG

EQYDALRRTRGDGNCFYRSFMFSYLEHILETQDRAEVERILKNIEQCKKTLSGLG

YIEFTFEDFFSMFIEELQNVLQGHGTSIGPEELLERTRDQTTSDYVVMFFRFVTS

GEIQRRAEFFEPFISGLTNSTVVQFCKSSVEPMGEESDHVHIIALSDALGVPIRV

MYLDRSSCDTGNLSVNHHDFIPAANSSEGDAAMGLNPADEKPYITLLYRPGHYDI

LYPK

SEQ ID NO: 16 ZmOTUB1 amino acid
MGDVPQAPHAAGGGEEWAGPDPNPSPSLGGCSDPVSVELSMGGDYYRACCGEPDP

DIPEGPKLPCVGDKEPLSSLAAEFQSGSPILQEKIKLLGEQYGALRRTRGDGNCF

YRSFMFSYLEHILETQDKAEADRIMVKIEECKKTLLSLGYIEFTFEDFFSIFIEL

LESVLQGHETPIGFVTSGEIQRRSDFFEPFISGLTNSTVVQFCKASVEPMGEESD

HVHIIALSDALGVPIRVMYLDRSSCDTGNLSVNHHDFIPSANDSEGDAATTPAPA

TEKPYITLLYRPGHYDILYPK

SEQ ID NO: 17 SbOTUB1 amino acid
MGDVPQAPHAAEGGGGLEEGAVPDPNPSPSLSLGGCSDPVSLELSMGGDYYRAC

CGDPDPDIPEGPKLPCVGEKEPLSSLAAEFQSGSPILQEKIKLLGEQYGALRRTR

GDGNCFYRSFMFSYLEHILETQDKAEADRIMVKIEDCKKTLLSLGYIEFTFEDFF

AIFIDMLESVLQGHETPIGFVTSGEIQRRSDFFEPFISGLTNSTVVQFCKASVEP

MGEESDHVHIIALSDALGVPIRVMYLDRSSCDTGNLSVNHHDFIPSSNASEGDAA

MTSTPDAEKPYITLLYRPGHYDILYPK

SEQ ID NO: 18 AtOTUB1 amino acid
MQNQIDMVKDEAEVAASISAIKGEEWGNCSSVEDQPSFQEEEAAKVPYVGDKEPL

SSLAAEYQSGSPILLEKIKILDSQYIGIRRTRGDGNCFFRSFMFSYLEHILESQD

RAEVDRIKVNVEKCRKTLQNLGYTDFTFEDFFALFLEQLDDILQGTEESISYDEL

VNRSRDQSVSDYIVMFFRFVTAGDIRTRADFFEPFITGLSNATVDQFCKSSVEPM

GEESDHIHITALSDALGVAIRVVYLDRSSCDSGGVTVNHHDFVPVGITNEKDEEA

SAPFITLLYRPGHYDILYPKPSCKVSDNVGK

SEQ ID NO: 19 GmOTUB1 amino acid
MQSKEAVVEDGEIKSVTAVGSEIDGWTNFGDDDIMQQQYTIQSEEAKKVPSVGDK

EPLSSLAAEYKSGSPILLEKIKVLDEQYAAIRRTRGDGNCFFRSFMFSYLEHVMK

CQDQAEVDRIQANVEKSRKALQTLGYADLTFEDFFALFLEQLESVIQGKETSISH

EELVLRSRDQSVSDYVVMFFRFVTSAAIQKRTEFFEPFILGLTNTTVEQFCKSSV

EPMGEESDHVHITALSDALGIPVRVVYLDRSSSDTGGVSVNHHDFMPVAGDLPNA

SCSSEKNIPFITLLYRPGHYDILYPK

-continued

SEQ ID NO: 20 brassica napus amino acid
mqnqndtvkddaelaasisaeqwgccsveepsfqddeaakvpyvgdkepmsslaa eyqagspillekikvldsqyvairrtrgdgncffrsfmfsylehilesqdgaevd riklnvekcrknlqnlgytdftfedffalfleqlddilqggeesisydelvnrsr dqsvsdyivmffrfvtageiktraeffepfitglsnttvdqfcktsvepmgeesd hihitalsdalgvairvvyldrsscdtgggvtvnhhdfvpvgsgtnekeeassaa pfitllyrpghydilypkvlenvek SEQ ID NO: 21 TuOTUB1 promoter sequence:
cagtaaaaagtttaaaattgacaacacaccaagaattcagcaatcaaatcaatgacacaatgaatagaaaagtt agcaatgcaattttttaggttcataagatattgcgagtaaccatgaaatcattgttgcattgcaaagagctaact atagaggtaacaccaactaagttttatactactagttatctcaatggttttattctccgcaaatctgcatcttgc ggattatacctgtgaaaagtattcttggactgatgacaatcattagaacagaacccagcacaaatttatcagta ggtcatcatatcacaaagcagacaacaaatcaagattaggtaagttgatgaagtggttggagttagtaaagaag tcatgtaaccaacaaatttagggcacgtgaaagtcttgcattgcatgaactgacatcttagttaaacaaagtta tcactcaagaatatagcgtatcggtgtatttattccaattatgtgagctcaagatgattgcaaagggaaagggg gaagggctataaagctatgaagataaacttttatatgagagtgtacagttttggatagtaacgcagcatgccaaa ttcgaaggttgatagtcagaatcgtgattctgaatcggatcggggccctaatggtagggtcgcatatcgcagaa tcttcactacgaaaatcacagaaacatagattttaccaaacagaatcatagaatcatgagttagtttggattgt caagtcgtagaatcgtacaacagaatcgcgattctgactacttttaacatattcactcctaatttgcactgaga aaaaaagataaatacagggaaataatttgcatggttacatcacacatctaaacaaagacaaatacgacaaata catatgattttctacactgcttgatgatactatgtctcatgtatgccaacttaagaatgcagtcaatgacacca cgaatctgcttcatacaaggaacacctactactgcaatatatattttttcgaaaggattactgcaatctatctac tttaagttacaggtagatatacgtgccctcgaaagatataagaattttagcactggagaacttcatcgccagcc ttattactccctccaatccgaattaattgatgcagcctctatacaatgacattatgctaagatcggagggagta ttctatatccatccttcacattatgctaagatcctcagcagcagatacaactcaagacctttgatgtgaacaat gaacaaaatagcttggaaaataataaatggacagtatgactaagataattggtattatgaaaatggaaagtaga tttcaggtatcaactagataactcggcaatacctatcttttctttggctcatggcaggtgtcagagaaatgtat cgatgttctaaaagagctggaagaactgtttctacataatcaaaatgtcctttccgttttcggcaatcgaccttt aaatggctcttttcaacgatatctcctcgggcatatccttcaccacttccacataacctctagtttgctcaatga agtgatcaacatcaaacacgtctgcaaaaccactgacaaagcattctgataagcacatgattagtttttgaaca gaagtgcactacatagaaacaacagtagaagccttcgtttcaccccaagtgactccagtacctagactcattcc agtatgcagcaacctcaaacttgggcagaaccattgtcgcgttcagaagacgtgcaaccgcaattccatcgcac agctgcagaacaattgcgccagaggccagaataattacaaccgaggaacttgtaacatagccaatcgacaacgc acaccactgcacaacattctatacaatgctacctatttcctaaagctaaatcatatgatcccactattgactcc acgagcctatacttgtcacttgtgcattcagtacatggccagatgatccaagtttaacagtacatacataagaa aaggaagtcttactccattacaaggaggataaaaccaagtttaacatacatcgcgccgcagctggttgaggccgc cgtagcaatctatcctgatgtagccattcctcgtcgacggagctgctgaaggagagcggggacagaaaccaatc atcaccacaacccaagccaatcctaaactctgaccgaaaaccacgaagcacacaaggcctcaccgggcattgcc gtctgccaccactcgcacggccgccactccgccaaacgccgctgcgcccatgagccgcgaccccgacggcga atgctccctgcgggaaaatcccaatgcgggggatctgtaacttccaggaagagtccagaagaacctggtatggc aggtcggggcggggcgcgtacctggaggccggtagggcgaagaaggatggggaggagcgcggggaggcgaggaa gaagaagagggcggcggcgaggaagagggccgggagaaggaggcgtatgtggtggggggccgcgcctgttcgcc -continued accacgcccccgccgacgccgctacctacgagaagcactggatctgatcgccggcggcgacgcggcgtcaccg
cgagcacggaagtacgacctgtccgccagaatgagggtcccacatgtaaataagggaccacctgtcatggatgg
ttatccagatcgagaggtggcgtgtgggaatggagcagggtggtggtccagcaggaacagcgttaacttcctga
aaatggaacgcgggcccgctgcgtcagccccacatgtcagggtcacgaagtacaccatgaaggtggatgacgcg
aagggcttatcttcaaaacgacacgcacatacccttttgtttcgcctgcggcgagatctccgactgccacaaaag
cgaaggtctcctccgcccgaatcaaagccgtcgtctcgaannnnnnnnnnnnnnnnnnnnnnnnnnnnnnnnn
nnnnnnnnnnnnnnnnnntccggcccccgaggacgcggcc SEQ ID NO: 22 HvOTUB1 promoter sequence:
aatacagaaagtacgaaactcaggtaaccacgaggaagttgcatcacgtctcctcaggtttaagtcattgactt
gggagtcctcggtgttcacacaaggtcaagatatctactggcttttcccccttcagagacagcaaagaaagcac
gcccaccactgtcctttctaacatgtgatttataggttgtccaatgctgtcaacactgcaacaaagcgatggcc
gctggtatgtgcagcatgtttgaaatcaaaatgcttgcatcagtatatgaaaatgtaacgatgagaagaggt
atacactggggagtatgattagtgaatgaagggaggttattcttccatccgctgcttgcttgagctgccaaacg
gaaggaatgagcagcggaataccaagtgtcatgtacaccttccttacagttaaagatcgcatgctcaacaccaa
tttgtttaagcttgcttgcttgccacgacgtaaaatatgaaaataaccactagtcacatagtccctccattctt
aaacattccaaccgtccgaaaatacttgtcatatgaattcatatatctagatgtaatttagttctagatatatc
cattttatatatttgtgcgataagtaatttcaggcggagggagtataagtttttaaagatttcactagggac
tacatacggatgtatatagacatactttagagtatagatacatccattttgctttgtatgcagtctgtagtgga
atctctaaaaaagacttatatttaagaacagagggagtagattactagcccaaacacggagtgatgaagaacat
ggcccgtgcaattggaagtgttgtttaatgtatcaaccgccagtgggtgattgatgcacactccactcgttggc
gcagaatgcatcatgcattgcatttggggtttctagttaagcataactctcattgacttgttaacaattgagat
ggacagttgttggaatcgattctccttctagaagcaaaattgaccagggcaacaagaaccaaacaacttcctag
ccaaagaaatgaataagcagctaagtatgtaaacattgcgatgcacacaataagaatccggttatggaacccaa
ctctacaacaaactatgtaaatgtggtgtatttcccagtgatggatcagattaatcacaggccattacaccacc
tgacagtagatcagtagctagtttctgagcaatgcaaaattcaaaaattatacatatatcccccccaaaaaattt
cctgcttgttagttatctaagaacaaagttttcaacctatctatacccctcaaatgttgagtttgggcctgggc
atatttccagttgcaaaaggaaatgccagaatgattcgctaggtagtaagtgtgcgtgtacatgtctgagctac
tatctgaactcaccgaaaacagtatccagaagaggccatgatgcattgttgtatgagtgataattgctctctga
atcaagaggatgtgcagcttgcgactctgatgaagaacggtttcttctgaagggcattacattatgcccactgc
agtagcaactcagccacaatgcgatctattagtcgctaccgataagaaggtggctgtgtagattggtccttgtg
ttatatgggctcacttgtgcagttgtgctacaacttgaactcacagaagcaatgttcagggagagctaatcccc
tccccagaatataatcctctcgatgagcatcccacatggccttagctagttggtctcctgccagtccagcagcc
gtgtagtttgcgaaggccctcctactcaagaccaatgtcttctgtagcccttgcattgttctcattgcagttac
catcttatccatatttccaaagaacgtggcaacataagcatcgctgttgactgaaacatagtagtcgagagcag
cttttgtgttgccatgcatcctctcaaaatcctcatgagtcaggagagacgatttagtatacatattttttgtag
atcgaagtgaagccctcgagttccattagcccatccccagcagctaaataaatgtttgtctctgtaggaatacc
tagtgcttggaggataaatgctgtttcacttggtgttagagggcactttccacggttcctccacagatgagcag
catcaccaatcaatacattcctgtcctccccacgtgcagcttcaatcgcatccagtgatttggaagaaagggca
ctgtattcacatcgactgtaggcaaccatatctggttcaaatctaaggtgaagtgataagaaaggttttggtat
tgcttggagaagcttcatagctttggcttctaccttcttgttcaactggagtgcattgtagcaaccttggcagt
aacaagctttcgcatgtgatggatatctgagaaaatacaggcatatacatcagcatggggaaaaggcagatcca aggtgaataattacaacagcgaaaagtttaaaattgacaacacaccaagaagtcagcaattaaatcaatgacac gatgaataggaaatttagcaatgcaattttttaggttcataagaaattgagagcaattaaatcataagacattgt tacatcgcaaagaactaactacagagtaacattaactaagtttacacaactagttatcttaaaggctttattct ccgcaaatccgcatcttgcagattatacctgtgaaaagtcttcttggactgatgacaatcattgaacagaaac cggcacaaatttatcagtaggtcatcgtatcgcaaagcagacaacaaatcaagattaggtaagttgaagtggtt ggagttagtaaagaattcatgtaaccaacaaatttaaggcacgtgaaagtcttgcattgtatgaaactatgaat tgacatcttagttaaacaaagttatcacgcgatagtatagtgtatcagtgtatttattctaattatgcatagtt tttaaggagtcgaggcgttttaaggcgttgagggggggct SEQ ID NO: 24: .ZmOTUB1 promoter sequence:
tcaatacatttggaaagtacaaatgaacatcacatcaaacatgtacaaacattagaacacaactcaaaagatgt agtattaaataaaggagaatgaggtcaagttataaaatgaactaatcctaattaggagttgattactctataag tgtttggaacatatctcaaaaaggtaaagtagtaatttaaacaagaaagagattaaatcataagatggacttat ctcatttaggaatttgattattctttaagtgttatctataattacataacctaattctattcatttcattgaga cctaaaagttaaaccaaaatgaattcatgtaacacatattattaatctcacaagattaaatatattttaactcc tagggcttttcattttttatttatttcattaaatgaataaatcaacatatacattaaacttatactctaggtgtaa aattaaagtgcacagaccatagatgaacttaatttatttggacagagaataatattatgaacattttacaattt gaaccactaaatttggagttcatatgaaaaagatatgaaataaacaagttttgaagttgaaatatgaaattagg gctaaatttgtgattaaataaaagtacagggggctatccaaaagaaaccaggggcctacgcgctaaaacagagg acgtcggttgatttcctaaaagccgagggtctcttaagtaaaacttacacgtgaaggggggtacggggtaacct cggccatcagatcagagatcaacgacaaggattagatcgcgtgggcgcgggcgcgtggacgcgactaacaggcg gggacggggcgtcagcgagtcagggcgggctgaccagccgggcccaggggcaggggcgcaggtgagggggagaa gggagagcggccggatctagatcggagcgctgcgattagatccgcaataatgaaacctaaaccgcacgatctcg gacgaacgcccgagatctatcgactgggggcggacacaaacgcggtggcgccgctcggtcccgcgccgacagtg agcggtggcgaagctctctgttcgcgcgggcagagcgagagagagggcgagggggtttggctgagggcgcaagt gagcgaggggaggtgggcgagcagggcgcggggctcaaaagggacgcaggcgcggggacgtggccggagaacgc gcggacgtgggcgcgtccaccgcgggggatcgtgggcgggaggttggggatgaccgacaggtgggctcggtggg acagagagagagagagagcgggcgcggagggaaaggaacgacgtcgacaactcggtcccacagagcagcgag agaggggagagagggcgcgctggagagacagacagacaggcggggtccgcctgtcagcgtgggcgggcgcggg cgcgcgcgcaagctgggccgacttgggctaactgggccagattggcttttctatttccagggaatttctattt gcttttttttatttattttctctagggttttcaattcaaattcaaatctagtttcaaattcaaaccaaatcaaac atgtgcaacaattcaagaatatttaggctcaatatgatgcaacatttcatgactcatatgttttgggcaaaata aaataaataatccctcactaattaaactaaccctaatcaaaagaggaagaggggggagagaaactagagagagag aaactagagtgagatagagaagagtaacacctgaatttggatgataatatgaaagaaatttttataccccaaatt cagggtgttacaatcgctgtgcactattttttgcgcgcgctgcacaggcgctgggcgtggggagggtgaagtcg tggtagcatcaggtgcccacattagattcttaatagattattattactagttggttgctcatactttgctacgg ttattatatactccatccgttccataatataaggcgtaaccattttttgttcttgtccccacaatataagacat gctctctctatgcatacgtacattaatgcagtgatatagagaaaattaaatatatttcttggtatttgaaccag aggtggttacgccttatatactaggacagagggagtatcatataaataggtatttagatatttattcaaatgta actattgtttatttctaaacactaaggtatgtgtggtctggtggttagctccaaatttctgaagcagggggcgt gggctcgagtagttgccctgcattttttttgcgcggtgtgatgggtgggcctagagtgtcagaaggtgaagctgt gatatcatcatgtgcccacattagattcttaatagattagtatagattattaattattactaggtatgtgtccg -continued cttgttgccacgaggctgagaagcgtggggaggggcgcctaagctacaaatataattttgtttatttgtaaac actaaagtatgtgtgatctgatggttagccctaaattttagagcacaggatgtgagtttgactgctcgttttg tactattttttgtgggctggacgtggggagagtgaagccgtggtaacactaggtgcccacattaggttcttaat agatagtagatagatagattgtttatttgtaaactatatgtgatctggtggttagtcctaaatttctaaagcat agtggtgtgggtttgagtgctcgttctccactattttttgcgctggacgtaaagagagtgaagtcgtagtagcac caggtacctacattagattcttaatagatagcaggggagtagaaatatatatatagaacttatatatatatgcc gaagctttgttttatacattattcttaaccgtttatttttaaataacatatatttttaatagcacgaaatagat gcaaatattttatggccttaaacaatttaaatagattttattttaattttttaggacttaattatacgacttttt tgaacgctataagtaaacggtaaataacaagggcttatcc SEQ ID NO: 25: SbOTUB1 promoter sequence:
tattcaacctgagagcactgtagcagccttgacagtatgaagcttttgcatatgaggggtttctgaaaacacac aaacatatatcaatttggcgcagaatcaacctcaagatgaacaactaacattacattaaaaaaattatcatacc aaagagcctaataggactgctgatagaaattgaagaacagaagggttaataaaataatttctaggatatacatt gtcattgccacaatcgtgaatcatagaatagctaaccacgcaaatctgtaggtacatacataagctggaaggac taaactactcgttaccttattatcttatttcactcaacctacatctttagagatagtaggaaactaaaagatt aggtaaattaaagtggttgctggttcgcaaaaaagtcatataaccaacaaataaaggatacccaaattctcata atatatagacaggcatcttcaccatcaaaattcatagtgtgtacgctctaaccaattaaggtcaggttcgttta ctgcaaagggacaaaaagaattgataaatgcagatcactacagcttttcacagtaagttctaagttgtaaataa aggaaatccagcaaactaaaattttaaaggtttacaaaaatatgctacactaatagttgttagaagtaggaagg ttatatttcaaacaatgaaatcaacaaaaacaccttatccatgtaaagtagcaattaccaactgcttggtcaca tcagatgctaacatctaaagcataaatgactaaataaatactgatttatacttcatcacggcttagttgtagta cttcacatatactagtcacttagtcaggaacagtaatgataaaactattatacttcataaactattttccctt cggtaggaataggaaatatgaacttcttataaactataatatagtacaaccaagatgccaatcttgtagtcgta caatattttattgctaactgatttattatcaccccttccaacatactaatacaatgagtcaatgaatatagaat aacatattctattagatgtcatgcaaaacccactgtaacttgtgaaacgaatcacttgtaagcatgagtaagag cattagtatattatggaaatggatggaaaatgcaaaggatctatgagatatacaagcagtacctatctcttctt tgattcatggcaggtgtcagtgagatgtattgatgctccaagagagctggaagtacacttttcaacataatcaaa atgtcctttccgtttactgcagtcaaccttaaacggctctttggatgctatctccacaggcaagtccttcataa cttccacatatcctctagtctgctcaatgaagtaatcaacatcgaaaacatctgcaaagccactgacagaacaa tccaataagaactactgtaagcatatttcaaacagaactgaactatagaacttcaatcatcataccctagactca ttccaataggcggcaacctcaaacttgggcagaatcatcgttgcgttcagaagacgtgcaacccccaattccgtc acatagctgcagaaccatcacaatagtatcatttagtggcccctccagaactcataagcacaagatatgaagtt atgaacaaaagaaagcacaattgctttatggaacatcaagatcttctgactgaaagttcagcactctcagtctc aggctcagagagtcactactccatgcagtgctgctacgatactgacaaccagagcatgtttcggctaaaatcaa tcatttgatctctacaggaaggaggaaactctaaccgaggtctcttaacgtacatcacgtcgcagctggttgag accaccgtagcagtctattcggatgtacccgttcctcctggacggagctgcacacacagcgcaggcgtcaatca tcagtacgtccaagtccagtatccaaattccaccccaaacagcgaggccttaccttgcactggtgccgtccgc caccacccgcacgggcgccactccaccaaccgccgctgcgcccatatgagccgcgagcccgaaggaggcagctc tctgctacaaaccgaatgcgggggttaaggaattgcgctagaacattctgagagggtctgggagtacacgagggg gcgaggcgcgtacccggggggcggggaggctgacgaagggcggcggcgacggcggcgacaggaggaagaagagga cgggcgcgaggaagagggacggtaggaggaaccggaggcggtgctgcgcgcaccacgccgccgccggtgacatg -continued gccggcggcgactcaccgtcgccggagccgccgggtgaggcgcctggatctgatcggccggtggcggcgtgtga tgaggaggagaaagaaatcgaatcccactagcacactgcgcacaccggagccgcaccagggccttgtttagttc caattttttttttcaaaatagaattagtagcacattcgtttgtatttgacaaatattgttcaatcatgaactaa ctaggcttaaaagattcgtctcgttaattccgactaaactgtataattagttttttattttcgtttatatttaat acttcatgtatgcgtctaaagatttgatgtgacggagaatctgaaaaattttacaaatttttttaagtaaaca aggcccgggcgtttcctctcagcagatgaaaaatgggtcccaggccacatgcgggtcccacacgtcatccacaa acagtgacacgtcgaaatggtgttggcctgttgggggcgtagagctggtagcctatagccaataggataggaaa caggtgggaccatgcttgagctaccccacatgtcagtctcacgggagtgtatccagttggagagggggttagac gttagtaaacggtgaacaacaagggcttatccgcaaaacgacacggacgtatttgccccgcttcccgtttccac ctgcgccgagatctcggaagagacgacgcaccgcaggatc SEQ ID NO: 26: GmOTUB1 promoter sequence:
tctgttaataatcaataatttgataattataattttttatcatacaagttaataatgactacacatctttatc aaaattgaaagaagattgaaatctccttaaatcaacttaactgattgtacaagttaaattaggatgcataaatt ataattacataattaaaattaatttctcaatatattttttgtctgaatttcatttctcatagtatatgttcact tgaaaaatatgataaatgaaactaaaataaaataaaaaatataataaataatgtgattagaaagaaagaaaaag acaaagaagaagaaaaagtaaatatatacatttttacatatttaggtcaaatgacttttttttttaatttgatc ttttattttctaaaaaaattatttttaatcttttatgtttttaaattgattcgaaatagtccttctgttaaaagc aaatttaacaccattaataatataaagataacccgccacaaaaacataatttcttttctgaaatatctccatac tataattaatacacatcaacaattttttaactcctactataatatttacaaagtttgaaaaaatacacaaaaaca tgttctaacctccatgaacctagaacatccccaacccataaccaaaaacaattgcaacaattcttaaaattggt ttagggcttctaaattgcatatctttacaagcaaaacccaaaaacaatctttgattttgattcaaaaacttgag agaatttacaaatcttgtattcaaaaccaaataaaaagttgcacaacaatctccctctagtgctccttccttcg ttgtgtcactactactgctacaatgattatgagtttgaatgctattatcatcattgttgtcgtcgcattgttca cttctgttgtcacaaattattttaatgatgtttccaacgacgaatgaaatccatcatattagaaaaaagtaaac aaacgagcacaaatatcatagatctaaaattaatctacaaattaaaaaaccaaacacatatatggtatcagtga gtgtttaaaaaaaaatactataagtgaaacccattgtgactctgatggtttcgatgatgacaaacataaactat tcaacgaaagtcacaaaatactaatagtagggactaatttgaatcattttaaataaaaaaataatcaaaataaa ctttataaaaaataaaagattaaattgaaaaaaataagataaagaatcaaatagataatttaacttatgtttta tttcttttcaaagttttcattctgtttgatatagaaacttattatgaatcttttaaaagagtgaaactgaagac cttgtggttagaattatataaattttcaagggcataattttacatttacaaggtttaaaactttcaaaatgaac gaaattattttatttgaaatgaaacattgtttcaatctaaatattttatcatcgatgttttaaaatgtagattc tattaaaaaaatatcatctcaatattatcctagggtgtattggattaagatttcaaaggattttaaaagacttt tttatgattaaaaagtcttgtggtattcaatcaagacttttataaaatataaacaaatcttgtggtattcaatt aagacaataaagattttttttttcagggcaacaaaatctgttggtattcaattgagatttcttaccacttttaaa atgtcttttggtattcaaaagtaaatagattttgatggattcttttgtggaatggattttgagagacttttttag ttagaaatacacataaaatactcctccaacaatctcacccaaacccttgagacttttcataatcttccaaagac tttttcttctcctgccgaacaagacacaaaccactaccaggtttattctcttacaacttttcaatcaattttac ctactttttaatgacaatcgatagtcaatattgttcatactatatgtatattacgcaaatcaaaagaaaaggt gctgtatatgcttcaagatttcgtattcatattgttttcaacgtccaggcaatgaatatgcatcaaaagaatga caattgatatgcatcaagatttcatattgctttttttagtactgtatatgcaaatcaaaataaaaaactttttt tttttttctgtttcttcaacttgttttttttacaacgtccattattattattattattttcttgtgttattatt -continued aaaatattaattattaatgtgttattattattttttttgacagcgtgttattattattattgtgttaataat tttttaattgttattgtgttattattattgttattttgttaatagttttttttaaatgattttatgatatatga gtattattttttatggaaaatgctaacatgtgcccttaagacacttgttagtgtattatgaacccattgttcaaa cacaagagcaggaacgagaagatgctaatatatggaggactaatataggttcatatatgagaagaaatgctaat aattaggcgaacatgaagtgagaatcactttgttattattttttttaggcaataatgactttgttattaaaaggt ttaaaatttctatcgttttttatttttctttattcaaacattataatttatttatcatcttttttcattcacttttg taacttccgttattttttttgtttaaaatgtattaatctttcaaaatcttaaaaatccataaagtactttgaaat cttaaaaatctgtgttagaaatccattaaaatcttgggttaagaatcctgattctaaaaagtcttttaaaaaaa atcttttaaaatcccacaaaatcaatacaatctcacataatctttttaaaatcttcaagattgttttttgtcaaaa tattctctcaaaatctcaatccaatacacttccttaaaaaaatatatttatgtacgattaattattaattactat aacttataaaaatcttctaattaattaacccgtcagcgcc SEQ ID NO: 27: BnOTUB1 promoter sequence:
tgtttaaatacatgtggtcactttcactatgtggattgtggaccctctcgtttattctaaagatggctttgtgg aattttttatagatacaaaaagtgggtaacatggaaatgtgcaacatcatattatcatcaccatctaatcatatg actgaaagtgaattgagtatatggcttttaggattggccaaagtaagcatgtaagattatgagccaatctgcaa tgagttttttttttatcttctatttctttattttgttcttctctctaattttcttttcactttaggcatgctat tattttgggaacgtgagattctttatgcctacttatgatcacttgtagttgtagctgtaccatgttttggttt tcaattatgaactttgataaaataacgttttccgaatcaactttgattatgaactttgattctttgtaaaaaaa aatcatattaagaaaaaattagtctgaaaatttgttagcttattcctaaatcgttataagaaaaattggttcca tcccaaataggtttatatttgttttaatataacgatggcatttgagttctacatggatgtcacttgtctaagac aattttcttatctttttttttgattaaatagagtatatcccagacctatggaaatatcaaactaatcttccaaa aagaagtatagctcacgagttagatcatttgcgggtatccaaataaagttcatactctatagtatagttccata tcttcgtgaccacacatatttagtgtcgtgggattgctttaaaccgaattgcttaactaaccggaattcgccta gatcactcatttgtttttttcttactccctccgttttatattgtaagtagttttagcaaaaaatgtttgtttcac aatataagtagttttcatatttcaatgcacatttctctttattgaatattgtgtaaccaatcaaataatgcta gctttttttataataggttgaatttattaattaaataatattttttacaaaagcaacaatttcttaatattagtg ttttttaactaaaactatttacaatatgaaacagagggagtatcatttaggtggtacatatacacacgtaaaatt ctatttccatcaaactgaattaaaattgttgacaaaattcattgtcatctattcttgtcatttacaaatttgac tctacacctaatatgcgaacttgtcctttcttcttctttttcacaacggaaccaatacgtgaacttcttttttaa taacatttttatttgtttttctggcaattgatcgagtgcatatgatcgaggagtttcccatgaatatcatatatg tgtcacttgatcaaatgatgggctaatcacatgctttacaatactcatgattgcaagccctgcaatctcttgga tccaaatgattattttcatttcttttcatcatgattgatcccacatttaattatttacatgatgatttcacgag aactaaaaagaagcaatttatatcaattcaatattatagaaaatttgctatagaaaaaccattcgttatcgtt ttcttaattttattttgtggcttttttcatatggctattccaatgcttttatgattattagcatgaacttgagca tgttctttatccccaaagaaagtaaactacagatacatcgtatgatattattgtgtattattaattattatgt acgatcgattttacaacatatatagaagagctgatgagtgttactgacgtaaatagtaattaatacatatatca cttaactatatatatgcataaagtcaagtttggttttgggttaaaaacgtacatcaaaccaaacataatagttc agtttatcttagtttaggtttgattatggtccagtagatcgtaatccaaggtcactatttttgttgacaatggt ttttttttctggttaaattttgattttttttttgttttaatttgcaagtccccgcatacactaaaagataaagc tcgatatatttgaattaaacgggaatataatagcatagattcaatcatgacgtattatcattctctagtgact ttttccacgctttcattaaaaaaagaacacttatctacatactgataacaactaacatagtataattaaggtcg

```
ttaagagtttagaaaaaaaatgcaaaaagaaagaataatagttgatgttcgtgtagattttggttactttctt gaacgagcaaggatcaaatcatcttcggaagaggagtatcaacctcacaagtcacaagaataataagctactc tacgcagaatagcaaaccgtcaaaaaaaatcaaatatttatcttttggacaatagttgatttgctataaatt tcctttacagtaaaaagttaagcaatttcttacggacataattatcacaacctcatgtttacttgtagcagagt caaatgaattcacgcgatcagcaataatcttattttttaacaaacagaaatagtggacatccatagatgatataa accttaattttgtttcaaattcaccacgaaacccttacattcgaaataagttataagctatcatatgttagtt cattaccacaggtccacaacatctgtgcttcatcagctggtatcagaaccatattaagtcttaaatattaatat atgaatcatcatgtgattattgttgtgcgtttatgttgctagtccaaattccgatttggtcgtttactaacatt cgcaaaagaggcccaaatattcggcccattctactaacatgatgtcgttccattattagcgaagccacatgcac gtcgttttaatttcccataaacgcttcgtctttctttattgtacattggaaaaaagccaaacgtctgttaccttt ttctgcccttccaatcaaattggtgtaaatcttttggtttcctcttttcagaaatttatttttccctaaagttt tgttttctttgtaaaaacattgcagagtgcccccaaaccg
```

CRISPR sequence information
RICE
EXAMPLE I; OTUB1 gene
SEQ ID NO: 28: OsOTUB1 CRISPR target sequence
tcagctggaaagtgttctgcagg SEQ ID NO: 29: OsOTUB1 CRISPR protospacer sequence
tcagctggaaagtgttctgc SEQ ID NO: 30: tracrRNA nucleotide sequence
GTTTTAGAGCTAGAAATAGCAAGTTAAAATAAGGCTAGTCCGTTATCAACTTGAAA

AAGTGGCACCGAGTCGGTGCTTTTTTTCAAGAGCTT

SEQ ID NO: 31: complete Os sgRNA nucleotide sequence
tcagctggaaagtgttctgcGTTTTAGAGCTAGAAATAGCAAGTTAAAATAAGGCTAGTCCGT

TATCAACTTGAAAAAGTGGCACCGAGTCGGTGCTTTTTTTCAAGAGCTT

SEQ ID NO: 32: OTUB1 Os sgRNA
GUUUUAGAGCUAGAAAUAGCAAGUUAAAAUAAGGCUAGUCCGUUAUCAACUUGA

AAAAGUGGCACCGAGUCGGUGC

SEQ ID NO: 33: complete OTUB1 CRISPR nucleic acid construct
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGtcagctggaaagtgttctgcGTTTTAGAGCTAGAA

ATAGCAAGTTAAAATAAGGCTAGTCCGTTATCAACTTGAAAAAGTGGCACCGAGTC

GGTGCTTTTTTTCAAGAGCTT

EXAMPLE II; OTUB1 gene
SEQ ID NO: 34: OsOTUB1 CRISPR target sequence
gactactaccactcgtgctgcgg SEQ ID NO: 35: OsOTUB1 protospacer sequence
gactactaccactcgtgctg SEQ ID NO: 36: OsOTUB1 sgRNA nucleic acid sequence
gactactaccactcgtgctgGTTTTAGAGCTAGAAATAGCAAGTTAAAATAAGGCTAGTCCG

TTATCAACTTGAAAAAGTGGCACCGAGTCGGTGCTTTTTTTCAAGAGCTT

SEQ ID NO: 37: OsOTUB1 U3-sgRNA cassette monocot plant, nucleic acid construct
TGGAATCGGCAGCAAAGGACGCGTTGACATTGTAGGACTATATTGCTCTAATAAA

GGAAGGAATCTTTAAACATACGAACAGATCACTTAAAGTTCTTCTGAAGCAACTTA

AAGTTATCAGGCATGCATGGATCTTGGAGGAATCAGATGTGCAGTCAGGGACCAT

AGCACAAGACAGGCGTCTTCTACTGGTGCTACCAGCAAATGCTGGAAGCCGGGA

ACACTGGGTACGTTGGAAACCACGTGTGATGTGAAGGAGTAAGATAAACTGTAGG

AGAAAAGCATTTCGTAGTGGGCCATGAAGCCTTTCAGGACATGTATTGCAGTATG

GGCCGGCCCATTACGCAATTGGACGACAACAAAGACTAGTATTAGTACCACCTCG

GCTATCCACATAGATCAAAGCTGGTTTAAAAGAGTTGTGCAGATGATCCGTGGCAg actactaccactcgtgctgGTTTTAGAGCTAGAAATAGCAAGTTAAAATAAGGCTAGTCCG

TTATCAACTTGAAAAAGTGGCACCGAGTCGGTGCTTTTTTTCAAGAGCTT
(non-capitalised letters are the protospacer sequence that binds the target sequence. bold sequence is the sgRNA coding sequence).

EXAMPLE III; OTUB1 gene
SEQ ID NO: 38: OsOTUB1 CRISPR target sequence
ccaccatgatttcagccctgagg SEQ ID NO: 39: OsOTUB1 protospacer sequence
ccaccatgatttcagccctg SEQ ID NO: 40: OsOTUB1 sgRNA nucleic acid sequence
ccaccatgatttcagccctgGTTTTAGAGCTAGAAATAGCAAGTTAAAATAAGGCTAGTCCG

TTATCAACTTGAAAAAGTGGCACCGAGTCGGTGCTTTTTTTCAAGAGCT

SEQ ID NO: 41 OsOTUB1 U6b-sgRNA cassette monocot plant, nucleic acid construct
TGGAATCGGCAGCAAAGGATGCAAGAACGAACTAAGCCGGACAAAAAAAAAGGA

GCACATATACAAACCGGTTTTATTCATGAATGGTCACGATGGATGATGGGGCTCA

GACTTGAGCTACGAGGCCGCAGGCGAGAGAAGCCTAGTGTGCTCTCTGCTTGTTT

GGGCCGTAACGGAGGATACGGCCGACGAGCGTGTACTACCGCGCGGGATGCCG

CTGGGCGCTGCGGGGCCGTTGGATGGGATCGGTGGGTCGCGGGAGCGTTGA

GGGGAGACAGGTTTAGTACCACCTCGCCTACCGAACAATGAAGAACCCACCTTAT

AACCCCGCGCGCTGCCGCTTGTGTTGccaccatgatttcagccctgGTTTTAGAGCTAGAA

ATAGCAAGTTAAAATAAGGCTAGTCCGTTATCAACTTGAAAAAGTGGCACCGAG

TCGGTGCTTTTTTTCAAGAGCT
(non-capitalised letters are the protospacer sequence that binds the target sequence. bold sequence is the sgRNA coding sequence).

EXAMPLE IV; OTUB1 promoter
SEQ ID NO: 42: target sequence
agcggcggtgggggaggaggtgg SEQ ID NO: 43; protospacer sequence
agcggcggtgggggaggagg SEQ ID NO: 44: full sgRNA sequence (protospacer sequence in bold (same for below sequences)
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

-continued

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGagcggcggtgggggaggaggGTTTTAGAGCTA

GAAATAGCAAGTTAAAATAAGGCTAGTCCGTTATCAACTTGAAAAAGTGGCACCGA

GTCGGTGCTTTTTTTCAAGAGCTT

EXAMPLE V; OTUB1 promoter
SEQ ID NO: 45: target sequence
Gggaggaggaggggggggggagg SEQ ID NO: 46 protospacer sequence
gggaggaggaggggggggg SEQ ID NO: 47: full sgRNA sequence
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGgggaggaggagggggggggggGTTTTAGAGCT

AGAAATAGCAAGTTAAAATAAGGCTAGTCCGTTATCAACTTGAAAAAGTGGCACCG

AGTCGGTGCTTTTTTTCAAGAGCTT

EXAMPLE VI; OTUB1 promoter
SEQ ID NO: 48: target sequence
Gggggggaggaggaggggggggg SEQ ID NO: 49 protospacer sequence
Ggggggaggaggaggggggg SEQ ID NO: 50: full sgRNA sequence
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGggggggaggaggagggggggGTTTTAGAGCT

AGAAATAGCAAGTTAAAATAAGGCTAGTCCGTTATCAACTTGAAAAAGTGGCACCG

AGTCGGTGCTTTTTTTCAAGAGCTT

EXAMPLE VII; OTUB1 promoter
SEQ ID NO: 51: target sequence
tcgaggggggaggaggagggggg SEQ ID NO: 52; protospacer sequence
tcgaggggggaggaggaggg SEQ ID NO: 53: full sgRNA sequence
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGtcgagggggaggaggagggGTTTTAGAGCTA

GAAATAGCAAGTTAAAATAAGGCTAGTCCGTTATCAACTTGAAAAAGTGGCACCGA

GTCGGTGCTTTTTTTCAAGAGCTT

EXAMPLE VIII; OTUB1 promoter
SEQ ID NO: 54: target sequence
Gtcgtcgagggggaggaggagg SEQ ID NO: 55; protospacer sequence
gtcgtcgagggggaggagg SEQ ID NO: 56: full sgRNA sequence
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGgtcgtcgagggggaggaggGTTTTAGAGCTA

GAAATAGCAAGTTAAAATAAGGCTAGTCCGTTATCAACTTGAAAAAGTGGCACCGA

GTCGGTGCTTTTTTTCAAGAGCTT

EXAMPLE IX; OTUB1 promoter
SEQ ID NO: 57: target sequence
ggcagccgcggcccccgagccgg SEQ ID NO: 58; protospacer sequence
ggcagccgcggcccccgagc SEQ ID NO: 59: full sgRNA sequence
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGggcagccgcggcccccgagcGTTTTAGAGCTAG

AAATAGCAAGTTAAAATAAGGCTAGTCCGTTATCAACTTGAAAAAGTGGCACCGAG

TCGGTGCTTTTTTTCAAGAGCTT

EXAMPLE X; OTUB1 promoter
SEQ ID NO: 60: target sequence
tcccggaggaggcggtgatgggg SEQ ID NO: 61; protospacer sequence
tcccggaggaggcggtgatg SEQ ID NO: 62: full sgRNA sequence
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGtcccggaggaggcggtgatgGTTTTAGAGCTAG

AAATAGCAAGTTAAAATAAGGCTAGTCCGTTATCAACTTGAAAAAGTGGCACCGAG

TCGGTGCTTTTTTTCAAGAGCTT

EXAMPLE XI; OTUB1 promoter
SEQ ID NO: 63: target sequence
cgcccggaagcgcaaggcggcgg SEQ ID NO: 64; protospacer sequence
cgcccggaagcgcaaggcgg SEQ ID NO: 65: full sgRNA sequence
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGcgcccggaagcgcaaggcggGTTTTAGAGCTA

GAAATAGCAAGTTAAAATAAGGCTAGTCCGTTATCAACTTGAAAAAGTGGCACCGA

GTCGGTGCTTTTTTTCAAGAGCTT

EXAMPLE XII; OTUB1 promoter
SEQ ID NO: 66: target sequence
gaagagaagaacacgcaccgcgg SEQ ID NO: 67; protospacer sequence
gaagagaagaacacgcaccg SEQ ID NO: 68: full sgRNA sequence
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGgaagagaagaacacgcaccgGTTTTAGAGCTA

GAAATAGCAAGTTAAAATAAGGCTAGTCCGTTATCAACTTGAAAAAGTGGCACCGA

GTCGGTGCTTTTTTTCAAGAGCTT

EXAMPLE XIII; OTUB1 promoter
SEQ ID NO: 69: target sequence
cccttacggcctccactctgagg SEQ ID NO: 70; protospacer sequence
cccttacggcctccactctg SEQ ID NO: 71: full sgRNA sequence
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGcccttacggcctccactctgGTTTTAGAGCTAGA

AATAGCAAGTTAAAATAAGGCTAGTCCGTTATCAACTTGAAAAAGTGGCACCGAGT

CGGTGCTTTTTTTCAAGAGCTT

EXAMPLE XIV; OTUB1 promoter
SEQ ID NO: 72: target sequence
cactttctccttatgacacgtgg SEQ ID NO: 73; protospacer sequence
cactttctccttatgacacg SEQ ID NO: 74: full sgRNA sequence
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGcactttctccttatgacacgGTTTTAGAGCTAGAA

ATAGCAAGTTAAAATAAGGCTAGTCCGTTATCAACTTGAAAAAGTGGCACCGAGTC

GGTGCTTTTTTTCAAGAGCTT

EXAMPLE XV; OTUB1 promoter
SEQ ID NO: 75: target sequence
tatataagctcgtcagaatgtgg SEQ ID NO: 76; protospacer sequence
tatataagctcgtcagaatg SEQ ID NO: 77: full sgRNA sequence
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGtatataagctcgtcagaatgGTTTTAGAGCTAGA

AATAGCAAGTTAAAATAAGGCTAGTCCGTTATCAACTTGAAAAAGTGGCACCGAGT

CGGTGCTTTTTTTCAAGAGCTT

EXAMPLE XVI; OTUB1 promoter
SEQ ID NO: 78: target sequence
cgagaagcactggatctgatcgg SEQ ID NO: 79; protospacer sequence
cgagaagcactggatctgat SEQ ID NO: 80: full sgRNA sequence
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGcgagaagcactggatctgatGTTTTAGAGCTAGA

AATAGCAAGTTAAAATAAGGCTAGTCCGTTATCAACTTGAAAAAGTGGCACCGAGT

CGGTGCTTTTTTTCAAGAGCTT

EXAMPLE XVII; OTUB1 promoter
SEQ ID NO: 81: target sequence
gagaggaggaagtagagcgcggg SEQ ID NO: 82; protospacer sequence
gagaggaggaagtagagcgc SEQ ID NO: 83: full sgRNA sequence
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGgagaggaggaagtagagcgcGTTTTAGAGCTA

GAAATAGCAAGTTAAAATAAGGCTAGTCCGTTATCAACTTGAAAAAGTGGCACCGA

GTCGGTGCTTTTTTTCAAGAGCTT

EXAMPLE XVIII; OTUB1 promoter
SEQ ID NO: 84: target sequence
taaacccaaaccacaaatcacgg SEQ ID NO: 85; protospacer sequence
taaacccaaaccacaaatca SEQ ID NO: 86: full sgRNA sequence
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGtaaacccaaaccacaaatcaGTTTTAGAGCTAG

AAATAGCAAGTTAAAATAAGGCTAGTCCGTTATCAACTTGAAAAAGTGGCACCGAG

TCGGTGCTTTTTTTCAAGAGCTT

EXAMPLE XIX; OTUB1 promoter
SEQ ID NO: 87: target sequence
atgtacccattcctcctcgacgg SEQ ID NO: 88; protospacer sequence
atgtacccattcctcctcga SEQ ID NO: 89: full sgRNA sequence
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGtatgtacccattcctcctcgaGTTTTAGAGCTAGA

AATAGCAAGTTAAAATAAGGCTAGTCCGTTATCAACTTGAAAAAGTGGCACCGAGT

CGGTGCTTTTTTTCAAGAGCTT

EXAMPLE XX; OTUB1 promoter
SEQ ID NO: 90: target sequence
aacgtacatcgcgtcgcagctgg SEQ ID NO: 91; protospacer sequence
aacgtacatcgcgtcgcagc SEQ ID NO: 92: full sgRNA sequence
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

-continued

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGaacgtacatcgcgtcgcagcGTTTTAGAGCTAG

AAATAGCAAGTTAAAATAAGGCTAGTCCGTTATCAACTTGAAAAAGTGGCACCGAG

TCGGTGCTTTTTTTCAAGAGCTT

EXAMPLE XXI; OTUB1 promoter
SEQ ID NO: 93: target sequence
actatcttactacttgtgcatgg SEQ ID NO: 94; protospacer sequence
actatcttactacttgtgca SEQ ID NO: 95: full sgRNA sequence
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGactatcttactacttgtgcaGTTTTAGAGCTAGAA

ATAGCAAGTTAAAATAAGGCTAGTCCGTTATCAACTTGAAAAAGTGGCACCGAGTC

GGTGCTTTTTTTCAAGAGCTT

EXAMPLE XXII; OTUB1 promoter
SEQ ID NO: 96 target sequence
tcggaagaataattacaaccagg SEQ ID NO: 97; protospacer sequence
tcggaagaataattacaacc SEQ ID NO: 98: full sgRNA sequence
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGtcggaagaataattacaaccGTTTTAGAGCTAGA

AATAGCAAGTTAAAATAAGGCTAGTCCGTTATCAACTTGAAAAAGTGGCACCGAGT

CGGTGCTTTTTTTCAAGAGCTT

-continued

EXAMPLE XXIII; OTUB1 promoter
SEQ ID NO: 99: target sequence
gtaggcagcaacctcaaacttgg SEQ ID NO: 100; protospacer sequence
gtaggcagcaacctcaaact SEQ ID NO: 101: full sgRNA sequence
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGgtaggcagcaacctcaaactGTTTTAGAGCTAG

AAATAGCAAGTTAAAATAAGGCTAGTCCGTTATCAACTTGAAAAAGTGGCACCGAG

TCGGTGCTTTTTTTCAAGAGCTT

Wild einkorn wheat
EXAMPLE I; OTUB1 gene
SEQ ID NO: 102 TuOTUB1 CRISPR target sequence
ttaaggcgaacacgaggagatgg SEQ ID NO: 103: protospacer sequence; TuOTUB1(double target)
ttaaggcgaacacgaggaga SEQ ID NO: 104: TuOTUB1 sgRNA nucleic acid
ttaaggcgaacacgaggagaGTTTTAGAGCTAGAAATAGCAAGTTAAAATAAGGCTAGTCC

GTTATCAACTTGAAAAAGTGGCACCGAGTCGGTGCTTTTTTTCAAGAGCTT

SEQ ID NO: 105 TuOTUB1; U6a-sgRNA cassette monocot plant, nucleic acid construct
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGttaaggcgaacacgaggagaGTTTTAGAGCTAG

AAATAGCAAGTTAAAATAAGGCTAGTCCGTTATCAACTTGAAAAAGTGGCACCG

AGTCGGTGCTTTTTTTCAAGAGCTT
(non-capitalised letters are the protospacer sequence that binds the target sequence. bold sequence is the sgRNA coding sequence).

EXAMPLE II; OTUB1 gene
SEQ ID NO: 106 TuOTUB1 CRISPR target sequence
attgctctgtcagatgcgttagg SEQ ID NO: 107: protospacer sequence; TuOTUB1(double target)
attgctctgtcagatgcgtt SEQ ID NO: 108: TuOTUB1 sgRNA nucleic acid
AttgctctgtcagatgcgttGTTTTAGAGCTAGAAATAGCAAGTTAAAATAAGGCTAGTCCGT

TATCAACTTGAAAAAGTGGCACCGAGTCGGTGCTTTTTTTCAAGAGCTT

-continued

SEQ ID NO: 109 TuOTUB1; U3-sgRNA cassette monocot plant, nucleic acid construct
TGGAATCGGCAGCAAAGGACGCGTTGACATTGTAGGACTATATTGCTCTAATAAA

GGAAGGAATCTTTAAACATACGAACAGATCACTTAAAGTTCTTCTGAAGCAACTTA

AAGTTATCAGGCATGCATGGATCTTGGAGGAATCAGATGTGCAGTCAGGGACCAT

AGCACAAGACAGGCGTCTTCTACTGGTGCTACCAGCAAATGCTGGAAGCCGGGA

ACACTGGGTACGTTGGAAACCACGTGTGATGTGAAGGAGTAAGATAAACTGTAGG

AGAAAAGCATTTCGTAGTGGGCCATGAAGCCTTTCAGGACATGTATTGCAGTATG

GGCCGGCCCATTACGCAATTGGACGACAACAAAGACTAGTATTAGTACCACCTCG

GCTATCCACATAGATCAAAGCTGGTTTAAAAGAGTTGTGCAGATGATCCGTGGCAa ttgctctgtcagatgcgttGTTTTAGAGCTAGAAATAGCAAGTTAAAATAAGGCTAGTCCGT

TATCAACTTGAAAAAGTGGCACCGAGTCGGTGCTTTTTTTCAAGAGCTT
(non-capitalised letters are the protospacer sequence that binds the target sequence. bold sequence is the sgRNA coding sequence).

Barley
EXAMPLE I; OTUB1 gene
SEQ ID NO: 110: HvOTUB1 CRISPR target sequence
ttaagacggacacgaggagatgg SEQ ID NO: 111: Hv OTUB1 protospacer
ttaagacggacacgaggaga SEQ ID NO: 112: Hv OTUB1 sgRNA nucleic acid
ttaagacggacacgaggagaGTTTTAGAGCTAGAAATAGCAAGTTAAAATAAGGCTAGTCC

GTTATCAACTTGAAAAAGTGGCACCGAGTCGGTGCTTTTTTTCAAGAGCTT

SEQ ID NO: 113: Hv OTUB1 U6a-sgRNA cassette monocot plant nucleic acid construct
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGttaagacggacacgaggagaGTTTTAGAGCTAG

AAATAGCAAGTTAAAATAAGGCTAGTCCGTTATCAACTTGAAAAAGTGGCACCG

AGTCGGTGCTTTTTTTCAAGAGCTT
(non-capitalised letters are the protospacer sequence that binds the target sequence. bold sequence is the sgRNA coding sequence).

EXAMPLE II: OTUB1 gene
SEQ ID NO: 114: HvOTUB1 CRISPR target sequence
Attgctctgtcagatgcgttagg SEQ ID NO: 115: Hv OTUB1 protospacer
attgctctgtcagatgcgtt SEQ ID NO: 116: Hv OTUB1 sgRNA nucleic acid
attgctctgtcagatgcgttGTTTTAGAGCTAGAAATAGCAAGTTAAAATAAGGCTAGTCCGT

TATCAACTTGAAAAAGTGGCACCGAGTCGGTGCTTTTTTTCAAGAGCTT

SEQ ID NO: 117: Hv OTUB1 sgRNA nucleic acid U3-sgRNA cassette monocot plant, nucleic acid construct
TGGAATCGGCAGCAAAGGACGCGTTGACATTGTAGGACTATATTGCTCTAATAAA

GGAAGGAATCTTTAAACATACGAACAGATCACTTAAAGTTCTTCTGAAGCAACTTA

-continued

```
AAGTTATCAGGCATGCATGGATCTTGGAGGAATCAGATGTGCAGTCAGGGACCAT

AGCACAAGACAGGCGTCTTCTACTGGTGCTACCAGCAAATGCTGGAAGCCGGGA

ACACTGGGTACGTTGGAAACCACGTGTGATGTGAAGGAGTAAGATAAACTGTAGG

AGAAAAGCATTTCGTAGTGGGCCATGAAGCCTTTCAGGACATGTATTGCAGTATG

GGCCGGCCCATTACGCAATTGGACGACAACAAAGACTAGTATTAGTACCACCTCG

GCTATCCACATAGATCAAAGCTGGTTTAAAAGAGTTGTGCAGATGATCCGTGGCAa ttgctctgtcagatgcgttGTTTTAGAGCTAGAAATAGCAAGTTAAAATAAGGCTAGTCCGT

TATCAACTTGAAAAAGTGGCACCGAGTCGGTGCTTTTTTTCAAGAGCTT
(non-capitalised letters are the protospacer sequence that binds the
target sequence. bold sequence is the sgRNA coding sequence).

Maize
EXAMPLE I; OTUB1 gene
SEQ ID NO: 118: ZmOTUB1 CRISPR target sequence
aagctttatgttttcctacctgg SEQ ID NO: 119: ZmOTUB1 protospacer sequence
aagctttatgttttcctacc SEQ ID NO: 120: ZmOTUB1 sgRNA nucleic acid sequence
aagctttatgttttcctaccGTTTTAGAGCTAGAAATAGCAAGTTAAAATAAGGCTAGTCCGTT

ATCAACTTGAAAAAGTGGCACCGAGTCGGTGCTTTTTTTCAAGAGCTT

SEQ ID NO: 121: ZmOTUB1 U6a-sgRNA cassette monocot plant, nucleic acid
construct
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGaagctttatgttttcctaccGTTTTAGAGCTAGAAA

TAGCAAGTTAAAATAAGGCTAGTCCGTTATCAACTTGAAAAAGTGGCACCGAGT

CGGTGCTTTTTTTCAAGAGCTT
(non-capitalised letters are the protospacer sequence that binds the
target sequence. bold sequence is the sgRNA coding sequence).

EXAMPLE II; OTUB1 gene
SEQ ID NO: 122: ZmOTUB1 CRISPR target sequence
attgccctatcagatgcactagg SEQ ID NO: 123: ZmOTUB1 protospacer sequence
attgccctatcagatgcact SEQ ID NO: 124: ZmOTUB1 sgRNA nucleic acid sequence
attgccctatcagatgcactGTTTTAGAGCTAGAAATAGCAAGTTAAAATAAGGCTAGTCCGT

TATCAACTTGAAAAAGTGGCACCGAGTCGGTGCTTTTTTTCAAGAGCTT

SEQ ID NO: 125: ZmOTUB1 U3-sgRNA cassette monocot plant, nucleic acid
construct
TGGAATCGGCAGCAAAGGACGCGTTGACATTGTAGGACTATATTGCTCTAATAAA

GGAAGGAATCTTTAAACATACGAACAGATCACTTAAAGTTCTTCTGAAGCAACTTA

AAGTTATCAGGCATGCATGGATCTTGGAGGAATCAGATGTGCAGTCAGGGACCAT

AGCACAAGACAGGCGTCTTCTACTGGTGCTACCAGCAAATGCTGGAAGCCGGGA

ACACTGGGTACGTTGGAAACCACGTGTGATGTGAAGGAGTAAGATAAACTGTAGG
```

-continued

AGAAAAGCATTTCGTAGTGGGCCATGAAGCCTTTCAGGACATGTATTGCAGTATG

GGCCGGCCCATTACGCAATTGGACGACAACAAAGACTAGTATTAGTACCACCTCG

GCTATCCACATAGATCAAAGCTGGTTTAAAAGAGTTGTGCAGATGATCCGTGGCAa ttgccctatcagatgcactGTTTTAGAGCTAGAAATAGCAAGTTAAAATAAGGCTAGTCCG

TTATCAACTTGAAAAAGTGGCACCGAGTCGGTGCTTTTTTTCAAGAGCTT
(non-capitalised letters are the protospacer sequence that binds the target sequence. bold sequence is the sgRNA coding sequence).

Sorghum
EXAMPLE I; OTUB1 gene
SEQ ID NO: 126: SbOTUB1 CRISPR target sequence
aagctttatgttctcctacttgg SEQ ID NO: 127: SbOTUB1 protospacer sequence
aagctttatgttctcctact SEQ ID NO: 128: SbOTUB1 sgRNA nucleic acid sequence
aagctttatgttctcctactGTTTTAGAGCTAGAAATAGCAAGTTAAAATAAGGCTAGTCCGTT

ATCAACTTGAAAAAGTGGCACCGAGTCGGTGCTTTTTTTCAAGAGCTT

SEQ ID NO: 129: SbOTUB1 U6a-sgRNA cassette monocot plant, nucleic acid construct
TGGAATCGGCAGCAAAGGATTTTTTCCTGTAGTTTTCCCACAACCATTTTTTACCAT

CCGAATGATAGGATAGGAAAAATATCCAAGTGAACAGTATTCCTATAAAATTCCCG

TAAAAAGCCTGCAATCCGAATGAGCCCTGAAGTCTGAACTAGCCGGTCACCTGTA

CAGGCTATCGAGATGCCATACAAGAGACGGTAGTAGGAACTAGGAAGACGATGG

TTGATTCGTCAGGCGAAATCGTCGTCCTGCAGTCGCATCTATGGGCCTGGACGGA

ATAGGGGAAAAAGTTGGCCGGATAGGAGGGAAAGGCCCAGGTGCTTACGTGCGA

GGTAGGCCTGGGCTCTCAGCACTTCGATTCGTTGGCACCGGGGTAGGATGCAAT

AGAGAGCAACGTTTAGTACCACCTCGCTTAGCTAGAGCAAACTGGACTGCCTTAT

ATGCGCGGGTGCTGGCTTGGCTGCCGaagctttatgttctcctactGTTTTAGAGCTAGAAA

TAGCAAGTTAAAATAAGGCTAGTCCGTTATCAACTTGAAAAAGTGGCACCGAGT

CGGTGCTTTTTTTCAAGAGCTT
(non-capitalised letters are the protospacer sequence that binds the target sequence. bold sequence is the sgRNA coding sequence).

EXAMPLE II; OTUB1 gene
SEQ ID NO: 130: SbOTUB1 CRISPR target sequence
tgttcacataattgccctatcgg SEQ ID NO: 131: SbOTUB1 protospacer sequence
tgttcacataattgccctat SEQ ID NO: 132: SbOTUB1 sgRNA nucleic acid sequence
tgttcacataattgccctatGTTTTAGAGCTAGAAATAGCAAGTTAAAATAAGGCTAGTCCGTT

ATCAACTTGAAAAAGTGGCACCGAGTCGGTGCTTTTTTTCAAGAGCTT

SEQ ID NO: 133: SbOTUB1 U3-sgRNA cassette monocot plant, nucleic acid construct
TGGAATCGGCAGCAAAGGACGCGTTGACATTGTAGGACTATATTGCTCTAATAAA

GGAAGGAATCTTTAAACATACGAACAGATCACTTAAAGTTCTTCTGAAGCAACTTA

AAGTTATCAGGCATGCATGGATCTTGGAGGAATCAGATGTGCAGTCAGGGACCAT

AGCACAAGACAGGCGTCTTCTACTGGTGCTACCAGCAAATGCTGGAAGCCGGGA

ACACTGGGTACGTTGGAAACCACGTGTGATGTGAAGGAGTAAGATAAACTGTAGG

AGAAAAGCATTTCGTAGTGGGCCATGAAGCCTTTCAGGACATGTATTGCAGTATG

GGCCGGCCCATTACGCAATTGGACGACAACAAAGACTAGTATTAGTACCACCTCG

GCTATCCACATAGATCAAAGCTGGTTTAAAAGAGTTGTGCAGATGATCCGTGGCAt

-continued gttcacataattgccctatGTTTTAGAGCTAGAAATAGCAAGTTAAAATAAGGCTAGTCCGT

TATCAACTTGAAAAAGTGGCACCGAGTCGGTGCTTTTTTTCAAGAGCTT
(non-capitalised letters are the protospacer sequence that binds the
target sequence. bold sequence is the sgRNA coding sequence).

Soybean
EXAMPLE I; OTUB1 gene
SEQ ID NO: 134: GmOTUB1 CRISPR target sequence
attcgtcgtactcgaggagatgg SEQ ID NO: 135: GmOTUB1 protospacer sequence
attcgtcgtactcgaggaga SEQ ID NO: 136: GmOTUB1 sgRNA nucleic acid sequence
attcgtcgtactcgaggagaGTTTTAGAGCTAGAAATAGCAAGTTAAAATAAGGCTAGTCCG

TTATCAACTTGAAAAAGTGGCACCGAGTCGGTGCTTTTTTTCAAGAGCT

SEQ ID NO: 137: GmOTUB1 U3b-sgRNA cassette monocot plant, nucleic acid
construct
TGGAATCGGCAGCAAAGGATTTACTTTAAATTTTTTCTTATGCAGCCTGTGATGGA

TAACTGAATCAAACAAATGGCGTCTGGGTTTAAGAAGATCTGTTTTGGCTATGTTG

GACGAAACAAGTGAACTTTTAGGATCAACTTCAGTTTATATATGGAGCTTATATCG

AGCAATAAGATAAGTGGGCTTTTTATGTAATTTAATGGGCTATCGTCCATAGATTCA

CTAATACCCATGCCCAGTACCCATGTATGCGTTTCATATAAGCTCCTAATTTCTCC

CACATCGCTCAAATCTAAACAAATCTTGTTGTATATATAACACTGAGGGAGCAACA

TTGGTCAattcgtcgtactcgaggagaGTTTTAGAGCTAGAAATAGCAAGTTAAAATAAGG

CTAGTCCGTTATCAACTTGAAAAAGTGGCACCGAGTCGGTGCTTTTTTTCAAGAG

CT
(non-capitalised letters are the protospacer sequence that binds the
target sequence. bold sequence is the sgRNA coding sequence).

EXAMPLE II; OTUB1 gene
SEQ ID NO: 138: GmOTUB1 CRISPR target sequence
tactgcccttctcagatgcattgg SEQ ID NO: 139: GmOTUB1 protospacer sequence
tactgcccttctcagatgcat SEQ ID NO: 140: GmOTUB1 sgRNA nucleic acid sequence
tactgcccttctcagatgcatGTTTTAGAGCTAGAAATAGCAAGTTAAAATAAGGCTAGTCCGT

TATCAACTTGAAAAAGTGGCACCGAGTCGGTGCTTTTTTTCAAGAGCT

SEQ ID NO: 141: GmOTUB1 U6-1-sgRNA cassette monocot plant, nucleic acid
construct
TGGAATCGGCAGCAAAGGAAGAAATCTCAAAATTCCGGCAGAACAATTTTGAATCT

CGATCCGTAGAAACGAGACGGTCATTGTTTTAGTTCCACCACGATTATATTTGAAA

TTTACGTGAGTGTGAGTGAGACTTGCATAAGAAAATAAAATCTTTAGTTGGGAAAA

AATTCAATAATATAAATGGGCTTGAGAAGGAAGCGAGGGATAGGCCTTTTTCTAAA

ATAGGCCCATTTAAGCTATTAACAATCTTCAAAAGTACCACAGCGCTTAGGTAAAG

AAAGCAGCTGAGTTTATATATGGTTAGAGACGAAGTAGTGATTGtactgcccttctcagatgc atGTTTTAGAGCTAGAAATAGCAAGTTAAAATAAGGCTAGTCCGTTATCAACTTG

AAAAAGTGGCACCGAGTCGGTGCTTTTTTTCAAGAGCT
(non-capitalised letters are the protospacer sequence that binds the
target sequence. bold sequence is the sgRNA coding sequence).

Brassica
EXAMPLE I; OTUB1 gene
SEQ ID NO: 142: BnOTUB1 CRISPR target sequence
atcaggcgaacaagaggagatgg -continued SEQ ID NO: 143: BnOTUB1 protospacer sequence
atcaggcgaacaagaggaga SEQ ID NO: 144: BnOTUB1 sgRNA nucleic acid sequence
atcaggcgaacaagaggagaGTTTTAGAGCTAGAAATAGCAAGTTAAAATAAGGCTAGTC

CGTTATCAACTTGAAAAAGTGGCACCGAGTCGGTGCTTTTTTTCAAGAGCT

SEQ ID NO: 145: BnOTUB1 U3b-sgRNA cassette monocot plant, nucleic acid
construct
TGGAATCGGCAGCAAAGGATTTACTTTAAATTTTTTCTTATGCAGCCTGTGATGGA

TAACTGAATCAAACAAATGGCGTCTGGGTTTAAGAAGATCTGTTTTGGCTATGTTG

GACGAAACAAGTGAACTTTTAGGATCAACTTCAGTTTATATATGGAGCTTATATCG

AGCAATAAGATAAGTGGGCTTTTTATGTAATTTAATGGGCTATCGTCCATAGATTCA

CTAATACCCATGCCCAGTACCCATGTATGCGTTTCATATAAGCTCCTAATTTCTCC

CACATCGCTCAAATCTAAACAAATCTTGTTGTATATATAACACTGAGGGAGCAACA

TTGGTCAatcaggcgaacaagaggagaGTTTTAGAGCTAGAAATAGCAAGTTAAAATAA

GGCTAGTCCGTTATCAACTTGAAAAAGTGGCACCGAGTCGGTGCTTTTTTTCAAG

AGCT
(non-capitalised letters are the protospacer sequence that binds the
target sequence. bold sequence is the sgRNA coding sequence).

EXAMPLE II: OTUB1 gene
SEQ ID NO: 146: BnOTUB1 CRISPR target sequence
tattcacataacagctttgtcgg SEQ ID NO: 147: BnOTUB1 protospacer sequence
tattcacataacagctttgt SEQ ID NO: 148: BnOTUB1 sgRNA nucleic acid sequence
tattcacataacagctttgtGTTTTAGAGCTAGAAATAGCAAGTTAAAATAAGGCTAGTCCGT

TATCAACTTGAAAAAGTGGCACCGAGTCGGTGCTTTTTTTCAAGAGCT

SEQ ID NO: 149: BnOTUB1 U6-1-sgRNA cassette monocot plant, nucleic acid
construct
TGGAATCGGCAGCAAAGGAAGAAATCTCAAAATTCCGGCAGAACAATTTTGAATCT

CGATCCGTAGAAACGAGACGGTCATTGTTTTAGTTCCACCACGATTATATTTGAAA

TTTACGTGAGTGTGAGTGAGACTTGCATAAGAAAATAAAATCTTTAGTTGGGAAAA

AATTCAATAATATAAATGGGCTTGAGAAGGAAGCGAGGGATAGGCCTTTTTCTAAA

ATAGGCCCATTTAAGCTATTAACAATCTTCAAAAGTACCACAGCGCTTAGGTAAAG

AAAGCAGCTGAGTTTATATATGGTTAGAGACGAAGTAGTGATTGtattcacataacagctttg tGTTTTAGAGCTAGAAATAGCAAGTTAAAATAAGGCTAGTCCGTTATCAACTTGA

AAAAGTGGCACCGAGTCGGTGCTTTTTTTCAAGAGCT
(non-capitalised letters are the protospacer sequence that binds the
target sequence. bold sequence is the sgRNA coding sequence).

SEQ ID NO: 150; Cas 9
atggctcctaagaagaagcggaaggttggtattcacggggtgcctgcggctgacaagaagtactccatcggcct cgacatcggcaccaacagcgtcggctgggcggtgatcaccgacgagtacaaggtcccgtccaagaagttcaagg tcctgggcaacacccgaccgccactccatcaagaagaacctcatcggcgccctcctcttcgactccggcgagacg gcggaggcgacccgcctcaagcgcaccgcccgccgccgctacacccgccgcaagaaccgcatctgctacctcca ggagatcttctccaacgagatggcgaaggtcgacgactccttcttccaccgcctcgaggagtccttcctcgtgg aggaggacaagaagcacgagcgccaccccatcttcggcaacatcgtcgacgaggtcgcctaccacgagaagtac cccactatctaccaccttcgtaagaagcttgttgactctactgataaggctgatcttcgtctcatctaccttgc tctcgctcacatgatcaagttccgtggtcacttccttatcgagggtgaccttaaccctgataactccgacgtgg acaagctcttcatccagctcgtccagacctacaaccagctcttcgaggagaacccctatcaacgcttccggtgtc -continued

```
gacgctaaggcgatcctttccgctaggctctccaagtccaggcgtctcgagaacctcatcgcccagctccctgg tgagaagaagaacggtcttttcggtaacctcatcgctctctccctcggtctgaccectaacttcaagtccaact tcgacctcgctgaggacgctaagcttcagctctccaaggatacctacgacgatgatctcgacaacctcctcgct cagattggagatcagtacgctgatctcttccttgctgctaagaacctctccgatgctatcctcctttcggatat ccttagggttaacactgagatcactaaggctcctctttctgcttccatgatcaagcgctacgacgagcaccacc aggacctcaccctcctcaaggctcttgttcgtcagcagctccccgagaagtacaaggagatcttcttcgaccag tccaagaacggctacgccggttacattgacggtggagctagccaggaggagttctacaagttcatcaagccaat ccttgagaagatggatggtactgaggagcttctcgttaagcttaaccgtgaggacctccttaggaagcagagga ctttcgataacggctctatccctcaccagatccaccttggtgagcttcacgccatccttcgtaggcaggaggac ttctaccctttcctcaaggacaaccgtgagaagatcgagaagatccttactttccgtattccttactacgttgg tcctcttgctcgtggtaactcccgtttcgcttggatgactaggaagtccgaggagactatcaccccttggaact tcgaggaggttgttgacaagggtgcttccgcccagtccttcatcgagcgcatgaccaacttcgacaagaacctc cccaacgagaaggtcctccccaagcactccctcctctacgagtacttcacggtctacaacgagctcaccaaggt caagtacgtcaccgagggtatgcgcaagcctgccttcctctccggcgagcagaagaaggctatcgttgacctcc tcttcaagaccaaccgcaaggtcaccgtcaagcagctcaaggaggactacttcaagaagatcgagtgcttcgac tccgtcgagatcagcggcgttgaggaccgtttcaacgcttctctcggtacctaccacgatctcctcaagatcat caaggacaaggacttcctcgacaacgaggagaacgaggacatcctcgaggacatcgtcctcactcttactctct tcgaggatagggagatgatcgaggagaggctcaagacttacgctcatctcttcgatgacaaggttatgaagcag ctcaagcgtcgccgttacaccggttggggtaggctctcccgcaagctcatcaacggtatcagggataagcagag cggcaagactatcctcgacttcctcaagtctgatggtttcgctaacaggaacttcatgcagctcatccacgatg actctcttaccttcaaggaggatattcagaaggctcaggtgtccggtcagggcgactctctccacgagcacatt gctaaccttgctggttcccctgctatcaagaagggcatccttcagactgttaaggttgtcgatgagcttgtcaa ggttatgggtcgtcacaagcctgagaacatcgtcatcgagatggctcgtgagaaccagactacccagaagggtc agaagaactcgagggagcgcatgaagaggattgaggagggtatcaaggagcttggttctcagatccttaaggag cacccctgtcgagaacacccagctccagaacgagaagctctacctctactacctccagaacggtagggatatgta cgttgaccaggagctcgacatcaacaggctttctgactacgacgtcgaccacattgttcctcagtctttcctta aggatgactccatcgacaacaaggtcctcacgaggtccgacaagaacaggggtaagtcggacaacgtccctctcc gaggaggttgtcaagaagatgaagaactactggaggcagcttctcaacgctaagctcattacccagaggaagtt cgacaacctcacgaaggctgagaggggtggcctttccgagcttgacaaggctggtttcatcaagaggcagcttg ttgagacgaggcagattaccaagcacgttgctcagatcctcgattctaggatgaacaccaagtacgacgagaac gacaagctcatccgcgaggtcaaggtgatcaccctcaagtccaagctcgtctccgacttccgcaaggacttcca gttctacaaggtccgcgagatcaacaactaccaccacgctcacgatgcttaccttaacgctgtcgttggtaccg ctcttatcaagaagtaccctaagcttgagtccgagttcgtctacggtgactacaaggtctacgacgttcgtaag atgatcgccaagtccgagcaggagatcggcaaggccaccgccaagtacttcttctactccaacatcatgaactt cttcaagaccgagatcaccctcgccaacggcgagatccgcaagcgccctcttatcgagacgaacggtgagactg gtgagatcgtttgggacaagggtcgcgacttcgctactgttcgcaaggtcctttctatgcctcaggttaacatc gtcaagaagaccgaggtccagaccggtggcttctccaaggagtctatccttccaaagagaaactcggacaagct catcgctaggaagaaggattgggaccctaagaagtacggtggtttcgactcccctactgtcgcctactccgtcc tcgtggtcgccaaggtgggagaagggtaagtcgaagaagctcaagtccgtcaaggagctcctcggcatcaccatc atggagcgctcctccttcgagaagaacccgatcgacttcctcgaggccaagggctacaaggaggtcaagaagga cctcatcatcaagctccccaagtactctctttttcgagctcgagaacggtcgtaagaggatgctggcttccgctg
```

-continued gtgagctccagaagggtaacgagcttgctcttccttccaagtacgtgaacttcctctacctcgcctcccactac gagaagctcaagggttcccctgaggataacgagcagaagcagctcttcgtggagcagcacaagcactacctcga cgagatcatcgagcagatctccgagttctccaagcgcgtcatcctcgctgacgctaacctcgacaaggtcctct ccgcctacaacaagcaccgcgacaagcccatccgcgagcaggccgagaacatcatccacctcttcacgctcacg aacctcggcgcccctgctgctttcaagtacttcgacaccaccatcgacaggaagcgttacacgtccaccaagga ggttctcgacgctactctcatccaccagtccatcaccggtctttacgagactcgtatcgacctttcccagcttg gtggtgataagcgtcctgctgccaccaaaaaggccggacaggctaagaaaaagaagtag SEQ ID NO: 151 Cys4-P2A-TaCas9 nucleic acid sequence
5'<u>ATGGACCACTACCTCGACATCAGGCTCAGGCCAGACCCAGAGTTCCCACCAGC</u>

<u>CCAGCTCATGTCCGTCCTCTTCGGCAAGCTCCACCAGGCCCTCGTGGCCCAGGG</u>

<u>CGGCGACAGGATCGGCGTGTCCTTCCCAGACCTCGACGAGTCCAGGTCCAGGCT</u>

<u>CGGCGAGAGGCTCCGCATCCACGCCTCCGCCGACGACCTCAGGGCCCTCCTCG</u>

<u>CCAGGCCGTGGCTGGAGGGCCTCAGGGACCACCTCCAGTTCGGCGAGCCAGCC</u>

<u>GTGGTGCCACACCCAACCCCATACAGGCAAGTGTCCAGGGTGCAAGCCAAGTCC</u>

<u>AACCCAGAGAGGCTCAGGAGGAGGCTCATGAGGAGGCACGACCTCTCCGAGGAA</u>

<u>GAGGCCAGGAAGCGCATCCCAGACACCGTGGCCAGGGCCCTCGACCTCCCATTC</u>

<u>GTGACCCTCAGGTCCCAGTCCACCGGCCAGCACTTCCGCCTCTTCATCAGGCAC</u>

<u>GGCCCACTCCAGGTGACCGCCGAGGAGGGCGGCTTTACCTGCTACGGCCTCTCC</u>

<u>AAGGGCGGCTTCGTGCCGTGGTTC</u>GGCTCCGGCGCCACCAACTTCTCCCTCCTC

AAGCAAGCCGGCGACGTGGAGGAGAACCCAGGCCCA*ATGGACAAGAAGTACTC*

*GATCGGCCTCGACATCGGGACGAACTCAGTTGGCTGGGCCGTGATCACCGACGA*

*GTACAAGGTGCCCTCTAAGAAGTTCAAGGTCCTGGGGAACACCGACCGCCATTCC*

*ATCAAGAAGAACCTCATCGGCGCTCTCCTGTTCGACAGCGGGGAGACCGCTGAG*

*GCTACGAGGCTCAAGAGAACCGCTAGGCGCCGGTACACGAGAAGGAAGAACAGG*

*ATCTGCTACCTCCAAGAGATTTTCTCCAACGAGATGGCCAAGGTTGACGATTCATT*

*CTTCCACCGCCTGGAGGAGTCTTTCCTCGTGGAGGAGGATAAGAAGCACGAGCG*

*GCATCCCATCTTCGGCAACATCGTGGACGAGGTTGCCTACCACGAGAAGTACCCT*

*ACGATCTACCATCTGCGGAAGAAGCTCGTGGACTCCACCGATAAGGCGGACCTC*

*AGACTGATCTACCTCGCTCTGGCCCACATGATCAAGTTCCGCGGCCATTTCCTGA*

*TCGAGGGGGATCTCAACCCAGACAACAGCGATGTTGACAAGCTGTTCATCCAACT*

*CGTGCAGACCTACAACCAACTCTTCGAGGAGAACCCGATCAACGCCTCTGGCGT*

*GGACGCGAAGGCTATCCTGTCCGCGAGGCTCTCGAAGTCCAGGAGGCTGGAGAA*

*CCTGATCGCTCAGCTCCCAGGCGAGAAGAAGAACGGCCTGTTCGGGAACCTCAT*

*CGCTCTCAGCCTGGGGCTCACCCCGAACTTCAAGTCGAACTTCGATCTCGCTGAG*

*GACGCCAAGCTGCAACTCTCCAAGGACACCTACGACGATGACCTCGATAACCTCC*

*TGGCCCAGATCGGCGATCAATACGCGGACCTGTTCCTCGCTGCCAAGAACCTGT*

*CGGACGCCATCCTCCTGTCAGATATCCTCCGCGTGAACACCGAGATCACGAAGG*

*CTCCACTCTCTGCCTCCATGATCAAGCGCTACGACGAGCACCATCAGGATCTGAC*

*CCTCCTGAAGGCGCTGGTCCGCCAACAGCTCCCGGAGAAGTACAAGGAGATTTT*

*CTTCGATCAGTCGAAGAACGGCTACGCTGGGTACATCGACGCGCGGGCCTCACA*

*AGAGGAGTTCTACAAGTTCATCAAGCCAATCCTGGAGAAGATGGACGGCACGGA*

-continued

```
GGAGCTCCTGGTGAAGCTCAACAGGGAGGACCTCCTGCGGAAGCAGAGAACCTT
CGATAACGGCAGCATCCCCCACCAAATCCATCTCGGGGAGCTGCACGCCATCCT
GAGAAGGCAAGAGGACTTCTACCCTTTCCTCAAGGATAACCGGGAGAAGATCGAG
AAGATCCTGACCTTCAGAATCCCATACTACGTCGGCCCTCTCGCGCGGGGGAACT
CAAGATTCGCTTGGATGACCCGCAAGTCTGAGGAGACCATCACGCCGTGGAACTT
CGAGGAGGTGGTGGACAAGGGCGCTAGCGCTCAGTCGTTCATCGAGAGGATGAC
CAACTTCGACAAGAACCTGCCCAACGAGAAGGTGCTCCCTAAGCACTCGCTCCTG
TACGAGTACTTCACCGTCTACAACGAGCTCACGAAGGTGAAGTACGTCACCGAGG
GCATGCGCAAGCCAGCGTTCCTGTCCGGGGAGCAGAAGAAGGCTATCGTGGACC
TCCTGTTCAAGACCAACCGGAAGGTCACGGTTAAGCAACTCAAGGAGGACTACTT
CAAGAAGATCGAGTGCTTCGATTCGGTCGAGATCAGCGGCGTTGAGGACCGCTT
CAACGCCAGCCTCGGGACCTACCACGATCTCCTGAAGATCATCAAGGATAAGGAC
TTCCTGGACAACGAGGAGAACGAGGATATCCTGGAGGACATCGTGCTGACCCTC
ACGCTGTTCGAGGACAGGGAGATGATCGAGGAGCGCCTGAAGACGTACGCCCAT
CTCTTCGATGACAAGGTCATGAAGCAACTCAAGCGCCGGAGATACACCGGCTGG
GGGAGGCTGTCCCGCAAGCTCATCAACGGCATCCGGGACAAGCAGTCCGGGAA
GACCATCCTCGACTTCCTCAAGAGCGATGGCTTCGCCAACAGGAACTTCATGCAA
CTGATCCACGATGACAGCCTCACCTTCAAGGAGGATATCCAAAAGGCTCAAGTGA
GCGGCCAGGGGGACTCGCTGCACGAGCATATCGCGAACCTCGCTGGCTCCCCC
GCGATCAAGAAGGGCATCCTCCAGACCGTGAAGGTTGTGGACGAGCTCGTGAAG
GTCATGGGCCGGCACAAGCCTGAGAACATCGTCATCGAGATGGCCAGAGAGAAC
CAAACCACGCAGAAGGGGCAAAAGAACTCTAGGGAGCGCATGAAGCGCATCGAG
GAGGGCATCAAGGAGCTGGGGTCCCAAATCCTCAAGGAGCACCCAGTGGAGAAC
ACCCAACTGCAGAACGAGAAGCTCTACCTGTACTACCTCCAGAACGGCAGGGATA
TGTACGTGGACCAAGAGCTGGATATCAACCGCCTCAGCGATTACGACGTCGATCA
TATCGTTCCCCAGTCTTTCCTGAAGGATGACTCCATCGACAACAAGGTCCTCACCA
GGTCGGACAAGAACCGCGGCAAGTCAGATAACGTTCCATCTGAGGAGGTCGTTA
AGAAGATGAAGAACTACTGGAGGCAGCTCCTGAACGCCAAGCTGATCACGCAAA
GGAAGTTCGACAACCTCACCAAGGCTGAGAGAGGCGGGCTCTCAGAGCTGGACA
AGGCCGGCTTCATCAAGCGGCAGCTGGTCGAGACCAGACAAATCACGAAGCACG
TTGCGCAAATCCTCGACTCTCGGATGAACACGAAGTACGATGAGAACGACAAGCT
GATCAGGGAGGTTAAGGTGATCACCCTGAAGTCTAAGCTCGTCTCCGACTTCAGG
AAGGATTTCCAGTTCTACAAGGTTCGCGAGATCAACAACTACCACCATGCCCATG
ACGCTTACCTCAACGCTGTGGTCGGCACCGCTCTGATCAAGAAGTACCCAAAGCT
GGAGTCCGAGTTCGTGTACGGGACTACAAGGTTTACGATGTGCGCAAGATGATC
GCCAAGTCGGAGCAAGAGATCGGCAAGGCTACCGCCAAGTACTTCTTCTACTCAA
ACATCATGAACTTCTTCAAGACCGAGATCACGCTGGCCAACGGCGAGATCCGGAA
GAGACCGCTCATCGAGACCAACGGCGAGACGGGGGAGATCGTGTGGGACAAGG
GCAGGGATTTCGCGACCGTCCGCAAGGTTCTCTCCATGCCCCAGGTGAACATCG
TCAAGAAGACCGAGGTCCAAACGGGCGGGTTCTCAAAGGAGTCTATCCTGCCTAA
```

-continued

GCGGAACAGCGACAAGCTCATCGCCAGAAAGAAGGACTGGGACCCAAAGAAGTA

CGGCGGGTTCGACAGCCCTACCGTGGCCTACTCGGTCCTGGTTGTGGCGAAGGT

TGAGAAGGGCAAGTCCAAGAAGCTCAAGAGCGTGAAGGAGCTCCTGGGGATCAC

CATCATGGAGAGGTCCAGCTTCGAGAAGAACCCAATCGACTTCCTGGAGGCCAA

GGGCTACAAGGAGGTGAAGAAGGACCTGATCATCAAGCTCCCGAAGTACTCTCTC

TTCGAGCTGGAGAACGGCAGGAAGAGAATGCTGGCTTCCGCTGGCGAGCTCCAG

AAGGGGAACGAGCTCGCGCTGCCAAGCAAGTACGTGAACTTCCTCTACCTGGCTT

CCCACTACGAGAAGCTCAAGGGCAGCCCGGAGGACAACGAGCAAAAGCAGCTGT

TCGTCGAGCAGCACAAGCATTACCTCGACGAGATCATCGAGCAAATCTCCGAGTT

CAGCAAGCGCGTGATCCTCGCCGACGCGAACCTGGATAAGGTCCTCTCCGCCTA

CAACAAGCACCGGGACAAGCCCATCAGAGAGCAAGCGGAGAACATCATCCATCT

CTTCACCCTGACGAACCTCGGCGCTCCTGCTGCTTTCAAGTACTTCGACACCACG

ATCGATCGGAAGAGATACACCTCCACGAAGGAGGTCCTGGACGCGACCCTCATC

CACCAGTCGATCACCGGCCTGTACGAGACGAGGATCGACCTCTCACAACTCGGC

GGGGATAAGAGACCCGCAGCAACCAAGAAGGCAGGGCAAGCAAAGAAGAAGAAG

TGA 3'

SEQ ID NO: 152; Outubain-like domain
PYVGDKEPLSTLAAEFQSGSPILQEKIKLLGEQYDALRRTRGDGNCFYRSFMFSYLEH

ILETQDKAEVERILKKIEQCKKTLADLGYIEFTFEDFFSIFIDQLESVLQGHESSIGAEELL

ERTRDQMVSDYVVMFFRFVTSGEIQRRAEFFEPFISGLTNSTVVQFCKASVEPMGEE

SDHVHIIALSDALGVPIRVMYLDRSSCDAGNISVNHHDFSPEANSSDGAAAAEKPYITL

LYRPGHYDILYP

SEQ ID NO: 153; Mutated OsOTUB1
ATGGGCGGGGACTACTACCACTCGTGCTGCGGCGACCCCGACCCCGACCTCCG

CGCGCCCGAGGGGCCCAAGCTGCCGTACGTCGGGGACAAGGAACCTCTCTCCA

CTTTAGCCGCCGAGTTTCAGTCTGGCAGCCCCATTTTACAGGAGAAAATAAAGTT

GCTTGGTGAACAGTATGATGCTTTAAGAAGGACACGAGGAGATGGAAACTGCTTT

TATCGAAGCTTTATGTTTTCCTACTTGGAACATATCCTAGAGACACAAGACAAAGC

TGAGGTTGAGCGCATTCTAAAAAAAATTGAGCAGTGCAAGAAGACTCTTGCAGAT

CTTGGATACATTGAGTTCACCTTTGAAGATTTCTTCTCT<u>GTCTTTATTGTTACTTTGT</u>

<u>GTGGCCCTCCTTACTTATCCTGTTCAATTGCTGTTTTGCAACTTATGCCAGATGTAT</u>

<u>TCCCTCTGAATAGTATGAAGATCTGTCCGATTATTTTCATGTATGCTTGTTTGCATT</u>

<u>TCCTTTTTAGATGTTCCTGGAATAATTTTTGTATGAGCTAGTTATAATGAGAGCTTG</u>

<u>TGCATTTTCCTGTCATGCAACAAATTAAATACTAGTGTCTAATCCTTGTGCATTGTT</u>

<u>AATAACTTTGAAAATGATTAGCCTTGAAGATTGGTCCATTATATATATGTTCACTTG</u>

<u>TTTCTTAGTTAGGATCACTCACCAGTCACCCTTCTGAAGTTCATAATGTATCACTTA</u>

TAAGTAAGCTAGCAAAACAAAATTTGGACTGTTTGTAGCCACCCAGAACCCAAATA

<u>GATGGATTTCACATTATTTTCTACTGGCTTTGGGAGTTATTTGATCGATGCTAGTAC</u>

<u>AACGTTGAAATTTGGGTAGTTGAGATGCATTTTTCACAAAGGACTCCTTTATTGGT</u>

<u>GCTTGATCTACAACTGGTGTTTTACTTTTTTACAAAAAAATGTAATCTCCTTGCAGT</u>

<u>GCACTCAAATTATTGCAACCTCCTTCCTTATGTTCCCACCCTCATTATTTTCAGATA</u>

TTCATTGATCAGCTGGAAAGTGTTCTGCAGGGACATGAATCCTCCATAGGGGCCG

```
AAGAGCTTCTAGAAAGAACCAGGGATCAGATGGTTTCTGATTATGTTGTCATGTTC

TTTAGGTTTGTCACCTCTGGTGAAATCCAAAGGAGGGCCGAGTTCTTCGAACCATT

CATCTCTGGCTTGACAAATTCGACTGTGGTTCAGTTCTGCAAGGCTTCCGTGGAG

CCGATGGGCGAGGAAAGTGACCATGTCCACATAATTGCCCTATCAGATGCGTTGG

GTGTGCCAATCCGTGTGATGTACCTAGACAGAAGCTCATGTGATGCTGGAAATAT

AAGTGTGAACCACCATGATTTCAGCCCTGAGGCCAATTCATCGGACGGTGCTGCT

GCTGCTGAGAAACCTTACATTACTTTGCTCTACCGTCCTGGTCACTACGACATTCT

CTACCCGAAGTGA
```

SEQ ID NO: 154; OsOTUB1 wtg mutation
```
MGGDYYHSCCGDPDPDLRAPEGPKLPYVGDKEPLSTLAAEFQSGSPILQEKIKLLGE

QYDALRRTRGDGNCFYRSFMFSYLEHILETQDKAEVERILKKIEQCKKTLADLGYIEFT

FEDFFSVFIVTLCGPPYLSCSIAVLQLMPDVFPLNSMKICPIIFMYACLHFLFRCSWNNF

CMS
```

SEQ ID NO: 155: NPT1 2.5 kb promoter sequence from IR66167-27-5-1-6
```
gagttgaagttgttgctgctgtcataagtactatctgctaaatgggcacactcctagcattattagaactgaga aatatcccaagcaatgaaagcgacaaaaaagtacccgtttgaagacatgattgacatggtcacatcaaacaccg gacatcaacatctaaatgtacataacaaggccaaaataattttcgatgctggttggtgctaccaagtcccacgt atgatacttaagaatcaatcatgaatattacaaatcaagtcaaactacgttatgtattgaactcttataattac tgcaacatatcacactggaatttcctatggtaattcctcgccagccttatcctacccatcccttgcagtatatt aagagcatcaacaacaaacatgattcaagacaactttttattaacactgaacaacataaattgggaacaaaacaa accacttggaggcatgattaggataatcggtattaaagaactggacatcacaattcacaactagatgttgaaat aatacctgtctcttctttggctcatggcaggtgtcagtgaaatatactgatgctccaagagagctggaagcacc gtttccacgtaatcaaaatgtccttttcgtttgctgcaatcaaccttaaagggctcttttgatgctatctcttc aggcatgtccttcacaacttccacataacctctggtttgctcaatgaagtaatcaacatcgaaaacgtctgcaa atccactgacagagaataccaataagtgatgaactaccttttgaacagaaataaactgcataactacaagtagc acagtcgttcatcttgtagagtgattctcatacctagattcattccagtaggcagcaacctcaaacttgggcag aaccattgttgcgttgagaaggcgcgcaaccgcaattccatcacatagctgaagaaacattcggaagaataatt acaaccaggagtaacataataacatagccagttgaaatcacattcgccttgcaatgtgaaaattttcataaata atctgaaaatttagttatgccactatatatcatgcaacctgcctccacgacattttaatcatggagtagaagat aaaacatatgatcccctcattgaccctactatcttactacttgtgcatggccgaacgatctaacagcgaaatc cagaaagccaacactcatttgatcccactaacaacggaagagagaaacgctagccgagatcgcttaacgtacat cgcgtcgcagctggttgagcccgccgtagcagtcgatccggatgtacccattcctcctcgacggagctgcagaa gaagaggaggttcaaaaccgcaatcaccaccacagtctcaagcagagatgtccactacccggatccttaaaccc aaaccacaaatcacggcgaggtctcacccggcattgccgcccgccaccaccccgcacgaccgccactccgccacc cgccgctgcgcccatatgacccgcgaccccgacgccgacggcgactcctccctaaagaccaaaagcgagtaagc gagatccgtaagcttctggaacaatctcgagcatcagctgcaagaggtgaggctgggccgcgtacctggaggtg ggaagagtgaagaagaaaggcggagaggagggtggagagaggaggaagtagagcgcggggcgaggaagatgac cggtaggaggatgcggacgcggctgcgcgccaccacgccgccggcgacgccgacgacgacatcgcctcgccgc gagaagcactggatctgatcggccgccgcctccacgccggagtggagagcatatataagctcgtcagaatgtgg gcccgtggctatgtgggcccaccatgtcatcgacgcttatcaagatcgagcggtggcgtgaggaaaccggtagg ggtgggggggctaaccaatcggaaacgcgtaataactcacccgcggttcactttctccttatgacacgtgggcc
```

-continued catctcttcctggacccacctgtcagttacccttacggcctccactctgaggatctaaacgtaaaaacgaattt atcggagggcttatccgcgaggggaaaaaaacgcgcacttatttctcgccttcgccgagatctcggaagagaag aacacgcaccgcggggagaggggagagaagcggaaagctccaccgaatcgaagcccccacacacgcgaagctgg cgcgggaggcggccgacgcgagcgcccggaagcgcaaggcggcgacggcggcggggagggcgacgccgcggcg acggtcccggaggaggcggtgatggggaggcggcggcggcagccgcggcccccgagccggtcgtcgagggggg aggagggggggggaggggttgaatcctaaccctagcggcggtggggaggaggtggtggagggtgctcggact ccgtgtcggtcgagctctcg SEQ ID NO: 156 DEP1 cDNA sequence:
atgggggaggaggcggtggtgatggaggcgccgaggcccaagtcgccgccgaggtacccggacctgtgcggccg gcggcggatgcagctggaggtgcagatcctgagccgcgagatcacgttcctcaaggatgagcttcacttccttg aaggagctcagcccgtttctcgttctggatgcattaaagagataaatgagtttgttggtacaaaacatgaccca ctaataccaacaaagagaaggaggcacagatcttgccgtcttttcggtggatcggatcaaaattgtgtatctg catttcatgtctttgctactgttgcaagtgctcacccaagtgcaaaagaccaaggtgcctcaattgttcttgca gctcatgctgcgacgagccatgctgtaagccaaactgcagtgcgtgctgcgctgggtcatgctgtagtccagac tgctgctcatgctgtaaacctaactgcagttgctgcaagacccttcttgctgcaaaccgaactgctcgtgctc ctgtccaagctgcagctcatgctgcgatacatcgtgctgcaaaccgagctgcacctgcttcaacatctttcat gcttcaaatccctgtacagctgcttcaagatcccttcatgcttcaagtcccagtgcaactgctctagcccccaat tgctgcacttgcacccttccaagctgtagctgcaagggctgtgcctgtccaagctgtggatgcaacggctgtgg ctgtccaagctgcggatgcaacggttgtggctgtccaagctgcggttgcaacggctgtggccttccaagctgcg gttgcaacggctgcggctcgtgctcttgcgcccaatgcaaacccgattgtggctcgtgctctaccaattgctgt agctgcaagccaagctgcaacggctgctgcggcgagcagtgctgccgctgcgcggactgcttctcctgctcgtg ccctcgttgctccagctgcttcaacatcttcaaatgctcctgcgctggctgctgctcgagcctgtgcaagtgcc cctgcacgacgcagtgcttcagctgccagtcgtcatgctgcaagcggcagccttcgtgctgcaagtgccagtcg tcttgctgcgaggggcagccttcctgctgcgagggacactgctgcagcctcccgaaaccgtcgtgccctgaatg ttcctgtgggtgtgtctggtcttgcaagaattgtacagagggttgtcgatgcccacggtgtcgtaacccatgct gtctcagtggttgcttatgttga SEQ ID NO: 157 DEP1 protein:
mgeeavvmeaprpksppryptdlcgrrrmqlevqilsreitflkdelhflegaqpvsrsgcikeinefvgtkhdp liptkrrrhrscrlfrwigsklcicisclcycckcspkckrprclncscsccdepcckpncsaccagsccspd ccscckpncscccktpscckpncscscpscsssccdtscckpsctcfnifscfkslyscfkipscfksqcncsspn cctctlpscsckgcacpscgcngcgcpscgcngcgcpscgcngcglpscgcngcscscaqckpdcgscstncc sckpscngccgeqccrcadcfscscprcsscfnifkcscagccsslckcpcttqcfscqssccckrqpscckcqs sccegqpscceghccslpkpscpecscgcvwscknctegcrcprcrnpcclsgclc SEQ ID NO: 158: dep1 cDNA sequence:
ATGGGGGAGGAGGCGGTGGTGATGGAGGCGCCGAGGCCCAAGTCGCCGCCGA

GGTACCCGGACCTGTGCGGCCGGCGGCGGATGCAGCTGGAGGTGCAGATCCTG

AGCCGCGAGATCACGTTCCTCAAGGATGAGCTTCACTTCCTTGAAGGAGCTCAGC

CCGTTTCTCGTTCTGGATGCATTAAAGAGATAAATGAGTTTGTTGGTACAAAACAT

GACCCACTAATACCAACAAAGAGAAGGAGGCACAGATCTTGCCGTCTTTTTCGGT

GGATCGGATCAAAATTGTGTATCTGCATTTCATGTCTTTGCTACTGTTGCAAGTGC

TCACCCAAGTGCAAAAGACCAAGGTGCCTCAATTGTTCTTGCAGCTCATGCTGCG

ACGAGCCATGCTGTAAGCCAAACTGCAGTGCGTGCTGCGCTGGGTCATGCTGCA

-continued

GTCCAGACTGCTGCTCATGCTGTAAACCTAACTGCAGTTGCTGCAAGACCCCTTC

TTGCTGCAAACCGAACTGCTCGTGCTCCTGTCCAAGCTGCAGCTCATGCTGCGAT

ACATCGTGCTGCAAACCGAGCTGCACCTGCTTCAACATCTAG

SEQ ID NO: 159 dep1 protein:
mgeeavvmeaprpkspprypdlcgrrrmqlevqilsreitflkdelhflegaqpvsrsgcikeinefvgtkhdp liptkrrrhrscrlfrwigsklcicisclcycckcspkckrprclncscssccdepcckpncsaccagsccspd ccscckpncscccktpscckpncscscpscssccdtscckpsctcfnif SEQ ID NO: 160 OsUBC13 cDNA
atggccaacagcaacctccccggcgaatcatcaaggagacgcagcgactcctcagcgagccagcgccgggaat cagcgcgtctccgtcggaggagaacatgcgctacttcaacgtcatgatccttggcccggcacagtcccctatg aaggtggagttttaagcttgaactctttttacctgaggaatatcctatggctgctccaaaggttaggttcctg accaaaatataccaccccaacattgacaagcttggtaggatatgccttgacattctcaaggacaaatggagccc agcccttcagattcggacagttcttttgagtatccaggcactcctaagtgcaccaaaccctgatgatcctctct ctgataacattgcaaagcactggaaagccaatgaagcagaagctgttgaaacagcaaaggagtggactcgcctg tatgccagcggtgcataa SEQ ID NO: 161 OsUBC13 protein:
Mansnlprriiketqrllsepapgisaspseenmryfnvmilgpaqspyeggvfklelflpeeypmaapkvrfl tkiyhpnidklgricldilkdkwspalqirtvllsiqallsapnpddplsdniakhwkaneaeavetakewtrl yasga SEQ ID NO: 162 OsUBC13 gDNA
atggccaacagcaacctccccggcgaatcatcaaggtcgcgcctccgatctgattgcctgggcgtagatctcc ccacgcctctaacccgattccccccttttcttttcttttttttttattttccctttctgtgctgatttttgt ttttgctgtctgtgtgttcgcgtctggtttggatctgcgcaggagacgcagcgactcctcagcgagccaggtgc gggcggttttttttttttttatgtatcgcggattttggcgatggtgttgtgttttccgtggtttgggttcgtg ttgttctgatggttttgggttggtttgtttgtgcagcgccgggaatcagcgcgtctccgtcggaggagaacatg cgctacttcaacgtcatgatccttggcccggcacagtccccctatgaaggtacggcacccgatggatacgttat ttgttgtagagggtgttacggctcccgatggatatgttatttgttgtagagggtggtcgattagggcgtttcta ggtataccgcagaattgggtgattctgtataaacccaattactagaagtgttaattatgtgtcagtcatggacg ggcacgcatttcgtaagcctgcttttgcttgattaggctggttcttttgcacttaccagttttagtttctcggg cggcgggcacttgcatgttctatgtgtctcatattccctttctagtatgaagttagtaatgctaaaacactagt gacttttagcaataatgttctaaactcggattatatacgtgacttataagtgcttttcttttatgtgttaactt gtttgatgctttgtgcggcaaaggttgcccttgattttccataaccaaattgatctcttcgatttatttgatta gactaattatgagtattgatattgttggcttttcatgttgtggtgtataatttaaatatttcctttcttaaacc ctttttgcgttaattcgggttggatatataatgggtgttaacagttagtagctttagatggtttattctattat catttggcttcctgatattgttctttctatcaggtggagtttttaagcttgaactctttttacctgaggaatat cctatggctgctccaaaggtaacaagacatagataaactttggttatgttttatatgatattatggggactgta taccttcaagctaattatgtcgtatttagaattgcgtgtggttatatactcatattaaaagtcaggacatttct gcattcattgacttgtgttgtgaagcggagcattaatttggtgacattggactcatgcatataaccaaatacag gaaagtagctgaaacatttaatttgtttgaaccattcttggcaaaaaaaattttattcttttatagcctaat ttttagttacccatatttaatcgtgtcgctctggaaccatcgttggttttatatgttatatgtgatgtcttgtt ggtaatagttttgttacatttgcttgatttccttttagggataatgcaaaccctgcctatttgagatgtaattt gcaatgagatcctgtgccaaggaccaaggttgtaagatatactttggtcctgtgggaacttttagctgtgtcc tgagcatcagcacgccattgcttctcttgaccgtctttttgcttcaagttcttaaaggtgttcttaacatcaca -continued ttgttcgtttggtgttcagccaaattataccttgattagttattttttagtctgtttggcttgacaatgtcat agattggaagggtgaagaaatattactcatatgttatacaaccataccggattattgtctacttcagtctccct aagtgtaaagctatataattcattattgtctacctcagtctccattttttctttgttgcgtatgcaggttaggt tcctgaccaaaatataccaccccaacattgacaaggtttgcagtcacattcctctttgttatttagtttacttc gtaatacattgtttattcattaataggtttacttttgtagcttggtaggatatgccttgacattctcaaggaca aatggagcccagcccttcagattcggacagttcttttgaggtctctcccccgttgcctgcacatgtgtattagc tttttatatcctgcacaaattccttgtctgctaagctgttgtcttattacgattgacatgatttctgttgaatt tgaattatttgttagcttacctgcatttagtaattttatcactgcccttgatgtgttttccaacaaaaactct tgagcattgtcaactattggaagttaggggtatcactttgctatacttaccttgtgacaacactcttttttttc agtatccaggcactcctaagtgcaccaaaccctgatgatcctctctctgataacattgcaaagcactggaaagc caatgaagcagaagctgttgaaacaggtaaattgaagctagcaatccagttaacagtgtctcccctcacactct gattttattggttgcctgataagcgatggtctggcatttgcagcaaaggagtggactcgcctgtatgccagcgg tgcataa SEQ ID NO: 163 U3 promoter sequence:
AAAGGAAGGAATCTTTAAACATACGAACAGATCACTTAAAGTTCTTCTGAAGCAAC

TTAAAGTTATCAGGCATGCATGGATCTTGGAGGAATCAGATGTGCAGTCAGGGAC

CATAGCACAAGACAGGCGTCTTCTACTGGTGCTACCAGCAAATGCTGGAAGCCGG

GAACACTGGGTACGTTGGAAACCACGTGTGATGTGAAGGAGTAAGATAAACTGTA

GGAGAAAAGCATTTCGTAGTGGGCCATGAAGCCTTTCAGGACATGTATTGCAGTA

TGGGCCGGCCCATTACGCAATTGGACGACAACAAAGACTAGTATTAGTACCACCT

CGGCTATCCACATAGATCAAAGCTGGTTTAAAAGAGTTGTGCAGATGATCCGTGG

CA

SEQ ID NO: 164 U6a promoter sequence:
TTTTTTCCTGTAGTTTTCCCACAACCATTTTTTACCATCCGAATGATAGGATAGGAA

AAATATCCAAGTGAACAGTATTCCTATAAAATTCCCGTAAAAAGCCTGCAATCCGA

ATGAGCCCTGAAGTCTGAACTAGCCGGTCACCTGTACAGGCTATCGAGATGCCAT

ACAAGAGACGGTAGTAGGAACTAGGAAGACGATGGTTGATTCGTCAGGCGAAATC

GTCGTCCTGCAGTCGCATCTATGGGCCTGGACGGAATAGGGGAAAAAGTTGGCC

GGATAGGAGGGAAAGGCCCAGGTGCTTACGTGCGAGGTAGGCCTGGGCTCTCA

GCACTTCGATTCGTTGGCACCGGGGTAGGATGCAATAGAGAGCAACGTTTAGTAC

CACCTCGCTTAGCTAGAGCAAACTGGACTGCCTTATATGCGCGGGTGCTGGCTTG

GCTGCCG

SEQ ID NO: 165 U6b promoter sequence:
TGCAAGAACGAACTAAGCCGGACAAAAAAAAAGGAGCACATATACAAACCGGTT

TTATTCATGAATGGTCACGATGGATGATGGGGCTCAGACTTGAGCTACGAGGCCG

CAGGCGAGAGAAGCCTAGTGTGCTCTCTGCTTGTTTGGGCCGTAACGGAGGATA

CGGCCGACGAGCGTGTACTACCGCGCGGGATGCCGCTGGGCGCTGCGGGGC

CGTTGGATGGGATCGGTGGGTCGCGGGAGCGTTGAGGGGAGACAGGTTTAGT

ACCACCTCGCCTACCGAACAATGAAGAACCCACCTTATAACCCCGCGCGCTGCCG

CTTGTGTTG

SEQ ID NO: 166 U3b in dicot plant
TTTACTTTAAATTTTTTCTTATGCAGCCTGTGATGGATAACTGAATCAAACAAATGG

CGTCTGGGTTTAAGAAGATCTGTTTTGGCTATGTTGGACGAAACAAGTGAACTTTT

AGGATCAACTTCAGTTTATATATGGAGCTTATATCGAGCAATAAGATAAGTGGGCT

TTTTATGTAATTTAATGGGCTATCGTCCATAGATTCACTAATACCCATGCCCAGTAC

CCATGTATGCGTTTCATATAAGCTCCTAATTTCTCCCACATCGCTCAAATCTAAACA

AATCTTGTTGTATATATAACACTGAGGGAGCAACATTGGTCA

SEQ ID NO: 167 U6-1 in dicot plant
AGAAATCTCAAAATTCCGGCAGAACAATTTTGAATCTCGATCCGTAGAAACGAGAC

GGTCATTGTTTTAGTTCCACCACGATTATATTTGAAATTTACGTGAGTGTGAGTGA

GACTTGCATAAGAAAATAAAATCTTTAGTTGGGAAAAAATTCAATAATATAAATGGG

CTTGAGAAGGAAGCGAGGGATAGGCCTTTTTCTAAAATAGGCCCATTTAAGCTATT

AACAATCTTCAAAAGTACCACAGCGCTTAGGTAAAGAAAGCAGCTGAGTTTATATA

TGGTTAGAGACGAAGTAGTGATTG

SEQ ID NO: 168; Cys4-P2A-TaCas9 nucleic acid sequence
5'<u>ATGGACCACTACCTCGACATCAGGCTCAGGCCAGACCCAGAGTTCCCACCAGC</u>

<u>CCAGCTCATGTCCGTCCTCTTCGGCAAGCTCCACCAGGCCCTCGTGGCCCAGGG</u>

<u>CGGCGACAGGATCGGCGTGTCCTTCCCAGACCTCGACGAGTCCAGGTCCAGGCT</u>

<u>CGGCGAGAGGCTCCGCATCCACGCCTCCGCCGACGACCTCAGGGCCCTCCTCG</u>

<u>CCAGGCCGTGGCTGGAGGGCCTCAGGGACCACCTCCAGTTCGGCGAGCCAGCC</u>

<u>GTGGTGCCACACCCAACCCCATACAGGCAAGTGTCCAGGGTGCAAGCCAAGTCC</u>

<u>AACCCAGAGAGGCTCAGGAGGAGGCTCATGAGGAGGCACGACCTCTCCGAGGAA</u>

<u>GAGGCCAGGAAGCGCATCCCAGACACCGTGGCCAGGGCCCTCGACCTCCCATTC</u>

<u>GTGACCCTCAGGTCCCAGTCCACCGGCCAGCACTTCCGCCTCTTCATCAGGCAC</u>

<u>GGCCCACTCCAGGTGACCGCCGAGGAGGGCGGCTTTACCTGCTACGGCCTCTCC</u>

<u>AAGGGCGGCTTCGTGCCGTGGTTC</u><u>GGCTCCGGC</u>GCCACCAACTTCTCCCTCCTC

AAGCAAGCCGGCGACGTGGAGGAGAACCCAGGCCCA*ATGGACAAGAAGTACTC*

*GATCGGCCTCGACATCGGGACGAACTCAGTTGGCTGGGCCGTGATCACCGACGA*

*GTACAAGGTGCCCTCTAAGAAGTTCAAGGTCCTGGGGAACACCGACCGCCATTCC*

*ATCAAGAAGAACCTCATCGGCGCTCTCCTGTTCGACAGCGGGGAGACCGCTGAG*

*GCTACGAGGCTCAAGAGAACCGCTAGGCGCCGGTACACGAGAAGGAAGAACAGG*

*ATCTGCTACCTCCAAGAGATTTTCTCCAACGAGATGGCCAAGGTTGACGATTCATT*

*CTTCCACCGCCTGGAGGAGTCTTTCCTCGTGGAGGAGGATAAGAAGCACGAGCG*

*GCATCCCATCTTCGGCAACATCGTGGACGAGGTTGCCTACCACGAGAAGTACCCT*

*ACGATCTACCATCTGCGGAAGAAGCTCGTGGACTCCACCGATAAGGCGGACCTC*

*AGACTGATCTACCTCGCTCTGGCCCACATGATCAAGTTCCGCGGCCATTTCCTGA*

*TCGAGGGGATCTCAACCCAGACAACAGCGATGTTGACAAGCTGTTCATCCAACT*

*CGTGCAGACCTACAACCAACTCTTCGAGGAGAACCCGATCAACGCCTCTGGCGT*

*GGACGCGAAGGCTATCCTGTCCGCGAGGCTCTCGAAGTCCAGGAGGCTGGAGAA*

*CCTGATCGCTCAGCTCCCAGGCGAGAAGAAGAACGGCCTGTTCGGGAACCTCAT*

*CGCTCTCAGCCTGGGGCTCACCCCGAACTTCAAGTCGAACTTCGATCTCGCTGAG*

*GACGCCAAGCTGCAACTCTCCAAGGACACCTACGACGATGACCTCGATAACCTCC*

-continued

```
TGGCCCAGATCGGCGATCAATACGCGGACCTGTTCCTCGCTGCCAAGAACCTGT

CGGACGCCATCCTCCTGTCAGATATCCTCCGCGTGAACACCGAGATCACGAAGG

CTCCACTCTCTGCCTCCATGATCAAGCGCTACGACGAGCACCATCAGGATCTGAC

CCTCCTGAAGGCGCTGGTCCGCCAACAGCTCCCGGAGAAGTACAAGGAGATTTT

CTTCGATCAGTCGAAGAACGGCTACGCTGGGTACATCGACGGCGGGGCCTCACA

AGAGGAGTTCTACAAGTTCATCAAGCCAATCCTGGAGAAGATGGACGGCACGGA

GGAGCTCCTGGTGAAGCTCAACAGGGAGGACCTCCTGCGGAAGCAGAGAACCTT

CGATAACGGCAGCATCCCCCACCAAATCCATCTCGGGGAGCTGCACGCCATCCT

GAGAAGGCAAGAGGACTTCTACCCTTTCCTCAAGGATAACGGGAGAAGATCGAG

AAGATCCTGACCTTCAGAATCCCATACTACGTCGGCCCTCTCGCGCGGGGGAACT

CAAGATTCGCTTGGATGACCCGCAAGTCTGAGGAGACCATCACGCCGTGGAACTT

CGAGGAGGTGGTGGACAAGGGCGCTAGCGCTCAGTCGTTCATCGAGAGGATGAC

CAACTTCGACAAGAACCTGCCCAACGAGAAGGTGCTCCCTAAGCACTCGCTCCTG

TACGAGTACTTCACCGTCTACAACGAGCTCACGAAGGTGAAGTACGTCACCGAGG

GCATGCGCAAGCCAGCGTTCCTGTCCGGGGAGCAGAAGAAGGCTATCGTGGACC

TCCTGTTCAAGACCAACCGGAAGGTCACGGTTAAGCAACTCAAGGAGGACTACTT

CAAGAAGATCGAGTGCTTCGATTCGGTCGAGATCAGCGGCGTTGAGGACCGCTT

CAACGCCAGCCTCGGGACCTACCACGATCTCCTGAAGATCATCAAGGATAAGGAC

TTCCTGGACAACGAGGAGAACGAGGATATCCTGGAGGACATCGTGCTGACCCTC

ACGCTGTTCGAGGACAGGGAGATGATCGAGGAGCGCCTGAAGACGTACGCCCAT

CTCTTCGATGACAAGGTCATGAAGCAACTCAAGCGCCGGAGATACACCGGCTGG

GGGAGGCTGTCCCGCAAGCTCATCAACGGCATCCGGGACAAGCAGTCCGGGAA

GACCATCCTCGACTTCCTCAAGAGCGATGGCTTCGCCAACAGGAACTTCATGCAA

CTGATCCACGATGACAGCCTCACCTTCAAGGAGGATATCCAAAAGGCTCAAGTGA

GCGGCCAGGGGGACTCGCTGCACGAGCATATCGCGAACCTCGCTGGCTCCCCC

GCGATCAAGAAGGGCATCCTCCAGACCGTGAAGGTTGTGGACGAGCTCGTGAAG

GTCATGGGCCGGCACAAGCCTGAGAACATCGTCATCGAGATGGCCAGAGAGAAC

CAAACCACGCAGAAGGGGCAAAAGAACTCTAGGGAGCGCATGAAGCGCATCGAG

GAGGGCATCAAGGAGCTGGGGTCCCAAATCCTCAAGGAGCACCCAGTGGAGAAC

ACCCAACTGCAGAACGAGAAGCTCTACCTGTACTACCTCCAGAACGGCAGGGATA

TGTACGTGGACCAAGAGCTGGATATCAACCGCCTCAGCGATTACGACGTCGATCA

TATCGTTCCCCAGTCTTTCCTGAAGGATGACTCCATCGACAACAAGGTCCTCACCA

GGTCGGACAAGAACCGCGGCAAGTCAGATAACGTTCCATCTGAGGAGGTCGTTA

AGAAGATGAAGAACTACTGGAGGCAGCTCCTGAACGCCAAGCTGATCACGCAAA

GGAAGTTCGACAACCTCACCAAGGCTGAGAGAGGCGGGCTCTCAGAGCTGGACA

AGGCCGGCTTCATCAAGCGGCAGCTGGTCGAGACCAGACAAATCACGAAGCACG

TTGCGCAAATCCTCGACTCTCGGATGAACACGAAGTACGATGAGAACGACAAGCT

GATCAGGGAGGTTAAGGTGATCACCCTGAAGTCTAAGCTCGTCTCCGACTTCAGG

AAGGATTTCCAGTTCTACAAGGTTCGCGAGATCAACAACTACCACCATGCCCATG

ACGCTTACCTCAACGCTGTGGTCGGCACCGCTCTGATCAAGAAGTACCCAAAGCT

GGAGTCCGAGTTCGTGTACGGGGACTACAAGGTTTACGATGTGCGCAAGATGATC
```

GCCAAGTCGGAGCAAGAGATCGGCAAGGCTACCGCCAAGTACTTCTTCTACTCAA

ACATCATGAACTTCTTCAAGACCGAGATCACGCTGGCCAACGGCGAGATCCGGAA

GAGACCGCTCATCGAGACCAACGGCGAGACGGGGGAGATCGTGTGGGACAAGG

GCAGGGATTTCGCGACCGTCCGCAAGGTTCTCTCCATGCCCCAGGTGAACATCG

TCAAGAAGACCGAGGTCCAAACGGGCGGGTTCTCAAAGGAGTCTATCCTGCCTAA

GCGGAACAGCGACAAGCTCATCGCCAGAAAGAAGGACTGGGACCCAAAGAAGTA

CGGCGGGTTCGACAGCCCTACCGTGGCCTACTCGGTCCTGGTTGTGGCGAAGGT

TGAGAAGGGCAAGTCCAAGAAGCTCAAGAGCGTGAAGGAGCTCCTGGGGATCAC

CATCATGGAGAGGTCCAGCTTCGAGAAGAACCCAATCGACTTCCTGGAGGCCAA

GGGCTACAAGGAGGTGAAGAAGGACCTGATCATCAAGCTCCCGAAGTACTCTCTC

TTCGAGCTGGAGAACGGCAGGAAGAGAATGCTGGCTTCCGCTGGCGAGCTCCAG

AAGGGGAACGAGCTCGCGCTGCCAAGCAAGTACGTGAACTTCCTCTACCTGGCTT

CCCACTACGAGAAGCTCAAGGGCAGCCCGGAGGACAACGAGCAAAAGCAGCTGT

TCGTCGAGCAGCACAAGCATTACCTCGACGAGATCATCGAGCAAATCTCCGAGTT

CAGCAAGCGCGTGATCCTCGCCGACGCGAACCTGGATAAGGTCCTCTCCGCCTA

CAACAAGCACCGGGACAAGCCCATCAGAGAGCAAGCGGAGAACATCATCCATCT

CTTCACCCTGACGAACCTCGGCGCTCCTGCTGCTTTCAAGTACTTCGACACCACG

ATCGATCGGAAGAGATACACCTCCACGAAGGAGGTCCTGGACGCGACCCTCATC

CACCAGTCGATCACCGGCCTGTACGAGACGAGGATCGACCTCTCACAACTCGGC

GGGGATAAGAGACCCGCAGCAACCAAGAAGGCAGGGCAAGCAAAGAAGAAGAAG

TGA 3'

SEQ ID NO: 169: Cys 4 endoribonuclease nucleic acid sequence
5'ATGGACCACTACCTCGACATCAGGCTCAGGCCAGACCCAGAGTTCCCACCAGC

CCAGCTCATGTCCGTCCTCTTCGGCAAGCTCCACCAGGCCCTCGTGGCCCAGGG

CGGCGACAGGATCGGCGTGTCCTTCCCAGACCTCGACGAGTCCAGGTCCAGGCT

CGGCGAGAGGCTCCGCATCCACGCCTCCGCCGACGACCTCAGGGCCCTCCTCG

CCAGGCCGTGGCTGGAGGGCCTCAGGGACCACCTCCAGTTCGGCGAGCCAGCC

GTGGTGCCACACCCAACCCCATACAGGCAAGTGTCCAGGGTGCAAGCCAAGTCC

AACCCAGAGAGGCTCAGGAGGAGGCTCATGAGGAGGCACGACCTCTCCGAGGAA

GAGGCCAGGAAGCGCATCCCAGACACCGTGGCCAGGGCCCTCGACCTCCCATTC

GTGACCCTCAGGTCCCAGTCCACCGGCCAGCACTTCCGCCTCTTCATCAGGCAC

GGCCCACTCCAGGTGACCGCCGAGGAGGGCGGCTTTACCTGCTACGGCCTCTCC

AAGGGCGGCTTCGTGCCGTGGTTC 3'

TABLE I

Primers used for sdRNA constructs

| Name | Forward primer | Reverse primer |
|---|---|---|
| 1 | Aacggcggtggggaaggagggttttagagctag aaat (SEQ ID NO: 170) | Cctcctcccccaccgccgctcggcagccaagcca gca (SEQ ID NO: 171) |
| 2 | Gggaggaggaggggggggggttttagagcta gaaat (SEQ ID NO: 172) | Cccccccccctcctcctccccggcagccaagcca gca (SEQ ID NO: 173) |

TABLE I-continued

Primers used for sdRNA constructs

| Name | Forward primer | Reverse primer |
|---|---|---|
| 3 | Gggggggaggaggaggggggggttttagagcta gaaat (SEQ ID NO: 174) | Cccccccctcctcctccccccccggcagccaagcca gca (SEQ ID NO: 175) |
| 4 | Tcgagggggggaggaggaggggttttagagctag aaat (SEQ ID NO: 176) | Ccctcctcctcccccctcgacggcagccaagcca gca (SEQ ID NO: 177) |
| 5 | Gtcgtcgagggggggaggagggttttagagctag aaat (SEQ ID NO: 178) | Cctcctcccccctcgacgaccggcagccaagcca gca (SEQ ID NO: 179) |
| 6 | Ggcagccgcggcccccgagcgttttagagctag aaat (SEQ ID NO: 180) | Gctcggggccgcggctgcccggcagccaagcc agca (SEQ ID NO: 181) |
| 7 | Tcccggaggaggcggtgatggttttagagctaga aat (SEQ ID NO: 182) | Catcaccgcctcctccgggacggcagccaagcca gca (SEQ ID NO: 183) |
| 8 | Cgcccggaagcgcaaggcgggttttagagctag aaat (SEQ ID NO: 184) | Ccgccttgcgcttccgggcgcggcagccaagcca gca (SEQ ID NO: 185) |
| 9 | Gaagagaagaacacgcaccggttttagagctag aaat (SEQ ID NO: 186) | Cggtgcgtgttcttctcttccggcagccaagcca gca (SEQ ID NO: 187) |
| 10 | cccttacggcctccactctggttttagagctaga aat (SEQ ID NO: 188) | Cagagtggaggccgtaagggcggcagccaagc cagca (SEQ ID NO: 189) |
| 11 | Cactttctccttatgacacggttttagagctag aaat (SEQ ID NO: 190) | Cgtgtcataaggagaaagtgcggcagccaagcc agca (SEQ ID NO: 191) |
| 12 | Tatataagctcgtcagaatggttttagagctag aaat (SEQ ID NO: 192) | Cattctgacgagcttatatacggcagccaagccag ca (SEQ ID NO: 193) |
| 13 | Cgagaagcactggatctgatgttttagagctaga aat (SEQ ID NO: 194) | Atcagatccagtgcttctcgcggcagccaagccag ca (SEQ ID NO: 195) |
| 14 | Gagaggaggaagtagagcgcgttttagagctag aaat (SEQ ID NO: 196) | Gcgctctacttcctcctctccggcagccaagcca gca (SEQ ID NO: 197) |
| 15 | Taaacccaaaccacaaatcagttttagagctaga aat (SEQ ID NO: 198) | Tgatttgtggtttgggtttacggcagccaagcca gca (SEQ ID NO: 199) |
| 16 | Atgtacccattcctcctcgagttttagagctag aaat (SEQ ID NO: 200) | Tcgaggaggaatgggtacatcggcagccaagcc agca (SEQ ID NO: 201) |
| 17 | Aacgtacatcgcgtcgcagcgttttagagctaga aat (SEQ ID NO: 202) | Gctgcgacgcgatgtacgttcggcagccaagcca gca (SEQ ID NO: 203) |
| 18 | Actatcttactacttgtgcagttttagagctag aaat (SEQ ID NO: 204) | Tgcacaagtagtaagatagtcggcagccaagcca gca (SEQ ID NO: 205) |
| 19 | Tcggaagaataattacaaccgttttagagctaga aat (SEQ ID NO: 206) | Ggttgtaattattcttccgacggcagccaagcca gca (SEQ ID NO: 207) |
| 20 | Gtaggcagcaacctcaaactgttttagagctaga aat (SEQ ID NO: 208) | Agtttgaggttgctgcctaccggcagccaagccag ca (SEQ ID NO: 209) |

RNAi nucleic acid sequence

SEQ ID NO: 210

TCTGGTGAAATCCAAAGGAGGGCCGAGTTCTTCGAACCATTCATCT

CTGGCTTGACAAATTCGACTGTGGTTCAGTTCTGCAAGGCTTCCGT

GGAGCCGATGGGCGAGGAAAGTGACCATGTCCACATAATTGCCCTA

TCAGATGCGTTGGGTGTGCCAATCCGTGTGATGTACCTAGACAGAA

GCTCATGTGATGCTGGAAATATAAGTGTGAACCACCATGATTTCAG

CCCTGAGGCCAATTCATCGGACGGTGCTGCTGCTGCTGAGAAACCT

TACATTACTTTGCTCTACCGTCCTGGTCACTACG

REFERENCES

1. Abe, A., Kosugi, S., Yoshida, K., Natsume, S., Takagi, H., Kanzaki, H., Matsumura, H., Mitsuoka, C., Tamiru, M., Innan, H., Cano, L., Kamoun, S. and Terauchi, R. (2012) Genome sequencing reveals agronomically important loci in rice using MutMap. *Nat Biotechnol,* 30, 174-178.
2. Alvarez-Venegas, R. and Avramova, Z. (2005) Methylation patterns of histone H3 Lys 4, Lys 9 and Lys 27 in transcriptionally active and inactive *Arabidopsis genes and in atx*1 mutants. *Nucleic Acids Res,* 33, 5199-5207.
3. Balakirev, M. Y., Tcherniuk, S. O., Jaquinod, M. and Chroboczek, J. (2003) Otubains: a new family of cysteine proteases in the ubiquitin pathway. *EMBO Rep,* 4, 517-522.
4. Che, R., Tong, H., Shi, B., Liu, Y., Fang, S., Liu, D., Xiao, Y., Hu, B., Liu, L., Wang, H., Zhao, M. and Chu, C.

(2016) Control of grain size and rice yield by GL2-mediated brassinosteroid responses. *Nat Plants,* 2

5. Dong, H., Dumenil, J., Lu, F. H., Na, L., Vanhaeren, H., Naumann, C., Klecker, M., Prior, R., Smith, C., McKenzie, N., Saalbach, G., Chen, L., Xia, T., Gonzalez, N., Seguela, M., Inze, D., Dissmeyer, N., Li, Y. and Bevan, M. W. (2017) Ubiquitylation activates a peptidase that promotes cleavage and destabilization of its activating E3 ligases and diverse growth regulatory proteins to limit cell proliferation in *Arabidopsis. Genes Dev,* 31, 197-208.

6. Du, L., Li, N., Chen, L., Xu, Y., Li, Y., Zhang, Y. and Li, C. (2014) The ubiquitin receptor DA1 regulates seed and organ size by modulating the stability of the ubiquitin-specific protease UBP15/SOD2 in *Arabidopsis. Plant Cell,* 26, 665-677.

7. Duan, P., Ni, S., Wang, J., Zhang, B., Xu, R., Wang, Y., Chen, H., Zhu, X. and Li, Y. (2016) Regulation of OsGRF4 by OsmiR396 controls grain size and yield in rice. *Nat Plants,* 2.

8. Duan, P., Rao, Y., Zeng, D., Yang, Y., Xu, R., Zhang, B., Dong, G., Qian, Q. and Li, Y. (2014) SMALL GRAIN 1, which encodes a mitogen-activated protein kinase kinase 4, influences grain size in rice. *Plant J,* 77, 547-557.

9. Duan, P., Xu, J., Zeng, D., Zhang, B., Geng, M., Zhang, G., Huang, K., Huang, L., Xu, R., Ge, S., Qian, Q. and Li, Y. (2017) Natural Variation in the Promoter of GSE5 Contributes to Grain Size Diversity in Rice. *Mol Plant,* 10, 685-694.

10. Fan, C., Xing, Y., Mao, H., Lu, T., Han, B., Xu, C., Li, X. and Zhang, Q. (2006) GS3, a major QTL for grain length and weight and minor QTL for grain width and thickness in rice, encodes a putative transmembrane protein. *Theor Appl Genet,* 112, 1164-1171.

11. Fang, N., Xu, R., Huang, L., Zhang, B., Duan, P., Li, N., Luo, Y. and Li, Y. (2016) SMALL GRAIN 11 Controls Grain Size, Grain Number and Grain Yield in Rice. *Rice (N Y),* 9, 64.

12. Herhaus, L., Al-Salihi, M., Macartney, T., Weidlich, S. and Sapkota, G. P. (2013) OTUB1 enhances TGFbeta signaling by inhibiting the ubiquitylation and degradation of active SMAD2/3. *Nat Commun,* 4, 2519.

13. Hisanaga, T., Kawade, K. and Tsukaya, H. (2015) Compensation: a key to clarifying the organ-level regulation of lateral organ size in plants. *J Exp Bot,* 66, 1055-1063.

14. Hu, J., Wang, Y., Fang, Y., Zeng, L., Xu, J., Yu, H., Shi, Z., Pan, J., Zhang, D., Kang, S., Zhu, L., Dong, G., Guo, L., Zeng, D., Zhang, G., Xie, L., Xiong, G., Li, J. and Qian, Q. (2015) A Rare Allele of GS2 Enhances Grain Size and Grain Yield in Rice. *Mol Plant,* 8, 1455-1465.

15. Hu, Z., He, H., Zhang, S., Sun, F., Xin, X., Wang, W., Qian, X., Yang, J. and Luo, X. (2012) A Kelch Motif-Containing Serine/Threonine Protein Phosphatase Determines the Large Grain QTL Trait in Rice. *J Integr Plant Biol,* 54, 979-990.

16. Huang, X., Qian, Q., Liu, Z., Sun, H., He, S., Luo, D., Xia, G., Chu, C., Li, J. and Fu, X. (2009) Natural variation at the DEP1 locus enhances grain yield in rice. *Nat Genet,* 41, 494-497.

17. Li, M., Tang, D., Wang, K., Wu, X., Lu, L., Yu, H., Gu, M., Yan, C. and Cheng, Z. (2011a) Mutations in the F-box gene LARGER PANICLE improve the panicle architecture and enhance the grain yield in rice. *Plant Biotechnol J,* 9, 1002-1013.

18. Li, N. and Li, Y. (2014) Ubiquitin-mediated control of seed size in plants. *Front Plant Sci,* 5, 332.

19. Li, N. and Li, Y. (2016) Signaling pathways of seed size control in plants. *Curr Opin Plant Biol,* 33, 23-32.

20. Li, S., Gao, F., Xie, K., Zeng, X., Cao, Y., Zeng, J., He, Z., Ren, Y., Li, W., Deng, Q., Wang, S., Zheng, A., Zhu, J., Liu, H., Wang, L. and Li, P. (2016) The OsmiR396c-OsGRF4-OsGIF1 regulatory module determines grain size and yield in Rice. *Plant Biotechnol J,* 14, 2134-2146.

21. Li, Y., Fan, C., Xing, Y., Jiang, Y., Luo, L., Sun, L., Shao, D., Xu, C., Li, X., Xiao, J., He, Y. and Zhang, Q. (2011b) Natural variation in GS5 plays an important role in regulating grain size and yield in rice. *Nat Genet,* 43, 1266-1269.

22. Li, Y., Zheng, L., Corke, F., Smith, C. and Bevan, M. W. (2008) Control of final seed and organ size by the DA1 gene family in *Arabidopsis thaliana. Genes Dev,* 22, 1331-1336.

23. Liu, S., Hua, L., Dong, S., Chen, H., Zhu, X., Jiang, J., Zhang, F., Li, Y., Fang, X. and Chen, F. (2015) OsMAPK6, a mitogen-activated protein kinase, influences rice grain size and biomass production. *Plant J,* 84, 672-681.

24. Mao, H., Sun, S., Yao, J., Wang, C., Yu, S., Xu, C., Li, X. and Zhang, Q. (2010) Linking differential domain functions of the GS3 protein to natural variation of grain size in rice. *Proc Natl Acad. Sci. USA,* 107, 19579-19584.

25. Nakada, S., Tai, I., Panier, S., Al-Hakim, A., Iemura, S., Juang, Y. C., O'Donnell, L., Kumakubo, A., Munro, M., Sicheri, F., Gingras, A. C., Natsume, T., Suda, T. and Durocher, D. (2010) Non-canonical inhibition of DNA damage-dependent ubiquitination by OTUB1. *Nature,* 466, 941-946.

26. Nijman, S. M., Luna-Vargas, M. P., Velds, A., Brummelkamp, T. R., Dirac, A. M., Sixma, T. K. and Bernards, R. (2005) A genomic and functional inventory of deubiquitinating enzymes. *Cell,* 123, 773-786.

27. Qi, P., Lin, Y. S., Song, X. J., Shen, J. B., Huang, W., Shan, J. X., Zhu, M. Z., Jiang, L., Gao, J. P. and Lin, H. X. (2012) The novel quantitative trait locus GL3.1 controls rice grain size and yield by regulating Cyclin-T1;3. *Cell Res,* 22, 1666-1680.

28. Shomura, A., Izawa, T., Ebana, K., Ebitani, T., Kanegae, H., Konishi, S. and Yano, M. (2008) Deletion in a gene associated with grain size increased yields during rice domestication. *Nat Genet,* 40, 1023-1028.

29. Si, L., Chen, J., Huang, X., Gong, H., Luo, J., Hou, Q., Zhou, T., Lu, T., Zhu, J., Shangguan, Y., Chen, E., Gong, C., Zhao, Q., Jing, Y., Zhao, Y., Li, Y., Cui, L., Fan, D., Lu, Y., Weng, Q., Wang, Y., Zhan, Q., Liu, K., Wei, X., An, K., An, G. and Han, B. (2016) OsSPL13 controls grain size in cultivated rice. *Nat Genet,* 48, 447-456.

30. Song, X. J., Huang, W., Shi, M., Zhu, M. Z. and Lin, H. X. (2007) A QTL for rice grain width and weight encodes a previously unknown RING-type E3 ubiquitin ligase. *Nat Genet,* 39, 623-630.

31. Sun, P., Zhang, W., Wang, Y., He, Q., Shu, F., Liu, H., Wang, J., Yuan, L. and Deng, H. (2016) OsGRF4 controls grain shape, panicle length and seed shattering in rice. *J Integr Plant Biol,* 58, 836-847.

32. Wang, S., Li, S., Liu, Q., Wu, K., Zhang, J., Wang, Y., Chen, X., Zhang, Y., Gao, C., Wang, F., Huang, H. and Fu, X. (2015a) The OsSPL16-GW7 regulatory module determines grain shape and simultaneously improves rice yield and grain quality. *Nat Genet,* 47, 949-954.

33. Wang, S., Wu, K., Yuan, Q., Liu, X., Liu, Z., Lin, X., Zeng, R., Zhu, H., Dong, G., Qian, Q., Zhang, G. and Fu, X. (2012) Control of grain size, shape and quality by OsSPL16 in rice. *Nat Genet,* 44, 950-954.

34. Wang, Y., Xiong, G., Hu, J., Jiang, L., Yu, H., Xu, J., Fang, Y., Zeng, L., Xu, E., Ye, W., Meng, X., Liu, R., Chen, H., Jing, Y., Zhu, X., Li, J. and Qian, Q. (2015b) Copy number variation at the GL7 locus contributes to grain size diversity in rice. *Nat Genet,* 47, 944-948.

35. Wang, Z., Li, N., Jiang, S., Gonzalez, N., Huang, X., Wang, Y., Inze, D. and Li, Y. (2016) SCF(SAP) controls organ size by targeting PPD proteins for degradation in *Arabidopsis thaliana. Nat Commun,* 7, 11192.

36. Weng, J., Gu, S., Wan, X., Gao, H., Guo, T., Su, N., Lei, C., Zhang, X., Cheng, Z., Guo, X., Wang, J., Jiang, L., Zhai, H. and Wan, J. (2008) Isolation and initial characterization of GWS, a major QTL associated with rice grain width and weight. *Cell Res,* 18, 1199-1209.

37. Wu, Y., Fu, Y., Zhao, S., Gu, P., Zhu, Z., Sun, C. and Tan, L. (2016) CLUSTERED PRIMARY BRANCH 1, a new allele of DWARF11, controls panicle architecture and seed size in rice. *Plant Biotechnol J,* 14, 377-386.

38. Xia, T., Li, N., Dumenil, J., Li, J., Kamenski, A., Bevan, M. W., Gao, F. and Li, Y. (2013) The Ubiquitin Receptor DA1 Interacts with the E3 Ubiquitin Ligase DA2 to Regulate Seed and Organ Size in *Arabidopsis. Plant Cell,* 25, 3347-3359.

39. Xu, Y., Jin, W., Li, N., Zhang, W., Liu, C., Li, C. and Li, Y. (2016) UBIQUITIN-SPECIFIC PROTEASE14 Interacts with ULTRAVIOLET-B I NSENSITIVE4 to Regulate Endoreduplication and Cell and Organ Growth in *Arabidopsis. Plant Cell,* 28, 1200-1214.

40. Yamamuro, C., Ihara, Y., Wu, X., Noguchi, T., Fujioka, S., Takatsuto, S., Ashikari, M., Kitano, H. and Matsuoka, M. (2000) Loss of function of a rice brassinosteroid insensitive1 homolog prevents internode elongation and bending of the lamina joint. *Plant Cell,* 12, 1591-1606.

41. Zhang, X., Wang, J., Huang, J., Lan, H., Wang, C., Yin, C., Wu, Y., Tang, H., Qian, Q., Li, J. and Zhang, H. (2012) Rare allele of OsPPKL1 associated with grain length causes extra-large grain and a significant yield increase in rice. *Proc Natl Acad. Sci. USA,* 109, 21534-21539.

42. Zhou, Y., Miao, J., Gu, H., Peng, X., Leburu, M., Yuan, F., Gao, Y., Tao, Y., Zhu, J., Gong, Z., Yi, C., Gu, M., Yang, Z. and Liang, G. (2015) Natural Variations in SLG7 Regulate Grain Shape in Rice. *Genetics,* 201, 1591-1599.

43. Zhao, M. et al. Regulation of OsmiR156h through alternative polyadenylation improves grain yield in rice. *PLOS One* 10, e0126154 (2015).

Bracha-Drori, K. et al. Detection of protein-protein interactions in plants using bimolecular fluorescence complementation. *Plant J* 40, 419-427 (2004).

Wang, F. et al. Biochemical insights on degradation of *Arabidopsis* DELLA proteins gained from a cell-free assay system. *Plant Cell* 21, 2378-2390 (2009).

Liu, Z. et al. BIK1 interacts with PEPRs to mediate ethylene-induced immunity. *Proc. Natl. Acad. Sci. USA* 110, 6205-6210 (2013).

Cermak, T. et al. Efficient design and assembly of custom TALEN and other TAL effector-based constructs for DNA targeting. Nucleic Acids Res. 39 (2011).

Neville E Sanjana, Le Cong, Yang Zhou, Margaret M Cunniff, Guoping Feng & Feng Zhang A transcription activator-like effector toolbox for genome engineering, Nature Protocols 7, 171-192 (2012).

Wiles, M. V., Qin, W., Cheng, A. W., Wang, H. CRISPR-Cas9-mediated genome editing and guide RNA design. *Mamm Genome* 26(9-10), 501-510 (2015).

Henikoff, S., Jill, B. J., Comai, L. TILLING. Traditional Mutagenesis Meets Functional Genomics. *Perspectives on Translational Biology.* 135(2), 630-636 (2004).

Comai, L., Young, K., Reynolds, S. H., Greene, E. A., Codomo, C. A., Enns, L. C., Johnson, J. E., Burtner, C., Odden A. R., Henikoff, S. Efficient discovery of DNA polymorphisms in natural populations by Ecotilling. *Plant J* 37(5), 778-786 (2004).

Komor, A. C., Kim, Y. B., Packer, M. S., Zuris, J. A., Liu, D. R. Programmable editing of a target base in genomic DNA without double-stranded DNA cleavage. *Nature* 533(7603), 420-424 (2016).

Nishida, K., Arazoe, T., Yachie, N., Banno, S., Kakimoto, M., Tabata, M., Mochizuki, M., Miyabe, A., Araki, M., Hara, K. Y., Shimatani, Z., Kondo, A. Targeted nucleotide editing using hybrid prokaryotic and vertebrate adaptive immune systems. *Science* 353(6305), aaf8729 (2016).

Clough, S. J., Bent A. F. Floral dip: a simplified method for *Agrobacterium*-mediate transformation of *Arabidopsis thaliana. Plant J.* 16(6), 735-743 (1998).

---

The invention claimed is:

1. A method of increasing grain yield in a plant, the method comprising reducing or abolishing the expression of at least one nucleic acid encoding a otubain-like protease (OTUB1) and/or reducing or abolishing the activity of OTUB1, wherein the method comprises introducing at least one mutation into at least one nucleic acid sequence encoding a OTUB1 polypeptide and/or the promoter of the OTUB1 polypeptide, wherein the at least one mutation reduces or abolishes the expression or activity of OTUB1 compared to a control plant; or wherein the mutation is a loss of function mutation; or wherein the method comprises using RNA interference to reduce or abolish the expression of a least one OTUB1 nucleic acid;

wherein the OTUB1 polypeptide comprises the amino acid sequence with SEQ ID NO: 1 or a functional variant or homologue thereof, wherein the homologue comprises an amino acid sequence selected from the group consisting of SEQ ID NO: 14 to 20, and the functional variant has at least 90% overall sequence identity to an amino acid sequence selected from the group consisting of SEQ ID NO: 1 and 14 to 20; and wherein the nucleic acid encoding an OTUB1 promoter comprises SEQ ID NO: 6 or a nucleic acid sequence selected from the group consisting of SEQ ID NO: 21, 22 and 24 to 27; and wherein the plant is selected from the group consisting of rice, wheat, maize, sorghum, barley, soybean and brassica.

2. A genetically altered [grain] plant, part thereof or [grain] plant cell, wherein said [grain] plant, part thereof or [grain] plant cell comprises at least one mutation in at least one nucleic acid encoding an OTUB1 polypeptide and/or the OTUB1 promoter, wherein the at least one mutation reduces or abolishes the expression or activity of OTUB1 compared to a control plant; or wherein the mutation is a loss of function mutation; or wherein the plant comprises an RNA interference construct that reduces or abolishes the expression of an OTUB1 polypeptide;

wherein the OTUB1 polypeptide comprises the amino acid sequence with SEQ ID NO: 1 or a functional variant or homologue thereof, wherein the homologue comprises an amino acid sequence selected from the group consisting of SEQ ID NO: 14 to 20, and the functional variant has at least 90% overall sequence identity to an amino acid sequence selected from the group consisting of SEQ ID NO: 1 and 14 to 20; and wherein the nucleic acid encoding an OTUB1 promoter comprises SEQ ID NO: 6 or [a functional variant or homologue thereof, wherein the homologue comprises] a nucleic acid sequence selected from the group consisting of SEQ ID NO: 21, 22 and 24 to 27; [and the functional variant has at least 90% overall sequence identity to a nucleic acid sequence selected from SEQ ID NO: 6, 21, 22 and 24 to 27] and wherein the plant is selected from the group consisting of rice, wheat, maize, sorghum, barley, soybean and brassica.

3. The plant part of claim 2, wherein said plant part is grain or a seed.

4. A method of producing a [grain] plant with increased grain yield, the method comprising introducing at least one mutation into at least one nucleic acid sequence encoding an OTUB1 polypeptide and/or the promoter of the OTUB1 polypeptide wherein the at least one mutation reduces or abolishes the expression or activity of OTUB1 compared to a control plant; or wherein the mutation is a loss of function mutation; or wherein the method comprises introducing and expressing in said plant an RNA interference construct that reduces or abolishes the expression of an OTUB1 nucleic acid;

wherein the OTUB1 polypeptide comprises the amino acid sequence with SEQ ID NO: 1 or a functional variant or homologue thereof, wherein the homologue comprises an amino acid sequence selected from the group consisting of SEQ ID NO: 14 to 20, and the functional variant has at least 90% overall sequence identity to an amino acid sequence selected from the group consisting of SEQ ID NO: 1 and 14 to 20; and wherein the nucleic acid encoding an OTUB1 promoter comprises SEQ ID NO: 6 or [a functional variant or homologue thereof, wherein the homologue comprises] a nucleic acid sequence selected from the group consisting of SEQ ID NO: 21, 22 and 24 to 27 [and the functional variant has at least 90% overall sequence identity to a nucleic acid sequence selected from of SEQ ID NO: 6, 21, 22 and 24 to 27]; and wherein the plant is selected from the group consisting of rice, wheat, maize, sorghum, barley, soybean and *brassica*.

5. The method of claim 4, wherein the method further comprises measuring a reduction in the expression of the OTUB1 nucleic acid and/or measuring a reduction in deubiquitinase activity of the OTUB1 polypeptide.

6. The method of claim 4, wherein the method further comprises regenerating a plant and screening for an increase in grain yield.

7. A plant, plant part or plant cell obtained or obtainable by the method of claim 4.

8. A method for identifying and/or selecting a plant that will have increased grain yield, compared to a control plant, the method comprising detecting in the plant or plant germplasm at least one polymorphism in the OTUB1 gene and/or OTUB1 promoter and selecting said plant or progeny thereof; and wherein the polymorphism reduces or abolishes the expression or activity of OTUB1 compared to a control plant; or wherein the polymorphism is a loss of function mutation, wherein the OTUB1 gene encodes an OTUB1 polypeptide comprising the amino acid sequence of SEQ ID NO: 1 or a functional variant or homologue thereof, wherein the homologue comprises an amino acid sequence selected from the group consisting of SEQ ID NO: 14 to 20, and the functional variant has at least 90% overall sequence identity to an amino acid sequence selected from the group consisting of SEQ ID NO: 1 and 14 to 20; and wherein the nucleic acid encoding an OTUB1 promoter comprises SEQ ID NO: 6 or a nucleic acid sequence selected from the group consisting of SEQ ID NO: 21, 22 and 24 to 27; and wherein the plant is selected from the group consisting of rice, wheat, maize, sorghum, barley, soybean and *brassica*.

9. The method of claim 8, wherein the method further comprises introgressing the chromosomal region comprising the at least one polymorphism in the OTUB1 gene and/or OTUB1 promoter into a second plant or plant germplasm to produce an introgressed plant or plant germplasm.

10. The genetically altered plant of claim 2, wherein the genetically altered plant, part thereof of plant cell further carries or expresses a nucleic acid sequence encoding a DEP-1 polypeptide, wherein the DEP-1 polypeptide comprises SEQ ID NO: 157 or 159 or a functional variant or homologue thereof, wherein the functional variant has at least 90% overall sequence identity to SEQ ID NO: 157 or 159.

11. The genetically altered grain plant of claim 2, wherein the at least one mutation reduces the deubiquitinase activity of OTUB1 compared to a control plant.

12. The method of claim 4, wherein the method reduces the deubiquitinase activity of OTUB1 compared to a control plant.

\* \* \* \* \*

SEQUENCE LISTING

```
<160> NUMBER OF SEQ ID NOS: 406

<210> SEQ ID NO 1
<211> LENGTH: 274
<212> TYPE: PRT
<213> ORGANISM: Oryza sativa

<400> SEQUENCE: 1

Met Gly Gly Asp Tyr Tyr His Ser Cys Cys Gly Asp Pro Asp Pro Asp
1               5                   10                  15

Leu Arg Ala Pro Glu Gly Pro Lys Leu Pro Tyr Val Gly Asp Lys Glu
                20                  25                  30

Pro Leu Ser Thr Leu Ala Ala Glu Phe Gln Ser Gly Ser Pro Ile Leu
            35                  40                  45

Gln Glu Lys Ile Lys Leu Leu Gly Glu Gln Tyr Asp Ala Leu Arg Arg
        50                  55                  60

Thr Arg Gly Asp Gly Asn Cys Phe Tyr Arg Ser Phe Met Phe Ser Tyr
65                  70                  75                  80

Leu Glu His Ile Leu Glu Thr Gln Asp Lys Ala Glu Val Glu Arg Ile
```

```
                    85                  90                  95
Leu Lys Lys Ile Glu Gln Cys Lys Lys Thr Leu Ala Asp Leu Gly Tyr
            100                 105                 110

Ile Glu Phe Thr Phe Glu Asp Phe Ser Ile Phe Ile Asp Gln Leu
            115                 120                 125

Glu Ser Val Leu Gln Gly His Glu Ser Ser Ile Gly Ala Glu Glu Leu
        130                 135                 140

Leu Glu Arg Thr Arg Asp Gln Met Val Ser Asp Tyr Val Val Met Phe
145                 150                 155                 160

Phe Arg Phe Val Thr Ser Gly Glu Ile Gln Arg Ala Glu Phe Phe
                165                 170                 175

Glu Pro Phe Ile Ser Gly Leu Thr Asn Ser Thr Val Val Gln Phe Cys
            180                 185                 190

Lys Ala Ser Val Glu Pro Met Gly Glu Ser Asp His Val His Ile
            195                 200                 205

Ile Ala Leu Ser Asp Ala Leu Gly Val Pro Ile Arg Val Met Tyr Leu
            210                 215                 220

Asp Arg Ser Ser Cys Asp Ala Gly Asn Ile Ser Val Asn His His Asp
225                 230                 235                 240

Phe Ser Pro Glu Ala Asn Ser Ser Asp Gly Ala Ala Ala Glu Lys
                245                 250                 255

Pro Tyr Ile Thr Leu Leu Tyr Arg Pro Gly His Tyr Asp Ile Leu Tyr
            260                 265                 270

Pro Lys

<210> SEQ ID NO 2
<211> LENGTH: 825
<212> TYPE: DNA
<213> ORGANISM: Oryza sativa

<400> SEQUENCE: 2
atgggcgggg actactacca ctcgtgctgc ggcgaccccg accccgacct ccgcgcgccc      60
gaggggccca gctgccgta cgtcggggac aaggaacctc tctccacttt agccgctgag     120
tttcagtctg gcagcccat tttacaggag aaaataaagt tgcttggtga acagtatgat     180 gcttttaagaa ggacacgagg agatggaaac tgcttttatc gaagctttat gttttcctac     240
ttggaacata tcctagagac acaagacaaa gctgaggttg agcgcattct aaaaaaaatt     300
gagcagtgca agaagactct tgcagatctt ggatacattg agttcacctt tgaagatttc     360
ttctctatat tcattgatca gctggaaagt gttctgcagg acatgaatc ctccataggg     420 gccgaagagc ttctagaaag aaccagggat cagatggttt ctgattatgt tgtcatgttc     480
tttaggtttg tcacctctgg tgaaatccaa aggagggcta gttcttcga accattcatc     540 tctggcttga caaattcgac tgtggttcag ttctgcaagg cttccgtgga gccgatgggc     600
gaggaaagtg accatgtcca cataattgcc ctatcagatg cgttgggtgt gccaatccgt     660
gtgatgtacc tagacagaag ctcatgtgat gctggaaata taagtgtgaa ccaccatgat     720
ttcagccctg aggccaattc atcggacggt gctgctgctg ctgagaaacc ttacattact     780
ttgctctacc gtcctggtca ctacgacatt ctctacccga agtga                     825

<210> SEQ ID NO 3
<211> LENGTH: 3825
<212> TYPE: DNA
<213> ORGANISM: Oryza sativa
```

```
<400> SEQUENCE: 3
atgggcgggg actactacca ctcgtgctgc ggcgacccog accccgacct ccgcgcgccc      60
gaggggccca agctgccgta cgtcggggac aaggtgagat gttgacgcct ctctctcttt     120
ctctgtctct ctcgctcgct ttgactcatc tgcgctttga ctcatctgcg gtcgatagat     180
ttgttcatgt ggtagaaatg ggtctgaatc gtggtaagac gcccagtgtt gccatgccag     240
tatccgctag ttgtgccagc aggtgaggcg atagatcagt cctgttagtc tagttggatg     300
ctgattgttg gtcatcatta ctgttgtatt ggtgctccat ttctatgtga attgacattt     360
taaggcgtct atacaagcag tgggactag aatttggata acaagtaaca atttccccct     420
attgcgtcat cttaaaggat aagaggagtt atcagatgct ggattttctc ctttattttt     480
agtcgtggtg cctggaataa tggagattgg ctgaacaagt tcatatcagt tgtgtccatt     540
ttcatcctct ggatggtcag tccttaagta ttgtcaggcg ctattgttgt gagttgtaac     600
tgttgtactt gattttttag cttcgttggt gaactgatgt ttggaggttc atgcagaagt     660
cagaaccatg gggaattaga atttggatga acagacagca attacctttc gtgttctctt     720
ctaggaaaag aagggtttat ctgttatcat ttgctggatg tgctccttac ttaatattta     780
tgcatggaat aatagagatg gccaaacaag tttgctccat agcgtattat gattctagga     840
taaaagtggt gtcatccttt aatcgtcaca cctaggacaa taaatgtgaa ggacgaactt     900
gttgatgcag aataatagcc tatgctagtc aattcagcac agaaactgag gttaaatgtg     960
tcccaaaagt ttcagttaag gttcacacta ggatttacac gaacagaaca atctgcaaa    1020
tatagtccat atgagaaggt ggagagctac atacacacaa tttcatatga atggaaaat    1080
gatgttggca ctaaacttgg atttaggtca agtagttaga tatttgatgc ctcaaattca    1140
ttttgttctg ttaattgcaa gcaccttttc acaatggagg acactaatgc attgctatga    1200
ttatctctgt gttgtacag ttattttagg ctatcgtatg actttcttct gctttcattt    1260
gtgttcatta ttgatatctt ttgaaccttg caggaacctc tctccacttt agccgctgag    1320
tttcagtctg gcagccccat tttacaggag aaaataaagg tccatatgga tttggcagtt    1380
ataatatgta atagacatat tttggttgat ctatcgtatc aatggatggt gcttcaattt    1440
gttcttataa tttcttgctt ggtctgcagt tgcttggtga acagtatgat gctttaagaa    1500
ggacacgagg agatgaaaac tgcttttatc gaagctttat gttttcctac ttggtattat    1560
ttttggtctg tttccataca aactttgact attttataag ctgatgatct tatcatttgc    1620
ttctaggaac atatcctaga gacacaagac aaagctgagg ttgagcgcat tctaaaaaaa    1680
attgagcagt gcaagaagac tcttgcagat cttggataca ttgagttcac cttttgaagat    1740
ttcttctctg taagtcttta ttgttacttt gtgtggtcct ccttacttat cctgttcaat    1800
tgctgttttg caacttatgc cagatgtatt ccctctgaat agtatgaaga tctgtccgat    1860
tattttcatg tatgcttgtt tgcatttcct ttttagatgt tcctggaata attttttgtat    1920
gagctagtta taatgagagc ttgtgcattt tcctgtcatg caacaaatta aatactagtg    1980
tctaatcctt gtgcattgtt aataactttg aaaatgatta gccttgaaga ttggtccatt    2040
atatatatgt tcacttgttt cttagttagg atcactcacc agtcacccctt ctgaagttca    2100
taatgtatca cttataagta agctagcaaa acaaaatttg gactgtttgt agccacccag    2160
aacccaaata gatggatttc acattatttt ctactggctt tgggagttat ttgatcgatg    2220
ctagtacaac gttgaaattt gggtagttga gatgcgtttt tcacaaagga ctcctttatt    2280
ggtgcttgat ctacaactgg tgttttactt ttttacaaaa aaatgtaatc tccttgcagt    2340
```

```
gcactcaaat tattgcaacc tccttcctta tgttcccacc ctcattattt tcagatattc      2400
attgatcagc tggaaagtgt tctgcaggga catgaatcct ccatagggta aatatcctag      2460
agttatattt gtatccttaa tgcatatgac caataatcat gtattaacaa caaagcaatt      2520
tttgtaattg tttataaagt atggcatgtc catcataaat gttttccttc tgtagtgaat      2580
ctattttgtt ttcctgtatc cttagggccg aagagcttct agaagaacc agggatcaga      2640 tggtttctga ttatggtttg tacatccaga tatgtgtagt atgcctttct ctgctttgct      2700
ctcattattt aactatgtct tctttagttg tcatgttctt taggtttgtc acctctggtg      2760
aaatccaaag gagggctgag ttcttcgaac cattcatctc tggcttgaca aattcgactg      2820
tggttcaggt tagctccata cttccatttt atgagggttt gtacagtcgt tggggaggta      2880
ttatgaggta caatacctcc aggtaccggg agttaccaca cataagcata aaatgtgtgg      2940
tgcctctcca aggaccacaa gaaatctctt cattatattt gtaatgcaca gagcagagag      3000
tacagacaaa tagacctgca ctctgcattt tcattaagta tttagatgtg agattattct      3060
atgttttatc tctcttgtta gtattttttg ctctgtttta taatggaagt tcattttctt      3120
gggaactgtc attcacaaaa caatgagtta tcgtaccctg ccatttagta gggaatttgg      3180
tggtaaaaaa ccattaactt tttcttcaat tttgtgcctt ctgcacaagg tgggataggg      3240
catatattgt ggaacaaaag agtgcacaat gactaattat ttagtatgca tcacactgga      3300
gtatgatata ctagtggaaa ggttatggca aaataccatg atagtagctt gatagattag      3360
caggtccgta agtatttttc caatgataat gtttttattca ttaaactgta gcaggataaa      3420
atctacttat gcacctttt ttcatgagta gcaaacaatg cattctctgg tttgaaaaac      3480
ttgttcaagt tgcagtgtgt tattccaatc cgtgtttgtg tgacaagcaa ttgctggagt      3540
tactgatcct gagttcaatt caatttgcag ttctgcaagg cttccgtgga gccgatgggc      3600
gaggaaagtg accatgtcca cataattgcc ctatcagatg cgttgggtgt gccaatccgt      3660
gtgatgtacc tagacagaag ctcatgtgat gctggaaata aagtgtgaa ccaccatgat      3720 ttcagccctg aggccaattc atcggacggt gctgctgctg ctgagaaacc ttacattact      3780
ttgctctacc gtcctggtca ctacgacatt ctctacccga agtga                     3825

<210> SEQ ID NO 4
<211> LENGTH: 825
<212> TYPE: DNA
<213> ORGANISM: Oryza sativa

<400> SEQUENCE: 4
atgggcgggg actactacca ctcgtgctgc ggcgaccccg accccgacct ccgcgcgccc        60
gaggggccca gctgccgta cgtcggggac aaggaacctc tctccacttt agccgctgag       120
tttcagtctg gcagccccat tttacaggag aaaataaagt tgcttggtga acagtatgat       180
gctttaagaa ggacacgagg agatggaaac tgcttttatc gaagctttat gttttcctac       240
ttggaacata tcctagagac acaagacaaa gctgaggttg agcgcattct aaaaaaaatt       300
gagcagtgca agaagactct tgcagatctt ggatacattg agttcacctt tgaagatttc       360
ttctctatat tcattgatca gctggaaagt gttctgcagg acatgaatc ctccataggg       420 gccgaagagc ttctagaaag aaccagggat cagatggttt ctgattatgt tgtcatgttc       480
tttaggtttg tcacctctgg tgaaatccaa aggagggccg agttcttcga accattcatc       540
tctggcttga caaattcgac tgtggttcag ttctgcaagg cttccgtgga gccgatgggc       600
```

| | | |
|---|---|---|
| gaggaaagtg accatgtcca cataattgcc ctatcagatg cgttgggtgt gccaatccgt | 660 | |
| gtgatgtacc tagacagaag ctcatgtgat gctggaaata taagtgtgaa ccaccatgat | 720 | |
| ttcagccctg aggccaattc atcggacggt gctgctgctg ctgagaaacc ttacattact | 780 | |
| ttgctctacc gtcctggtca ctacgacatt ctctacccga agtga | 825 | |

```
<210> SEQ ID NO 5
<211> LENGTH: 3824
<212> TYPE: DNA
<213> ORGANISM: Oryza sativa

<400> SEQUENCE: 5
```

| | | |
|---|---|---|
| atgggcgggg actactacca ctcgtgctgc ggcgaccccg accccgacct ccgcgcgccc | 60 | |
| gagggcccca agctgccgta cgtcggggac aaggtgagat gttgacgcct ctctctctct | 120 | |
| ctgtctctct cgctcgcttt gactcatctg cgctttgact catctgcggt cgatagattt | 180 | |
| gttcatgtgg tagaaatggg tctgaatcgt ggtaagacgc ccagtgttgc catgccagta | 240 | |
| tccgctagtt gtgccagcag gtgaggcgat agatcagtcc tgttagtcta gttggatgct | 300 | |
| gattgttggt catcattact gttgtattgg tgctccattt ctatgtgaat tgacattta | 360 | |
| aggcgtctat acaagcagtg gggactagaa tttggataac aagtaacaat ttccccttat | 420 | |
| tgcgtcatct taaaggataa gaggagttat cagatgctgg attttctcct ttattttag | 480 | |
| tcgtggtgcc tggaataatg gagattggct gaacaagttc atatcagttg tgtccatttt | 540 | |
| catcctctgg atggtcagtc cttaagtatt gtcaggcgct attgttgtga gttgtaactg | 600 | |
| ttgtacttga ttttttagct tcgttggtga actgatgttt ggaggttcat gcagaagtca | 660 | |
| gaaccatggg gaattagaat ttggatgaac agacagcaat tacctttcgt gttctcttct | 720 | |
| aggaaaagaa gggtttatct gttatcattt gctggatgtg ctccttactt aatatttatg | 780 | |
| catggaataa tagagatggc caaacaagtt tgctccatag cgtattatga ttctaggata | 840 | |
| aaagtggtgt catcctttaa tcgtcacacc taggacaata aatgtgaagg acgaacttgt | 900 | |
| tgatgcagaa taatagccta tgctagtcaa ttcagcacag aaactgaggt taaatgtgtc | 960 | |
| ccaaaagttt cagttaaggt tcacactagg atttacacga acagaacaaa tctgcaaata | 1020 | |
| tagtccatat gagaaggtgg agagctacat acacacaatt tcatatgaaa tggaaaatga | 1080 | |
| tgttggcact aaactggat ttaggtcaag tagttagata tttgatgcct caaatttatt | 1140 | |
| ttgttctgtt aattgcaagc accttttcac aatggaggac actaatgcat tgctatgatt | 1200 | |
| atctctgtgt ttgtacagtt atttaggct atcgtatgac tttcttctgc tttcatttgt | 1260 | |
| gttcattatt gatatctttt gaaccttgca ggaacctctc tccactttag ccgctgagtt | 1320 | |
| tcagtctggc agccccattt tacaggagaa aataaaggtc catatggatt tggcagttat | 1380 | |
| aatatgtaat agacatattt tggttgatct atcgtatcaa tggatggtgc ttcaatttgt | 1440 | |
| tcttataatt tcttgcttgg tctccagttg cttggtgaac agtatgatgc tttaagaagg | 1500 | |
| acacgaggag atggaaactg cttttatcga agctttatgt tttcctactt ggtattattt | 1560 | |
| ttggtctgtt tccatacaaa ctttgactat tttataagct gatgatctta tcatttgctt | 1620 | |
| ctaggaacat atcctagaga cacaagacaa agctgaggtt gagcgcattc taaaaaaaat | 1680 | |
| tgagcagtgc aagaagactc ttgcagatct tggatacatt gagttcaccct tgaagattt | 1740 | |
| cttctctgta agtctttatt gttactttgt gtggtcctcc ttacttatcc tgttcaattt | 1800 | |
| ctgttttgca acttatgcca gatgtattcc ctctgaatag tatgaagatc tgtccgatta | 1860 | |
| ttttcatgta tgcttgtttg catttccttt ttagatgttc ctggaataat ttttgtatga | 1920 | |

```
gctagttata atgagagctt gtgcattttc ctgtcatgca acaaattaaa tactagtgtc    1980
taatccttgt gcattgttaa taactttgaa aatgattagc cttgaagatt ggtccattat    2040
atatatgttc acttgtttct tagttaggat cactcaccag tcacccttct gaagttcata    2100
atgtatcact tataagtaag ctagcaaaac aaaatttgga ctgtttgtag ccacccagaa    2160
cccaaataga tggatttcac attattttct actggctttg ggagttattt gatcgatgct    2220
agtacaacgt tgaaattttg ggtagttgag atgcattttt cacaaaggac tcctttattg    2280
gtgcttgatc tacaactggt gttttacttt tttacaaaaa aatgtaatct ccttgcagtg    2340
cactcaaatt attgcaacct ccttccttat gttcccaccc tcattatttt cagatattca    2400
ttgatcagct ggaaagtgtt ctgcagggac atgaatcctc catagggtaa atatcctaga    2460
gttatatttg tatccttaat gcatatgacc aataatcatg tattaacaac aaagcatttt    2520
ttgtaattgt ttataaagta tggcatgtcc atcataaatg ttttccttct gtagtgaatc    2580
tattttgttt tcctgtatcc ttagggccga agagcttcta gaaagaacca gggatcagat    2640
ggtttctgat tatggtttgt acatccagat atgtgtagta tgcctttctc tgctttgctc    2700
tcattattta actatgtctt ctttagttgt catgttcttt aggtttgtca cctctggtga    2760
aatccaaagg agggccgagt tcttcgaacc attcatctct ggcttgacaa attcgactgt    2820
ggttcaggtt agctccatac ttccattgta tgagggtttg tacagttgtt ggggaggtat    2880
tatgaggtac aatacctcca ggtaccggga gttaccacac ataagcataa aatgtgtggt    2940
gcctctccaa ggaccacaag aaatctcttc attatatttg taatgcacag agcagagagt    3000
acagacaaat agacctgcac tctgcatttt cattaagtat ttagatgtga gattattcta    3060
tgttttatct ctcttgttag tattttttgc tctgttttat aatggaagtt cattttcttg    3120
ggaactgtca ttcacaaaac aatgagttat cgtaccctgc catttagtag ggaatttggt    3180
ggtaaaaaac cattaacttt ttcttcaatt ttgtgccttc tgcacaaggt gggataggggc    3240 atatattgtg gaacaaaaga gtgcacaatg actaattatt tagtatgcat cacactggag    3300
tatgatatac tagtggaaag gttatggcaa aataccatga tagtagcttg atagattagc    3360
aggtccgtaa gtatttttcc aatgataatg ttttattcat taaactgtag caggataaaa    3420
tctacttatg cacctttttt tcatgagtag caaacaatgc attctctggt ttgaaaaact    3480
tgttcaagtt gcagtgtgtt attccaatcc gtgtttgtgt gacaagcaat tgctggagtt    3540
actgatcctg agttcaattc aatttgcagt tctgcaaggc ttccgtggag ccgatgggcg    3600
aggaaagtga ccatgtccac ataattgccc tatcagatgc gttgggtgtg ccaatccgtg    3660
tgatgtacct agacagaagc tcatgtgatg ctggaaatat aagtgtgaac caccatgatt    3720
tcagccctga ggccaattca tcggacggtg ctgctgctgc tgagaaacct tacattactt    3780
tgctctaccg tcctggtcac tacgacattc tctacccgaa gtga                    3824
```

<210> SEQ ID NO 6
<211> LENGTH: 2462
<212> TYPE: DNA
<213> ORGANISM: Oryza sativa

<400> SEQUENCE: 6

```
gagttgaagt tgttgctgct gtcataagta ctatctgcta aatgggcaca ctcctagcat      60
tattagaact gagaaatatc ccaagcaatg aaagcgacaa aaaagtaccc gtttgaagac     120
atgattgaca tggtcacatc aaacaccgga catcaacatc taaatgtaca taacaaggcc     180
```

| | |
|---|---|
| aaaataattt tcgatgctgg ttggtgctac caagtcccac gtatgatact taagaatcaa | 240 |
| tcatgaatat tacaaatcaa gtcaaactac gttatgtatt gaactcttat aattactgca | 300 |
| acatatcaca ctggaatttc ctatggtaat tcctcgccag ccttatccta cccatccctt | 360 |
| gcagtatatt aagagcatca acaacaaaca tgattcaaga caactttat taacactgaa | 420 |
| caacataaat tgggaacaaa acaaaccact tggaggcatg attaggataa tcggtattaa | 480 |
| agaactggac atcacaattc acaactagat gttgaaataa tacctgtctc ttctttggct | 540 |
| catggcaggt gtcagtgaaa tatactgatg ctccaagaga gctggaagca ccgtttccac | 600 |
| gtaatcaaaa tgtccttttc gtttgctgca atcaaccta aagggctctt ttgatgctat | 660 |
| ctcttcaggc atgtccttta caacttccac ataacctctg gtttgctcaa tgaagtaatc | 720 |
| aacatcgaaa acgtctgcaa atccactgac agagaatacc aataagtgat gaactacctt | 780 |
| ttgaacagaa ataaactgca taactacaag tagcacagtc gttcatcttg tagagtgatt | 840 |
| ctcataccta gattcattcc agtaggcagc aacctcaaac ttgggcagaa ccattgttgc | 900 |
| gttgagaagg cgcgcaaccg caattccatc acatagctga agaaacattc ggaagaataa | 960 |
| ttacaaccag gagtaacata ataacatagc cagttgaaat cacattcgcc ttgcaatgtg | 1020 |
| aaaattttca taaataatct gaaaatttag ttatgccact atatatcatg caacctgcct | 1080 |
| ccacgacatt ttaatcatgg agtagaagat aaaacatatg atcccctca ttgaccctac | 1140 |
| tatcttacta cttgtgcatg gccgaacgat ctaacagcga aatccagaaa gccaacactc | 1200 |
| atttgatccc actaacaacg gaagagagaa acgctagccg agatcgctta acgtacatcg | 1260 |
| cgtcgcagct ggttgagccc gccgtagcag tcgatccgga tgtacccatt cctcctcgac | 1320 |
| ggagctgcag aagaagagga ggttcaaaac cgcaatcacc accacagtct caagcagaga | 1380 |
| tgtccactac ccggatcctt aaacccaaac cacaaatcac ggcgaggtct cacccggcat | 1440 |
| tgccgcccgc caccacccgc acgaccgcca ctccgccacc cgccgctgcg cccatatgac | 1500 |
| ccgcgacccc gacgccgacg gcgactcctc cctaaagacc aaaagcgagt aagcgagatc | 1560 |
| cgtaagcttc tggaacaatc tcgagcatca gctgcaagag gtgaggctgg gccgcgtacc | 1620 |
| tggaggtggg aagagtgaag aagaaaggcg gagaggaggg tggagagagg aggaagtaga | 1680 |
| gcgcggggc gaggaagatg accggtagga ggatgcggac gcggctgcgc gcccaccacg | 1740 |
| ccgccggcga cgccgacgac gacatcgcct cgccgcgaga agcactggat ctgatcggcc | 1800 |
| gccgcctcca cgccggagtg gagagcgtat ataagctcgt cagaatgtgg gcccgtggct | 1860 |
| atgtgggccc accatgtcat cgacgcttat caagatcgag cggtggcgtg aggaaaccgg | 1920 |
| tagggtggg ggggctaacc aatcggaaac gcgtaataac tcacccgcgg ttcactttct | 1980 |
| ccttatgaca cgtgggccca tctcttcctg gacccacctg tcagttaccc ttacggcctc | 2040 |
| cactctgagg atctaaacgt aaaaacgaat ttatcggagg gcttatccgc gaggggaaaa | 2100 |
| aaacgcgcac ttatttctcg ccttcgccga gatctcggaa gagaagaaca cgcaccgcgg | 2160 |
| ggagagggga gagaagcgga aagctccacc gaatcgaagc cccacacac gcgaagctgg | 2220 |
| cgcgggaggc ggccgacgcg agcgcccgga agcgcaaggc ggcggacggc ggcggggagg | 2280 |
| gcgacgccgc ggcgacggtc ccggaggagg cggtgatggg ggaggcggcg gcggcagccg | 2340 |
| cggcccccga gccggtcgtc gagggggag gagggggggg ggagggggttg aatcctaacc | 2400 |
| ctagcggcgg tgggggagga ggtggtggag ggtgctcgga ctccgtgtcg gtcgagctct | 2460 |
| cg | 2462 |

<210> SEQ ID NO 7
<211> LENGTH: 837
<212> TYPE: DNA
<213> ORGANISM: Triticum urartu

<400> SEQUENCE: 7

| | | | | | |
|---|---|---|---|---|---|
| atgggcgggg | actactacca | cgcctgctgc | ggcgacccgg | accccgacca | caagcccgag | 60 |
| ggaccccagg | tgccgtacat | cggtaacaag | gaacctctct | ccgccttagc | agcagagttc | 120 |
| cagtctggca | gccccatttt | acaggagaaa | ataaagttgc | ttggtgaaca | atatgatgct | 180 |
| ttaaggcgaa | cacgaggaga | tggaaactgc | ttttatcgaa | gctttatgtt | ctcctacctg | 240 |
| gaacatatcc | tagagacaca | agatagagct | gaggttgagc | gcatcctaaa | aaacattgaa | 300 |
| cagtgcaaga | tgacactttc | aggtcttgga | tacattgaat | tcacttttga | agacttcttc | 360 |
| tctatgttca | ttgaggagct | gcaaaatgtt | ctgcagggac | acgaaacttc | tattgggcct | 420 |
| gaagaacttc | tagaaagaac | cagggatcaa | acgacttctg | attatgttgt | catgttcttt | 480 |
| aggtttgtta | cctctggtga | aattcaaagg | agggctgagt | tctttgaacc | atttatttct | 540 |
| ggcttgacaa | attcgaccgt | ggctcagttt | tgcaagtctt | ctgtggagcc | aatgggcgag | 600 |
| gaaagcgacc | atgtgcacat | tattgctctg | tcagatgcgt | tagggggtgcc | aatccgcgtg | 660 |
| atgtacctag | accgaagctc | ctgtgacaca | ggcaatctaa | gtgtgaacca | ccatgatttc | 720 |
| attcctgcag | ccaattcctc | tgaaggtgat | gctgcaatgg | gattaaatcc | ggctgaggag | 780 |
| aaaccttaca | ttactctgct | ctaccggcct | ggtcactatg | atattctcta | cccaaag | 837 |

<210> SEQ ID NO 8
<211> LENGTH: 840
<212> TYPE: DNA
<213> ORGANISM: Hordeum vulgare

<400> SEQUENCE: 8

| | | | | | |
|---|---|---|---|---|---|
| atgggcgggg | actactacca | cgcctgctgc | ggcgacccog | accccgaccc | caagcccgag | 60 |
| ggaccccagg | tgccgtacat | cggtaacaag | gaacctctct | ccgccttagc | agcagagttc | 120 |
| cagtctggca | gccccatttt | acaggagaaa | ataaagttgc | ttggtgaaca | atatgatgct | 180 |
| ttaagacgga | cacgaggaga | tggaaactgc | ttttatcgaa | gctttatgtt | ctcctacctg | 240 |
| gaacatatcc | ttgagacaca | agacagagct | gaggttgagc | gcatcctaaa | aaacattgaa | 300 |
| caatgcaaga | agacactttc | aggtcttgga | tacattgagt | tcacttttga | ggacttcttc | 360 |
| tctatgttca | ttgaggagct | gcaaaatgtt | ctgcagggac | acggaacttc | tattgggcct | 420 |
| gaagaacttc | tagaaagaac | cagggatcag | acgacttctg | attatgttgt | catgttcttt | 480 |
| agatttgtta | cctctggtga | aattcaaagg | agggctgagt | tctttgaacc | atttatttct | 540 |
| ggcttgacaa | attcgaccgt | ggttcagttt | tgcaagtctt | ctgtggagcc | aatgggcgag | 600 |
| gaaagtgacc | atgtgcacat | tattgctctg | tcagatgcgt | tagggggtgcc | aatccgcgtg | 660 |
| atgtacctag | accgaagctc | ttgtgacaca | ggcaatctaa | gtgtgaacca | ccatgatttc | 720 |
| atccctgcag | ccaattcctc | tgaaggtgat | gctgcaatgg | gattaaatcc | tgctgatgag | 780 |
| aaaccttaca | ttactctgct | ctaccggcct | ggtcactatg | acattctcta | cccgaagtga | 840 |

<210> SEQ ID NO 9
<211> LENGTH: 891
<212> TYPE: DNA
<213> ORGANISM: Zea mays

<400> SEQUENCE: 9

| | |
|---|---|
| atgggcgacg ttccacaggc gccgcacgct gcgggaggtg gagaagagtg ggcggggccg | 60 |
| gaccctaacc ctagcccgag cctcggcggc tgctcggacc ccgtgtcggt ggagctctcc | 120 |
| atgggcgggg actactaccg cgcctgctgc ggcgagcccg atcccgacat ccccgagggg | 180 |
| cccaagctgc cgtgcgttgg ggacaaggaa cctctctcct ctttagcagc tgagtttcag | 240 |
| tctggcagcc ccattttaca agagaaaatt aagttgcttg gcgagcaata tggtgcttta | 300 |
| agacgtacac gtggagatgg aaactgcttt tatcgaagct ttatgttttc ctacctggaa | 360 |
| cacatcctag agacacaaga caaagctgag gctgatcgca tcatggtaaa aattgaggaa | 420 |
| tgcaagaaaa cactcctctc tcttggatat attgagttca cttttgagga cttcttttcg | 480 |
| atattcattg aactgctgga agtgttctg cagggacatg aaactcctat agggtttgtc | 540 |
| acttctggtg aaattcaaag gaggtctgac ttctttgaac cgttcatatc tggcttgaca | 600 |
| aattcaaccg tggttcagtt ctgcaaggct ctgtgaaac ctatgggtga ggaaagtgac | 660 |
| catgtgcaca taattgccct atcagatgca ctaggcgtac caatccgtgt tatgtaccta | 720 |
| gaccgaagct cgtgtgacac tggcaacctg agcgtgaatc accacgattt catcccgtcg | 780 |
| gccaatgatt cggagggtga tgcggccacg cacctgctc ctgccacaga gaaaccgtac | 840 |
| atcactttgc tctaccgtcc tggccactac gatattctct acccaaagtg a | 891 |

<210> SEQ ID NO 10
<211> LENGTH: 909
<212> TYPE: DNA
<213> ORGANISM: Sorghum bicolor

<400> SEQUENCE: 10

| | |
|---|---|
| atgggcgacg tgccccaggc gccgcacgcc gcggaaggag gaggaggagg actggaggag | 60 |
| ggggcggtgc ccgaccctaa ccctagcccg agcctgagcc tcggcggctg ctcggacccc | 120 |
| gtgtcgctgg agctctccat gggcgggac tactaccgcg cctgctgcgg cgaccccgac | 180 |
| cccgacatcc ccgaggggcc caagctgccg tgcgttgggg aaaaggaacc tctctcctct | 240 |
| ttagcagccg agtttcagtc tggcagcccc attttacaag agaaaattaa gttgcttggc | 300 |
| gaacaatatg gtgctttaag acggacacgt ggagatggaa actgctttta tcgaagcttt | 360 |
| atgttctcct acttggaaca catcctagag acacaagaca agctgaggc tgatcgcatc | 420 |
| atggtaaaaa ttgaggattg caagaagacg ctcctgtctc ttggatatat tgagttcact | 480 |
| tttgaggatt ctttgcgat attcattgat atgctggaaa gtgttctgca gggacatgaa | 540 |
| actcctatag ggtttgtcac ttctggtgaa attcaaagga ggtctgactt ctttgaacca | 600 |
| ttcatatctg gcttgacaaa ttcaactgtg gttcagttct gcaaggcttc tgtggaacct | 660 |
| atgggtgagg aaagtgacca tgttcacata attgccctat cggatgcact aggtgtacct | 720 |
| atccgtgtta tgtacctaga ccgaagctcg tgtgatactg gcaatctgag tgtgaatcac | 780 |
| catgatttca tcccttcgtc caatgcttct gagggtgatg ctgcgatgac atctactcct | 840 |
| gacgctgaga aaccttacat cactttgctc taccgtcctg gtcactatga tattctctac | 900 |
| ccaaagtga | 909 |

<210> SEQ ID NO 11
<211> LENGTH: 918
<212> TYPE: DNA
<213> ORGANISM: Arabidopsis thaliana

<400> SEQUENCE: 11

| | |
|---|---|
| atgcagaatc agattgatat ggtgaaggat gaagcggaag tagctgcatc gatttcagca | 60 |

```
attaagggtg aagaatgggg aaattgttca tcagtggaag atcaaccatc ttttcaagaa        120
gaagaagctg ctaaagttcc ttatgttggt gataaggaac ctctgtctag tttagctgca        180
gagtatcaat cagggagtcc cattttgctg gagaagatta agatactgga cagtcaatat        240
atcggaatcc ggcgaacaag aggagatgga aattgcttct tccgaagttt atgttctct         300 taccttgagc atatattgga atcacaagat cgtgctgaag tcgatcgtat caaggtcaat        360
gttgagaaat gtagaaagac tctgcaaaac ttaggttata cagattttac atttgaggac        420 ttcttttgcgt tgttccttga gcaactagat gacattctcc aaggaactga agagtctata       480
agctacgatg agctggttaa cagaagtaga gatcagtcag tctcagatta cattgtaatg        540
ttctttaggt ttgttactgc tggtgatata cgaacgcgtg ccgattttt cgagcctttt         600 ataacaggct tatcaaatgc aacagtggat cagtttttgca agtcctcggt cgaaccaatg       660
ggggaagaga gtgaccatat tcacataact gctttgtcgg acgcacttgg tgttgcaatc       720
cgtgttgtgt atcttgaccg tagctcatgt gatagtgggg gcgtcactgt gaatcatcat       780
gactttgttc ctgtgggcat taccaatgag aaagatgaag aagcttctgc tccatttata       840
accttgctgt atcgtccagg ccattacgat atcctctacc ccaagccatc ttgtaaggta       900
tcagacaatg tggggaaa                                                     918

<210> SEQ ID NO 12
<211> LENGTH: 906
<212> TYPE: DNA
<213> ORGANISM: Glycine max

<400> SEQUENCE: 12
atgcagagta agaagctgt tgtggaagat ggggaaataa agagtgtgac tgctgtaggg       60
tctgaaattg atgggtggac caattttggg gacgatgaca taatgcagca gcagtataca      120
attcagtctg aagaggctaa gaaagttcca tctgtgggcg acaaggaacc actgagtagc      180
ttagctgctg aatataaatc aggcagtcct atcttgctgg agaaaataaa ggtgcttgat      240
gagcaatacg ctgccattcg tcgtactcga ggagatggaa actgcttctt tcgaagcttt      300
atgttttcat atcttgagca tgttatgaaa tgtcaagacc aagcagaagt tgatcgtatc      360
caagccaatg ttgaaaaaag tagaaaagca ctgcagacct tgggttatgc agacttgact      420
tttgaagatt tttttgcgtt attccttgag cagctgaaat ctgttattca agggaaagag      480
acttccataa gtcatgaaga gcttgttctt agaagccgag atcagtcagt atctgattat      540
gtcgttatgt tcttcagatt tgttacctct gccgcaatac aaaagcgcac agaatttttt      600
gaaccattca tactaggctt aactaataca acggtcgagc agttttgcaa atcatctgtt      660
gaaccaatgg gtgaagagag cgaccatgtg cacattactg ccctttcaga tgcattgggc      720
attccagtcc gtgttgtgta ccttgaccgc agctcaagtg atactggtgg tgtcagtgta      780
aatcatcatg atttcatgcc agtggctggt gatctcccaa atgctagttg cagctctgaa      840
aagaacattc ctttcatcac actactatat cgtcctggtc actatgacat cctctatcca      900
aaatga                                                                 906

<210> SEQ ID NO 13
<211> LENGTH: 903
<212> TYPE: DNA
<213> ORGANISM: Brassica napus

<400> SEQUENCE: 13
```

```
atgcagaatc agaatgatac ggtgaaggat gatgcggagc tcgctgcttc catctcggct    60
gaacaatggg gatgctgttc agtggaggaa ccatcttttc aagatgatga agctgctaaa   120
gttccttatg ttggtgataa ggagcctatg tctagtttag ctgcagagta ccaagcaggg   180
agccccattt tgcttgagaa gataaaggta ctggacagtc aatatgttgc aatcaggcga   240
acaagaggag atggaaactg cttcttccga agttttatgt tctcttacct tgagcatatt   300
ttggaatcac aagatggtgc tgaagttgac cgtatcaagc tcaatgttga aaaatgtaga   360
aagaatctgc agaacttagg ctacacagat ttcacatttg aggacttctt tgcgttgttc   420
cttgagcaac tagatgacat cctccaagga ggcgaagagt ctataagcta tgatgagctg   480
gttaacagaa gtagagatca gtctgtttcc gactacattg tgatgttctt caggtttgtt   540
actgctggtg aaataaaaac gcgtgctgag ttcttcgagc cttttataac aggattatct   600
aataccacag tggatcagtt ttgcaagaca tcagttgaac cgatggggga agagagtgac   660
catattcaca taacagcttt gtcggacgcg cttggtgttg caatcccggt tgtgtatctt   720
gaccgtagct catgtgatac tggaggtggt gtcactgtga accatcacga ctttgttccc   780
gttggcagtg gcactaatga gaaagaagaa gcttcttctg ctgctcccct tataacattg   840
ctctatcgtc caggccatta cgatatcctc taccccaagg tattggagaa tgtggaaaaa   900
tga                                                                903
```

<210> SEQ ID NO 14
<211> LENGTH: 279
<212> TYPE: PRT
<213> ORGANISM: Triticum urartu

<400> SEQUENCE: 14

```
Met Gly Gly Asp Tyr Tyr His Ala Cys Cys Gly Asp Pro Asp Pro Asp
1               5                   10                  15

His Lys Pro Glu Gly Pro Gln Val Pro Tyr Ile Gly Asn Lys Glu Pro
            20                  25                  30

Leu Ser Ala Leu Ala Ala Glu Phe Gln Ser Gly Ser Pro Ile Leu Gln
        35                  40                  45

Glu Lys Ile Lys Leu Leu Gly Glu Gln Tyr Asp Ala Leu Arg Arg Thr
    50                  55                  60

Arg Gly Asp Gly Asn Cys Phe Tyr Arg Ser Phe Met Phe Ser Tyr Leu
65                  70                  75                  80

Glu His Ile Leu Glu Thr Gln Asp Arg Ala Glu Val Glu Arg Ile Leu
                85                  90                  95

Lys Asn Ile Glu Gln Cys Lys Met Thr Leu Ser Gly Leu Gly Tyr Ile
            100                 105                 110

Glu Phe Thr Phe Glu Asp Phe Ser Met Phe Ile Glu Glu Leu Gln
        115                 120                 125

Asn Val Leu Gln Gly His Glu Thr Ser Ile Gly Pro Glu Glu Leu Leu
    130                 135                 140

Glu Arg Thr Arg Asp Gln Thr Thr Ser Asp Tyr Val Val Met Phe Phe
145                 150                 155                 160

Arg Phe Val Thr Ser Gly Glu Ile Gln Arg Arg Ala Glu Phe Phe Glu
                165                 170                 175

Pro Phe Ile Ser Gly Leu Thr Asn Ser Thr Val Ala Gln Phe Cys Lys
            180                 185                 190

Ser Ser Val Glu Pro Met Gly Glu Glu Ser Asp His Val His Ile Ile
        195                 200                 205
```

```
Ala Leu Ser Asp Ala Leu Gly Val Pro Ile Arg Val Met Tyr Leu Asp
    210                 215                 220

Arg Ser Ser Cys Asp Thr Gly Asn Leu Ser Val Asn His His Asp Phe
225                 230                 235                 240

Ile Pro Ala Ala Asn Ser Ser Glu Gly Asp Ala Ala Met Gly Leu Asn
                245                 250                 255

Pro Ala Glu Glu Lys Pro Tyr Ile Thr Leu Leu Tyr Arg Pro Gly His
            260                 265                 270

Tyr Asp Ile Leu Tyr Pro Lys
        275

<210> SEQ ID NO 15
<211> LENGTH: 279
<212> TYPE: PRT
<213> ORGANISM: Hordeum vulgare

<400> SEQUENCE: 15

Met Gly Gly Asp Tyr Tyr His Ala Cys Cys Gly Asp Pro Asp Pro Asp
1               5                   10                  15

Pro Lys Pro Glu Gly Pro Gln Val Pro Tyr Ile Gly Asn Lys Glu Pro
            20                  25                  30

Leu Ser Ala Leu Ala Ala Glu Phe Gln Ser Gly Ser Pro Ile Leu Gln
        35                  40                  45

Glu Lys Ile Lys Leu Leu Gly Glu Gln Tyr Asp Ala Leu Arg Arg Thr
50                  55                  60

Arg Gly Asp Gly Asn Cys Phe Tyr Arg Ser Phe Met Phe Ser Tyr Leu
65                  70                  75                  80

Glu His Ile Leu Glu Thr Gln Asp Arg Ala Glu Val Glu Arg Ile Leu
                85                  90                  95

Lys Asn Ile Glu Gln Cys Lys Lys Thr Leu Ser Gly Leu Gly Tyr Ile
            100                 105                 110

Glu Phe Thr Phe Glu Asp Phe Phe Ser Met Phe Ile Glu Glu Leu Gln
        115                 120                 125

Asn Val Leu Gln Gly His Gly Thr Ser Ile Gly Pro Glu Glu Leu Leu
130                 135                 140

Glu Arg Thr Arg Asp Gln Thr Thr Ser Asp Tyr Val Val Met Phe Phe
145                 150                 155                 160

Arg Phe Val Thr Ser Gly Glu Ile Gln Arg Arg Ala Glu Phe Phe Glu
                165                 170                 175

Pro Phe Ile Ser Gly Leu Thr Asn Ser Thr Val Val Gln Phe Cys Lys
            180                 185                 190

Ser Ser Val Glu Pro Met Gly Glu Glu Ser Asp His Val His Ile Ile
        195                 200                 205

Ala Leu Ser Asp Ala Leu Gly Val Pro Ile Arg Val Met Tyr Leu Asp
    210                 215                 220

Arg Ser Ser Cys Asp Thr Gly Asn Leu Ser Val Asn His His Asp Phe
225                 230                 235                 240

Ile Pro Ala Ala Asn Ser Ser Glu Gly Asp Ala Ala Met Gly Leu Asn
                245                 250                 255

Pro Ala Asp Glu Lys Pro Tyr Ile Thr Leu Leu Tyr Arg Pro Gly His
            260                 265                 270

Tyr Asp Ile Leu Tyr Pro Lys
        275

<210> SEQ ID NO 16
```

```
<211> LENGTH: 296
<212> TYPE: PRT
<213> ORGANISM: Zea mays

<400> SEQUENCE: 16
```

| Met<br>1 | Gly | Asp | Val | Pro<br>5 | Gln | Ala | Pro | His | Ala<br>10 | Ala | Gly | Gly | Glu | Glu<br>15 |
|---|---|---|---|---|---|---|---|---|---|---|---|---|---|---|
| Trp | Ala | Gly | Pro<br>20 | Asp | Pro | Asn | Pro<br>25 | Ser | Pro | Ser | Leu | Gly<br>30 | Gly | Cys | Ser |
| Asp | Pro | Val<br>35 | Ser | Val | Glu | Leu | Ser<br>40 | Met | Gly | Gly | Asp | Tyr<br>45 | Tyr | Arg | Ala |
| Cys | Cys<br>50 | Gly | Glu | Pro | Asp | Pro<br>55 | Asp | Ile | Pro | Glu | Gly<br>60 | Pro | Lys | Leu | Pro |
| Cys<br>65 | Val | Gly | Asp | Lys | Glu<br>70 | Pro | Leu | Ser | Ser | Leu<br>75 | Ala | Ala | Glu | Phe | Gln<br>80 |
| Ser | Gly | Ser | Pro | Ile<br>85 | Leu | Gln | Glu | Lys | Ile<br>90 | Lys | Leu | Leu | Gly | Glu<br>95 | Gln |
| Tyr | Gly | Ala | Leu<br>100 | Arg | Arg | Thr | Arg | Gly<br>105 | Asp | Gly | Asn | Cys | Phe<br>110 | Tyr | Arg |
| Ser | Phe | Met<br>115 | Phe | Ser | Tyr | Leu | Glu<br>120 | His | Ile | Leu | Glu | Thr<br>125 | Gln | Asp | Lys |
| Ala | Glu<br>130 | Ala | Asp | Arg | Ile | Met<br>135 | Val | Lys | Ile | Glu | Glu<br>140 | Cys | Lys | Lys | Thr |
| Leu<br>145 | Leu | Ser | Leu | Gly | Tyr<br>150 | Ile | Glu | Phe | Thr | Phe<br>155 | Glu | Asp | Phe | Phe | Ser<br>160 |
| Ile | Phe | Ile | Glu | Leu<br>165 | Leu | Glu | Ser | Val | Leu<br>170 | Gln | Gly | His | Glu | Thr<br>175 | Pro |
| Ile | Gly | Phe | Val<br>180 | Thr | Ser | Gly | Glu | Ile<br>185 | Gln | Arg | Arg | Ser | Asp<br>190 | Phe | Phe |
| Glu | Pro | Phe<br>195 | Ile | Ser | Gly | Leu | Thr<br>200 | Asn | Ser | Thr | Val | Val<br>205 | Gln | Phe | Cys |
| Lys<br>210 | Ala | Ser | Val | Glu | Pro<br>215 | Met | Gly | Glu | Glu | Ser<br>220 | Asp | His | Val | His | Ile |
| Ile<br>225 | Ala | Leu | Ser | Asp | Ala<br>230 | Leu | Gly | Val | Pro | Ile<br>235 | Arg | Val | Met | Tyr | Leu<br>240 |
| Asp | Arg | Ser | Ser | Cys<br>245 | Asp | Thr | Gly | Asn | Leu<br>250 | Ser | Val | Asn | His | His<br>255 | Asp |
| Phe | Ile | Pro | Ser<br>260 | Ala | Asn | Asp | Ser | Glu<br>265 | Gly | Asp | Ala | Ala | Thr<br>270 | Thr | Pro |
| Ala | Pro | Ala<br>275 | Thr | Glu | Lys | Pro | Tyr<br>280 | Ile | Thr | Leu | Leu | Tyr<br>285 | Arg | Pro | Gly |
| His | Tyr<br>290 | Asp | Ile | Leu | Tyr | Pro<br>295 | Lys | | | | | | | | |

```
<210> SEQ ID NO 17
<211> LENGTH: 302
<212> TYPE: PRT
<213> ORGANISM: Sorghum bicolor

<400> SEQUENCE: 17
```

| Met<br>1 | Gly | Asp | Val | Pro<br>5 | Gln | Ala | Pro | His | Ala<br>10 | Ala | Glu | Gly | Gly | Gly<br>15 |
|---|---|---|---|---|---|---|---|---|---|---|---|---|---|---|
| Gly | Leu | Glu | Glu<br>20 | Gly | Ala | Val | Pro<br>25 | Asp | Pro | Asn | Pro | Ser<br>30 | Pro | Ser | Leu |
| Ser | Leu | Gly<br>35 | Gly | Cys | Ser | Asp | Pro<br>40 | Val | Ser | Leu | Glu | Leu<br>45 | Ser | Met | Gly |

Gly Asp Tyr Tyr Arg Ala Cys Cys Gly Asp Pro Asp Pro Asp Ile Pro
    50                  55                  60

Glu Gly Pro Lys Leu Pro Cys Val Gly Glu Lys Glu Pro Leu Ser Ser
65                  70                  75                  80

Leu Ala Ala Glu Phe Gln Ser Gly Ser Pro Ile Leu Gln Glu Lys Ile
                85                  90                  95

Lys Leu Leu Gly Glu Gln Tyr Gly Ala Leu Arg Arg Thr Arg Gly Asp
            100                 105                 110

Gly Asn Cys Phe Tyr Arg Ser Phe Met Phe Ser Tyr Leu Glu His Ile
            115                 120                 125

Leu Glu Thr Gln Asp Lys Ala Glu Ala Asp Arg Ile Met Val Lys Ile
            130                 135                 140

Glu Asp Cys Lys Lys Thr Leu Leu Ser Leu Gly Tyr Ile Glu Phe Thr
145                 150                 155                 160

Phe Glu Asp Phe Phe Ala Ile Phe Ile Asp Met Leu Glu Ser Val Leu
                165                 170                 175

Gln Gly His Glu Thr Pro Ile Gly Phe Val Thr Ser Gly Glu Ile Gln
            180                 185                 190

Arg Arg Ser Asp Phe Phe Glu Pro Phe Ile Ser Gly Leu Thr Asn Ser
            195                 200                 205

Thr Val Val Gln Phe Cys Lys Ala Ser Val Glu Pro Met Gly Glu Glu
    210                 215                 220

Ser Asp His Val His Ile Ile Ala Leu Ser Asp Ala Leu Gly Val Pro
225                 230                 235                 240

Ile Arg Val Met Tyr Leu Asp Arg Ser Ser Cys Asp Thr Gly Asn Leu
                245                 250                 255

Ser Val Asn His His Asp Phe Ile Pro Ser Ser Asn Ala Ser Glu Gly
            260                 265                 270

Asp Ala Ala Met Thr Ser Thr Pro Asp Ala Glu Lys Pro Tyr Ile Thr
            275                 280                 285

Leu Leu Tyr Arg Pro Gly His Tyr Asp Ile Leu Tyr Pro Lys
            290                 295                 300

<210> SEQ ID NO 18
<211> LENGTH: 306
<212> TYPE: PRT
<213> ORGANISM: Arabidopsis thaliana

<400> SEQUENCE: 18

Met Gln Asn Gln Ile Asp Met Val Lys Asp Glu Ala Glu Val Ala Ala
1               5                   10                  15

Ser Ile Ser Ala Ile Lys Gly Glu Glu Trp Gly Asn Cys Ser Ser Val
            20                  25                  30

Glu Asp Gln Pro Ser Phe Gln Glu Glu Ala Ala Lys Val Pro Tyr
            35                  40                  45

Val Gly Asp Lys Glu Pro Leu Ser Ser Leu Ala Ala Tyr Gln Ser
        50                  55                  60

Gly Ser Pro Ile Leu Leu Glu Lys Ile Lys Ile Leu Asp Ser Gln Tyr
65                  70                  75                  80

Ile Gly Ile Arg Arg Thr Arg Gly Asp Gly Asn Cys Phe Phe Arg Ser
                85                  90                  95

Phe Met Phe Ser Tyr Leu Glu His Ile Leu Glu Ser Gln Asp Arg Ala
            100                 105                 110

Glu Val Asp Arg Ile Lys Val Asn Val Glu Lys Cys Arg Lys Thr Leu

```
                 115                 120                 125
Gln Asn Leu Gly Tyr Thr Asp Phe Thr Phe Glu Asp Phe Ala Leu
        130                 135                 140
Phe Leu Glu Gln Leu Asp Asp Ile Leu Gln Gly Thr Glu Glu Ser Ile
145                 150                 155                 160
Ser Tyr Asp Glu Leu Val Asn Arg Ser Arg Asp Gln Ser Val Ser Asp
                165                 170                 175
Tyr Ile Val Met Phe Phe Arg Phe Val Thr Ala Gly Asp Ile Arg Thr
            180                 185                 190
Arg Ala Asp Phe Phe Glu Pro Phe Ile Thr Gly Leu Ser Asn Ala Thr
        195                 200                 205
Val Asp Gln Phe Cys Lys Ser Ser Val Glu Pro Met Gly Glu Glu Ser
210                 215                 220
Asp His Ile His Ile Thr Ala Leu Ser Asp Ala Leu Gly Val Ala Ile
225                 230                 235                 240
Arg Val Val Tyr Leu Asp Arg Ser Ser Cys Asp Ser Gly Gly Val Thr
                245                 250                 255
Val Asn His His Asp Phe Val Pro Val Gly Ile Thr Asn Glu Lys Asp
            260                 265                 270
Glu Glu Ala Ser Ala Pro Phe Ile Thr Leu Leu Tyr Arg Pro Gly His
        275                 280                 285
Tyr Asp Ile Leu Tyr Pro Lys Pro Ser Cys Lys Val Ser Asp Asn Val
        290                 295                 300
Gly Lys
305

<210> SEQ ID NO 19
<211> LENGTH: 301
<212> TYPE: PRT
<213> ORGANISM: Glycine max

<400> SEQUENCE: 19

Met Gln Ser Lys Glu Ala Val Val Glu Asp Gly Glu Ile Lys Ser Val
1               5                   10                  15
Thr Ala Val Gly Ser Glu Ile Asp Gly Trp Thr Asn Phe Gly Asp Asp
                20                  25                  30
Asp Ile Met Gln Gln Gln Tyr Thr Ile Gln Ser Glu Glu Ala Lys Lys
            35                  40                  45
Val Pro Ser Val Gly Asp Lys Glu Pro Leu Ser Ser Leu Ala Ala Glu
        50                  55                  60
Tyr Lys Ser Gly Ser Pro Ile Leu Leu Glu Lys Ile Lys Val Leu Asp
65                  70                  75                  80
Glu Gln Tyr Ala Ala Ile Arg Arg Thr Arg Gly Asp Gly Asn Cys Phe
                85                  90                  95
Phe Arg Ser Phe Met Phe Ser Tyr Leu Glu His Val Met Lys Cys Gln
            100                 105                 110
Asp Gln Ala Glu Val Asp Arg Ile Gln Ala Asn Val Glu Lys Ser Arg
        115                 120                 125
Lys Ala Leu Gln Thr Leu Gly Tyr Ala Asp Leu Thr Phe Glu Asp Phe
    130                 135                 140
Phe Ala Leu Phe Leu Glu Gln Leu Glu Ser Val Ile Gln Gly Lys Glu
145                 150                 155                 160
Thr Ser Ile Ser His Glu Glu Leu Val Leu Arg Ser Arg Asp Gln Ser
                165                 170                 175
```

Val Ser Asp Tyr Val Val Met Phe Phe Arg Phe Val Thr Ser Ala Ala
            180                 185                 190

Ile Gln Lys Arg Thr Glu Phe Phe Glu Pro Phe Ile Leu Gly Leu Thr
            195                 200                 205

Asn Thr Thr Val Glu Gln Phe Cys Lys Ser Ser Val Glu Pro Met Gly
            210                 215                 220

Glu Glu Ser Asp His Val His Ile Thr Ala Leu Ser Asp Ala Leu Gly
225                 230                 235                 240

Ile Pro Val Arg Val Tyr Leu Asp Arg Ser Ser Asp Thr Gly
            245                 250                 255

Gly Val Ser Val Asn His His Asp Phe Met Pro Val Ala Gly Asp Leu
            260                 265                 270

Pro Asn Ala Ser Cys Ser Ser Glu Lys Asn Ile Pro Phe Ile Thr Leu
            275                 280                 285

Leu Tyr Arg Pro Gly His Tyr Asp Ile Leu Tyr Pro Lys
            290                 295                 300

<210> SEQ ID NO 20
<211> LENGTH: 300
<212> TYPE: PRT
<213> ORGANISM: Brassica napus

<400> SEQUENCE: 20

Met Gln Asn Gln Asn Asp Thr Val Lys Asp Asp Ala Glu Leu Ala Ala
1               5                   10                  15

Ser Ile Ser Ala Glu Gln Trp Gly Cys Cys Ser Val Glu Glu Pro Ser
            20                  25                  30

Phe Gln Asp Asp Glu Ala Ala Lys Val Pro Tyr Val Gly Asp Lys Glu
            35                  40                  45

Pro Met Ser Ser Leu Ala Ala Glu Tyr Gln Ala Gly Ser Pro Ile Leu
        50                  55                  60

Leu Glu Lys Ile Lys Val Leu Asp Ser Gln Tyr Val Ala Ile Arg Arg
65              70                  75                  80

Thr Arg Gly Asp Gly Asn Cys Phe Phe Arg Ser Phe Met Phe Ser Tyr
                85                  90                  95

Leu Glu His Ile Leu Glu Ser Gln Asp Gly Ala Glu Val Asp Arg Ile
            100                 105                 110

Lys Leu Asn Val Glu Lys Cys Arg Lys Asn Leu Gln Asn Leu Gly Tyr
            115                 120                 125

Thr Asp Phe Thr Phe Glu Asp Phe Phe Ala Leu Phe Leu Glu Gln Leu
        130                 135                 140

Asp Asp Ile Leu Gln Gly Gly Glu Glu Ser Ile Ser Tyr Asp Glu Leu
145             150                 155                 160

Val Asn Arg Ser Arg Asp Gln Ser Val Ser Asp Tyr Ile Val Met Phe
                165                 170                 175

Phe Arg Phe Val Thr Ala Gly Glu Ile Lys Thr Arg Ala Glu Phe Phe
            180                 185                 190

Glu Pro Phe Ile Thr Gly Leu Ser Asn Thr Thr Val Asp Gln Phe Cys
            195                 200                 205

Lys Thr Ser Val Glu Pro Met Gly Glu Glu Ser Asp His Ile His Ile
        210                 215                 220

Thr Ala Leu Ser Asp Ala Leu Gly Val Ala Ile Arg Val Val Tyr Leu
225             230                 235                 240

Asp Arg Ser Ser Cys Asp Thr Gly Gly Val Thr Val Asn His His
                245                 250                 255

```
Asp Phe Val Pro Val Gly Ser Gly Thr Asn Glu Lys Glu Glu Ala Ser
            260                 265                 270

Ser Ala Ala Pro Phe Ile Thr Leu Leu Tyr Arg Pro Gly His Tyr Asp
        275                 280                 285

Ile Leu Tyr Pro Lys Val Leu Glu Asn Val Glu Lys
        290                 295                 300

<210> SEQ ID NO 21
<211> LENGTH: 3000
<212> TYPE: DNA
<213> ORGANISM: Triticum urartu
<220> FEATURE:
<221> NAME/KEY: misc_feature
<222> LOCATION: (2927)..(2978)
<223> OTHER INFORMATION: n is a, c, g, or t

<400> SEQUENCE: 21
cagtaaaaag tttaaaattg acaacacacc aagaattcag caatcaaatc aatgacacaa      60
tgaatagaaa agttagcaat gcaatttta ggttcataag atattgcgag taaccatgaa     120
atcattgttg cattgcaaag agctaactat agaggtaaca ccaactaagt ttatactact     180
agttatctca atggttttat tctccgcaaa tctgcatctt gcggattata cctgtgaaaa     240
gtattcttgg actgatgaca atcattagaa cagaacccag cacaaattta tcagtaggtc     300
atcatatcac aaagcagaca acaaatcaag attaggtaag ttgatgaagt ggttggagtt     360
agtaaagaag tcatgtaacc aacaaattta gggcacgtga aagtcttgca ttgcatgaac     420
tgacatctta gttaaacaaa gttatcactc aagaatatag cgtatcggtg tatttattcc     480
aattatgtga gctcaagatg attgcaaagg aaaggggga agggctataa agctatgaag     540
ataactttta tatgagagtg tacagttttg gatagtaacg cagcatgcca aattcgaagg     600
ttgatagtca gaatcgtgat tctgaatcgg atcgggccc taatggtagg gtcgcatatc     660
gcagaatctt cactacgaaa atcacagaaa catagatttt accaaacaga atcatagaat     720
catgagttag tttggattgt caagtcgtag aatcgtacaa cagaatcgcg attctgacta     780
cttttaacat attcactcct aatttgcact gagaaaaaaa agataaatac agggaaataa     840
tttgcatggt tacatcacac atctaaacaa agacaaatac gacaaataca tatgattttc     900
tacactgctt gatgatacta tgtctcatgt atgccaactt aagaatgcag tcaatgacac     960
cacgaatctg cttcatacaa ggaacaccta ctactgcaat atatatttt cgaaaggatt    1020 actgcaatct atctacttta agttacaggt agatatacgt gccctcgaaa gatataagaa    1080
ttttagcact ggagaacttc atcgccagcc ttattactcc ctccaatccg aattaattga    1140
tgcagcctct atacaatgac attatgctaa gatcggaggg agtattctat atccatcctt    1200
cacattatgc taagatcctc agcagcagat acaactcaag acctttgatg tgaacaatga    1260
acaaaatagc ttggaaaata ataaatggac agtatgacta agataattgg tattatgaaa    1320
atggaaagta gatttcaggt atcaactaga taactcggca atacctatct tttctttggc    1380
tcatggcagg tgtcagagaa atgtatcgat gttctaaaag agctggaaga actgtttcta    1440
cataatcaaa atgtcctttc cgttttcggc aatcgaccct aaatggctct ttcaacgata    1500
tctcctcggg catatccttc accacttcca cataacctct agtttgctca atgaagtgat    1560
caacatcaaa cacgtctgca aaaccactga caaagcattc tgataagcac atgattagtt    1620
tttgaacaga agtgcactac atagaaacaa cagtagaagc cttcgtttca ccccaagtga    1680
ctccagtacc tagactcatt ccagtatgca gcaacctcaa acttgggcag aaccattgtc    1740
```

```
gcgttcagaa gacgtgcaac cgcaattcca tcgcacagct gcagaacaat tgcgccagag   1800
gccagaataa ttacaaccga ggaacttgta acatagccaa tcgacaacgc acaccactgc   1860
acaacattct atacaatgct acctatttcc taaagctaaa tcatatgatc ccactattga   1920
ctccacgagc ctatacttgt cacttgtgca ttcagtacat ggccagatga tccaagttta   1980
acagtacata cataagaaaa ggaagtctta ctccattaca aggaggataa accaagttta   2040
acatacatcg cgccgcagct ggttgaggcc gccgtagcaa tctatcctga tgtagccatt   2100
cctcgtcgac ggagctgctg aaggagagcg gggacagaaa ccaatcatca ccacaaccca   2160
agccaatcct aaactctgac cgaaaaccac gaagcacaca aggcctcacc gggcattgcc   2220
gtctgccacc actcgcacgg ccgccactcc gccaaacgcc gctgcgccca tatgagccgc   2280
gacccccacg gcgaatgctc cctgcgggaa aatcccaatg cggggatct gtaacttcca   2340 ggaagagtcc agaagaacct ggtatggcag gtcggggcgg ggcgcgtacc tggaggccgg   2400
tagggcgaag aaggatgggg aggagcgcgg ggaggcgagg aagaagaaga gggcggcggc   2460
gaggaagagg gccgggagaa ggaggcgtat gtggtggggg gccgcgcctg ttcgccacca   2520
cgccccccgc cgacgccgct acctacgaga agcactggat ctgatcgccg gcggcgacgc   2580
ggcgtcaccg cgagcacgga agtacgacct gtccgccaga atgagggtcc cacatgtaaa   2640
taagggacca cctgtcatgg atggttatcc agatcgagag gtggcgtgtg ggaatggagc   2700
agggtggtgg tccagcagga acagcgttaa cttcctgaaa atggaacgcg ggcccgctgc   2760
gtcagcccca catgtcaggg tcacgaagta caccatgaag gtggatgacg cgaagggctt   2820
atcttcaaaa cgacacgcac atacccttg tttcgcctgc ggcgagatct ccgactgcca   2880
caaaagcgaa ggtctcctcc gcccgaatca aagccgtcgt ctcgaannnn nnnnnnnnn   2940 nnnnnnnnnn nnnnnnnnnn nnnnnnnnnn nnnnnnntc cggcccccga ggacgcggcc   3000
```

<210> SEQ ID NO 22
<211> LENGTH: 3000
<212> TYPE: DNA
<213> ORGANISM: Hordeum vulgare

<400> SEQUENCE: 22

```
aatacagaaa gtacgaaact caggtaacca cgaggaagtt gcatcacgtc tcctcaggtt     60
taagtcattg acttgggagt cctcggtgtt cacacaaggt caagatatct actggctttt    120
cccccttcag agacagcaaa gaaagcacgc ccaccactgt cctttctaac atgtgattta    180
taggttgtcc aatgctgtca acactgcaac aaagcgatgg ccgctggtat gtgcagcatg    240
tttgaaatca aaatgcttgc atcagtatat atgaaaatgt aacgatgaga agaggtatac    300
actggggagt atgattagtg aatgaaggga ggttattctt ccatccgctg cttgcttgag    360
ctgccaaacg gaaggaatga gcagcggaat accaagtgtc atgtacacct tccttacagt    420
taaagatcgc atgctcaaca ccaatttgtt taagcttgct tgcttgccac gacgtaaaat    480
atgaaaataa ccactagtca catagtccct ccattcttaa acattccaac cgtccgaaaa    540
tacttgtcat atgaattcat atatctagat gtaatttagt tctagatata tccatttta    600 tatatttgtg cgataagtaa tttcaggcgg agggagtata agttttttaa agatttcact    660
agggactaca tacggatgta tatagacata ctttagagta tagatacatc cattttgctt    720
tgtatgcagt ctgtagtgga atctctaaaa aagactttata tttaagaaca gagggagtag    780
attactagcc caaacacgga gtgatgaaga acatggcccg tgcaattgga agtgttgttt    840
```

```
aatgtatcaa ccgccagtgg gtgattgatg cacactccac tcgttggcgc agaatgcatc    900
atgcattgca tttggggttt ctagttaagc ataactctca ttgacttgtt aacaattgag    960
atggacagtt gttggaatcg attctccttc tagaagcaaa attgaccagg gcaacaagaa   1020
ccaaacaact tcctagccaa agaaatgaat aagcagctaa gtatgtaaac attgcgatgc   1080
acacaataag aatccggtta tggaacccaa ctctacaaca aactatgtaa atgtggtgta   1140
tttcccagtg atggatcaga ttaatcacag gccattacac cacctgacag tagatcagta   1200 gctagttttct gagcaatgca aaattcaaaa attatacata tatcccccca aaaaatttcc   1260
tgcttgttag ttatctaaga acaaagtttt caacctatct ataccctca aatgttgagt    1320 ttgggcctgg gcatatttcc agttgcaaaa ggaaatgcca gaatgattcg ctaggtagta   1380
agtgtgcgtg tacatgtctg agctactatc tgaactcacc gaaaacagta tccagaagag   1440
gccatgatgc attgttgtat gagtgataat tgctctctga atcaagagga tgtgcagctt   1500
gcgactctga tgaagaacgg tttcttctga agggcattac attatgccca ctgcagtagc   1560
aactcagcca caatgcgatc tattagtcgc taccgataag aaggtggctg tgtagattgg   1620
tccttgtgtt atatgggctc acttgtgcag ttgtgctaca acttgaactc acagaagcaa   1680
tgttcaggga gagctaatcc cctccccaga atataatcct ctcgatgagc atcccacatg   1740
gccttagcta gttggtctcc tgccagtcca gcagccgtgt agtttgcgaa ggccctccta   1800
ctcaagacca atgtcttctg tagcccttgc attgttctca ttgcagttac catcttatcc   1860
atatttccaa agaacgtggc aacataagca tcgctgttga ctgaaacata gtagtcgaga   1920
gcagcttttg tgttgccatg catcctctca aaatcctcat gagtcaggag agacgattta   1980
gtatacatat ttttgtagat cgaagtgaag ccctcgagtt ccattagccc atccccagca   2040
gctaaataaa tgtttgtctc tgtaggaata cctagtgctt ggaggataaa tgctgtttca   2100
cttggtgtta gagggcactt tccacggttc ctccacagat gagcagcatc accaatcaat   2160
acattcctgt cctccccacg tgcagcttca atcgcatcca gtgatttgga agaaagggca   2220
ctgtattcac atcgactgta ggcaaccata tctggttcaa atctaaggtg aagtgataag   2280
aaaggttttg gtattgcttg gagaagcttc atagctttgg cttctacctt cttgttcaac   2340
tggagtgcat tgtagcaacc ttggcagtaa caagctttcg catgtgatgg atatctgaga   2400
aaatacaggc atatacatca gcatggggaa aaggcagatc caaggtgaat aattacaaca   2460
gcgaaaagtt taaaattgac aacacaccaa gaagtcagca attaaatcaa tgacacgatg   2520
aataggaaat ttagcaatgc aattttagg ttcataagaa attgagagca attaaatcat    2580
aagacattgt tacatcgcaa agaactaact acagagtaac attaactaag tttacacaac   2640
tagttatctt aaaggcttta ttctccgcaa atccgcatct tgcagattat acctgtgaaa   2700
agtcttcttg gactgatgac aatcattaga acagaaaccg gcacaaattt atcagtaggt   2760
catcgtatcg caaagcagac aacaaatcaa gattaggtaa gttgaagtgg ttggagttag   2820
taaagaattc atgtaaccaa caaatttaag gcacgtgaaa gtcttgcatt gtatgaaact   2880
atgaattgac atcttagtta aacaaagtta tcacgcgata gtatagtgta tcagtgtatt   2940
tattctaatt atgcatagtt tttaaggagt cgaggcgttt taaggcgttg aggggggggct   3000
```

<210> SEQ ID NO 23
<211> LENGTH: 22
<212> TYPE: DNA
<213> ORGANISM: Artificial Sequence
<220> FEATURE:
<223> OTHER INFORMATION: SRS5-QR primer

<400> SEQUENCE: 23

```
tcaaaaccag acacacaaac tg                                             22
```

<210> SEQ ID NO 24
<211> LENGTH: 3000
<212> TYPE: DNA
<213> ORGANISM: Zea mays

<400> SEQUENCE: 24

```
tcaatacatt tggaaagtac aaatgaacat cacatcaaac atgtacaaac attagaacac    60
aactcaaaag atgtagtatt aaataaagga gaatgaggtc aagttataaa atgaactaat   120
cctaattagg agttgattac tctataagtg tttggaacat atctcaaaaa ggtaaagtag   180
taatttaaac aagaaagaga ttaaatcata agatggactt atctcattta ggaatttgat   240
tattctttaa gtgttatcta taattacata acctaattct attcatttca ttgagaccta   300
aaagttaaac caaatgaat tcatgtaaca catattatta atctcacaag attaaatata   360
ttttaactcc tagggctttc attttatttt atttcattaa atgaataaat caacatatac   420
attaaactta tactctaggt gtaaaattaa agtgcacaga ccatagatga acttaattta   480
tttggacaga gaataatatt atgaacattt tacaatttga accactaaat ttggagttca   540
tatgaaaaag atatgaaata aacaagtttt gaagttgaaa tatgaaatta gggctaaatt   600
tgtgattaaa taaagtaca gggggctatc caaagaaac caggggccta cgcgctaaaa    660
cagaggacgt cgggttgatt tcctaaaagc cgagggtctc ttaagtaaaa cttacacgtg   720
aagggggtac ggggtaacct cggccatcag atcagagatc aacgacaagg attagatcgc   780
gtgggcgcgg gcgcgtggac gcgactaaca ggcggggacg gggcgtcagc gagtcagggc   840
gggctgacca gccgggccca ggggcagggg cgcaggtgag ggggagaagg gagagcggcc   900
ggatctagat cggagcgctg cgattagatc cgcaataatg aaacctaaac cgcacgatct   960
cggacgaacg cccgagatct atcgactggg ggcggacaca aacgcggtgg cgccgctcgg  1020
tcccgcgccg acagtgagcg gtggcgaagc tctctgttcg cgcgggcaga gcgagagaga  1080
gggcgagggg gtttggctga gggcgcaagt gagcgagggg aggtgggcga gcagggcgcg  1140
gggctcaaaa gggacgcagg cgcggggacg tggccggaga acgcgcggac gtgggcgcgt  1200
ccaccgcggg ggatcgtggg cgggaggttg gggatgaccg acaggtgggc tcggtgggac  1260
agagagagag agagagagcg ggcgcggagg gaaaggaacg acgtcgacaa ctcggtccca  1320
cagagcagcg agagagggg agagagggcg cgctggagag acagacagac aggcggggtc  1380
cgcctgtcag cgtgggcggg cgcgggcgcg cgcgcaagct gggccgactt gggctaactg  1440
ggccagattg gcttttctcta tttccaggga atttctattt gcttttttta tttatttct   1500
ctagggtttt caattcaaat tcaaatctag tttcaaattc aaaccaaatc aaacatgtgc  1560
aacaattcaa gaatatttag gctcaatatg atgcaacatt tcatgactca tatgttttgg  1620
gcaaaataaa ataaataatc cctcactaat taaactaacc ctaatcaaaa gaggaagagg  1680
gggagagaaa ctagagagag agaaactaga gtgagataga gaagagtaac acctgaattt  1740
ggatgataat atgaaagaaa ttttataccc caaattcagg gtgttacaat cgctgtgcac  1800
tattttttgc gcgcgctgca caggcgctgg gcgtggggag ggtgaagtcg tggtagcatc  1860
aggtgcccac attagattct taatagatta ttattactag ttggttgctc atactttgct  1920
acggttatta tatactccat ccgttccata atataaggcg taaccatttt ttgttcttgt  1980
```

```
cccacaata taagacatgc tctctctatg catacgtaca ttaatgcagt gatatagaga    2040
aaattaaata tatttcttgg tatttgaacc agaggtggtt acgccttata tactaggaca    2100
gagggagtat catataaata ggtatttaga tatttattca aatgtaacta ttgtttattt    2160
ctaaacacta aggtatgtgt ggtctggtgg ttagctccaa atttctgaag caggggggcgt   2220 gggctcgagt agttgccctg cattttttg cgcggtgtga tgggtgggcc tagagtgtca    2280
gaaggtgaag ctgtgatatc atcatgtgcc cacattagat tcttaataga ttagtataga   2340
ttattaatta ttactaggta tgtgtccgct tgttgccacg aggctgagaa gcgtggggag   2400
gggcgcctaa gctacaaata taattttttgt ttatttgtaa acactaaagt atgtgtgatc   2460
tgatggttag ccctaaatttt ttagagcaca ggatgtgagt ttgactgctc gttttgtact   2520 atttttttgtg ggctggacgt ggggagagtg aagccgtggt aacactaggt gcccacatta   2580
ggttcttaat agatagtaga tagatagatt gtttatttgt aaactatatg tgatctggtg    2640
gttagtccta aatttctaaa gcatagtggt gtgggtttga gtgctcgttc tccactattt   2700
ttgcgctgga cgtaaagaga gtgaagtcgt agtagcacca ggtacctaca ttagattctt   2760
aatagatagc aggggagtag aaatatatat atagaactta tatatatatg ccgaagcttt   2820
gttttataca ttattcttaa ccgtttattt ttaaataaca tatattttta atagcacgaa    2880
atagatgcaa atatttttat ggccttaaac aatttaaata gatttttattt taattttttag  2940 gacttaatta tacgacttttt tgaacgctat aagtaaacgg taaataacaa gggcttatcc    3000
```

<210> SEQ ID NO 25
<211> LENGTH: 3000
<212> TYPE: DNA
<213> ORGANISM: Sorghum bicolor

<400> SEQUENCE: 25

```
tattcaacct gagagcactg tagcagcctt gacagtatga agcttttgca tatgaggggt    60
ttctgaaaac acacaaacat atatcaattt ggcgcagaat caacctcaag atgaacaact    120
aacattacat taaaaaaatt atcataccaa agagcctaat aggactgctg atagaaattg    180
aagaacagaa gggttaataa aataatttct aggatataca ttgtcattgc cacaatcgtg    240
aatcatagaa tagctaacca cgcaaatctg taggtacata cataagctgg aaggactaaa    300
ctactcgtta ccttattatc ttatttcact caacctacat ctttagaaga tagtaggaaa    360
ctaaaagatt aggtaaatta aagtggttgc tggttcgcaa aaaagtcata taaccaacaa    420
ataaaggata cccaaattct cataatatat agacaggcat cttcaccatc aaaattcata    480
gtgtgtacgc tctaaccaat taaggtcagg ttcgtttact gcaaagggac aaaaagaatt    540
gataaatgca gatcactaca gcttttcaca gtaagttcta agttgtaaat aaaggaaatc    600
cagcaaacta aaattttaaa ggtttacaaa aatatgctac actaatagtt gttagaagta    660
ggaaggttat atttcaaaca atgaaatcaa caaaacacc ttatccatgt aaagtagcaa    720
ttaccaactg cttggtcaca tcagatgcta acatctaaag cataaatgac taaataaata    780
ctgatttata cttcatcacg gcttagttgt agtactttca catatactag tcacttagtc    840
aggaacagta atgataaaac tattatactt cataaactat tttcccttcg gtaggaatag    900
gaaatatgaa cttcttataa actataatat agtacaacca agatgccaat cttgtagtcg    960
tacaatattt tattgctaac tgatttatta tcaccccttc caacatacta atacaatgag    1020
tcaatgaata tagaataaca tattctatta gatgtcatgc aaaacccact gtaacttgtg    1080
aaacgaatca cttgtaagca tgagtaagag cattagtata ttatggaaat ggatggaaaa    1140
```

-continued

```
tgcaaaggat ctatgagata tacaagcagt acctatctct tctttgattc atggcaggtg   1200
tcagtgagat gtattgatgc tccaagagag ctggaagtac actttcaaca taatcaaaat   1260
gtcctttccg tttactgcag tcaaccttaa acggctcttt ggatgctatc tccacaggca   1320
agtccttcat aacttccaca tatcctctag tctgctcaat gaagtaatca acatcgaaaa   1380
catctgcaaa gccactgaca gaacaatcca ataagaacta ctgtaagcat atttcaaaca   1440
gaactgaact atagaacttc aatcatcata cctagactta ttccaatagg cggcaacctc   1500
aaacttgggc agaatcatcg ttgcgttcag aagacgtgca accccaattc cgtcacatag   1560
ctgcagaacc atcacaatag tatcatttag tggcccctcc agaactcata agcacaagat   1620
atgaagttat gaacaaaaga agcacaatt gctttatgga acatcaagat cttctgactg   1680
aaagttcagc actctcagtc tcaggctcag agagtcacta ctccatgcag tgctgctacg   1740
atactgacaa ccagagcatg tttcggctaa aatcaatcat ttgatctcta caggaaggag   1800
gaaactctaa ccgaggtctc ttaacgtaca tcacgtcgca gctggttgag accaccgtag   1860
cagtctattc ggatgtaccc gttcctcctg gacggagctg cacacacagc gcaggcgtca   1920
atcatcagta cgtccaagtc cagtatccaa attccacccc caaacagcga ggccttacct   1980
tgcactggtg ccgtccgcca ccacccgcac gggcgccact ccaccaaccg ccgctgcgcc   2040
catatgagcc gcgagcccga aggaggcagc tctctgctac aaaccgaatg cggggttaag   2100
gaattgcgct agaacattct gagagggtct gggagtacac gaggggggcga ggcgcgtacc   2160 cggggggcggg gaggctgacg aagggcggcg gcgacggcgg cgacaggagg aagaagagga   2220
cgggcgcgag gaagagggac ggtaggagga accggaggcg gtgctgcgcg caccacgccg   2280
ccgccggtga catggccggc ggcgactcac cgtcgccgga gccgccgggt gaggcgcctg   2340
gatctgatcg gccggtggcg gcgtgtgatg aggaggagaa agaaatcgaa tcccactagc   2400
acactgcgca caccggagcc gcaccagggc cttgtttagt tccaattttt ttttcaaaa    2460 tagaattagt agcacattcg tttgtatttg acaaatattg ttcaatcatg aactaactag   2520
gcttaaaaga ttcgtctcgt taattccgac taaactgtat aattagtttt tatttcgtt    2580 tatatttaat acttcatgta tgcgtctaaa gatttgatgt gacggagaat ctgaaaaatt   2640
ttacaaattt ttttaagta aacaaggccc gggcgtttcc tctcagcaga tgaaaaatgg    2700
gtcccaggcc acatgcgggt cccacacgtc atccacaaac agtgacacgt cgaaatggtg   2760
ttggcctgtt gggggcgtag agctggtagc ctatagccaa taggatagga aacaggtggg   2820
accatgcttg agctaccccc acatgtcagt ctcacgggta tgtatccagt tggagagggg   2880
ttagacgtta gtaaacggtg aacaacaagg gcttatccgc aaaacgacac ggacgtattt   2940
gccccgcttc ccgtttccac ctgcgccgag atctcggaag agacgacgca ccgcaggatc   3000
```

<210> SEQ ID NO 26
<211> LENGTH: 3000
<212> TYPE: DNA
<213> ORGANISM: Glycine max

<400> SEQUENCE: 26

```
tctgttaata atcaataatt tgataattat aatttttta tcatacaagt taataatgac     60
tacacatctt tatcaaaatt gaaagaagat tgaaatctcc ttaaatcaac ttaactgatt   120
gtacaagtta aattaggatg cataaattat aattacataa ttaaaattaa tttctcaata   180 tatttttgt ctgaatttca tttctcatag tatatgttca cttgaaaaat atgataaatg    240
```

```
aaactaaaat aaaataaaaa atataataaa taatgtgatt agaagaaag aaaaagacaa      300 aagaagaaga aaaagtaaat atatacattt ttacatattt aggtcaaatg acttttttt      360 taatttgatc ttttatttc taaaaaatt attttaatct tttatgtttt taaattgatt       420
cgaaatagtc cttctgttaa aagcaaattt aacaccatta ataatataaa gataacccgc     480
cacaaaaaca taatttcttt tctgaaatat ctccatacta taattaatac acatcaacaa     540
tttttaactc ctactataat atttacaaag tttgaaaaaa tacacaaaaa catgttctaa     600
cctccatgaa cctagaacat ccccaaccca taaccaaaaa caattgcaac aattcttaaa     660
attggtttag ggcttctaaa ttgcatatct ttacaagcaa aacccaaaaa caatctttga     720
ttttgattca aaaacttgag agaatttaca aatcttgtat tcaaaaccaa ataaaaagtt     780
gcacaacaat ctccctctag tgctccttcc ttcgttgtgt cactactact gctacaatga     840
ttatgagttt gaatgctatt atcatcattg ttgtcgtcgc attgttcact tctgttgtca     900
caaattattt taatgatgtt tccaacgacg aatgaaatcc atcatattag aaaaagtaa      960 acaaacgagc acaaatatca tagatctaaa attaatctac aaattaaaaa accaaacaca     1020
tatatggtat cagtgagtgt ttaaaaaaaa atactataag tgaaacccat tgtgactctg     1080
atggtttcga tgatgacaaa cataaactat tcaacgaaag tcacaaaata ctaatagtag     1140
ggactaattt gaatcatttt aaataaaaaa ataatcaaaa taaactttat aaaaaataaa     1200
agattaaatt gaaaaaaata agataaagaa tcaaatagat aatttaactt atgttttatt     1260
tcttttcaaa gttttcattc tgtttgatat agaaacttat tatgaatctt ttaaaagagt     1320
gaaactgaag accttgtggt tagaattata taaattttca agggcataat tttacattta     1380
caaggtttaa aactttcaaa atgaacgaaa ttattttatt tgaaatgaaa cattgtttca     1440
atctaaatat tttatcatcg atgttttaaa atgtagattc tattaaaaaa atatcatctc     1500
aatattatcc tagggtgtat tggattaaga tttcaaagga ttttaaaaga cttttttatg     1560 attaaaagt cttgtggtat tcaatcaaga cttttataaa atataaacaa atcttgtggt      1620
attcaattaa gacaataaag atttttttt cagggcaaca aaatctgttg gtattcaatt      1680
gagatttctt accactttta aaatgtcttt tggtattcaa aagtaaatag attttgatgg     1740
attcttttgt ggaatggatt ttgagagact ttttagttag aaatacacat aaaatactcc     1800
tccaacaatc tcacccaaac ccttgagact tttcataatc ttccaaagac ttttttcttct    1860 cctgccgaac aagacacaaa ccactaccag gtttattctc ttacaacttt tcaatcaatt     1920
ttacctactt tttaatgaca atcgatagtc aatattgttc atactatatg tatattacgc     1980
aaatcaaaag aaaagggtgc tgtatatgct tcaagatttc gtattcatat tgtttccaac     2040
gtccaggcaa tgaatatgca tcaaaagaat gacaattgat atgcatcaag atttcatatt     2100
gctttttttt agtactgtat atgcaaatca aaataaaaaa cttttttttt tttctgtttc     2160
ttcaacttgt tttttttaca acgtccatta ttattattat tattttcttg tgttattatt     2220
aaaatattaa ttattaatgt gttattatta ttttttttgac agcgtgttat tattattatt    2280
attgtgttaa taatttttta attgttattg tgttattatt attgttattt tgttaatagt     2340 ttttttttaaa tgatttatg atatgagt attattttta tggaaaatgc taacatgtgc       2400
ccttaagaca cttgttagtg tattatgaac ccattgttca aacacaagag caggaacgag     2460
aagatgctaa tatatggagg actaatatag gttcatatat gagaagaaat gctaataatt     2520
aggcgaacat gaagtgagaa tcactttgtt attattttt taggcaataa tgactttgtt     2580
attaaaaggt ttaaaatttc tatcgttttt attttcttta ttcaaacatt ataatttatt     2640
```

| | | | | |
|---|---|---|---|---|
| tatcatcttt | ttcattcact | tttgtaactt | ccgttatttt | tttgtttaaa atgtattaat | 2700 |
| ctttcaaaat | cttaaaaatc | cataaagtac | tttgaaatct | taaaaatctg tgttagaaat | 2760 |
| ccattaaaat | cttgggttaa | gaatcctgat | tctaaaaagt | cttttaaaaa aaatctttta | 2820 |
| aaatcccaca | aaatcaatac | aatctcacat | aatcttttaa | aatcttcaag attgttttg | 2880 |
| tcaaaatatt | ctctcaaaat | ctcaatccaa | tacacttcct | taaaaaatat atttatgtac | 2940 |
| gattaattat | taattactat | aacttataaa | aatcttctaa | ttaattaacc cgtcagcgcc | 3000 |

<210> SEQ ID NO 27
<211> LENGTH: 3000
<212> TYPE: DNA
<213> ORGANISM: Brassica napus

<400> SEQUENCE: 27

| | | | | |
|---|---|---|---|---|
| tgtttaaata | catgtggtca | ctttcactat | gtggattgtg | gaccctctcg tttattctaa | 60 |
| agatggcttt | gtggaatttt | tatagataca | aaaagtgggt | aacatggaaa tgtgcaacat | 120 |
| catattatca | tcaccatcta | atcatatgac | tgaaagtgaa | ttgagtatat ggcttttagg | 180 |
| attggccaaa | gtaagcatgt | aagattatga | gccaatctgc | aatgagtttt tttttttatct | 240 |
| tctatttctt | tattttgttc | ttctctctaa | ttttcttttc | actttaggca tgctattatt | 300 |
| tttgggaacg | tgagattctt | tatgcctact | tatgatcact | tgtagttgta gctgtaccat | 360 |
| gttttggttt | tcaattatga | actttgataa | aataacgttt | tccgaatcaa ctttgattat | 420 |
| gaactttgat | tctttgtaaa | aaaaaatcat | attaagaaaa | aattagtctg aaaatttgtt | 480 |
| agcttattcc | taaatcgtta | taagaaaaat | tggttccatc | ccaaataggt ttatatttgt | 540 |
| tttaatataa | cgatggcatt | tgagttctac | atggatgtca | cttgtctaag acaattttct | 600 |
| tatcttttt | tttgattaaa | tagagtatat | cccagaccta | tggaaatatc aaactaatct | 660 |
| tccaaaaaga | agtatagctc | acgagttaga | tcatttgcgg | gtatccaaat aaagttcata | 720 |
| ctctatagta | tagttccata | tcttcgtgac | cacacatatt | tagtgtcgtg ggattgcttt | 780 |
| aaaccgaatt | gcttaactaa | ccggaattcg | cctagatcac | tcatttgttt ttcttactc | 840 |
| cctccgtttt | atattgtaag | tagttttagc | aaaaaatgtt | tgtttcacaa tataagtagt | 900 |
| tttcatattt | caatgcacat | tttctctttta | ttgaatattg | tgtaaccaat caaataatgc | 960 |
| tagcttttt | ataataggtt | gaatttatta | attaaataat | attttttaca aaagcaacaa | 1020 |
| tttcttaata | ttagtgtttt | taactaaaac | tatttacaat | atgaaacaga gggagtatca | 1080 |
| tttaggtggt | acatatacac | acgtaaaatt | ctatttccat | caaactgaat taaaattgtt | 1140 |
| gacaaaattc | attgtcatct | attcttgtca | tttacaaatt | tgactctaca cctaatatgc | 1200 |
| gaacttgtcc | tttcttcttc | tttttcacaa | cggaaccaat | acgtgaactt cttttttaata | 1260 |
| acatttatt | tgttttctg | gcaattgatc | gagtgcatat | gatcgaggag tttcccatga | 1320 |
| atatcatata | tgtgtcactt | gatcaaatga | tgggctaatc | acatgcttta caatactcat | 1380 |
| gattgcaagc | cctgcaatct | cttggatcca | aatgattatt | ttcatttctt ttcatcatga | 1440 |
| ttgatcccac | atttaattat | ttacatgatg | atttcacgag | aactaaaaaa gaagcaattt | 1500 |
| atatcaattc | aatattatag | aaaatttgct | atagaaaaac | cattcgttat cgttttctta | 1560 |
| attttatttt | gtggcttttt | catatggcta | ttccaatgct | tttatgatta ttagcatgaa | 1620 |
| cttgagcatg | ttctttatcc | cccaaagaaa | gtaaactaca | gatacatcgt atgatattat | 1680 |
| tgtgtattat | taattattat | gtacgatcga | ttttacaaca | tatatagaag agctgatgag | 1740 |

```
tgttactgac gtaaatagta attaatacat atatcactta actatatata tgcataaagt    1800
caagtttggt tttgggttaa aaacgtacat caaaccaaac ataatagttc agtttatctt    1860
agtttaggtt tgattatggt ccagtagatc gtaatccaag gtcactattt ttgttgacaa    1920 tggtttttttt tctggttaaa ttttgatttt tttttttgttt ttaatttgca agtccccgca    1980
tacactaaaa gataaagctc gatatatttg aattaaacgg gaatataata gcatagattc    2040
aatcatggac gtattatcat tctctagtga cttttccac gctttcatta aaaaaagaac    2100
acttatctac atactgataa caactaacat agtataatta aggtcgttaa gagtttagaa    2160
aaaaaatgca aaagaaaga ataatagttg atgttcgtgt agattttttgg ttactttctt    2220 gaacgagcaa ggatcaaaat catcttcgga agaggagtat caacctcaca agtcacaaga    2280
ataataagct actctacgca gaatagcaaa ccgtcaaaaa aaatcaaaat atttatcttt    2340
ttggacaata gttgatttgc tataaatttc ctttacagta aaagttaag caatttctta    2400 cggacataat tatcacaacc tcatgtttac ttgtagcaga gtcaaatgaa ttcacgcgat    2460
cagcaataat cttatttta acaaacagaa atagtggaca tccatagatg atataaacct    2520
taatttttgt ttcaaattca ccacgaaacc cttacattcg aaataagtta taagctatca    2580
tatgttagtt cattaccaca ggtccacaac atctgtgctt catcagctgg tatcagaacc    2640
atattaagtc ttaaatatta atatatgaat catcatgtga ttattgttgt gcgtttatgt    2700
tgctagtcca aattccgatt tggtcgttta ctaacattcg caaagagc ccaaatattc    2760 ggcccattct actaacatga tgtcgttcca ttattagcga agccacatgc acgtcgtttt    2820
aatttcccat aaacgcttcg tctttctttt ttgtacattg gaaaaagcc aaacgtctgt    2880 taccttttct gccccttccaa tcaaattggt gtaaatcttt tggttttcctc ttttttcagaa    2940 atttatttttc cctaaagttt tgttttcttt gtaaaaacat tgcagagtgc ccccaaaccg    3000
```

```
<210> SEQ ID NO 28
<211> LENGTH: 23
<212> TYPE: DNA
<213> ORGANISM: Artificial Sequence
<220> FEATURE:
<223> OTHER INFORMATION: OsOTUB1 CRISPR target sequence

<400> SEQUENCE: 28
tcagctggaa agtgttctgc agg                                             23

<210> SEQ ID NO 29
<211> LENGTH: 20
<212> TYPE: DNA
<213> ORGANISM: Artificial Sequence
<220> FEATURE:
<223> OTHER INFORMATION: OsOTUB1 CRISPR protospacer sequence

<400> SEQUENCE: 29
tcagctggaa agtgttctgc                                                 20

<210> SEQ ID NO 30
<211> LENGTH: 92
<212> TYPE: DNA
<213> ORGANISM: Artificial Sequence
<220> FEATURE:
<223> OTHER INFORMATION: tracrRNA nucleotide sequence

<400> SEQUENCE: 30
gttttagagc tagaaatagc aagttaaaat aaggctagtc cgttatcaac ttgaaaaagt    60
ggcaccgagt cggtgctttt tttcaagagc tt                                   92
```

<210> SEQ ID NO 31
<211> LENGTH: 112
<212> TYPE: DNA
<213> ORGANISM: Artificial Sequence
<220> FEATURE:
<223> OTHER INFORMATION: Complete Os sgRNA nucleotide sequence

<400> SEQUENCE: 31

```
tcagctggaa agtgttctgc gttttagagc tagaaatagc aagttaaaat aaggctagtc      60
cgttatcaac ttgaaaaagt ggcaccgagt cggtgctttt tttcaagagc tt             112
```

<210> SEQ ID NO 32
<211> LENGTH: 76
<212> TYPE: RNA
<213> ORGANISM: Artificial Sequence
<220> FEATURE:
<223> OTHER INFORMATION: OTUB1 Os sgRNA

<400> SEQUENCE: 32

```
guuuuagagc uagaaauagc aaguuaaaau aaggcuaguc cguuaucaac uugaaaaagu      60
ggcaccgagu cggugc                                                      76
```

<210> SEQ ID NO 33
<211> LENGTH: 578
<212> TYPE: DNA
<213> ORGANISM: Artificial Sequence
<220> FEATURE:
<223> OTHER INFORMATION: complete OTUB1 CRISPR nucleic acid construct

<400> SEQUENCE: 33

```
tggaatcggc agcaaaggat ttttttcctgt agttttccca caaccatttt ttaccatccg     60
aatgatagga taggaaaaat atccaagtga acagtattcc tataaaattc ccgtaaaaag    120
cctgcaatcc gaatgagccc tgaagtctga actagccggt cacctgtaca ggctatcgag    180
atgccataca agagacggta gtaggaacta ggaagacgat ggttgattcg tcaggcgaaa    240
tcgtcgtcct gcagtcgcat ctatgggcct ggacggaata ggggaaaaag ttggccggat    300
aggagggaaa ggcccaggtg cttacgtgcg aggtaggcct gggctctcag cacttcgatt    360
cgttggcacc ggggtaggat gcaatagaga gcaacgttta gtaccacctc gcttagctag    420
agcaaactgg actgccttat atgcgcgggt gctggcttgg ctgccgtcag ctggaaagtg    480
ttctgcgttt tagagctaga aatagcaagt taaataagg ctagtccgtt atcaacttga     540
aaaagtggca ccgagtcggt gctttttttc aagagctt                            578
```

<210> SEQ ID NO 34
<211> LENGTH: 23
<212> TYPE: DNA
<213> ORGANISM: Artificial Sequence
<220> FEATURE:
<223> OTHER INFORMATION: OsOTUB1 CRISPR target sequence

<400> SEQUENCE: 34

```
gactactacc actcgtgctg cgg                                              23
```

<210> SEQ ID NO 35
<211> LENGTH: 20
<212> TYPE: DNA
<213> ORGANISM: Artificial Sequence
<220> FEATURE:
<223> OTHER INFORMATION: OsOTUB1 protospacer sequence -continued

```
<400> SEQUENCE: 35
gactactacc actcgtgctg                                                    20

<210> SEQ ID NO 36
<211> LENGTH: 112
<212> TYPE: DNA
<213> ORGANISM: Artificial Sequence
<220> FEATURE:
<223> OTHER INFORMATION: OsOTUB1 sgRNA nucleic acid sequence

<400> SEQUENCE: 36
gactactacc actcgtgctg gttttagagc tagaaatagc aagttaaaat aaggctagtc        60
cgttatcaac ttgaaaaagt ggcaccgagt cggtgctttt tttcaagagc tt              112

<210> SEQ ID NO 37
<211> LENGTH: 552
<212> TYPE: DNA
<213> ORGANISM: Artificial Sequence
<220> FEATURE:
<223> OTHER INFORMATION: OsOTUB1 U3-sgRNA casette monocot plant, nucleic
      acid construct

<400> SEQUENCE: 37
tggaatcggc agcaaaggac gcgttgacat tgtaggacta tattgctcta ataaggaag         60 gaatctttaa acatacgaac agatcactta aagttcttct gaagcaactt aaagttatca      120
ggcatgcatg gatcttggag gaatcagatg tgcagtcagg gaccatagca caagacaggc      180
gtcttctact ggtgctacca gcaaatgctg gaagccggga acactgggta cgttggaaac      240
cacgtgtgat gtgaaggagt aagataaact gtaggagaaa agcatttcgt agtgggccat      300
gaagcctttc aggacatgta ttgcagtatg ggccggccca ttacgcaatt ggacgacaac      360
aaagactagt attagtacca cctcggctat ccacatagat caaagctggt ttaaaagagt      420
tgtgcagatg atccgtggca gactactacc actcgtgctg gttttagagc tagaaatagc      480
aagttaaaat aaggctagtc cgttatcaac ttgaaaaagt ggcaccgagt cggtgctttt      540
tttcaagagc tt                                                          552

<210> SEQ ID NO 38
<211> LENGTH: 23
<212> TYPE: DNA
<213> ORGANISM: Artificial Sequence
<220> FEATURE:
<223> OTHER INFORMATION: OsOTUB1 CRISPR target sequence

<400> SEQUENCE: 38
ccaccatgat tcagccctg agg                                                23

<210> SEQ ID NO 39
<211> LENGTH: 20
<212> TYPE: DNA
<213> ORGANISM: Artificial Sequence
<220> FEATURE:
<223> OTHER INFORMATION: OsOTUB1 protospacer sequence

<400> SEQUENCE: 39
ccaccatgat ttcagccctg                                                   20

<210> SEQ ID NO 40
<211> LENGTH: 111
<212> TYPE: DNA
<213> ORGANISM: Artificial Sequence
<220> FEATURE:
```

<223> OTHER INFORMATION: OsOTUB1 sgRNA nucleic acid sequence

<400> SEQUENCE: 40

| ccaccatgat ttcagccctg gttttagagc tagaaatagc aagttaaaat aaggctagtc | 60 |
| cgttatcaac ttgaaaaagt ggcaccgagt cggtgctttt tttcaagagc t | 111 |

<210> SEQ ID NO 41
<211> LENGTH: 463
<212> TYPE: DNA
<213> ORGANISM: Artificial Sequence
<220> FEATURE:
<223> OTHER INFORMATION: OsOTUB1 U6b-sgRNA cassette monocot plant, nucleic acid construct

<400> SEQUENCE: 41

| tggaatcggc agcaaaggat gcaagaacga actaagccgg acaaaaaaaa aaggagcaca | 60 |
| tatacaaacc ggttttattc atgaatggtc acgatggatg atggggctca gacttgagct | 120 |
| acgaggccgc aggcgagaga agcctagtgt gctctctgct tgtttgggcc gtaacggagg | 180 |
| atacggccga cgagcgtgta ctaccgcgcg ggatgccgct gggcgctgcg ggggccgttg | 240 |
| gatggggatc ggtgggtcgc gggagcgttg aggggagaca ggtttagtac cacctcgcct | 300 |
| accgaacaat gaagaaccca ccttataacc ccgcgcgctg ccgcttgtgt tgccaccatg | 360 |
| atttcagccc tggttttaga gctagaaata gcaagtaaaa ataaggctag tccgttatca | 420 |
| acttgaaaaa gtggcaccga gtcggtgctt ttttcaaga gct | 463 |

<210> SEQ ID NO 42
<211> LENGTH: 23
<212> TYPE: DNA
<213> ORGANISM: Artificial Sequence
<220> FEATURE:
<223> OTHER INFORMATION: target sequence

<400> SEQUENCE: 42

| agcggcggtg ggggaggagg tgg | 23 |

<210> SEQ ID NO 43
<211> LENGTH: 20
<212> TYPE: DNA
<213> ORGANISM: Artificial Sequence
<220> FEATURE:
<223> OTHER INFORMATION: protospacer sequence

<400> SEQUENCE: 43

| agcggcggtg ggggaggagg | 20 |

<210> SEQ ID NO 44
<211> LENGTH: 578
<212> TYPE: DNA
<213> ORGANISM: Artificial Sequence
<220> FEATURE:
<223> OTHER INFORMATION: full sgRNA sequence

<400> SEQUENCE: 44

| tggaatcggc agcaaaggat tttttcctgt agtttcccca caaccatttt ttaccatccg | 60 |
| aatgatagga taggaaaaat atccaagtga acagtattcc tataaaattc ccgtaaaaag | 120 |
| cctgcaatcc gaatgagccc tgaagtctga actagccggt cacctgtaca ggctatcgag | 180 |
| atgccataca agagacggta gtaggaacta ggaagacgat ggttgattcg tcaggcgaaa | 240 |
| tcgtcgtcct gcagtcgcat ctatgggcct ggacggaata ggggaaaaag ttggccggat | 300 |

| | |
|---|---|
| aggagggaaa ggcccaggtg cttacgtgcg aggtaggcct gggctctcag cacttcgatt | 360 |
| cgttggcacc ggggtaggat gcaatagaga gcaacgttta gtaccacctc gcttagctag | 420 |
| agcaaactgg actgccttat atgcgcgggt gctggcttgg ctgccgagcg gcggtgggg | 480 |
| aggagggttt tagagctaga aatagcaagt taaaataagg ctagtccgtt atcaacttga | 540 |
| aaaagtggca ccgagtcggt gcttttttc aagagctt | 578 |

<210> SEQ ID NO 45
<211> LENGTH: 23
<212> TYPE: DNA
<213> ORGANISM: Artificial Sequence
<220> FEATURE:
<223> OTHER INFORMATION: target sequence

<400> SEQUENCE: 45
gggaggagga gggggggggg agg                                         23

<210> SEQ ID NO 46
<211> LENGTH: 20
<212> TYPE: DNA
<213> ORGANISM: Artificial Sequence
<220> FEATURE:
<223> OTHER INFORMATION: protospacer sequence

<400> SEQUENCE: 46
gggaggagga gggggggggg                                             20

<210> SEQ ID NO 47
<211> LENGTH: 578
<212> TYPE: DNA
<213> ORGANISM: Artificial Sequence
<220> FEATURE:
<223> OTHER INFORMATION: full sgRNA sequence

<400> SEQUENCE: 47

| | |
|---|---|
| tggaatcggc agcaaaggat ttttcctgt agttttccca caaccatttt ttaccatccg | 60 |
| aatgatagga taggaaaaat atccaagtga acagtattcc tataaaattc ccgtaaaaag | 120 |
| cctgcaatcc gaatgagccc tgaagtctga actagccggt cacctgtaca ggctatcgag | 180 |
| atgccataca agagacggta gtaggaacta ggaagacgat ggttgattcg tcaggcgaaa | 240 |
| tcgtcgtcct gcagtcgcat ctatgggcct ggacggaata ggggaaaaag ttggccggat | 300 |
| aggagggaaa ggcccaggtg cttacgtgcg aggtaggcct gggctctcag cacttcgatt | 360 |
| cgttggcacc ggggtaggat gcaatagaga gcaacgttta gtaccacctc gcttagctag | 420 |
| agcaaactgg actgccttat atgcgcgggt gctggcttgg ctgccgggga ggaggaggg | 480 |
| ggggggttt tagagctaga aatagcaagt taaaataagg ctagtccgtt atcaacttga | 540 |
| aaaagtggca ccgagtcggt gcttttttc aagagctt | 578 |

<210> SEQ ID NO 48
<211> LENGTH: 23
<212> TYPE: DNA
<213> ORGANISM: Artificial Sequence
<220> FEATURE:
<223> OTHER INFORMATION: target sequence

<400> SEQUENCE: 48 gggggggagga ggagggggggg ggg                                       23

<210> SEQ ID NO 49
<211> LENGTH: 20

```
<212> TYPE: DNA
<213> ORGANISM: Artificial Sequence
<220> FEATURE:
<223> OTHER INFORMATION: protospacer sequence

<400> SEQUENCE: 49 gggggggagga ggagggggggg                                                  20

<210> SEQ ID NO 50
<211> LENGTH: 578
<212> TYPE: DNA
<213> ORGANISM: Artificial Sequence
<220> FEATURE:
<223> OTHER INFORMATION: full sgRNA sequence

<400> SEQUENCE: 50
tggaatcggc agcaaaggat tttttcctgt agttttccca caaccatttt ttaccatccg        60
aatgatagga taggaaaaat atccaagtga acagtattcc tataaaattc ccgtaaaaag      120
cctgcaatcc gaatgagccc tgaagtctga actagccggt cacctgtaca ggctatcgag      180
atgccataca agagacggta gtaggaacta ggaagacgat ggttgattcg tcaggcgaaa      240
tcgtcgtcct gcagtcgcat ctatgggcct ggacggaata ggggaaaaag ttggccggat      300
aggagggaaa ggcccaggtg cttacgtgcg aggtaggcct gggctctcag cacttcgatt      360
cgttggcacc ggggtaggat gcaatagaga gcaacgttta gtaccacctc gcttagctag      420
agcaaactgg actgccttat atgcgcgggt gctggcttgg ctgccggggg ggaggaggag      480
gggggggttt tagagctaga aatagcaagt taaaataagg ctagtccgtt atcaacttga      540
aaaagtggca ccgagtcggt gcttttttc aagagctt                               578

<210> SEQ ID NO 51
<211> LENGTH: 23
<212> TYPE: DNA
<213> ORGANISM: Artificial Sequence
<220> FEATURE:
<223> OTHER INFORMATION: target sequence

<400> SEQUENCE: 51 tcgaggggggg aggaggaggg ggg                                               23

<210> SEQ ID NO 52
<211> LENGTH: 20
<212> TYPE: DNA
<213> ORGANISM: Artificial Sequence
<220> FEATURE:
<223> OTHER INFORMATION: protospacer sequence

<400> SEQUENCE: 52
tcgagggggg aggaggaggg                                                    20

<210> SEQ ID NO 53
<211> LENGTH: 578
<212> TYPE: DNA
<213> ORGANISM: Artificial Sequence
<220> FEATURE:
<223> OTHER INFORMATION: full sgRNA sequence

<400> SEQUENCE: 53
tggaatcggc agcaaaggat tttttcctgt agttttccca caaccatttt ttaccatccg        60
aatgatagga taggaaaaat atccaagtga acagtattcc tataaaattc ccgtaaaaag      120
cctgcaatcc gaatgagccc tgaagtctga actagccggt cacctgtaca ggctatcgag      180
```

| atgccataca agagacggta gtaggaacta ggaagacgat ggttgattcg tcaggcgaaa | 240 |
| tcgtcgtcct gcagtcgcat ctatgggcct ggacggaata ggggaaaaag ttggccggat | 300 |
| aggagggaaa ggcccaggtg cttacgtgcg aggtaggcct gggctctcag cacttcgatt | 360 |
| cgttggcacc ggggtaggat gcaatagaga gcaacgttta gtaccacctc gcttagctag | 420 |
| agcaaactgg actgccttat atgcgcgggt gctggcttgg ctgccgtcga ggggggagga | 480 |
| ggaggggttt tagagctaga aatagcaagt taaataagg ctagtccgtt atcaacttga | 540 |
| aaaagtggca ccgagtcggt gcttttttc aagagctt | 578 |

```
<210> SEQ ID NO 54
<211> LENGTH: 23
<212> TYPE: DNA
<213> ORGANISM: Artificial Sequence
<220> FEATURE:
<223> OTHER INFORMATION: target sequence

<400> SEQUENCE: 54
```

| gtcgtcgagg ggggaggagg agg | 23 |

```
<210> SEQ ID NO 55
<211> LENGTH: 20
<212> TYPE: DNA
<213> ORGANISM: Artificial Sequence
<220> FEATURE:
<223> OTHER INFORMATION: protospacer sequence

<400> SEQUENCE: 55
```

| gtcgtcgagg ggggaggagg | 20 |

```
<210> SEQ ID NO 56
<211> LENGTH: 578
<212> TYPE: DNA
<213> ORGANISM: Artificial Sequence
<220> FEATURE:
<223> OTHER INFORMATION: full gsRNA sequence

<400> SEQUENCE: 56
```

| tggaatcggc agcaaaggat ttttcctgt agttttccca caaccatttt ttaccatccg | 60 |
| aatgatagga taggaaaaat atccaagtga acagtattcc tataaaattc ccgtaaaaag | 120 |
| cctgcaatcc gaatgagccc tgaagtctga actagccggt cacctgtaca ggctatcgag | 180 |
| atgccataca agagacggta gtaggaacta ggaagacgat ggttgattcg tcaggcgaaa | 240 |
| tcgtcgtcct gcagtcgcat ctatgggcct ggacggaata ggggaaaaag ttggccggat | 300 |
| aggagggaaa ggcccaggtg cttacgtgcg aggtaggcct gggctctcag cacttcgatt | 360 |
| cgttggcacc ggggtaggat gcaatagaga gcaacgttta gtaccacctc gcttagctag | 420 |
| agcaaactgg actgccttat atgcgcgggt gctggcttgg ctgccggtcg tcgagggggg | 480 |
| aggagggttt tagagctaga aatagcaagt taaataagg ctagtccgtt atcaacttga | 540 |
| aaaagtggca ccgagtcggt gcttttttc aagagctt | 578 |

```
<210> SEQ ID NO 57
<211> LENGTH: 23
<212> TYPE: DNA
<213> ORGANISM: Artificial Sequence
<220> FEATURE:
<223> OTHER INFORMATION: target sequence

<400> SEQUENCE: 57
```

| ggcagccgcg gccccgagc cgg | 23 |

<210> SEQ ID NO 58
<211> LENGTH: 20
<212> TYPE: DNA
<213> ORGANISM: Artificial Sequence
<220> FEATURE:
<223> OTHER INFORMATION: protospacer sequence

<400> SEQUENCE: 58
ggcagccgcg gcccccgagc                                               20

<210> SEQ ID NO 59
<211> LENGTH: 578
<212> TYPE: DNA
<213> ORGANISM: Artificial Sequence
<220> FEATURE:
<223> OTHER INFORMATION: full sgRNA sequence

<400> SEQUENCE: 59
tggaatcggc agcaaaggat ttttcctgt agttttccca caaccatttt ttaccatccg    60
aatgatagga taggaaaaat atccaagtga acagtattcc tataaaattc ccgtaaaaag  120
cctgcaatcc gaatgagccc tgaagtctga actagccggt cacctgtaca ggctatcgag  180
atgccataca agagacggta gtaggaacta ggaagacgat ggttgattcg tcaggcgaaa  240
tcgtcgtcct gcagtcgcat ctatgggcct ggacggaata ggggaaaaag ttggccggat  300
aggagggaaa ggcccaggtg cttacgtgcg aggtaggcct gggctctcag cacttcgatt  360
cgttggcacc ggggtaggat gcaatagaga gcaacgttta gtaccacctc gcttagctag  420
agcaaactgg actgccttat atgcgcgggt gctggcttgg ctgccgggca gccgcggccc  480
ccgagcgttt tagagctaga aatagcaagt taaataagg ctagtccgtt atcaacttga  540
aaaagtggca ccgagtcggt gcttttttc aagagctt                           578

<210> SEQ ID NO 60
<211> LENGTH: 23
<212> TYPE: DNA
<213> ORGANISM: Artificial Sequence
<220> FEATURE:
<223> OTHER INFORMATION: target sequence

<400> SEQUENCE: 60
tcccggagga ggcggtgatg ggg                                           23

<210> SEQ ID NO 61
<211> LENGTH: 20
<212> TYPE: DNA
<213> ORGANISM: Artificial Sequence
<220> FEATURE:
<223> OTHER INFORMATION: protospacer sequence

<400> SEQUENCE: 61
tcccggagga ggcggtgatg                                               20

<210> SEQ ID NO 62
<211> LENGTH: 578
<212> TYPE: DNA
<213> ORGANISM: Artificial Sequence
<220> FEATURE:
<223> OTHER INFORMATION: full sgRNA sequence

<400> SEQUENCE: 62
tggaatcggc agcaaaggat ttttcctgt agttttccca caaccatttt ttaccatccg    60

```
aatgatagga taggaaaaat atccaagtga acagtattcc tataaaattc ccgtaaaaag    120
cctgcaatcc gaatgagccc tgaagtctga actagccggt cacctgtaca ggctatcgag    180
atgccataca agagacggta gtaggaacta ggaagacgat ggttgattcg tcaggcgaaa    240
tcgtcgtcct gcagtcgcat ctatgggcct ggacggaata ggggaaaaag ttggccggat    300
aggagggaaa ggcccaggtg cttacgtgcg aggtaggcct gggctctcag cacttcgatt    360
cgttggcacc ggggtaggat gcaatagaga gcaacgttta gtaccacctc gcttagctag    420
agcaaactgg actgccttat atgcgcgggt gctggcttgg ctgccgtccc ggaggaggcg    480
gtgatggttt tagagctaga aatagcaagt taaaataagg ctagtccgtt atcaacttga    540
aaaagtggca ccgagtcggt gcttttttc aagagctt                            578
```

<210> SEQ ID NO 63
<211> LENGTH: 23
<212> TYPE: DNA
<213> ORGANISM: Artificial Sequence
<220> FEATURE:
<223> OTHER INFORMATION: target sequence
<400> SEQUENCE: 63

```
cgcccggaag cgcaaggcgg cgg                                            23
```

<210> SEQ ID NO 64
<211> LENGTH: 20
<212> TYPE: DNA
<213> ORGANISM: Artificial Sequence
<220> FEATURE:
<223> OTHER INFORMATION: protospacer sequence
<400> SEQUENCE: 64

```
cgcccggaag cgcaaggcgg                                                20
```

<210> SEQ ID NO 65
<211> LENGTH: 578
<212> TYPE: DNA
<213> ORGANISM: Artificial Sequence
<220> FEATURE:
<223> OTHER INFORMATION: full sgRNA sequence
<400> SEQUENCE: 65

```
tggaatcggc agcaaaggat tttttcctgt agttttccca caaccatttt ttaccatccg    60
aatgatagga taggaaaaat atccaagtga acagtattcc tataaaattc ccgtaaaaag    120
cctgcaatcc gaatgagccc tgaagtctga actagccggt cacctgtaca ggctatcgag    180
atgccataca agagacggta gtaggaacta ggaagacgat ggttgattcg tcaggcgaaa    240
tcgtcgtcct gcagtcgcat ctatgggcct ggacggaata ggggaaaaag ttggccggat    300
aggagggaaa ggcccaggtg cttacgtgcg aggtaggcct gggctctcag cacttcgatt    360
cgttggcacc ggggtaggat gcaatagaga gcaacgttta gtaccacctc gcttagctag    420
agcaaactgg actgccttat atgcgcgggt gctggcttgg ctgccgcgcc cggaagcgca    480
aggcgggttt tagagctaga aatagcaagt taaaataagg ctagtccgtt atcaacttga    540
aaaagtggca ccgagtcggt gcttttttc aagagctt                            578
```

<210> SEQ ID NO 66
<211> LENGTH: 23
<212> TYPE: DNA
<213> ORGANISM: Artificial Sequence
<220> FEATURE:
<223> OTHER INFORMATION: target sequence

<400> SEQUENCE: 66
gaagagaaga acacgcaccg cgg                                              23

<210> SEQ ID NO 67
<211> LENGTH: 20
<212> TYPE: DNA
<213> ORGANISM: Artificial Sequence
<220> FEATURE:
<223> OTHER INFORMATION: protospacer sequence

<400> SEQUENCE: 67
gaagagaaga acacgcaccg                                                  20

<210> SEQ ID NO 68
<211> LENGTH: 578
<212> TYPE: DNA
<213> ORGANISM: Artificial Sequence
<220> FEATURE:
<223> OTHER INFORMATION: full sgRNA sequence

<400> SEQUENCE: 68
tggaatcggc agcaaaggat tttttcctgt agttttccca caaccatttt ttaccatccg      60
aatgatagga taggaaaaat atccaagtga acagtattcc tataaaattc ccgtaaaaag     120
cctgcaatcc gaatgagccc tgaagtctga actagccggt cacctgtaca ggctatcgag    180
atgccataca agagacggta gtaggaacta ggaagacgat ggttgattcg tcaggcgaaa    240
tcgtcgtcct gcagtcgcat ctatgggcct ggacggaata ggggaaaaag ttggccggat    300
aggagggaaa ggcccaggtg cttacgtgcg aggtaggcct gggctctcag cacttcgatt    360
cgttggcacc ggggtaggat gcaatagaga gcaacgttta gtaccacctc gcttagctag    420
agcaaactgg actgccttat atgcgcgggt gctggcttgg ctgccggaag agaagaacac    480
gcaccggttt tagagctaga aatagcaagt taaaataagg ctagtccgtt atcaacttga    540
aaaagtggca ccgagtcggt gctttttttc aagagctt                            578

<210> SEQ ID NO 69
<211> LENGTH: 23
<212> TYPE: DNA
<213> ORGANISM: Artificial Sequence
<220> FEATURE:
<223> OTHER INFORMATION: target sequence

<400> SEQUENCE: 69
cccttacggc ctccactctg agg                                              23

<210> SEQ ID NO 70
<211> LENGTH: 20
<212> TYPE: DNA
<213> ORGANISM: Artificial Sequence
<220> FEATURE:
<223> OTHER INFORMATION: protospacer sequence

<400> SEQUENCE: 70
cccttacggc ctccactctg                                                  20

<210> SEQ ID NO 71
<211> LENGTH: 578
<212> TYPE: DNA
<213> ORGANISM: Artificial Sequence
<220> FEATURE:
<223> OTHER INFORMATION: full sgRNA sequence

<400> SEQUENCE: 71

```
tggaatcggc agcaaaggat tttttcctgt agttttccca caaccatttt ttaccatccg    60
aatgatagga taggaaaaat atccaagtga acagtattcc tataaaattc ccgtaaaaag   120
cctgcaatcc gaatgagccc tgaagtctga actagccggt cacctgtaca ggctatcgag   180
atgccataca agagacggta gtaggaacta ggaagacgat ggttgattcg tcaggcgaaa   240
tcgtcgtcct gcagtcgcat ctatgggcct ggacggaata ggggaaaaag ttggccggat   300
aggagggaaa ggcccaggtg cttacgtgcg aggtaggcct gggctctcag cacttcgatt   360
cgttggcacc ggggtaggat gcaatagaga gcaacgttta gtaccacctc gcttagctag   420
agcaaactgg actgccttat atgcgcgggt gctggcttgg ctgccgccct tacggcctcc   480
actctggttt tagagctaga aatagcaagt taaataagg ctagtccgtt atcaacttga   540
aaaagtggca ccgagtcggt gcttttttc aagagctt                           578
```

<210> SEQ ID NO 72
<211> LENGTH: 23
<212> TYPE: DNA
<213> ORGANISM: Artificial Sequence
<220> FEATURE:
<223> OTHER INFORMATION: target sequence

<400> SEQUENCE: 72

```
cactttctcc ttatgacacg tgg                                           23
```

<210> SEQ ID NO 73
<211> LENGTH: 20
<212> TYPE: DNA
<213> ORGANISM: Artificial Sequence
<220> FEATURE:
<223> OTHER INFORMATION: protospacer sequence

<400> SEQUENCE: 73

```
cactttctcc ttatgacacg                                               20
```

<210> SEQ ID NO 74
<211> LENGTH: 578
<212> TYPE: DNA
<213> ORGANISM: Artificial Sequence
<220> FEATURE:
<223> OTHER INFORMATION: full sgRNA sequence

<400> SEQUENCE: 74

```
tggaatcggc agcaaaggat tttttcctgt agttttccca caaccatttt ttaccatccg    60
aatgatagga taggaaaaat atccaagtga acagtattcc tataaaattc ccgtaaaaag   120
cctgcaatcc gaatgagccc tgaagtctga actagccggt cacctgtaca ggctatcgag   180
atgccataca agagacggta gtaggaacta ggaagacgat ggttgattcg tcaggcgaaa   240
tcgtcgtcct gcagtcgcat ctatgggcct ggacggaata ggggaaaaag ttggccggat   300
aggagggaaa ggcccaggtg cttacgtgcg aggtaggcct gggctctcag cacttcgatt   360
cgttggcacc ggggtaggat gcaatagaga gcaacgttta gtaccacctc gcttagctag   420
agcaaactgg actgccttat atgcgcgggt gctggcttgg ctgccgcact ttctccttat   480
gacacggttt tagagctaga aatagcaagt taaataagg ctagtccgtt atcaacttga   540
aaaagtggca ccgagtcggt gcttttttc aagagctt                           578
```

<210> SEQ ID NO 75
<211> LENGTH: 23

```
<212> TYPE: DNA
<213> ORGANISM: Artificial Sequence
<220> FEATURE:
<223> OTHER INFORMATION: target sequence

<400> SEQUENCE: 75
tatataagct cgtcagaatg tgg                                              23

<210> SEQ ID NO 76
<211> LENGTH: 20
<212> TYPE: DNA
<213> ORGANISM: Artificial Sequence
<220> FEATURE:
<223> OTHER INFORMATION: protospacer sequence

<400> SEQUENCE: 76
tatataagct cgtcagaatg                                                  20

<210> SEQ ID NO 77
<211> LENGTH: 578
<212> TYPE: DNA
<213> ORGANISM: Artificial Sequence
<220> FEATURE:
<223> OTHER INFORMATION: full sgRNA sequence

<400> SEQUENCE: 77
tggaatcggc agcaaaggat ttttccctgt agttttccca caaccatttt ttaccatccg      60
aatgatagga taggaaaaat atccaagtga acagtattcc tataaaattc ccgtaaaaag     120
cctgcaatcc gaatgagccc tgaagtctga actagccggt cacctgtaca ggctatcgag     180
atgccataca agagacggta gtaggaacta ggaagacgat ggttgattcg tcaggcgaaa     240
tcgtcgtcct gcagtcgcat ctatgggcct ggacggaata ggggaaaaag ttggccggat     300
aggagggaaa ggcccaggtg cttacgtgcg aggtaggcct gggctctcag cacttcgatt     360
cgttggcacc ggggtaggat gcaatagaga gcaacgttta gtaccacctc gcttagctag     420
agcaaactgg actgccttat atgcgcgggt gctggcttgg ctgccgtata taagctcgtc     480
agaatggttt tagagctaga aatagcaagt taaaataagg ctagtccgtt atcaacttga     540
aaaagtggca ccgagtcggt gcttttttc aagagctt                             578

<210> SEQ ID NO 78
<211> LENGTH: 23
<212> TYPE: DNA
<213> ORGANISM: Artificial Sequence
<220> FEATURE:
<223> OTHER INFORMATION: target sequence

<400> SEQUENCE: 78
cgagaagcac tggatctgat cgg                                              23

<210> SEQ ID NO 79
<211> LENGTH: 20
<212> TYPE: DNA
<213> ORGANISM: Artificial Sequence
<220> FEATURE:
<223> OTHER INFORMATION: protospacer sequence

<400> SEQUENCE: 79
cgagaagcac tggatctgat                                                  20

<210> SEQ ID NO 80
<211> LENGTH: 578
<212> TYPE: DNA
```

<213> ORGANISM: Artificial Sequence
<220> FEATURE:
<223> OTHER INFORMATION: full sgRNA sequence

<400> SEQUENCE: 80

```
tggaatcggc agcaaaggat tttttcctgt agttttccca caaccatttt ttaccatccg      60
aatgatagga taggaaaaat atccaagtga acagtattcc tataaaattc ccgtaaaaag     120
cctgcaatcc gaatgagccc tgaagtctga actagccggt cacctgtaca ggctatcgag     180
atgccataca agagacggta gtaggaacta ggaagacgat ggttgattcg tcaggcgaaa     240
tcgtcgtcct gcagtcgcat ctatgggcct ggacggaata ggggaaaaag ttggccggat     300
aggagggaaa ggcccaggtg cttacgtgcg aggtaggcct gggctctcag cacttcgatt     360
cgttggcacc ggggtaggat gcaatagaga gcaacgttta gtaccacctc gcttagctag     420
agcaaactgg actgccttat atgcgcgggt gctggcttgg ctgccgcgag aagcactgga     480
tctgatgttt tagagctaga aatagcaagt taaataagg ctagtccgtt atcaacttga      540
aaaagtggca ccgagtcggt gcttttttc aagagctt                              578
```

<210> SEQ ID NO 81
<211> LENGTH: 23
<212> TYPE: DNA
<213> ORGANISM: Artificial Sequence
<220> FEATURE:
<223> OTHER INFORMATION: target sequence

<400> SEQUENCE: 81

```
gagaggagga agtagagcgc ggg                                              23
```

<210> SEQ ID NO 82
<211> LENGTH: 20
<212> TYPE: DNA
<213> ORGANISM: Artificial Sequence
<220> FEATURE:
<223> OTHER INFORMATION: protospacer sequence

<400> SEQUENCE: 82

```
gagaggagga agtagagcgc                                                  20
```

<210> SEQ ID NO 83
<211> LENGTH: 578
<212> TYPE: DNA
<213> ORGANISM: Artificial Sequence
<220> FEATURE:
<223> OTHER INFORMATION: full sgRNA sequence

<400> SEQUENCE: 83

```
tggaatcggc agcaaaggat tttttcctgt agttttccca caaccatttt ttaccatccg      60
aatgatagga taggaaaaat atccaagtga acagtattcc tataaaattc ccgtaaaaag     120
cctgcaatcc gaatgagccc tgaagtctga actagccggt cacctgtaca ggctatcgag     180
atgccataca agagacggta gtaggaacta ggaagacgat ggttgattcg tcaggcgaaa     240
tcgtcgtcct gcagtcgcat ctatgggcct ggacggaata ggggaaaaag ttggccggat     300
aggagggaaa ggcccaggtg cttacgtgcg aggtaggcct gggctctcag cacttcgatt     360
cgttggcacc ggggtaggat gcaatagaga gcaacgttta gtaccacctc gcttagctag     420
agcaaactgg actgccttat atgcgcgggt gctggcttgg ctgccggaga ggaggaagta     480
gagcgcgttt tagagctaga aatagcaagt taaataagg ctagtccgtt atcaacttga      540
aaaagtggca ccgagtcggt gcttttttc aagagctt                              578
```

-continued

<210> SEQ ID NO 84
<211> LENGTH: 23
<212> TYPE: DNA
<213> ORGANISM: Artificial Sequence
<220> FEATURE:
<223> OTHER INFORMATION: target sequence

<400> SEQUENCE: 84
taaacccaaa ccacaaatca cgg                                            23

<210> SEQ ID NO 85
<211> LENGTH: 20
<212> TYPE: DNA
<213> ORGANISM: Artificial Sequence
<220> FEATURE:
<223> OTHER INFORMATION: protospacer sequence

<400> SEQUENCE: 85
taaacccaaa ccacaaatca                                                20

<210> SEQ ID NO 86
<211> LENGTH: 578
<212> TYPE: DNA
<213> ORGANISM: Artificial Sequence
<220> FEATURE:
<223> OTHER INFORMATION: full sgRNA sequence

<400> SEQUENCE: 86
tggaatcggc agcaaaggat ttttcctgt agttttccca caaccatttt ttaccatccg     60
aatgatagga taggaaaaat atccaagtga acagtattcc tataaaattc ccgtaaaaag    120
cctgcaatcc gaatgagccc tgaagtctga actagccggt cacctgtaca ggctatcgag    180
atgccataca agagacggta gtaggaacta ggaagacgat ggttgattcg tcaggcgaaa    240
tcgtcgtcct gcagtcgcat ctatgggcct ggacggaata ggggaaaaag ttggccggat    300
aggagggaaa ggcccaggtg cttacgtgcg aggtaggcct gggctctcag cacttcgatt    360
cgttggcacc ggggtaggat gcaatagaga gcaacgttta gtaccacctc gcttagctag    420
agcaaactgg actgccttat atgcgcgggt gctggcttgg ctgccgtaaa cccaaaccac    480
aaatcagttt tagagctaga aatagcaagt taaataagg ctagtccgtt atcaacttga     540
aaaagtggca ccgagtcggt gcttttttc aagagctt                             578

<210> SEQ ID NO 87
<211> LENGTH: 23
<212> TYPE: DNA
<213> ORGANISM: Artificial Sequence
<220> FEATURE:
<223> OTHER INFORMATION: target sequence

<400> SEQUENCE: 87
atgtacccat tcctcctcga cgg                                            23

<210> SEQ ID NO 88
<211> LENGTH: 20
<212> TYPE: DNA
<213> ORGANISM: Artificial Sequence
<220> FEATURE:
<223> OTHER INFORMATION: protospacer sequence

<400> SEQUENCE: 88
atgtacccat tcctcctcga                                                20

<210> SEQ ID NO 89
<211> LENGTH: 579
<212> TYPE: DNA
<213> ORGANISM: Artificial Sequence
<220> FEATURE:
<223> OTHER INFORMATION: full sgRNA sequence

<400> SEQUENCE: 89

```
tggaatcggc agcaaaggat tttttcctgt agttttccca caaccatttt ttaccatccg    60
aatgatagga taggaaaaat atccaagtga acagtattcc tataaaattc ccgtaaaaag   120
cctgcaatcc gaatgagccc tgaagtctga actagccggt cacctgtaca ggctatcgag   180
atgccataca agagacggta gtaggaacta ggaagacgat ggttgattcg tcaggcgaaa   240
tcgtcgtcct gcagtcgcat ctatgggcct ggacggaata ggggaaaaag ttggccggat   300
aggagggaaa ggcccaggtg cttacgtgcg aggtaggcct gggctctcag cacttcgatt   360
cgttggcacc ggggtaggat gcaatagaga gcaacgttta gtaccacctc gcttagctag   420
agcaaactgg actgccttat atgcgcgggt gctggcttgg ctgccgtatg tacccattcc   480
tcctcgagtt ttagagctag aaatagcaag ttaaaataag gctagtccgt tatcaacttg   540
aaaaagtggc accgagtcgg tgcttttttt caagagctt                          579
```

<210> SEQ ID NO 90
<211> LENGTH: 23
<212> TYPE: DNA
<213> ORGANISM: Artificial Sequence
<220> FEATURE:
<223> OTHER INFORMATION: target sequence

<400> SEQUENCE: 90

```
aacgtacatc gcgtcgcagc tgg                                             23
```

<210> SEQ ID NO 91
<211> LENGTH: 20
<212> TYPE: DNA
<213> ORGANISM: Artificial Sequence
<220> FEATURE:
<223> OTHER INFORMATION: protospacer sequence

<400> SEQUENCE: 91

```
aacgtacatc gcgtcgcagc                                                 20
```

<210> SEQ ID NO 92
<211> LENGTH: 578
<212> TYPE: DNA
<213> ORGANISM: Artificial Sequence
<220> FEATURE:
<223> OTHER INFORMATION: full sgRNA sequence

<400> SEQUENCE: 92

```
tggaatcggc agcaaaggat tttttcctgt agttttccca caaccatttt ttaccatccg    60
aatgatagga taggaaaaat atccaagtga acagtattcc tataaaattc ccgtaaaaag   120
cctgcaatcc gaatgagccc tgaagtctga actagccggt cacctgtaca ggctatcgag   180
atgccataca agagacggta gtaggaacta ggaagacgat ggttgattcg tcaggcgaaa   240
tcgtcgtcct gcagtcgcat ctatgggcct ggacggaata ggggaaaaag ttggccggat   300
aggagggaaa ggcccaggtg cttacgtgcg aggtaggcct gggctctcag cacttcgatt   360
cgttggcacc ggggtaggat gcaatagaga gcaacgttta gtaccacctc gcttagctag   420
agcaaactgg actgccttat atgcgcgggt gctggcttgg ctgccgaacg tacatcgcgt   480
```
cgcagcgttt tagagctaga aatagcaagt taaaataagg ctagtccgtt atcaacttga      540
aaaagtggca ccgagtcggt gcttttttc aagagctt                              578

<210> SEQ ID NO 93
<211> LENGTH: 23
<212> TYPE: DNA
<213> ORGANISM: Artificial Sequence
<220> FEATURE:
<223> OTHER INFORMATION: target sequence

<400> SEQUENCE: 93
actatcttac tacttgtgca tgg                                              23

<210> SEQ ID NO 94
<211> LENGTH: 20
<212> TYPE: DNA
<213> ORGANISM: Artificial Sequence
<220> FEATURE:
<223> OTHER INFORMATION: protospacer

<400> SEQUENCE: 94
actatcttac tacttgtgca                                                  20

<210> SEQ ID NO 95
<211> LENGTH: 578
<212> TYPE: DNA
<213> ORGANISM: Artificial Sequence
<220> FEATURE:
<223> OTHER INFORMATION: full sgRNA sequence

<400> SEQUENCE: 95
tggaatcggc agcaaaggat tttttcctgt agttttccca caaccatttt ttaccatccg      60
aatgatagga taggaaaaat atccaagtga acagtattcc tataaaattc ccgtaaaaag     120
cctgcaatcc gaatgagccc tgaagtctga actagccggt cacctgtaca ggctatcgag    180
atgccataca agagacggta gtaggaacta ggaagacgat ggttgattcg tcaggcgaaa    240
tcgtcgtcct gcagtcgcat ctatgggcct ggacggaata ggggaaaaag ttggccggat    300
aggagggaaa ggcccaggtg cttacgtgcg aggtaggcct gggctctcag cacttcgatt    360
cgttggcacc ggggtaggat gcaatagaga gcaacgttta gtaccacctc gcttagctag    420
agcaaactgg actgccttat atgcgcgggt gctggcttgg ctgccgacta tcttactact    480
tgtgcagttt tagagctaga aatagcaagt taaaataagg ctagtccgtt atcaacttga    540
aaaagtggca ccgagtcggt gcttttttc aagagctt                              578

<210> SEQ ID NO 96
<211> LENGTH: 23
<212> TYPE: DNA
<213> ORGANISM: Artificial Sequence
<220> FEATURE:
<223> OTHER INFORMATION: target sequence

<400> SEQUENCE: 96
tcggaagaat aattacaacc agg                                              23

<210> SEQ ID NO 97
<211> LENGTH: 20
<212> TYPE: DNA
<213> ORGANISM: Artificial Sequence
<220> FEATURE:
<223> OTHER INFORMATION: protospacer sequence

<400> SEQUENCE: 97
tcggaagaat aattacaacc                                             20

<210> SEQ ID NO 98
<211> LENGTH: 578
<212> TYPE: DNA
<213> ORGANISM: Artificial Sequence
<220> FEATURE:
<223> OTHER INFORMATION: full sgRNA sequence

<400> SEQUENCE: 98
tggaatcggc agcaaaggat ttttcctgt agttttccca caaccatttt ttaccatccg   60
aatgatagga taggaaaaat atccaagtga acagtattcc tataaaattc ccgtaaaaag  120
cctgcaatcc gaatgagccc tgaagtctga actagccggt cacctgtaca ggctatcgag  180
atgccataca agagacggta gtaggaacta ggaagacgat ggttgattcg tcaggcgaaa  240
tcgtcgtcct gcagtcgcat ctatgggcct ggacggaata ggggaaaaag ttggccggat  300
aggagggaaa ggcccaggtg cttacgtgcg aggtaggcct gggctctcag cacttcgatt  360
cgttggcacc ggggtaggat gcaatagaga gcaacgttta gtaccacctc gcttagctag  420
agcaaactgg actgccttat atgcgcgggt gctggcttgg ctgccgtcgg aagaataatt  480
acaaccgttt tagagctaga aatagcaagt taaataagg ctagtccgtt atcaacttga  540
aaaagtggca ccgagtcggt gctttttttc aagagctt                         578

<210> SEQ ID NO 99
<211> LENGTH: 23
<212> TYPE: DNA
<213> ORGANISM: Artificial Sequence
<220> FEATURE:
<223> OTHER INFORMATION: target sequence

<400> SEQUENCE: 99
gtaggcagca acctcaaact tgg                                         23

<210> SEQ ID NO 100
<211> LENGTH: 20
<212> TYPE: DNA
<213> ORGANISM: Artificial Sequence
<220> FEATURE:
<223> OTHER INFORMATION: protospacer sequence

<400> SEQUENCE: 100
gtaggcagca acctcaaact                                             20

<210> SEQ ID NO 101
<211> LENGTH: 578
<212> TYPE: DNA
<213> ORGANISM: Artificial Sequence
<220> FEATURE:
<223> OTHER INFORMATION: full sgRNA sequence

<400> SEQUENCE: 101
tggaatcggc agcaaaggat ttttcctgt agttttccca caaccatttt ttaccatccg   60
aatgatagga taggaaaaat atccaagtga acagtattcc tataaaattc ccgtaaaaag  120
cctgcaatcc gaatgagccc tgaagtctga actagccggt cacctgtaca ggctatcgag  180
atgccataca agagacggta gtaggaacta ggaagacgat ggttgattcg tcaggcgaaa  240
tcgtcgtcct gcagtcgcat ctatgggcct ggacggaata ggggaaaaag ttggccggat  300
aggagggaaa ggcccaggtg cttacgtgcg aggtaggcct gggctctcag cacttcgatt  360

-continued

```
cgttggcacc ggggtaggat gcaatagaga gcaacgttta gtaccacctc gcttagctag      420
agcaaactgg actgccttat atgcgcgggt gctggcttgg ctgccggtag gcagcaacct      480
caaactgttt tagagctaga aatagcaagt taaataagg ctagtccgtt atcaacttga       540
aaaagtggca ccgagtcggt gctttttttc aagagctt                              578
```

<210> SEQ ID NO 102
<211> LENGTH: 23
<212> TYPE: DNA
<213> ORGANISM: Artificial Sequence
<220> FEATURE:
<223> OTHER INFORMATION: TuOUTB1 CRISPR target sequence

<400> SEQUENCE: 102

```
ttaaggcgaa cacgaggaga tgg                                               23
```

<210> SEQ ID NO 103
<211> LENGTH: 20
<212> TYPE: DNA
<213> ORGANISM: Artificial Sequence
<220> FEATURE:
<223> OTHER INFORMATION: protospacer sequence; TuOTUB1 (double target)

<400> SEQUENCE: 103

```
ttaaggcgaa cacgaggaga                                                   20
```

<210> SEQ ID NO 104
<211> LENGTH: 112
<212> TYPE: DNA
<213> ORGANISM: Artificial Sequence
<220> FEATURE:
<223> OTHER INFORMATION: TuOTUB1 sgRNA nucleic acid

<400> SEQUENCE: 104

```
ttaaggcgaa cacgaggaga gttttagagc tagaaatagc aagttaaaat aaggctagtc      60
cgttatcaac ttgaaaaagt ggcaccgagt cggtgctttt tttcaagagc tt             112
```

<210> SEQ ID NO 105
<211> LENGTH: 578
<212> TYPE: DNA
<213> ORGANISM: Artificial Sequence
<220> FEATURE:
<223> OTHER INFORMATION: TuOTUB1; U6a-sgRNA cassette monocot plant,
      nucleic acid construct

<400> SEQUENCE: 105

```
tggaatcggc agcaaaggat tttttcctgt agttttccca caaccatttt ttaccatccg      60
aatgatagga taggaaaaat atccaagtga acagtattcc tataaaattc ccgtaaaaag     120
cctgcaatcc gaatgagccc tgaagtctga actagccggt cacctgtaca ggctatcgag     180
atgccataca agagacggta gtaggaacta ggaagacgat ggttgattcg tcaggcgaaa     240
tcgtcgtcct gcagtcgcat ctatgggcct ggacggaata ggggaaaaag ttggccggat     300
aggagggaaa ggcccaggtg cttacgtgcg aggtaggcct gggctctcag cacttcgatt     360
cgttggcacc ggggtaggat gcaatagaga gcaacgttta gtaccacctc gcttagctag     420
agcaaactgg actgccttat atgcgcgggt gctggcttgg ctgccgttaa ggcgaacacg     480
aggagagttt tagagctaga aatagcaagt taaataagg ctagtccgtt atcaacttga      540
aaaagtggca ccgagtcggt gctttttttc aagagctt                             578
```

```
<210> SEQ ID NO 106
<211> LENGTH: 23
<212> TYPE: DNA
<213> ORGANISM: Artificial Sequence
<220> FEATURE:
<223> OTHER INFORMATION: TuOUTB1 CRISPR sequence

<400> SEQUENCE: 106
attgctctgt cagatgcgtt agg                                              23

<210> SEQ ID NO 107
<211> LENGTH: 20
<212> TYPE: DNA
<213> ORGANISM: Artificial Sequence
<220> FEATURE:
<223> OTHER INFORMATION: protospacer sequence; TuOTUB1 (double target)

<400> SEQUENCE: 107
attgctctgt cagatgcgtt                                                  20

<210> SEQ ID NO 108
<211> LENGTH: 112
<212> TYPE: DNA
<213> ORGANISM: Artificial Sequence
<220> FEATURE:
<223> OTHER INFORMATION: TuOTUB1 sgRNA nucleic acid

<400> SEQUENCE: 108
attgctctgt cagatgcgtt gttttagagc tagaaatagc aagttaaaat aaggctagtc      60
cgttatcaac ttgaaaaagt ggcaccgagt cggtgctttt tttcaagagc tt             112

<210> SEQ ID NO 109
<211> LENGTH: 552
<212> TYPE: DNA
<213> ORGANISM: Artificial Sequence
<220> FEATURE:
<223> OTHER INFORMATION: TuOUTB1; U3-sgRNA cassette monocot plant,
      nucleic acid construct

<400> SEQUENCE: 109
tggaatcggc agcaaaggac gcgttgacat tgtaggacta tattgctcta ataaggaag       60 gaatctttaa acatacgaac agatcactta agttcttct gaagcaactt aaagttatca     120
ggcatgcatg gatcttggag gaatcagatg tgcagtcagg gaccatagca caagacaggc    180
gtcttctact ggtgctacca gcaaatgctg gaagccggga acactgggta cgttggaaac    240
cacgtgtgat gtgaaggagt aagataaact gtaggagaaa agcatttcgt agtgggccat    300
gaagcctttc aggacatgta ttgcagtatg ggccggccca ttacgcaatt ggacgacaac    360
aaagactagt attagtacca cctcggctat ccacatagat caaagctggt ttaaaagagt    420
tgtgcagatg atccgtggca attgctctgt cagatgcgtt gttttagagc tagaaatagc    480
aagttaaaat aaggctagtc cgttatcaac ttgaaaaagt ggcaccgagt cggtgctttt    540
tttcaagagc tt                                                        552

<210> SEQ ID NO 110
<211> LENGTH: 23
<212> TYPE: DNA
<213> ORGANISM: Artificial Sequence
<220> FEATURE:
<223> OTHER INFORMATION: HvOTUB1 CRISPR target sequence

<400> SEQUENCE: 110
ttaagacgga cacgaggaga tgg                                              23
```

```
<210> SEQ ID NO 111
<211> LENGTH: 20
<212> TYPE: DNA
<213> ORGANISM: Artificial Sequence
<220> FEATURE:
<223> OTHER INFORMATION: Hv OTUB1 protospacer

<400> SEQUENCE: 111
ttaagacgga cacgaggaga                                              20

<210> SEQ ID NO 112
<211> LENGTH: 112
<212> TYPE: DNA
<213> ORGANISM: Artificial Sequence
<220> FEATURE:
<223> OTHER INFORMATION: Hv OTUB1 sgRNA nucleic acid

<400> SEQUENCE: 112
ttaagacgga cacgaggaga gttttagagc tagaaatagc aagttaaaat aaggctagtc    60
cgttatcaac ttgaaaaagt ggcaccgagt cggtgctttt tttcaagagc tt           112

<210> SEQ ID NO 113
<211> LENGTH: 578
<212> TYPE: DNA
<213> ORGANISM: Artificial Sequence
<220> FEATURE:
<223> OTHER INFORMATION: Hv OTUB1 U6a-sgRNA cassete monocot plant
      nucleic acid construct

<400> SEQUENCE: 113
tggaatcggc agcaaaggat tttttcctgt agttttccca caaccatttt ttaccatccg    60
aatgatagga taggaaaaat atccaagtga acagtattcc tataaaattc ccgtaaaaag   120
cctgcaatcc gaatgagccc tgaagtctga actagccggt cacctgtaca ggctatcgag   180
atgccataca agagacggta gtaggaacta ggaagacgat ggttgattcg tcaggcgaaa   240
tcgtcgtcct gcagtcgcat ctatgggcct ggacggaata ggggaaaaag ttggccggat   300
aggagggaaa ggcccaggtg cttacgtgcg aggtaggcct gggctctcag cacttcgatt   360
cgttggcacc ggggtaggat gcaatagaga gcaacgttta gtaccacctc gcttagctag   420
agcaaactgg actgccttat atgcgcgggt gctggcttgg ctgccgttaa gacggacacg   480
aggagagttt tagagctaga aatagcaagt taaataagg ctagtccgtt atcaacttga    540
aaaagtggca ccgagtcggt gcttttttc aagagctt                            578

<210> SEQ ID NO 114
<211> LENGTH: 23
<212> TYPE: DNA
<213> ORGANISM: Artificial Sequence
<220> FEATURE:
<223> OTHER INFORMATION: HvOTUB1 CRISPR target sequence

<400> SEQUENCE: 114
attgctctgt cagatgcgtt agg                                           23

<210> SEQ ID NO 115
<211> LENGTH: 20
<212> TYPE: DNA
<213> ORGANISM: Artificial Sequence
<220> FEATURE:
<223> OTHER INFORMATION: Hv OTUB1 protospacer

<400> SEQUENCE: 115
```

```
attgctctgt cagatgcgtt                                              20

<210> SEQ ID NO 116
<211> LENGTH: 112
<212> TYPE: DNA
<213> ORGANISM: Artificial Sequence
<220> FEATURE:
<223> OTHER INFORMATION: Hv OTUB1 sgRNA nucleic acid

<400> SEQUENCE: 116
attgctctgt cagatgcgtt gttttagagc tagaaatagc aagttaaaat aaggctagtc    60
cgttatcaac ttgaaaaagt ggcaccgagt cggtgctttt tttcaagagc tt          112

<210> SEQ ID NO 117
<211> LENGTH: 552
<212> TYPE: DNA
<213> ORGANISM: Artificial Sequence
<220> FEATURE:
<223> OTHER INFORMATION: Hv OTUB1 sgRNA nucleic acid U3-sgRNA cassette
      monocot plant, nucleic acid construct

<400> SEQUENCE: 117
tggaatcggc agcaaaggac gcgttgacat tgtaggacta tattgctcta ataaaggaag    60
gaatctttaa acatacgaac agatcactta aagttcttct gaagcaactt aaagttatca   120
ggcatgcatg gatcttggag gaatcagatg tgcagtcagg gaccatagca caagacaggc   180
gtcttctact ggtgctacca gcaaatgctg gaagccggga acactgggta cgttggaaac   240
cacgtgtgat gtgaaggagt aagataaact gtaggagaaa agcatttcgt agtgggccat   300
gaagcctttc aggacatgta ttgcagtatg ggccggccca ttacgcaatt ggacgacaac   360
aaagactagt attagtacca cctcggctat ccacatagat caaagctggt ttaaaagagt   420
tgtgcagatg atccgtggca attgctctgt cagatgcgtt gttttagagc tagaaatagc   480
aagttaaaat aaggctagtc cgttatcaac ttgaaaaagt ggcaccgagt cggtgctttt   540
tttcaagagc tt                                                      552

<210> SEQ ID NO 118
<211> LENGTH: 23
<212> TYPE: DNA
<213> ORGANISM: Artificial Sequence
<220> FEATURE:
<223> OTHER INFORMATION: ZmOTUB1 CRISPR target sequence

<400> SEQUENCE: 118
aagctttatg ttttcctacc tgg                                           23

<210> SEQ ID NO 119
<211> LENGTH: 20
<212> TYPE: DNA
<213> ORGANISM: Artificial Sequence
<220> FEATURE:
<223> OTHER INFORMATION: ZmOTUB1 protospacer sequence

<400> SEQUENCE: 119
aagctttatg ttttcctacc                                               20

<210> SEQ ID NO 120
<211> LENGTH: 112
<212> TYPE: DNA
<213> ORGANISM: Artificial Sequence
<220> FEATURE:
<223> OTHER INFORMATION: ZmOTUB1 sgRNA nucleic acid sequence
```

<400> SEQUENCE: 120

```
aagctttatg ttttcctacc gttttagagc tagaaatagc aagttaaaat aaggctagtc      60
cgttatcaac ttgaaaaagt ggcaccgagt cggtgctttt tttcaagagc tt             112
```

<210> SEQ ID NO 121
<211> LENGTH: 578
<212> TYPE: DNA
<213> ORGANISM: Artificial Sequence
<220> FEATURE:
<223> OTHER INFORMATION: ZmOTUB1 U6a-sgRNA cassette monocot plant, nucleic acid construct

<400> SEQUENCE: 121

```
tggaatcggc agcaaaggat ttttccctgt agttttccca caaccatttt ttaccatccg     60
aatgatagga taggaaaaat atccaagtga acagtattcc tataaaattc ccgtaaaaag    120
cctgcaatcc gaatgagccc tgaagtctga actagccggt cacctgtaca ggctatcgag    180
atgccataca agagacggta gtaggaacta ggaagacgat ggttgattcg tcaggcgaaa    240
tcgtcgtcct gcagtcgcat ctatgggcct ggacggaata ggggaaaaag ttggccggat    300
aggagggaaa ggcccaggtg cttacgtgcg aggtaggcct gggctctcag cacttcgatt    360
cgttggcacc ggggtaggat gcaatagaga gcaacgttta gtaccacctc gcttagctag    420
agcaaactgg actgccttat atgcgcgggt gctggcttgg ctgccgaagc tttatgtttt    480
cctaccgttt tagagctaga aatagcaagt taaataagg ctagtccgtt atcaacttga    540
aaaagtggca ccgagtcggt gcttttttc aagagctt                             578
```

<210> SEQ ID NO 122
<211> LENGTH: 23
<212> TYPE: DNA
<213> ORGANISM: Artificial Sequence
<220> FEATURE:
<223> OTHER INFORMATION: ZmOTUB1 CRISPR target sequence

<400> SEQUENCE: 122

```
attgccctat cagatgcact agg                                             23
```

<210> SEQ ID NO 123
<211> LENGTH: 20
<212> TYPE: DNA
<213> ORGANISM: Artificial Sequence
<220> FEATURE:
<223> OTHER INFORMATION: ZmOTUB1 protospacer sequence

<400> SEQUENCE: 123

```
attgccctat cagatgcact                                                 20
```

<210> SEQ ID NO 124
<211> LENGTH: 112
<212> TYPE: DNA
<213> ORGANISM: Artificial Sequence
<220> FEATURE:
<223> OTHER INFORMATION: ZmOTUB1 sgRNA nucleic acid sequence

<400> SEQUENCE: 124

```
attgccctat cagatgcact gttttagagc tagaaatagc aagttaaaat aaggctagtc     60
cgttatcaac ttgaaaaagt ggcaccgagt cggtgctttt tttcaagagc tt            112
```

<210> SEQ ID NO 125
<211> LENGTH: 552

```
<212> TYPE: DNA
<213> ORGANISM: Artificial Sequence
<220> FEATURE:
<223> OTHER INFORMATION: ZmOTUB1 U3-sgRNA cassette monocot plant,
      nucleic acid construct

<400> SEQUENCE: 125
tggaatcggc agcaaaggac gcgttgacat tgtaggacta tattgctcta ataaaggaag      60
gaatctttaa acatacgaac agatcactta aagttcttct gaagcaactt aaagttatca     120
ggcatgcatg gatcttggag gaatcagatg tgcagtcagg gaccatagca caagacaggc     180
gtcttctact ggtgctacca gcaaatgctg gaagccggga acactgggta cgttggaaac     240
cacgtgtgat gtgaaggagt aagataaact gtaggagaaa agcatttcgt agtgggccat     300
gaagcctttc aggacatgta ttgcagtatg ggccggccca ttcgcaatt ggacgacaac      360
aaagactagt attagtacca cctcggctat ccacatagat caaagctggt ttaaaagagt     420
tgtgcagatg atccgtggca attgccctat cagatgcact gttttagagc tagaaatagc     480
aagttaaaat aaggctagtc cgttatcaac ttgaaaaagt ggcaccgagt cggtgctttt     540
tttcaagagc tt                                                         552

<210> SEQ ID NO 126
<211> LENGTH: 23
<212> TYPE: DNA
<213> ORGANISM: Artificial Sequence
<220> FEATURE:
<223> OTHER INFORMATION: SbOTUB1 CRISPR target sequence

<400> SEQUENCE: 126
aagctttatg ttctcctact tgg                                              23

<210> SEQ ID NO 127
<211> LENGTH: 20
<212> TYPE: DNA
<213> ORGANISM: Artificial Sequence
<220> FEATURE:
<223> OTHER INFORMATION: SbOTUB1 protospacer sequence

<400> SEQUENCE: 127
aagctttatg ttctcctact                                                  20

<210> SEQ ID NO 128
<211> LENGTH: 112
<212> TYPE: DNA
<213> ORGANISM: Artificial Sequence
<220> FEATURE:
<223> OTHER INFORMATION: SbOTUB1 sgRNA nucleic acid sequence

<400> SEQUENCE: 128
aagctttatg ttctcctact gttttagagc tagaaatagc aagttaaaat aaggctagtc      60
cgttatcaac ttgaaaaagt ggcaccgagt cggtgctttt tttcaagagc tt             112

<210> SEQ ID NO 129
<211> LENGTH: 578
<212> TYPE: DNA
<213> ORGANISM: Artificial Sequence
<220> FEATURE:
<223> OTHER INFORMATION: SbOTUB1 U6a-sgRNA cassette monocot plant,
      nucleic acid construct

<400> SEQUENCE: 129
tggaatcggc agcaaaggat ttttcctgt agttttccca caaccatttt ttaccatccg       60
```

-continued

```
aatgatagga taggaaaaat atccaagtga acagtattcc tataaaattc ccgtaaaaag     120
cctgcaatcc gaatgagccc tgaagtctga actagccggt cacctgtaca ggctatcgag     180
atgccataca agagacggta gtaggaacta ggaagacgat ggttgattcg tcaggcgaaa     240
tcgtcgtcct gcagtcgcat ctatgggcct ggacggaata ggggaaaaag ttggccggat     300
aggagggaaa ggcccaggtg cttacgtgcg aggtaggcct gggctctcag cacttcgatt     360
cgttggcacc ggggtaggat gcaatagaga gcaacgttta gtaccacctc gcttagctag     420
agcaaactgg actgccttat atgcgcgggt gctggcttgg ctgccgaagc tttatgttct     480
cctactgttt tagagctaga aatagcaagt taaaataagg ctagtccgtt atcaacttga     540
aaaagtggca ccgagtcggt gcttttttc aagagctt                              578

<210> SEQ ID NO 130
<211> LENGTH: 23
<212> TYPE: DNA
<213> ORGANISM: Artificial Sequence
<220> FEATURE:
<223> OTHER INFORMATION: SbOTUB1 CRISPR target sequence

<400> SEQUENCE: 130
tgttcacata attgccctat cgg                                             23

<210> SEQ ID NO 131
<211> LENGTH: 20
<212> TYPE: DNA
<213> ORGANISM: Artificial Sequence
<220> FEATURE:
<223> OTHER INFORMATION: SbOTUB1 protospacer sequence

<400> SEQUENCE: 131
tgttcacata attgccctat                                                 20

<210> SEQ ID NO 132
<211> LENGTH: 112
<212> TYPE: DNA
<213> ORGANISM: Artificial Sequence
<220> FEATURE:
<223> OTHER INFORMATION: SbOTUB1 sgRNA nucleic acid sequence

<400> SEQUENCE: 132
tgttcacata attgccctat gttttagagc tagaaatagc aagttaaaat aaggctagtc     60
cgttatcaac ttgaaaaagt ggcaccgagt cggtgctttt tttcaagagc tt             112

<210> SEQ ID NO 133
<211> LENGTH: 552
<212> TYPE: DNA
<213> ORGANISM: Artificial Sequence
<220> FEATURE:
<223> OTHER INFORMATION: SbOTUB1 U3-sgRNA cassette monocot plant,
      nucleic acid construct

<400> SEQUENCE: 133
tggaatcggc agcaaaggac gcgttgacat tgtaggacta tattgctcta ataaaggaag     60
gaatctttaa acatacgaac agatcactta aagttcttct gaagcaactt aaagttatca     120
ggcatgcatg gatcttggag gaatcagatg tgcagtcagg gaccatagca caagacaggc     180
gtcttctact ggtgctacca gcaaatgctg gaagccggga acactgggta cgttggaaac     240
cacgtgtgat gtgaaggagt aagataaact gtaggagaaa agcatttcgt agtgggccat     300
gaagcctttc aggacatgta ttgcagtatg ggccggccca ttacgcaatt ggacgacaac     360
```

```
aaagactagt attagtacca cctcggctat ccacatagat caaagctggt ttaaaagagt    420
tgtgcagatg atccgtggca tgttcacata attgccctat gttttagagc tagaaatagc    480
aagttaaaat aaggctagtc cgttatcaac ttgaaaaagt ggcaccgagt cggtgctttt    540
tttcaagagc tt                                                        552
```

<210> SEQ ID NO 134
<211> LENGTH: 23
<212> TYPE: DNA
<213> ORGANISM: Artificial Sequence
<220> FEATURE:
<223> OTHER INFORMATION: GmOTUB1 CRISPR target sequence

<400> SEQUENCE: 134

```
attcgtcgta ctcgaggaga tgg                                             23
```

<210> SEQ ID NO 135
<211> LENGTH: 20
<212> TYPE: DNA
<213> ORGANISM: Artificial Sequence
<220> FEATURE:
<223> OTHER INFORMATION: GmOTUB1 protospacer sequence

<400> SEQUENCE: 135

```
attcgtcgta ctcgaggaga                                                 20
```

<210> SEQ ID NO 136
<211> LENGTH: 111
<212> TYPE: DNA
<213> ORGANISM: Artificial Sequence
<220> FEATURE:
<223> OTHER INFORMATION: GmOTUB1 sgRNA nucleic acid sequence

<400> SEQUENCE: 136

```
attcgtcgta ctcgaggaga gttttagagc tagaaatagc aagttaaaat aaggctagtc    60
cgttatcaac ttgaaaaagt ggcaccgagt cggtgctttt tttcaagagc t            111
```

<210> SEQ ID NO 137
<211> LENGTH: 455
<212> TYPE: DNA
<213> ORGANISM: Artificial Sequence
<220> FEATURE:
<223> OTHER INFORMATION: GmOTUB1 U3b-sgRNA cassette monocot plant,
      nucleic acid construct

<400> SEQUENCE: 137

```
tggaatcggc agcaaaggat ttactttaaa ttttttctta tgcagcctgt gatggataac     60
tgaatcaaac aaatggcgtc tgggtttaag aagatctgtt ttggctatgt tggacgaaac    120
aagtgaactt ttaggatcaa cttcagttta tatatggagc ttatatcgag caataagata    180
agtgggcttt ttatgtaatt taatgggcta tcgtccatag attcactaat acccatgccc    240
agtacccatg tatgcgtttc atataagctc ctaatttctc ccacatcgct caaatctaaa    300
caaatcttgt tgtatatata acactgaggg agcaacattg gtcaattcgt cgtactcgag    360
gagagtttta gagctagaaa tagcaagtta aaataaggct agtccgttat caacttgaaa    420
aagtggcacc gagtcggtgc tttttttcaa gagct                               455
```

<210> SEQ ID NO 138
<211> LENGTH: 23
<212> TYPE: DNA
<213> ORGANISM: Artificial Sequence
<220> FEATURE:

<223> OTHER INFORMATION: GmOTUB1 CRISPR target sequence

<400> SEQUENCE: 138 tactgcccctt tcagatgcat tgg                                          23

<210> SEQ ID NO 139
<211> LENGTH: 20
<212> TYPE: DNA
<213> ORGANISM: Artificial Sequence
<220> FEATURE:
<223> OTHER INFORMATION: GMOTUB1 protospacer sequence

<400> SEQUENCE: 139 tactgcccctt tcagatgcat                                              20

<210> SEQ ID NO 140
<211> LENGTH: 111
<212> TYPE: DNA
<213> ORGANISM: Artificial Sequence
<220> FEATURE:
<223> OTHER INFORMATION: GmOTUB1 sgRNA nucleic acid sequence

<400> SEQUENCE: 140 tactgcccctt tcagatgcat gttttagagc tagaaatagc aagttaaaat aaggctagtc    60
cgttatcaac ttgaaaaagt ggcaccgagt cggtgctttt tttcaagagc t            111

<210> SEQ ID NO 141
<211> LENGTH: 435
<212> TYPE: DNA
<213> ORGANISM: Artificial Sequence
<220> FEATURE:
<223> OTHER INFORMATION: GmOTUB1 U6-1-sgRNA cassette monocot plant,
      nucleic acid construct

<400> SEQUENCE: 141
tggaatcggc agcaaaggaa gaaatctcaa aattccggca gaacaattt gaatctcgat      60 ccgtagaaac gagacggtca ttgttttagt tccaccacga ttatatttga aatttacgtg   120
agtgtgagtg agacttgcat aagaaaataa aatctttagt tgggaaaaaa ttcaataata   180
taaatgggct tgagaaggaa gcgagggata ggcctttttc taaataggc ccatttaagc    240 tattaacaat cttcaaaagt accacagcgc ttaggtaaag aaagcagctg agtttatata   300
tggttagaga cgaagtagtg attgtactgc cctttcagat gcatgtttta gagctagaaa   360
tagcaagtta aaataaggct agtccgttat caacttgaaa agtggcacc gagtcggtgc    420 tttttttcaa gagct                                                   435

<210> SEQ ID NO 142
<211> LENGTH: 23
<212> TYPE: DNA
<213> ORGANISM: Artificial Sequence
<220> FEATURE:
<223> OTHER INFORMATION: BnOTUB1 CRISPR target sequence

<400> SEQUENCE: 142
atcaggcgaa caagaggaga tgg                                           23

<210> SEQ ID NO 143
<211> LENGTH: 20
<212> TYPE: DNA
<213> ORGANISM: Artificial Sequence
<220> FEATURE:
<223> OTHER INFORMATION: BnOTUB1 protospacer sequence

```
<400> SEQUENCE: 143
atcaggcgaa caagaggaga                                               20

<210> SEQ ID NO 144
<211> LENGTH: 111
<212> TYPE: DNA
<213> ORGANISM: Artificial Sequence
<220> FEATURE:
<223> OTHER INFORMATION: BnOTUB1 sgRNA nucleic acid sequence

<400> SEQUENCE: 144
atcaggcgaa caagaggaga gttttagagc tagaaatagc aagttaaaat aaggctagtc   60
cgttatcaac ttgaaaaagt ggcaccgagt cggtgctttt tttcaagagc t           111

<210> SEQ ID NO 145
<211> LENGTH: 455
<212> TYPE: DNA
<213> ORGANISM: Artificial Sequence
<220> FEATURE:
<223> OTHER INFORMATION: BnOTUB1 U3b-sgRNA cassette monocot plant,
      nucleic acid construct

<400> SEQUENCE: 145
tggaatcggc agcaaaggat ttactttaaa ttttttctta tgcagcctgt gatggataac   60
tgaatcaaac aaatggcgtc tgggtttaag aagatctgtt ttggctatgt tggacgaaac  120
aagtgaactt ttaggatcaa cttcagttta tatatggagc ttatatcgag caataagata  180
agtgggcttt ttatgtaatt taatgggcta tcgtccatag attcactaat acccatgccc  240
agtacccatg tatgcgtttc atataagctc ctaatttctc ccacatcgct caaatctaaa  300
caaatcttgt tgtatatata acactgaggg agcaacattg gtcaatcagg cgaacaagag  360
gagagtttta gagctagaaa tagcaagtta aaataaggct agtccgttat caacttgaaa  420
aagtggcacc gagtcggtgc ttttttttcaa gagct                            455

<210> SEQ ID NO 146
<211> LENGTH: 23
<212> TYPE: DNA
<213> ORGANISM: Artificial Sequence
<220> FEATURE:
<223> OTHER INFORMATION: BnOTUB1 CRISPR target sequence

<400> SEQUENCE: 146
tattcacata acagctttgt cgg                                           23

<210> SEQ ID NO 147
<211> LENGTH: 20
<212> TYPE: DNA
<213> ORGANISM: Artificial Sequence
<220> FEATURE:
<223> OTHER INFORMATION: BnOTUB1 protospacer sequence

<400> SEQUENCE: 147
tattcacata acagctttgt                                               20

<210> SEQ ID NO 148
<211> LENGTH: 111
<212> TYPE: DNA
<213> ORGANISM: Artificial Sequence
<220> FEATURE:
<223> OTHER INFORMATION: BnOTUB1 sgRNA nucleic acid sequence

<400> SEQUENCE: 148
```

```
tattcacata acagctttgt gttttagagc tagaaatagc aagttaaaat aaggctagtc    60
cgttatcaac ttgaaaaagt ggcaccgagt cggtgctttt tttcaagagc t            111
```

<210> SEQ ID NO 149
<211> LENGTH: 435
<212> TYPE: DNA
<213> ORGANISM: Artificial Sequence
<220> FEATURE:
<223> OTHER INFORMATION: BnOTUB1 U6-1-sgRNA cassette monocot plant,
      nucleic acid construct

<400> SEQUENCE: 149

```
tggaatcggc agcaaaggaa gaaatctcaa aattccggca gaacaatttt gaatctcgat    60
ccgtagaaac gagacggtca ttgttttagt tccaccacga ttatatttga aatttacgtg   120
agtgtgagtg agacttgcat aagaaaataa aatctttagt tgggaaaaaa ttcaataata   180
taaatgggct tgagaaggaa gcgagggata ggcctttttc taaaataggc ccatttaagc   240
tattaacaat cttcaaaagt accacagcgc ttaggtaaag aaagcagctg agtttatata   300
tggttagaga cgaagtagtg attgtattca cataacagct ttgtgtttta gagctagaaa   360
tagcaagtta aaataaggct agtccgttat caacttgaaa aagtggcacc gagtcggtgc   420 ttttttttcaa gagct                                                   435
```

<210> SEQ ID NO 150
<211> LENGTH: 4203
<212> TYPE: DNA
<213> ORGANISM: Artificial Sequence
<220> FEATURE:
<223> OTHER INFORMATION: Cas9

<400> SEQUENCE: 150

```
atggctccta agaagaagcg gaaggttggt attcacgggg tgcctgcggc tgacaagaag    60
tactccatcg gcctcgacat cggcaccaac agcgtcggct gggcggtgat caccgacgag   120
tacaaggtcc cgtccaagaa gttcaaggtc ctgggcaaca ccgaccgcca ctccatcaag   180
aagaacctca cggcgcccct cctcttcgac tccggcgaga cggcggaggc gacccgcctc   240
aagcgcaccg cccgccgccg ctacacccgc cgcaagaacc gcatctgcta cctccaggag   300
atcttctcca acgagatggc gaaggtcgac gactccttct ccaccgcct cgaggagtcc   360 ttcctcgtgg aggaggacaa gaagcacgag cgccacccca tcttcggcaa catcgtcgac   420
gaggtcgcct accacgagaa gtaccccact atctaccacc ttcgtaagaa gcttgttgac   480
tctactgata aggctgatct tcgtctcatc taccttgctc tcgctcacat gatcaagttc   540
cgtggtcact tccttatcga gggtgacctt aaccctgata actccgacgt ggacaagctc   600
ttcatccagc tcgtccagac ctacaaccag ctcttcgagg agaaccctat caacgcttcc   660
ggtgtcgacg ctaaggcgat cctttccgct aggctctcca gtccaggcg tctcgagaac   720 ctcatcgccc agctccctgg tgagaagaag acggtctttt cggtaacct catcgctctc   780 tccctcggtc tgacccctaa cttcaagtcc aacttcgacc tcgctgagga cgctaagctt   840
cagctctcca aggataccta cgacgatgat ctcgacaacc tcctcgctca gattggagat   900
cagtacgctg atctcttcct tgctgctaag aacctctccg atgctatcct cctttcggat   960
atccttaggg ttaacactga tcactaag gctcctcttt ctgcttccat gatcaagcgc   1020
tacgacgagc accaccagga cctcaccctc ctcaaggctc ttgttcgtca gcagctcccc   1080
gagaagtaca aggagatctt cttcgaccag tccaagaacg gctacgccgg ttacattgac   1140
```

```
ggtggagcta gccaggagga gttctacaag ttcatcaagc caatccttga gaagatggat   1200
ggtactgagg agcttctcgt taagcttaac cgtgaggacc tccttaggaa gcagaggact   1260
ttcgataacg gctctatccc tcaccagatc caccttggtg agcttcacgc catccttcgt   1320
aggcaggagg acttctaccc tttcctcaag gacaaccgtg agaagatcga gaagatcctt   1380
actttccgta ttccttacta cgttggtcct cttgctcgtg gtaactcccg tttcgcttgg   1440
atgactagga agtccgagga gactatcacc ccttggaact tcgaggaggt tgttgacaag   1500
ggtgcttccg cccagtcctt catcgagcgc atgaccaact tcgacaagaa cctccccaac   1560
gagaaggtcc tccccaagca ctccctcctc tacgagtact tcacggtcta caacgagctc   1620
accaaggtca agtacgtcac cgagggtatg cgcaagcctg ccttcctctc cggcgagcag   1680
aagaaggcta tcgttgacct cctcttcaag accaaccgca aggtcaccgt caagcagctc   1740
aaggaggact acttcaagaa gatcgagtgc ttcgactccg tcgagatcag cggcgttgag   1800
gaccgtttca acgcttctct cggtacctac cacgatctcc tcaagatcat caaggacaag   1860
gacttcctcg acaacgagga gaacgaggac atcctcgagg acatcgtcct cactcttact   1920
ctcttcgagg ataggagat gatcgaggag aggctcaaga cttacgctca tctcttcgat   1980
gacaaggtta tgaagcagct caagcgtcgc cgttacaccg gttggggtag gctctcccgc   2040
aagctcatca cggtatcag ggataagcag agcggcaaga ctatcctcga cttcctcaag   2100
tctgatggtt tcgctaacag gaacttcatg cagctcatcc acgatgactc tcttaccttc   2160
aaggaggata ttcagaaggc tcaggtgtcc ggtcagggcg actctctcca cgagcacatt   2220
gctaaccttg ctggttcccc tgctatcaag aagggcatcc ttcagactgt taaggttgtc   2280
gatgagcttg tcaaggttat gggtcgtcac aagcctgaga acatcgtcat cgagatggct   2340
cgtgagaacc agactaccca gaagggtcag aagaactcga gggagcgcat gaagaggatt   2400
gaggagggta tcaaggagct tggttctcag atccttaagg agcaccctgt cgagaacacc   2460
cagctccaga acgagaagct ctacctctac tacctccaga acggtaggga tatgtacgtt   2520
gaccaggagc tcgacatcaa caggcttcct gactacgacg tcgaccacat tgttcctcag   2580
tctttcctta aggatgactc catcgacaac aaggtcctca cgaggtccga caagaacagg   2640
ggtaagtcgg acaacgtccc cttccgaggag gttgtcaaga agatgaagaa ctactggagg   2700
cagcttctca acgctaagct cattacccag aggaagttcg acaacctcac gaaggctgag   2760
aggggtggcc tttccgagct tgacaaggct ggtttcatca agaggcagct tgttgagacg   2820
aggcagatta ccaagcacgt tgctcagatc ctcgattcta ggatgaacac caagtacgac   2880
gagaacgaca agctcatccg cgaggtcaag gtgatcaccc tcaagtccaa gctcgtctcc   2940
gacttccgca aggacttcca gttctacaag gtccgcgaga tcaacaacta ccaccacgct   3000
cacgatgctt accttaacgc tgtcgttggt accgctctta tcaagaagta ccctaagctt   3060
gagtccgagt tcgtctacgg tgactacaag gtctacgacg ttcgtaagat gatcgccaag   3120
tccgagcagg agatcggcaa ggccaccgcc aagtacttct tctactccaa catcatgaac   3180
ttcttcaaga ccgagatcac cctcgccaac ggcgagatcc gcaagcgccc tcttatcgag   3240
acgaacggtg agactggtga gatcgtttgg gacaagggtc gcgacttcgc tactgttcgc   3300
aaggtccttt ctatgcctca ggttaacatc gtcaagaaga ccgaggtcca gaccggtggc   3360
ttctccaagg agtctatcct tccaaagaga aactcggaca agctcatcgc taggaagaag   3420
gattgggacc ctaagaagta cggtggtttc gactccccta ctgtcgccta ctccgtcctc   3480
gtggtcgcca aggtggagaa gggtaagtcg aagaagctca agtccgtcaa ggagctcctc   3540
```

```
ggcatcacca tcatggagcg ctcctccttc gagaagaacc cgatcgactt cctcgaggcc    3600
aagggctaca aggaggtcaa gaaggacctc atcatcaagc tccccaagta ctctcttttc    3660
gagctcgaga cgtcgtaa gaggatgctg gcttccgctg gtgagctcca gaagggtaac      3720
gagcttgctc ttccttccaa gtacgtgaac ttcctctacc tcgcctccca ctacgagaag    3780
ctcaagggtt cccctgagga taacgagcag aagcagctct tcgtggagca gcacaagcac    3840
tacctcgacg agatcatcga gcagatctcc gagttctcca gcgcgtcat cctcgctgac     3900 gctaacctcg acaaggtcct ctccgcctac aacaagcacc gcgacaagcc catccgcgag    3960
caggccgaga acatcatcca cctcttcacg ctcacgaacc tcggcgcccc tgctgctttc    4020
aagtacttcg acaccaccat cgacaggaag cgttacacgt ccaccaagga ggttctcgac    4080
gctactctca tccaccagtc catcaccggt ctttacgaga ctcgtatcga cctttcccag    4140
cttggtggtg ataagcgtcc tgctgccacc aaaaaggccg acaggctaa gaaaaagaag     4200 tag                                                                  4203

<210> SEQ ID NO 151
<211> LENGTH: 4782
<212> TYPE: DNA
<213> ORGANISM: Artificial Sequence
<220> FEATURE:
<223> OTHER INFORMATION: Cys4-P2A-TaCas9 nucleic acid sequence

<400> SEQUENCE: 151
atggaccact acctcgacat caggctcagg ccagacccag agttcccacc agcccagctc      60
atgtccgtcc tcttcggcaa gctccaccag gccctcgtgg cccagggcgg cgacaggatc     120
ggcgtgtcct tcccagacct cgacgagtcc aggtccaggc tcggcgagag gctccgcatc     180
cacgcctccg ccgacgacct cagggccctc ctcgccaggc cgtggctgga gggcctcagg     240
gaccacctcc agttcggcga gccagccgtg gtgccacacc caaccccata caggcaagtg     300
tccagggtgc aagccaagtc caacccagag aggctcagga ggaggctcat gaggaggcac     360
gacctctccg aggaagaggc caggaagcgc atcccagaca ccgtggccag ggccctcgac     420
ctcccattcg tgaccctcag gtcccagtcc accggccagc acttccgcct cttcatcagg     480
cacggcccac tccaggtgac cgccgaggag ggcggctta cctgctacgg cctctccaag     540
ggcggcttcg tgccgtggtt cggctccggc gccaccaact tctccctcct caagcaagcc     600
ggcgacgtgg aggagaaccc aggcccaatg acaagaagt actcgatcgg cctcgacatc      660
gggacgaact cagttggctg ggccgtgatc accgacgagt acaaggtgcc ctctaagaag     720
ttcaaggtcc tggggaacac cgaccgccat tccatcaaga gaaacctcat cggcgctctc     780
ctgttcgaca gcggggagac cgctgaggct acgaggctca gagaaccgc taggcgccgg      840 tacacgagaa ggaagaacag gatctgctac ctccaagaga ttttctccaa cgagatggcc     900
aaggttgacg attcattctt ccaccgcctg gaggagtctt tcctcgtgga ggaggataag    960
aagcacgagc ggcatcccat cttcggcaac atcgtggacg aggttgccta ccacgagaag    1020
taccctacga tctaccatct gcggaagaag ctcgtggact ccaccgataa ggcggacctc    1080
agactgatct acctcgctct ggcccacatg atcaagttcc gcggccattt cctgatcgag    1140
ggggatctca acccagacaa cagcgatgtt gacaagctgt tcatccaact cgtgcagacc    1200
tacaaccaac tcttcgagga aacccgatc aacgcctctg gcgtggacgc gaaggctatc    1260
ctgtccgcga ggctctcgaa gtccaggagg ctggagaacc tgatcgctca gctcccaggc    1320
```

```
gagaagaaga acggcctgtt cgggaacctc atcgctctca gcctgggsct caccccgaac   1380
ttcaagtcga acttcgatct cgctgaggac gccaagctgc aactctccaa ggacacctac   1440
gacgatgacc tcgataacct cctggcccag atcggcgatc aatacgcgga cctgttcctc   1500
gctgccaaga acctgtcgga cgccatcctc ctgtcagata tcctccgcgt gaacaccgag   1560
atcacgaagg ctccactctc tgcctccatg atcaagcgct acgacgagca ccatcaggat   1620
ctgaccctcc tgaaggcgct ggtccgccaa cagctcccgg agaagtacaa ggagattttc   1680
ttcgatcagt cgaagaacgg ctacgctggg tacatcgacg gcggggcctc acaagaggag   1740
ttctacaagt tcatcaagcc aatcctggag aagatggacg gcacggagga gctcctggtg   1800
aagctcaaca gggaggacct cctgcggaag cagagaacct cgataacggc agcatcccc   1860 caccaaatcc atctcgggga gctgcacgcc atcctgagaa ggcaagagga cttctaccct   1920
ttcctcaagg ataaccggga agatcgagaa gatcctga ccttcagaat cccatactac   1980
gtcggccctc tcgcgcgggg gaactcaaga ttcgcttgga tgacccgcaa gtctgaggag   2040
accatcacgc cgtggaactt cgaggaggtg gtggacaagg gcgctagcgc tcagtcgttc   2100
atcgagagga tgaccaactt cgacaagaac ctgcccaacg agaaggtgct ccctaagcac   2160
tcgctcctgt acgagtactt caccgtctac aacgagctca cgaaggtgaa gtacgtcacc   2220
gagggcatgc gcaagccagc gttcctgtcc ggggagcaga agaaggctat cgtggacctc   2280
ctgttcaaga ccaaccggaa ggtcacggtt aagcaactca aggaggacta cttcaagaag   2340
atcgagtgct tcgattcggt cgagatcagc ggcgttgagg accgcttcaa cgccagcctc   2400
gggacctacc acgatctcct gaagatcatc aaggataagg acttcctgga caacgaggag   2460
aacgaggata tcctggagga catcgtgctg accctcacgc tgttcgagga cagggagatg   2520
atcgaggagc gcctgaagac gtacgccat ctcttcgatg acaaggtcat gaagcaactc   2580
aagcgccgga gataccaccgg ctgggggagg ctgtcccgca agctcatcaa cggcatccgg   2640
gacaagcagt ccgggaagac catcctcgac ttcctcaaga gcgatggctt cgccaacagg   2700
aacttcatgc aactgatcca cgatgacagc ctcaccttca aggaggatat ccaaaaggct   2760
caagtgagcg gccaggggga ctcgctgcac gagcatatcg cgaacctcgc tggctccccc   2820
gcgatcaaga agggcatcct ccagaccgtg aaggttgtgg acgagctcgt gaaggtcatg   2880
ggccggcaca agcctgagaa catcgtcatc gagatggcca gagagaacca aaccacgcag   2940 aagggcaaa agaactctag ggagcgcatg aagcgcatcg aggagggcat caaggagctg   3000
gggtcccaaa tcctcaagga gcacccagtg agaacacccc aactgcagaa cgagaagctc   3060
tacctgtact acctccagaa cggcagggat atgtacgtgg accaagagct ggatatcaac   3120
cgcctcagcg attacgacgt cgatcatatc gttccccagt cttttcctgaa ggatgactcc   3180 atcgacaaca aggtcctcac caggtcggac aagaaccgcg gcaagtcaga taacgttcca   3240
tctgaggagg tcgttaagaa gatgaagaac tactggaggc agctcctgaa cgccaagctg   3300
atcacgcaaa ggaagttcga caacctcacc aaggctgaga gaggcgggct ctcagagctg   3360
gacaaggccg gcttcatcaa gcggcagctg gtcgagacca gacaaatcac gaagcacgtt   3420
gcgcaaatcc tcgactctcg gatgaacacg aagtacgatg agaacgacaa gctgatcagg   3480
gaggttaagg tgatcacccct gaagtctaag ctcgtctccg acttcaggaa ggatttccag   3540
ttctacaagg ttcgcgagat caacaactac caccatgccc atgacgctta cctcaacgct   3600
gtggtcggca ccgctctgat caagaagtac ccaaagctgg agtccgagtt cgtgtacggg   3660
gactacaagg tttacgatgt gcgcaagatg atcgccaagt cggagcaaga gatcggcaag   3720
```

-continued

```
gctaccgcca agtacttctt ctactcaaac atcatgaact tcttcaagac cgagatcacg    3780
ctggccaacg gcgagatccg aagagaccg ctcatcgaga ccaacggcga gacggggag    3840 atcgtgtggg acaagggcag ggatttcgcg accgtccgca aggttctctc catgccccag    3900
gtgaacatcg tcaagaagac cgaggtcaa acgggcgggt tctcaaagga gtctatcctg    3960
cctaagcgga acagcgacaa gctcatcgcc agaaagaagg actgggaccc aaagaagtac    4020
ggcgggttcg acagccctac cgtggcctac tcggtcctgg ttgtggcgaa ggttgagaag    4080
ggcaagtcca agaagctcaa gagcgtgaag gagctcctgg ggatcaccat catggagagg    4140
tccagcttcg agaagaaccc aatcgacttc ctggaggcca agggctacaa ggaggtgaag    4200
aaggacctga tcatcaagct cccgaagtac tctctcttcg agctggagaa cggcaggaag    4260
agaatgctgg cttccgctgg cgagctccag aaggggaacg agctcgcgct gccaagcaag    4320
tacgtgaact tcctctacct ggcttcccac tacgagaagc tcaagggcag cccggaggac    4380
aacgagcaaa agcagctgtt cgtcgagcag cacaagcatt acctcgacga gatcatcgag    4440
caaatctccg agttcagcaa gcgcgtgatc ctcgccgacg cgaacctgga taaggtcctc    4500
tccgcctaca caagcaccg ggacaagccc atcagagagc aagcggagaa catcatccat    4560
ctcttcaccc tgacgaacct cggcgctcct gctgctttca agtacttcga caccacgatc    4620
gatcggaaga gatacacctc cacgaaggag gtcctggacg cgaccctcat ccaccagtcg    4680
atcaccggcc tgtacgagac gaggatcgac ctctcacaac tcggcgggga taagagaccc    4740
gcagcaacca gaaggcagg gcaagcaaag aagaagaagt ga    4782
```

<210> SEQ ID NO 152
<211> LENGTH: 248
<212> TYPE: PRT
<213> ORGANISM: Artificial Sequence
<220> FEATURE:
<223> OTHER INFORMATION: Outubain-like domain

<400> SEQUENCE: 152

```
Pro Tyr Val Gly Asp Lys Glu Pro Leu Ser Thr Leu Ala Ala Glu Phe
1               5                  10                  15

Gln Ser Gly Ser Pro Ile Leu Gln Glu Lys Ile Lys Leu Leu Gly Glu
            20                  25                  30

Gln Tyr Asp Ala Leu Arg Arg Thr Arg Gly Asp Gly Asn Cys Phe Tyr
        35                  40                  45

Arg Ser Phe Met Phe Ser Tyr Leu Glu His Ile Leu Glu Thr Gln Asp
    50                  55                  60

Lys Ala Glu Val Glu Arg Ile Leu Lys Lys Ile Glu Gln Cys Lys Lys
65                  70                  75                  80

Thr Leu Ala Asp Leu Gly Tyr Ile Glu Phe Thr Phe Glu Asp Phe Phe
                85                  90                  95

Ser Ile Phe Ile Asp Gln Leu Glu Ser Val Leu Gln Gly His Glu Ser
            100                 105                 110

Ser Ile Gly Ala Glu Glu Leu Leu Glu Arg Thr Arg Asp Gln Met Val
        115                 120                 125

Ser Asp Tyr Val Val Met Phe Phe Arg Phe Val Thr Ser Gly Glu Ile
    130                 135                 140

Gln Arg Arg Ala Glu Phe Phe Glu Pro Phe Ile Ser Gly Leu Thr Asn
145                 150                 155                 160

Ser Thr Val Val Gln Phe Cys Lys Ala Ser Val Glu Pro Met Gly Glu
                165                 170                 175
```

-continued

```
Glu Ser Asp His Val His Ile Ile Ala Leu Ser Asp Ala Leu Gly Val
            180                 185                 190

Pro Ile Arg Val Met Tyr Leu Asp Arg Ser Ser Cys Asp Ala Gly Asn
        195                 200                 205

Ile Ser Val Asn His His Asp Phe Ser Pro Glu Ala Asn Ser Ser Asp
    210                 215                 220

Gly Ala Ala Ala Glu Lys Pro Tyr Ile Thr Leu Leu Tyr Arg Pro
225                 230                 235                 240

Gly His Tyr Asp Ile Leu Tyr Pro
                245

<210> SEQ ID NO 153
<211> LENGTH: 1466
<212> TYPE: PRT
<213> ORGANISM: Artificial Sequence
<220> FEATURE:
<223> OTHER INFORMATION: Mutated OsTUB1

<400> SEQUENCE: 153

Ala Thr Gly Gly Gly Cys Gly Gly Gly Ala Cys Thr Ala Cys Thr
1               5                   10                  15

Ala Cys Cys Ala Cys Thr Cys Gly Thr Gly Cys Thr Gly Cys Gly Gly
            20                  25                  30

Cys Gly Ala Cys Cys Cys Gly Ala Cys Cys Cys Gly Ala Cys
        35                  40                  45

Cys Thr Cys Cys Gly Cys Gly Cys Cys Cys Gly Ala Gly Gly
    50                  55                  60

Gly Gly Cys Cys Cys Ala Ala Gly Cys Thr Gly Cys Cys Gly Thr Ala
65                  70                  75                  80

Cys Gly Thr Cys Gly Gly Gly Ala Cys Ala Ala Gly Ala Ala
        85                  90                  95

Cys Cys Thr Cys Thr Cys Thr Cys Cys Ala Cys Thr Thr Thr Ala Gly
    100                 105                 110

Cys Cys Gly Cys Cys Gly Ala Gly Thr Thr Thr Cys Ala Gly Thr Cys
        115                 120                 125

Thr Gly Gly Cys Ala Gly Cys Cys Cys Ala Thr Thr Thr Ala
    130                 135                 140

Cys Ala Gly Gly Ala Gly Ala Ala Ala Thr Ala Ala Ala Gly Thr
145                 150                 155                 160

Thr Gly Cys Thr Thr Gly Gly Thr Gly Ala Ala Cys Ala Gly Thr Ala
        165                 170                 175

Thr Gly Ala Thr Gly Cys Thr Thr Ala Gly Ala Ala Gly Gly
    180                 185                 190

Ala Cys Ala Cys Gly Ala Gly Gly Ala Gly Ala Thr Gly Gly Ala Ala
        195                 200                 205

Ala Cys Thr Gly Cys Thr Thr Thr Thr Ala Thr Cys Gly Ala Ala Gly
        210                 215                 220

Cys Thr Thr Thr Ala Thr Gly Thr Thr Thr Cys Cys Thr Ala Cys
225                 230                 235                 240

Thr Thr Gly Gly Ala Ala Cys Ala Thr Cys Cys Thr Ala Gly
            245                 250                 255

Ala Gly Ala Cys Ala Cys Ala Ala Gly Ala Cys Ala Ala Ala Gly Cys
                260                 265                 270

Thr Gly Ala Gly Gly Thr Thr Gly Ala Gly Cys Gly Cys Ala Thr Thr
            275                 280                 285
```

```
Cys Thr Ala Ala Ala Ala Ala Ala Thr Thr Gly Ala Gly Cys
    290             295             300
Ala Gly Thr Gly Cys Ala Ala Gly Ala Ala Gly Ala Cys Thr Cys Thr
305             310             315             320
Thr Gly Cys Ala Gly Ala Thr Cys Thr Thr Gly Gly Ala Thr Ala Cys
                325             330             335
Ala Thr Thr Gly Ala Gly Thr Thr Cys Ala Cys Cys Thr Thr Gly
            340             345             350
Ala Ala Gly Ala Thr Thr Thr Cys Thr Thr Cys Thr Cys Thr Gly Thr
            355             360             365
Cys Thr Thr Thr Ala Thr Thr Gly Thr Thr Ala Cys Thr Thr Thr Gly
    370             375             380
Thr Gly Thr Gly Gly Cys Cys Cys Thr Cys Cys Thr Ala Cys Thr
385             390             395             400
Thr Ala Thr Cys Cys Thr Gly Thr Thr Cys Ala Ala Thr Thr Gly Cys
            405             410             415
Thr Gly Thr Thr Thr Thr Gly Cys Ala Ala Cys Thr Thr Ala Thr Gly
            420             425             430
Cys Cys Ala Gly Ala Thr Gly Thr Ala Thr Thr Cys Cys Cys Thr Cys
    435             440             445
Thr Gly Ala Ala Thr Ala Gly Thr Ala Thr Gly Ala Ala Gly Ala Thr
    450             455             460
Cys Thr Gly Thr Cys Cys Gly Ala Thr Thr Ala Thr Thr Thr Thr Cys
465             470             475             480
Ala Thr Gly Thr Ala Thr Gly Cys Thr Thr Gly Thr Thr Thr Gly Cys
            485             490             495
Ala Thr Thr Thr Cys Cys Thr Thr Thr Thr Thr Ala Gly Ala Thr Gly
            500             505             510
Thr Thr Cys Cys Thr Gly Gly Ala Ala Thr Ala Ala Thr Thr Thr Thr
    515             520             525
Thr Gly Thr Ala Thr Gly Ala Gly Cys Thr Ala Gly Thr Thr Ala Thr
    530             535             540
Ala Ala Thr Gly Ala Gly Ala Gly Cys Thr Thr Gly Thr Gly Cys Ala
545             550             555             560
Thr Thr Thr Thr Cys Cys Thr Gly Thr Cys Ala Thr Gly Cys Ala Ala
                565             570             575
Cys Ala Ala Ala Thr Thr Ala Ala Thr Ala Cys Thr Ala Gly Thr
            580             585             590
Gly Thr Cys Thr Ala Ala Thr Cys Thr Thr Gly Thr Gly Cys Ala
    595             600             605
Thr Thr Gly Thr Thr Ala Ala Thr Ala Ala Cys Thr Thr Gly Ala
    610             615             620
Ala Ala Ala Thr Gly Ala Thr Ala Gly Cys Cys Thr Thr Gly Ala
625             630             635             640
Ala Gly Ala Thr Thr Gly Gly Thr Cys Ala Thr Ala Thr Ala
            645             650             655
Thr Ala Thr Ala Thr Gly Thr Cys Ala Cys Thr Gly Thr Thr
            660             665             670
Thr Cys Thr Thr Ala Gly Thr Thr Ala Gly Gly Ala Thr Cys Ala Cys
    675             680             685
Thr Cys Ala Cys Cys Ala Gly Thr Cys Ala Cys Cys Cys Thr Thr Cys
    690             695             700
```

Thr Gly Ala Ala Gly Thr Thr Cys Ala Thr Ala Thr Gly Thr Ala
705                 710                 715                 720

Thr Cys Ala Cys Thr Thr Ala Thr Ala Ala Gly Thr Ala Ala Gly Cys
            725                 730                 735

Thr Ala Gly Cys Ala Ala Ala Ala Cys Ala Ala Ala Ala Thr Thr Thr
                740                 745                 750

Gly Gly Ala Cys Thr Gly Thr Thr Gly Thr Ala Gly Cys Cys Ala
            755                 760                 765

Cys Cys Cys Ala Gly Ala Ala Cys Cys Cys Ala Ala Thr Ala Gly
770                 775                 780

Ala Thr Gly Gly Ala Thr Thr Cys Ala Cys Ala Thr Thr Ala Thr
785                 790                 795                 800

Thr Thr Thr Cys Thr Ala Cys Thr Gly Gly Cys Thr Thr Gly Gly
                805                 810                 815

Gly Ala Gly Thr Thr Ala Thr Thr Gly Ala Thr Cys Gly Ala Thr
            820                 825                 830

Gly Cys Thr Ala Gly Thr Ala Cys Ala Ala Cys Gly Thr Gly Ala
            835                 840                 845

Ala Ala Thr Thr Thr Gly Gly Gly Thr Ala Gly Thr Thr Gly Ala Gly
850                 855                 860

Ala Thr Gly Cys Ala Thr Thr Thr Thr Cys Ala Cys Ala Ala Ala
865                 870                 875                 880

Gly Gly Ala Cys Thr Cys Cys Thr Thr Thr Ala Thr Thr Gly Gly Thr
                885                 890                 895

Gly Cys Thr Thr Gly Ala Thr Cys Thr Ala Cys Ala Ala Cys Thr Gly
            900                 905                 910

Gly Thr Gly Thr Thr Thr Thr Ala Cys Thr Thr Thr Thr Thr Thr Ala
            915                 920                 925

Cys Ala Ala Ala Ala Ala Ala Thr Gly Thr Ala Ala Thr Cys Thr
930                 935                 940

Cys Cys Thr Thr Gly Cys Ala Gly Thr Gly Cys Ala Cys Thr Cys Ala
945                 950                 955                 960

Ala Ala Thr Thr Ala Thr Thr Gly Cys Ala Ala Cys Cys Thr Cys Cys
                965                 970                 975

Thr Thr Cys Cys Thr Thr Ala Thr Gly Thr Cys Cys Cys Ala Cys
            980                 985                 990

Cys Cys Thr Cys Ala Thr Thr Ala Thr Thr Thr Thr Cys Ala Gly Ala
            995                 1000                1005

Thr Ala Thr Thr Cys Ala Thr Thr Gly Ala Thr Cys Ala Gly Cys
    1010                1015                1020

Thr Gly Gly Ala Ala Ala Gly Thr Gly Thr Thr Cys Thr Gly Cys
    1025                1030                1035

Ala Gly Gly Gly Ala Cys Ala Thr Gly Ala Ala Thr Cys Cys Thr
    1040                1045                1050

Cys Cys Ala Thr Ala Gly Gly Gly Gly Cys Cys Gly Ala Ala Gly
    1055                1060                1065

Ala Gly Cys Thr Thr Cys Thr Ala Gly Ala Ala Ala Gly Ala Ala
    1070                1075                1080

Cys Cys Ala Gly Gly Gly Ala Thr Cys Ala Gly Ala Thr Gly Gly
    1085                1090                1095

Thr Thr Thr Cys Thr Gly Ala Thr Thr Ala Thr Gly Thr Thr Gly
    1100                1105                1110

Thr Cys Ala Thr Gly Thr Thr Cys Thr Thr Thr Ala Gly Gly Thr

```
    1115                1120                1125

Thr Thr  Gly Thr Cys Ala Cys  Cys Thr Cys Thr Gly  Gly Thr Gly
    1130                1135                1140

Ala Ala  Ala Thr Cys Cys Ala  Ala Ala Gly Gly Ala  Gly Gly Gly
    1145                1150                1155

Cys Cys  Gly Ala Gly Thr Thr  Cys Thr Thr Cys Gly  Ala Ala Cys
    1160                1165                1170

Cys Ala  Thr Thr Cys Ala Thr  Cys Thr Cys Thr Gly  Gly Cys Thr
    1175                1180                1185

Thr Gly  Ala Cys Ala Ala Ala  Thr Thr Cys Gly Ala  Cys Thr Gly
    1190                1195                1200

Thr Gly  Gly Thr Thr Cys Ala  Gly Thr Thr Cys Thr  Gly Cys Ala
    1205                1210                1215

Ala Gly  Gly Cys Thr Thr Cys  Cys Gly Thr Gly Gly  Ala Gly Cys
    1220                1225                1230

Cys Gly  Ala Thr Gly Gly Gly  Cys Gly Ala Gly Gly  Ala Ala Ala
    1235                1240                1245

Gly Thr  Gly Ala Cys Cys Ala  Thr Gly Thr Cys Cys  Ala Cys Ala
    1250                1255                1260

Thr Ala  Ala Thr Thr Gly Cys  Cys Cys Thr Ala Thr  Cys Ala Gly
    1265                1270                1275

Ala Thr  Gly Cys Gly Thr Thr  Gly Gly Gly Thr Gly  Thr Gly Cys
    1280                1285                1290

Cys Ala  Ala Thr Cys Cys Gly  Thr Gly Thr Gly Ala  Thr Gly Thr
    1295                1300                1305

Ala Cys  Cys Thr Ala Gly Ala  Cys Ala Gly Ala Ala  Gly Cys Thr
    1310                1315                1320

Cys Ala  Thr Gly Thr Gly Ala  Thr Gly Cys Thr Gly  Gly Ala Ala
    1325                1330                1335

Ala Thr  Ala Thr Ala Ala Gly  Thr Gly Thr Gly Ala  Ala Cys Cys
    1340                1345                1350

Ala Cys  Cys Ala Thr Gly Ala  Thr Thr Thr Cys Ala  Gly Cys Cys
    1355                1360                1365

Cys Thr  Gly Ala Gly Gly Cys  Cys Ala Ala Thr Thr  Cys Ala Thr
    1370                1375                1380

Cys Gly  Gly Ala Cys Gly Gly  Thr Gly Cys Thr Gly  Cys Thr Gly
    1385                1390                1395

Cys Thr  Gly Cys Thr Gly Ala  Gly Ala Ala Ala Cys  Cys Thr Thr
    1400                1405                1410

Ala Cys  Ala Thr Thr Ala Cys  Thr Thr Thr Gly Cys  Thr Cys Thr
    1415                1420                1425

Ala Cys  Cys Gly Thr Cys Cys  Thr Gly Gly Thr Cys  Ala Cys Thr
    1430                1435                1440

Ala Cys  Gly Ala Cys Ala Thr  Thr Cys Thr Cys Thr  Ala Cys Cys
    1445                1450                1455

Cys Gly  Ala Ala Gly Thr Gly  Ala
    1460                1465
```

<210> SEQ ID NO 154
<211> LENGTH: 179
<212> TYPE: PRT
<213> ORGANISM: Artificial Sequence
<220> FEATURE:
<223> OTHER INFORMATION: OsOTUB1 wtg mutation

<400> SEQUENCE: 154

```
Met Gly Gly Asp Tyr Tyr His Ser Cys Cys Gly Asp Pro Asp
1               5                   10                  15

Leu Arg Ala Pro Glu Gly Pro Lys Leu Pro Tyr Val Gly Asp Lys Glu
            20                  25                  30

Pro Leu Ser Thr Leu Ala Ala Glu Phe Gln Ser Gly Ser Pro Ile Leu
        35                  40                  45

Gln Glu Lys Ile Lys Leu Leu Gly Glu Gln Tyr Asp Ala Leu Arg Arg
    50                  55                  60

Thr Arg Gly Asp Gly Asn Cys Phe Tyr Arg Ser Phe Met Phe Ser Tyr
65                  70                  75                  80

Leu Glu His Ile Leu Glu Thr Gln Asp Lys Ala Glu Val Glu Arg Ile
                85                  90                  95

Leu Lys Lys Ile Glu Gln Cys Lys Lys Thr Leu Ala Asp Leu Gly Tyr
            100                 105                 110

Ile Glu Phe Thr Phe Glu Asp Phe Phe Ser Val Phe Ile Val Thr Leu
        115                 120                 125

Cys Gly Pro Pro Tyr Leu Ser Cys Ser Ile Ala Val Leu Gln Leu Met
    130                 135                 140

Pro Asp Val Phe Pro Leu Asn Ser Met Lys Ile Cys Pro Ile Ile Phe
145                 150                 155                 160

Met Tyr Ala Cys Leu His Phe Leu Phe Arg Cys Ser Trp Asn Asn Phe
                165                 170                 175

Cys Met Ser
```

<210> SEQ ID NO 155
<211> LENGTH: 2462
<212> TYPE: DNA
<213> ORGANISM: Artificial Sequence
<220> FEATURE:
<223> OTHER INFORMATION: NPT1 2.5kb promoter sequence from IR66167-27-5-1-6

<400> SEQUENCE: 155

| gagttgaagt tgttgctgct gtcataagta ctatctgcta aatgggcaca ctcctagcat | 60 |
| tattagaact gagaaatatc ccaagcaatg aaagcgacaa aaaagtaccc gtttgaagac | 120 |
| atgattgaca tggtcacatc aaacaccgga catcaacatc taaatgtaca taacaaggcc | 180 |
| aaaataattt tcgatgctgg ttggtgctac caagtcccac gtatgatact taagaatcaa | 240 |
| tcatgaatat tacaaatcaa gtcaaactac gttatgtatt gaactcttat aattactgca | 300 |
| acatatcaca ctggaatttc ctatggtaat tcctcgccag ccttatccta cccatccctt | 360 |
| gcagtatatt aagagcatca acaacaaaca tgattcaaga caactttat taacactgaa | 420 |
| caacataaat tgggaacaaa acaaaccact tggaggcatg attaggataa tcggtattaa | 480 |
| agaactggac atcacaattc acactagat gttgaaataa tacctgtctc ttctttggct | 540 |
| catggcaggt gtcagtgaaa tatactgatg ctccaagaga gctggaagca ccgtttccac | 600 |
| gtaatcaaaa tgtccttttc gtttgctgca atcaaccta aagggctctt tgatgctat | 660 |
| ctcttcaggc atgtccttca caacttccac ataacctctg gtttgctcaa tgaagtaatc | 720 |
| aacatcgaaa acgtctgcaa atccactgac agagaatacc aataagtgat gaactacctt | 780 |
| ttgaacagaa ataaactgca taactacaag tagcacagtc gttcatcttg tagagtgatt | 840 |
| ctcataccta gattcattcc agtaggcagc aacctcaaac ttgggcagaa ccattgttgc | 900 |
| gttgagaagg cgcgcaaccg caattccatc acatagctga agaaacattc ggaagaataa | 960 |

```
ttacaaccag gagtaacata ataacatagc cagttgaaat cacattcgcc ttgcaatgtg    1020
aaaattttca taaataatct gaaaatttag ttatgccact atatatcatg caacctgcct    1080
ccacgacatt ttaatcatgg agtagaagat aaaacatatg atcccctca ttgaccctac     1140
```

<sub>(line above: "atcccctca" preserved as visible)</sub>

```
tatcttacta cttgtgcatg ccgaacgat ctaacagcga atccagaaa gccaacactc      1200 atttgatccc actaacaacg gaagagagaa acgctagccg agatcgctta acgtacatcg    1260
cgtcgcagct ggttgagccc gccgtagcag tcgatccgga tgtacccatt cctcctcgac    1320
ggagctgcag aagaagagga ggttcaaaac cgcaatcacc accacagtct caagcagaga    1380
tgtccactac ccggatcctt aaacccaaac cacaaatcac ggcgaggtct cacccggcat    1440
tgccgcccgc caccacccgc acgaccgcca ctccgccacc cgccgctgcg cccatatgac    1500
ccgcgacccc gacgccgacg cgcgactcctc cctaaagacc aaaagcgagt aagcgagatc   1560
cgtaagcttc tggaacaatc tcgagcatca gctgcaagag gtgaggctgg gccgcgtacc    1620
tggaggtggg aagagtgaag aagaaaggcg gagaggaggg tggagagagg aggaagtaga    1680
gcgcgggggc gaggaagatg accggtagga ggatgcggac gcggctgcgc gcccaccacg    1740
ccgccggcga cgccgacgac gacatcgcct cgccgcgaga agcactggat ctgatcggcc    1800
gccgcctcca cgccggagtg gagagcatat ataagctcgt cagaatgtgg gcccgtggct    1860
atgtgggccc accatgtcat cgacgcttat caagatcgag cggtggcgtg aggaaaccgg    1920 tagggggtggg ggggctaacc aatcggaaac gcgtaataac tcacccgcgg ttcactttct   1980
ccttatgaca cgtgggccca tctcttcctg gacccacctg tcagttaccc ttacggcctc    2040
cactctgagg atctaaacgt aaaaacgaat ttatcggagg gcttatccgc gaggggaaaa    2100
aaacgcgcac ttatttctcg ccttcgccga gatctcggaa gagaagaaca cgcaccgcgg    2160
ggagagggga gagaagcgga aagctccacc gaatcgaagc ccccacacac gcgaagctgg    2220
cgcgggaggc ggccgacgcg agcgcccgga agcgcaaggc ggcggacggc ggcggggagg    2280
gcgacgccgc ggcgacggtc ccggaggagg cggtgatggg ggaggcggcg gcggcagccg    2340
cggcccccga gccggtcgtc gagggggggag gagggggggg ggaggggttg aatcctaacc    2400
ctagcggcgg tggggagga ggtggtggag ggtgctcgga ctccgtgtcg gtcgagctct      2460
cg                                                                   2462
```

<210> SEQ ID NO 156
<211> LENGTH: 1281
<212> TYPE: DNA
<213> ORGANISM: Oryza sativa

<400> SEQUENCE: 156

```
atggggagg aggcggtggt gatggaggcg ccgaggccca agtcgccgcc gaggtacccg      60
gacctgtgcg gccggcggcg gatgcagctg gaggtgcaga tcctgagccg cgagatcacg    120
ttcctcaagg atgagcttca cttccttgaa ggagctcagc ccgtttctcg ttctggatgc    180
attaaagaga taaatgagtt tgttggtaca aaacatgacc cactaatacc aacaaagaga    240
aggaggcaca gatcttgccg tctttttcgg tggatcggat caaaattgtg tatctgcatt    300
tcatgtcttt gctactgttg caagtgctca cccagtgcaa aagaccaag gtgcctcaat     360 tgttcttgca gctcatgctg cgacgagcca tgctgtaagc caaactgcag tgcgtgctgc    420
gctgggtcat gctgtagtcc agactgctgc tcatgctgta aacctaactg cagttgctgc    480
aagacccctt cttgctgcaa accgaactgc tcgtgctcct gtccaagctg cagctcatgc    540
```

```
tgcgatacat cgtgctgcaa accgagctgc acctgcttca acatctttc atgcttcaaa      600 tccctgtaca gctgcttcaa gatcccttca tgcttcaagt cccagtgcaa ctgctctagc      660
cccaattgct gcacttgcac ccttccaagc tgtagctgca agggctgtgc ctgtccaagc      720
tgtggatgca acggctgtgg ctgtccaagc tgcggatgca acggttgtgg ctgtccaagc      780
tgcggttgca acggctgtgg ccttccaagc tgcggttgca acggctgcgg ctcgtgctct      840
tgcgcccaat gcaaacccga ttgtggctcg tgctctacca attgctgtag ctgcaagcca      900
agctgcaacg gctgctgcgg cgagcagtgc tgccgctgcg cggactgctt ctcctgctcg      960
tgccctcgtt gctccagctg cttcaacatc ttcaaatgct cctgcgctgg ctgctgctcg      1020
agcctgtgca agtgcccctg cacgacgcag tgcttcagct gccagtcgtc atgctgcaag      1080
cggcagcctt cgtgctgcaa gtgccagtcg tcttgctgcg agggcagcc ttcctgctgc      1140 gagggacact gctgcagcct cccgaaaccg tcgtgccctg aatgttcctg tgggtgtgtc      1200
tggtcttgca agaattgtac agagggttgt cgatgcccac ggtgtcgtaa cccatgctgt      1260
ctcagtggtt gcttatgttg a                                                1281
```

<210> SEQ ID NO 157
<211> LENGTH: 426
<212> TYPE: PRT
<213> ORGANISM: Oryza sativa

<400> SEQUENCE: 157

```
Met Gly Glu Glu Ala Val Val Met Glu Ala Pro Arg Pro Lys Ser Pro
1               5                   10                  15

Pro Arg Tyr Pro Asp Leu Cys Gly Arg Arg Met Gln Leu Glu Val
            20                  25                  30

Gln Ile Leu Ser Arg Glu Ile Thr Phe Leu Lys Asp Glu Leu His Phe
        35                  40                  45

Leu Glu Gly Ala Gln Pro Val Ser Arg Ser Gly Cys Ile Lys Glu Ile
    50                  55                  60

Asn Glu Phe Val Gly Thr Lys His Asp Pro Leu Ile Pro Thr Lys Arg
65                  70                  75                  80

Arg Arg His Arg Ser Cys Arg Leu Phe Arg Trp Ile Gly Ser Lys Leu
                85                  90                  95

Cys Ile Cys Ile Ser Cys Leu Cys Tyr Cys Lys Cys Ser Pro Lys
            100                 105                 110

Cys Lys Arg Pro Arg Cys Leu Asn Cys Ser Cys Ser Ser Cys Cys Asp
        115                 120                 125

Glu Pro Cys Cys Lys Pro Asn Cys Ser Ala Cys Cys Ala Gly Ser Cys
    130                 135                 140

Cys Ser Pro Asp Cys Cys Ser Cys Cys Lys Pro Asn Cys Ser Cys
145                 150                 155                 160

Lys Thr Pro Ser Cys Cys Lys Pro Asn Cys Ser Cys Ser Cys Pro Ser
                165                 170                 175

Cys Ser Ser Cys Cys Asp Thr Ser Cys Cys Lys Pro Ser Cys Thr Cys
            180                 185                 190

Phe Asn Ile Phe Ser Cys Phe Lys Ser Leu Tyr Ser Cys Phe Lys Ile
        195                 200                 205

Pro Ser Cys Phe Lys Ser Gln Cys Asn Cys Ser Pro Asn Cys Cys
    210                 215                 220

Thr Cys Thr Leu Pro Ser Cys Ser Cys Lys Gly Cys Ala Cys Pro Ser
225                 230                 235                 240
```

Cys Gly Cys Asn Gly Cys Gly Cys Pro Ser Cys Gly Cys Asn Gly Cys
                245                 250                 255

Gly Cys Pro Ser Cys Gly Cys Asn Gly Cys Gly Leu Pro Ser Cys Gly
            260                 265                 270

Cys Asn Gly Cys Gly Ser Cys Ser Cys Ala Gln Cys Lys Pro Asp Cys
        275                 280                 285

Gly Ser Cys Ser Thr Asn Cys Cys Ser Cys Lys Pro Ser Cys Asn Gly
    290                 295                 300

Cys Cys Gly Glu Gln Cys Arg Cys Ala Asp Cys Phe Ser Cys Ser
305                 310                 315                 320

Cys Pro Arg Cys Ser Ser Cys Phe Asn Ile Phe Lys Cys Ser Cys Ala
                325                 330                 335

Gly Cys Cys Ser Ser Leu Cys Lys Cys Pro Cys Thr Thr Gln Cys Phe
            340                 345                 350

Ser Cys Gln Ser Ser Cys Cys Lys Arg Gln Pro Ser Cys Cys Lys Cys
        355                 360                 365

Gln Ser Ser Cys Cys Glu Gly Gln Pro Ser Cys Cys Glu Gly His Cys
    370                 375                 380

Cys Ser Leu Pro Lys Pro Ser Cys Pro Glu Cys Ser Cys Gly Cys Val
385                 390                 395                 400

Trp Ser Cys Lys Asn Cys Thr Glu Gly Cys Arg Cys Pro Arg Cys Arg
                405                 410                 415

Asn Pro Cys Cys Leu Ser Gly Cys Leu Cys
            420                 425

<210> SEQ ID NO 158
<211> LENGTH: 588
<212> TYPE: DNA
<213> ORGANISM: Oryza sativa

<400> SEQUENCE: 158
atgggggagg aggcggtggt gatggaggcg ccgaggccca gtcgccgcc gaggtacccg      60
gacctgtgcg gccggcggcg gatgcagctg gaggtgcaga tcctgagccg cgagatcacg     120
ttcctcaagg atgagcttca cttccttgaa ggagctcagc ccgtttctcg ttctggatgc     180
attaaagaga taaatgagtt tgttggtaca aaacatgacc cactaatacc aacaaagaga     240
aggaggcaca gatcttgccg tcttttttcgg tggatcggat caaaattgtg tatctgcatt    300
tcatgtcttt gctactgttg caagtgctca cccaagtgca aagaccaag gtgcctcaat      360
tgttcttgca gctcatgctg cgacgagcca tgctgtaagc caaactgcag tgcgtgctgc     420
gctgggtcat gctgcagtcc agactgctgc tcatgctgta aacctaactg cagttgctgc    480
aagaccccctt cttgctgcaa accgaactgc tcgtgctcct gtccaagctg cagctcatgc    540
tgcgatacat cgtgctgcaa accgagctgc acctgcttca acatctag                  588

<210> SEQ ID NO 159
<211> LENGTH: 196
<212> TYPE: PRT
<213> ORGANISM: Oryza sativa

<400> SEQUENCE: 159

Met Gly Glu Glu Ala Val Val Met Glu Ala Pro Arg Pro Lys Ser Pro
1               5                   10                  15

Pro Arg Tyr Pro Asp Leu Cys Gly Arg Arg Met Gln Leu Glu Val
            20                  25                  30

Gln Ile Leu Ser Arg Glu Ile Thr Phe Leu Lys Asp Glu Leu His Phe

```
                35                  40                  45
Leu Glu Gly Ala Gln Pro Val Ser Arg Ser Gly Cys Ile Lys Glu Ile
 50                  55                  60

Asn Glu Phe Val Gly Thr Lys His Asp Pro Leu Ile Pro Thr Lys Arg
 65                  70                  75                  80

Arg Arg His Arg Ser Cys Arg Leu Phe Arg Trp Ile Gly Ser Lys Leu
                 85                  90                  95

Cys Ile Cys Ile Ser Cys Leu Cys Tyr Cys Lys Cys Ser Pro Lys
            100                 105                 110

Cys Lys Arg Pro Arg Cys Leu Asn Cys Ser Cys Ser Ser Cys Cys Asp
        115                 120                 125

Glu Pro Cys Cys Lys Pro Asn Cys Ser Ala Cys Ala Gly Ser Cys
130                 135                 140

Cys Ser Pro Asp Cys Cys Ser Cys Cys Lys Pro Asn Cys Ser Cys
145                 150                 155                 160

Lys Thr Pro Ser Cys Cys Lys Pro Asn Cys Ser Cys Ser Cys Pro Ser
                165                 170                 175

Cys Ser Ser Cys Cys Asp Thr Ser Cys Cys Lys Pro Ser Cys Thr Cys
            180                 185                 190

Phe Asn Ile Phe
            195

<210> SEQ ID NO 160
<211> LENGTH: 462
<212> TYPE: DNA
<213> ORGANISM: Oryza sativa

<400> SEQUENCE: 160
atggccaaca gcaacctccc ccggcgaatc atcaaggaga cgcagcgact cctcagcgag      60
ccagcgccgg gaatcagcgc gtctccgtcg gaggagaaca tgcgctactt caacgtcatg     120
atccttggcc cggcacagtc cccctatgaa ggtggagttt ttaagcttga actcttttta     180
cctgaggaat atcctatggc tgctccaaag gttaggttcc tgaccaaaat ataccacccc     240
aacattgaca agcttggtag atatgccttt gacattctca aggacaaatg gagcccagcc     300
cttcagattc ggacagttct tttgagtatc caggcactcc taagtgcacc aaaccctgat     360
gatcctctct ctgataacat tgcaaagcac tggaaagcca atgaagcaga agctgttgaa     420
acagcaaagg agtggactcg cctgtatgcc agcggtgcat aa                       462

<210> SEQ ID NO 161
<211> LENGTH: 153
<212> TYPE: PRT
<213> ORGANISM: Oryza sativa

<400> SEQUENCE: 161

Met Ala Asn Ser Asn Leu Pro Arg Arg Ile Ile Lys Glu Thr Gln Arg
 1               5                  10                  15

Leu Leu Ser Glu Pro Ala Pro Gly Ile Ser Ala Ser Pro Ser Glu Glu
             20                  25                  30

Asn Met Arg Tyr Phe Asn Val Met Ile Leu Gly Pro Ala Gln Ser Pro
         35                  40                  45

Tyr Glu Gly Gly Val Phe Lys Leu Glu Leu Phe Leu Pro Glu Glu Tyr
     50                  55                  60

Pro Met Ala Ala Pro Lys Val Arg Phe Leu Thr Lys Ile Tyr His Pro
 65                  70                  75                  80
```

```
Asn Ile Asp Lys Leu Gly Arg Ile Cys Leu Asp Ile Leu Lys Asp Lys
             85                  90                  95

Trp Ser Pro Ala Leu Gln Ile Arg Thr Val Leu Leu Ser Ile Gln Ala
            100                 105                 110

Leu Leu Ser Ala Pro Asn Pro Asp Asp Pro Leu Ser Asp Asn Ile Ala
            115                 120                 125

Lys His Trp Lys Ala Asn Glu Ala Glu Ala Val Glu Thr Ala Lys Glu
            130                 135                 140

Trp Thr Arg Leu Tyr Ala Ser Gly Ala
145                 150

<210> SEQ ID NO 162
<211> LENGTH: 2597
<212> TYPE: DNA
<213> ORGANISM: Oryza sativa

<400> SEQUENCE: 162
```

| | | | | | |
|---|---|---|---|---|---|
| atggccaaca | gcaacctccc | ccggcgaatc | atcaaggtcg | cgcctccgat | ctgattgcct | 60 |
| gggcgtagat | ctccccacgc | tctaacccg | attccccct | tttctttttct | ttttttttt | 120 |
| attttccctt | tctgtgctga | ttttttgttt | ttgctgtctg | tgtgttcgcg | tctggtttgg | 180 |
| atctgcgcag | gagacgcagc | gactcctcag | cgagccaggt | gcgggcggtt | tttttttttt | 240 |
| ttatgtatcg | cggattttgg | cgatggtgtt | gtgttttcc | gtggtttggg | ttcgtgttgt | 300 |
| tctgatggtt | ttgggttggt | ttgtttgtgc | agcgccggga | atcagcgcgt | ctccgtcgga | 360 |
| ggagaacatg | cgctacttca | acgtcatgat | ccttggcccg | gcacagtccc | cctatgaagg | 420 |
| tacggcaccc | gatggatacg | ttatttgttg | tagagggtgt | tacggctccc | gatggatatg | 480 |
| ttatttgttg | tagagggtgg | tcgattaggg | cgtttctagg | tataccgcag | aattgggtga | 540 |
| ttctgtataa | acccaattac | tagaagtgtt | aattatgtgt | cagtcatgga | cgggcacgca | 600 |
| tttcgtaagc | ctgcttttgc | ttgattaggc | tggttctttt | gcacttacca | gttttagttt | 660 |
| ctcgggcggc | gggcacttgc | atgttctatg | tgtctcatat | tccctttcta | gtatgaagtt | 720 |
| agtaatgcta | aaacactagt | gacttttagc | aataatgttc | taaactcgga | ttatatacgt | 780 |
| gacttataag | tgcttttctt | ttatgtgtta | acttgtttga | tgctttgtgc | ggcaaaggtt | 840 |
| gcccttgatt | ttccataacc | aaattgatct | cttcgattta | tttgattaga | ctaattatga | 900 |
| gtattgatat | tgttggcttt | tcatgttgtg | gtgtataatt | taaatatttc | ctttcttaaa | 960 |
| cccttttgc | gttaattcgg | gttggatata | taatgggtgt | taacagttag | tagctttaga | 1020 |
| tggtttattc | tattatcatt | tggcttcctg | atattgttct | ttctatcagg | tggagttttt | 1080 |
| aagcttgaac | tcttttttacc | tgaggaatat | cctatggctg | ctccaaaggt | aacaagacat | 1140 |
| agataaactt | tggttatgtt | ttatatgata | ttatggggac | tgtatacctt | caagctaatt | 1200 |
| atgtcgtatt | tagaattgcg | tgtggttata | tactcatatt | aaaagtcagg | acatttctgc | 1260 |
| attcattgac | ttgtgttgtg | aagcggagca | ttaatttggt | gacattggac | tcatgcatat | 1320 |
| aaccaaatac | aggaaagtag | ctgaaacatt | taatttgttt | gaaccattct | ttggcaaaaa | 1380 |
| aaaatttta | ttcttttatag | cctaattttt | agttacccat | atttaatcgt | gtcgctctgg | 1440 |
| aaccatcgtt | ggtttatat | gttatatgtg | atgtcttgtt | ggtaatagtt | ttgttacatt | 1500 |
| tgcttgattt | ccttttaggg | ataatgcaaa | ccctgcctat | ttgagatgta | atttgcaatg | 1560 |
| agatcctgtg | ccaaggacca | aggttgtaag | atatactttt | ggtcctgtgg | gaacttttag | 1620 |
| ctgtgtcctg | agcatcagca | cgccattgct | tctcttgacc | gtctttttgc | ttcaagttct | 1680 |

```
taaaggtgtt cttaacatca cattgttcgt ttggtgttca gccaaattat accttgatta    1740 gttattttt tagtctgttt ggcttgacaa tgtcatagat tggaagggtg aagaaatatt    1800
actcatatgt tatacaacca taccggatta ttgtctactt cagtctccct aagtgtaaag    1860
ctatataatt cattattgtc tacctcagtc tccatttttt ctttgttgcg tatgcaggtt    1920
aggttcctga ccaaaatata ccaccccaac attgacaagg tttgcagtca cattcctctt    1980
tgttatttag tttacttcgt aatacattgt ttattcatta ataggtttac ttttgtagct    2040
tggtaggata tgccttgaca ttctcaagga caaatggagc ccagcccttc agattcggac    2100
agttcttttg aggtctctcc cccgttgcct gcacatgtgt attagctttt tatatcctgc    2160
acaaattcct tgtctgctaa gctgttgtct tattacgatt gacatgattt ctgttgaatt    2220
tgaattattt gttagcttac ctgcatttag taattttatc actgcccttg atgtgttttt    2280
ccaacaaaaa ctcttgagca ttgtcaacta ttggaagtta ggggtatcac tttgctatac    2340
ttaccttgtg acaacactct ttttttcag tatccaggca ctcctaagtg caccaaaccc    2400
tgatgatcct ctctctgata acattgcaaa gcactgaaaa gccaatgaag cagaagctgt    2460
tgaaacaggt aaattgaagc tagcaatcca gttaacagtg tctcccctca cactctgatt    2520
ttattggttg cctgataagc gatggtctgg catttgcagc aaaggagtgg actcgcctgt    2580
atgccagcgg tgcataa                                                  2597
```

<210> SEQ ID NO 163
<211> LENGTH: 388
<212> TYPE: DNA
<213> ORGANISM: Artificial Sequence
<220> FEATURE:
<223> OTHER INFORMATION: U3 promoter sequence

<400> SEQUENCE: 163

```
aaaggaagga atctttaaac atacgaacag atcacttaaa gttcttctga agcaacttaa     60
agttatcagg catgcatgga tcttggagga atcagatgtg cagtcaggga ccatagcaca    120
agacaggcgt cttctactgg tgctaccagc aaatgctgga agccgggaac actgggtacg    180
ttggaaacca cgtgtgatgt gaaggagtaa gataaactgt aggagaaaag catttcgtag    240
tgggccatga agcctttcag gacatgtatt gcagtatggg ccggcccatt acgcaattgg    300
acgacaacaa agactagtat tagtaccacc tcggctatcc acatagatca aagctggttt    360
aaaagagttg tgcagatgat ccgtggca                                       388
```

<210> SEQ ID NO 164
<211> LENGTH: 447
<212> TYPE: DNA
<213> ORGANISM: Artificial Sequence
<220> FEATURE:
<223> OTHER INFORMATION: U6a promoter sequence

<400> SEQUENCE: 164

```
tttttttcctg tagtttttccc acaaccattt tttaccatcc gaatgatagg ataggaaaaa    60
tatccaagtg aacagtattc ctataaaatt cccgtaaaaa gcctgcaatc cgaatgagcc    120
ctgaagtctg aactagccgg tcacctgtac aggctatcga gatgccatac aagagacggt    180
agtaggaact aggaagacga tggttgattc gtcaggcgaa atcgtcgtcc tgcagtcgca    240
tctatgggcc tggacggaat aggggaaaaa gttggccgga taggagggaa aggcccaggt    300
gcttacgtgc gaggtaggcc tgggctctca gcacttcgat tcgttggcac cggggtagga    360
tgcaatagag agcaacgttt agtaccacct cgcttagcta gagcaaactg gactgcctta    420
```
tatgcgcggg tgctggcttg gctgccg                                          447

<210> SEQ ID NO 165
<211> LENGTH: 333
<212> TYPE: DNA
<213> ORGANISM: Artificial Sequence
<220> FEATURE:
<223> OTHER INFORMATION: U6b promoter sequence

<400> SEQUENCE: 165
tgcaagaacg aactaagccg acaaaaaaa aaaggagcac atatacaaac cggtttatt       60 catgaatggt cacgatggat gatgggctc agacttgagc tacgaggccg caggcgagag     120
aagcctagtg tgctctctgc ttgtttgggc cgtaacggag gatacggccg acgagcgtgt   180
actaccgcgc gggatgccgc tgggcgctgc ggggcccgtt ggatggggat cggtgggtcg   240
cgggagcgtt gaggggagac aggtttagta ccacctcgcc taccgaacaa tgaagaaccc   300
accttataac cccgcgcgct gccgcttgtg ttg                                  333

<210> SEQ ID NO 166
<211> LENGTH: 325
<212> TYPE: DNA
<213> ORGANISM: Artificial Sequence
<220> FEATURE:
<223> OTHER INFORMATION: U3b in dicot plant

<400> SEQUENCE: 166
tttactttaa attttttctt atgcagcctg tgatggataa ctgaatcaaa caaatggcgt     60
ctgggtttaa gaagatctgt tttggctatg ttggacgaaa caagtgaact tttaggatca   120
acttcagttt atatatggag cttatatcga gcaataagat aagtgggctt tttatgtaat   180
ttaatgggct atcgtccata gattcactaa tacccatgcc cagtacccat gtatgcgttt   240
catataagct cctaatttct cccacatcgc tcaaatctaa acaaatcttg ttgtatatat   300
aacactgagg gagcaacatt ggtca                                           325

<210> SEQ ID NO 167
<211> LENGTH: 305
<212> TYPE: DNA
<213> ORGANISM: Artificial Sequence
<220> FEATURE:
<223> OTHER INFORMATION: U6-1 in dicot plant

<400> SEQUENCE: 167
agaaatctca aaattccggc agaacaattt tgaatctcga tccgtagaaa cgagacggtc     60
attgttttag ttccaccacg attatatttg aaatttacgt gagtgtgagt gagacttgca   120
taagaaaata aaatctttag ttgggaaaaa attcaataat ataaatgggc ttgagaagga   180
agcgagggat aggccttttt ctaaaatagg cccatttaag ctattaacaa tcttcaaaag   240
taccacagcg cttaggtaaa gaaagcagct gagtttatat atggttagag acgaagtagt   300
gattg                                                                 305

<210> SEQ ID NO 168
<211> LENGTH: 4782
<212> TYPE: DNA
<213> ORGANISM: Artificial Sequence
<220> FEATURE:
<223> OTHER INFORMATION: Cys4-P2A-TaCas9 nucleic acid sequence

<400> SEQUENCE: 168

```
atggaccact acctcgacat caggctcagg ccagacccag agttcccacc agcccagctc    60
atgtccgtcc tcttcggcaa gctccaccag gccctcgtgg cccagggcgg cgacaggatc   120
ggcgtgtcct tcccagacct cgacgagtcc aggtccaggc tcggcgagag gctccgcatc   180
cacgcctccg ccgacgacct cagggccctc ctcgccaggc cgtggctgga gggcctcagg   240
gaccacctcc agttcggcga gccagccgtg gtgccacacc caaccccata caggcaagtg   300
tccagggtgc aagccaagtc aacccagag aggctcagga ggaggctcat gaggaggcac    360
gacctctccg aggaagaggc caggaagcgc atcccagaca ccgtggccag ggccctcgac   420
ctcccattcg tgaccctcag gtccagtcc accggccagc acttccgcct cttcatcagg    480
cacggcccac tccaggtgac cgccgaggag ggcggcttta cctgctacgg cctctccaag   540
ggcggcttcg tgccgtggtt cggctccggc gccaccaact tctccctcct caagcaagcc   600
ggcgacgtgg aggagaaccc aggcccaatg acaagaagt actcgatcgg cctcgacatc    660
gggacgaact cagttggctg ggccgtgatc accgacgagt acaaggtgcc ctctaagaag   720
ttcaaggtcc tgggaacac cgaccgccat tccatcaaga agaacctcat cggcgctctc    780
ctgttcgaca gcggggagac cgctgaggct acgaggctca agaaccgc taggcgccgg    840
tacacgaaga ggaagaacag gatctgctac ctccaagaga ttttctccaa cgagatggcc   900
aaggttgacg attcattctt ccaccgcctg gaggagtctt tcctcgtgga ggaggataag   960
aagcacgagc ggcatcccat cttcggcaac atcgtggacg aggttgccta ccacgagaag  1020
taccctacga tctaccatct gcggaagaag ctcgtggact ccaccgataa ggcggacctc  1080
agactgatct acctcgctct ggcccacatg atcaagttcc gcggccattt cctgatcgag  1140
ggggatctca acccagacaa cagcgatgtt gacaagctgt tcatccaact cgtgcagacc  1200
tacaaccaac tcttcgagga gaacccgatc aacgcctctg gcgtggacgc gaaggctatc  1260
ctgtccgcga ggctctcgaa gtccaggagg ctggagaacc tgatcgctca gctcccaggc  1320
gagaagaaga acggcctgtt cgggaacctc atcgctctca gcctggggct caccccgaac  1380
ttcaagtcga acttcgatct cgctgaggac gccaagctgc aactctccaa ggacacctac  1440
gacgatgacc tcgataacct cctggcccag atcggcgatc aatacgcgga cctgttcctc  1500
gctgccaaga acctgtcgga cgccatcctc ctgtcagata tcctccgcgt gaacaccgag  1560
atcacgaagg ctccactctc tgcctccatg atcaagcgct acgacgagca ccatcaggat  1620
ctgaccctcc tgaaggcgct ggtccgccaa cagctcccgg agaagtacaa ggagattttc  1680
ttcgatcagt cgaagaacgg ctacgctggg tacatcgacg gcggggcctc acaagaggag  1740
ttctacaagt tcatcaagcc aatcctggag aagatggacg gcacggagga gctcctggtg  1800
aagctcaaca gggaggacct cctgcggaag cagagaacct tcgataacgg cagcatcccc  1860
caccaaatcc atctcgggga gctgcacgcc atcctgagaa ggcaagagga cttctaccct  1920
ttcctcaagg ataaccggga gaagatcgag aagatcctga ccttcagaat cccatactac  1980
gtcggccctc tcgcgcgggg gaactcaaga ttcgcttgga tgacccgcaa gtctgaggag  2040
accatcacgc cgtggaactt cgaggaggtg gtggacaagg gcgctagcgc tcagtcgttc  2100
atcgagagga tgaccaactt cgacaagaac ctgcccaacg agaaggtgct ccctaagcac  2160
tcgctcctgt acgagtactt caccgtctac aacgagctca cgaaggtgaa gtacgtcacc  2220
gagggcatgc gcaagccagc gttcctgtcc ggggagcaga agaaggctat cgtggacctc  2280
ctgttcaaga ccaaccggaa ggtcacggtt aagcaactca aggaggacta cttcaagaag  2340
atcgagtgct tcgattcggt cgagatcagc ggcgttgagg accgcttcaa cgccagcctc  2400
```

```
gggacctacc acgatctcct gaagatcatc aaggataagg acttcctgga caacgaggag    2460
aacgaggata tcctggagga catcgtgctg accctcacgc tgttcgagga cagggagatg    2520
atcgaggagc gcctgaagac gtacgcccat ctcttcgatg acaaggtcat gaagcaactc    2580
aagcgccgga gatacaccgg ctgggggagg ctgtcccgca agctcatcaa cggcatccgg    2640
gacaagcagt ccgggaagac catcctcgac ttcctcaaga gcgatggctt cgccaacagg    2700
aacttcatgc aactgatcca cgatgacagc ctcaccttca aggaggatat ccaaaaggct    2760
caagtgagcg gccaggggga ctcgctgcac gagcatatcg cgaacctcgc tggctccccc    2820
gcgatcaaga agggcatcct ccagaccgtg aaggttgtgg acgagctcgt gaaggtcatg    2880
ggccggcaca agcctgagaa catcgtcatc gagatggcca gagagaacca aaccacgcag    2940
aaggggcaaa agaactctag ggagcgcatg aagcgcatcg aggagggcat caaggagctg    3000
gggtcccaaa tcctcaagga gcacccagtg gagaacaccc aactgcagaa cgagaagctc    3060
tacctgtact acctccagaa cggcagggat atgtacgtgg accaagagct ggatatcaac    3120
cgcctcagcg attacgacgt cgatcatatc gttccccagt cttttcctgaa ggatgactcc    3180 atcgacaaca aggtcctcac caggtcggac aagaaccgcg gcaagtcaga taacgttcca    3240
tctgaggagg tcgttaagaa gatgaagaac tactggaggc agctcctgaa cgccaagctg    3300
atcacgcaaa ggaagttcga caacctcacc aaggctgaga gaggcgggct ctcagagctg    3360
gacaaggccg gcttcatcaa gcggcagctg gtcgagacca gacaaatcac gaagcacgtt    3420
gcgcaaatcc tcgactctcg gatgaacacg aagtacgatg agaacgacaa gctgatcagg    3480
gaggttaagg tgatcaccct gaagtctaag ctcgtctccg acttcaggaa ggatttccag    3540
ttctacaagg ttcgcgagat caacaactac caccatgccc atgacgctta cctcaacgct    3600
gtggtcggca ccgctctgat caagaagtac ccaaagctgg agtccgagtt cgtgtacggg    3660
gactacaagg tttacgatgt gcgcaagatg atcgccaagt cggagcaaga gatcggcaag    3720
gctaccgcca agtacttctt ctactcaaac atcatgaact tcttcaagac cgagatcacg    3780
ctggccaacg gcgagatccg gaagagaccg ctcatcgaga ccaacggcga gacggggggag    3840 atcgtgtggg acaagggcag ggatttcgcg accgtccgca aggttctctc catgccccag    3900
gtgaacatcg tcaagaagac cgaggtccaa acgggcgggt tctcaaagga gtctatcctg    3960
cctaagcgga acagcgacaa gctcatcgcc agaaagaagg actgggaccc aaagaagtac    4020
ggcgggttcg acagccctac cgtggcctac tcggtcctgg ttgtggcgaa ggttgagaag    4080
ggcaagtcca agaagctcaa gagcgtgaag gagctcctgg ggatcaccat catggagagg    4140
tccagcttcg agaagaaccc aatcgacttc ctggaggcca agggctacaa ggaggtgaag    4200
aaggacctga tcatcaagct cccgaagtac tctctcttcg agctggagaa cggcaggaag    4260
agaatgctgg cttccgctgg cgagctccag aagggggaacg agctcgcgct gccaagcaag    4320
tacgtgaact tcctctacct ggcttcccac tacgagaagc tcaagggcag cccggaggac    4380
aacgagcaaa agcagctgtt cgtcgagcag cacaagcatt acctcgacga gatcatcgag    4440
caaatctccg agttcagcaa gcgcgtgatc ctcgccgacg cgaacctgga taaggtcctc    4500
tccgcctaca caagcaccg ggacaagccc atcagagagc aagcggagaa catcatccat    4560
ctcttcaccc tgacgaacct cggcgctcct gctgctttca agtacttcga caccacgatc    4620
gatcggaaga gatacaccct cacgaaggag gtcctggacg cgacccctcat ccaccagtcg    4680 atcaccggcc tgtacgagac gaggatcgac ctctcacaac tcggcgggga taagagaccc    4740
```

```
gcagcaacca agaaggcagg gcaagcaaag aagaagaagt ga            4782
```

<210> SEQ ID NO 169
<211> LENGTH: 561
<212> TYPE: DNA
<213> ORGANISM: Artificial Sequence
<220> FEATURE:
<223> OTHER INFORMATION: Cys 4 endoribonuclease nucleic acid sequence

<400> SEQUENCE: 169

```
atggaccact acctcgacat caggctcagg ccagacccag agttcccacc agcccagctc    60
atgtccgtcc tcttcggcaa gctccaccag gccctcgtgg cccagggcgg cgacaggatc   120
ggcgtgtcct tcccagacct cgacgagtcc aggtccaggc tcggcgagag gctccgcatc   180
cacgcctccg ccgacgacct cagggccctc ctcgccaggc cgtggctgga gggcctcagg   240
gaccacctcc agttcggcga ccagccgtg gtgccacacc caaccccata caggcaagtg    300
tccagggtgc aagccaagtc caacccagag aggctcagga ggaggctcat gaggaggcac   360
gacctctccg aggaagaggc caggaagcgc atcccagaca ccgtgccag ggccctcgac     420
ctcccattcg tgaccctcag gtccagtcc accggccagc acttccgcct cttcatcagg    480
cacggcccac tccaggtgac cgccgaggag ggcggcttta cctgctacgg cctctccaag   540
ggcggcttcg tgccgtggtt c                                             561
```

<210> SEQ ID NO 170
<211> LENGTH: 37
<212> TYPE: DNA
<213> ORGANISM: Artificial Sequence
<220> FEATURE:
<223> OTHER INFORMATION: fwd primer 1

<400> SEQUENCE: 170

```
agcggcggtg ggggaggagg gttttagagc tagaaat                             37
```

<210> SEQ ID NO 171
<211> LENGTH: 37
<212> TYPE: DNA
<213> ORGANISM: Artificial Sequence
<220> FEATURE:
<223> OTHER INFORMATION: rev primer 1

<400> SEQUENCE: 171

```
cctcctcccc caccgccgct cggcagccaa gccagca                             37
```

<210> SEQ ID NO 172
<211> LENGTH: 37
<212> TYPE: DNA
<213> ORGANISM: Artificial Sequence
<220> FEATURE:
<223> OTHER INFORMATION: fwd primer 2

<400> SEQUENCE: 172

```
gggaggagga gggggggggg gttttagagc tagaaat                             37
```

<210> SEQ ID NO 173
<211> LENGTH: 37
<212> TYPE: DNA
<213> ORGANISM: Artificial Sequence
<220> FEATURE:
<223> OTHER INFORMATION: rev primer 2

<400> SEQUENCE: 173

```
cccccccccc tcctcctccc cggcagccaa gccagca                             37
```

<210> SEQ ID NO 174
<211> LENGTH: 37
<212> TYPE: DNA
<213> ORGANISM: Artificial Sequence
<220> FEATURE:
<223> OTHER INFORMATION: fwd primer 3

<400> SEQUENCE: 174 gggggggagga ggaggggggg gttttagagc tagaaat                                37

<210> SEQ ID NO 175
<211> LENGTH: 37
<212> TYPE: DNA
<213> ORGANISM: Artificial Sequence
<220> FEATURE:
<223> OTHER INFORMATION: rev primer 3

<400> SEQUENCE: 175
ccccccctcc tcctccccccc cggcagccaa gccagca                                37

<210> SEQ ID NO 176
<211> LENGTH: 37
<212> TYPE: DNA
<213> ORGANISM: Artificial Sequence
<220> FEATURE:
<223> OTHER INFORMATION: fwd primer 4

<400> SEQUENCE: 176 tcgaggggg aggaggaggg gttttagagc tagaaat                                  37

<210> SEQ ID NO 177
<211> LENGTH: 37
<212> TYPE: DNA
<213> ORGANISM: Artificial Sequence
<220> FEATURE:
<223> OTHER INFORMATION: rev primer 4

<400> SEQUENCE: 177
ccctcctcct ccccccctcga cggcagccaa gccagca                                37

<210> SEQ ID NO 178
<211> LENGTH: 37
<212> TYPE: DNA
<213> ORGANISM: Artificial Sequence
<220> FEATURE:
<223> OTHER INFORMATION: fwd primer 5

<400> SEQUENCE: 178
gtcgtcgagg ggggaggagg gttttagagc tagaaat                                 37

<210> SEQ ID NO 179
<211> LENGTH: 37
<212> TYPE: DNA
<213> ORGANISM: Artificial Sequence
<220> FEATURE:
<223> OTHER INFORMATION: rev primer 5

<400> SEQUENCE: 179
cctcctcccc cctcgacgac cggcagccaa gccagca                                 37

<210> SEQ ID NO 180
<211> LENGTH: 37
<212> TYPE: DNA
<213> ORGANISM: Artificial Sequence
<220> FEATURE:

<223> OTHER INFORMATION: fwd primer 6

<400> SEQUENCE: 180
ggcagccgcg gcccccgagc gttttagagc tagaaat       37

<210> SEQ ID NO 181
<211> LENGTH: 37
<212> TYPE: DNA
<213> ORGANISM: Artificial Sequence
<220> FEATURE:
<223> OTHER INFORMATION: rev primer 6

<400> SEQUENCE: 181 gctcggggc cgcggctgcc cggcagccaa gccagca       37

<210> SEQ ID NO 182
<211> LENGTH: 37
<212> TYPE: DNA
<213> ORGANISM: Artificial Sequence
<220> FEATURE:
<223> OTHER INFORMATION: fwd primer 7

<400> SEQUENCE: 182
tcccggagga ggcggtgatg gttttagagc tagaaat       37

<210> SEQ ID NO 183
<211> LENGTH: 37
<212> TYPE: DNA
<213> ORGANISM: Artificial Sequence
<220> FEATURE:
<223> OTHER INFORMATION: rev primer 7

<400> SEQUENCE: 183
catcaccgcc tcctccggga cggcagccaa gccagca       37

<210> SEQ ID NO 184
<211> LENGTH: 37
<212> TYPE: DNA
<213> ORGANISM: Artificial Sequence
<220> FEATURE:
<223> OTHER INFORMATION: fwd primer 8

<400> SEQUENCE: 184
cgcccggaag cgcaaggcgg gttttagagc tagaaat       37

<210> SEQ ID NO 185
<211> LENGTH: 37
<212> TYPE: DNA
<213> ORGANISM: Artificial Sequence
<220> FEATURE:
<223> OTHER INFORMATION: rev primer 8

<400> SEQUENCE: 185
ccgccttgcg cttccgggcg cggcagccaa gccagca       37

<210> SEQ ID NO 186
<211> LENGTH: 37
<212> TYPE: DNA
<213> ORGANISM: Artificial Sequence
<220> FEATURE:
<223> OTHER INFORMATION: fwd primer 9

<400> SEQUENCE: 186
gaagagaaga acacgcaccg gttttagagc tagaaat       37

-continued

```
<210> SEQ ID NO 187
<211> LENGTH: 37
<212> TYPE: DNA
<213> ORGANISM: Artificial Sequence
<220> FEATURE:
<223> OTHER INFORMATION: rev primer 9

<400> SEQUENCE: 187
cggtgcgtgt tcttctcttc cggcagccaa gccagca                              37

<210> SEQ ID NO 188
<211> LENGTH: 37
<212> TYPE: DNA
<213> ORGANISM: Artificial Sequence
<220> FEATURE:
<223> OTHER INFORMATION: fwd primer 10

<400> SEQUENCE: 188
cccttacggc ctccactctg gttttagagc tagaaat                              37

<210> SEQ ID NO 189
<211> LENGTH: 37
<212> TYPE: DNA
<213> ORGANISM: Artificial Sequence
<220> FEATURE:
<223> OTHER INFORMATION: rev primer 10

<400> SEQUENCE: 189
cagagtggag gccgtaaggg cggcagccaa gccagca                              37

<210> SEQ ID NO 190
<211> LENGTH: 37
<212> TYPE: DNA
<213> ORGANISM: Artificial Sequence
<220> FEATURE:
<223> OTHER INFORMATION: fwd primer 11

<400> SEQUENCE: 190
cactttctcc ttatgacacg gttttagagc tagaaat                              37

<210> SEQ ID NO 191
<211> LENGTH: 37
<212> TYPE: DNA
<213> ORGANISM: Artificial Sequence
<220> FEATURE:
<223> OTHER INFORMATION: rev primer 11

<400> SEQUENCE: 191
cgtgtcataa ggagaaagtg cggcagccaa gccagca                              37

<210> SEQ ID NO 192
<211> LENGTH: 37
<212> TYPE: DNA
<213> ORGANISM: Artificial Sequence
<220> FEATURE:
<223> OTHER INFORMATION: fwd primer 12

<400> SEQUENCE: 192
tatataagct cgtcagaatg gttttagagc tagaaat                              37

<210> SEQ ID NO 193
<211> LENGTH: 37
<212> TYPE: DNA
<213> ORGANISM: Artificial Sequence
<220> FEATURE:
<223> OTHER INFORMATION: rev primer 12
```

<400> SEQUENCE: 193
cattctgacg agcttatata cggcagccaa gccagca                                37

<210> SEQ ID NO 194
<211> LENGTH: 37
<212> TYPE: DNA
<213> ORGANISM: Artificial Sequence
<220> FEATURE:
<223> OTHER INFORMATION: fwd primer 13

<400> SEQUENCE: 194
cgagaagcac tggatctgat gttttagagc tagaaat                                37

<210> SEQ ID NO 195
<211> LENGTH: 37
<212> TYPE: DNA
<213> ORGANISM: Artificial Sequence
<220> FEATURE:
<223> OTHER INFORMATION: rev primer 13

<400> SEQUENCE: 195
atcagatcca gtgcttctcg cggcagccaa gccagca                                37

<210> SEQ ID NO 196
<211> LENGTH: 37
<212> TYPE: DNA
<213> ORGANISM: Artificial Sequence
<220> FEATURE:
<223> OTHER INFORMATION: fwd primer 14

<400> SEQUENCE: 196
gagaggagga agtagagcgc gttttagagc tagaaat                                37

<210> SEQ ID NO 197
<211> LENGTH: 37
<212> TYPE: DNA
<213> ORGANISM: Artificial Sequence
<220> FEATURE:
<223> OTHER INFORMATION: rev primer 14

<400> SEQUENCE: 197
gcgctctact tcctcctctc cggcagccaa gccagca                                37

<210> SEQ ID NO 198
<211> LENGTH: 37
<212> TYPE: DNA
<213> ORGANISM: Artificial Sequence
<220> FEATURE:
<223> OTHER INFORMATION: fwd primer 15

<400> SEQUENCE: 198
taaacccaaa ccacaaatca gttttagagc tagaaat                                37

<210> SEQ ID NO 199
<211> LENGTH: 37
<212> TYPE: DNA
<213> ORGANISM: Artificial Sequence
<220> FEATURE:
<223> OTHER INFORMATION: rev primer 15

<400> SEQUENCE: 199
tgatttgtgg tttgggttta cggcagccaa gccagca                                37

<210> SEQ ID NO 200
<211> LENGTH: 37

```
<212> TYPE: DNA
<213> ORGANISM: Artificial Sequence
<220> FEATURE:
<223> OTHER INFORMATION: fwd primer 16

<400> SEQUENCE: 200
atgtacccat tcctcctcga gttttagagc tagaaat                              37

<210> SEQ ID NO 201
<211> LENGTH: 37
<212> TYPE: DNA
<213> ORGANISM: Artificial Sequence
<220> FEATURE:
<223> OTHER INFORMATION: rev primer 16

<400> SEQUENCE: 201
tcgaggagga atgggtacat cggcagccaa gccagca                              37

<210> SEQ ID NO 202
<211> LENGTH: 37
<212> TYPE: DNA
<213> ORGANISM: Artificial Sequence
<220> FEATURE:
<223> OTHER INFORMATION: fwd primer 17

<400> SEQUENCE: 202
aacgtacatc gcgtcgcagc gttttagagc tagaaat                              37

<210> SEQ ID NO 203
<211> LENGTH: 37
<212> TYPE: DNA
<213> ORGANISM: Artificial Sequence
<220> FEATURE:
<223> OTHER INFORMATION: rev primer 17

<400> SEQUENCE: 203
gctgcgacgc gatgtacgtt cggcagccaa gccagca                              37

<210> SEQ ID NO 204
<211> LENGTH: 37
<212> TYPE: DNA
<213> ORGANISM: Artificial Sequence
<220> FEATURE:
<223> OTHER INFORMATION: fwd primer 18

<400> SEQUENCE: 204
actatcttac tacttgtgca gttttagagc tagaaat                              37

<210> SEQ ID NO 205
<211> LENGTH: 37
<212> TYPE: DNA
<213> ORGANISM: Artificial Sequence
<220> FEATURE:
<223> OTHER INFORMATION: rev primer 18

<400> SEQUENCE: 205
tgcacaagta gtaagatagt cggcagccaa gccagca                              37

<210> SEQ ID NO 206
<211> LENGTH: 37
<212> TYPE: DNA
<213> ORGANISM: Artificial Sequence
<220> FEATURE:
<223> OTHER INFORMATION: fwd primer 19

<400> SEQUENCE: 206
```

```
tcggaagaat aattacaacc gttttagagc tagaaat                                37
```

<210> SEQ ID NO 207
<211> LENGTH: 37
<212> TYPE: DNA
<213> ORGANISM: Artificial Sequence
<220> FEATURE:
<223> OTHER INFORMATION: rev primer 19

<400> SEQUENCE: 207

```
ggttgtaatt attcttccga cggcagccaa gccagca                                37
```

<210> SEQ ID NO 208
<211> LENGTH: 37
<212> TYPE: DNA
<213> ORGANISM: Artificial Sequence
<220> FEATURE:
<223> OTHER INFORMATION: fwd primer 20

<400> SEQUENCE: 208

```
gtaggcagca acctcaaact gttttagagc tagaaat                                37
```

<210> SEQ ID NO 209
<211> LENGTH: 37
<212> TYPE: DNA
<213> ORGANISM: Artificial Sequence
<220> FEATURE:
<223> OTHER INFORMATION: rev primer 20

<400> SEQUENCE: 209

```
agtttgaggt tgctgcctac cggcagccaa gccagca                                37
```

<210> SEQ ID NO 210
<211> LENGTH: 310
<212> TYPE: DNA
<213> ORGANISM: Artificial Sequence
<220> FEATURE:
<223> OTHER INFORMATION: RNAi nucleic acid sequence

<400> SEQUENCE: 210

```
tctggtgaaa tccaaaggag ggccgagttc ttcgaaccat tcatctctgg cttgacaaat       60
tcgactgtgg ttcagttctg caaggcttcc gtggagccga tgggcgagga aagtgaccat      120
gtccacataa ttgccctatc agatgcgttg ggtgtgccaa tccgtgtgat gtacctagac      180
agaagctcat gtgatgctgg aaatataagt gtgaaccacc atgatttcag ccctgaggcc      240
aattcatcgg acggtgctgc tgctgctgag aaaccttaca ttactttgct ctaccgtcct      300
ggtcactacg                                                              310
```

<210> SEQ ID NO 211
<211> LENGTH: 248
<212> TYPE: PRT
<213> ORGANISM: Artificial Sequence
<220> FEATURE:
<223> OTHER INFORMATION: Otubain-like domain

<400> SEQUENCE: 211

```
Pro Tyr Val Gly Asp Lys Glu Pro Leu Ser Thr Leu Ala Ala Glu Phe
1               5                   10                  15

Gln Ser Gly Ser Pro Ile Leu Gln Glu Lys Ile Lys Leu Leu Gly Glu
            20                  25                  30

Gln Tyr Asp Ala Leu Arg Arg Thr Arg Gly Asp Gly Asn Cys Phe Tyr
        35                  40                  45
```

```
Arg Ser Phe Met Phe Ser Tyr Leu Glu His Ile Leu Glu Thr Gln Asp
    50                  55                  60

Lys Ala Glu Val Glu Arg Ile Leu Lys Lys Ile Glu Gln Cys Lys Lys
65                  70                  75                  80

Thr Leu Ala Asp Leu Gly Tyr Ile Glu Phe Thr Phe Glu Asp Phe Phe
                    85                  90                  95

Ser Ile Phe Ile Asp Gln Leu Glu Ser Val Leu Gln Gly His Glu Ser
                100                 105                 110

Ser Ile Gly Ala Glu Glu Leu Leu Glu Arg Thr Arg Asp Gln Met Val
            115                 120                 125

Ser Asp Tyr Val Val Met Phe Phe Arg Phe Val Thr Ser Gly Glu Ile
    130                 135                 140

Gln Arg Arg Ala Glu Phe Phe Glu Pro Phe Ile Ser Gly Leu Thr Asn
145                 150                 155                 160

Ser Thr Val Val Gln Phe Cys Lys Ala Ser Val Glu Pro Met Gly Glu
                165                 170                 175

Glu Ser Asp His Val His Ile Ile Ala Leu Ser Asp Ala Leu Gly Val
                180                 185                 190

Pro Ile Arg Val Met Tyr Leu Asp Arg Ser Ser Cys Asp Ala Gly Asn
            195                 200                 205

Ile Ser Val Asn His His Asp Phe Ser Pro Glu Ala Asn Ser Ser Asp
    210                 215                 220

Gly Ala Ala Ala Ala Glu Lys Pro Tyr Ile Thr Leu Leu Tyr Arg Pro
225                 230                 235                 240

Gly His Tyr Asp Ile Leu Tyr Pro
                245

<210> SEQ ID NO 212
<211> LENGTH: 230
<212> TYPE: PRT
<213> ORGANISM: Artificial Sequence
<220> FEATURE:
<223> OTHER INFORMATION: Otubain-like domain

<400> SEQUENCE: 212

Ser Pro Ile Leu Gln Glu Lys Ile Lys Leu Leu Gly Glu Gln Tyr Asp
1               5                   10                  15

Ala Leu Arg Arg Thr Arg Gly Asp Gly Asn Cys Phe Tyr Arg Ser Phe
                20                  25                  30

Met Phe Ser Tyr Leu Glu His Ile Leu Glu Thr Gln Asp Lys Ala Glu
            35                  40                  45

Val Glu Arg Ile Leu Lys Lys Ile Glu Gln Cys Lys Lys Thr Leu Ala
    50                  55                  60

Asp Leu Gly Tyr Ile Glu Phe Thr Phe Glu Asp Phe Phe Ser Ile Phe
65                  70                  75                  80

Ile Asp Gln Leu Glu Ser Val Leu Gln Gly His Glu Ser Ser Ile Gly
                85                  90                  95

Ala Glu Glu Leu Leu Glu Arg Thr Arg Asp Gln Met Val Ser Asp Tyr
            100                 105                 110

Val Val Met Phe Phe Arg Phe Val Thr Ser Gly Glu Ile Gln Arg Arg
        115                 120                 125

Ala Glu Phe Phe Glu Pro Phe Ile Ser Gly Leu Thr Asn Ser Thr Val
    130                 135                 140

Val Gln Phe Cys Lys Ala Ser Val Glu Pro Met Gly Glu Glu Ser Asp
145                 150                 155                 160
```

```
His Val His Ile Ile Ala Leu Ser Asp Ala Leu Gly Val Pro Ile Arg
            165                 170                 175

Val Met Tyr Leu Asp Arg Ser Ser Cys Asp Ala Gly Asn Ile Ser Val
        180                 185                 190

Asn His His Asp Phe Ser Pro Glu Ala Asn Ser Ser Asp Gly Ala Ala
        195                 200                 205

Ala Ala Glu Lys Pro Tyr Ile Thr Leu Leu Tyr Arg Pro Gly His Tyr
    210                 215                 220

Asp Ile Leu Tyr Pro Lys
225                 230

<210> SEQ ID NO 213
<211> LENGTH: 271
<212> TYPE: PRT
<213> ORGANISM: Homo sapiens

<400> SEQUENCE: 213

Met Ala Ala Glu Glu Pro Gln Gln Gln Lys Gln Glu Pro Leu Gly Ser
1               5                   10                  15

Asp Ser Glu Gly Val Asn Cys Leu Ala Tyr Asp Glu Ala Ile Met Ala
            20                  25                  30

Gln Gln Asp Arg Ile Gln Glu Ile Ala Val Gln Asn Pro Leu Val
        35                  40                  45

Ser Glu Arg Leu Glu Leu Ser Val Leu Tyr Lys Glu Tyr Ala Glu Asp
50                  55                  60

Asp Asn Ile Tyr Gln Gln Lys Ile Lys Asp Leu His Lys Lys Tyr Ser
65                  70                  75                  80

Tyr Ile Arg Lys Thr Arg Pro Asp Gly Asn Cys Phe Tyr Arg Ala Phe
                85                  90                  95

Gly Phe Ser His Leu Glu Ala Leu Ile Asp Asp Ser Lys Glu Leu Gln
            100                 105                 110

Arg Phe Lys Ala Val Ser Ala Lys Ser Lys Glu Asp Leu Val Ser Gln
        115                 120                 125

Gly Phe Thr Glu Phe Thr Ile Glu Asp Phe His Asn Thr Phe Met Asp
    130                 135                 140

Leu Ile Glu Gln Val Glu Lys Gln Thr Ser Val Ala Asp Leu Leu Ala
145                 150                 155                 160

Ser Phe Asn Asp Gln Ser Thr Ser Asp Tyr Leu Val Val Tyr Leu Arg
                165                 170                 175

Leu Leu Thr Ser Gly Tyr Leu Gln Arg Glu Ser Lys Phe Phe Glu His
            180                 185                 190

Phe Ile Glu Gly Gly Arg Thr Val Lys Glu Phe Cys Gln Gln Glu Val
        195                 200                 205

Glu Pro Met Cys Lys Glu Ser Asp His Ile His Ile Ile Ala Leu Ala
    210                 215                 220

Gln Ala Leu Ser Val Ser Ile Gln Val Glu Tyr Met Asp Arg Gly Glu
225                 230                 235                 240

Gly Gly Thr Thr Asn Pro His Ile Phe Pro Glu Gly Ser Glu Pro Lys
                245                 250                 255

Val Tyr Leu Leu Tyr Arg Pro Gly His Tyr Asp Ile Leu Tyr Lys
            260                 265                 270

<210> SEQ ID NO 214
<211> LENGTH: 271
<212> TYPE: PRT
<213> ORGANISM: Mus musculus
```

<400> SEQUENCE: 214

| Met<br>1 | Ala | Ala | Glu | Glu<br>5 | Pro | Gln | Gln | Lys | Gln<br>10 | Glu | Pro | Leu | Gly | Ser<br>15 |

Asp Ser Glu Gly Val Asn Cys Leu Ala Tyr Asp Glu Ala Ile Met Ala
            20                  25                  30

Gln Gln Asp Arg Ile Gln Glu Ile Ala Val Gln Asn Pro Leu Val
        35                  40                  45

Ser Glu Arg Leu Glu Leu Ser Val Leu Tyr Lys Glu Tyr Ala Glu Asp
50                  55                  60

Asp Asn Ile Tyr Gln Gln Lys Ile Lys Asp Leu His Lys Lys Tyr Ser
65                  70                  75                  80

Tyr Ile Arg Lys Thr Arg Pro Asp Gly Asn Cys Phe Tyr Arg Ala Phe
                85                  90                  95

Gly Phe Ser His Leu Glu Ala Leu Ile Asp Asp Ser Lys Glu Leu Gln
                100                 105                 110

Arg Phe Lys Ala Val Ser Ala Lys Ser Lys Glu Asp Leu Val Ser Gln
            115                 120                 125

Gly Phe Thr Glu Phe Thr Ile Glu Asp Phe His Asn Thr Phe Met Asp
130                 135                 140

Leu Ile Glu Gln Val Glu Lys Gln Thr Ser Val Ala Asp Leu Leu Ala
145                 150                 155                 160

Ser Phe Asn Asp Gln Ser Thr Ser Asp Tyr Leu Val Val Tyr Leu Arg
                165                 170                 175

Leu Leu Thr Ser Gly Tyr Leu Gln Arg Glu Ser Lys Phe Phe Glu His
                180                 185                 190

Phe Ile Glu Gly Gly Arg Thr Val Lys Glu Phe Cys Gln Gln Glu Val
            195                 200                 205

Glu Pro Met Cys Lys Glu Ser Asp His Ile His Ile Ala Leu Ala
210                 215                 220

Gln Ala Leu Ser Val Ser Ile Gln Val Glu Tyr Met Asp Arg Gly Glu
225                 230                 235                 240

Gly Gly Thr Thr Asn Pro His Val Phe Pro Glu Gly Ser Glu Pro Lys
                245                 250                 255

Val Tyr Leu Leu Tyr Arg Pro Gly His Tyr Asp Ile Leu Tyr Lys
            260                 265                 270

<210> SEQ ID NO 215
<211> LENGTH: 306
<212> TYPE: PRT
<213> ORGANISM: Arabidopsis thaliana

<400> SEQUENCE: 215

Met Gln Asn Gln Ile Asp Met Val Lys Asp Glu Ala Glu Val Ala Ala
1               5                   10                  15

Ser Ile Ser Ala Ile Lys Gly Glu Glu Trp Gly Asn Cys Ser Ser Val
            20                  25                  30

Glu Asp Gln Pro Ser Phe Gln Glu Glu Ala Ala Lys Val Pro Tyr
        35                  40                  45

Val Gly Asp Lys Glu Pro Leu Ser Ser Leu Ala Ala Glu Tyr Gln Ser
50                  55                  60

Gly Ser Pro Ile Leu Leu Glu Lys Ile Lys Ile Leu Asp Ser Gln Tyr
65                  70                  75                  80

Ile Gly Ile Arg Arg Thr Arg Gly Asp Gly Asn Cys Phe Phe Arg Ser
                85                  90                  95

```
Phe Met Phe Ser Tyr Leu Glu His Ile Leu Glu Ser Gln Asp Arg Ala
            100                 105                 110

Glu Val Asp Arg Ile Lys Val Asn Val Glu Lys Cys Arg Lys Thr Leu
            115                 120                 125

Gln Asn Leu Gly Tyr Thr Asp Phe Thr Phe Glu Asp Phe Phe Ala Leu
130                 135                 140

Phe Leu Glu Gln Leu Asp Asp Ile Leu Gln Gly Thr Glu Glu Ser Ile
145                 150                 155                 160

Ser Tyr Asp Glu Leu Val Asn Arg Ser Arg Asp Gln Ser Val Ser Asp
                165                 170                 175

Tyr Ile Val Met Phe Phe Arg Phe Val Thr Ala Gly Asp Ile Arg Thr
            180                 185                 190

Arg Ala Asp Phe Phe Glu Pro Phe Ile Thr Gly Leu Ser Asn Ala Thr
            195                 200                 205

Val Asp Gln Phe Cys Lys Ser Ser Val Glu Pro Met Gly Glu Glu Ser
210                 215                 220

Asp His Ile His Ile Thr Ala Leu Ser Asp Ala Leu Gly Val Ala Ile
225                 230                 235                 240

Arg Val Val Tyr Leu Asp Arg Ser Ser Cys Asp Ser Gly Gly Val Thr
                245                 250                 255

Val Asn His His Asp Phe Val Pro Val Gly Ile Thr Asn Glu Lys Asp
            260                 265                 270

Glu Glu Ala Ser Ala Pro Phe Ile Thr Leu Leu Tyr Arg Pro Gly His
            275                 280                 285

Tyr Asp Ile Leu Tyr Pro Lys Pro Ser Cys Lys Val Ser Asp Asn Val
            290                 295                 300

Gly Lys
305

<210> SEQ ID NO 216
<211> LENGTH: 301
<212> TYPE: PRT
<213> ORGANISM: Glycine max

<400> SEQUENCE: 216

Met Gln Ser Lys Glu Ala Val Val Glu Asp Gly Glu Ile Lys Ser Val
1               5                   10                  15

Thr Ala Val Gly Ser Glu Ile Asp Gly Trp Thr Asn Phe Gly Asp Asp
            20                  25                  30

Asp Ile Met Gln Gln Gln Tyr Thr Ile Gln Ser Glu Glu Ala Lys Lys
            35                  40                  45

Val Pro Ser Val Gly Asp Lys Glu Pro Leu Ser Ser Leu Ala Ala Glu
50                  55                  60

Tyr Lys Ser Gly Ser Pro Ile Leu Leu Glu Lys Ile Lys Val Leu Asp
65                  70                  75                  80

Glu Gln Tyr Ala Ala Ile Arg Arg Thr Arg Gly Asp Gly Asn Cys Phe
                85                  90                  95

Phe Arg Ser Phe Met Phe Ser Tyr Leu Glu His Val Met Lys Cys Gln
            100                 105                 110

Asp Gln Ala Glu Val Asp Arg Ile Gln Ala Asn Val Glu Lys Ser Arg
            115                 120                 125

Lys Ala Leu Gln Thr Leu Gly Tyr Ala Asp Leu Thr Phe Glu Asp Phe
130                 135                 140

Phe Ala Leu Phe Leu Glu Gln Leu Glu Ser Val Ile Gln Gly Lys Glu
```

```
                145                 150                 155                 160
Thr Ser Ile Ser His Glu Glu Leu Val Leu Arg Ser Arg Asp Gln Ser
                165                 170                 175

Val Ser Asp Tyr Val Val Met Phe Phe Arg Phe Val Thr Ser Ala Ala
                180                 185                 190

Ile Gln Lys Arg Thr Glu Phe Phe Glu Pro Phe Ile Leu Gly Leu Thr
                195                 200                 205

Asn Thr Thr Val Glu Gln Phe Cys Lys Ser Ser Val Glu Pro Met Gly
    210                 215                 220

Glu Glu Ser Asp His Val His Ile Thr Ala Leu Ser Asp Ala Leu Gly
225                 230                 235                 240

Ile Pro Val Arg Val Val Tyr Leu Asp Arg Ser Ser Ser Asp Thr Gly
                245                 250                 255

Gly Val Ser Val Asn His His Asp Phe Met Pro Val Ala Gly Asp Leu
                260                 265                 270

Pro Asn Ala Ser Cys Ser Ser Glu Lys Asn Ile Pro Phe Ile Thr Leu
                275                 280                 285

Leu Tyr Arg Pro Gly His Tyr Asp Ile Leu Tyr Pro Lys
    290                 295                 300

<210> SEQ ID NO 217
<211> LENGTH: 296
<212> TYPE: PRT
<213> ORGANISM: Zea mays

<400> SEQUENCE: 217

Met Gly Asp Val Pro Gln Ala Pro His Ala Ala Gly Gly Gly Glu Glu
1               5                   10                  15

Trp Ala Gly Pro Asp Pro Asn Pro Ser Pro Ser Leu Gly Gly Cys Ser
                20                  25                  30

Asp Pro Val Ser Val Glu Leu Ser Met Gly Gly Asp Tyr Tyr Arg Ala
                35                  40                  45

Cys Cys Gly Glu Pro Asp Pro Asp Ile Pro Glu Gly Pro Lys Leu Pro
            50                  55                  60

Cys Val Gly Asp Lys Glu Pro Leu Ser Ser Leu Ala Ala Glu Phe Gln
65                  70                  75                  80

Ser Gly Ser Pro Ile Leu Gln Glu Lys Ile Lys Leu Leu Gly Glu Gln
                85                  90                  95

Tyr Gly Ala Leu Arg Arg Thr Arg Gly Asp Gly Asn Cys Phe Tyr Arg
                100                 105                 110

Ser Phe Met Phe Ser Tyr Leu Glu His Ile Leu Glu Thr Gln Asp Lys
            115                 120                 125

Ala Glu Ala Asp Arg Ile Met Val Lys Ile Glu Glu Cys Lys Lys Thr
    130                 135                 140

Leu Leu Ser Leu Gly Tyr Ile Glu Phe Thr Phe Glu Asp Phe Phe Ser
145                 150                 155                 160

Ile Phe Leu Glu Leu Leu Glu Ser Val Leu Gln Gly His Glu Thr Pro
                165                 170                 175

Ile Gly Phe Val Thr Ser Gly Glu Ile Gln Arg Arg Ser Asp Phe Phe
                180                 185                 190

Glu Pro Phe Ile Ser Gly Leu Thr Asn Ser Thr Val Val Gln Phe Cys
                195                 200                 205

Lys Ala Ser Val Glu Pro Met Gly Glu Glu Ser Asp His Val His Ile
    210                 215                 220
```

```
Ile Ala Leu Ser Asp Ala Leu Gly Val Pro Ile Arg Val Met Tyr Leu
225                 230                 235                 240

Asp Arg Ser Ser Cys Asp Thr Gly Asn Leu Ser Val Asn His His Asp
            245                 250                 255

Phe Ile Pro Ser Ala Asn Asp Ser Glu Gly Asp Ala Ala Thr Thr Pro
            260                 265                 270

Ala Pro Ala Thr Glu Lys Pro Tyr Ile Thr Leu Leu Tyr Arg Pro Gly
        275                 280                 285

His Tyr Asp Ile Leu Tyr Pro Lys
290                 295
```

<210> SEQ ID NO 218
<211> LENGTH: 302
<212> TYPE: PRT
<213> ORGANISM: Sorghum bicolor

<400> SEQUENCE: 218

```
Met Gly Asp Val Pro Gln Ala Pro His Ala Glu Gly Gly Gly Gly Gly
1               5                   10                  15

Gly Leu Glu Glu Gly Ala Val Pro Asp Pro Asn Pro Ser Pro Ser Leu
            20                  25                  30

Ser Leu Gly Gly Cys Ser Asp Pro Val Ser Leu Glu Leu Ser Met Gly
        35                  40                  45

Gly Asp Tyr Tyr Arg Ala Cys Cys Gly Asp Pro Asp Pro Asp Ile Pro
50                  55                  60

Glu Gly Pro Lys Leu Pro Cys Val Gly Glu Lys Glu Pro Leu Ser Ser
65                  70                  75                  80

Leu Ala Ala Glu Phe Gln Ser Gly Ser Pro Ile Leu Gln Glu Lys Ile
                85                  90                  95

Lys Leu Leu Gly Glu Gln Tyr Gly Ala Leu Arg Arg Thr Arg Gly Asp
            100                 105                 110

Gly Asn Cys Phe Tyr Arg Ser Phe Met Phe Ser Tyr Leu Glu His Ile
        115                 120                 125

Leu Glu Thr Gln Asp Lys Ala Glu Ala Asp Arg Ile Met Val Lys Ile
130                 135                 140

Glu Asp Cys Lys Lys Thr Leu Leu Ser Leu Gly Tyr Ile Glu Phe Thr
145                 150                 155                 160

Phe Glu Asp Phe Phe Ala Ile Phe Ile Asp Met Leu Glu Ser Val Leu
                165                 170                 175

Gln Gly His Glu Thr Pro Ile Gly Phe Val Thr Ser Gly Glu Ile Gln
            180                 185                 190

Arg Arg Ser Asp Phe Phe Glu Pro Phe Ile Ser Gly Leu Thr Asn Ser
        195                 200                 205

Thr Val Val Gln Phe Cys Lys Ala Ser Val Glu Pro Met Gly Glu Glu
210                 215                 220

Ser Asp His Val His Ile Ile Ala Leu Ser Asp Ala Leu Gly Val Pro
225                 230                 235                 240

Ile Arg Val Met Tyr Leu Asp Arg Ser Ser Cys Asp Thr Gly Asn Leu
                245                 250                 255

Ser Val Asn His His Asp Phe Ile Pro Ser Ser Asn Ala Ser Glu Gly
            260                 265                 270

Asp Ala Ala Met Thr Ser Thr Pro Asp Ala Glu Lys Pro Tyr Ile Thr
        275                 280                 285

Leu Leu Tyr Arg Pro Gly His Tyr Asp Ile Leu Tyr Pro Lys
290                 295                 300
```

<210> SEQ ID NO 219
<211> LENGTH: 279
<212> TYPE: PRT
<213> ORGANISM: Hordeum vulgare

<400> SEQUENCE: 219

Met Gly Gly Asp Tyr Tyr His Ala Cys Cys Gly Asp Pro Asp Pro Asp
1               5                   10                  15

Pro Lys Pro Glu Gly Pro Gln Val Pro Tyr Ile Gly Asn Lys Glu Pro
            20                  25                  30

Leu Ser Ala Leu Ala Ala Glu Phe Gln Ser Gly Ser Pro Ile Leu Gln
        35                  40                  45

Glu Lys Ile Lys Leu Leu Gly Glu Gln Tyr Asp Ala Leu Arg Arg Thr
    50                  55                  60

Arg Gly Asp Gly Asn Cys Phe Tyr Arg Ser Phe Met Phe Ser Tyr Leu
65                  70                  75                  80

Glu His Ile Leu Glu Thr Gln Asp Arg Ala Glu Val Glu Arg Ile Leu
                85                  90                  95

Lys Asn Ile Glu Gln Cys Lys Lys Thr Leu Ser Gly Leu Gly Tyr Ile
            100                 105                 110

Glu Phe Thr Phe Glu Asp Phe Phe Ser Met Phe Ile Glu Glu Leu Gln
        115                 120                 125

Asn Val Leu Gln Gly His Gly Thr Ser Ile Gly Pro Glu Glu Leu Leu
    130                 135                 140

Glu Arg Thr Arg Asp Gln Thr Thr Ser Asp Tyr Val Val Met Phe Phe
145                 150                 155                 160

Arg Glu Val Thr Ser Gly Glu Ile Gln Arg Arg Ala Glu Phe Phe Glu
                165                 170                 175

Pro Phe Ile Ser Gly Leu Thr Asn Ser Thr Val Val Gln Phe Cys Lys
            180                 185                 190

Ser Ser Val Glu Pro Met Gly Glu Glu Ser Asp His Val His Ile Ile
        195                 200                 205

Ala Leu Ser Asp Ala Leu Gly Val Pro Ile Arg Val Met Tyr Leu Asp
    210                 215                 220

Arg Ser Ser Cys Asp Thr Gly Asn Leu Ser Val Asn His His Asp Phe
225                 230                 235                 240

Ile Pro Ala Ala Asn Ser Ser Glu Gly Asp Ala Ala Met Gly Leu Asn
                245                 250                 255

Pro Ala Asp Glu Lys Pro Tyr Ile Thr Leu Leu Tyr Arg Pro Gly His
            260                 265                 270

Tyr Asp Ile Leu Tyr Pro Lys
        275

<210> SEQ ID NO 220
<211> LENGTH: 279
<212> TYPE: PRT
<213> ORGANISM: Triticum urartu

<400> SEQUENCE: 220

Met Gly Gly Asp Tyr Tyr His Ala Cys Cys Gly Asp Pro Asp Pro Asp
1               5                   10                  15

Pro Lys Pro Glu Gly Pro Gln Val Pro Tyr Ile Gly Asn Lys Glu Pro
            20                  25                  30

Leu Ser Ala Leu Ala Ala Glu Phe Gln Ser Gly Ser Pro Ile Leu Gln
        35                  40                  45

```
Glu Lys Ile Lys Leu Leu Gly Glu Gln Tyr Asp Ala Leu Arg Arg Thr
         50                  55                  60

Arg Gly Asp Gly Asn Cys Phe Tyr Arg Ser Phe Met Phe Ser Tyr Leu
 65                  70                  75                  80

Glu His Ile Leu Glu Thr Gln Asp Arg Ala Glu Val Glu Arg Ile Leu
                 85                  90                  95

Lys Asn Ile Glu Gln Cys Lys Lys Thr Leu Ser Gly Leu Gly Tyr Ile
                100                 105                 110

Glu Phe Thr Phe Glu Asp Phe Phe Ser Met Phe Ile Glu Glu Leu Gln
            115                 120                 125

Asn Val Leu Gln Gly His Glu Thr Ser Ile Gly Pro Glu Glu Leu Leu
        130                 135                 140

Glu Arg Thr Arg Asp Gln Thr Thr Ser Asp Tyr Val Val Met Phe Phe
145                 150                 155                 160

Arg Glu Val Thr Ser Gly Glu Ile Gln Arg Arg Ala Glu Phe Phe Glu
                165                 170                 175

Pro Phe Ile Ser Gly Leu Thr Asn Ser Thr Val Ala Gln Phe Cys Lys
            180                 185                 190

Ser Ser Val Glu Pro Met Gly Glu Ser Asp His Val His Ile Ile
        195                 200                 205

Ala Leu Ser Asp Ala Leu Gly Val Pro Ile Arg Val Met Tyr Leu Asp
    210                 215                 220

Arg Ser Ser Cys Asp Thr Gly Asn Leu Ser Val Asn His His Asp Phe
225                 230                 235                 240

Ile Pro Ala Ala Asn Ser Ser Glu Gly Asp Ala Ala Met Gly Leu Asn
                245                 250                 255

Pro Ala Glu Glu Lys Pro Tyr Ile Thr Leu Leu Tyr Arg Pro Gly His
            260                 265                 270

Tyr Asp Ile Leu Tyr Pro Lys
        275

<210> SEQ ID NO 221
<211> LENGTH: 274
<212> TYPE: PRT
<213> ORGANISM: Oryza sativa

<400> SEQUENCE: 221

Met Gly Gly Asp Tyr Tyr His Ser Cys Cys Gly Asp Pro Asp Pro Asp
 1               5                  10                  15

Leu Arg Ala Pro Glu Gly Pro Lys Leu Pro Tyr Val Gly Asp Lys Glu
             20                  25                  30

Pro Leu Ser Thr Leu Ala Ala Glu Phe Gln Ser Gly Ser Pro Ile Leu
         35                  40                  45

Gln Glu Lys Ile Lys Leu Leu Gly Glu Gln Tyr Asp Ala Leu Arg Arg
     50                  55                  60

Thr Arg Gly Asp Gly Asn Cys Phe Tyr Arg Ser Phe Met Phe Ser Tyr
 65                  70                  75                  80

Leu Glu His Ile Leu Glu Thr Gln Asp Lys Ala Glu Val Glu Arg Ile
                 85                  90                  95

Leu Lys Lys Ile Glu Gln Cys Lys Lys Thr Leu Ala Asp Leu Gly Tyr
                100                 105                 110

Ile Glu Phe Thr Phe Glu Asp Phe Phe Ser Ile Phe Ile Asp Gln Leu
            115                 120                 125

Glu Ser Val Leu Gln Gly His Glu Ser Ser Ile Gly Ala Glu Glu Leu
```

```
Leu Glu Arg Thr Arg Asp Gln Met Val Ser Asp Tyr Val Val Met Phe
145                 150                 155                 160

Phe Arg Glu Val Thr Ser Gly Glu Ile Gln Arg Arg Ala Glu Phe Phe
                165                 170                 175

Glu Pro Phe Ile Ser Gly Leu Thr Asn Ser Thr Val Val Gln Phe Cys
                180                 185                 190

Lys Ala Ser Val Glu Pro Met Gly Glu Glu Ser Asp His Val His Ile
                195                 200                 205

Ile Ala Leu Ser Asp Ala Leu Gly Val Pro Ile Arg Val Met Tyr Leu
                210                 215                 220

Asp Arg Ser Ser Cys Asp Ala Gly Asn Ile Ser Val Asn His His Asp
225                 230                 235                 240

Phe Ser Pro Glu Ala Asn Ser Ser Asp Gly Ala Ala Ala Ala Glu Lys
                245                 250                 255

Pro Tyr Ile Thr Leu Leu Tyr Arg Pro Gly His Tyr Asp Ile Leu Tyr
                260                 265                 270

Pro Lys
```

```
<210> SEQ ID NO 222
<211> LENGTH: 80
<212> TYPE: DNA
<213> ORGANISM: Artificial Sequence
<220> FEATURE:
<223> OTHER INFORMATION: ZH11

<400> SEQUENCE: 222
attcattgat cagctggaaa gtgttctgca gggacatgaa tcctccatag ggtaaatatc    60
ctagagttat atttgtatcc                                               80

<210> SEQ ID NO 223
<211> LENGTH: 73
<212> TYPE: DNA
<213> ORGANISM: Artificial Sequence
<220> FEATURE:
<223> OTHER INFORMATION: osotub1-C1

<400> SEQUENCE: 223
attcattgat cagctggaaa gtgtggacat gaatcctcca tagggtaaat atcctagagt    60
tatatttgta tcc                                                      73

<210> SEQ ID NO 224
<211> LENGTH: 54
<212> TYPE: DNA
<213> ORGANISM: Artificial Sequence
<220> FEATURE:
<223> OTHER INFORMATION: osotub1-C2

<400> SEQUENCE: 224
attcattgat cagctggaaa gtgtaatttg tatcctagag ttatatttgt atcc          54

<210> SEQ ID NO 225
<211> LENGTH: 67
<212> TYPE: DNA
<213> ORGANISM: Artificial Sequence
<220> FEATURE:
<223> OTHER INFORMATION: osotub1-C3

<400> SEQUENCE: 225
attcattgat cagctggaaa gtgtgaatcc tccatagggt aaatatccta gagttatatt    60
``` tgtatcc 67

<210> SEQ ID NO 226
<211> LENGTH: 274
<212> TYPE: PRT
<213> ORGANISM: Artificial Sequence
<220> FEATURE:
<223> OTHER INFORMATION: osOTUB1.1

<400> SEQUENCE: 226

Met Gly Gly Asp Tyr Tyr His Ser Cys Cys Gly Asp Pro Asp Pro Asp
1               5                   10                  15

Leu Arg Ala Pro Glu Gly Pro Lys Leu Pro Tyr Val Gly Asp Lys Glu
            20                  25                  30

Pro Leu Ser Thr Leu Ala Ala Glu Phe Gln Ser Gly Ser Pro Ile Leu
        35                  40                  45

Gln Glu Lys Ile Lys Leu Leu Gly Glu Gln Tyr Asp Ala Leu Arg Arg
    50                  55                  60

Thr Arg Gly Asp Gly Asn Cys Phe Tyr Arg Ser Phe Met Phe Ser Tyr
65                  70                  75                  80

Leu Glu His Ile Leu Glu Thr Gln Asp Lys Ala Glu Val Glu Arg Ile
                85                  90                  95

Leu Lys Lys Ile Glu Gln Cys Lys Lys Thr Leu Ala Asp Leu Gly Tyr
            100                 105                 110

Ile Glu Phe Thr Phe Glu Asp Phe Phe Ser Ile Phe Ile Asp Gln Leu
        115                 120                 125

Glu Ser Val Leu Gln Gly His Glu Ser Ser Ile Gly Ala Glu Glu Leu
    130                 135                 140

Leu Glu Arg Thr Arg Asp Gln Met Val Ser Asp Tyr Val Val Met Phe
145                 150                 155                 160

Phe Arg Phe Val Thr Ser Gly Glu Ile Gln Arg Arg Ala Glu Phe Phe
                165                 170                 175

Glu Pro Phe Ile Ser Gly Leu Thr Asn Ser Thr Val Val Gln Phe Cys
            180                 185                 190

Lys Ala Ser Val Glu Pro Met Gly Glu Glu Ser Asp His Val His Ile
        195                 200                 205

Ile Ala Leu Ser Asp Ala Leu Gly Val Pro Ile Arg Val Met Tyr Leu
    210                 215                 220

Asp Arg Ser Ser Cys Asp Ala Gly Asn Ile Ser Val Asn His His Asp
225                 230                 235                 240

Phe Ser Pro Glu Ala Asn Ser Ser Asp Gly Ala Ala Ala Glu Lys
                245                 250                 255

Pro Tyr Ile Thr Leu Leu Tyr Arg Pro Gly His Tyr Asp Ile Leu Tyr
            260                 265                 270

Pro Lys

<210> SEQ ID NO 227
<211> LENGTH: 136
<212> TYPE: PRT
<213> ORGANISM: Artificial Sequence
<220> FEATURE:
<223> OTHER INFORMATION: osotub1-C1

<400> SEQUENCE: 227

Met Gly Gly Asp Tyr Tyr His Ser Cys Cys Gly Asp Pro Asp Pro Asp
1               5                   10                  15

Leu Arg Ala Pro Glu Gly Pro Lys Leu Pro Tyr Val Gly Asp Lys Glu
            20                  25                  30

Pro Leu Ser Thr Leu Ala Ala Glu Phe Gln Ser Gly Ser Pro Ile Leu
        35                  40                  45

Gln Glu Lys Ile Lys Leu Leu Gly Glu Gln Tyr Asp Ala Leu Arg Arg
    50                  55                  60

Thr Arg Gly Asp Gly Asn Cys Phe Tyr Arg Ser Phe Met Phe Ser Tyr
65                  70                  75                  80

Leu Glu His Ile Leu Glu Thr Gln Asp Lys Ala Glu Val Glu Arg Ile
                85                  90                  95

Leu Lys Lys Ile Glu Gln Cys Lys Lys Thr Leu Ala Asp Leu Gly Tyr
            100                 105                 110

Ile Glu Phe Thr Phe Glu Asp Phe Phe Ser Ile Phe Ile Asp Gln Leu
        115                 120                 125

Glu Ser Val Asp Met Asn Pro Pro
    130                 135

<210> SEQ ID NO 228
<211> LENGTH: 27
<212> TYPE: DNA
<213> ORGANISM: Artificial Sequence
<220> FEATURE:
<223> OTHER INFORMATION: OsSPL1 fwd primer

<400> SEQUENCE: 228
cgagctcatg tcgagtgggc tcaagaa                                            27

<210> SEQ ID NO 229
<211> LENGTH: 28
<212> TYPE: DNA
<213> ORGANISM: Artificial Sequence
<220> FEATURE:
<223> OTHER INFORMATION: OsSPL1 rev primer

<400> SEQUENCE: 229
cgggatcctc acttggggcc tgaacgca                                           28

<210> SEQ ID NO 230
<211> LENGTH: 29
<212> TYPE: DNA
<213> ORGANISM: Artificial Sequence
<220> FEATURE:
<223> OTHER INFORMATION: OsSPL2 fwd primer

<400> SEQUENCE: 230
gcgtcgacaa tggattggga cgccaagat                                          29

<210> SEQ ID NO 231
<211> LENGTH: 28
<212> TYPE: DNA
<213> ORGANISM: Artificial Sequence
<220> FEATURE:
<223> OTHER INFORMATION: OsSPL2 rev primer

<400> SEQUENCE: 231
cgggatccct accacgatga gaaaggaa                                           28

<210> SEQ ID NO 232
<211> LENGTH: 29
<212> TYPE: DNA
<213> ORGANISM: Artificial Sequence
<220> FEATURE:
<223> OTHER INFORMATION: OsSPL3 fwd primer

```
<400> SEQUENCE: 232
gcgtcgacaa tgggttcttt tgggatgga                                              29

<210> SEQ ID NO 233
<211> LENGTH: 28
<212> TYPE: DNA
<213> ORGANISM: Artificial Sequence
<220> FEATURE:
<223> OTHER INFORMATION: OsSPL3 rev primer

<400> SEQUENCE: 233
cgggatccct ataatgcaaa tagaatct                                               28

<210> SEQ ID NO 234
<211> LENGTH: 29
<212> TYPE: DNA
<213> ORGANISM: Artificial Sequence
<220> FEATURE:
<223> OTHER INFORMATION: OsSPL4 fwd primer

<400> SEQUENCE: 234
gcgtcgacaa tggattggat gcctcctcc                                              29

<210> SEQ ID NO 235
<211> LENGTH: 28
<212> TYPE: DNA
<213> ORGANISM: Artificial Sequence
<220> FEATURE:
<223> OTHER INFORMATION: OsSPL4 rev primer

<400> SEQUENCE: 235
cgggatcctt aatgaaatga catgcagc                                               28

<210> SEQ ID NO 236
<211> LENGTH: 27
<212> TYPE: DNA
<213> ORGANISM: Artificial Sequence
<220> FEATURE:
<223> OTHER INFORMATION: OsSPL5 fwd primer

<400> SEQUENCE: 236
cgagctcatg gcggtgccag cggcggc                                                27

<210> SEQ ID NO 237
<211> LENGTH: 28
<212> TYPE: DNA
<213> ORGANISM: Artificial Sequence
<220> FEATURE:
<223> OTHER INFORMATION: OsSPL5 rev primer

<400> SEQUENCE: 237
cgggatccct agatgaaatc cacctcga                                               28

<210> SEQ ID NO 238
<211> LENGTH: 29
<212> TYPE: DNA
<213> ORGANISM: Artificial Sequence
<220> FEATURE:
<223> OTHER INFORMATION: OsSPL6 fwd primer

<400> SEQUENCE: 238
gcgtcgacaa tggaggctgc ccgggtcgg                                              29

<210> SEQ ID NO 239
```

```
<211> LENGTH: 28
<212> TYPE: DNA
<213> ORGANISM: Artificial Sequence
<220> FEATURE:
<223> OTHER INFORMATION: OsSPL6 rev primer

<400> SEQUENCE: 239
cgggatcctc acattggtcc acgttcta                                          28

<210> SEQ ID NO 240
<211> LENGTH: 30
<212> TYPE: DNA
<213> ORGANISM: Artificial Sequence
<220> FEATURE:
<223> OTHER INFORMATION: OsSPL7 fwd primer

<400> SEQUENCE: 240
gcgtcgacaa tggaaggaaa cggctgcggc                                        30

<210> SEQ ID NO 241
<211> LENGTH: 28
<212> TYPE: DNA
<213> ORGANISM: Artificial Sequence
<220> FEATURE:
<223> OTHER INFORMATION: OsSPL7 rev primer

<400> SEQUENCE: 241
cgggatcctc agaccacgcg ggcgccct                                          28

<210> SEQ ID NO 242
<211> LENGTH: 29
<212> TYPE: DNA
<213> ORGANISM: Artificial Sequence
<220> FEATURE:
<223> OTHER INFORMATION: OsSPL8 fwd primer

<400> SEQUENCE: 242
gcgtcgacaa tgatgaacgt tccatccgc                                         29

<210> SEQ ID NO 243
<211> LENGTH: 28
<212> TYPE: DNA
<213> ORGANISM: Artificial Sequence
<220> FEATURE:
<223> OTHER INFORMATION: OsSPL8 rev primer

<400> SEQUENCE: 243
cgggatccct agtgatcgaa gtcgagat                                          28

<210> SEQ ID NO 244
<211> LENGTH: 31
<212> TYPE: DNA
<213> ORGANISM: Artificial Sequence
<220> FEATURE:
<223> OTHER INFORMATION: OsSPL9 fwd primer

<400> SEQUENCE: 244
gcgtcgacaa tggacgcccc cggcggcggc g                                      31

<210> SEQ ID NO 245
<211> LENGTH: 28
<212> TYPE: DNA
<213> ORGANISM: Artificial Sequence
<220> FEATURE:
<223> OTHER INFORMATION: OsSPL9 rev primer

<400> SEQUENCE: 245
```

```
cgggatccct atgatgagta gttcctag                                            28

<210> SEQ ID NO 246
<211> LENGTH: 28
<212> TYPE: DNA
<213> ORGANISM: Artificial Sequence
<220> FEATURE:
<223> OTHER INFORMATION: OsSPL10

<400> SEQUENCE: 246
ggactagtat gatgagcggt aggatgaa                                            28

<210> SEQ ID NO 247
<211> LENGTH: 28
<212> TYPE: DNA
<213> ORGANISM: Artificial Sequence
<220> FEATURE:
<223> OTHER INFORMATION: OsSPL10 rev primer

<400> SEQUENCE: 247
cgggatccct acatgaagtc gacctcga                                            28

<210> SEQ ID NO 248
<211> LENGTH: 29
<212> TYPE: DNA
<213> ORGANISM: Artificial Sequence
<220> FEATURE:
<223> OTHER INFORMATION: OsSPL11 fwd primer

<400> SEQUENCE: 248
gcgtcgacaa tggagtgcaa ccccgtctc                                           29

<210> SEQ ID NO 249
<211> LENGTH: 28
<212> TYPE: DNA
<213> ORGANISM: Artificial Sequence
<220> FEATURE:
<223> OTHER INFORMATION: OsSPL11 rev primer

<400> SEQUENCE: 249
cgggatcctc aatgtatctg gttcagac                                            28

<210> SEQ ID NO 250
<211> LENGTH: 29
<212> TYPE: DNA
<213> ORGANISM: Artificial Sequence
<220> FEATURE:
<223> OTHER INFORMATION: OsSPL12 fwd primer

<400> SEQUENCE: 250
gcgtcgacaa tggcttcttt tgggatgaa                                           29

<210> SEQ ID NO 251
<211> LENGTH: 28
<212> TYPE: DNA
<213> ORGANISM: Artificial Sequence
<220> FEATURE:
<223> OTHER INFORMATION: OsSPL12 rev primer

<400> SEQUENCE: 251
ggactagttc agtgcagatg gccatagc                                            28

<210> SEQ ID NO 252
<211> LENGTH: 27
<212> TYPE: DNA
```

```
<213> ORGANISM: Artificial Sequence
<220> FEATURE:
<223> OTHER INFORMATION: OsSPL13 fwd primer

<400> SEQUENCE: 252
cgagctcatg gaccgcaagg acaaggc                                               27

<210> SEQ ID NO 253
<211> LENGTH: 28
<212> TYPE: DNA
<213> ORGANISM: Artificial Sequence
<220> FEATURE:
<223> OTHER INFORMATION: OsSPL13 rev primer

<400> SEQUENCE: 253
cgggatcctt atctgatctg aacggcg                                               28

<210> SEQ ID NO 254
<211> LENGTH: 29
<212> TYPE: DNA
<213> ORGANISM: Artificial Sequence
<220> FEATURE:
<223> OTHER INFORMATION: OsSPL15 fwd primer

<400> SEQUENCE: 254
gcgtcgacaa tgcagaggga agtggggcc                                             29

<210> SEQ ID NO 255
<211> LENGTH: 28
<212> TYPE: DNA
<213> ORGANISM: Artificial Sequence
<220> FEATURE:
<223> OTHER INFORMATION: OsSPL15 rev primer

<400> SEQUENCE: 255
cgggatcctt atatcgtacc aaaatcca                                              28

<210> SEQ ID NO 256
<211> LENGTH: 27
<212> TYPE: DNA
<213> ORGANISM: Artificial Sequence
<220> FEATURE:
<223> OTHER INFORMATION: OsSPL16 fwd primer

<400> SEQUENCE: 256
gtcgacaatg gagtgggatc tcaagat                                               27

<210> SEQ ID NO 257
<211> LENGTH: 26
<212> TYPE: DNA
<213> ORGANISM: Artificial Sequence
<220> FEATURE:
<223> OTHER INFORMATION: OsSPL16 rev primer

<400> SEQUENCE: 257
ggatccctac tgccatgaga acggca                                                26

<210> SEQ ID NO 258
<211> LENGTH: 29
<212> TYPE: DNA
<213> ORGANISM: Artificial Sequence
<220> FEATURE:
<223> OTHER INFORMATION: OsSPL17 fwd primer

<400> SEQUENCE: 258
gcgtcgacaa tggcgaccgg cggcagcgg                                             29
```

<210> SEQ ID NO 259
<211> LENGTH: 28
<212> TYPE: DNA
<213> ORGANISM: Artificial Sequence
<220> FEATURE:
<223> OTHER INFORMATION: OsSPL17 rev primer

<400> SEQUENCE: 259
cgggatccct acagagacca gttcatgg         28

<210> SEQ ID NO 260
<211> LENGTH: 27
<212> TYPE: DNA
<213> ORGANISM: Artificial Sequence
<220> FEATURE:
<223> OTHER INFORMATION: OsSPL18 fwd primer

<400> SEQUENCE: 260
cgagctcatg gattgggatc tcaagat         27

<210> SEQ ID NO 261
<211> LENGTH: 28
<212> TYPE: DNA
<213> ORGANISM: Artificial Sequence
<220> FEATURE:
<223> OTHER INFORMATION: OsSPL18 rev primer

<400> SEQUENCE: 261
cgggatccct actgccacga gaatggga         28

<210> SEQ ID NO 262
<211> LENGTH: 27
<212> TYPE: DNA
<213> ORGANISM: Artificial Sequence
<220> FEATURE:
<223> OTHER INFORMATION: OsSPL19 fwd primer

<400> SEQUENCE: 262
cgagctcatg gagtgggcgg cggcggc         27

<210> SEQ ID NO 263
<211> LENGTH: 27
<212> TYPE: DNA
<213> ORGANISM: Artificial Sequence
<220> FEATURE:
<223> OTHER INFORMATION: OsSPL19 rev primer

<400> SEQUENCE: 263
cgggatccct acacctgcca agagaat         27

<210> SEQ ID NO 264
<211> LENGTH: 20
<212> TYPE: DNA
<213> ORGANISM: Artificial Sequence
<220> FEATURE:
<223> OTHER INFORMATION: OsOTUB1 fwd primer

<400> SEQUENCE: 264
gattgaggag acgagccatc         20

<210> SEQ ID NO 265
<211> LENGTH: 20
<212> TYPE: DNA
<213> ORGANISM: Artificial Sequence
<220> FEATURE:

```
<223> OTHER INFORMATION: OsOTUB1 rev primer

<400> SEQUENCE: 265 cttttttcaga tctgcgctcc                                              20

<210> SEQ ID NO 266
<211> LENGTH: 20
<212> TYPE: DNA
<213> ORGANISM: Artificial Sequence
<220> FEATURE:
<223> OTHER INFORMATION: OsSPL14 fwd primer

<400> SEQUENCE: 266
cattgggttt gtgcattcag                                               20

<210> SEQ ID NO 267
<211> LENGTH: 20
<212> TYPE: DNA
<213> ORGANISM: Artificial Sequence
<220> FEATURE:
<223> OTHER INFORMATION: OsSPL14 rev primer

<400> SEQUENCE: 267
caacgaccca tattccaacc                                               20

<210> SEQ ID NO 268
<211> LENGTH: 20
<212> TYPE: DNA
<213> ORGANISM: Artificial Sequence
<220> FEATURE:
<223> OTHER INFORMATION: OsUBC13 fwd primer

<400> SEQUENCE: 268
ggggtgactt gaggtagtgg                                               20

<210> SEQ ID NO 269
<211> LENGTH: 20
<212> TYPE: DNA
<213> ORGANISM: Artificial Sequence
<220> FEATURE:
<223> OTHER INFORMATION: OsUBC13 rev primer

<400> SEQUENCE: 269
gcgacttcag ttctccacct                                               20

<210> SEQ ID NO 270
<211> LENGTH: 20
<212> TYPE: DNA
<213> ORGANISM: Artificial Sequence
<220> FEATURE:
<223> OTHER INFORMATION: OsTB1 fwd primer

<400> SEQUENCE: 270
gaaccactca tcgtccacca                                               20

<210> SEQ ID NO 271
<211> LENGTH: 20
<212> TYPE: DNA
<213> ORGANISM: Artificial Sequence
<220> FEATURE:
<223> OTHER INFORMATION: OsTB1 rev primer

<400> SEQUENCE: 271
ctgatcctgc tgatgctgct                                               20
```

```
<210> SEQ ID NO 272
<211> LENGTH: 20
<212> TYPE: DNA
<213> ORGANISM: Artificial Sequence
<220> FEATURE:
<223> OTHER INFORMATION: DEP1 fwd primer

<400> SEQUENCE: 272
gcgagatcac gttcctcaag                                               20

<210> SEQ ID NO 273
<211> LENGTH: 20
<212> TYPE: DNA
<213> ORGANISM: Artificial Sequence
<220> FEATURE:
<223> OTHER INFORMATION: DEP1 rev primer

<400> SEQUENCE: 273
tgcagtttgg cttacagcat                                               20

<210> SEQ ID NO 274
<211> LENGTH: 20
<212> TYPE: DNA
<213> ORGANISM: Artificial Sequence
<220> FEATURE:
<223> OTHER INFORMATION: OsRCN2 fwd primer

<400> SEQUENCE: 274
caaccccacg gtgaagatga                                               20

<210> SEQ ID NO 275
<211> LENGTH: 20
<212> TYPE: DNA
<213> ORGANISM: Artificial Sequence
<220> FEATURE:
<223> OTHER INFORMATION: OsRCN2 rev primer

<400> SEQUENCE: 275
acctgtggat gccgatgttt                                               20

<210> SEQ ID NO 276
<211> LENGTH: 20
<212> TYPE: DNA
<213> ORGANISM: Artificial Sequence
<220> FEATURE:
<223> OTHER INFORMATION: OsMADS34 fwd primer

<400> SEQUENCE: 276
gagatcgacg tagaggcagc                                               20

<210> SEQ ID NO 277
<211> LENGTH: 20
<212> TYPE: DNA
<213> ORGANISM: Artificial Sequence
<220> FEATURE:
<223> OTHER INFORMATION: OsMADS34 rev primer

<400> SEQUENCE: 277
taggccatcc actcaggagg                                               20

<210> SEQ ID NO 278
<211> LENGTH: 20
<212> TYPE: DNA
<213> ORGANISM: Artificial Sequence
<220> FEATURE:
<223> OTHER INFORMATION: Os11g47870 fwd primer
```

-continued

<400> SEQUENCE: 278
agctgcacat cgtggactac                                                20

<210> SEQ ID NO 279
<211> LENGTH: 20
<212> TYPE: DNA
<213> ORGANISM: Artificial Sequence
<220> FEATURE:
<223> OTHER INFORMATION: Os11g47870 rev primer

<400> SEQUENCE: 279
ttgcagcaat ggcttggaac                                                20

<210> SEQ ID NO 280
<211> LENGTH: 20
<212> TYPE: DNA
<213> ORGANISM: Artificial Sequence
<220> FEATURE:
<223> OTHER INFORMATION: Os06g38294 fwd primer

<400> SEQUENCE: 280
tcgttcttgt ggtggaggtg                                                20

<210> SEQ ID NO 281
<211> LENGTH: 20
<212> TYPE: DNA
<213> ORGANISM: Artificial Sequence
<220> FEATURE:
<223> OTHER INFORMATION: Os06g38294 rev primer

<400> SEQUENCE: 281
aggtagatgg cgtaggtggt                                                20

<210> SEQ ID NO 282
<211> LENGTH: 20
<212> TYPE: DNA
<213> ORGANISM: Artificial Sequence
<220> FEATURE:
<223> OTHER INFORMATION: Actin1 fwd primer

<400> SEQUENCE: 282
ccactatgtt ccctggcatt                                                20

<210> SEQ ID NO 283
<211> LENGTH: 20
<212> TYPE: DNA
<213> ORGANISM: Artificial Sequence
<220> FEATURE:
<223> OTHER INFORMATION: Actin1 rev primer

<400> SEQUENCE: 283
gtactcagcc ttggcaatcc                                                20

<210> SEQ ID NO 284
<211> LENGTH: 59
<212> TYPE: DNA
<213> ORGANISM: Artificial Sequence
<220> FEATURE:
<223> OTHER INFORMATION: DEP1-GATC-motif fwd primer

<400> SEQUENCE: 284
aatttattcc cttgctgttt catttcgtac gtactccgcg ctcgggatgc ggccatagc    59

<210> SEQ ID NO 285
<211> LENGTH: 59

```
<212> TYPE: DNA
<213> ORGANISM: Artificial Sequence
<220> FEATURE:
<223> OTHER INFORMATION: DEP1-GATC-motif rev primer

<400> SEQUENCE: 285
gctatggccg catcccgagc gcggagtacg tacgaaatga aacagcaagg gaataaatt       59

<210> SEQ ID NO 286
<211> LENGTH: 30
<212> TYPE: DNA
<213> ORGANISM: Artificial Sequence
<220> FEATURE:
<223> OTHER INFORMATION: pOsOTUB1.1 fwd primer

<400> SEQUENCE: 286
gaattcgagt tgaagttgtt gctgctgtca                                       30

<210> SEQ ID NO 287
<211> LENGTH: 25
<212> TYPE: DNA
<213> ORGANISM: Artificial Sequence
<220> FEATURE:
<223> OTHER INFORMATION: pOsOTUB1.1 rev primer

<400> SEQUENCE: 287
ggtacccgag agctcgaccg acacg                                            25

<210> SEQ ID NO 288
<211> LENGTH: 28
<212> TYPE: DNA
<213> ORGANISM: Artificial Sequence
<220> FEATURE:
<223> OTHER INFORMATION: gOsOTUB1.1 fwd primer

<400> SEQUENCE: 288
cccgggatgg gcggggacta ctaccact                                         28

<210> SEQ ID NO 289
<211> LENGTH: 29
<212> TYPE: DNA
<213> ORGANISM: Artificial Sequence
<220> FEATURE:
<223> OTHER INFORMATION: gOsOTUB1.1 rev primer

<400> SEQUENCE: 289
gtcgactcac ttcggggtag agaatgtcg                                        29

<210> SEQ ID NO 290
<211> LENGTH: 30
<212> TYPE: DNA
<213> ORGANISM: Artificial Sequence
<220> FEATURE:
<223> OTHER INFORMATION: gOsOTUB1.2 fwd primer

<400> SEQUENCE: 290
cccgggatgt tttcctactt ggtattattt                                       30

<210> SEQ ID NO 291
<211> LENGTH: 29
<212> TYPE: DNA
<213> ORGANISM: Artificial Sequence
<220> FEATURE:
<223> OTHER INFORMATION: gOsOTUB1.2 rev primer

<400> SEQUENCE: 291
```
gtcgactcac ttcggggtag agaatgtcg                                              29

<210> SEQ ID NO 292
<211> LENGTH: 28
<212> TYPE: DNA
<213> ORGANISM: Artificial Sequence
<220> FEATURE:
<223> OTHER INFORMATION: OsOTUB1.1-OE fwd primer

<400> SEQUENCE: 292
cccgggatgg gcggggacta ctaccact                                               28

<210> SEQ ID NO 293
<211> LENGTH: 28
<212> TYPE: DNA
<213> ORGANISM: Artificial Sequence
<220> FEATURE:
<223> OTHER INFORMATION: OsOTUB1.1-OE rev primer

<400> SEQUENCE: 293
gtcgactcac ttcgggtaga gaatgtcg                                               28

<210> SEQ ID NO 294
<211> LENGTH: 30
<212> TYPE: DNA
<213> ORGANISM: Artificial Sequence
<220> FEATURE:
<223> OTHER INFORMATION: OsOTUB1.2-OE fwd primer

<400> SEQUENCE: 294
cccgggatgt tttcctactt ggaacatatc                                             30

<210> SEQ ID NO 295
<211> LENGTH: 28
<212> TYPE: DNA
<213> ORGANISM: Artificial Sequence
<220> FEATURE:
<223> OTHER INFORMATION: OsOTUB1.2-OE rev primer

<400> SEQUENCE: 295
gtcgactcac ttcgggtaga gaatgtcg                                               28

<210> SEQ ID NO 296
<211> LENGTH: 28
<212> TYPE: DNA
<213> ORGANISM: Artificial Sequence
<220> FEATURE:
<223> OTHER INFORMATION: OsOTUB1.1-GFP fwd primer

<400> SEQUENCE: 296
cccgggatgg gcggggacta ctaccact                                               28

<210> SEQ ID NO 297
<211> LENGTH: 28
<212> TYPE: DNA
<213> ORGANISM: Artificial Sequence
<220> FEATURE:
<223> OTHER INFORMATION: OsOTUB1.1-GFP rev primer

<400> SEQUENCE: 297
gtcgaccttc gggtagagaa tgtcgtag                                               28

<210> SEQ ID NO 298
<211> LENGTH: 30
<212> TYPE: DNA
<213> ORGANISM: Artificial Sequence

```
<220> FEATURE:
<223> OTHER INFORMATION: OsOTUB1.2-GFP fwd primer

<400> SEQUENCE: 298
cccgggatgt tttcctactt ggaacatatc                                    30

<210> SEQ ID NO 299
<211> LENGTH: 28
<212> TYPE: DNA
<213> ORGANISM: Artificial Sequence
<220> FEATURE:
<223> OTHER INFORMATION: OsOTUB1.2-GFP rev primer

<400> SEQUENCE: 299
gtcgaccttc gggtagagaa tgtcgtag                                      28

<210> SEQ ID NO 300
<211> LENGTH: 36
<212> TYPE: DNA
<213> ORGANISM: Artificial Sequence
<220> FEATURE:
<223> OTHER INFORMATION: CRISPR-OsOTUB1 fwd primer

<400> SEQUENCE: 300
cagctggaaa gtgttctgcg ttttagagct agaaat                             36

<210> SEQ ID NO 301
<211> LENGTH: 36
<212> TYPE: DNA
<213> ORGANISM: Artificial Sequence
<220> FEATURE:
<223> OTHER INFORMATION: CRISPR-OsOTUB1 rev primer

<400> SEQUENCE: 301
gcagaacact ttccagctgc ggcagccaag ccagca                             36

<210> SEQ ID NO 302
<211> LENGTH: 30
<212> TYPE: DNA
<213> ORGANISM: Artificial Sequence
<220> FEATURE:
<223> OTHER INFORMATION: OsUBC13-OE fwd primer

<400> SEQUENCE: 302
gtcgacatgg ccaacagcaa cctcccccgg                                    30

<210> SEQ ID NO 303
<211> LENGTH: 30
<212> TYPE: DNA
<213> ORGANISM: Artificial Sequence
<220> FEATURE:
<223> OTHER INFORMATION: OsUBC13-OE rev primer

<400> SEQUENCE: 303
ctgcagttat gcaccgctgg catacaggcg                                    30

<210> SEQ ID NO 304
<211> LENGTH: 28
<212> TYPE: DNA
<213> ORGANISM: Artificial Sequence
<220> FEATURE:
<223> OTHER INFORMATION: RNAi-OSUBC13-L fwd primer

<400> SEQUENCE: 304
actagtcccg gcgaatcatc aaggagac                                      28
```

```
<210> SEQ ID NO 305
<211> LENGTH: 28
<212> TYPE: DNA
<213> ORGANISM: Artificial Sequence
<220> FEATURE:
<223> OTHER INFORMATION: RNAi-OsUBC13-L rev primer

<400> SEQUENCE: 305
agatctgaac tgtccgaatc tgaagggc                                            28

<210> SEQ ID NO 306
<211> LENGTH: 28
<212> TYPE: DNA
<213> ORGANISM: Artificial Sequence
<220> FEATURE:
<223> OTHER INFORMATION: RNAi-OsUBC13-R fwd primer

<400> SEQUENCE: 306
tctagacccg gcgaatcatc aaggagac                                            28

<210> SEQ ID NO 307
<211> LENGTH: 28
<212> TYPE: DNA
<213> ORGANISM: Artificial Sequence
<220> FEATURE:
<223> OTHER INFORMATION: RNAi-OsUBC13-R rev primer

<400> SEQUENCE: 307
ggatccgaac tgtccgaatc tgaagggc                                            28

<210> SEQ ID NO 308
<211> LENGTH: 30
<212> TYPE: DNA
<213> ORGANISM: Artificial Sequence
<220> FEATURE:
<223> OTHER INFORMATION: OsSPL14-OE fwd primer

<400> SEQUENCE: 308
gaattcctat ggagatggcc agtggaggag                                          30

<210> SEQ ID NO 309
<211> LENGTH: 31
<212> TYPE: DNA
<213> ORGANISM: Artificial Sequence
<220> FEATURE:
<223> OTHER INFORMATION: OsSPL14-OE rev primer

<400> SEQUENCE: 309
ggatccccta cagagaccaa tccatcgtgt t                                        31

<210> SEQ ID NO 310
<211> LENGTH: 27
<212> TYPE: DNA
<213> ORGANISM: Artificial Sequence
<220> FEATURE:
<223> OTHER INFORMATION: RNAi-OsSPL14-L fwd primer

<400> SEQUENCE: 310
actagtaaga acaaggggaa gggcgtg                                             27

<210> SEQ ID NO 311
<211> LENGTH: 26
<212> TYPE: DNA
<213> ORGANISM: Artificial Sequence
<220> FEATURE:
<223> OTHER INFORMATION: RNAi-OsSPL14-L rev primer
```

<400> SEQUENCE: 311
agatctaaag gggtttgcgg cctcct                                               26

<210> SEQ ID NO 312
<211> LENGTH: 27
<212> TYPE: DNA
<213> ORGANISM: Artificial Sequence
<220> FEATURE:
<223> OTHER INFORMATION: RNAi-OsSPL14-R fwd primer

<400> SEQUENCE: 312
tctagaaaga acaaggggaa gggcgtg                                              27

<210> SEQ ID NO 313
<211> LENGTH: 26
<212> TYPE: DNA
<213> ORGANISM: Artificial Sequence
<220> FEATURE:
<223> OTHER INFORMATION: RNAi-OsSPL14-R rev primer

<400> SEQUENCE: 313
ggatccaaag gggtttgcgg cctcct                                               26

<210> SEQ ID NO 314
<211> LENGTH: 28
<212> TYPE: DNA
<213> ORGANISM: Artificial Sequence
<220> FEATURE:
<223> OTHER INFORMATION: BD-OsOTUB1.1 fwd primer

<400> SEQUENCE: 314
ggatccatgg gcggggacta ctaccact                                             28

<210> SEQ ID NO 315
<211> LENGTH: 28
<212> TYPE: DNA
<213> ORGANISM: Artificial Sequence
<220> FEATURE:
<223> OTHER INFORMATION: BD-OsOTUB1.1 rev primer

<400> SEQUENCE: 315
gaattctcac ttcgggtaga gaatgtcg                                             28

<210> SEQ ID NO 316
<211> LENGTH: 29
<212> TYPE: DNA
<213> ORGANISM: Artificial Sequence
<220> FEATURE:
<223> OTHER INFORMATION: BD-OsOTUBdC fwd primer

<400> SEQUENCE: 316
ggatccatgt tggaacatat cctagagac                                            29

<210> SEQ ID NO 317
<211> LENGTH: 28
<212> TYPE: DNA
<213> ORGANISM: Artificial Sequence
<220> FEATURE:
<223> OTHER INFORMATION: BD-OsOTUBdC rev primer

<400> SEQUENCE: 317
gaattctcac ttcgggtaga gaatgtcg                                             28

<210> SEQ ID NO 318

-continued

<210> SEQ ID NO 318
<211> LENGTH: 30
<212> TYPE: DNA
<213> ORGANISM: Artificial Sequence
<220> FEATURE:
<223> OTHER INFORMATION: AD-OsUBC13 fwd primer

<400> SEQUENCE: 318
ggatccatgg ccaacagcaa cctcccccgg                                        30

<210> SEQ ID NO 319
<211> LENGTH: 27
<212> TYPE: DNA
<213> ORGANISM: Artificial Sequence
<220> FEATURE:
<223> OTHER INFORMATION: AD-OsUBC13 rev primer

<400> SEQUENCE: 319
gtcgactgca ccgctggcat acaggcg                                           27

<210> SEQ ID NO 320
<211> LENGTH: 29
<212> TYPE: DNA
<213> ORGANISM: Artificial Sequence
<220> FEATURE:
<223> OTHER INFORMATION: BD-OsSPL14dN2 fwd primer

<400> SEQUENCE: 320
gaattcatgc cgccgcggtg ccaggtgga                                         29

<210> SEQ ID NO 321
<211> LENGTH: 31
<212> TYPE: DNA
<213> ORGANISM: Artificial Sequence
<220> FEATURE:
<223> OTHER INFORMATION: BD-OsSPL14dN2 rev primer

<400> SEQUENCE: 321 ggatcccta cagagaccaa tccatcgtgt t                                       31

<210> SEQ ID NO 322
<211> LENGTH: 29
<212> TYPE: DNA
<213> ORGANISM: Artificial Sequence
<220> FEATURE:
<223> OTHER INFORMATION: cYFP-OsOTUB1.1 fwd primer

<400> SEQUENCE: 322
gtcgacaatg ggcggggact actaccact                                         29

<210> SEQ ID NO 323
<211> LENGTH: 28
<212> TYPE: DNA
<213> ORGANISM: Artificial Sequence
<220> FEATURE:
<223> OTHER INFORMATION: cYFP-OsOTUB1.1 fwd primer

<400> SEQUENCE: 323
ggatcctcac ttcgggtaga gaatgtcg                                          28

<210> SEQ ID NO 324
<211> LENGTH: 31
<212> TYPE: DNA
<213> ORGANISM: Artificial Sequence
<220> FEATURE:
<223> OTHER INFORMATION: nYFP-OsUBC13 fwd primer

<400> SEQUENCE: 324
gtcgacaatg gccaacagca acctcccccg g                                      31

<210> SEQ ID NO 325
<211> LENGTH: 30
<212> TYPE: DNA
<213> ORGANISM: Artificial Sequence
<220> FEATURE:
<223> OTHER INFORMATION: nYFP-OsUBC13 rev primer

<400> SEQUENCE: 325
ggatccttat gcaccgctgg catacaggcg                                        30

<210> SEQ ID NO 326
<211> LENGTH: 28
<212> TYPE: DNA
<213> ORGANISM: Artificial Sequence
<220> FEATURE:
<223> OTHER INFORMATION: nYFP-OsSPL14 fwd primer

<400> SEQUENCE: 326
gagctcatgg agatggccag tggaggag                                          28

<210> SEQ ID NO 327
<211> LENGTH: 30
<212> TYPE: DNA
<213> ORGANISM: Artificial Sequence
<220> FEATURE:
<223> OTHER INFORMATION: nYFP-OsSPL14 rev primer

<400> SEQUENCE: 327
ggatccctac agagaccaat ccatcgtgtt                                        30

<210> SEQ ID NO 328
<211> LENGTH: 29
<212> TYPE: DNA
<213> ORGANISM: Artificial Sequence
<220> FEATURE:
<223> OTHER INFORMATION: nYFP-OsSPL14dN1 fwd primer

<400> SEQUENCE: 328
gagctcatgg caggcggcgg cggcactgg                                         29

<210> SEQ ID NO 329
<211> LENGTH: 30
<212> TYPE: DNA
<213> ORGANISM: Artificial Sequence
<220> FEATURE:
<223> OTHER INFORMATION: nYFP-OsSPL14dN1 rev primer

<400> SEQUENCE: 329
ggatccctac agagaccaat ccatcgtgtt                                        30

<210> SEQ ID NO 330
<211> LENGTH: 29
<212> TYPE: DNA
<213> ORGANISM: Artificial Sequence
<220> FEATURE:
<223> OTHER INFORMATION: nYFP-OsSPL14dN2 fwd primer

<400> SEQUENCE: 330
gagctcatgc cgccgcggtg ccaggtgga                                         29

<210> SEQ ID NO 331
<211> LENGTH: 30
<212> TYPE: DNA

```
<213> ORGANISM: Artificial Sequence
<220> FEATURE:
<223> OTHER INFORMATION: nYFP-OsSPL14dN2 rev primer

<400> SEQUENCE: 331
ggatccctac agagaccaat ccatcgtgtt                                           30

<210> SEQ ID NO 332
<211> LENGTH: 29
<212> TYPE: DNA
<213> ORGANISM: Artificial Sequence
<220> FEATURE:
<223> OTHER INFORMATION: nYFP-OsSPL14dN3 fwd primer

<400> SEQUENCE: 332
gagctcatga gctttacgtt ggatttctc                                            29

<210> SEQ ID NO 333
<211> LENGTH: 30
<212> TYPE: DNA
<213> ORGANISM: Artificial Sequence
<220> FEATURE:
<223> OTHER INFORMATION: nYFP-OsSPL14dN3 rev primer

<400> SEQUENCE: 333
ggatccctac agagaccaat ccatcgtgtt                                           30

<210> SEQ ID NO 334
<211> LENGTH: 30
<212> TYPE: DNA
<213> ORGANISM: Artificial Sequence
<220> FEATURE:
<223> OTHER INFORMATION: nYFP-OsSPL14dN4 fwd primer

<400> SEQUENCE: 334
gagctcatgt gggatactac tacccacagt                                           30

<210> SEQ ID NO 335
<211> LENGTH: 30
<212> TYPE: DNA
<213> ORGANISM: Artificial Sequence
<220> FEATURE:
<223> OTHER INFORMATION: nYFP-OsSPL14dN4 rev primer

<400> SEQUENCE: 335
ggatccctac agagaccaat ccatcgtgtt                                           30

<210> SEQ ID NO 336
<211> LENGTH: 28
<212> TYPE: DNA
<213> ORGANISM: Artificial Sequence
<220> FEATURE:
<223> OTHER INFORMATION: nYFP-OsSPL14dC1 fwd primer

<400> SEQUENCE: 336
gagctcatgg agatggccag tggaggag                                             28

<210> SEQ ID NO 337
<211> LENGTH: 29
<212> TYPE: DNA
<213> ORGANISM: Artificial Sequence
<220> FEATURE:
<223> OTHER INFORMATION: nYFP-OsSPL14dC1 rev primer

<400> SEQUENCE: 337
ggatccctac catggctggg ttgacagaa                                            29
```

<210> SEQ ID NO 338
<211> LENGTH: 28
<212> TYPE: DNA
<213> ORGANISM: Artificial Sequence
<220> FEATURE:
<223> OTHER INFORMATION: nYFP-OsSPL14dC2 fwd primer

<400> SEQUENCE: 338
gagctcatgg agatggccag tggaggag         28

<210> SEQ ID NO 339
<211> LENGTH: 29
<212> TYPE: DNA
<213> ORGANISM: Artificial Sequence
<220> FEATURE:
<223> OTHER INFORMATION: nYFP-OsSPL14dC2 rev primer

<400> SEQUENCE: 339
ggatccctat ctgaacctgc gatgctcac        29

<210> SEQ ID NO 340
<211> LENGTH: 28
<212> TYPE: DNA
<213> ORGANISM: Artificial Sequence
<220> FEATURE:
<223> OTHER INFORMATION: nYFP-OsSPL14dC3 fwd primer

<400> SEQUENCE: 340
gagctcatgg agatggccag tggaggag         28

<210> SEQ ID NO 341
<211> LENGTH: 29
<212> TYPE: DNA
<213> ORGANISM: Artificial Sequence
<220> FEATURE:
<223> OTHER INFORMATION: nYFP-OsSPL14dC3 fwd primer

<400> SEQUENCE: 341
ggatccctac ggcggcggcg gcggcggcg        29

<210> SEQ ID NO 342
<211> LENGTH: 28
<212> TYPE: DNA
<213> ORGANISM: Artificial Sequence
<220> FEATURE:
<223> OTHER INFORMATION: nYFP-OsSPL14dC4 fwd primer

<400> SEQUENCE: 342
gagctcatgg agatggccag tggaggag         28

<210> SEQ ID NO 343
<211> LENGTH: 29
<212> TYPE: DNA
<213> ORGANISM: Artificial Sequence
<220> FEATURE:
<223> OTHER INFORMATION: nYFP-OsSPL14dC4 rev primer

<400> SEQUENCE: 343
ggatccctat gccgcggcgg cgtcctcga        29

<210> SEQ ID NO 344
<211> LENGTH: 29
<212> TYPE: DNA
<213> ORGANISM: Artificial Sequence
<220> FEATURE:

```
<223> OTHER INFORMATION: nYFP-SBP fwd primer

<400> SEQUENCE: 344
gagctcatgc cgccgcggtg ccaggtgga                                      29

<210> SEQ ID NO 345
<211> LENGTH: 29
<212> TYPE: DNA
<213> ORGANISM: Artificial Sequence
<220> FEATURE:
<223> OTHER INFORMATION: nYFP-SBP rev primer

<400> SEQUENCE: 345
ggatccctag gtttgcggcc tcctccggc                                      29

<210> SEQ ID NO 346
<211> LENGTH: 28
<212> TYPE: DNA
<213> ORGANISM: Artificial Sequence
<220> FEATURE:
<223> OTHER INFORMATION: YFP-SPL14dSBP-1 fwd primer

<400> SEQUENCE: 346
gagctcatgg agatggccag tggaggag                                       28

<210> SEQ ID NO 347
<211> LENGTH: 41
<212> TYPE: DNA
<213> ORGANISM: Artificial Sequence
<220> FEATURE:
<223> OTHER INFORMATION: YFP-SPL14dSBP-1 rev primer

<400> SEQUENCE: 347
gcgtgatgcc aaagggggttt gcacgcccctt cccttgttc t                       41

<210> SEQ ID NO 348
<211> LENGTH: 21
<212> TYPE: DNA
<213> ORGANISM: Artificial Sequence
<220> FEATURE:
<223> OTHER INFORMATION: YFP-SPL14dSBP-2 fwd primer

<400> SEQUENCE: 348
caaacccctt tggcatcacg c                                              21

<210> SEQ ID NO 349
<211> LENGTH: 30
<212> TYPE: DNA
<213> ORGANISM: Artificial Sequence
<220> FEATURE:
<223> OTHER INFORMATION: YFP-SPL14dSBP-2 rev primer

<400> SEQUENCE: 349
ggatccctac agagaccaat ccatcgtgtt                                     30

<210> SEQ ID NO 350
<211> LENGTH: 284
<212> TYPE: PRT
<213> ORGANISM: Artificial Sequence
<220> FEATURE:
<223> OTHER INFORMATION: C.elegans alignment

<400> SEQUENCE: 350
```

Met Ala Asn Glu Pro Gln Lys Ser Asp Asp Asn Gly Gln Ala Ala Glu
1               5                   10                  15

```
Ala Val Val Thr Asp Asp Glu Ile Val Leu Gln Asp Gln Gln Leu Lys
            20                  25                  30

Thr Ile Glu Asp Glu Gln Lys Ser Val Pro Leu Val Ala Thr Leu Ala
        35                  40                  45

Pro Phe Ser Ile Leu Cys Ala Glu Tyr Asp Asn Glu Thr Ser Ala Ala
50                  55                  60

Phe Leu Ser Lys Ala Thr Glu Leu Ser Glu Val Tyr Gly Glu Ile Arg
65                  70                  75                  80

Tyr Ile Arg Gly Asp Gly Asn Cys Phe Tyr Arg Ala Ile Leu Val Gly
                85                  90                  95

Leu Ile Glu Ile Met Leu Lys Asp Arg Ala Arg Leu Glu Lys Phe Ile
            100                 105                 110

Ala Ser Ser Arg Asp Trp Thr Arg Thr Leu Val Glu Leu Gly Phe Pro
        115                 120                 125

Asp Trp Thr Cys Thr Asp Phe Cys Asp Phe Phe Ile Glu Phe Leu Glu
130                 135                 140

Lys Ile His Ser Gly Val His Thr Glu Glu Ala Val Tyr Thr Ile Leu
145                 150                 155                 160

Asn Asp Asp Gly Ser Ala Asn Tyr Ile Leu Met Phe Arg Leu Ile
                165                 170                 175

Thr Ser Ala Phe Leu Lys Gln Asn Ser Glu Glu Tyr Ala Pro Phe Ile
        180                 185                 190

Asp Glu Gly Met Thr Val Ala Gln Tyr Cys Glu Gln Glu Ile Glu Pro
                195                 200                 205

Met Trp Lys Asp Ala Asp His Leu Ala Ile Asn Ser Leu Ile Lys Ala
210                 215                 220

Ala Gly Thr Arg Val Arg Ile Glu Tyr Met Asp Arg Thr Ala Ala Pro
225                 230                 235                 240

Asn Gly Gly Trp His Tyr Asp Ile Pro Ser Asp Gln Gln Ile Ala
                245                 250                 255

Pro Glu Ile Thr Leu Leu Tyr Arg Pro Gly His Tyr Asp Val Ile Tyr
                260                 265                 270

Lys Lys Asp Ser Thr Glu Ala Ser Glu Ile Glu Asn
            275                 280

<210> SEQ ID NO 351
<211> LENGTH: 234
<212> TYPE: PRT
<213> ORGANISM: Artificial Sequence
<220> FEATURE:
<223> OTHER INFORMATION: OTUB2 alignment

<400> SEQUENCE: 351

Met Ser Glu Thr Ser Phe Asn Leu Ile Ser Lys Cys Asp Ile Leu
1               5                   10                  15

Ser Ile Leu Arg Asp His Pro Glu Asn Arg Ile Tyr Arg Lys Ile
            20                  25                  30

Glu Glu Leu Ser Lys Arg Phe Thr Ala Ile Arg Lys Thr Lys Gly Asp
        35                  40                  45

Gly Asn Cys Phe Tyr Arg Ala Leu Gly Tyr Ser Tyr Leu Glu Ser Leu
50                  55                  60

Leu Gly Lys Ser Arg Glu Ile Phe Lys Phe Lys Glu Arg Val Leu Gln
65                  70                  75                  80

Thr Pro Asn Asp Leu Leu Ala Ala Gly Phe Glu Glu His Lys Phe Arg
                85                  90                  95
```

Asn Phe Phe Asn Ala Phe Tyr Ser Val Val Glu Leu Val Glu Lys Asp
                100                 105                 110

Gly Ser Val Ser Ser Leu Leu Lys Val Phe Asn Asp Gln Ser Ala Ser
            115                 120                 125

Asp His Ile Val Gln Phe Leu Arg Leu Leu Thr Ser Ala Phe Ile Arg
        130                 135                 140

Asn Arg Ala Asp Phe Phe Arg His Phe Ile Asp Glu Glu Met Asp Ile
145                 150                 155                 160

Lys Asp Phe Cys Thr His Glu Val Glu Pro Met Ala Thr Glu Cys Asp
                165                 170                 175

His Ile Gln Ile Thr Ala Leu Ser Gln Ala Leu Ser Ile Ala Leu Gln
            180                 185                 190

Val Glu Tyr Val Asp Glu Met Asp Thr Ala Leu Asn His His Val Phe
        195                 200                 205

Pro Glu Ala Ala Thr Pro Ser Val Tyr Leu Leu Tyr Lys Thr Ser His
210                 215                 220

Tyr Asn Ile Leu Tyr Ala Ala Asp Lys His
225                 230

<210> SEQ ID NO 352
<211> LENGTH: 263
<212> TYPE: PRT
<213> ORGANISM: Artificial Sequence
<220> FEATURE:
<223> OTHER INFORMATION: Mus musculus alignment

<400> SEQUENCE: 352

Met Ala Ala Glu Glu Pro Gln Gln Gln Lys Gln Glu Pro Leu Gly Ser
1               5                   10                  15

Asp Ser Glu Gly Val Asn Cys Leu Ala Tyr Asp Glu Ala Met Ser Glu
            20                  25                  30

Thr Ser Phe Asn Leu Ile Ser Glu Lys Cys Asp Ile Leu Ser Ile Leu
        35                  40                  45

Arg Asp His Pro Glu Asn Arg Ile Tyr Gln Arg Lys Ile Gln Glu Leu
50                  55                  60

Ser Lys Arg Phe Thr Ser Ile Arg Lys Thr Lys Gly Asp Gly Asn Cys
65                  70                  75                  80

Phe Tyr Arg Ala Leu Gly Tyr Ser Tyr Leu Glu Ser Leu Leu Gly Lys
                85                  90                  95

Ser Arg Glu Ile Leu Lys Phe Lys Glu Arg Val Leu Gln Thr Pro Asn
            100                 105                 110

Asp Leu Leu Ala Ala Gly Phe Glu Glu His Lys Phe Arg Asn Phe Phe
        115                 120                 125

Asn Ala Phe Tyr Ser Val Val Glu Leu Val Glu Lys Asp Ser Ser Val
130                 135                 140

Ser Ser Leu Leu Lys Val Phe Asn Asp Gln Ser Ser Ser Asp Arg Ile
145                 150                 155                 160

Val Gln Phe Leu Arg Leu Leu Thr Ser Ala Phe Ile Arg Asn Arg Ala
                165                 170                 175

Asp Phe Phe Arg His Phe Ile Asp Glu Glu Met Asp Ile Lys Asp Phe
            180                 185                 190

Cys Thr His Glu Val Glu Pro Met Ala Met Glu Cys Asp His Val Gln
        195                 200                 205

Ile Thr Ala Leu Ser Gln Ala Leu Asn Ile Ala Leu Gln Val Glu Tyr
210                 215                 220

```
Val Asp Glu Met Asp Thr Ala Leu Asn His His Val Phe Pro Glu Ala
225                 230                 235                 240

Ala Ile Pro Ser Val Tyr Leu Leu Tyr Lys Thr Ser His Tyr Asn Ile
            245                 250                 255

Leu Tyr Ala Ala Glu Lys His
            260
```

<210> SEQ ID NO 353
<211> LENGTH: 256
<212> TYPE: PRT
<213> ORGANISM: Artificial Sequence
<220> FEATURE:
<223> OTHER INFORMATION: OTUB1 alignment

<400> SEQUENCE: 353

```
Met Glu Pro Phe Thr His Asn Asp Gly Asn Arg Asp Glu Leu Ile Met
1               5                   10                  15

Ala Gln Gln Asp Arg Ile Gln Gln Glu Ile Ala Val Gln Asn Pro Leu
            20                  25                  30

Val Ser Glu Arg Leu Glu Leu Ser Val Leu Tyr Lys Glu Tyr Ala Glu
        35                  40                  45

Asp Asp Asn Ile Tyr Gln Gln Lys Ile Lys Asp Leu His Lys Lys Tyr
50                  55                  60

Ser Tyr Ile Arg Lys Thr Arg Pro Asp Gly Asn Cys Phe Tyr Arg Ala
65                  70                  75                  80

Phe Gly Phe Ser His Leu Glu Ala Leu Leu Asp Asp Ser Lys Glu Leu
                85                  90                  95

Gln Arg Phe Lys Ala Val Ser Ala Lys Ser Lys Glu Asp Leu Val Ser
            100                 105                 110

Gln Gly Phe Thr Glu Phe Thr Ile Glu Asp Phe His Asn Thr Phe Met
        115                 120                 125

Asp Leu Ile Glu Gln Val Glu Lys Gln Thr Ser Val Ala Asp Leu Leu
130                 135                 140

Ala Ser Phe Asn Asp Gln Ser Thr Ser Asp Tyr Leu Val Val Tyr Leu
145                 150                 155                 160

Arg Leu Leu Thr Ser Gly Tyr Leu Gln Arg Glu Ser Lys Phe Phe Glu
                165                 170                 175

His Phe Ile Glu Gly Gly Arg Thr Val Lys Glu Phe Cys Gln Gln Glu
            180                 185                 190

Val Glu Pro Met Cys Lys Glu Ser Asp His Ile His Ile Ala Leu
        195                 200                 205

Ala Gln Ala Leu Ser Val Ser Ile Gln Val Glu Tyr Met Asp Arg Gly
    210                 215                 220

Glu Gly Gly Thr Thr Asn Pro His Ile Phe Pro Glu Gly Ser Glu Pro
225                 230                 235                 240

Lys Val Tyr Leu Leu Tyr Arg Pro Gly His Tyr Asp Ile Leu Tyr Lys
                245                 250                 255
```

<210> SEQ ID NO 354
<211> LENGTH: 262
<212> TYPE: PRT
<213> ORGANISM: Artificial Sequence
<220> FEATURE:
<223> OTHER INFORMATION: D.melanogaster alignment

<400> SEQUENCE: 354

```
Met Glu Pro Phe Thr His Asn Asp Gly Asn Arg Asp Glu Leu Ile Ile
1               5                   10                  15
```

Gln Gln Lys Arg Asp Ile Glu Lys Glu Ile Ser Asp Thr Thr Pro Leu
            20                  25                  30

Val Ser Glu Gln Leu Pro Leu Thr Cys Leu Tyr Ala Glu Tyr Ser Gly
                35                  40                  45

Asp Glu Ile Phe Thr Ala Lys Ile Gln Asp Leu Ser Lys Lys Tyr Lys
 50                  55                  60

Phe Ile Arg Arg Thr Arg Pro Asp Gly Asn Cys Phe Phe Arg Ala Phe
 65                  70                  75                  80

Ala Tyr Ser Tyr Leu Glu Tyr Leu Ile Ser Asn Thr Ser Ala Tyr Gln
                85                  90                  95

Glu Phe Lys Lys Leu Ala Glu Glu Ser Lys Glu Lys Leu Val Gln Leu
                100                 105                 110

Gly Phe Pro Ser Phe Thr Leu Glu Asp Phe His Glu Thr Phe Met Glu
                115                 120                 125

Val Ile Gln Arg Val Ser Pro Asp Asn Ala Gly Gly His Ser Thr Val
130                 135                 140

Gln Asp Glu Leu His Lys Ile Phe Asn Glu Gln Gly Tyr Ser Asp Tyr
145                 150                 155                 160

Val Val Val Tyr Leu Arg Leu Ile Thr Ser Gly Lys Leu Gln Glu Glu
                165                 170                 175

Ala Asp Phe Tyr Gln Asn Phe Ile Glu Gly Asp Leu Thr Ile Glu Ala
                180                 185                 190

Phe Arg His Leu Glu Val Glu Pro Met Tyr Lys Glu Ser Asp His Ile
                195                 200                 205

His Ile Ile Ala Leu Cys Thr Ala Leu Gly Ala Gly Val Arg Val Glu
                210                 215                 220

Tyr Leu Asp Arg Gly Glu Gly Gly Thr Val Lys Ala His Asp Phe Pro
225                 230                 235                 240

Glu Gly Ser Glu Pro Arg Ile Tyr Leu Ile Tyr Arg Pro Gly His Tyr
                245                 250                 255

Asp Ile Leu Tyr Pro Asn
                260

<210> SEQ ID NO 355
<211> LENGTH: 296
<212> TYPE: PRT
<213> ORGANISM: Artificial Sequence
<220> FEATURE:
<223> OTHER INFORMATION: C.reinhardtii alignment

<400> SEQUENCE: 355

Met Ala Ser Thr Glu Pro Ala Ala Glu Pro Pro Val Ala Gly Ser Glu
1               5                   10                  15

Ala Pro Asp Arg Pro Ser Asp Glu Ala Ile Leu Gln Gln Gln Asn Gln
                20                  25                  30

Ile Arg Ala Glu Gln Ala Lys Val Ser Glu Tyr Val Gly Gln Glu Glu
            35                  40                  45

Asn Leu Gly Ala Leu Lys Ala Glu Tyr Glu Asn Gly Asn Gln Asn Phe
 50                  55                  60

Val Gln Lys Ile Gly Lys Leu Glu Glu Arg Tyr Arg Thr Phe Arg Arg
 65                  70                  75                  80

Thr Arg Gly Asp Gly Asn Cys Phe Phe Arg Gly Phe Ile Tyr Ala Tyr
                85                  90                  95

Leu Glu Gly Leu Leu Gln Asn Ser Asp Leu Ala Glu Ala Asn Arg Phe
                100                 105                 110

-continued

```
Met Ser Val Val Gln Ser Trp Lys Ala Lys Leu Val Glu Gly Gly Phe
        115                 120                 125

Gln Glu Leu Val Phe Glu Asp Ala Met Glu Leu Leu Leu Glu Gln Val
    130                 135                 140

Lys Glu Val Thr Lys Ala Ser Asp Gln Phe Ala Gln Glu Lys Leu Leu
145                 150                 155                 160

Val Asn Met Arg Asp Asp Met Val Ser Asn Met Ile Val Met Phe Leu
                165                 170                 175

Arg Leu Val Thr Ser Cys Glu Val Gln Arg Arg Glu Asp Phe Phe
                180                 185                 190

Pro Phe Ile Leu Gly Met Tyr Asp Glu Pro Pro Ala Thr Val Glu Leu
            195                 200                 205

Phe Cys Gln Arg His Val Glu Pro Met Gly Glu Glu Ser Asp His Leu
        210                 215                 220

His Ile Val Ala Val Thr Glu Ala Leu Gln Ile Pro Val Arg Val Val
225                 230                 235                 240

Tyr Leu Asp Ser Ser Gly Leu Pro Ala Gly Gly Gly Gly Gly Gly Ala
                245                 250                 255

Gly Ala Leu Glu Ala Ser Cys His Asp Phe Val Pro Asp Ser Cys Pro
            260                 265                 270

Pro Gly Thr Ala Pro Arg Val His Leu Leu Tyr Arg Pro Gly His Tyr
        275                 280                 285

Asp Ile Leu Tyr Ala Lys Ser Gly
    290                 295

<210> SEQ ID NO 356
<211> LENGTH: 318
<212> TYPE: PRT
<213> ORGANISM: Artificial Sequence
<220> FEATURE:
<223> OTHER INFORMATION: Zea mays alignment

<400> SEQUENCE: 356

Met Gly Asp Val Pro Gln Ala Pro His Ala Ala Gly Gly Glu Glu
1               5                   10                  15

Trp Ala Gly Pro Asp Pro Asn Pro Ser Pro Ser Leu Gly Gly Cys Ser
                20                  25                  30

Asp Pro Val Ser Val Glu Leu Ser Met Gly Gly Asp Tyr Tyr Arg Ala
            35                  40                  45

Cys Cys Gly Glu Pro Asp Pro Asp Ile Pro Glu Gly Pro Lys Leu Pro
50                  55                  60

Cys Val Gly Asp Lys Glu Pro Leu Ser Ser Leu Ala Ala Glu Phe Gln
65                  70                  75                  80

Ser Gly Ser Pro Ile Leu Gln Glu Lys Ile Lys Leu Leu Gly Glu Gln
                85                  90                  95

Tyr Gly Ala Leu Arg Arg Thr Arg Gly Asp Gly Asn Cys Phe Tyr Arg
            100                 105                 110

Ser Phe Met Phe Ser Tyr Leu Glu His Ile Leu Glu Thr Gln Asp Lys
        115                 120                 125

Ala Glu Ala Asp Arg Ile Met Val Lys Ile Glu Cys Lys Lys Thr
    130                 135                 140

Leu Leu Ser Leu Gly Tyr Ile Glu Phe Thr Phe Glu Asp Phe Ser
145                 150                 155                 160

Ile Phe Ile Glu Leu Leu Glu Ser Val Leu Gln Gly His Glu Thr Pro
                165                 170                 175
```

```
Ile Gly Pro Glu Glu Leu Leu Glu Arg Thr Arg Asp Pro Gln Val Ser
            180                 185                 190

Asp Tyr Val Val Met Phe Phe Arg Phe Val Thr Ser Gly Glu Ile Gln
            195                 200                 205

Arg Arg Ser Asp Phe Phe Glu Pro Phe Ile Ser Gly Leu Thr Asn Ser
210                 215                 220

Thr Val Val Gln Phe Cys Lys Ala Ser Val Glu Pro Met Gly Glu Glu
225                 230                 235                 240

Ser Asp His Val His Ile Ile Ala Leu Ser Asp Ala Leu Gly Val Pro
            245                 250                 255

Ile Arg Val Met Tyr Leu Asp Arg Ser Ser Cys Asp Thr Gly Asn Leu
            260                 265                 270

Ser Val Asn His His Asp Phe Ile Pro Ser Ala Asn Asp Ser Glu Gly
            275                 280                 285

Asp Ala Ala Thr Thr Pro Ala Pro Ala Thr Glu Lys Pro Tyr Ile Thr
            290                 295                 300

Leu Leu Tyr Arg Pro Gly His Tyr Asp Ile Leu Tyr Pro Lys
305                 310                 315

<210> SEQ ID NO 357
<211> LENGTH: 274
<212> TYPE: PRT
<213> ORGANISM: Artificial Sequence
<220> FEATURE:
<223> OTHER INFORMATION: LOC_Os08g42540 alignment

<400> SEQUENCE: 357

Met Gly Gly Asp Tyr Tyr His Ser Cys Cys Gly Asp Pro Asp Pro Asp
1               5                   10                  15

Leu Arg Ala Pro Glu Gly Pro Lys Leu Pro Tyr Val Gly Asp Lys Glu
            20                  25                  30

Pro Leu Ser Thr Leu Ala Ala Glu Phe Gln Ser Gly Ser Pro Ile Leu
        35                  40                  45

Gln Glu Lys Ile Lys Leu Leu Gly Glu Gln Tyr Asp Ala Leu Arg Arg
    50                  55                  60

Thr Arg Gly Asp Gly Asn Cys Phe Tyr Arg Ser Phe Met Phe Ser Tyr
65                  70                  75                  80

Leu Glu His Ile Leu Glu Thr Gln Asp Lys Ala Glu Val Glu Arg Ile
            85                  90                  95

Leu Lys Lys Ile Glu Gln Cys Lys Lys Thr Leu Ala Asp Leu Gly Tyr
            100                 105                 110

Ile Glu Phe Thr Phe Glu Asp Phe Ser Ile Phe Ile Asp Gln Leu
            115                 120                 125

Glu Ser Val Leu Gln Gly His Glu Ser Ser Ile Gly Ala Glu Glu Leu
        130                 135                 140

Leu Glu Arg Thr Arg Asp Gln Met Val Ser Asp Tyr Val Val Met Phe
145                 150                 155                 160

Phe Arg Phe Val Thr Ser Gly Glu Ile Gln Arg Arg Ala Glu Phe Phe
            165                 170                 175

Glu Pro Phe Ile Ser Gly Leu Thr Asn Ser Thr Val Val Gln Phe Cys
            180                 185                 190

Lys Ala Ser Val Glu Pro Met Gly Glu Glu Ser Asp His Val His Ile
            195                 200                 205

Ile Ala Leu Ser Asp Ala Leu Gly Val Pro Ile Arg Val Met Tyr Leu
210                 215                 220
```

Asp Arg Ser Ser Cys Asp Ala Gly Asn Ile Ser Val Asn His His Asp
225                 230                 235                 240

Phe Ser Pro Glu Ala Asn Ser Ser Asp Gly Ala Ala Ala Glu Lys
                245                 250                 255

Pro Tyr Ile Thr Leu Leu Tyr Arg Pro Gly His Tyr Asp Ile Leu Tyr
            260                 265                 270

Pro Lys

<210> SEQ ID NO 358
<211> LENGTH: 320
<212> TYPE: PRT
<213> ORGANISM: Artificial Sequence
<220> FEATURE:
<223> OTHER INFORMATION: Hordeum vulgare alignment

<400> SEQUENCE: 358

Met Gly Asp Ala Pro Pro Ala Pro Ala Pro Leu Val Glu Gly Gly
1               5                   10                  15

Gly Ser Asp Gly Ala Gly Pro Asp Pro Asn Ser His Arg Leu Ser Pro
                20                  25                  30

Glu Pro Val Ser Val Glu Leu Ser Met Gly Gly Asp Tyr Tyr His Ala
            35                  40                  45

Cys Cys Gly Asp Pro Asp Pro Asp Pro Lys Pro Glu Gly Pro Gln Val
50                  55                  60

Pro Tyr Ile Gly Asn Lys Glu Pro Leu Ser Ala Leu Ala Ala Glu Phe
65                  70                  75                  80

Gln Ser Gly Ser Pro Ile Leu Gln Glu Lys Ile Lys Leu Leu Gly Glu
                85                  90                  95

Gln Tyr Asp Ala Leu Arg Arg Thr Arg Gly Asp Gly Asn Cys Phe Tyr
            100                 105                 110

Arg Ser Phe Met Phe Ser Tyr Leu Glu His Ile Leu Glu Thr Gln Asp
            115                 120                 125

Arg Ala Glu Val Glu Arg Ile Leu Lys Asn Ile Glu Gln Cys Lys Lys
130                 135                 140

Thr Leu Ser Gly Thr Gly Tyr Ile Glu Phe Thr Phe Glu Asp Phe Phe
145                 150                 155                 160

Ser Met Phe Ile Glu Glu Leu Gln Asn Val Leu Gln Gly His Gly Thr
                165                 170                 175

Ser Ile Gly Pro Glu Glu Leu Leu Glu Arg Thr Arg Asp Gln Thr Thr
            180                 185                 190

Ser Asp Tyr Val Val Met Phe Phe Arg Phe Val Thr Ser Gly Glu Ile
        195                 200                 205

Gln Arg Arg Ala Glu Phe Phe Glu Pro Phe Ile Ser Gly Leu Thr Asn
210                 215                 220

Ser Thr Val Val Gln Phe Cys Lys Ser Ser Val Glu Pro Met Gly Glu
225                 230                 235                 240

Glu Ser Asp His Val His Ile Ile Ala Leu Ser Asp Ala Leu Gly Val
                245                 250                 255

Pro Ile Arg Val Met Tyr Leu Asp Arg Ser Ser Cys Asp Thr Gly Asn
            260                 265                 270

Leu Ser Cys Asn His His Asp Phe Ile Pro Ala Ala Asn Ser Ser Glu
        275                 280                 285

Gly Asp Ala Ala Met Gly Leu Asn Pro Ala Asp Glu Lys Pro Tyr Ile
290                 295                 300

```
Thr Leu Leu Tyr Tyr Arg Pro Gly His Tyr Asp Ile Leu Tyr Pro Lys
305                 310                 315                 320

<210> SEQ ID NO 359
<211> LENGTH: 320
<212> TYPE: PRT
<213> ORGANISM: Artificial Sequence
<220> FEATURE:
<223> OTHER INFORMATION: Triticum urartu alignment

<400> SEQUENCE: 359

Met Gly Asp Ala Pro Pro Ala Pro Ala Pro Leu Val Glu Gly Gly
1               5                   10                  15

Gly Ser Asp Gly Ala Gly Pro Asp Pro Asn Ser His Arg Leu Ser Pro
                20                  25                  30

Glu Pro Val Ser Val Glu Leu Ser Met Gly Gly Asp Tyr Tyr His Ala
            35                  40                  45

Cys Cys Gly Asp Pro Asp Pro Asp Pro Lys Pro Glu Gly Pro Gln Val
        50                  55                  60

Pro Tyr Ile Gly Asn Lys Glu Pro Leu Ser Ala Leu Ala Ala Glu Phe
65                  70                  75                  80

Gln Ser Gly Ser Pro Ile Leu Gln Glu Lys Ile Lys Leu Leu Gly Glu
                85                  90                  95

Gln Tyr Asp Ala Leu Arg Arg Thr Arg Gly Asp Gly Asn Cys Phe Tyr
            100                 105                 110

Arg Ser Phe Met Phe Ser Tyr Leu Glu His Ile Leu Glu Thr Gln Asp
        115                 120                 125

Arg Ala Glu Val Glu Arg Ile Leu Lys Asn Ile Glu Gln Cys Lys Lys
    130                 135                 140

Thr Leu Ser Gly Thr Gly Tyr Ile Glu Phe Thr Phe Glu Asp Phe Phe
145                 150                 155                 160

Ser Met Phe Ile Glu Glu Leu Gln Asn Val Leu Gln Gly His Glu Thr
                165                 170                 175

Ser Ile Gly Pro Glu Glu Leu Leu Glu Arg Thr Arg Asp Gln Thr Thr
            180                 185                 190

Ser Asp Tyr Val Val Met Phe Phe Arg Phe Val Thr Ser Gly Glu Ile
        195                 200                 205

Gln Arg Arg Ala Glu Phe Phe Glu Pro Phe Ile Ser Gly Leu Thr Asn
    210                 215                 220

Ser Thr Val Val Gln Phe Cys Lys Ser Ser Val Glu Pro Met Gly Glu
225                 230                 235                 240

Glu Ser Asp His Val His Ile Ile Ala Leu Ser Asp Ala Leu Gly Val
                245                 250                 255

Pro Ile Arg Val Met Tyr Leu Asp Arg Ser Ser Cys Thr Gly Asn
            260                 265                 270

Leu Ser Cys Asn His His Asp Phe Ile Pro Ala Ala Asn Ser Ser Glu
        275                 280                 285

Gly Asp Ala Ala Met Gly Leu Asn Pro Ala Glu Glu Lys Pro Tyr Ile
    290                 295                 300

Thr Leu Leu Tyr Tyr Arg Pro Gly His Tyr Asp Ile Leu Tyr Pro Lys
305                 310                 315                 320

<210> SEQ ID NO 360
<211> LENGTH: 306
<212> TYPE: PRT
<213> ORGANISM: Artificial Sequence
<220> FEATURE:
```

<223> OTHER INFORMATION: A.thaliana alignment

<400> SEQUENCE: 360

Met Gln Asn Gln Ile Asp Met Val Lys Asp Glu Ala Glu Val Ala Ala
1               5                   10                  15

Ser Ile Ser Ala Ile Lys Gly Glu Glu Trp Gly Asn Cys Ser Ser Val
            20                  25                  30

Glu Asp Gln Pro Ser Phe Gln Glu Glu Ala Ala Lys Val Pro Tyr
        35                  40                  45

Val Gly Asp Lys Glu Pro Leu Ser Ser Leu Ala Ala Glu Tyr Gln Ser
    50                  55                  60

Gly Ser Pro Ile Leu Leu Glu Lys Ile Lys Ile Leu Asp Ser Gln Tyr
65                  70                  75                  80

Ile Gly Ile Arg Arg Thr Arg Gly Asp Gly Asn Cys Phe Phe Arg Ser
                85                  90                  95

Phe Met Phe Ser Tyr Leu Glu His Ile Leu Glu Ser Gln Asp Arg Ala
            100                 105                 110

Glu Val Asp Arg Ile Lys Val Asn Val Glu Lys Cys Arg Lys Thr Leu
        115                 120                 125

Gln Asn Leu Gly Tyr Thr Asp Phe Thr Phe Glu Asp Phe Phe Ala Leu
    130                 135                 140

Phe Leu Glu Gln Leu Asp Asp Ile Leu Gln Gly Thr Glu Glu Ser Ile
145                 150                 155                 160

Ser Tyr Asp Glu Leu Val Asn Arg Ser Arg Asp Gln Ser Val Ser Asp
                165                 170                 175

Tyr Ile Val Met Phe Phe Arg Phe Val Thr Ala Gly Asp Ile Arg Thr
            180                 185                 190

Arg Ala Asp Phe Phe Glu Pro Phe Ile Thr Gly Leu Ser Asn Ala Thr
        195                 200                 205

Val Asp Gln Phe Cys Lys Ser Ser Val Glu Pro Met Gly Glu Glu Ser
    210                 215                 220

Asp His Ile His Ile Thr Ala Leu Ser Asp Ala Leu Gly Val Ala Ile
225                 230                 235                 240

Arg Val Val Tyr Leu Asp Arg Ser Ser Cys Asp Ser Gly Gly Val Thr
                245                 250                 255

Val Asn His His Asp Phe Val Pro Val Gly Ile Thr Asn Glu Lys Asp
            260                 265                 270

Glu Glu Ala Ser Ala Pro Phe Ile Thr Leu Leu Tyr Arg Pro Gly His
        275                 280                 285

Tyr Asp Ile Leu Tyr Pro Lys Pro Ser Cys Lys Val Ser Asp Asn Val
    290                 295                 300

Gly Lys
305

<210> SEQ ID NO 361
<211> LENGTH: 301
<212> TYPE: PRT
<213> ORGANISM: Artificial Sequence
<220> FEATURE:
<223> OTHER INFORMATION: Glycine max alignment

<400> SEQUENCE: 361

Met Gln Ser Lys Glu Ala Val Val Glu Asp Gly Glu Ile Lys Ser Val
1               5                   10                  15

Thr Ala Val Gly Ser Glu Ile Asp Gly Trp Thr Asn Phe Gly Asp Asp
            20                  25                  30

Asp Ile Met Gln Gln Gln Tyr Thr Ile Gln Ala Glu Glu Ala Lys Lys
             35                  40                  45

Val Pro Phe Val Gly Asp Lys Glu Pro Leu Ser Ser Leu Ala Ala Glu
 50                  55                  60

Tyr Lys Leu Gly Ser Pro Ile Leu Leu Glu Lys Ile Lys Val Leu Asp
 65                  70                  75                  80

Glu Gln Tyr Ala Ala Ile Arg Arg Thr Arg Gly Asp Gly Asn Cys Phe
                 85                  90                  95

Phe Arg Ser Phe Met Phe Ser Tyr Leu Glu His Ile Met Glu Cys Gln
            100                 105                 110

Asp Gln Ala Glu Ile Asp Arg Ile Gln Ala Asn Val Glu Lys Ser Arg
            115                 120                 125

Lys Ala Leu Gln Thr Leu Gly Tyr Ala Asp Leu Thr Phe Glu Asp Phe
130                 135                 140

Phe Ala Leu Phe Leu Glu Gln Leu Glu Ser Val Ile Gln Gly Lys Glu
145                 150                 155                 160

Thr Ser Ile Ser His Glu Leu Val Leu Arg Ser Arg Asp Gln Ser
                165                 170                 175

Ile Ser Asp Tyr Val Val Met Phe Phe Arg Phe Val Thr Ser Ala Glu
            180                 185                 190

Ile Gln Lys Arg Ala Glu Phe Phe Glu Pro Phe Ile Leu Gly Leu Thr
            195                 200                 205

Asn Thr Thr Val Glu Gln Phe Cys Lys Ser Ser Val Glu Pro Met Gly
            210                 215                 220

Glu Glu Ser Asp His Met His Ile Thr Ala Leu Ser Asp Ala Leu Gly
225                 230                 235                 240

Ile Pro Ile Arg Val Val Tyr Leu Asp Arg Ser Ser Cys Asp Thr Gly
            245                 250                 255

Gly Val Ser Val Asn His His Asp Phe Met Pro Val Ala Gly Asp Leu
            260                 265                 270

Pro Asn Ala Ser Cys Ser Ser Glu Lys Asn Ile Pro Phe Ile Thr Leu
            275                 280                 285

Leu Tyr Arg Pro Gly His Tyr Asp Ile Leu Tyr Thr Lys
            290                 295                 300

<210> SEQ ID NO 362
<211> LENGTH: 20
<212> TYPE: DNA
<213> ORGANISM: Artificial Sequence
<220> FEATURE:
<223> OTHER INFORMATION: WTG1-dF primer

<400> SEQUENCE: 362
cacaaagtaa caataaagtc                                              20

<210> SEQ ID NO 363
<211> LENGTH: 24
<212> TYPE: DNA
<213> ORGANISM: Artificial Sequence
<220> FEATURE:
<223> OTHER INFORMATION: WTG1-dR primer

<400> SEQUENCE: 363
gctgatgatc ttatcatttg cttc                                         24

<210> SEQ ID NO 364
<211> LENGTH: 18

<212> TYPE: DNA
<213> ORGANISM: Artificial Sequence
<220> FEATURE:
<223> OTHER INFORMATION: WTG1-F1 primer

<400> SEQUENCE: 364
atgggcgggg actactac                                                         18

<210> SEQ ID NO 365
<211> LENGTH: 20
<212> TYPE: DNA
<213> ORGANISM: Artificial Sequence
<220> FEATURE:
<223> OTHER INFORMATION: WTG1-R1 primer

<400> SEQUENCE: 365
tcacttcggg tagagaatgt                                                       20

<210> SEQ ID NO 366
<211> LENGTH: 40
<212> TYPE: DNA
<213> ORGANISM: Artificial Sequence
<220> FEATURE:
<223> OTHER INFORMATION: C99-WTG1-GF primer

<400> SEQUENCE: 366
agcgcaacga attcgagctc ggtcacatca acaccggac                                  40

<210> SEQ ID NO 367
<211> LENGTH: 40
<212> TYPE: DNA
<213> ORGANISM: Artificial Sequence
<220> FEATURE:
<223> OTHER INFORMATION: C99-WTG1-GR primer

<400> SEQUENCE: 367
ggccagtgcc aagcttagca gcaacatcaa ctaggggcct                                 40

<210> SEQ ID NO 368
<211> LENGTH: 34
<212> TYPE: DNA
<213> ORGANISM: Artificial Sequence
<220> FEATURE:
<223> OTHER INFORMATION: 003-CDSWTG1-F primer

<400> SEQUENCE: 368
gcaggaattc aagcttatgg gcggggacta ctac                                       34

<210> SEQ ID NO 369
<211> LENGTH: 36
<212> TYPE: DNA
<213> ORGANISM: Artificial Sequence
<220> FEATURE:
<223> OTHER INFORMATION: 003-CDSWTG1-R primer

<400> SEQUENCE: 369
agtcactatg gtcgactcac ttcgggtaga gaatgt                                     36

<210> SEQ ID NO 370
<211> LENGTH: 40
<212> TYPE: DNA
<213> ORGANISM: Artificial Sequence
<220> FEATURE:
<223> OTHER INFORMATION: C43-CDSWTG1-F primer

<400> SEQUENCE: 370
tgaactatac aaaggcgcgc caatgggcgg ggactactac    40

<210> SEQ ID NO 371
<211> LENGTH: 42
<212> TYPE: DNA
<213> ORGANISM: Artificial Sequence
<220> FEATURE:
<223> OTHER INFORMATION: C43-CDSWTG1-R primer

<400> SEQUENCE: 371
cgctctagaa ctagttaatt aatcacttcg ggtagagaat gt    42

<210> SEQ ID NO 372
<211> LENGTH: 36
<212> TYPE: DNA
<213> ORGANISM: Artificial Sequence
<220> FEATURE:
<223> OTHER INFORMATION: proWTG1-F primer

<400> SEQUENCE: 372
cggggcgtaa tctagatgct accaagtccc acgtat    36

<210> SEQ ID NO 373
<211> LENGTH: 36
<212> TYPE: DNA
<213> ORGANISM: Artificial Sequence
<220> FEATURE:
<223> OTHER INFORMATION: proWTG1-R primer

<400> SEQUENCE: 373
ggatcgatcc tctagaaaag cttcgataaa agcagt    36

<210> SEQ ID NO 374
<211> LENGTH: 38
<212> TYPE: DNA
<213> ORGANISM: Artificial Sequence
<220> FEATURE:
<223> OTHER INFORMATION: MBP-WTG1-F primer

<400> SEQUENCE: 374
tcggatcctc tagagtcgac atgggcgggg actactac    38

<210> SEQ ID NO 375
<211> LENGTH: 38
<212> TYPE: DNA
<213> ORGANISM: Artificial Sequence
<220> FEATURE:
<223> OTHER INFORMATION: MBP-WTG1-R primer

<400> SEQUENCE: 375
ggccagtgcc aagcttgctc acttcgggta gagaatgt    38

<210> SEQ ID NO 376
<211> LENGTH: 40
<212> TYPE: DNA
<213> ORGANISM: Artificial Sequence
<220> FEATURE:
<223> OTHER INFORMATION: MBP-wtg1-F primer

<400> SEQUENCE: 376
tcggatcctc tagagtcgac atgggcgggg actactacca    40

<210> SEQ ID NO 377
<211> LENGTH: 41
<212> TYPE: DNA
<213> ORGANISM: Artificial Sequence

```
<220> FEATURE:
<223> OTHER INFORMATION: MBP-wtg1-R primer

<400> SEQUENCE: 377
ggccagtgcc aagcttgcct agctcataca aaaattattc c                          41

<210> SEQ ID NO 378
<211> LENGTH: 40
<212> TYPE: DNA
<213> ORGANISM: Artificial Sequence
<220> FEATURE:
<223> OTHER INFORMATION: MBP-WTG1-MutF primer

<400> SEQUENCE: 378
tcggatcctc tagagtcgac atgggcgggg actactacca                            40

<210> SEQ ID NO 379
<211> LENGTH: 47
<212> TYPE: DNA
<213> ORGANISM: Artificial Sequence
<220> FEATURE:
<223> OTHER INFORMATION: MBP-WTG1-MutR primer

<400> SEQUENCE: 379
ggccagtgcc aagcttgctc acttcgggta gagaatgtcg tagcgac                    47

<210> SEQ ID NO 380
<211> LENGTH: 25
<212> TYPE: DNA
<213> ORGANISM: Artificial Sequence
<220> FEATURE:
<223> OTHER INFORMATION: MBP-WTG1-MutF1 primer

<400> SEQUENCE: 380
gaggagaagg aaacagcttt tatcg                                            25

<210> SEQ ID NO 381
<211> LENGTH: 25
<212> TYPE: DNA
<213> ORGANISM: Artificial Sequence
<220> FEATURE:
<223> OTHER INFORMATION: MBP-WTG1-MutR1 primer

<400> SEQUENCE: 381
cgataaaagc tgtttccttc tcctc                                            25

<210> SEQ ID NO 382
<211> LENGTH: 22
<212> TYPE: DNA
<213> ORGANISM: Artificial Sequence
<220> FEATURE:
<223> OTHER INFORMATION: ACTIN1-F primer

<400> SEQUENCE: 382
acatcgccct ggactatgac ca                                               22

<210> SEQ ID NO 383
<211> LENGTH: 21
<212> TYPE: DNA
<213> ORGANISM: Artificial Sequence
<220> FEATURE:
<223> OTHER INFORMATION: ACTIN1-R primer

<400> SEQUENCE: 383
gtcgtactca gccttggcaa t                                                21
```

<210> SEQ ID NO 384
<211> LENGTH: 20
<212> TYPE: DNA
<213> ORGANISM: Artificial Sequence
<220> FEATURE:
<223> OTHER INFORMATION: WTG1-QF primer

<400> SEQUENCE: 384
tggttcagtt ctgcaaggct                                       20

<210> SEQ ID NO 385
<211> LENGTH: 20
<212> TYPE: DNA
<213> ORGANISM: Artificial Sequence
<220> FEATURE:
<223> OTHER INFORMATION: WTG1-QR primer

<400> SEQUENCE: 385
ccaggacggt agagcaaagt                                       20

<210> SEQ ID NO 386
<211> LENGTH: 22
<212> TYPE: DNA
<213> ORGANISM: Artificial Sequence
<220> FEATURE:
<223> OTHER INFORMATION: LIC-QF primer

<400> SEQUENCE: 386
ggagtttcga gcgtatctgg aa                                    22

<210> SEQ ID NO 387
<211> LENGTH: 22
<212> TYPE: DNA
<213> ORGANISM: Artificial Sequence
<220> FEATURE:
<223> OTHER INFORMATION: LIC-QR primer

<400> SEQUENCE: 387
tggacagagg aagcaggaga ct                                    22

<210> SEQ ID NO 388
<211> LENGTH: 20
<212> TYPE: DNA
<213> ORGANISM: Artificial Sequence
<220> FEATURE:
<223> OTHER INFORMATION: BRD1-QF primer

<400> SEQUENCE: 388
tcaaccttcc tggaaccaac                                       20

<210> SEQ ID NO 389
<211> LENGTH: 20
<212> TYPE: DNA
<213> ORGANISM: Artificial Sequence
<220> FEATURE:
<223> OTHER INFORMATION: BRD1-QR primer

<400> SEQUENCE: 389
tctgtgagct tctccctggt                                       20

<210> SEQ ID NO 390
<211> LENGTH: 20
<212> TYPE: DNA
<213> ORGANISM: Artificial Sequence
<220> FEATURE:
<223> OTHER INFORMATION: BZR1-QF primer

```
<400> SEQUENCE: 390
gacaacaacg aggtgctcaa                                              20

<210> SEQ ID NO 391
<211> LENGTH: 20
<212> TYPE: DNA
<213> ORGANISM: Artificial Sequence
<220> FEATURE:
<223> OTHER INFORMATION: BZR1-QR primer

<400> SEQUENCE: 391
gcttacatcc cttgcggtag                                              20

<210> SEQ ID NO 392
<211> LENGTH: 21
<212> TYPE: DNA
<213> ORGANISM: Artificial Sequence
<220> FEATURE:
<223> OTHER INFORMATION: D1-QF primer

<400> SEQUENCE: 392
cggccctaga ccagaaactt g                                            21

<210> SEQ ID NO 393
<211> LENGTH: 21
<212> TYPE: DNA
<213> ORGANISM: Artificial Sequence
<220> FEATURE:
<223> OTHER INFORMATION: D1-QR primer

<400> SEQUENCE: 393
cttccctgga gcgtctcatg c                                            21

<210> SEQ ID NO 394
<211> LENGTH: 30
<212> TYPE: DNA
<213> ORGANISM: Artificial Sequence
<220> FEATURE:
<223> OTHER INFORMATION: D2-QF primer

<400> SEQUENCE: 394
agctgcctgg cactaggctc tacagatcac                                   30

<210> SEQ ID NO 395
<211> LENGTH: 30
<212> TYPE: DNA
<213> ORGANISM: Artificial Sequence
<220> FEATURE:
<223> OTHER INFORMATION: D2-QR primer

<400> SEQUENCE: 395
atgttgtcgg agatgagctc gtcggtgagc                                   30

<210> SEQ ID NO 396
<211> LENGTH: 19
<212> TYPE: DNA
<213> ORGANISM: Artificial Sequence
<220> FEATURE:
<223> OTHER INFORMATION: D11-QF primer

<400> SEQUENCE: 396
tggcgatgac attccgatg                                               19

<210> SEQ ID NO 397
```

```
<211> LENGTH: 21
<212> TYPE: DNA
<213> ORGANISM: Artificial Sequence
<220> FEATURE:
<223> OTHER INFORMATION: D11-QR primer

<400> SEQUENCE: 397
gcaactgcaa acctgtcagg a                                              21

<210> SEQ ID NO 398
<211> LENGTH: 22
<212> TYPE: DNA
<213> ORGANISM: Artificial Sequence
<220> FEATURE:
<223> OTHER INFORMATION: D61-QF primer

<400> SEQUENCE: 398
gttggacggc cttacgttta tc                                             22

<210> SEQ ID NO 399
<211> LENGTH: 20
<212> TYPE: DNA
<213> ORGANISM: Artificial Sequence
<220> FEATURE:
<223> OTHER INFORMATION: D61-QR primer

<400> SEQUENCE: 399
gctggtaaac tccagcaagc                                                20

<210> SEQ ID NO 400
<211> LENGTH: 22
<212> TYPE: DNA
<213> ORGANISM: Artificial Sequence
<220> FEATURE:
<223> OTHER INFORMATION: GS2-QF primer

<400> SEQUENCE: 400
gccatttccc ctttcaagct at                                             22

<210> SEQ ID NO 401
<211> LENGTH: 22
<212> TYPE: DNA
<213> ORGANISM: Artificial Sequence
<220> FEATURE:
<223> OTHER INFORMATION: GS2-QR primer

<400> SEQUENCE: 401
gaccatgaat cccttccctt tg                                             22

<210> SEQ ID NO 402
<211> LENGTH: 20
<212> TYPE: DNA
<213> ORGANISM: Artificial Sequence
<220> FEATURE:
<223> OTHER INFORMATION: GL7-QF primer

<400> SEQUENCE: 402
cacagggaag atgcaaggtg                                                20

<210> SEQ ID NO 403
<211> LENGTH: 20
<212> TYPE: DNA
<213> ORGANISM: Artificial Sequence
<220> FEATURE:
<223> OTHER INFORMATION: GL7-QR primer

<400> SEQUENCE: 403
```

```
ggccccgtgt tgaggaatat                                              20

<210> SEQ ID NO 404
<211> LENGTH: 20
<212> TYPE: DNA
<213> ORGANISM: Artificial Sequence
<220> FEATURE:
<223> OTHER INFORMATION: SPL13-QF primer

<400> SEQUENCE: 404
ccgccgttcc agatcagata                                              20

<210> SEQ ID NO 405
<211> LENGTH: 20
<212> TYPE: DNA
<213> ORGANISM: Artificial Sequence
<220> FEATURE:
<223> OTHER INFORMATION: SPL13-QR primer

<400> SEQUENCE: 405
aagaagggac gtaggtggtg                                              20

<210> SEQ ID NO 406
<211> LENGTH: 19
<212> TYPE: DNA
<213> ORGANISM: Artificial Sequence
<220> FEATURE:
<223> OTHER INFORMATION: SRS5-QF primer

<400> SEQUENCE: 406
gagttcgacg atggtgacg                                               19
```